US011667697B2

(12) United States Patent
Crowe, Jr. et al.

(10) Patent No.: US 11,667,697 B2
(45) Date of Patent: Jun. 6, 2023

(54) HUMAN ORTHOPOXVIRUS ANTIBODIES AND METHODS OF USE THEREFOR

(71) Applicant: Vanderbilt University, Nashville, TN (US)

(72) Inventors: James E. Crowe, Jr., Nashville, TN (US); Iuliia Gilchuk, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 248 days.

(21) Appl. No.: 16/343,107

(22) PCT Filed: Oct. 18, 2017

(86) PCT No.: PCT/US2017/057150
§ 371 (c)(1),
(2) Date: Apr. 18, 2019

(87) PCT Pub. No.: WO2018/075621
PCT Pub. Date: Apr. 26, 2018

(65) Prior Publication Data
US 2020/0071389 A1 Mar. 5, 2020

Related U.S. Application Data

(60) Provisional application No. 62/410,207, filed on Oct. 19, 2016.

(51) Int. Cl.
*A61K 39/42* (2006.01)
*C07K 16/08* (2006.01)
(Continued)

(52) U.S. Cl.
CPC ............ *C07K 16/081* (2013.01); *A61P 31/20* (2018.01); *G01N 33/56983* (2013.01); *A61K 2039/505* (2013.01); *A61K 2039/507* (2013.01); *A61K 2039/545* (2013.01); *C07K 2317/24* (2013.01); *C07K 2317/33* (2013.01); *C07K 2317/565* (2013.01); *C07K 2317/76* (2013.01); *G01N 2333/065* (2013.01)

(58) Field of Classification Search
None
See application file for complete search history.

(56) References Cited

U.S. PATENT DOCUMENTS 7,850,965 B2 * 12/2010 Jensen .................... A61P 31/14 424/133.1
7,914,788 B2 * 3/2011 Chen .................... C07K 14/005 424/141.1

(Continued)

FOREIGN PATENT DOCUMENTS

WO WO-2007065433 A2 * 6/2007 .............. A61P 31/12

OTHER PUBLICATIONS

Rudikoff et al., "Single amino acid substitution altering antigen-binding specificity," Proc Natl Acad Sci USA 79:1979-1983 (Year: 1982).*

(Continued)

*Primary Examiner* — M Franco G Salvoza
(74) *Attorney, Agent, or Firm* — Parker Highlander PLLC

(57) ABSTRACT

The present disclosure is directed to antibodies binding to and neutralizing Poxvirus and methods for use thereof.

20 Claims, 16 Drawing Sheets

Specification includes a Sequence Listing.

(51) Int. Cl.
*A61P 31/20* (2006.01)
*G01N 33/569* (2006.01)
*A61K 39/00* (2006.01)

(56) References Cited

U.S. PATENT DOCUMENTS

| | | | |
|---|---|---|---|
| 8,673,307 | B1 | 3/2014 | Nussenzweig et al. |
| 2003/0207349 | A1 | 11/2003 | Baker et al. |
| 2008/0069822 | A1* | 3/2008 | Jensen ............... A61P 31/14 424/159.1 |
| 2010/0166768 | A1 | 7/2010 | Sleeman et al. |
| 2011/0158984 | A1 | 6/2011 | Jensen et al. |
| 2012/0058906 | A1 | 3/2012 | Smider et al. |
| 2016/0176953 | A1 | 6/2016 | Purcell Ngambo et al. |

OTHER PUBLICATIONS

Benhia et al., "Unusual Features of Vaccinia Virus Extracellular Virion Form Neutralization Resistance Revealed in Human Antibody Response to the Smallpox Vaccine," Journal of Virolog, vol. 87, No. 3: 1569-1585 (Year: 2013).*

Matho et al., "Structural and Functional Characterization of Anti-A33 Antibodies Reveal a Potent Cross-Species Orthopoxviruses Neutralizer," PLoS Patho 11(9): e1005148 (Year: 2015).*

Benhnia. Mohammed Rafii-El-Idrissi, et al. "Vaccinia virus extracellular enveloped virion neutralization in vitro and protection in vivo depend on complement." *Journal of Virology* 83.3 (2009): 1201-1215.

International Preliminary Report on Patentability issued in International Application No. PCT/US2017/057150, dated May 2, 2019.

International Search Report and Written Opinion issued in International Application No. PCT/US17/57150, dated Mar. 26, 2018.

Lantto, Johan, et al. "Capturing the natural diversity of the human antibody response against vaccinia virus." *Journal of Virology* 85.4 (2011): 1820-1833.

Lustig, Shlomo, et al. "Combinations of polyclonal or monoclonal antibodies to proteins of the outer membranes of the two infectious forms of vaccinia virus protect mice against a lethal respiratory challenge." *Journal of Virology* 79.21 (2005): 13454-13462.

McCausland, Megan M., et al. "Combination therapy of vaccinia virus infection with human anti-H3 and anti-B5 monoclonal antibodies in a small animal model." *Antiviral Therapy* 15.4 (2010): 661.

Moss. Bernard. "Smallpox vaccines: targets of protective immunity." *Immunological Reviews* 239.1 (2011): 8-26.

Zaitseva. Marina, el al "Passive immunotherapies protect WRvFire and IHD-J-Luc vaccinia virus-infected mice from lethality bv reducing viral loads in the upper respiratory tract and internal organs." *Journal of Virology* 85.17 (2011): 9147-9158.

* cited by examiner

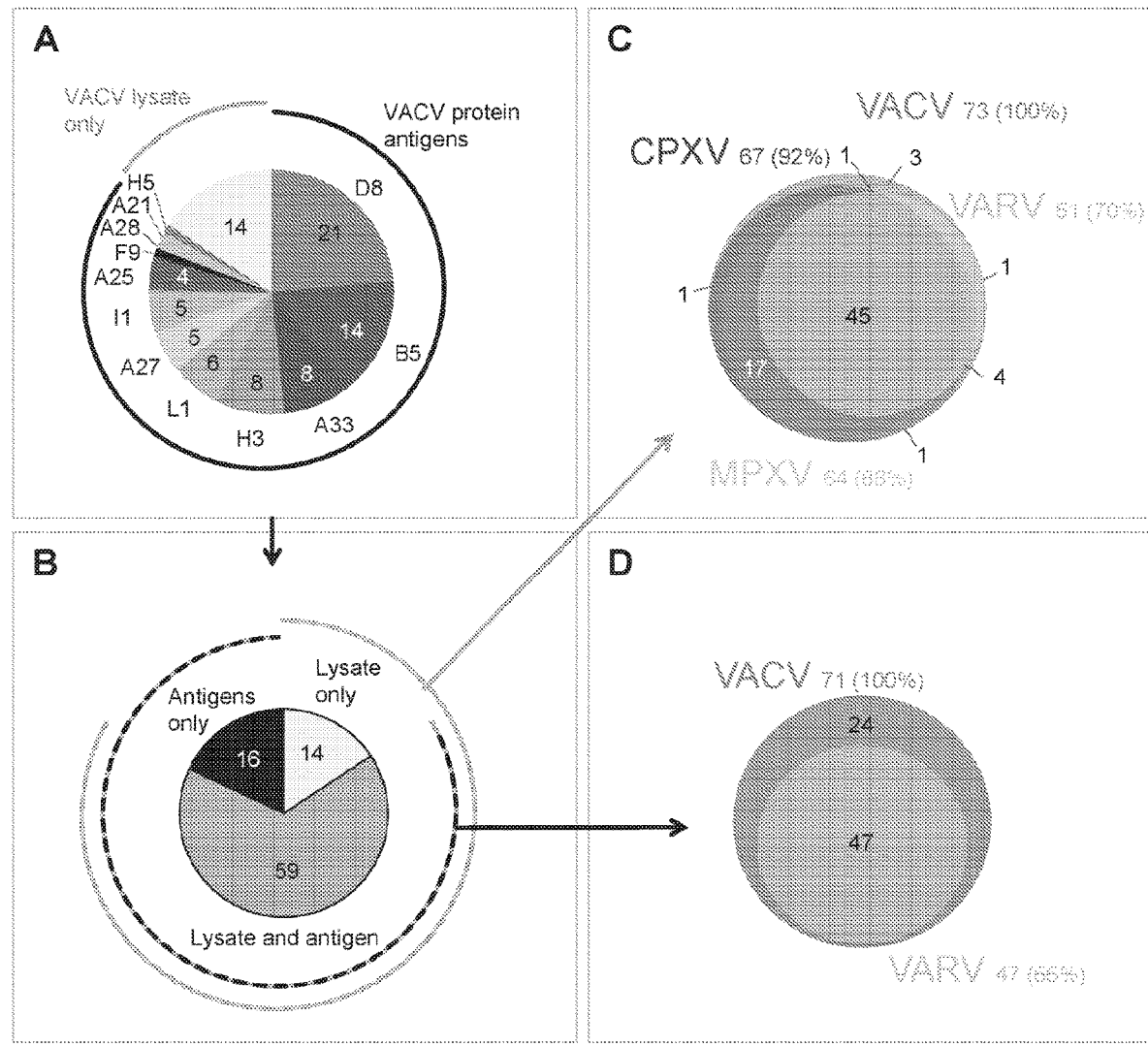
FIGS. 1A-D

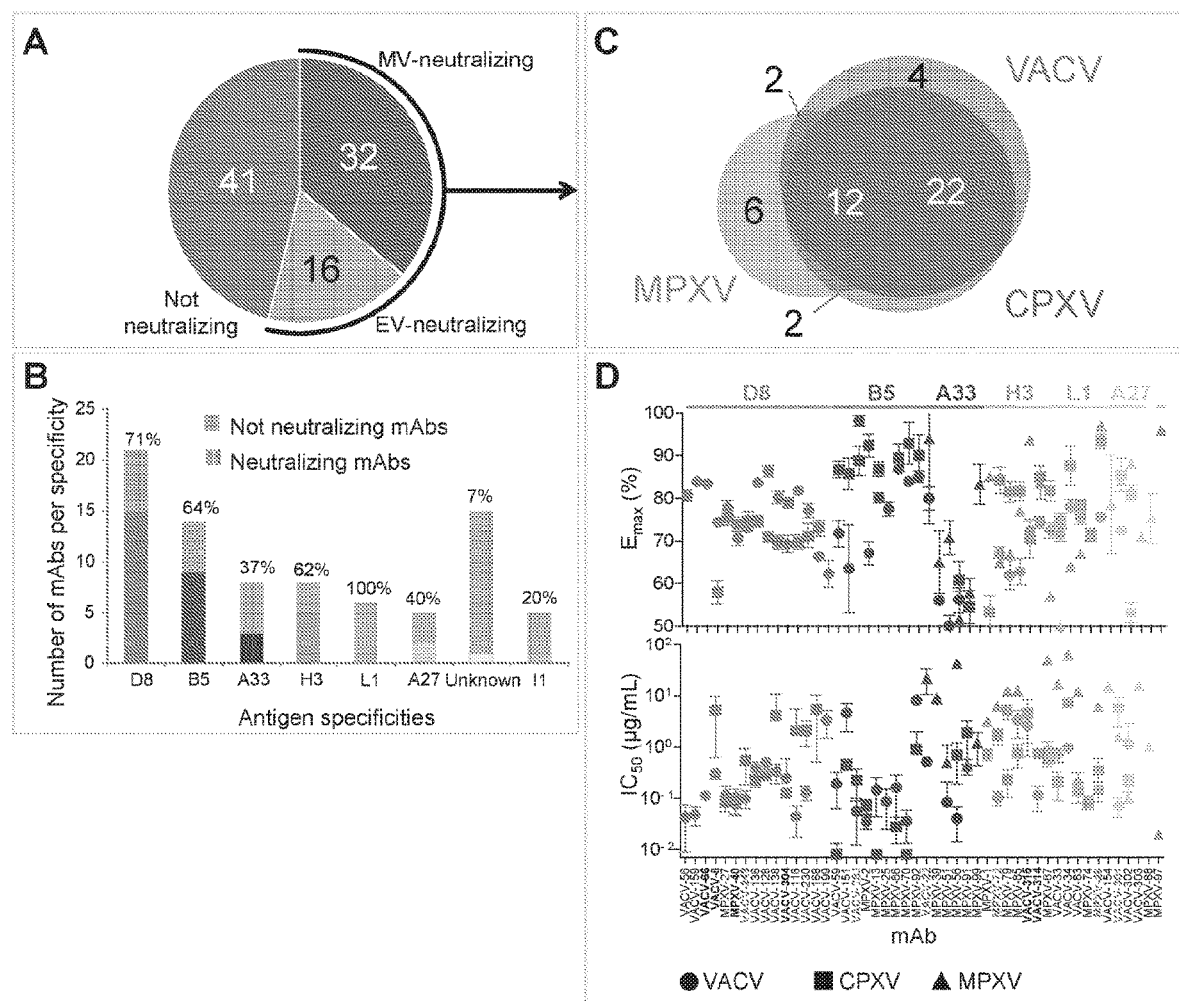
FIGS. 2A-D

FIGS. 3A-B

A
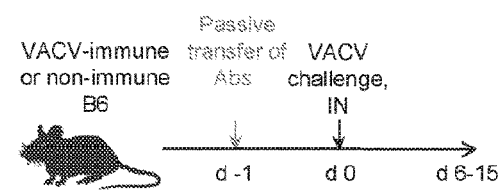
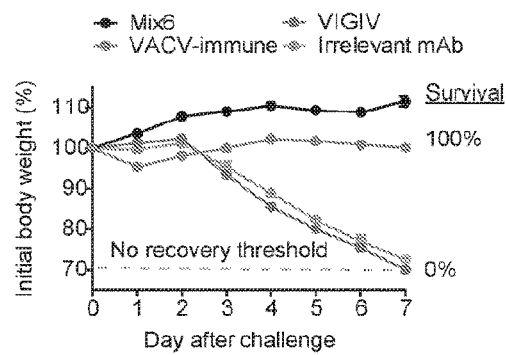
B
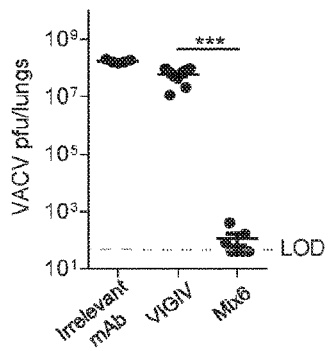
C
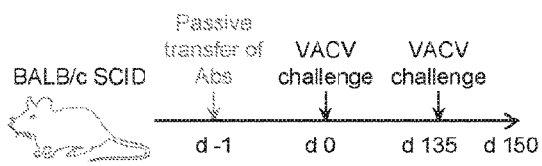
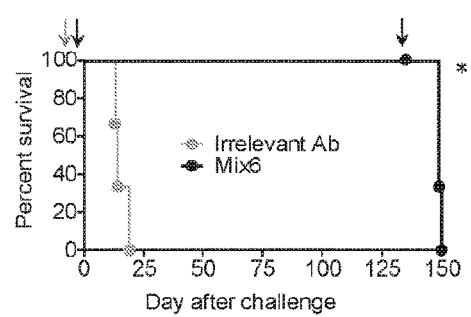
D
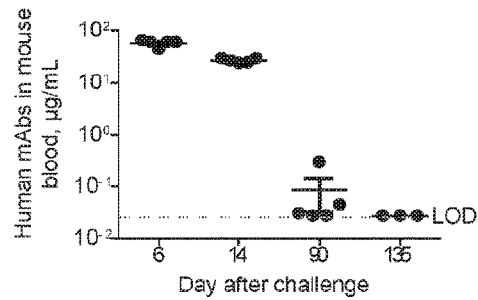
FIGS. 4A-D

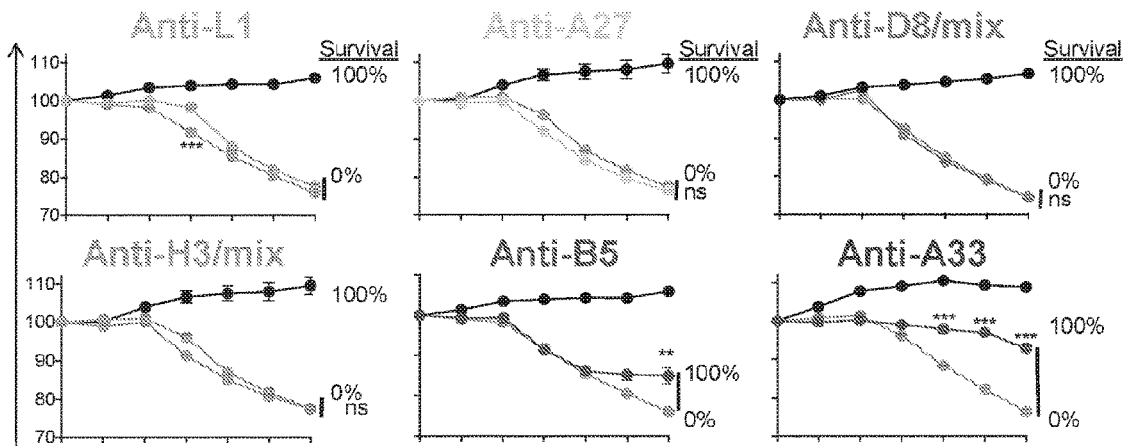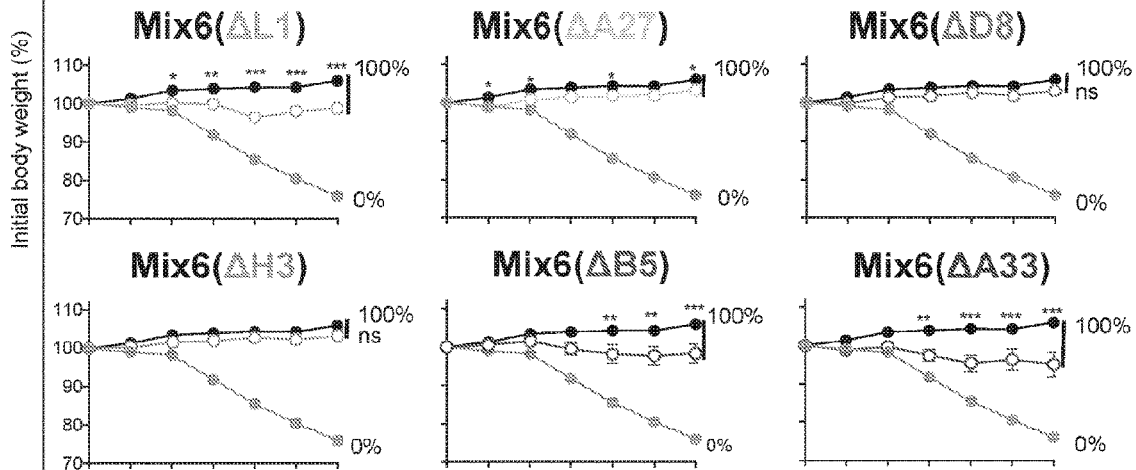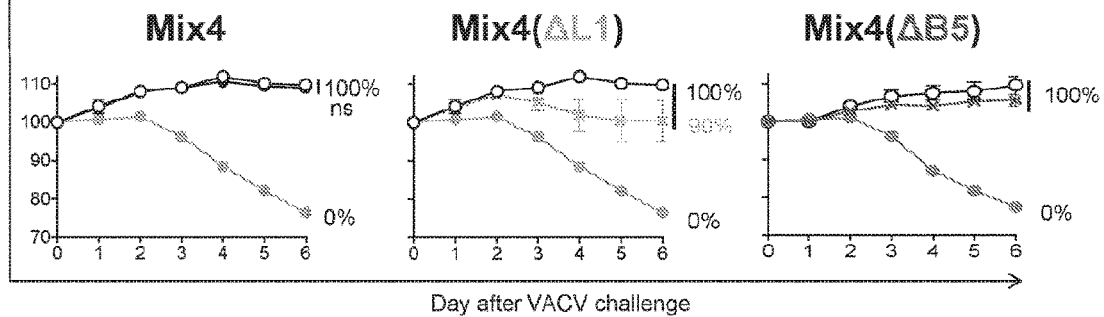
FIGS. 5A-C

MV neutralization

VACV △ Mix6
CPXV ○ Mix4
MPXV □ VIGIV
VARV

Neutralization (%) vs Antibody concentration (µg/mL)

*FIG. 10*

*EV neutralization*

FIG. 10 (Cont'd)

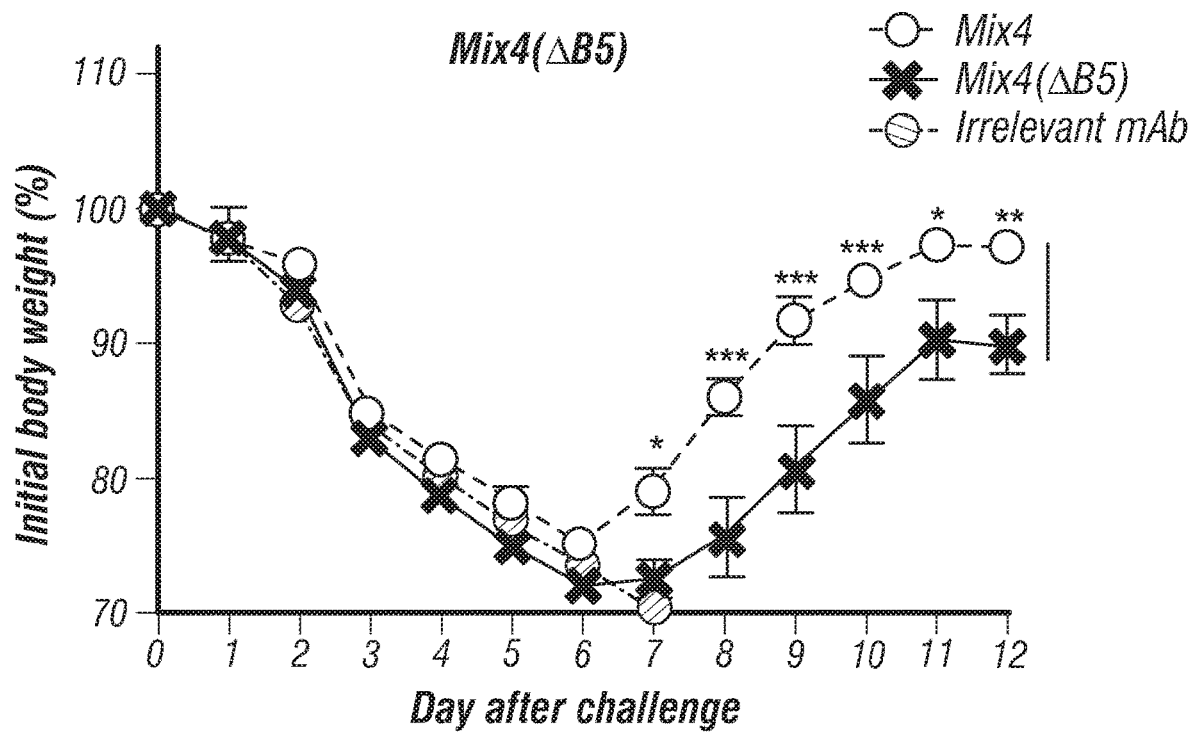
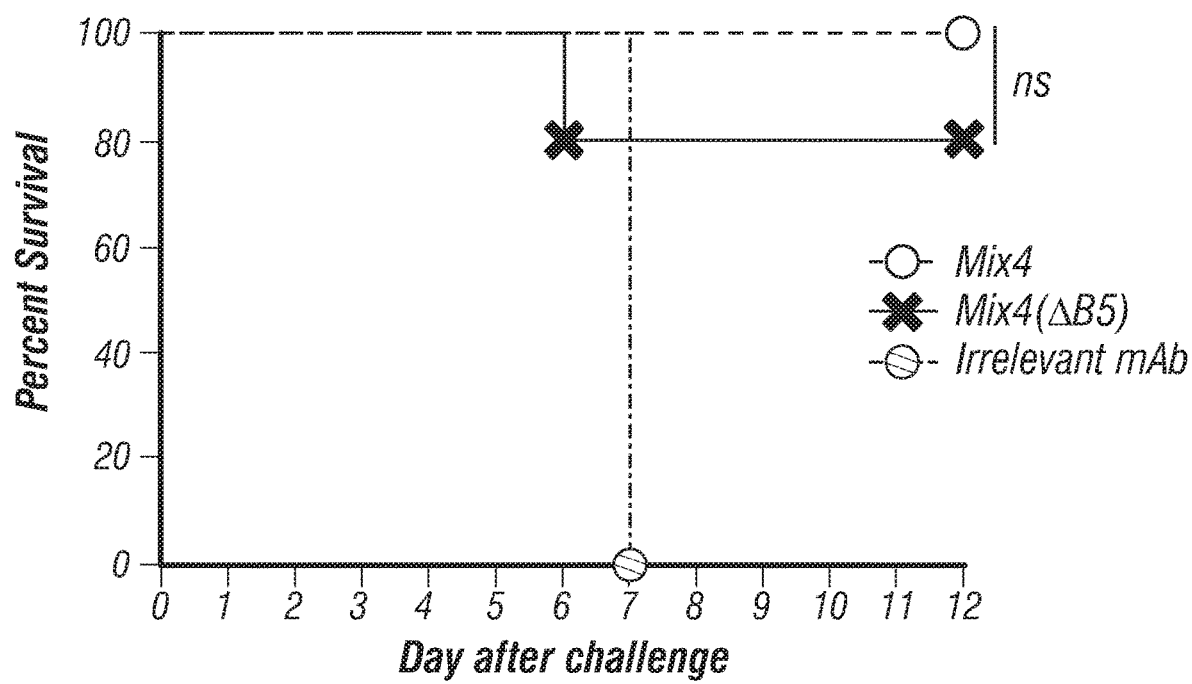
FIG. 12B

SEQUENCE LISTING

<160> NUMBER OF SEQ ID NOS: 943

<210> SEQ ID NO 1
<211> LENGTH: 367
<212> TYPE: DNA
<213> ORGANISM: Artificial sequence

```
<220> FEATURE:
<223> OTHER INFORMATION: Synthetic oligonucleotide

<400> SEQUENCE: 1
caggtgcagc tacagcagtg gggcgcagga ctgttgaagc cttcggagac cctgtccctc    60
acctgcgctg gctatggtgg gtccttcagt ggttatttct ggagctggat ccgccagccc   120
ccagggaagg gctggaatg gattggggag atcaatcata gtggcagcac cgactacaac    180
ccgtccctca agagtcgagt caccatatca ctggacacgt ccaagaccca gttctccctg   240
aagctgagct ctgtgaccgc cgcggacacg gctgtctatt actgtgcgag agtgatgact   300
ggaattacga attactacta ctattacggt atggacgtct ggggccaagg gaccacggtc   360
accttct                                                             367

<210> SEQ ID NO 2
<211> LENGTH: 328
<212> TYPE: DNA
<213> ORGANISM: Artificial sequence
<220> FEATURE:
<223> OTHER INFORMATION: Synthetic oligonucleotide

<400> SEQUENCE: 2
gacatccagt tgacccagtc tccatccttc ctgtctgcat ctgtaggaga cagagtcacc    60
atcacttgcc gggccagtca ggacattagc agttatttag cctggtatca gcaaaaacca   120
gggaaagccc ctaagctcct gatctatgct gcatccactt tgcaaagtgg ggtcccctca   180
aggttcagcg gcagtgaatc tgggacagaa ttcactctca caatcagcag cctgcagcct   240
gaaaattttg caacttatta ctgtcaacac cttaatagtt accccggggg gtacactttt   300
ggccagggga ccaaggtgga tatcaaaa                                      328

<210> SEQ ID NO 3
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 3
caggtgcagc tacagcagtg gggcgcagga ctgttgaagc cttcggagac cctctcactc    60
acctgtgctg tctatggtgg gtccttcagt ggttactact ggagctggat ccgccagccc   120
ccagggaagg gctggagtg gattggggaa atcaatcata gtggaagcac caactacaac    180
ccgtccctca agagtcgagt caccatatca gtagacacgt ccaagagcca gttctccctg   240
aagctgagct ctgtgaccgc cgcggacacg gctgtgtatt actgtgcgag agccacccag   300
ggttcgggga cctataagtt attcttttac tcctacggta tggacgtctg gggccaaggg   360
accacggtca ccgtctcctc a                                             381

<210> SEQ ID NO 4
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 4
gacatccaga tgacccagtc tccttccacc ctgtctgcat ctgtaggaga cagagtcacc    60
atcacttgcc gggccagtca gagtattact agctggttgg cctggtatca gcagaaacca   120
```

| | |
|---|---|
| gggaaagccc ctaagctcct gatctataag gcgtctagtt tagaaagtgg ggtcccatca | 180 |
| aggttcagcg gcagtggatc tgggacagaa ttcactctca ccatcagcag cctgcagcct | 240 |
| gatgattttg caacttatta ctgccaacag tataatagtt atccgtacac ttttggccag | 300 |
| gggacacgac tggagattaa a | 321 |

<210> SEQ ID NO 5
<211> LENGTH: 370
<212> TYPE: DNA
<213> ORGANISM: Artificial sequence
<220> FEATURE:
<223> OTHER INFORMATION: Synthetic oligonucleotide

<400> SEQUENCE: 5

| | |
|---|---|
| cagctgcagc tgcaggagtc gggcccagga ctggtgaagc cttcggagac cctgtccctc | 60 |
| acctgcactg tctctggtga ctccatcagc agtaataatt actactgggg ctggatccgc | 120 |
| cagcccccag ggaagggact ggagtggatt gggagtatct attacagtgg gagcacctac | 180 |
| tacaaccgt ccctcaagag tcgagtcacc atatccgtag acacgtccaa gaaccagttc | 240 |
| tccctgaagc tgagctctgt gaccgccgca gacacggctg tgtattactg tgcgagacac | 300 |
| cgtcgagtat tactatggtt cggggagttc caactctggg gccagggaac cctggtcacc | 360 |
| gtctcctcag | 370 |

<210> SEQ ID NO 6
<211> LENGTH: 334
<212> TYPE: DNA
<213> ORGANISM: Artificial sequence
<220> FEATURE:
<223> OTHER INFORMATION: Synthetic oligonucleotide

<400> SEQUENCE: 6

| | |
|---|---|
| cagtctgccc tgacgcagcc gccctcagtg tctggggccc cagggcagag ggtcaccatc | 60 |
| tcctgcactg ggagcagctc caacatcggg gcaggttatg atgtacactg gtaccagcag | 120 |
| cttccaggaa cagcccccaa actcctcatc tatggtaaca tcaatcggcc ctcaggggtc | 180 |
| cctgaccgat tctctggctc caagtctggc acctcagcct ccctggccat cactgggctc | 240 |
| caggctgagg atgaggctga ttattactgc cagtcctatg acagcagcct gagtggtgcc | 300 |
| ttattcggcg agggacccca gctgaccgtc ctat | 334 |

<210> SEQ ID NO 7
<211> LENGTH: 349
<212> TYPE: DNA
<213> ORGANISM: Artificial sequence
<220> FEATURE:
<223> OTHER INFORMATION: Synthetic oligonucleotide

<400> SEQUENCE: 7

| | |
|---|---|
| caggtgcagc tgcaggagtc gggcccagga ctggtgaagc cttcggagac cctgtccctc | 60 |
| acctgcactg tctctggtgg ctccatgagt agttacttct ggagctggat ccggcagccc | 120 |
| ccagggaagg gactggagtg gattgggtat atctcttaca gtgggggcac caactacaac | 180 |
| ccctccctca gagtcgagt caccatatca gtagacacgt ccaagaacca gttctccctg | 240 |
| aagctgacct ctgtgaccgc tgcggacacg gccgtttatt actgtgcgag agaggaccgc | 300 |
| ggctcgcctg actattgggg ccagggaacc ctggtcaccg tctcctcag | 349 |

<210> SEQ ID NO 8
<211> LENGTH: 331

```
<212> TYPE: DNA
<213> ORGANISM: Artificial sequence
<220> FEATURE:
<223> OTHER INFORMATION: Synthetic oligonucleotide

<400> SEQUENCE: 8
cagtctgtgt tgacgcagcc gccctcagtg tctgcggccc caggacggaa ggtcaccatc    60
tcctgctctg gaagcagctc aacattggg aataattatg tatcctggta ccagcagctc   120
ccaggaacag cccccaaact cctcatttat gacaattata gcgaccctc agggattcct   180
gaccgattct ctggctccaa gtctggcacg tcagccaccc tgggcatcac cggactccag   240
actgggacg aggccgatta ttactgcgga acatgggatc tcagcctgag tgctggggtg    300
ttcggcggag ggaccaagct gaccgtccta g                                  331

<210> SEQ ID NO 9
<211> LENGTH: 358
<212> TYPE: DNA
<213> ORGANISM: Artificial sequence
<220> FEATURE:
<223> OTHER INFORMATION: Synthetic oligonucleotide

<400> SEQUENCE: 9
caggtgcagc tggtgcagtc tggggctgag gtgaagaagc ctggggcctc agtgaaggtc    60
tcctgcaagg cttctggata caccttcacc agttatgata tcaactgggt gcgacaggcc   120
actggacaag ggcttgagtg gctgggatgg atgaaccta acagtggtaa cacaaagtct   180
gcacagaagg tcaagggcag agtcaccatg accagggaca cctccataag cacagcctac   240
atggagctga gcagcctgag atctgaggac acggccgtgt attactgtgc gagaaccccc   300
tttgatggta gtggttatta ttactggggc cagggaaccc tggtcaccgt ctcctcag    358

<210> SEQ ID NO 10
<211> LENGTH: 334
<212> TYPE: DNA
<213> ORGANISM: Artificial sequence
<220> FEATURE:
<223> OTHER INFORMATION: Synthetic oligonucleotide

<400> SEQUENCE: 10
gatattgtga tgactcagtc tccactctcc ctgtccgtca cccctggaga gccggcctcc    60
atctcctgca ggtcgagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattattgca tgcaagctct acaaactccg   300
ggggcttcgg ccctggacca aggtggatat caaa                               334

<210> SEQ ID NO 11
<211> LENGTH: 356
<212> TYPE: DNA
<213> ORGANISM: Artificial sequence
<220> FEATURE:
<223> OTHER INFORMATION: Synthetic oligonucleotide

<400> SEQUENCE: 11
caggtgcagc tggtgcagtc tggggctgag gtgaagaagc ctggggcctc agtgaaggtc    60
tcctgcaagg cttctggata caccttcacc agttatgata tcaactgggt gcgacaggcc   120
actggacaag ggcttgagtg gctgggatgg atgaaccta acagtggtaa cacaaagtct   180
```

```
gcacagaagg tcaagggcag agtcaccatg accagggaca cctccataag cacagcctac    240
atggagctga gcagcctgag atctgaggac acggccgtgt attactgtgc gagaaccccc    300
tttgatgata ttggttatta ttactggggc cagggaaccc tggtcaccgt ctcctc       356
```

<210> SEQ ID NO 12
<211> LENGTH: 337
<212> TYPE: DNA
<213> ORGANISM: Artificial sequence
<220> FEATURE:
<223> OTHER INFORMATION: Synthetic oligonucleotide

<400> SEQUENCE: 12

```
gatattgtga tgactcagtc tccactctcc ctgtccgtca cccctggaga gccggcctcc    60
atctcctgca ggtcgagtca gagcctcctg catagtaatg gatacaacta tttggattgg   120
tacctgcaga agccagggca gtctccacag ctcctgatct atttgggttc taatcgggcc   180
tccggggtcc ctgacaggtt cattggcagt ggatcaggca cagattttac actgaaaatc   240
agcatagtgg aggctgagga tgttggggtt tattattgca tgcaagctct acaaactccg   300
ggggctttcg gccctgggac caaggtggat atcaaaa                            337
```

<210> SEQ ID NO 13
<211> LENGTH: 352
<212> TYPE: DNA
<213> ORGANISM: Artificial sequence
<220> FEATURE:
<223> OTHER INFORMATION: Synthetic oligonucleotide

<400> SEQUENCE: 13

```
gaggtccagc tggtacagtc tggggctgag gtgaagaagc ctggggctac agtgaaaatc    60
tcctgcaagg tttctggata caccttcacc gactactaca tgcactgggt gcaacaggcc   120
cctggaaaag ggcttaagtg gatgggactt cttgatcctc tagatggtga aacaatatac   180
tcagagaagt tccagggcaa agtcaccata accgcggaca catctacaga cacagcctac   240
atggaactga gcagcctgag atctgaggac acggccgtgt attactgtgc aagagagttg   300
actggttacc tcaactactg ggccaggga accctggtca ccgtctcctc ag            352
```

<210> SEQ ID NO 14
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 14

```
gacatccaga tgacccagtc tccatcctcc ctgtctgcat ctgtaggaga cagagtcacc    60
atcacttgcc gggcgagtcc cggcattttgc aattatttag cctggtatca acataaacca   120
gggaaagttc ctaaactcct gatctatgct gcatccactt tgcaatcagg gtcccatct    180 cggttcactg gcgttggatc tgggacaaat ttcactctca ccatcaacaa tttgcctcct   240
gaaaatgttg caacttatta ctgtcaaaag tataacagtg cccctcacac gttcggccaa   300
gggacaaaag tggatatcaa a                                             321
```

<210> SEQ ID NO 15
<211> LENGTH: 365
<212> TYPE: DNA
<213> ORGANISM: Artificial sequence
<220> FEATURE:
<223> OTHER INFORMATION: Synthetic oligonucleotide

<400> SEQUENCE: 15

```
caggtcacct tgaaggagtc tggtcctgtg ctggtgaacc ccacagagac cctcacgctg      60
acctgcaccg tctctggatt ctcactcagc aatgctagaa tgcgtgtgag ctggatccgt     120
cagcccccag ggaaggccct ggagtggctt gcacacattt tttcgaatga cgaaaaatcc    180
tacagcacat ctctgaagag caggctcacc atctccaagg acacctccaa aagccaggtg    240
gtccttacca tgaccaacat ggaccctgtg acacagcct catattactg tgcccggatg     300 agggggagt acaactcgta ctactttgac tcctggggcc agggaaccct ggtcaccgtc     360
tcctc                                                                365
```

<210> SEQ ID NO 16
<211> LENGTH: 323
<212> TYPE: DNA
<213> ORGANISM: Artificial sequence
<220> FEATURE:
<223> OTHER INFORMATION: Synthetic oligonucleotide

<400> SEQUENCE: 16

```
tcctatgagc tgacacagcc accctcggtg tcagtgtccc caggacagac ggccaggatc      60
acctgctctg gagatgcatt gccaaaccaa tatgcttatt ggtaccagca gaagccaggc    120
caggcccctg tgctggtgat atataaagac agtgagaggc cctcagggat ccctgagcga    180
ttctctggct ccagctcagg gacaacagtc acgttgacca tcagtggagt ccaggcagaa    240
gacgaggctg actattactg tcaatcagca gacagcagtg gtacttctgt ggtattcggc    300
ggagggaccc aggtgaccgt cct                                            323
```

<210> SEQ ID NO 17
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 17

```
caggtgcagc tggtgcagtc tggggctgag gtgaagaagc ctggggcctc agtgaaggtt      60
tcctgcaagg catctggata caccttcgcc agctacgaca ttcactgtgt gcgacaggcc    120
cctggacaag ggtttgaatg gatggtaggg agctactctg gcaatggtaa cacaggctat    180
gcacagaagt tccagggcag agtcaccatg accagggaca cgtccacgag cacagcctac    240
atggagctga gcagtcagag atctgaggac atagatgtgt actactgtgc gagtagggat    300
attgtggtgg tgactgctac ccgctccccc tttgactact ggggccaggg aaccctggtc    360
accgtctcct ca                                                        372
```

<210> SEQ ID NO 18
<211> LENGTH: 328
<212> TYPE: DNA
<213> ORGANISM: Artificial sequence
<220> FEATURE:
<223> OTHER INFORMATION: Synthetic oligonucleotide

<400> SEQUENCE: 18

```
gaaattgtgt tgacgcagtc tccaggcacc ctgtctttgt ctccagggga aagagccacc      60
ctctcctgca gggccagtca gagtgttacc agcascuct tagccuggya ccagcaaaaa     120
cctggccagg ctccaaggct cctcatctat agtgcatcca gcagggccac tggcatccca    180
```

```
gacaggttca gtggcagtgg gtctgggaca gacttcactc tcaccatcag cagactggag    240
cctgaagatt ttgcagtgta ttactgtcag caatatggta gctcacctcc gtacactttt    300
ggccagggga ccaaggtgga tatcaaaa                                        328

<210> SEQ ID NO 19
<211> LENGTH: 373
<212> TYPE: DNA
<213> ORGANISM: Artificial sequence
<220> FEATURE:
<223> OTHER INFORMATION: Synthetic oligonucleotide

<400> SEQUENCE: 19
caggtgcagc tgcaggagtc gggcccagga ctggtgaagc cttcggagac cctgtccctc     60
acctgcactg tctctggtgg ctccatcagt agtttctact ggagctggat ccggcagccc    120
ccaggaaagg gactggagtg gattgggtat atctattaca gtgggagcac caactacaac    180
ccctccctca gagtcgagt caccatatca gtagacacgt ccaagaacca gttctccctg    240
aagctgagct ctgtgaccgc tgcggacacg gccgtgtatt actgtgcgag actaagaggg    300
aactatgcta gtagtggtta ttactacaac tttgactact ggggccaggg aaccctggtc    360
accgtctcct cag                                                       373

<210> SEQ ID NO 20
<211> LENGTH: 306
<212> TYPE: DNA
<213> ORGANISM: Artificial sequence
<220> FEATURE:
<223> OTHER INFORMATION: Synthetic oligonucleotide

<400> SEQUENCE: 20
cagtctgtgg tgacgcagcc gccctcagtg tctgcggccc caggacagaa ggtcaccatc     60
tcctgctctg gaagcagctc aacattggg aataattatg tatcctggta ccagcagctc    120
ccaggaacag ccccccaaact cctcatttat gacaataata gcgaccctc agggattcct    180 gaccgattct ctggctccaa gtctggcacg tcagccaccc tgggcatcac cggactccag    240
actggggacg aggccgatta ttactgcgga acatgggata gcagcctgag tgcttatgtc    300
tcggaa                                                               306

<210> SEQ ID NO 21
<211> LENGTH: 370
<212> TYPE: DNA
<213> ORGANISM: Artificial sequence
<220> FEATURE:
<223> OTHER INFORMATION: Synthetic oligonucleotide

<400> SEQUENCE: 21
cagctgcagc tgcaggagtc gggcccagga ctggtgaagc cttcggagac cctgtccctc     60
acctgcactg tctctggtgg ctccatcagc agtagtagtt actactgggg ctggatccgc    120
cagcccccag ggaaggggct ggagtggatt gggagtatct attatcgtgg gagcacctac    180
tacaacccgt ccctcaagag tcgaatcacc atatccgtag acacgtccaa gaaccagttc    240
tccctgaagc tgaggtctgt gaccgccgca gacacggctg tgtattactg tgcgagacat    300
ttgcgagtat tactatggtt cggggagtta ttggaatggg gccaagggac cacggtcacc    360
gtctcctcag                                                           370

<210> SEQ ID NO 22
<211> LENGTH: 334
```

<212> TYPE: DNA
<213> ORGANISM: Artificial sequence
<220> FEATURE:
<223> OTHER INFORMATION: Synthetic oligonucleotide

<400> SEQUENCE: 22

```
cagtctgccc tgacgcagcc gccctcagtg tctggggccc cagggcagag ggtcacaatc    60
tcctgcactg ggagcagctc aacatcggg gcagattatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc cagtcccatg acagcagcct gagtggttat   300
gtcttcggaa ctgggaccaa ggtcaccgtc ctat                                334
```

<210> SEQ ID NO 23
<211> LENGTH: 352
<212> TYPE: DNA
<213> ORGANISM: Artificial sequence
<220> FEATURE:
<223> OTHER INFORMATION: Synthetic oligonucleotide

<400> SEQUENCE: 23

```
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag ggcttgagtg gatgggatgg atcaacccaa acagtggtgg cacaaactat   180
gcacagaagt tcagggcag gtcaccatg accaggaca cgcccatcag cacagcctac   240
atggagctga gcaggctgag atctgacgac acggccgtgt attactgtgc gagagtgccc   300
ccygatagca gcagctggaa gtggggccag ggaaccctgg tcaccgtctc ct           352
```

<210> SEQ ID NO 24
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 24

```
gatattgtga tgactcagtc tccactctcc ctgcccgtca cccctggaga gccggcctcc    60
atctcctgca ggtctagtca gagcctcctg catagaaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300
ccgacgtcgg ccaaggac                                                 318
```

<210> SEQ ID NO 25
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 25

```
gaggtgcagc tggtggagtc tggggggaggc ctggtcaagc ctgggggggtc cctgagactc    60
tcctgtgcag cctctggatt caccttcagt agctatagca tgaactgggt ccgccagcct   120
ccagggaagg ggctggagtg gtctcatcc attactagta gtagtagtta catatactac   180
```

```
gcagactcag tgaagggccg attcaccatc tccagagaca acgccaagaa ctcactgtat    240
ctgcaaatga acagcctgag agccgaggac acggctgtgt attattgtgc gagccgaccg    300
ggtatagcac cagctggccc ccaggcggag ggctactggg gccagggaac cctggtcacc    360
ttc                                                                  363
```

```
<210> SEQ ID NO 26
<211> LENGTH: 273
<212> TYPE: DNA
<213> ORGANISM: Artificial sequence
<220> FEATURE:
<223> OTHER INFORMATION: Synthetic oligonucleotide

<400> SEQUENCE: 26
gaaatagtga tgacgcagtc tccagccacc ctgtctgtgt ctccagggga aagagccacc     60
ctctcctgca gggccagtca gagtgtcagc agcaacttag cctggtacca gcagaaacct    120
ggccaggctc ccaggctcct catctatggt gcatccacca gggccactgg catcccagcc    180
aggttcagtg ccagtgggtc tgggacagag ttcactctca ccatcagcag cctgcagcct    240
gaagattttg cagtgtatta ctgtcagcag tat                                 273
```

```
<210> SEQ ID NO 27
<211> LENGTH: 353
<212> TYPE: DNA
<213> ORGANISM: Artificial sequence
<220> FEATURE:
<223> OTHER INFORMATION: Synthetic oligonucleotide

<400> SEQUENCE: 27
caggtccagc tggtacagtc tggggctgag gtgaagaagc ctggggcctc agtgaaggtc     60
tcctgcaagg tctccggata caccctcact gaattatcca tgcactgggt gcgacaggct    120
cctggaaaag ggcttgagtg gctgggaggt tttgatcctg aagatggtga acaatctac     180 gcacagaagt tccagggcag agtcaccatg accgaggaca catctacaga cacagcctac    240
atggaactga gcagcctgag atctgaggac acggccgtgt attactgtgc aagagaaagc    300
tggctcaggg ggtttgacta ctggggccag ggaaccctgg tcaccgtctc ctc           353
```

```
<210> SEQ ID NO 28
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 28
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcctctat ggtgcatcca gcagggccac tggcatccca    180
gacaggttca gtggcagtgg gtctgggaca gacttcactc tcaccatcag cagactggag    240
cctgaaaatt ttgcagtgta ttactgtcag cagtatggta gctctcctcg acgttcggc     300 caagggacca aggtggatat caaaa                                          325
```

```
<210> SEQ ID NO 29
<211> LENGTH: 361
<212> TYPE: DNA
<213> ORGANISM: Artificial sequence
<220> FEATURE:
<223> OTHER INFORMATION: Synthetic oligonucleotide
```

<400> SEQUENCE: 29

```
caagtgcagc tggtggagtc gggcccagga ctggtgaagc cttcacagac cctgtccctc    60
acctgcactg tctctggtgg ctccatcagc cgtggtattt actactggag ctggatccgg   120
cagcccgccg ggaagggact ggagtggatt gggcgtatct ataccagtgg gagcaccaac   180
tacaacccct ccctcaagag tcgagtcacc atatcagtag acacgtccaa gaaccagttc   240
tccctgaagc tgagctctgt gaccgccgca gacacggccg tgtattactg tgcgagagat   300
ggctggtacg gtggtactt agatctctgg ggccgtggca ccctggtcac cgtctcctca   360
g                                                                  361
```

<210> SEQ ID NO 30
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 30

```
gaaatagtga tgacgcagtc tccagccacc ctgtctgtgt ctccagggga aagagccacc    60
ctctcctgca gggccagtca gagtgttagc agcgacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggccgggtac tttcggcgga   300
gggaccaagg tggatatcaa aa                                           322
```

<210> SEQ ID NO 31
<211> LENGTH: 373
<212> TYPE: DNA
<213> ORGANISM: Artificial sequence
<220> FEATURE:
<223> OTHER INFORMATION: Synthetic oligonucleotide

<400> SEQUENCE: 31

```
gaggtgcagc tggtggagtc tgggggaggc ttggtccagc ctgggggtc cctgagactc     60
tcctgtgtag tctctggatt cacctttagt aattattgga tgagttgggt ccgccaggct   120
ccagggaagg ggctggagtg gtggccaac ataaagcaag atggtagtaa gaatactat    180
gtggactctg tgacgggccg attcaccatc tccagagaca acgccaagaa ctcactgtat   240
ctgcaaatga acagcctgag agccgaggac acggctgtgt attactgtgc gaccttaaat   300
cttgaattag cagtggatgc tatctcggag gcccttaagt ggggccaggg aaccctggtc   360
accgtctcct cag                                                     373
```

<210> SEQ ID NO 32
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 32

```
tcctatgagc tgacacagcc accctcggtg tcagtgtccc caggacagac ggccaggatc    60
acctgctctg gagatgcatt gccaaaacaa tttgcttatt ggtaccagca gaagccaggc   120
caggcccctg tagtgatgat atataaagac agtgagaggc cctcagggat ccctgagcga   180
```
ttctctggct ccagttcagg gacaacagtc acgttgacca tcagtggagt ccaggcagaa   240
gacgaggctg actattactg tcaatcagta gacaacagtg gtacttatga ggtgttcggc   300
ggagggaccc agctgaccgt cctat                                        325

<210> SEQ ID NO 33
<211> LENGTH: 367
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (354)..(354)
<223> OTHER INFORMATION: n is a, c, g, or t

<400> SEQUENCE: 33
caggtgcagc tacagcagtg gggcgcagga ctgttgaagc cttcggagac cctgtccctc    60
acctgtgatg tctatggtgg gtccttcagt ggttactact ggagctggat ccgccagccc   120
ccagggaagg ggctggagtg gattgggaaa tcaatcata gtggaagcac cacctacacc    180
ccgtccctca ggagtcgagt caccatatca gtagacacgt ccaagaacca gttctccctg   240
aagctgagct ctgtgaccgc cgcggacacg gctgtgtatt actgtgcgag agttttgtca   300
gggtggctac catttcccaa ctactactac tacatggacg tctgggcaa aggnaccacg   360 gtcacct                                                            367

<210> SEQ ID NO 34
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 34
gacatccaga tgactcagtc tccatcgtcc ctgcctgcat ctgtaggaga cagggtcacc    60
atcacttgcc gggcaagtca ggacattaga aataatttag gctggtatca gcagaagcca   120
gggaaagccc ctgagcgcct gatctatgga acctccaatt tgcagagtgg ggtcccgtca   180
aggttcagcg gcagtggatc tgggacagaa ttcactctca caatcagcag cctgcagcct   240
gaagattttg caacttatta ctgtctacag cataatagtt accctcccac gttcggccgc   300
gggaccaagg tggaaatcaa ac                                           322

<210> SEQ ID NO 35
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 35
caggtccagc tggtgcagtc tggggctgag gtgaagaagc ctgggtcctc agtgaaggtc    60
tcctgcaagg tttctggagg caccttcagc agtttagcta tcaactgggt gcgacaggcc   120
cctggacagg gcttgagtg gatgggaggc atcatcccca tctttggtaa agcaaactac   180
gcacagaagt tccagggcag agtgtcaatt atcgcggacg aatccacgag cacagcctac   240
atggacctga gcagcctgag atttgaggac acggccgtgt attactgtgc gactggtggg   300
aacattaggg ttcatgattt tgatatctgg ggccaaggga cactggtcat cgtctcttca   360

```
<210> SEQ ID NO 36
<211> LENGTH: 342
<212> TYPE: DNA
<213> ORGANISM: Artificial sequence
<220> FEATURE:
<223> OTHER INFORMATION: Synthetic oligonucleotide

<400> SEQUENCE: 36
gatgttgtga tgactcagtc tccactctcc ctgcccgtca cccttggaca gccggcctcc    60
atctcctgca ggtctagtca aagcctcgta acagcgatg  gaaataccta cttgaattgg   120
tttcagcaga ggccaggcca atctccaagg cgcctaattt ataaggtttc taaccgggac   180
tctggggtcc cagacagatt cagcggcagt gggtcaggca ctgatttcac actgaacatc   240
agcagggtgg aggctgagga tgttggggtt tattactgca tgcaaggtac acactggcct   300
ccgaggtgga cgttcggcca agggaccaag gtggatatca aa                      342

<210> SEQ ID NO 37
<211> LENGTH: 373
<212> TYPE: DNA
<213> ORGANISM: Artificial sequence
<220> FEATURE:
<223> OTHER INFORMATION: Synthetic oligonucleotide

<400> SEQUENCE: 37
caggtgcagc tacagcagtg gggcgcagga ctgttgaagc cttcggagac cctgtccctc    60
acctgcgctg tctatggtgg gtccttcagt ggttactact ggagctggat tcgccagccc   120
ccagggaagg ggctggagtg gattggggaa atcaattaca gtggaagcac cgactacaac   180
ccgtccctcg agagtcgagt caccatatca gtaracgcgt ccaagaacca cttctccctg   240
aacttgaact ctgtgaccgc cgcggacacg gttgtgtatt actgtgcgag aatttcaagc   300
ggctggattg gatttccccg ataccactac tacttggacg tctggggcaa agggaccacg   360
gtcaccgtct cct                                                      373

<210> SEQ ID NO 38
<211> LENGTH: 213
<212> TYPE: DNA
<213> ORGANISM: Artificial sequence
<220> FEATURE:
<223> OTHER INFORMATION: Synthetic oligonucleotide

<400> SEQUENCE: 38
tcctatgagc tgacacagcc acccgcggtg tcagtgtccc caggacagac agccaggatc    60
agctgctctg gagatgtact gagagataat tatgctgact ggtacccgca aaagccaggc   120
caggcccctg tgctggtgat atataaagat gaacaatccc tgggtgtcgg cggagggacc   180
cagctgaccg tcctagatcg gaagagcgtc gtg                                213

<210> SEQ ID NO 39
<211> LENGTH: 391
<212> TYPE: DNA
<213> ORGANISM: Artificial sequence
<220> FEATURE:
<223> OTHER INFORMATION: Synthetic oligonucleotide

<400> SEQUENCE: 39
caggtccagc tggtgcagtc tggggctgag gtgaagaagc ctgggtcctc agtgaaggtc    60
tcctgcaagg cttctggaga gaccttcagc agatatgctt tcagctgggt gcgactggcc   120
cctggacaag gccttgagtg gttgggaagg atcatccctt tcattgatat accaaactac   180
```

| | |
|---|---|
| gcacagaagt tccaggggag agtcaccatt accgcggaca atccacgag cacagcctac | 240 |
| atggagctga gtagcctgag atctgaagac acggccgtct attactgtgc gagttcgctc | 300 |
| ccctccacat attactttgg ttcggggaat tatccctggg gaaactggct cgacccctgg | 360 |
| ggccagggaa ccctggtcac cgtctcctca g | 391 |

<210> SEQ ID NO 40
<211> LENGTH: 330
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (15)..(15)
<223> OTHER INFORMATION: n is a, c, g, or t

<400> SEQUENCE: 40

| | |
|---|---|
| cagtctgtgg tgacncagcc gccctcagtg tctgcggccc ccggacagaa cgtcaccatc | 60 |
| tcctgctctg gaagcagctc caacattggg aataattatg tatcctggta ccatcagctc | 120 |
| ccaggaacag cccccaaact cctcatttat gacaatgata agcgaccctc agggattcct | 180 |
| gaccgattct ctggctccaa gtctggcacg tcagccaccc tgggcatcac cggactccag | 240 |
| actggggacg aggccgatta ttactgcgga acatgggata gcagcctgag tgaagtagtg | 300 |
| ttcggcggag ggacccaggt gaccgtccta | 330 |

<210> SEQ ID NO 41
<211> LENGTH: 342
<212> TYPE: DNA
<213> ORGANISM: Artificial sequence
<220> FEATURE:
<223> OTHER INFORMATION: Synthetic oligonucleotide

<400> SEQUENCE: 41

| | |
|---|---|
| caggtgcagc tacagcagtg gggcgcagga ctgttgatat cttcggagac cctgtcmctc | 60 |
| acctgtggtg tgtatggtgg gtccttcagt ggttactact ggacctggat ccgtcagccc | 120 |
| cccgggaagg ggctggagtg gattggtgaa atcaattatg ttggaagcac caactacaac | 180 |
| ccgtccctca agagtcgagt caccatgtca gtagacacgt ccaagaacca cttctccctg | 240 |
| agcctgagct ctgtgaccgc cgctgacacg gctgtctatt actgtgcgag aggccttcgt | 300 |
| ggaaatagtg tctgctttga ctggggccct ggaaccctgg tc | 342 |

<210> SEQ ID NO 42
<211> LENGTH: 319
<212> TYPE: DNA
<213> ORGANISM: Artificial sequence
<220> FEATURE:
<223> OTHER INFORMATION: Synthetic oligonucleotide

<400> SEQUENCE: 42

| | |
|---|---|
| gagttagtga tgacgcagtc tccagccacc ctgtctgtgt ctccagggga aagagcctcc | 60 |
| ctctcctgca gggccagtca gagtgttagc agcaacttag cctggtacca gcagaaacct | 120 |
| ggccaggctc ccaggctcct catctatggt gcatccacca gggccactgg tctcccagcc | 180 |
| aggttcagtg gcagtgggtc tgggacagag ttcactctca ccatcagcag cctgcagtct | 240 |
| gaagattttg caatttatta ctgtcagcag tataataact ggccgagaac ttttggccag | 300 |
| gggaccaagg tggatatca | 319 |

<210> SEQ ID NO 43
<211> LENGTH: 383
<212> TYPE: DNA
<213> ORGANISM: Artificial sequence
<220> FEATURE:
<223> OTHER INFORMATION: Synthetic oligonucleotide

<400> SEQUENCE: 43

| gaggtgcagc tggtggagtc tgggggaggc ttggtacagc ctggggagtc tctgaagatc | 60 |
| tcctgtgcag cctctggatt caccttcagt agctttagca tgaactgggt ccgccaggct | 120 |
| ccagggaagg ggctggagtg ggtttcatac attagtagta gtagtagtac catatactac | 180 |
| gcagactctg tgaagggccg attcaccatc tccagagaca atgccaagaa ctcactgtat | 240 |
| ctacaaatga acagcctgag agacgaggac acggctgtgt attactgtgc gagacggtca | 300 |
| gttggttgta gtggtggtaa ctgctacgca tactactacg gtatggacgt ctggggccaa | 360 |
| gggaccacgg tcaccgtctc ctc | 383 |

<210> SEQ ID NO 44
<211> LENGTH: 337
<212> TYPE: DNA
<213> ORGANISM: Artificial sequence
<220> FEATURE:
<223> OTHER INFORMATION: Synthetic oligonucleotide

<400> SEQUENCE: 44

| gatattgtga tgactcagtc tccactctcc ctgcccgtca cccctggaga gccggcctcc | 60 |
| atctcctgca ggtctagtca gaacctcctg catagtaatg gatacaacta tttggattgg | 120 |
| tacctgcaga agccagggca gtctccacag ctcctgatct atttgggttc taatcgggcc | 180 |
| tccggggtcc ctgacaggtt cagtggcagt ggatcaggca cagattttac actgaaaatc | 240 |
| agcagagtgg aggctgagga tgttggactt tattactgca tgcaagctct acaaactcct | 300 |
| atcaccttcg gccaagggac acgactggag attaaaa | 337 |

<210> SEQ ID NO 45
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 45

| caggtgcagc tggtgcagtc tgggggaggc ttggtcaagc ctggagggtc cctgagactc | 60 |
| tcctgtgcag cctctggatt caccttcagt gactactaca tgagctggat ccgccaggct | 120 |
| ccagggaagg ggctggagtg ggtttcatac attagtacta gtggtagtac catatactac | 180 |
| gcagactctg tgaagggccg attcaccatc tccagggaca cgccaagaa ctcactgtat | 240 |
| ctgcaaatga acagcctgag agccgaggac acggccatgt attactgtgc gagagatggt | 300 |
| gatggttcgg ggagttatac ccctccttac tattactacg gtctggacgt ctggggccaa | 360 |
| gggaccacgg tcaccgtctc ctca | 384 |

<210> SEQ ID NO 46
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 46

| | |
|---|---|
| gacatccaga tgacccagtc tccatcctcc ctgtctgcat ctgtaggaga cagagtcacc | 60 |
| atcacttgcc gggcaagtca gagcattcgc aactatttaa attggtatca gcagaaatca | 120 |
| gggaaagccc ctaagctcct gatctatgct gcatccagtt tgcaaagtgg ggtcccatca | 180 |
| aggttcagtg gcagtggatc tgggacagat ttcactctca ccatcagcag tctgcaccct | 240 |
| gaagattttg caacttacta ctgtcaacag agttacagta cccctccgct cactttcggc | 300 |
| ggagggacca aggtagagat caaac | 325 |

<210> SEQ ID NO 47
<211> LENGTH: 345
<212> TYPE: DNA
<213> ORGANISM: Artificial sequence
<220> FEATURE:
<223> OTHER INFORMATION: Synthetic oligonucleotide

<400> SEQUENCE: 47

| | |
|---|---|
| gaggtgcagc tggtggagtc tgggggaggc ctggtcaagc ctgggggtc cctgagactc | 60 |
| tcctgtgcag cctctggatt caccttcagt agctatagca tgaactgggt ccgccagcct | 120 |
| ccagggaagg gctggagtg gtctcatcc attactagta gtagtagtta catatactac | 180 |
| gcagactcag tgaagggccg attcaccatc tccagagaca cgccaagaa ctcactgtat | 240 |
| ctgcaaatga acagcctgag agccgaggac acggctgtgt attattgtgc gagccgaccg | 300 |
| ggtatagcac cagctggccc cccaggcgga gggctactgg ggccc | 345 |

<210> SEQ ID NO 48
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 48

| | |
|---|---|
| gaaattgtgt tgacgcagtc tccaggcacc ctgtctttgt ctccagggga aagagccacc | 60 |
| ctctcctgca gggccagtca gagtgttagc agcagctact tagcctggta ccagcagaaa | 120 |
| cctggccagg ctcccaggct cctcatctat ggtgcatccc gcagggccac tggcatccca | 180 |
| gacaggttca gtgccagtgg gtctgggaca gacttcactc tcaccatcag cagactggag | 240 |
| cctgaagatt ttgcagtgta ttactgtcag cagtatggta gctcaccgta cacttttggc | 300 |
| cggggggaccc aggtggatat caaaa | 325 |

<210> SEQ ID NO 49
<211> LENGTH: 362
<212> TYPE: DNA
<213> ORGANISM: Artificial sequence
<220> FEATURE:
<223> OTHER INFORMATION: Synthetic oligonucleotide

<400> SEQUENCE: 49

| | |
|---|---|
| gaggtgcagc tggtggagtc tgggggaggc ctggtcaagc ctgggggtc cctgagactc | 60 |
| tcctgtgcag cctctggatt caccttcagt agttatagca tgaactgggt ccgccaggct | 120 |
| ccagggaagg gctggagtg gtctcatcc attagtagta ttagtagcta catatactac | 180 |
| gcagactcag tcaagggccg attcaccatc tccagagaca cgccaagaa ctcactgtat | 240 |
| ctgcaaatga acagcctgag agccgaggac acggctgtgt attattgtgc gagagatagg | 300 |
| ccacggtcaa ggcccaattc ggggagttat ttctggtact actacggtat ggacgtctgg | 360 |
| gg | 362 |

<210> SEQ ID NO 50
<211> LENGTH: 300
<212> TYPE: DNA
<213> ORGANISM: Artificial sequence
<220> FEATURE:
<223> OTHER INFORMATION: Synthetic oligonucleotide

<400> SEQUENCE: 50

| tcctatgagc tgactcagcc accctcggtg tcagtggccc caggacagac ggccaggatt | 60 |
| acctgtgggg gaaacaacat tggaagtaaa agtgtgcact ggtaccagca gaagccaggc | 120 |
| caggcccctg tgctggtcgt ctatgatgat agcgaccggc cctcaggat ccctgagcga | 180 |
| ttctctggct ccaactctgg gaacacggcc accctgacca tcagcagggt cgaagccggg | 240 |
| gatgaggccg actattactg tcaggtgtgg gatagtaata gtgatcatcg ggtatcggcg | 300 |

<210> SEQ ID NO 51
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 51

| caggtccagc tggtgcagtc tggggctgag gtgaagaagc ctgggtcctc agtgaaggtc | 60 |
| tcctgcaagg cttctggagg caccttcagc acctatgcta tcaactgggt gcgacaggcc | 120 |
| cctggacaag gcttgagtg gatgggaagg atcatcccta tccttggtac ggcaaactac | 180 |
| gcacagaagt tccagggcag agtcacgatt accgcggaca aatccacgag cacagcctac | 240 |
| atggagctga gcagcctgag atctgaggac acggccgtgt attactgtgc gagacggggg | 300 |
| ggcgagggcg ccgcacacgg tatggacgtc tggggccaag gaccacggt caccgtctcc | 360 |
| tca | 363 |

<210> SEQ ID NO 52
<211> LENGTH: 338
<212> TYPE: DNA
<213> ORGANISM: Artificial sequence
<220> FEATURE:
<223> OTHER INFORMATION: Synthetic oligonucleotide

<400> SEQUENCE: 52

| gatattgtga tgactcagtc tccactctcc ctgcccgtca cccctggaga gccggcctcc | 60 |
| atctcctgca ggtctagtca gagcctcctg catagtaatg gatacaacta tttggattgg | 120 |
| tacctgcaga agccagggca gtctccacag ctcctgatct atttgggttc taatcgggcc | 180 |
| tccggggtcc ctgacaggtt cagtggcagt ggatcaggca cagattttac actgaaaatc | 240 |
| agcagagtgg aggctgagga tgttggggtt tattactgct tgcaggctct acaaactctt | 300 |
| ccgatcacct tcggccaagg gacacgactg gagattaa | 338 |

<210> SEQ ID NO 53
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 53

| caggtccagc ttgtgcagtc tggggctgag gtgaagaagc ctggggcctc agtgaaggtc | 60 |

```
tcctgcaaga cttctggata caccttcact acctatgctg ttcattgggt gcgccaggcc    120
cccggacaaa ggcttgagtg gatgggatgg atcaaccctg cgatggtga cacaagatat     180 gcccagaagt tccaggacag agtcaccatt agtagtgaca catccgcgac cacagtgtac    240
atggaactga gcagcctgag atctgaggac acggctgtgt atttctgtgc gagacctcgt    300
gccagtctat tacgatattt tgactggctg tttgaacagt ggggccagga aaccctggtc    360
accgtctcct ca                                                          372

<210> SEQ ID NO 54
<211> LENGTH: 328
<212> TYPE: DNA
<213> ORGANISM: Artificial sequence
<220> FEATURE:
<223> OTHER INFORMATION: Synthetic oligonucleotide

<400> SEQUENCE: 54
gaaattgtgt tgacgcagtc tccaggcacc ctgtctttgt ctccagggga cagagccacc     60
ctctcctgcg gggccagtca gagcattcac cacaactacg tagcctggta ccagcagaga    120
cctggccagg ctcccaggct cctcatcttt ggtgcttcca gtagggccac tggcatccca    180
gacaggttca ctggcagtgg gtctgggaca gaattcactc tcaccatcaa cagactggag    240
cctgaagatt ttgcagtgta ttactgtcag cagtatggca actcagttcc gtactccttt    300
ggccagggga ccaaggtgga tatcaaaa                                         328

<210> SEQ ID NO 55
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 55
caggtgcagc tacagcagtg gggcgcagga ctgttgaagc cttcggagac cctgtccctc     60
acctgtgctg tctatggtgg gtccttcacg aactactact ggagctggat ccgccagttc    120
ccagggaagg gctggagta cattggggaa atcgatcata gtggaagcgc caactacaac    180
ccgtccctga agagtcgagt caccatatca ctagacacgt ccaagaacca attctccctg    240
aggctgagct ctgtgaccgc cgcggacacg gctgtgtatt tctgtgcgag ggatgtctat    300
ggttcgggga cttattactg gttcgatccc tggggccagg gaaccctg                  348

<210> SEQ ID NO 56
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 56
gacatcgtga tgacccagtc tccttccacc ctgtctgcat ctgtaggaga cagagtcacc     60
atcacttgcc gggccagtca gagtattagt agctggttgg cctggtatca gcagaaacca    120
gggaaagccc ctaaactcct gatctatgat gcctccagtt tggaaagtgg ggtcccatca    180
aggttcagcg gcagtggatc tgggacagaa ttcactctca ccatcagcag cctgcggcct    240
gatgattttg caacttatta ctgccaacag tataatactt attcttggtg gacgttcggc    300
caagggacca aggtggaaat caaac                                            325
```

<210> SEQ ID NO 57
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 57

| | |
|---|---|
| gacatccaga tgacccagtc tccaacctcc ctgtctgcat ctgtaggaga cagagtcacc | 60 |
| atcacttgcc gggcaagtca gaggattagc agccatttaa attggtatca acagaaacca | 120 |
| gggaaagccc ctaaactcct gatttatgtc gcatccagtt tgcaaagtgg ggtcccatca | 180 |
| aggttcagtg gcagtggatc tgggacagat tacactctca ccatcagcag tctgcaacct | 240 |
| gaagattttg caacttactt ctgtcaacag agttacacta ccccgtacac ttttggccag | 300 |
| gggaccaacc tgcaaatgaa ac | 322 |

<210> SEQ ID NO 58
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 58

| | |
|---|---|
| caggtgcagc tgcaggagtc gggcccagga ctggtgaagc cttcggagac cctgtccctc | 60 |
| acctgygctg tctctggtgg ctccatcagc actagaacct ggtggacttg ggtccgccag | 120 |
| cccccaggga aggggctgga gtggattgga gaaatctatc agagtgggag caccaactac | 180 |
| aacccgtccc tcaagagtcg agtcaccata tcaatagaca cgtccaagaa ccagttctcc | 240 |
| ctgaagctga gctctgtgac cgccgcggac acggccctgt attactgtgc gagaagtggc | 300 |
| agatatagca gtgtcactcc ttttgactac tggggccagg gaaccctggt cact | 354 |

<210> SEQ ID NO 59
<211> LENGTH: 319
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (120)..(120)
<223> OTHER INFORMATION: n is a, c, g, or t

<400> SEQUENCE: 59

| | |
|---|---|
| gaaattgtgt tgacacagtc cccagccacc ctgtctttg tctccgggca aagagccacc | 60 |
| ctctcctgca gggccagtca agtattggc aactacttag cctggtacca acagaaaccn | 120 |
| ggccaggctc ccaggctcct catctatgat gcatccaaca gggccactgg catcccagcc | 180 |
| aggttcagtg gcagtgggtc tgggacagac ttcactctca ccatcagcag cctagagcct | 240 |
| gaagattttg cagtttatta ctgtcagcag cgtagccact ggccggcttt cggccctggg | 300 |
| accaaggtgg atatcaaaa | 319 |

<210> SEQ ID NO 60
<211> LENGTH: 382
<212> TYPE: DNA
<213> ORGANISM: Artificial sequence
<220> FEATURE:
<223> OTHER INFORMATION: Synthetic oligonucleotide

<400> SEQUENCE: 60

```
caggtgcagc tggtggagtc tggggggaggc gtggtccagc ctggggaggtc tctgaagatc    60 tcctgtgcag cctctggatt caccttcagt gactctggct tacactgggt ccgccaggct   120
ccaggcaagg ggctggagtg cgtggcattt atatggtatg atggaagtac taaatactat   180
gcagactccg tgaagggccg attcaccatc tccagagaca attccaggaa cacactgtat   240
cttcaaatga agagcctgag agccgaggac acggctgtgt attactgtgc gagagagcta   300
ggatattgta gtggtggtac ctgctactcc atgggtgctt ttgatatctg gggccaaggg   360
acactggtca ccgtctctca gt                                            382
```

<210> SEQ ID NO 61
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 61

```
cagtctgtgc tgactcagcc tgcctccgtg tctgggtctc ctggacagtc gatcaccatc    60
tcctgcactg gaaccagcag tgatgttggg agttataacc ttgtctcctg gtaccaacag   120
cacccaggca aagcccccaa actcatgatt tatgaggtca gtaagcggcc ctcagggggtt   180 tctaatcgct tctctggctc caagtctgac aacacggcct ccctgacaat ctctgggctc   240
caggctgagg acgaggctga ttattactgc tgctcatatg taggtagtag cacttccgtg   300
ttcggcggag ggacccaggt gaccgtccta                                    330
```

<210> SEQ ID NO 62
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 62

```
gaggtgcagc tggtggagtc tggggggaggc ttggtaaagc ctggggggtc ccttagactc    60
tcctgtgcag cctctagttt cattttcagt gacgcctgga tgaagtgggt ccgccaggct   120
ccagggaagg ggctggagtg ggtcggccat tttaaaacca aaactgatgg tgggacaaca   180
gactacgctg cacccgtgaa aggcagattc agcatctcaa gagatgattc aaaatccacg   240
ctgcatgtgc aaatgaacag cctgaaaacc gaggacacag ccgtgtatta ctgtaccaca   300 gccgggggcaa gttacgtc                                                318
```

<210> SEQ ID NO 63
<211> LENGTH: 279
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (271)..(271)
<223> OTHER INFORMATION: n is a, c, g, or t

<400> SEQUENCE: 63

```
gaaattgtgt tgacgcagtc tccaggcacc ctgtctttgt ctccaggggga aagagccacc    60 ctctcctgca gggccagtca gagtgttagc aacacgtact tagcctggta ccagcagaaa   120
cctggccagg ctcccaggct cctcatctat gctgcatcca cagggccac tggcatccca   180 gacaggttca gtggcagtgg gtctgggaca gacttcactc tcaccatcag cagactggag   240
```
cctgaagatt ttgcagtgta ttactgtcaa ncagtatgg          279

<210> SEQ ID NO 64
<211> LENGTH: 376
<212> TYPE: DNA
<213> ORGANISM: Artificial sequence
<220> FEATURE:
<223> OTHER INFORMATION: Synthetic oligonucleotide

<400> SEQUENCE: 64
caggtccagc ttgtgcagtc tggggctgag gtgaagaagc ctggggcctc agtgaaggtc      60
tcctgcaagg cttctggata caccttcact aaatatacta tacattgggt gcgccaggcc     120
cccggacaaa ggcttgagtg ggtgggaggg atctacgctg ctatggcaa cacaagatac      180
tcacagaagt tccagggcag agtcaccatt accaggaca catccgcgag cacagcctac      240
atggagctga gcagcctgag atctgaagac acggctgtgt atttctgtgc gagagatttc    300
gaggatttcg attcctggac tggttattat tcatggcttc actggggcca gggaaccctg     360
gtcaccgtct cctcag                                                     376

<210> SEQ ID NO 65
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 65
gaaattgtgt tgacgcagtc tcccggcacc ctgtctttgt ctccagggga aagagccacc      60
ctctcctgca gggccagtca gagtgttagc agcaccact tagcctggta ccagcaaaaa      120
cctggccagg ctcccaggct cctcatctat ggtgcctcca gcagggccac tggcatccca    180
gacaggttca gtggcagtgg gtctgggaca gacttcactc tcaccatcac cagactggag     240
cctgaagatt ttgcaatgta tttctgtcag cagtatgata gctccccttc gatcaccttc     300
ggccaaggga cacgactgga gattaaa                                         327

<210> SEQ ID NO 66
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 66
caggtgcagc tacagcagtg gggcgcagga ctgttgaagc cttcggagac cctgtccctc      60
acctgygctg tccatggtgg gtccttcagt ggttacttct ggagctggat ccgccagccc     120
ccagggaagg ggctggaatg gattgggaa atgaatcata gtggcagcac caactataac      180
ccatccctca agagtcgagt caccatatca gtagacacgt ccaagaagca gttctccctg     240
aagctgaact ctgtgaccgc cgcggacacg gctgtgtatt actgtgcgag aacagctcgt    300
acggtgaggt actttgaaaa ctggggccag ggaaccctgg tcaccgtctc ctca           354

<210> SEQ ID NO 67
<211> LENGTH: 340
<212> TYPE: DNA
<213> ORGANISM: Artificial sequence
<220> FEATURE:
<223> OTHER INFORMATION: Synthetic oligonucleotide

<400> SEQUENCE: 67

```
gacatcgtga tgacccagtc tccagactcc ctggctgtgt ctctgggcga gagggccacc    60
atcaactgca agtccagcca gactgtttta tacaactcca acaattacag ctacttaact   120
tggtaccagc agaaaccagg acagcctcct agggtgctca tttactgggc atctacccgg   180
gaatccgggg tccctgaccg attcagtggc agcgggtctg ggacagattt cactctcacc   240
atcagcagcc tgcaggctga aaatgtggcc ctttattact gtcagcagta ttacagtact   300
ccttggacgt tcggccaagg gaccaaggtg gatatcaaaa                         340
```

<210> SEQ ID NO 68
<211> LENGTH: 382
<212> TYPE: DNA
<213> ORGANISM: Artificial sequence
<220> FEATURE:
<223> OTHER INFORMATION: Synthetic oligonucleotide

<400> SEQUENCE: 68

```
caggtgcagc tggtggagtc tgggggaggc ttggtcaagc ctggagggtc tctgaagatc    60
tcctgtgcag ccaacagatt caccttcagc aactactaca tgagctggat ccgccagggt   120
ccagggaagg agccggagtg gatttcatac attagtagta agagtcgtta cacaaattac   180
gcagactctg tgaagggccg attcaccatc tccagagaca acaccaagaa ttcactgttt   240
ctgcaaatga acgacctgcg agccgaggac acggctgtct attactgtgc gagaggggg    300
ggatattgtg gcggtactac ttgttccatg gacatgcttt tgatatctg ggtcaaggg    360
acagtggtca ccgtctcttc ag                                            382
```

<210> SEQ ID NO 69
<211> LENGTH: 293
<212> TYPE: DNA
<213> ORGANISM: Artificial sequence
<220> FEATURE:
<223> OTHER INFORMATION: Synthetic oligonucleotide

<400> SEQUENCE: 69

```
gaagttgtgt tgacgcagtc tccaggcacc ctgtctttgt ctccagggga aagagccacc    60
ctctcctgca gggccagtca gagtgtgacc agcagctact tagcctggta ccaacagaag   120
cctggccagg ctcccaggct cctcatctat ggtgcatcta tcaggtccac tgacatccca   180
gacaggttca gtggcagtga gtctgggaca gacttcactt acaccatcag cagaccggag   240
catgaagatt ttgctctgta tttctgtcag cagtatggta gctcaccgta cac           293
```

<210> SEQ ID NO 70
<211> LENGTH: 355
<212> TYPE: DNA
<213> ORGANISM: Artificial sequence
<220> FEATURE:
<223> OTHER INFORMATION: Synthetic oligonucleotide

<400> SEQUENCE: 70

```
caagtgcagc tggtggagtc gggcccagga ctggtgaagc cttcggggac gctgtccctc    60
acctgcgctg tctctggtgg ctccatcagc agtagtaact ggtggagttg ggtccgccag   120
cccccaggga aggggctgga gtggattggg gaaatctatc atagtgggag caccaactac   180
accccgtccc tcaagagtcg agtcaccata tcattagaca gtccaagaa ccagttctcc    240
ctgaagctga gctctgtgac cgccgcggac acggccatgt attactgtgc gagaaacttc   300
tatcccggat acctccagta ctgggggccag ggcaccctgg tcaccgtctc ctcag       355
```

<210> SEQ ID NO 71
<211> LENGTH: 221
<212> TYPE: DNA
<213> ORGANISM: Artificial sequence
<220> FEATURE:
<223> OTHER INFORMATION: Synthetic oligonucleotide

<400> SEQUENCE: 71

```
cagtctgctc tgacccagcc tgccagtgtg agtggatctc ctggacagtc tattaccatt      60
tcttgtaccg gaaccattag cgacgtgggc gggtacaact acgtgagctg gtaccagcag     120
cacccaggca aggctcccaa actgatgatc tatgacgtga acaagcggcc ttcagggggtc    180
agcaatagat tctcaggaag caaatccggc aatactgtac g                         221
```

<210> SEQ ID NO 72
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 72

```
caggtgcagc tggtggagtc tgggggaggc gtggtccagc ctggggagtc tctgaagatc      60
tcctgtgcag cctctggatt caccttcagt agctatggca tgcactgggt ccgccaggct     120
ccaggcaagg ggctggagtg ggtggcagtt atatggtatg atggaattaa taaatactat     180
gcagactccg tgaagggccg attcaccatc tccagagaca attccaagaa cacgctgtat     240
ctgcaaatga acagcctgag agctgaggac acggctgtgt attactgtgc gaaagaggcg     300
ggtggtggtg actgctattc caactacttt cactactggg gccagggaac cctggtcacc     360
gtctcctca                                                              369
```

<210> SEQ ID NO 73

<400> SEQUENCE: 73

000

<210> SEQ ID NO 74
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 74

```
caggtgcagc tggtggagtc tgggggaggc gtggtccagc ctggggaggtc cctgagactc      60
tcctgtgcag cgtctggatt caccttcagt aactctggca tgcactgggt ccgccaggct     120
ccaggcaagg ggctggagtg ggtggcagtt atatggtttg atggaactaa taaatactat     180
gcagactccg tgaagggccg attcaccatc tccagagaca attccaagaa cacgctgtat     240
ctgcaaatga acagcctgag agccgaggac acggctgtat attactgtgc gagagtgcct     300
tgtggtggtg actgctattc cgggtacctc cagcactggg gccagggcac cctggtcacc     360
gtctcctca                                                              369
```

<210> SEQ ID NO 75
<211> LENGTH: 328
<212> TYPE: DNA
<213> ORGANISM: Artificial sequence

```
<220> FEATURE:
<223> OTHER INFORMATION: Synthetic oligonucleotide

<400> SEQUENCE: 75
gcaatagtga tgacgcagtc tccagccacc ctgtctgtgt ctccagggga aagagccacc    60
ctctcctgca gggccagtca gagtgttagc agcaccttag cctggtacca gcagaaacct   120
ggccaggctc ccaggctcct catctatggt gcatccacca aggccactgg tatcccagcc   180
aggttcagtg gcagtgggtc tgggacagag ttcactctca ccatcagcag cctgcagtct   240
gaagattttg cagtttatta ctgtcagcac tataataact ggcctcccct gctcactttc   300
ggcggaggga ccaaggtgga tatcaaat                                      328

<210> SEQ ID NO 76
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 76
gaggtgcagc tggtggagtc cggggggaggc ttagttcagc ctggggagtc tctgaagatc    60
tcctgtgcag ccactggatt caccttcagt agctactgga tgcactgggt ccgccaagct   120
ccagggaagg gactggtgtg ggtctcaggt attaatagtg atggcagtag cacaagttac   180
gcggactccg tgaagggccg attcaccatc gccagagaca cgccaaggg cacgctgtat    240 ctgcaaatga acagtctgag agccgaggac acggctgtat attactgtgc aagagtcggc   300
gccgtccgta tagcagcagc tgcccctgac tactggggcc agggaaccct ggtcaccgtc   360
tcctca                                                              366

<210> SEQ ID NO 77
<211> LENGTH: 340
<212> TYPE: DNA
<213> ORGANISM: Artificial sequence
<220> FEATURE:
<223> OTHER INFORMATION: Synthetic oligonucleotide

<400> SEQUENCE: 77
gacatcgtga tgacccagtc tccagactcc ctggctgtgt ctctgggcga gagggccacc    60
atcaactgca gtccagcca gagtgtttta tacagctcca acaataagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtact   300
ccgtggacgt tcggccaagg gaccaaggtg gatatcaaaa                         340

<210> SEQ ID NO 78
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 78
caggtgcagc tacagcagtg gggcgcagga ctgttgaagc cttcggagac cctgtccctc    60
acctgtgcta tttatggtgg gtccctcagt ggtcagtact ggagttggat ccgccagccc   120
cccgggaggg gcctggagtg gattggggag atccatcata agggacgcac caactacaac   180
```
ccgtccctca agagtcgagt caccatatca attgacacgt cgcagaggca gttctccctg    240
aggctgacct ctgtgagcgc cgcggacacg gctgtgtatt actgtgcgag tggaaactac    300
agactgggcc agggaaccct ggtcaccttc    330

<210> SEQ ID NO 79
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 79
gatgttgtgc tgactcagtc tccactcacc ctgcccgtca cccttggaca gccggcctcc     60
atctcctgca ggtctagtca aagcctcgta tacagtgatg gagacaccta cttgaattgg    120
tttcagcaga ggccaggcca agctccgagg cgcctaattt ataaggtttc taaacgggac    180
tttggggtcc cagacagatt cagcggcagt gggtcaggca ctgatttcac actgagaatc    240
agcagggtgg aggctgagga tgttggggtt tattactgca tgcaaggtac acactggcct    300
cgaacttttg gccaggggac ccaagtggat attaaa                              336

<210> SEQ ID NO 80
<211> LENGTH: 382
<212> TYPE: DNA
<213> ORGANISM: Artificial sequence
<220> FEATURE:
<223> OTHER INFORMATION: Synthetic oligonucleotide

<400> SEQUENCE: 80
cagctgcagc tgcaggagtc gggcccagga ctggtgaagc cttcggagac cctgtccctc     60
tcctgcaccg tctctggtgg ctccatcaac agtcgtactt actactgggg ctggatccgc    120
cagcccccag ggaaggggcc ggagtggatt gggactgtct ttcataatgt gagcaccttg    180
tacacctcgt ccctcaggag tcgagtcacc atctccgtag acacctccaa gaaccggttc    240
tccctgaaat tgacctctgt gaccgccgcg gacacggctg tttatttctg tgggagacta    300
actccgcgca atttatttcg tgggacgtta gtgagatggg tcgaccctg gggccaggga    360 atcctggtca ccgtctcctc ag                                             382

<210> SEQ ID NO 81
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 81
gaaatagtgt tggcgcagtc tccaggcacc ctgtctttgt ctccagggga aagagccacc     60
ctctcctgca gggccagtca caatcttaac agcaactact tagcctggta ccagcagaaa    120
cctggccagg ctcccaggct cctcatctat ggtgcatcca gcagggccac tggcatccca    180
gacaggttca ctggcagtgg gtctgggaca gacttcactc tcaccatcag cagactggag    240
cctgaagatt ttgcagtgta ttactgtcag cagtatgctg gctcactcac tttcggcgga    300
gggaccaagg tggatatcaa aa                                             322

<210> SEQ ID NO 82
<211> LENGTH: 387
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (379)..(379)
<223> OTHER INFORMATION: n is a, c, g, or t

<400> SEQUENCE: 82

```
caggtacagc tgcagcagtc aggtccagga ctggtgaagc cctcgcagac cctgtcactc    60
acctgtgcca tctccgggga cagtgtctct agcaacagtg ctgcttggat ctggatcagg   120
cagtccccat cgagaggcct tgagtggctg ggaacgacat actacaggtc cgagtggtat   180
agtgattatc cagcatctgt gaaaagtcga gtaaccatca acgcagacac atccaagaac   240
cagttctccc tgcagctgaa ctctgtgact cccgaggaca cggctgtgta ttattgtgca   300
agaataaccg tcgggtataa cagccctcac ctgcgggtaa ctcgaggctg gctcgacccc   360
tggggcccag ggaaccctng tcacctc                                       387
```

<210> SEQ ID NO 83
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 83

```
gacatcgtga tgacccagtc tccagactcc ctggctgtgt ctctgggcga gagggccacc    60
atcaactgca gtccagcca gagtgtttta tacagctcca acaataagaa ctacattgca   120
tggtaccagc agaagccagg acaggctcct aagctgctca tttactgggc atctacccgg   180
gaatccgggg tccctgaccg attcagtggc agcgggtctg ggacaaattt cactctcgcc   240
atcagcagcc tgcaggctga agatgtggca gtttattact gtcagcaata ttatagttct   300
cccctcactt tcggcggagg gaccaaggtg gatatcaaa                          339
```

<210> SEQ ID NO 84
<211> LENGTH: 340
<212> TYPE: DNA
<213> ORGANISM: Artificial sequence
<220> FEATURE:
<223> OTHER INFORMATION: Synthetic oligonucleotide

<400> SEQUENCE: 84

```
caggtgcagc tggtggagtc tgggggaggc gtggtccagc ctggaggtc tctgaagatc    60 tcctgtgcag cctctggatt caccttcagt acctatacta tgcactgggt ccgccaggct   120
ccaggcaagg ggctagagtg ggtggcaact atatcatatg atggcattaa tgaatactac   180
gcagactccg tgaagggccg attccaccatc ttcagagaca attccaagaa catgctgtat   240
ctgcaaatga acagcctgag acctgaggac acggctatgt tttactgtgc gagagggagg   300
ggagtggtga tgactgctat taccagacga cttctggggc                         340
```

<210> SEQ ID NO 85
<211> LENGTH: 330
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or t

<400> SEQUENCE: 85

```
cagtctgtgc tgactcagcc nccctcagcg tctgggaccc cggggcagag ggtcaccatc    60
tcttgttctg gaagcagctc caacatcgga attaattatg tacactggta ccagcagctc   120
ccaggaacgg cccccaaact cctcatctat aggaataatc agcggccctc aggggtccct   180
gaccgattct ctggctccaa gtctggcacc tcagcctccc tggccatcag tgggctccgg   240
tccgaggatg aggctgatta ttactgtgca gcatgggatg acagcctgag tggtaaagtg   300
ttcggcggag ggacccaggt gaccgtccta                                    330
```

<210> SEQ ID NO 86
<211> LENGTH: 342
<212> TYPE: DNA
<213> ORGANISM: Artificial sequence
<220> FEATURE:
<223> OTHER INFORMATION: Synthetic oligonucleotide

<400> SEQUENCE: 86

```
caggtgcagc tggtggagtc tgggggaggc gtggtccagc ctgggaggtc tctgaagatc    60
tcctgtgtag cctctggatt caccttcagc agttatgcaa tacactgggt ccgccaggct   120
ccaggcaagg ggctagagtg ggtggcgttt atctcaaatg atggaagtag taaaaagttg   180
gcagactccg tgaagggccg attcaccatc tccagagaca attccaagaa cacgctgtat   240
ctgcaaatga acagcctgag agctgaggac acggctgtat attattgtgc gagagcggat   300
cgagggtact ttggccactg gggccaggga accctggtca cc                      342
```

<210> SEQ ID NO 87

<400> SEQUENCE: 87

000

<210> SEQ ID NO 88
<211> LENGTH: 355
<212> TYPE: DNA
<213> ORGANISM: Artificial sequence
<220> FEATURE:
<223> OTHER INFORMATION: Synthetic oligonucleotide

<400> SEQUENCE: 88

```
caggtgcagc tggtgcagtc gggcccagga ctggtgaagc cttcggagac actgtccctc    60
acctgcactg tctctggtgg ctccatcagt agttactact ggagctggat ccggcagccc   120
ccagggaagg gactggagta cattgggcat atctattaca cgggggggcac caagtacaac   180
ccctccctca ggagtcgcgt caccatatca gtagacacgt ccaagaacca gttctccctg   240
aagctgacct ctgtgaccgc cgcagacacg gccgtgtatt actgtgcgag actggccggg   300
agaaaacctg acgcggactc ctggggccag ggaaccctgg tcaccgtctc ctcag        355
```

<210> SEQ ID NO 89
<211> LENGTH: 328
<212> TYPE: DNA
<213> ORGANISM: Artificial sequence
<220> FEATURE:
<223> OTHER INFORMATION: Synthetic oligonucleotide

<400> SEQUENCE: 89

```
cagcctgtgc tgactcagga gccctcactg actgtgtccc caggagggac agtcactctc    60
acctgtgctt ccagcactgg agcagtcacc agtggttttct ttccaaactg gctccagcag  120
```
aaacctggac aagctcccag ggcactgatt tatagtacaa acaacaaaca ctcctggacc    180
cctgcccggt tctcaggctc cctccttggg ggcaaagctg ccctgacact gtcaggtgtg    240
cagcctgagg acgaggctga gtattactgc ctgctctact atggtggtgt cgtggtattc    300
ggcggaggga ccaagctgac cgtcctag                                      328

<210> SEQ ID NO 90
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 90
gaggtgcagc tgttggagtc tgggggaggc ttggtacagc ctgggggtc tctgaagctc      60 tcctgtgcag cctctggatt catctttagc aactatgcca tgggctgggt ccgccaggct    120
ccagggaagg ggctggagtg gtctcagct cttagtgcta gtgatggtgt cacttcctac    180
gcagactccg tgaagggccg gttcaccatc tccagagaca attccaagaa cacgatgtat    240
ttgcaaatga acaggctgag aaccgaagac acggccatat atttctgtgc gaaaggccgc    300
gctcgggtaa acaacatcta ccgctacttt gaccactggg gccagggaac cctggtcacc    360
gtctcctca                                                           369

<210> SEQ ID NO 91
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 91
cagtctgtgc tgactcagcc tgcctccgtg tctgggtctc ctggacagtc gatcaccatc     60
tcctgcactg gaaccagcag tgacgttggt gcttatacct ttgtctcctg gtaccaacat    120
cacccgggca agcccccaa actcatcatt tatgaggtca gtaatcggcc ctccggggtt     180
tctgatcgct tctctggctc caagtctggc aacacggcct ccctgaccat ctctgggctc    240
caggctgagg acgaggctga ttattactgc aattcatata caaccaccag tccctgggtg    300
ttcggcggag ggacccagct gaccgtccta                                    330

<210> SEQ ID NO 92
<211> LENGTH: 352
<212> TYPE: DNA
<213> ORGANISM: Artificial sequence
<220> FEATURE:
<223> OTHER INFORMATION: Synthetic oligonucleotide

<400> SEQUENCE: 92
gaggtgcagc tgttggagtc tgggggaggc ttggtacagc ctggggagtc tctgaagatc     60
tcctgtgcag tctctggatt ctcctttaag agttatgcca tgagctgggt ccgccaggct    120
ccagggaagg ggctcgagtg gtctccact attggtgtga gtggtgctag cacatacttc    180
gcagaccccg tgaagggccg attcacaatc tccagagaca actccaagga cactctgtat    240
ctgcaaatga acagcctgag agccgaggac acggccgtct attactgtgc gagagacaca    300
tattactatg atagtagaat ctggtacttc ggtctctggg gccgtggcac cc           352

<210> SEQ ID NO 93

<400> SEQUENCE: 93

000

<210> SEQ ID NO 94
<211> LENGTH: 379
<212> TYPE: DNA
<213> ORGANISM: Artificial sequence
<220> FEATURE:
<223> OTHER INFORMATION: Synthetic oligonucleotide

<400> SEQUENCE: 94

| caggtccagc tggtgcagtc tggggctgag gtgaagaagc ctgggtcctc agtgaaggtc | 60 |
| tcctgcaagg cttctggagg caccttcagc agctatgtta tcagttgggt gcgacaggcc | 120 |
| cctggacaag ggcctgagtg gatgggaagg atcatcgtta tgcttggtgt aacaaactac | 180 |
| gcacagaagt tccagggcag agtctcgatt accgcggaca atccacaaa cacagcctac | 240 |
| atggagctga acagcctgag atctgaggac acggccgtgt attactgtgc gagggccgtc | 300 |
| attactatgg ttcggggaga tatacccctc gggtggttcg accctgggg ccagggaacc | 360 |
| ctggtcaccg tctcctcag | 379 |

<210> SEQ ID NO 95
<211> LENGTH: 300
<212> TYPE: DNA
<213> ORGANISM: Artificial sequence
<220> FEATURE:
<223> OTHER INFORMATION: Synthetic oligonucleotide

<400> SEQUENCE: 95

| gaaattgtgt tgacgcagtc tccaggcacc ctgtctttgt ctccagggga aagagccacc | 60 |
| ctctcctgca gggccagtca gagtgttaga agcaactact tagcctggta ccagcagaaa | 120 |
| cctggccagg ctcccaggct cctcttctat ggtgcatcca gcagggccac tggcatccca | 180 |
| gacaggttca gtggcagtgg gtctgcgaca gacttcactc tcaccatcag cagactggag | 240 |
| cctgaagatt ttgcagtgta ttactgtcag cagtatggta gctcaccccc gacgtcggcc | 300 |

<210> SEQ ID NO 96
<211> LENGTH: 370
<212> TYPE: DNA
<213> ORGANISM: Artificial sequence
<220> FEATURE:
<223> OTHER INFORMATION: Synthetic oligonucleotide

<400> SEQUENCE: 96

| caggtcacct tgaaggagtc tggtcctacg ctggtgaaac ccacacagac cctcacgctg | 60 |
| acctgcacct tctctgggtt ctcaatcaac acaggtggac agggtgtggg ctggatccgg | 120 |
| cagcccccag gaaaggccct ggagtggctt gcgctcattt attgggatga tgataagcgc | 180 |
| tacagcccgg ctctgaggag cagactcacc atcaccaagg gcacctccaa aaaccaggtg | 240 |
| gtcctaacaa tgaccaaaat ggaccctgtg gacacagcca catattactg tgcacaccgt | 300 |
| tcagtggctg gtaggaggga cttggctttt gatatctggg gccaagggac cctggtcacc | 360 |
| gtctcctcag | 370 |

<210> SEQ ID NO 97
<211> LENGTH: 315
<212> TYPE: DNA
<213> ORGANISM: Artificial sequence
<220> FEATURE:
<223> OTHER INFORMATION: Synthetic oligonucleotide

<400> SEQUENCE: 97

```
cagtctgtgc tgactcagcc tgcctccgtg tctgggtctc ctggacagtc gatcaccatc      60
tcctgcactg gaaccaccag tgacattggt acttatgact atgtctcctg gtatcaacag     120
cacccaggca gagcccccaa actcatgatt tatgatgtca gtaagcggcc ctcagggggtt    180 tctggtcgct ctctctggctc caagtctggc aacacggcct ccctgaccat ctctggcctc    240
cagactgagg acgagtctca ttattatctg cagcttcata taccaagcgg cctcacttgg    300
gtgttcggcg gaggg                                                     315
```

<210> SEQ ID NO 98
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 98

```
gaggtgcagc tggtggagtc tgggggaggc ttggtaaagc ctggggagtc tctgaagatc      60
tcctgtgcag cctctggttt cagtttcaat aacgcctgga tgaactgggt ccgccaggct     120
ccagggaagg ggctggagtg ggtcggccgt attaaaactc atgctgatgg tgggacaact    180
gactacgctg cacccgtgac aggcagattc accatctcga gagatgattc aaaaaacacg    240
ctgtctctcc aaatgagcag cctgaaaacc gaggacacag ccgtgtatta ctgtaccaca    300
agttttacgt tcccccgcag gatctttgct tactggggcc agggaaccct ggtc          354
```

<210> SEQ ID NO 99
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 99

```
gaaattgtgt tgacacagtc tccagccacc ctgtctttgt ctccagggga aagagccacc      60
ctctcctgca gggccagtca gagtgttagc agctacttag cctggtacca acaaaaacct     120
ggccaggctc ccagactcct catctatgat acatccaaca gggccactgg catcccagcc    180
aggttcagtg gcagtgggtc tgggacagac ttcactctca ccatcagcag cctagagcct    240
gaggatcttg cagtttatta ctgtcaactt cgaaacagct ggcctccaac tttcggccct    300
gggaccaagg tggatatcaa a                                              321
```

<210> SEQ ID NO 100
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 100

```
caggttcagc tggtgcagtc tggagctgag gtgaagaagc ctggggcctc agtgaaggtc      60
tcctgcaagg cctctggtta ttcctttaga agcaacggca tcagctgggt gcgacaggcc     120
cctggacaag gatttgagtg gctgggatgg atcgccgctt acaatggtga cacaaaatat    180
gtgcagaagt tcagggcag actcaccatg accacggaca cttccacgga cacagcctac    240
atggagctgt ggagcctgag atctgacgac acggccgtct attactgtgc gagagatccc    300
```

```
aaactgggga gaaagggaag tgcttttgat atctggggcc aagggacact ggtcatcgtc      360
tcgtca                                                                 366

<210> SEQ ID NO 101
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 101
gaaattgtgt tgacacagtc tccagccacc ctgtctttgt ctccagggg aagagccacc        60 ctctcctgca gggccagtca gagtgttggc aactacttaa cttggtacca acagaaacct      120
ggccaggctc ccaggctcct catctttgat ggtccacca gggccactgg catcccagcc       180
aggttcagtg gcagtgggtc tgggacagac ttcactctca ccatcagcag cctagagcct     240
gaagattttg cagtttatta ctgtctacag cgtagcgact tgtacacttt tggccagggg    300
accaaggtgg atatcaaa                                                   318

<210> SEQ ID NO 102
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 102
gaggtgcagc tgttggagtc tgggggaggc ttggtacagc ctggggagtc tctgaagatc       60
tcctgtgtag gctctgaatt cacatttagt agttatgcca tgagctgggt ccgccagcct     120
ccagggaagg gctggagtg gtctcaggt attagtgata gtggtggaag attgtacgtc       180
gcagactccg tgaagggccg cttcaccgtc tccagagaca attccaagaa cacgctgtat    240
ctggaaatga atagcctgag aggcgaggac acggccatat attactgtgc gaaagaccgg    300
gttgtgggag caacttaccc gcggggcgtt tttgatatct ggggccaagg gacaatggtc   360
accgtctctt ca                                                         372

<210> SEQ ID NO 103

<400> SEQUENCE: 103

000

<210> SEQ ID NO 104
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 104
cagctgcagc tgcaggagtc gggcccagga ctggtgaagc cttcggagac cctgtccctc      60
acctgcactg tctctggtgg ctccatcagc agtggtggtt actactgggg ctggatccgc    120
cagcccccag gaagggggct ggagtggatt gcgagtatct attatagtgg gagcacctac    180
tacaacccgt ccctcaagag tcgagtcacc atatcagtag acacgtccaa gacccagttc   240
tccctgaagc tgagctctgt gaccgccgcg gacacggccg tgtattattg tgcgaggcag   300
agcagctcga cgggggggctt ccactactgg ggccaggga ccctggtcac cgtctcctca   360
```

<210> SEQ ID NO 105
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 105

```
cagtctgtgc tgacgcagcc gccctcagtg tctggggccc cagggcagag ggtcaccatc      60
tcctgcactg ggagcagctc caacatcggg gcaggttatg atgtacactg gtaccagcat     120
cttccaggaa cagcccccaa actcctcatc tatggtaaca gcaatcggcc ctcaggggtc     180
cctgaccgat tctctggctc caagtctggc acctcagcct ccctggccat cactgggctc     240
caggctgagg atgaggctaa ttattactgc cagtcctatg acagcagcct gagtggtcgg     300
gaggtgttcg gcggagggac ccagctgacc gtccta                               336
```

<210> SEQ ID NO 106
<211> LENGTH: 370
<212> TYPE: DNA
<213> ORGANISM: Artificial sequence
<220> FEATURE:
<223> OTHER INFORMATION: Synthetic oligonucleotide

<400> SEQUENCE: 106

```
caagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt cttagttgga atagtggtag cataggctat     180
gcggactctg tgaagggccg attcaccatc tccagagaca acgccaagaa ctccctgtat     240
ctgcaaatga acagtctgag agctgaggac acggccttgt attactgtgc aaaagagacc     300
gagaaatatt actatgatag tagtggttat gactactggg gccagggaac cctggtcacc     360
gtctcctcag                                                            370
```

<210> SEQ ID NO 107
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 107

```
gaaattgtgt tgactcagtc tccaggcacc ctgtctttgt ctccagggga aagagccacc      60
ctctcctgca gggccagtca gagtgttagc agcatctact agcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gccgagggac ttttggccag     300
gggaccaagc tggagatcaa ac                                              322
```

<210> SEQ ID NO 108
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 108

```
caggtgcagc tggtgcagtc tggaggaggc ctgatccagc ctgggggtc cctgagactc      60
```

```
tcctgtgtag tctctgggtt caacgtcgct actaattata tgagtttggg tccgccaggct    120 ccagggaagg ggctggagtg ggtctcagtt atttatagcg gcggtagtac atactacgca    180
gactccgtga agggccgatt caccatctcc agagacaatt ccaagaacac ggtgtttctt    240
caaatgaaca gcctgagacc cgaagacacg gccgcgtatt attgtgcgaa ggggggagga    300
ttgggtctgg actactgggg ccagggaacc ctggtcaccg tctcctca                 348
```

<210> SEQ ID NO 109
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 109

```
cagtctgccc tgactcagcc tccctccgcg tccgggtctc ctggacagtc agtcaccatc     60
acatgcactg gaagcagcag tgacgttggt ggttataact atgtgtcctg gtaccaacaa    120
cacccaggca aagcccccaa agtcgtgatt tatgaggtca ataagcggcc ctcaggggtc    180
cctcatcgct tctctggctc caagtctggc aacacggcct ccctgaccgt ctctggcctc    240
caggctgagg atgaggctga ttattactgc agctcatatg caggcaccga aaccgtggca    300
ttcggcggag ggaccaagct gaccgtccta c                                   331
```

<210> SEQ ID NO 110
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 110

```
caggtccagc tggtgcagtc tggggctgag gtgaagaagc ctgggtcctc agtgaaggtc     60
tcctgcaagg cttctggagg cagattcagc actcaacata tcaactggat gcgacaggcc    120
cctggacatg gacttgagtg gatgggaggg atcatcccca tctttgctac agcagactac    180
gcacagaagt tccagggcag aatcacaatt accgcggacg aatctaccag cacagcctac    240
atggaaatga gcagcctgag atctgaggac acggccatat attattgtgg tgtctacaat    300
gcaaactggg gccagggaac cctggtc                                        327
```

<210> SEQ ID NO 111
<211> LENGTH: 303
<212> TYPE: DNA
<213> ORGANISM: Artificial sequence
<220> FEATURE:
<223> OTHER INFORMATION: Synthetic oligonucleotide

<400> SEQUENCE: 111

```
gatattgtga tgactcagtc tccactctcc ctgcccgtca cccctggaga gccggcctcc     60
ttctcctgta ggtctagtca gagcctcctg cattataatg gaaataacta tttgaattgg    120
tacctgcaga agccagggca gtctccacaa ctcctgatct atttgggttc taatcgggcc    180
tccggggtcc ctgacaggtt cagtggcagt ggatcaggca cagatttac actgaaaatc     240 agtaaagtgg aggctgacga tgttgggatt tactactgca tgcaagctcg acacaccccg    300
tgg                                                                  303
```

<210> SEQ ID NO 112

```
<211> LENGTH: 345
<212> TYPE: DNA
<213> ORGANISM: Artificial sequence
<220> FEATURE:
<223> OTHER INFORMATION: Synthetic oligonucleotide

<400> SEQUENCE: 112
caggtgcagc tggtggagtc tgggggaggc gtggtccagc ctgggaggtc cctgagactc      60
tcctgtgcag cctctggatt caccttcagt agctatagta tgcactgggt ccgccaggct     120
ccaggcaagg ggcttgaatg ggtggcagtt atatcatttg atgggagaag taattactac     180
gcagactccg tgaggggccg cttcaccatc tccagagaca actccaagaa aacgatgtat     240
ctgcaaatga acagcctgag acttgcggac acggctgtgt attactgtgc gagaggtgga     300
ataggtgccc cggacccccc ggagcggtat ggacgtctgg ggccc                     345

<210> SEQ ID NO 113
<211> LENGTH: 322
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (291)..(291)
<223> OTHER INFORMATION: n is a, c, g, or t

<400> SEQUENCE: 113
gacattcaga tgatccagtc tccatcctcc ctgtctgcat ctgtaggaga cagagtcacc      60
atctcctgcc aggcgactca agacattagc aactctgtaa attggtatca gcagaaacca     120
gggaaagccc ccaaactcct gatctacgat gcgtccactt tggaaacagg ggtcccttca     180
aggttcagtg gagtggatc tgggacacat tttactttca ccatcagcag cctgcagcct     240
gaagacattg caacatatta ctgtcaacag tttcatagtc tccctccgac ntttggccag     300
gggcccaagg ggatatccaa ac                                              322

<210> SEQ ID NO 114
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 114
caggttcagc tggtgcagtc tggagctgag gtgaagaagc ctggggcctc agtgaaggtc      60
tcctgcaagg cttctggtta caccttacg agccacggta tcatctgggt gcgacaggcc     120
cctggacaag ggcttgagtg gatgggatgg atcagcgttt acaatgacaa cacaaactct     180
gcacagaagt tccaggacag agtcaccatg accacagcca tccacgag cacagcctac     240 atggagctga ggagcctgag atctgacgac acggccgttt attactgtgc gagaagtagc     300
agtggccccc ggtattacta ctacggtatg gacgtctggg gccaagggac cacgtcacct     360

<210> SEQ ID NO 115
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 115
cagtctgtgg tgacgcagcc gccctcagtg tctggggccc cagggcagag ggtcaccatc      60
```

```
tcctgcactg ggagcagctc aacatcggg gcaggttatg ctgtacactg gtactaccag    120
cttccaggaa tagcccccaa actcctcatc tttggtaaca acaatcggcc ctcagggggtc    180 cctgaccgct tctctggctc caagtctggc acctcagcct ccctggccat cactgggctc    240
caggctgagg atgaggctga ttattactgc cagtcctatg acagcagcct gagtggttgg    300
gtgttcggcg agggacccaa ggtgaccgtc cta                                 333

<210> SEQ ID NO 116
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 116
gaggtgcagc tgttggagtc tgggggaggc ttggtacagc ctggggagtc tctgagactc    60
tcctgtgcag cctctggatt cacccttagg aactatgcca tgagctgggt ccgccagact   120
ccagggaagg ggctggagtg ggtctcagct attagtggta gtggtggtag cacatactac   180
gcagactccg tgaagggccg gttcaccatc tccagagaca cttccaagaa cacgctgtat   240
gtgcaaatga acagcctgag agccgaggac acggccgtat attactgtgc gaaaataaga   300
ttagatagta gtggttattc aggtgctttt gatatctggg gccaagggac aagggtcacc   360
gtctcctca                                                           369

<210> SEQ ID NO 117
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 117
tcctatgagc tgacacagcc accctcggtg tcagtgtccc caggacagac ggccaggatc    60
acctgctctg gagatgcatt gccaaagcaa tatgcttctt ggtaccagca gaagccaggc   120
caggcccctg tgctggtgat atataaagac agtgagaggc cctcagggat ccctgagcga   180
ttctctggct ccagctcagg gacaacagtc acgttgacca tcagtggagt ccaggcagaa   240
gacgaggctg actattactg tcaatcagca gacagcagtg gtacttatcc ggtggttttc   300
ggcggaggga cccagctgac cgtccta                                       327

<210> SEQ ID NO 118
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 118
caggtccagc tggtgcagtc tggggctgag gtgaagaagc ctgggtcctc agtgaaggtc    60
tcctgcaagg cttctggagg caccttcagc agctatgcta tcagttgggt gcgacaggcc   120
cctggacaag gcttgagtg gatgggaggg atcatcccta tctttggtac agcaaactac   180
gcacagaagt tccagggcag agtcacgatt accgcggacg aatccacggg cacagcctac   240
atggagctga ccagcctgag atctgaggac acggccatat attactgtgc gagagcgtcg   300
gagcagtggc tggcctcaat caactggttc gaccctggg gccagggaac cctggtcacc   360
```

-continued

| | |
|---|---|
| gtctcctca | 369 |

<210> SEQ ID NO 119
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 119

| | |
|---|---|
| cagtctgccc tgactcagcc tgcctccgtg tctgggtctc ctggacagtc gatcaccatc | 60 |
| tcctgcactg gaaccagcag tgatgttggg agttataacc ttgtctcctg gtaccaacaa | 120 |
| cacccaggca aagcccccaa actcatgatt tatgaggtca gtaagcggcc ctcagggggtt | 180 |
| tctaatcgct tctctgcctc caagtctggc aacacggcct ccctgacaat ctctgggctc | 240 |
| caggctgagg acgaggctga ttattactgc tgctcatatg caggtagtag cactttggtg | 300 |
| ttcggcggag ggacccaggt caccgtccta | 330 |

<210> SEQ ID NO 120
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 120

| | |
|---|---|
| gaggtgcagc tgttggagtc tgggggaggc ttggtacagc ctgggggggtc cctgagactc | 60 |
| tcctgtgcag cctctggatt cagcttcagc agctatgcca tgagttgggt ccgccaggct | 120 |
| ccagggaagg gactggagtg ggtctcaggg attggtaata gtggtgatag acatttttac | 180 |
| gcagactccg cgaagggccg gttcaccatc tttagagaca attccaacaa taggttgtat | 240 |
| ctgcaaatga acagcctgag agccgcggac acggccgtgt attactgtgc gaagtggggc | 300 |
| agatttgaaa gtggcgcctt tgggggccag ggagtcctgg tcaccgtctc ctca | 354 |

<210> SEQ ID NO 121
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 121

| | |
|---|---|
| tcctatgagc tgacacagtc accctcggtg tcagtgtccc caggacagac ggccaggatc | 60 |
| acctgctctg gagatgcatt gccagagcag tatgcttatt ggtaccagca gaagccaggc | 120 |
| caggccccag tgttggtaat atataaagac agtgagaggc cctcagggat ccctgagcga | 180 |
| ttctctggct ccggctcagg gacaacagtc acgttgacca ttactggagt ccaggcagaa | 240 |
| gacgaggctg actattactg tcaatccgca gacaacagtg gtacttatga agtcttcgga | 300 |
| actgggacca aggtcaccgt ccta | 324 |

<210> SEQ ID NO 122
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 122

| | |
|---|---|
| cagctgcagc tgcaggagtc gggcccagga ctggtgaagc cttcggagac cctgtccctc | 60 |

```
acctgcactg tctctggtgg ctccatcatc agtagtagtt actactgggg ctggatccgc    120
cagcccccag ggaaggggct ggagtggctt gggagtatct attatagtgg gagcacctac    180
tacaacccgt ccctcaagag tcgagtcacc atatccgtag acacgtccaa gaaccagttc    240
tccctgaagg tgacctctgt gaccgccgca gacacggctg tgtattactg tgcgagacaa    300
atttccaaag cagcagctgg ttctattgac tactggggcc agggaaccct ggtcaccgtc    360
tcc                                                                  363

<210> SEQ ID NO 123
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 123
gatattgtga tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtctccacag ctcctgatct atttgggttc taatcgggcc    180
tccggggtct ctgacaggtt cagtggcagt ggatcaggca cagattttac actgaaaatc    240
agcagagtag aggctgagga tgttggggtt tattactgca tgcaagctct acaaactccg    300
atcaccttcg gccaagggac acgactggag attaaa                              336

<210> SEQ ID NO 124
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 124
gaggtgcagc tgttggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcagct atcagtggca ctggtggaaa tacatactac    180
gcagactccg tgaagggccg gttcaccatc tccagagaca gtccaagaa cacgctatat     240 ctgcaaatgc acagcctgag agccgaggac acggccgtat attactgtgc gacgtccctg    300
atatggtggc tacagtctga ctactggggc cagggaaccc tggtcaccgt ctcctca       357

<210> SEQ ID NO 125
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 125
gacatccaga tgacccagtc tccatcctcc ctgtctgcat ctgtaggaga cagagtcacc     60
atcacttgcc gggcaagtca gagcattgcc agctatttaa tttggtatca gcagaaacca    120
gggaacgccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctcaaac gttcggccaa    300
gggaccaagg tggatatcaa a                                              321
```

<210> SEQ ID NO 126
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 126

| | | | | | |
|---|---|---|---|---|---|
| gaggtgcagc | tggtgcagtc | tggagcagag | gtgaaaaagc | ccggggagtc | tctgaagatc | 60 |
| tcctgtaagg | gttctggata | cagctttacc | aaccactgga | tcgcctgggt | gcgccaggtg | 120 |
| cccgggaaag | gcctggattg | gatggggatc | atctatcctg | gtgactctga | tatcagatac | 180 |
| agcccgtcct | tccaaggcca | ggtcaccatt | tcagccgaca | actccatcaa | caccgcctac | 240 |
| ttgcagtgga | ggagcctgaa | ggcctcggac | accgccatgt | attactgtgc | gagagccatg | 300 |
| acgacggtga | ctccttttga | ctactggggc | cagggaaccc | tggtcacctt | ctcc | 354 |

<210> SEQ ID NO 127
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 127

| | | | | | |
|---|---|---|---|---|---|
| tcctatgagc | tgactcaggc | accctcagtg | gccgtgtctt | caggacagac | agccagcatc | 60 |
| acctgctctg | gagataaatt | gggggataca | tatactttct | ggtatcagca | gaagccaggc | 120 |
| cagtcccctg | tggtggtcat | ctatcaagat | accaagcggc | cctcagggat | ccctgagcga | 180 |
| ttctctggct | ccaactctgg | gaacacagcc | actctgacca | tcaccgggac | ccagtctatg | 240 |
| gatgaagmtg | actattactg | tcaggcgtgg | gacagcgcca | ctgtggtttt | cggcggaggg | 300 |
| acccaggtga | ccgtccta | | | | | 318 |

<210> SEQ ID NO 128
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 128

| | | | | | |
|---|---|---|---|---|---|
| cagctgcagc | tgcaggagtc | gggcccagga | ctggtgaagc | cttcggagac | cctgtccctc | 60 |
| acctgcactg | tctctggtgg | ctccatcagc | agtaggaatt | tcttctgggc | gtggatccgc | 120 |
| cagcccccag | ggaagggact | ggagttcatt | gggagtattt | tttatagtgg | gggcacctac | 180 |
| tacaacccgt | ccctcaagag | tcgactctcc | atatccgtag | acacgtctag | gaaccagttc | 240 |
| tccctgaggc | tgagttctgt | gaccgccgca | gatacggctg | tatactactg | tgcgagacat | 300 |
| atgattgtag | tcctaccagg | tgtcccgatt | ccacctcgt | tcgacccctg | gggccaggga | 360 |
| accctg | | | | | | 366 |

<210> SEQ ID NO 129
<211> LENGTH: 345
<212> TYPE: DNA
<213> ORGANISM: Artificial sequence
<220> FEATURE:
<223> OTHER INFORMATION: Synthetic oligonucleotide

<400> SEQUENCE: 129

| | | | | | |
|---|---|---|---|---|---|
| gacatcgtga | tgacccagtc | gccagactcc | ctggctgtgt | ctctgggcga | gagggccacc | 60 |

| atcaactgca agtccagtca gagtgtttta tccaactcca acaataagaa ctacttagct | 120 |
| tggtaccagc agaaaccagg acagcctcct aggctgctca tttactgggc atctgcccgg | 180 |
| gaatccgggg tccctgaccg attcagtggc agcgggtctg ggacagattt cactctcacc | 240 |
| atcatcagcc tgcagcctga agatgtggca gtttattact gtcagcagta ttatagtcct | 300 |
| cctgcggagc tctctttcgg cggagggacc aaggtggata tcaaa | 345 |

<210> SEQ ID NO 130
<211> LENGTH: 303
<212> TYPE: DNA
<213> ORGANISM: Artificial sequence
<220> FEATURE:
<223> OTHER INFORMATION: Synthetic oligonucleotide

<400> SEQUENCE: 130

| caggtgcagc tggtggagtc tgggggaggc gtggtccagc ctggggaggtc cctgagactc | 60 |
| tcctgtgcag cgtctggatt caccttcagt aactatggcc tgcactgggt ccgccaggct | 120 |
| ccaggcaagg ggctggagtg ggtggcactt atatggtttg atggaagtaa taaatactat | 180 |
| gcagactccg tgaagggccg attcaccatc tccagagaca attccaagaa cacactgtat | 240 |
| ctgcaaatga acagcctgac agccgaggac acggctgtgt attactgtgc gagagagaca | 300 |
| gta | 303 |

<210> SEQ ID NO 131
<211> LENGTH: 258
<212> TYPE: DNA
<213> ORGANISM: Artificial sequence
<220> FEATURE:
<223> OTHER INFORMATION: Synthetic oligonucleotide

<400> SEQUENCE: 131

| tcctatgagc tgactcagcc acccgcggtg tcagtggccc caggaaagac ggccaggatt | 60 |
| acctgtgggg gagacgacat tggatttaaa ggtgtgcact ggtaccagca gaagccaggc | 120 |
| caggcccctg tactggtcgt ctatgatgat cgcgaccggc cctcagggat ccctgaccga | 180 |
| ttatctggct ccaactctgg gaacacggcc accctgacca tcagcagggt cgaagccggg | 240 |
| gatgaggccg actattac | 258 |

<210> SEQ ID NO 132
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 132

| gaggtgcagc tggtggagtc tgggggaggc ttggtccagc ctggggagtc tctgaagatc | 60 |
| tcctgttcag cctctggatt caccttcagt gactatgcta tgcactgggt ccgccaggct | 120 |
| ccagggcagg gactgcaata tgtttcagct attagtagta atggacatag tacatattat | 180 |
| gcagactccg tgaagggcag attcaccttc tccagagaca attccaagaa tacgctgtat | 240 |
| cttcaaatga gcagtctgag acctgaagac acggctgtat attactgtgt gaggtgtctg | 300 |
| cttcggggac ttattagccc ctttgactac tggggccagg aaccctggt c | 351 |

<210> SEQ ID NO 133
<211> LENGTH: 331
<212> TYPE: DNA

-continued

```
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (312)..(312)
<223> OTHER INFORMATION: n is a, c, g, or t

<400> SEQUENCE: 133
cagtctgtgc tgactcagcc accctcggtg tctgaagccc ccaggcagag ggtcaccatc      60
tcctgttctg gaagcagctc caacatcgga aataatgctg taaactggta ccagcagctc     120
ccaggaaagg ctcccaaact cctcatctat tatgatgatc tgctgccctc agggtctct      180 gaccgcttct ctggctcaaa gtctgggacc acagcctccc tgactatctc gggccctag     240 cctgaggacg aggctgattt ttactgttca acatgggact acagcctcag tgctcgggtg     300
ttcggcggag gnacccaggt gaccgtccta g                                    331

<210> SEQ ID NO 134
<211> LENGTH: 361
<212> TYPE: DNA
<213> ORGANISM: Artificial sequence
<220> FEATURE:
<223> OTHER INFORMATION: Synthetic oligonucleotide

<400> SEQUENCE: 134
caggttcagc tggtgcagtc tgggggaggt gtagtccagc ctggagtc cctcacactc       60 tcctgttcag cctctggatt catcttcact agatatggtc tccactgggt ccgccaggct    120
ccaggcaagg gctagagtg gtggcagtt atttcatctg atggaacgaa tagacactac      180
gcagactccg tgaagggccg attcaccgtc tccagagaca attccaaaag cacattatat    240
gtgcagatga acagcctgag aaatgaggac acggctgtat attactgtgc gagactaagt    300
ctagaagcgg cgtggtactt cgatctctgg ggccgtggta ccctggtcac cgtctcctca    360
g                                                                     361

<210> SEQ ID NO 135
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 135
cagtctgtgg tgacgcagcc gccctcagtg tctggggccc cagggcagag ggtcaccatc     60
tcctgcactg ggagcagctc caacatcggg gcaggttatg atgtacactg gtaccagcat   120
cttccaggaa cagcccccaa agtcctcatc tatggcaaca ccaatcggcc ctcagggtc    180 cctgaccggt tctctggctc taagtctggc acctcagcct ccctggccat cactgggctc   240
caggctgagg atgaggctga ttattactgc cagtcctatg caacagcct gaatggccct   300 tgggtcttcg gaactgggac ccag                                            324

<210> SEQ ID NO 136
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 136
gaggtgcagc tgttggagtc tggggggaggc ttggtacagc ctggggagtc cctgaaactc    60
```

```
tcctgtgcag cctctggatt cacctttagc agctatgcca tgaactgggt ccgccaggct    120
ccagggaagg ggctggagtg ggtctcaggt attagtggta gtggtggtag cacatactac    180
gcagactccg tgaagggccg gttcaccgtc tccagagaca attccaagaa cacgctgtat    240
ctgcaaatga acagcctgag agccgaggac acggccgtat attactgtgc gaaagacaac    300
aactactact actacggtat ggacgtctgg ggccaaggga ccacggtcac cgtctcctca    360
```

<210> SEQ ID NO 137
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 137

```
gccatccaga tgacccagtc tccatcctcc ctgtctgcat ctgtaggaga cagagtcacc     60
atcacttgcc gggcaagtca gggcattaga aatgatttag ctggtatcag cagaaaccca    120
gggaaagccc ctaagctcct gatctatgct gcatccagtt tacaaagtgg ggtcccatca    180
aggttcagcg gcagtggatc tggcacagat ttcactctca ccatcagcag cctgcagcct    240
gaagattttg caacttatta ctgtctacaa gattacaatt atcctcgaat gttcggccaa    300
gggaccaagg tggatatcaa a                                              321
```

<210> SEQ ID NO 138
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 138

```
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcagtt atatggtttg atggaagtaa taaatactat    180
gcagactccg tgaagggccg attcaccatc tccagagaca attccaagaa cacgctgtat    240
ctccaaatga acagcctgag agccgaggac acggctgtgt attactgtgc gagagtcgcc    300
cgggactaca gtaacatctt tgatgctttt gatatctggg gccaagggac actggtcacc    360
gtctcctca                                                            369
```

<210> SEQ ID NO 139
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 139

```
gacatccaga tgacccagtc tccatcctcc ctgtctgcat ctgtaggaga cagagtcacc     60
atcacttgcc gggcaagtcg gagcattagc acctatttaa attggtatca gcagaaacca    120
gggaaagccc ctaagctcct gatctatgct gcatccagtt tgcacagtgg ggtcccatca    180
aggttcagtg gcagtggatc tgggacagat ttcactctca ccatcagcag tctgcaacct    240
gaagattttg caacttacta ctgtcaacag agttacagta ccccgatcac cttcggccaa    300
gggacacgac tggagattaa a                                              321
```

<210> SEQ ID NO 140
<211> LENGTH: 294
<212> TYPE: DNA
<213> ORGANISM: Artificial sequence
<220> FEATURE:
<223> OTHER INFORMATION: Synthetic oligonucleotide

<400> SEQUENCE: 140
actgtctctg gtggctccat cagcagtaga agttactact ggggctggat ccgccagccc    60
ccagggaagg ggctggagtg gattgggagt atctattata gtgggagcac ctactacaac   120
ccgtctctca agagtcgagt caccatatcc gtagacacgt ccaagaacca gttctccctg   180
aagctgagct ctgtgaccgc cgcagacacg gctgtgtatt actgtgtgag aatagccgta   240
gcagcagctg gcacagacta ctggggccag ggaaccctgg tcaccgtctc ctca          294

<210> SEQ ID NO 141
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 141
gagatagtga tgacgcagtc tccagacacc ctgtctgtgt ctccagggga aagagccacc    60
gtctcctgca gggccagtca gagtattagc agcaacttag cctggtacca gcagaaacct   120
ggccaggctc ccaggctcct catctatggt gcatccacca gggccattgg tatcccagcc   180
aggttcagtg gcagtgggtc tgggacagag ttcactctca ccatcagcag cctgcagtct   240
gaagattttg cagtttatta ctgtcagcag tataataact ggcctccgta cacttttggc   300
caggggacca aggtggatat caaaa                                         325

<210> SEQ ID NO 142
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 142
caggtgcagc tggtgcagtc tggggctgag gtgaagaagc ctggggcctc agtgaaggtc    60
tcctgcaagg cttctggata caacctcacc acctatgata tcgtttgggt gcgacaggcc   120
gctggacaag gcttgagtg gatgggatgg atgaatccta aaagtggtaa cacagcctac   180
gcagagaggt tccagggcag agtcaccatg accaggaaca cctccataag cacagcctac   240
atggagctga gcagcctgag atctgaggac acggccgtgt attactgtgc gagaagtctg   300
gattcattac gattttttgga gtggttccac cagaactact actacttcat ggacgtctgg   360
ggcaaaggga ccacggtcac c                                             381

<210> SEQ ID NO 143
<211> LENGTH: 310
<212> TYPE: DNA
<213> ORGANISM: Artificial sequence
<220> FEATURE:
<223> OTHER INFORMATION: Synthetic oligonucleotide

<400> SEQUENCE: 143
gaaattgtgt tgacacagtc tccagccacc ctgtctttgt ctccagggga aagagccacc    60
ctctcctgca gggccagtca gactattggc ggctacttag cctggtatca acagatacct   120

```
ggccaggctc ccaggctcct catctatgat gcatccaaca gggccactgg catcccagcc    180
aggttcagtg gcagtgggtc tgggacagac ttcactctca ccatcagcag cctggagcct    240
gaagattttg cagttttatta ctgtcagctg cgtagcactt tcggcggagg gaccaaggtg    300
gatatcaaaa                                                            310
```

<210> SEQ ID NO 144
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 144

```
gaggtgcagc tggtggagtc tgggggaggc ttggtacagc cagggcggtc cctgagactc     60
tcctgtaaag cctctggaat ccccttttggt gattatgcta tgacctggtt ccgccaggct    120
ccagggaagg gactggagtg ggtaggtttc attaagagca aagcttatgg tgggacaccg    180
gaatacgccg cgtctktgaa gggcagattc accatctcaa gagataattc cagaagcacc    240
gcctacctgc aaatgaacag cctgaaaacc gacgacacag ccgtgtatta ctgtagtgca    300
acattgacta gaggggagct gttttgactac tggggccagg gaaccctggt caccgtctcc    360
tca                                                                   363
```

<210> SEQ ID NO 145
<211> LENGTH: 303
<212> TYPE: DNA
<213> ORGANISM: Artificial sequence
<220> FEATURE:
<223> OTHER INFORMATION: Synthetic oligonucleotide

<400> SEQUENCE: 145

```
gaaattgtgt tgacacagtc tccagacacc ctgtctttgt ctctagggga aagagccacc     60
ctctcctgca gggccagtca gagtgttagt aactacttag cctggtatca acagaaacct    120
ggccaggctc ccaggctcct catctatgat gcgtccagca gggccactgg catcccagcc    180
aggttcagtg gcagtgggtc tgggacagac ttcactctca ccatcagcag cctagagcct    240
gaagattttg cagttttatta ctgtcagcag cgttccaact ggccgctcac tttcggcgga    300
gga                                                                   303
```

<210> SEQ ID NO 146
<211> LENGTH: 382
<212> TYPE: DNA
<213> ORGANISM: Artificial sequence
<220> FEATURE:
<223> OTHER INFORMATION: Synthetic oligonucleotide

<400> SEQUENCE: 146

```
caggtgcagc tgcaggagtc gggcccagga ctggtgaagc cttcggagac cctgtccctc     60
acctgsactg tctctggtga ctccgtcaac agtggtagtt tctactggag ctggatccgg    120
caggccccag ggaagggact ggagtggatt ggttttatct attacagtgg gaccaccaac    180
tacaacccct ccctcaagag acgagtcacc atatcattaa tcacgtccaa gaaccagttt    240
tccctgaggc tgggctctgt gaccgctgcg gacacggccg tctattactg tgtgagagag    300
tggcctaggc actatgataa tagaggttac cacacgttgc cggggacctg gggccaggga    360
accctggtca ccgtctcctc ag                                              382
```

<210> SEQ ID NO 147
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 147

```
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaaccttct gatctataag gcgtctactt tagaaagtgg ggtcccatca     180
cggttcagcg gcagtggatc tgggacagag ttcactctca ccatcaacag cctgcaccct    240
gatgattttg caacttatta ctgccaacaa tataatactg attcttcccg gacgttcggc    300
caagggacca aggtggatat caaaa                                          325
```

<210> SEQ ID NO 148
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 148

```
caggtgcagc tggtggagtc tgggggaggc gtggtccagc ctgggaggtc cctgagactc      60
tcctgtacag cctctggatt caacttcagt tactatggca tacactgggt ccgccaggct    120
ccaggcaagg ggctgcagtg ggtggcactt atatcatatg atggaagtga taaatactat    180
gcagactccg tgaagggccg attcaccgtc tccagagact attccaagaa cacactgttt    240
ctgcaaatga acagcctgag aggtgacgat acggctgtgt attattgtca aatggttaag    300 gtgcctttt atttctgggg ccaagggaca atggtcaccc tctcctcc                 348
```

<210> SEQ ID NO 149
<211> LENGTH: 261
<212> TYPE: DNA
<213> ORGANISM: Artificial sequence
<220> FEATURE:
<223> OTHER INFORMATION: Synthetic oligonucleotide

<400> SEQUENCE: 149

```
tctggagatg aattgccaaa aagatatgct tattggtacc agcagaagtc aggccaggcc      60
cctgtgctgg tcatctatga ggacaccaaa cgaccctccg ggatccctga agattctct    120 ggctccagct cagggacagt ggccaccttg actatcagcg gggcccaggt ggacgatgaa    180
gctgactact actgttactc aacagacagt actagtaatc ataagagggt gttcggcgga    240
gggacccagg tgaccgtcct a                                              261
```

<210> SEQ ID NO 150
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 150

```
caggtgcagc tggtgcagtc tggggctgag gtgaagaagc ctgggtcctc ggtgaaggtc      60
tcctgcaagg gttctggaga cagcttcaga agttatgcta tcagttgggt gcgacaggcc    120
cctggacaag ggcttgagtg gatgggaggg atcatcccta ggtttggtac aacaaactac    180
```

```
gcacagaagt tccaggacag agtcacgatt accgcagaca agtccacgac tacagcctac    240
atggaactgc gcagcctcaa atgtgaggac acgggcgtgt attactgtgc gaggccacaa    300
agtgcctacg atttcgggcc ttttgaccac tggggccagg aaccctggt caccgtctcc     360 tca                                                                  363
```

<210> SEQ ID NO 151
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 151

```
tcctatgagc tgactcagcc accctcactg tcagtggccc caggaaagac ggccagaatt     60
acctgtgggg gagacaacat tggaagtaaa ggtgttcact ggtaccagca gaagccaggc    120
caggcccctg tggtagtcat ctcttatgat agcgaccggc cctcagggat ccctgagcga    180
ttctctggct ccaattctgg ggacacggcc accctgacca tcagcagggt cgaagccggg    240
gatgaggccg actattactg tcacgtgtgg catactacta ctgatcatta tgtcttcgga    300
actgggacca aggtcacc                                                  318
```

<210> SEQ ID NO 152
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 152

```
caggtgcagc tggtggagtc tgggggaggc gtggtccagc ctgggaggtc cctgagactc     60
tcctgtgccg cgtttggatt caccatcagt agctatggca tgcactgggt ccgccaggct    120
ccaggcaagg ggctggagtg ggtggcattt atatggtatg atggaactaa taatactat    180 gcagactccg tgaagggccg attcaccatc tccagagaca attccaagaa cacgctgtat    240
ctgcaaatga acagcctcag agccgaggac acggccgtgt attactgtgt gaggacccag    300
caggttatac gccctttttt cgaccactgg ggccagggaa ccctggtcac cgtctcctca    360
```

<210> SEQ ID NO 153
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 153

```
gaaatagtga tgacgcagtc tccagccacc ctgtctgtgt ctccagggga tagagtcacc     60
ctctcctgca gggccagtca gagtattagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca gcatcagcag cctgcagtct    240
gaagattttg cagtttatta ctgtcagcag tataaaaact ggcctccgtg gacgttcggc    300
caagggacca aggtggatat caaaa                                          325
```

<210> SEQ ID NO 154
<211> LENGTH: 387
<212> TYPE: DNA

<213> ORGANISM: Artificial sequence
<220> FEATURE:
<223> OTHER INFORMATION: Synthetic oligonucleotide

<400> SEQUENCE: 154

```
caggtgcagc tggtgcagtc tggggctgag gtgaagaagc ctgggtcctc ggtgaaggtc    60
tcctgcaaga cttctggagg caccttcagc aattattcta tcacctgggt gcgacaggcc   120
cctggacaag gcttgagtg gatgggaggg atcatcccta tctctggaac agcaaaatac   180
gcacagaagt tccagggcag agtcacgatt agcgcggaca atccacgag cacagcctac   240
atggaactga gcagcctgag atctgaggac acggccgtat attactgtgc gagagactgt   300
tacggggttt tttggagtgg ttattttagc aggtgccact cggtatgga cgtctggggc   360
caagggacca cggtcaccgt ctcctca                                       387
```

<210> SEQ ID NO 155
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 155

```
gaaattgagt tgacgcagtc tccaggcacc ctgtctttgt ctccagggga aagagccacc    60
ctctcctgca gggccagtca gagcgttaga agcagccact tagcctggta ccagcagaaa   120
cctggccagg ctcccaggct cctcatctat ggtgcatcca acagggccac tggcatccca   180
gacagattca gtggcagtgg gactgggaca gacttcactc tcaccatcag cagactggag   240
cctgaagatt ttgcagtgta ttactgtcag cagtatggtg gctcaccttt gctcactttc   300
ggcggaggga ccaaggtgga tatcaaa                                       327
```

<210> SEQ ID NO 156
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 156

```
gaggtgcagc tgttggagtc tgggggaggc ttggtacagc ctgggggtc cctgaaactc     60
tcctgtgcag cctctggatt cacatttagc aactatgcca tgagctgggt ccgccaggct   120
ccagggaagg gctggagtg gtctcagct tttagtggca ctggtggtag cacatactac    180
gcagactccg tgaagggccg gttcagcatc tccagagaca attccaagaa cacgctgtat   240
ctgcaaatga acagcctgag agtcgaggac acggccgtat attactgtgc gaaagatagg   300
ggaatagtgg gaactacccg atttgactcc tggggccagg gaaccctggt caccgtctcc   360
tca                                                                 363
```

<210> SEQ ID NO 157
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 157

```
gaaatagtga tgacgcagtc tccagccacc ctgtctgtgt ctccagggga aagagccacc    60
ctctcctgca gggccagtca gagtgttagc agcaacttag cctggtacca gcagaaacct   120
```

```
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tatagtaact ggcctccgat caccttcggc    300
caagggacac gactggagat taaa                                           324
```

```
<210> SEQ ID NO 158
<211> LENGTH: 393
<212> TYPE: DNA
<213> ORGANISM: Artificial sequence
<220> FEATURE:
<223> OTHER INFORMATION: Synthetic oligonucleotide

<400> SEQUENCE: 158
caggtgcagc tggtggagtc tgggggaggc ttggtccagc ctggggagtc tctgaagatc     60
tcctgtgtag cctctggctt cgccttcagt ggctctgcta tgcactgggt ccgccaggct    120
tccgggaaag gctggagtg gcttggccgt ataagaaata gccgaacaa ctacgcgaca     180 gcatatgctg cgtcggtgaa aggcaggttc accatctcca gagatgattc aaagaacacg    240
gcgtatctac aaatgaacag cctgaaaacc gaggacgcgg gcgtgtatta ttgtactaga    300
cgaatggacc atgctcgtcg gcccgctcgg gaggactact acaacaacgg tatggacatc    360
tggggccaag ggaccacggt caccgtctcc tca                                 393
```

```
<210> SEQ ID NO 159
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 159
gaaattgtgt tgacgcagtc tccaggcacc ctgtctttgt ctccagggga aagagccacc     60
ctctcctgca gggccagtca gagtgttagc agcagcttct tagcctggta ccagcacaaa    120
cctggccagg ctcccaggct cctcatctat gatgcgtcca gcagggccac tggcatccca    180
gacaggttca gtggcagtgg gtctgggca gagtacactc tcaccatcag cagactggag     240
cctgaagact ttgcagtgta ttactgtcag cagtatagta gctcacccac cttcggccct    300
gggaccaaag gtggatatca a                                              321
```

```
<210> SEQ ID NO 160
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 160
caggtgcagc tggtggagtc tgggggaggc gtggtccagc ctgggggtc cctgagactc       60 tcctgtgcag cgtctggatt cagcttcagt aactatggcg tgcactgggt ccgccaggct    120
ccaggcaggg cgctggagtg ggtcgctttt atacggtttg atggaactga taaatactat    180
gcagactccg tggagggccg attcaccatc tccagagaca attccaagaa cacactgtat    240
ctccaaatga acaacctgag agctgaggac acggctgtgt attactgtgc gaaggatttg    300
gcgatgatga ttgcaaaccc ccttgactgc tggggccagg gaatcctggt caccgtctcc    360
tca                                                                  363
```

<210> SEQ ID NO 161
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 161

| | | | | | |
|---|---|---|---|---|---|
| gaaatagtga | tgacgcagtc | tccagccacc | ctgtctgtgt | ctccagggga | aagagccacc | 60 |
| ctctcctgca | gggccagtca | gagtgttagt | agcaacttag | cctggtacca | gcagaaacct | 120 |
| ggccaggctc | ccaggctcct | catctatgat | gcatccacca | gggccactgg | tatcccagtc | 180 |
| aggttcagtg | gcagtgggtc | tgggacagag | ttcactctca | ccatcagcag | cctgcagtct | 240 |
| gaagattttg | caatttatta | ctgtcagcag | tataaaaact | gggggacgtt | cggccaaggg | 300 |
| accaaggtgg | atatcaaa | | | | | 318 |

<210> SEQ ID NO 162
<211> LENGTH: 349
<212> TYPE: DNA
<213> ORGANISM: Artificial sequence
<220> FEATURE:
<223> OTHER INFORMATION: Synthetic oligonucleotide

<400> SEQUENCE: 162

| | | | | | |
|---|---|---|---|---|---|
| caggtccagc | tggtgcagtc | tggggctgag | gtgaagaagc | ctgggtcctc | ggtgaaggtc | 60 |
| tcctgcaagg | cttctggagg | cactttcaac | agttttgcta | tcacctgggt | gcgacaggcc | 120 |
| cctggacaag | ggcttgagtg | gatggggggg | atcattcctc | tctttggtac | cacgaactac | 180 |
| gcacagaagt | tccaggacag | agtcacgatt | accacggacg | attccatgag | tacatttac | 240 |
| atggagttga | aaagcctgag | atctgaggac | acggccgtct | attactgtgc | gagagtgttc | 300 |
| tccgcggctg | gacactgggg | ccagggaacc | ctggtcaccg | tctcctcag | | 349 |

<210> SEQ ID NO 163
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 163

| | | | | | |
|---|---|---|---|---|---|
| gacatccaga | tgaccccttc | tccatcctcc | ctgtctgcat | ctgtaggaga | cagagtcacc | 60 |
| atcacttgcc | gggcaagtca | gagcattgcc | agctatttaa | tttgggatca | gcagaaacca | 120 |
| gggaacgccc | ctaagctcct | gatctatgct | gcatccagtt | tgcaaagtgg | ggtcccatca | 180 |
| aggttcagtg | gcagtggatc | tgggacagat | ttcactctca | ccatcggcag | tctgcaacct | 240 |
| gaagattttg | caacttacta | ctgtcaacag | agttacagta | cccctcaaac | gttcggccaa | 300 |
| gggaccaagg | tggatatcaa | aa | | | | 322 |

<210> SEQ ID NO 164
<211> LENGTH: 390
<212> TYPE: DNA
<213> ORGANISM: Artificial sequence
<220> FEATURE:
<223> OTHER INFORMATION: Synthetic oligonucleotide

<400> SEQUENCE: 164

| | | | | | |
|---|---|---|---|---|---|
| caggtgcagc | tggtggagtc | tgggggaggc | gtggtccagc | ctgggaggtc | cctgagactc | 60 |
| tcctgtgcag | cctctggatt | caccttccgt | agctatgcta | tgcactgggt | ccgccaggct | 120 |

```
ccaggcaagg ggctagagtg ggtggcagtt atctcatatg atgcgaataa tgaatactac    180
gcagactccg tgaagggccg attcaccatc tccagagaca attccaagaa cacgctgtat    240
ctgcaaatga acaccctgag acctgaggac acggctgtat attactgtgc gagagggctc    300
attccttccg cagagcagtg gcaggccagg gggggacctg attactacta ctactacggt    360
atggccgtct ggggccaagg gaccacggtc                                      390
```

<210> SEQ ID NO 165

<400> SEQUENCE: 165

000

<210> SEQ ID NO 166
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 166

```
caggtccagc tggtgcagtc tggggctgag gtgaagaagc ctgggtcctc agtgaaggtc    60
tcctgcaagg cttctggagc caccttcagc agctatgttt tcagctgggt gcgacaggcc    120
cctggacaag gccttgagtg gatgggaagg atcctcccta tccttgatat accaaactac    180
gcacagaagt tccagggcag agtcacgatt accgcggaca aatccacgag cacagcctac    240
atggagctgg gcagcctgag atctgaggac acggccgtgt attactgtgc gagaggcgga    300
ggcgcagtga ctggacgggg gtattatttt gactactggg gccagggaac cctggtcacc    360
ttctcc                                                                366
```

<210> SEQ ID NO 167
<211> LENGTH: 290
<212> TYPE: DNA
<213> ORGANISM: Artificial sequence
<220> FEATURE:
<223> OTHER INFORMATION: Synthetic oligonucleotide

<400> SEQUENCE: 167

```
gacatccaga tgacccagtc tccatcctcc ctgtctgcat ctgtaggaga cagagtcacc    60
atcacttgcc gggcaagtca gagcattagc agctatttac attggtatca acagagacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctcccac                290
```

<210> SEQ ID NO 168
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 168

```
caggtccagc tggtgcagtc tggggctgag gtgaagaagc ctgggtcctc ggtgaaggtc    60
tcctgcaagc tttccggagg caccctcaac agttatgctg tcagctgggt gcgacaggcc    120
ccgggacaag gccttgagtg gataggaagg atcatcccta tggttggcat ggcacactat    180
gcacagaagt ttcagggcag agtcacaatt accgcggaca aatccacgag ttcagtctac    240
```

```
atggagctga gtaccctgag atccgaagac acggccatgt atcattgtgc gagagagcag      300
aagttggtgg ggggggggctg gttcgacccc tggggccagg gaaccctggt cacc           354
```

<210> SEQ ID NO 169
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 169

```
gaaattgtat tgacgcagtc tccaggcacc ctgtctttgt ctccagggga aagcgccacc      60
ctctcctgca gggccagtca gagtgttaac agcgactact tagcctggta ccaacagaag     120
cctggccagg ctcccaggct cctcatctat ggtgtatcca gcagggccac tggcatccca     180
gacaggttca gtggcagtgg gtctgagaca gacttcactc tcaccattag tagactggag     240
cctgaagatt ttggtgtatt ttactgtcag cagtatggtc actcaccgta cacttttggc     300
caggggacca aggtggatat caaa                                             324
```

<210> SEQ ID NO 170
<211> LENGTH: 373
<212> TYPE: DNA
<213> ORGANISM: Artificial sequence
<220> FEATURE:
<223> OTHER INFORMATION: Synthetic oligonucleotide

<400> SEQUENCE: 170

```
caggtccagc tggtgcagtc tggggctgag gtgaagaagc ctgggtcctc ggtgaaggtc      60
tcctgcaagg cttctggagg cacctcagc aattctgcta tcaactgggt gcgacaggcc     120
cctggacaag gcttgagtg gatgggaagg atcatccta tccttggtat accaaactac      180
gcacagaagt tcgagggcag agtcacgatt accgcggaca atccacgag cacagcctac     240 atggagctga acagcctgag atctgaggac acggccgtgt attactgtgc gagccctcag     300
agagtattac gattttttgca gtggtcaccc tttgactact ggggccaggg aaccctggtc     360
accgtctcct cag                                                         373
```

<210> SEQ ID NO 171
<211> LENGTH: 294
<212> TYPE: DNA
<213> ORGANISM: Artificial sequence
<220> FEATURE:
<223> OTHER INFORMATION: Synthetic oligonucleotide

<400> SEQUENCE: 171

```
gaaattgtgt tgacgcagtc tccaggcacc ctgtctttgt ctccagggga aagagttacc      60
ctctcctgca gggccagtca gagtgttagc agcagctact tagcctggta ccagcagaaa     120
cctggccagg ctcccaggct cctcatctat gatgtattaa gcagagccac tggcatccca     180
gacaggttca gtggcagtgg gtctgggaca gacttcactc tcaccatcag cagactggag     240
cctgaagatt ttgcagtgta tttctgtcag cagtatgcta tctcacctaa cact            294
```

<210> SEQ ID NO 172
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 172

```
caggtgcagc tggtggagtc tgggggaggc gtggtccagc ctgggaggtc cctgagactc    60
tcctgtgcag cctctggatt cagcctcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagaggggtt   300
cgaatgacta caagccttga ctactgggc cagggaaccc tggtcaccgt ctcctca       357
```

<210> SEQ ID NO 173
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 173

```
cagtctgtgc tgactcagcc tgcctccgtg tctgggtctc ctggacagtc gatcaccatc    60
tcctgcactg gaaccagcag tgacgttggt ggttataact atgtctcctg gtaccaacag   120
cacccaggca aagcccccaa actcatgatt tatgatgtca gtaagcggcc ctcagggggtt  180
tctaatcgct tctctggctc caagtctggc aacacggcct ccctgaccat ctctgggctc   240
caggctgacg acgaggctga ttattactgc agctcatata accatcag cactttaggg    300
gtgttcggcg agggacccca ggtgaccgtc cta                                 333
```

<210> SEQ ID NO 174
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 174

```
caggtgcagc tgcaggagtc gggcccagga ctggtgaagc cttcggagac cctgtccctc    60
acctgcattg tctctggtgg ctccatcagt agttactact ggagttggat ccggcaatcc   120
ccagggaagg gactggagtg gattgggtat atgtctcaca gtgggagcac caactacaac   180
ccctccctca agagtcgagt caccatatca gtagacatgt ccaagaacca gttttccctg   240
aagttgacct ctgtgaccgc tgcggacacg gccgcgtatt attgtgcgag aggagtgggt   300
ggcgtttacg atattttgac tggttattgg ggcccaact ggttcgaccc ctggggccmg   360
ggaaccctgg tc                                                       372
```

<210> SEQ ID NO 175
<211> LENGTH: 337
<212> TYPE: DNA
<213> ORGANISM: Artificial sequence
<220> FEATURE:
<223> OTHER INFORMATION: Synthetic oligonucleotide

<400> SEQUENCE: 175

```
cagtctgtgg tgacgcagcc gccctcagtg tctggggccc cagggcagag ggtcaccatc    60
tcctgcactg ggagcagctc caacatcggg gcaggttatg atgtacactg gtaccaacag   120
cttccaggaa cagccccaa actcctcatc tatgctaaca ccaatcggcc ctcaggggtc   180
cctgaccgat tctctggctc caagtctgac acctcagcct ccctggccat cactgggctc   240
caggctgagg atgagggtga ttattactgc cagtcctttg acagcagcct gagggggttcc  300
```

```
gtggtattcg gcggagggac ccaggtgacc gtcctag                              337
```

<210> SEQ ID NO 176
<211> LENGTH: 365
<212> TYPE: DNA
<213> ORGANISM: Artificial sequence
<220> FEATURE:
<223> OTHER INFORMATION: Synthetic oligonucleotide

<400> SEQUENCE: 176

```
caggtgcagc tggtggagtc tgggggaggc ttggtcaagc ctggggagtc tctgaagatc    60
tcctgttcag tctctggatt caccttcagt gactactaca tgagctggat ccgccagact   120
ccagggaagg ggctggagtg gatttcatac attagtggtg gtggtaatac catatactat   180
acagactctg tgaagggccg attccacatc tccagggaca actccaagaa gtcactgtat   240
ctgcaaatga acagcctgag agccgaggac acggccgtgt attactgtgc gcggaacctt   300
agggctgcag gtgttaatta tttctacttc tactacatgg acgtctgggg caaaggacca   360
cggtc                                                                365
```

<210> SEQ ID NO 177
<211> LENGTH: 300
<212> TYPE: DNA
<213> ORGANISM: Artificial sequence
<220> FEATURE:
<223> OTHER INFORMATION: Synthetic oligonucleotide

<400> SEQUENCE: 177

```
gaaattgtgt tgacacagtc tccagccacc ctgtctttgt ctccagggga aagagccacc    60
ctctcctgca gggccagtca gagtgttagc agctccttag cctggtatca acagagacct   120
ggccgggcgc ccaggctcct catctatgat gcatccaata gggccactgg catcccagcc   180
aggttcagtg gcagtgggtc tgggacagac ttcaatctca ccatcagcag cctggagcct   240
gaagattttg cagtttatta ctgtcagcag cgtggcaagt ggcctccgtg gacgtcggcc   300
```

<210> SEQ ID NO 178
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 178

```
caggtgcagc tggtgcagtc tggggctgag gtgaagaagc ctggggcctc agtgaaggtc    60
tcctgcaagg catctggata cacctcgatg agcgactata taaatgggt gcgacaggcc   120
cctggacaag ggcttgagtg gatgggaata atgaaccctc ttggtggcag cacaagctac   180
gcacagaagt tgcagggcag agtcaccatg accagggaca cgtccacgag cacagtgtac   240
atggagctga gcagcctgag atctgacgac acggccgtct attattgtgt agttagtagt   300
ggttttcaac agtggttcga cccctggggc cagggaaccc tggtcaccgt ctcttca      357
```

<210> SEQ ID NO 179
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 179

```
gaaatagtga tgacgcattc tccagccacc ctgtctgtgt ctccagggga aagagccatc    60
ctctcctgca gggccagtca gagtctcacc accaacttag cctggtacca gcagaaacct   120
ggccaggctc ccaggctcct catctatcgt gcatccacca gggccactgg tatcccagcc   180
aggttcagtg gcagtgggtc tgggacagag ttcactctca ccatcagcag cctgcaatct   240
gaagattttg caatttatta ctgtcaacag tataataact ggcctcggac gttcggccaa   300
gggaccaagg tggatatcaa a                                             321
```

```
<210> SEQ ID NO 180
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 180
```

Gln Val Gln Leu Gln Gln Trp Gly Ala Gly Leu Leu Lys Pro Ser Glu
1               5                   10                  15

Thr Leu Ser Leu Thr Cys Ala Gly Tyr Gly Gly Ser Phe Ser Gly Tyr
            20                  25                  30

Phe Trp Ser Trp Ile Arg Gln Pro Pro Gly Lys Gly Leu Glu Trp Ile
        35                  40                  45

Gly Glu Ile Asn His Ser Gly Ser Thr Asp Tyr Asn Pro Ser Leu Lys
50                  55                  60

Ser Arg Val Thr Ile Ser Leu Asp Thr Ser Lys Thr Gln Phe Ser Leu
65                  70                  75                  80

Lys Leu Ser Ser Val Thr Ala Ala Asp Thr Ala Val Tyr Tyr Cys Ala
                85                  90                  95

Arg Val Met Thr Gly Ile Thr Asn Tyr Tyr Tyr Tyr Gly Met Asp
            100                 105                 110

Val Trp Gly Gln Gly Thr Thr Val Thr Phe
        115                 120

```
<210> SEQ ID NO 181
<211> LENGTH: 109
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid

<400> SEQUENCE: 181
```

Asp Ile Gln Leu Thr Gln Xaa Pro Ser Phe Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Glu Ser Gly Thr Xaa Phe Thr Leu Thr Ile Ser Ser Leu Gln Pro
65                  70                  75                  80

-continued

Glu Asn Phe Ala Thr Tyr Tyr Cys Gln His Leu Asn Ser Tyr Pro Arg
                85                  90                  95

Gly Tyr Thr Phe Gly Gln Gly Thr Lys Val Asp Ile Lys
            100                 105

<210> SEQ ID NO 182
<211> LENGTH: 127
<212> TYPE: PRT
<213> ORGANISM: Artificial sequence
<220> FEATURE:
<223> OTHER INFORMATION: Synthetic amino acid sequence

<400> SEQUENCE: 182

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Ser Gln Phe Ser Leu
65                  70                  75                  80

Lys Leu Ser Ser Val Thr Ala Ala Asp Thr Ala Val Tyr Tyr Cys Ala
                85                  90                  95

Arg Ala Thr Gln Gly Ser Gly Thr Tyr Lys Leu Phe Phe Tyr Ser Tyr
            100                 105                 110

Gly Met Asp Val Trp Gly Gln Gly Thr Thr Val Thr Val Ser Ser
        115                 120                 125

<210> SEQ ID NO 183
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 183

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Thr Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Tyr
                85                  90                  95

Thr Phe Gly Gln Gly Thr Arg Leu Glu Ile Lys
            100                 105

<210> SEQ ID NO 184
<211> LENGTH: 123
<212> TYPE: PRT
<213> ORGANISM: Artificial sequence
<220> FEATURE:
<223> OTHER INFORMATION: Synthetic amino acid sequence

<400> SEQUENCE: 184

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Asn
            20                  25                  30

Asn Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Arg Arg Val Leu Leu Trp Phe Gly Glu Phe Gln Leu
            100                 105                 110

Trp Gly Gln Gly Thr Leu Val Thr Val Ser Ser
        115                 120

<210> SEQ ID NO 185
<211> LENGTH: 111
<212> TYPE: PRT
<213> ORGANISM: Artificial sequence
<220> FEATURE:
<223> OTHER INFORMATION: Synthetic amino acid sequence

<400> SEQUENCE: 185

Gln Ser Ala Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ile Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ala Leu Phe Gly Gly Gly Thr Gln Leu Thr Val Leu
            100                 105                 110

<210> SEQ ID NO 186
<211> LENGTH: 116
<212> TYPE: PRT
<213> ORGANISM: Artificial sequence
<220> FEATURE:
<223> OTHER INFORMATION: Synthetic amino acid sequence

<400> SEQUENCE: 186

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Met Ser Ser Tyr
            20                  25                  30

Phe Trp Ser Trp Ile Arg Gln Pro Pro Gly Lys Gly Leu Glu Trp Ile
        35                  40                  45

Gly Tyr Ile Ser Tyr Ser Gly Gly Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Glu Asp Arg Gly Ser Pro Asp Tyr Trp Gly Gln Gly Thr Leu Val
            100                 105                 110

Thr Val Ser Ser
        115

<210> SEQ ID NO 187
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 187

Gln Ser Val Leu Thr Gln Pro Pro Ser Val Ser Ala Ala Pro Gly Arg
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Tyr Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Leu Ser Leu
                85                  90                  95

Ser Ala Gly Val Phe Gly Gly Gly Thr Lys Leu Thr Val Leu
            100                 105                 110

<210> SEQ ID NO 188
<211> LENGTH: 119
<212> TYPE: PRT
<213> ORGANISM: Artificial sequence
<220> FEATURE:
<223> OTHER INFORMATION: Synthetic amino acid sequence

<400> SEQUENCE: 188

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Leu
        35                  40                  45

Gly Trp Met Asn Pro Asn Ser Gly Asn Thr Lys Ser Ala Gln Lys Val
    50                  55                  60

Lys Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Pro Phe Asp Gly Ser Gly Tyr Tyr Tyr Trp Gly Gln Gly
            100                 105                 110

Thr Leu Val Thr Val Ser Ser
        115

<210> SEQ ID NO 189

<211> LENGTH: 111
<212> TYPE: PRT
<213> ORGANISM: Artificial sequence
<220> FEATURE:
<223> OTHER INFORMATION: Synthetic amino acid sequence

<400> SEQUENCE: 189

Asp Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gly Ala Ser Ala Leu Asp Gln Gly Gly Tyr Gln
            100                 105                 110

<210> SEQ ID NO 190
<211> LENGTH: 118
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (67)..(67)
<223> OTHER INFORMATION: Xaa can be any naturally occurring amino acid

<400> SEQUENCE: 190

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Leu
        35                  40                  45

Gly Trp Met Asn Pro Asn Ser Gly Asn Thr Lys Ser Ala Gln Lys Val
    50                  55                  60

Lys Gly Xaa Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Pro Phe Asp Asp Ile Gly Tyr Tyr Tyr Trp Gly Gln Gly
            100                 105                 110

Thr Leu Val Thr Val Ser
        115

<210> SEQ ID NO 191
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 191

Asp Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Ser
                    20                  25                  30

Asn Gly Tyr Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
        50                  55                  60

Asp Arg Phe Ile Gly Ser Gly Ser Gly Thr Asp Phe Thr Leu Lys Ile
65                  70                  75                  80

Ser Ile Val Glu Ala Glu Asp Val Gly Val Tyr Tyr Cys Met Gln Ala
                85                  90                  95

Leu Gln Thr Pro Gly Ala Phe Gly Pro Gly Thr Lys Val Asp Ile Lys
            100                 105                 110

<210> SEQ ID NO 192
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 192

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
                20                  25                  30

Tyr Met His Trp Val Gln Gln Ala Pro Gly Lys Gly Leu Lys Trp Met
            35                  40                  45

Gly Leu Leu Asp Pro Leu Asp Gly Glu Thr Ile Tyr Ser Glu Lys Phe
        50                  55                  60

Gln Gly Lys Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Leu Thr Gly Tyr Leu Asn Tyr Trp Gly Gln Gly Thr Leu
            100                 105                 110

Val Thr Val Ser Ser
        115

<210> SEQ ID NO 193
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Arg Ala Ser Pro Gly Ile Cys Asn Tyr
                20                  25                  30

Leu Ala Trp Tyr Gln His Lys Pro Gly Lys Val Pro Lys Leu Leu Ile
            35                  40                  45

Tyr Ala Ala Ser Thr Leu Gln Ser Gly Val Pro Ser Arg Phe Thr Gly
        50                  55                  60

Val Gly Ser Gly Thr Asn Phe Thr Leu Thr Ile Asn Asn Leu Pro Pro
65                  70                  75                  80

Glu Asn Val Ala Thr Tyr Tyr Cys Gln Lys Tyr Asn Ser Ala Pro His

```
                    85                  90                  95

Thr Phe Gly Gln Gly Thr Lys Val Asp Ile Lys
            100                 105

<210> SEQ ID NO 194
<211> LENGTH: 121
<212> TYPE: PRT
<213> ORGANISM: Artificial sequence
<220> FEATURE:
<223> OTHER INFORMATION: Synthetic amino acid sequence

<400> SEQUENCE: 194

Gln Val Thr Leu Lys Glu Ser Gly Pro Val Leu Val Asn Pro Thr Glu
1               5                   10                  15

Thr Leu Thr Leu Thr Cys Thr Val Ser Gly Phe Ser Leu Ser Asn Ala
            20                  25                  30

Arg Met Arg Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Ser Tyr Tyr
                85                  90                  95

Cys Ala Arg Met Arg Gly Glu Tyr Asn Ser Tyr Tyr Phe Asp Ser Trp
            100                 105                 110

Gly Gln Gly Thr Leu Val Thr Val Ser
        115                 120

<210> SEQ ID NO 195
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 195

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Asn Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Ser
                85                  90                  95

Val Val Phe Gly Gly Gly Thr Gln Val Thr Val
            100                 105

<210> SEQ ID NO 196
<211> LENGTH: 120
<212> TYPE: PRT
<213> ORGANISM: Artificial sequence
<220> FEATURE:
<223> OTHER INFORMATION: Synthetic amino acid sequence

<400> SEQUENCE: 196
```

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Ala Ser Tyr
            20                  25                  30

Asp Ile His Cys Val Arg Gln Ala Pro Gly Gln Gly Phe Glu Trp Met
            35                  40                  45

Val Gly Ser Tyr Ser Gly Asn Gly Asn Thr Gly Tyr Ala Gln Lys Phe
50                  55                  60

Gln Gly Arg Val Thr Met Thr Arg Asp Thr Ser Ser Thr Ala Tyr
65                  70                  75                  80

Met Glu Leu Ser Ser Gln Arg Ser Glu Asp Ile Asp Val Tyr Tyr Cys
                85                  90                  95

Ala Ser Arg Asp Ile Val Val Thr Ala Thr Arg Ser Pro Phe Asp
            100                 105                 110

Tyr Trp Gly Gln Gly Thr Leu Val
            115                 120
```

<210> SEQ ID NO 197
<211> LENGTH: 109
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid

<400> SEQUENCE: 197

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Xaa
            20                  25                  30

Tyr Leu Ala Xaa Xaa Gln Gln Lys Pro Gly Gln Ala Pro Arg Leu Leu
            35                  40                  45

Ile Tyr Ser Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Tyr Thr Phe Gly Gln Gly Thr Lys Val Asp Ile Lys
            100                 105
```

<210> SEQ ID NO 198
<211> LENGTH: 124
<212> TYPE: PRT
<213> ORGANISM: Artificial sequence
<220> FEATURE:
<223> OTHER INFORMATION: Synthetic amino acid sequence

<400> SEQUENCE: 198

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Phe
            20                  25                  30
```

Tyr Trp Ser Trp Ile Arg Gln Pro Pro Gly Lys Gly Leu Glu Trp Ile
                35                  40                  45

Gly Tyr Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Arg Gly Asn Tyr Ala Ser Ser Gly Tyr Tyr Tyr Asn Phe Asp
                100                 105                 110

Tyr Trp Gly Gln Gly Thr Leu Val Thr Val Ser Ser
                115                 120

<210> SEQ ID NO 199
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 199

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
                35                  40                  45

Ile Tyr Asp Asn Asn Lys Arg Pro Ser Gly Ile Pro Asp Arg Phe Ser
            50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Ser Glu Thr Gly Thr Lys Val Thr Val Leu
                100                 105                 110

<210> SEQ ID NO 200
<211> LENGTH: 123
<212> TYPE: PRT
<213> ORGANISM: Artificial sequence
<220> FEATURE:
<223> OTHER INFORMATION: Synthetic amino acid sequence

<400> SEQUENCE: 200

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
                35                  40                  45

Trp Ile Gly Ser Ile Tyr Tyr Arg Gly Ser Thr Tyr Tyr Asn Pro Ser
            50                  55                  60

Leu Lys Ser Arg Ile Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg His Leu Arg Val Leu Leu Trp Phe Gly Glu Leu Leu Glu

Trp Gly Gln Gly Thr Thr Val Thr Val Ser Ser
        115                  120

<210> SEQ ID NO 201
<211> LENGTH: 111
<212> TYPE: PRT
<213> ORGANISM: Artificial sequence
<220> FEATURE:
<223> OTHER INFORMATION: Synthetic amino acid sequence

<400> SEQUENCE: 201

Gln Ser Ala Leu Thr Gln Pro Pro Ser Val Ser Gly Ala Pro Gly Gln
1              5                10              15

Arg Val Thr Ile Ser Cys Thr Gly Ser Ser Ser Asn Ile Gly Ala Asp
          20              25              30

Tyr Asp Val His Trp Tyr Gln Gln Leu Pro Gly Thr Ala Pro Lys Leu
        35              40              45

Leu Ile Tyr Gly Asn Ser Asn Arg Pro Ser Gly Val Pro Asp Arg Phe
    50              55              60

Ser Gly Ser Lys Ser Gly Thr Ser Ala Ser Leu Ala Ile Thr Gly Leu
65              70              75              80

Gln Ala Glu Asp Glu Ala Asp Tyr Tyr Cys Gln Ser His Asp Ser Ser
        85              90              95

Leu Ser Gly Tyr Val Phe Gly Thr Gly Thr Lys Val Thr Val Leu
        100            105            110

<210> SEQ ID NO 202
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 202

Gln Val Gln Leu Val Gln Ser Gly Ala Glu Val Lys Lys Pro Gly Ala
1              5                10              15

Ser Val Lys Val Ser Cys Lys Ala Ser Gly Tyr Thr Phe Thr Gly Tyr
          20              25              30

Tyr Met His Trp Val Arg Gln Ala Pro Gly Gln Gly Leu Glu Trp Met
        35              40              45

Gly Trp Ile Asn Pro Asn Ser Gly Gly Thr Asn Tyr Ala Gln Lys Phe
    50              55              60

Gln Gly Arg Val Thr Met Thr Arg Asp Thr Pro Ile Ser Thr Ala Tyr
65              70              75              80

Met Glu Leu Ser Arg Leu Arg Ser Asp Asp Thr Ala Val Tyr Tyr Cys
        85              90              95

Ala Arg Val Pro Pro Asp Ser Ser Ser Trp Lys Trp Gly Gln Gly Thr
        100            105            110

Leu Val Thr Val Ser
        115

<210> SEQ ID NO 203
<211> LENGTH: 106
<212> TYPE: PRT
<213> ORGANISM: Artificial sequence
<220> FEATURE:
<223> OTHER INFORMATION: Synthetic amino acid sequence

<400> SEQUENCE: 203

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Thr Ser Ala Lys Asp
            100                 105
```

```
<210> SEQ ID NO 204
<211> LENGTH: 121
<212> TYPE: PRT
<213> ORGANISM: Artificial sequence
<220> FEATURE:
<223> OTHER INFORMATION: Synthetic amino acid sequence

<400> SEQUENCE: 204

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Pro Pro Gly Lys Gly Leu Glu Trp Val
            35                  40                  45

Ser Ser Ile Thr Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Arg Pro Gly Ile Ala Pro Ala Gly Pro Gln Ala Glu Gly Tyr
            100                 105                 110

Trp Gly Gln Gly Thr Leu Val Thr Phe
            115                 120
```

```
<210> SEQ ID NO 205
<211> LENGTH: 91
<212> TYPE: PRT
<213> ORGANISM: Artificial sequence
<220> FEATURE:
<223> OTHER INFORMATION: Synthetic amino acid sequence

<400> SEQUENCE: 205

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Ala
        50                  55                  60

Ser Gly Ser Gly Thr Glu Phe Thr Leu Thr Ile Ser Ser Leu Gln Pro
```

```
                65                  70                  75                  80

Glu Asp Phe Ala Val Tyr Tyr Cys Gln Gln Tyr
                85                  90
```

<210> SEQ ID NO 206
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 206

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Leu
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Leu Arg Gly Phe Asp Tyr Trp Gly Gln Gly Thr
                100                 105                 110

Leu Val Thr Val Ser
        115
```

<210> SEQ ID NO 207
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 207

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Leu Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asn Phe Ala Val Tyr Tyr Cys Gln Gln Tyr Gly Ser Ser Pro
                85                  90                  95

Arg Thr Phe Gly Gln Gly Thr Lys Val Asp Ile Lys
                100                 105
```

<210> SEQ ID NO 208
<211> LENGTH: 120
<212> TYPE: PRT
<213> ORGANISM: Artificial sequence
<220> FEATURE:
<223> OTHER INFORMATION: Synthetic amino acid sequence

<400> SEQUENCE: 208

```
Gln Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Ser Arg Gly
            20                  25                  30

Ile Tyr Tyr Trp Ser Trp Ile Arg Gln Pro Ala Gly Lys Gly Leu Glu
        35                  40                  45

Trp Ile Gly Arg Ile Tyr Thr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Trp Tyr Gly Trp Tyr Leu Asp Leu Trp Gly Arg
                100                 105                 110

Gly Thr Leu Val Thr Val Ser Ser
            115                 120

<210> SEQ ID NO 209
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 209

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asp
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Gly
                85                  90                  95

Thr Phe Gly Gly Gly Thr Lys Val Asp Ile Lys
                100                 105

<210> SEQ ID NO 210
<211> LENGTH: 124
<212> TYPE: PRT
<213> ORGANISM: Artificial sequence
<220> FEATURE:
<223> OTHER INFORMATION: Synthetic amino acid sequence

<400> SEQUENCE: 210

Glu Val Gln Leu Val Glu Ser Gly Gly Gly Leu Val Gln Pro Gly Gly
1               5                   10                  15

Ser Leu Arg Leu Ser Cys Val Val Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Lys Lys Tyr Tyr Val Asp Ser Val
    50                  55                  60

Thr Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Val Tyr Tyr Cys
                    85                  90                  95

Ala Thr Leu Asn Leu Glu Leu Ala Val Asp Ala Ile Ser Glu Ala Leu
                100                 105                 110

Lys Trp Gly Gln Gly Thr Leu Val Thr Val Ser Ser
            115                 120

<210> SEQ ID NO 211
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 211

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Phe Ala
            20                  25                  30

Tyr Trp Tyr Gln Gln Lys Pro Gly Gln Ala Pro Val Val Met Ile Tyr
        35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Val Asp Asn Ser Gly Thr Tyr
                85                  90                  95

Glu Val Phe Gly Gly Gly Thr Gln Leu Thr Val Leu
                100                 105

<210> SEQ ID NO 212
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 212

Gln Val Gln Leu Gln Gln Trp Gly Ala Gly Leu Leu Lys Pro Ser Glu
1               5                   10                  15

Thr Leu Ser Leu Thr Cys Asp Val Tyr Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Tyr Thr Pro Ser Leu Arg
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Leu Ser Gly Trp Leu Pro Phe Pro Asn Tyr Tyr Tyr Met
                100                 105                 110

Asp Val Trp Gly Lys Gly Thr Thr Val Thr
            115                 120

<210> SEQ ID NO 213
<211> LENGTH: 107
```

```
<212> TYPE: PRT
<213> ORGANISM: Artificial sequence
<220> FEATURE:
<223> OTHER INFORMATION: Synthetic amino acid sequence

<400> SEQUENCE: 213

Asp Ile Gln Met Thr Gln Ser Pro Ser Ser Leu Pro Ala Ser Val Gly
1               5                   10                  15

Asp Arg Val Thr Ile Thr Cys Arg Ala Ser Gln Asp Ile Arg Asn Asn
            20                  25                  30

Leu Gly Trp Tyr Gln Gln Lys Pro Gly Lys Ala Pro Glu Arg Leu Ile
        35                  40                  45

Tyr Gly Thr Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Phe Gly Arg Gly Thr Lys Val Glu Ile Lys
            100                 105

<210> SEQ ID NO 214
<211> LENGTH: 120
<212> TYPE: PRT
<213> ORGANISM: Artificial sequence
<220> FEATURE:
<223> OTHER INFORMATION: Synthetic amino acid sequence

<400> SEQUENCE: 214

Gln Val Gln Leu Val Gln Ser Gly Ala Glu Val Lys Lys Pro Gly Ser
1               5                   10                  15

Ser Val Lys Val Ser Cys Lys Val Ser Gly Gly Thr Phe Ser Ser Leu
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Lys Ala Asn Tyr Ala Gln Lys Phe
    50                  55                  60

Gln Gly Arg Val Ser Ile Ile Ala Asp Glu Ser Thr Ser Thr Ala Tyr
65                  70                  75                  80

Met Asp Leu Ser Ser Leu Arg Phe Glu Asp Thr Ala Val Tyr Tyr Cys
                85                  90                  95

Ala Thr Gly Gly Asn Ile Arg Val His Asp Phe Asp Ile Trp Gly Gln
            100                 105                 110

Gly Thr Leu Val Ile Val Ser Ser
        115                 120

<210> SEQ ID NO 215
<211> LENGTH: 114
<212> TYPE: PRT
<213> ORGANISM: Artificial sequence
<220> FEATURE:
<223> OTHER INFORMATION: Synthetic amino acid sequence

<400> SEQUENCE: 215

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Asn Ser
            20                  25                  30

Asp Gly Asn Thr Tyr Leu Asn Trp Phe Gln Gln Arg Pro Gly Gln Ser
```

```
            35                  40                  45
Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Asn Ile
 65                  70                  75                  80

Ser Arg Val Glu Ala Glu Asp Val Gly Val Tyr Tyr Cys Met Gln Gly
                 85                  90                  95

Thr His Trp Pro Pro Arg Trp Thr Phe Gly Gln Gly Thr Lys Val Asp
                100                 105                 110

Ile Lys

<210> SEQ ID NO 216
<211> LENGTH: 124
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (72)..(72)
<223> OTHER INFORMATION: Xaa can be any naturally occurring amino acid

<400> SEQUENCE: 216

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Pro Pro Gly Lys Gly Leu Glu Trp Ile
             35                  40                  45

Gly Glu Ile Asn Tyr Ser Gly Ser Thr Asp Tyr Asn Pro Ser Leu Glu
 50                  55                  60

Ser Arg Val Thr Ile Ser Val Xaa Ala Ser Lys Asn His Phe Ser Leu
 65                  70                  75                  80

Asn Leu Asn Ser Val Thr Ala Ala Asp Thr Val Val Tyr Tyr Cys Ala
                 85                  90                  95

Arg Ile Ser Ser Gly Trp Ile Gly Phe Pro Arg Tyr His Tyr Tyr Leu
                100                 105                 110

Asp Val Trp Gly Lys Gly Thr Thr Val Thr Val Ser
            115                 120

<210> SEQ ID NO 217
<211> LENGTH: 71
<212> TYPE: PRT
<213> ORGANISM: Artificial sequence
<220> FEATURE:
<223> OTHER INFORMATION: Synthetic amino acid sequence

<400> SEQUENCE: 217

Ser Tyr Glu Leu Thr Gln Pro Pro Ala Val Ser Val Ser Pro Gly Gln
 1               5                  10                  15

Thr Ala Arg Ile Ser Cys Ser Gly Asp Val Leu Arg Asp Asn Tyr Ala
                 20                  25                  30

Asp Trp Tyr Pro Gln Lys Pro Gly Gln Ala Pro Val Leu Val Ile Tyr
             35                  40                  45

Lys Asp Glu Gln Ser Leu Gly Val Gly Gly Thr Gln Leu Thr Val
 50                  55                  60

Leu Asp Arg Lys Ser Val Val
 65                  70
```

```
<210> SEQ ID NO 218
<211> LENGTH: 130
<212> TYPE: PRT
<213> ORGANISM: Artificial sequence
<220> FEATURE:
<223> OTHER INFORMATION: Synthetic amino acid sequence

<400> SEQUENCE: 218

Gln Val Gln Leu Val Gln Ser Gly Ala Glu Val Lys Lys Pro Gly Ser
1               5                   10                  15

Ser Val Lys Val Ser Cys Lys Ala Ser Gly Glu Thr Phe Ser Arg Tyr
            20                  25                  30

Ala Phe Ser Trp Val Arg Leu Ala Pro Gly Gln Gly Leu Glu Trp Leu
        35                  40                  45

Gly Arg Ile Ile Pro Phe Ile Asp Ile Pro Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Leu Pro Ser Thr Tyr Tyr Phe Gly Ser Gly Asn Tyr Pro
            100                 105                 110

Trp Gly Asn Trp Leu Asp Pro Trp Gly Gln Gly Thr Leu Val Thr Val
        115                 120                 125

Ser Ser
    130

<210> SEQ ID NO 219
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 219

Gln Ser Val Val Thr Gln Pro Pro Ser Val Ser Ala Ala Pro Gly Gln
1               5                   10                  15

Asn Val Thr Ile Ser Cys Ser Gly Ser Ser Asn Ile Gly Asn Asn
            20                  25                  30

Tyr Val Ser Trp Tyr His Gln Leu Pro Gly Thr Ala Pro Lys Leu Leu
        35                  40                  45

Ile Tyr Asp Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Glu Val Val Phe Gly Gly Gly Thr Gln Val Thr Val Leu
            100                 105                 110

<210> SEQ ID NO 220
<211> LENGTH: 114
<212> TYPE: PRT
<213> ORGANISM: Artificial sequence
<220> FEATURE:
<223> OTHER INFORMATION: Synthetic amino acid sequence

<400> SEQUENCE: 220

Gln Val Gln Leu Gln Gln Trp Gly Ala Gly Leu Leu Ile Ser Ser Glu
```

```
                1               5                  10                  15
            Thr Leu Ser Leu Thr Cys Gly Val Tyr Gly Gly Ser Phe Ser Gly Tyr
                            20                  25                  30

Tyr Trp Thr Trp Ile Arg Gln Pro Pro Gly Lys Gly Leu Glu Trp Ile
                        35                  40                  45

Gly Glu Ile Asn Tyr Val Gly Ser Thr Asn Tyr Asn Pro Ser Leu Lys
                50                  55                  60

Ser Arg Val Thr Met Ser Val Asp Thr Ser Lys Asn His Phe Ser Leu
            65                  70                  75                  80

Ser Leu Ser Ser Val Thr Ala Ala Asp Thr Ala Val Tyr Tyr Cys Ala
                            85                  90                  95

Arg Gly Leu Arg Gly Asn Ser Val Cys Phe Asp Trp Gly Pro Gly Thr
                        100                 105                 110

Leu Val
```

<210> SEQ ID NO 221
<211> LENGTH: 106
<212> TYPE: PRT
<213> ORGANISM: Artificial sequence
<220> FEATURE:
<223> OTHER INFORMATION: Synthetic amino acid sequence

<400> SEQUENCE: 221

```
            Glu Leu Val Met Thr Gln Ser Pro Ala Thr Leu Ser Val Ser Pro Gly
            1               5                   10                  15

Glu Arg Ala Ser Leu Ser Cys Arg Ala Ser Gln Ser Val Ser Ser Asn
                            20                  25                  30

Leu Ala Trp Tyr Gln Gln Lys Pro Gly Gln Ala Pro Arg Leu Leu Ile
                        35                  40                  45

Tyr Gly Ala Ser Thr Arg Ala Thr Gly Leu Pro Ala Arg Phe Ser Gly
                50                  55                  60

Ser Gly Ser Gly Thr Glu Phe Thr Leu Thr Ile Ser Ser Leu Gln Ser
            65                  70                  75                  80

Glu Asp Phe Ala Ile Tyr Tyr Cys Gln Gln Tyr Asn Asn Trp Pro Arg
                            85                  90                  95

Thr Phe Gly Gln Gly Thr Lys Val Asp Ile
                        100                 105
```

<210> SEQ ID NO 222
<211> LENGTH: 127
<212> TYPE: PRT
<213> ORGANISM: Artificial sequence
<220> FEATURE:
<223> OTHER INFORMATION: Synthetic amino acid sequence

<400> SEQUENCE: 222

```
            Glu Val Gln Leu Val Glu Ser Gly Gly Gly Leu Val Gln Pro Gly Glu
            1               5                   10                  15

Ser Leu Lys Ile Ser Cys Ala Ala Ser Gly Phe Thr Phe Ser Ser Phe
                            20                  25                  30

Ser Met Asn Trp Val Arg Gln Ala Pro Gly Lys Gly Leu Glu Trp Val
                        35                  40                  45

Ser Tyr Ile Ser Ser Ser Ser Thr Ile Tyr Tyr Ala Asp Ser Val
                50                  55                  60

Lys Gly Arg Phe Thr Ile Ser Arg Asp Asn Ala Lys Asn Ser Leu Tyr
            65                  70                  75                  80

Leu Gln Met Asn Ser Leu Arg Asp Glu Asp Thr Ala Val Tyr Tyr Cys
```

85                  90                  95

Ala Arg Arg Ser Val Gly Cys Ser Gly Gly Asn Cys Tyr Ala Tyr Tyr
                100                 105                 110

Tyr Gly Met Asp Val Trp Gly Gln Gly Thr Thr Val Thr Val Ser
            115                 120                 125

<210> SEQ ID NO 223
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 223

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Ala
                85                  90                  95

Leu Gln Thr Pro Ile Thr Phe Gly Gln Gly Thr Arg Leu Glu Ile Lys
                100                 105                 110

<210> SEQ ID NO 224
<211> LENGTH: 128
<212> TYPE: PRT
<213> ORGANISM: Artificial sequence
<220> FEATURE:
<223> OTHER INFORMATION: Synthetic amino acid sequence

<400> SEQUENCE: 224

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Thr Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Arg Asp Gly Asp Gly Ser Gly Ser Tyr Thr Pro Tyr Tyr Tyr
                100                 105                 110

Tyr Gly Leu Asp Val Trp Gly Gln Gly Thr Thr Val Thr Val Ser Ser
            115                 120                 125

<210> SEQ ID NO 225
<211> LENGTH: 108
<212> TYPE: PRT
<213> ORGANISM: Artificial sequence
<220> FEATURE:

-continued

<223> OTHER INFORMATION: Synthetic amino acid sequence

<400> SEQUENCE: 225

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Tyr
            20                  25                  30

Leu Asn Trp Tyr Gln Gln Lys Ser Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu His Pro
65                  70                  75                  80

Glu Asp Phe Ala Thr Tyr Tyr Cys Gln Gln Ser Tyr Ser Thr Pro Pro
                85                  90                  95

Leu Thr Phe Gly Gly Gly Thr Lys Val Glu Ile Lys
            100                 105

<210> SEQ ID NO 226
<211> LENGTH: 115
<212> TYPE: PRT
<213> ORGANISM: Artificial sequence
<220> FEATURE:
<223> OTHER INFORMATION: Synthetic amino acid sequence

<400> SEQUENCE: 226

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Pro Pro Gly Lys Gly Leu Glu Trp Val
        35                  40                  45

Ser Ser Ile Thr Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Arg Pro Gly Ile Ala Pro Ala Gly Pro Pro Gly Gly Gly Leu
            100                 105                 110

Leu Gly Pro
        115

<210> SEQ ID NO 227
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 227

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser

```
                    50                  55                  60
Ala Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                     85                  90                  95

Tyr Thr Phe Gly Arg Gly Thr Gln Val Asp Ile Lys
                100                 105
```

<210> SEQ ID NO 228
<211> LENGTH: 120
<212> TYPE: PRT
<213> ORGANISM: Artificial sequence
<220> FEATURE:
<223> OTHER INFORMATION: Synthetic amino acid sequence

<400> SEQUENCE: 228

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
             35                  40                  45

Ser Ser Ile Ser Ser Ile Ser Ser Tyr Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Pro Arg Ser Arg Pro Asn Ser Gly Ser Tyr Phe Trp
                100                 105                 110

Tyr Tyr Tyr Gly Met Asp Val Trp
            115                 120
```

<210> SEQ ID NO 229
<211> LENGTH: 100
<212> TYPE: PRT
<213> ORGANISM: Artificial sequence
<220> FEATURE:
<223> OTHER INFORMATION: Synthetic amino acid sequence

<400> SEQUENCE: 229

```
Ser Tyr Glu Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
             35                  40                  45

Asp Asp Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Asn Ser Asp His
                 85                  90                  95

Arg Val Ser Ala
            100
```

<210> SEQ ID NO 230
<211> LENGTH: 121

```
<212> TYPE: PRT
<213> ORGANISM: Artificial sequence
<220> FEATURE:
<223> OTHER INFORMATION: Synthetic amino acid sequence

<400> SEQUENCE: 230

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ala Ile Asn Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Glu Gly Ala Ala His Gly Met Asp Val Trp Gly
            100                 105                 110

Gln Gly Thr Thr Val Thr Val Ser Ser
        115                 120

<210> SEQ ID NO 231
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 231

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Leu Gln Thr Leu Pro Ile Thr Phe Gly Gln Gly Thr Arg Leu Glu Ile
            100                 105                 110

<210> SEQ ID NO 232
<211> LENGTH: 124
<212> TYPE: PRT
<213> ORGANISM: Artificial sequence
<220> FEATURE:
<223> OTHER INFORMATION: Synthetic amino acid sequence

<400> SEQUENCE: 232

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Thr Tyr
            20                  25                  30

Ala Val His Trp Val Arg Gln Ala Pro Gly Gln Arg Leu Glu Trp Met
```

```
                35                  40                  45
Gly Trp Ile Asn Pro Gly Asp Gly Asp Thr Arg Tyr Ala Gln Lys Phe
 50                  55                  60

Gln Asp Arg Val Thr Ile Ser Ser Asp Thr Ser Ala Thr Thr Val Tyr
 65                  70                  75                  80

Met Glu Leu Ser Ser Leu Arg Ser Glu Asp Thr Ala Val Tyr Phe Cys
                 85                  90                  95

Ala Arg Pro Arg Ala Ser Leu Leu Arg Tyr Phe Asp Trp Leu Phe Glu
                100                 105                 110

Gln Trp Gly Gln Glu Thr Leu Val Thr Val Ser Ser
            115                 120
```

<210> SEQ ID NO 233
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 233

```
Glu Ile Val Leu Thr Gln Ser Pro Gly Thr Leu Ser Leu Ser Pro Gly
  1               5                  10                  15

Asp Arg Ala Thr Leu Ser Cys Gly Ala Ser Gln Ser Ile His His Asn
             20                  25                  30

Tyr Val Ala Trp Tyr Gln Arg Pro Gly Gln Ala Pro Arg Leu Leu
         35                  40                  45

Ile Phe Gly Ala Ser Ser Arg Ala Thr Gly Ile Pro Asp Arg Phe Thr
 50                  55                  60

Gly Ser Gly Ser Gly Thr Glu Phe Thr Leu Thr Ile Asn Arg Leu Glu
 65                  70                  75                  80

Pro Glu Asp Phe Ala Val Tyr Tyr Cys Gln Gln Tyr Gly Asn Ser Val
                 85                  90                  95

Pro Tyr Ser Phe Gly Gln Gly Thr Lys Val Asp Ile Lys
                100                 105
```

<210> SEQ ID NO 234
<211> LENGTH: 116
<212> TYPE: PRT
<213> ORGANISM: Artificial sequence
<220> FEATURE:
<223> OTHER INFORMATION: Synthetic amino acid sequence

<400> SEQUENCE: 234

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Thr Asn Tyr
             20                  25                  30

Tyr Trp Ser Trp Ile Arg Gln Phe Pro Gly Lys Gly Leu Glu Tyr Ile
         35                  40                  45

Gly Glu Ile Asp His Ser Gly Ser Ala Asn Tyr Asn Pro Ser Leu Lys
 50                  55                  60

Ser Arg Val Thr Ile Ser Leu Asp Thr Ser Lys Asn Gln Phe Ser Leu
 65                  70                  75                  80

Arg Leu Ser Ser Val Thr Ala Ala Asp Thr Ala Val Tyr Phe Cys Ala
                 85                  90                  95

Arg Asp Val Tyr Gly Ser Gly Thr Tyr Tyr Trp Phe Asp Pro Trp Gly
                100                 105                 110
```

Gln Gly Thr Leu
        115

<210> SEQ ID NO 235
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 235

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Arg Ile Ser Ser His
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Ser Tyr Thr Thr Pro Tyr
                85                  90                  95

Thr Phe Gly Gln Gly Thr Asn Leu Gln Met Lys
            100                 105

<210> SEQ ID NO 236
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 236

Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Thr Arg
            20                  25                  30

Thr Trp Trp Thr Trp Val Arg Gln Pro Pro Gly Lys Gly Leu Glu Trp
        35                  40                  45

Ile Gly Glu Ile Tyr Gln Ser Gly Ser Thr Asn Tyr Asn Pro Ser Leu
    50                  55                  60

Lys Ser Arg Val Thr Ile Ser Ile Asp Thr Ser Lys Asn Gln Phe Ser
65                  70                  75                  80

Leu Lys Leu Ser Ser Val Thr Ala Ala Asp Thr Ala Leu Tyr Tyr Cys
                85                  90                  95

Ala Arg Ser Gly Arg Tyr Ser Ser Val Thr Pro Phe Asp Tyr Trp Gly
            100                 105                 110

Gln Gly Thr Leu Val Thr
        115

<210> SEQ ID NO 237
<211> LENGTH: 106
<212> TYPE: PRT
<213> ORGANISM: Artificial sequence
<220> FEATURE:
<223> OTHER INFORMATION: Synthetic amino acid sequence

<400> SEQUENCE: 237

Glu Ile Val Leu Thr Gln Ser Pro Ala Thr Leu Val Phe Val Ser Gly

```
                1               5                  10                 15
            Gln Arg Ala Thr Leu Ser Cys Arg Ala Ser Gln Ser Ile Gly Asn Tyr
                            20                  25                 30

Leu Ala Trp Tyr Gln Gln Lys Pro Gly Gln Ala Pro Arg Leu Leu Ile
                        35                  40                  45

Tyr Asp Ala Ser Asn Arg Ala Thr Gly Ile Pro Ala Arg Phe Ser Gly
                50                  55                  60

Ser Gly Ser Gly Thr Asp Phe Thr Leu Thr Ile Ser Ser Leu Glu Pro
            65                  70                  75                  80

Glu Asp Phe Ala Val Tyr Tyr Cys Gln Gln Arg Ser His Trp Pro Ala
                            85                  90                  95

Phe Gly Pro Gly Thr Lys Val Asp Ile Lys
                        100                 105

<210> SEQ ID NO 238
<211> LENGTH: 127
<212> TYPE: PRT
<213> ORGANISM: Artificial sequence
<220> FEATURE:
<223> OTHER INFORMATION: Synthetic amino acid sequence

<400> SEQUENCE: 238

Gln Val Gln Leu Val Glu Ser Gly Gly Gly Val Val Gln Pro Gly Arg
            1               5                  10                  15

Ser Leu Lys Ile Ser Cys Ala Ala Ser Gly Phe Thr Phe Ser Asp Ser
                            20                  25                  30

Gly Leu His Trp Val Arg Gln Ala Pro Gly Lys Gly Leu Glu Cys Val
                        35                  40                  45

Ala Phe Ile Trp Tyr Asp Gly Ser Thr Lys Tyr Tyr Ala Asp Ser Val
                50                  55                  60

Lys Gly Arg Phe Thr Ile Ser Arg Asp Asn Ser Arg Asn Thr Leu Tyr
            65                  70                  75                  80

Leu Gln Met Lys Ser Leu Arg Ala Glu Asp Thr Ala Val Tyr Tyr Cys
                            85                  90                  95

Ala Arg Glu Leu Gly Tyr Cys Ser Gly Gly Thr Cys Tyr Ser Met Gly
                        100                 105                 110

Ala Phe Asp Ile Trp Gly Gln Gly Thr Leu Val Thr Val Ser Gln
                    115                 120                 125

<210> SEQ ID NO 239
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 239

Gln Ser Val Leu Thr Gln Pro Ala Ser Val Ser Gly Ser Pro Gly Gln
            1               5                  10                  15

Ser Ile Thr Ile Ser Cys Thr Gly Thr Ser Ser Asp Val Gly Ser Tyr
                            20                  25                  30

Asn Leu Val Ser Trp Tyr Gln Gln His Pro Gly Lys Ala Pro Lys Leu
                        35                  40                  45

Met Ile Tyr Glu Val Ser Lys Arg Pro Ser Gly Val Ser Asn Arg Phe
                50                  55                  60

Ser Gly Ser Lys Ser Asp Asn Thr Ala Ser Leu Thr Ile Ser Gly Leu
            65                  70                  75                  80
```

```
Gln Ala Glu Asp Glu Ala Asp Tyr Tyr Cys Ser Tyr Val Gly Ser
                85                  90                  95

Ser Thr Ser Val Phe Gly Gly Gly Thr Gln Val Thr Val Leu
            100                 105                 110

<210> SEQ ID NO 240
<211> LENGTH: 106
<212> TYPE: PRT
<213> ORGANISM: Artificial sequence
<220> FEATURE:
<223> OTHER INFORMATION: Synthetic amino acid sequence

<400> SEQUENCE: 240

Glu Val Gln Leu Val Glu Ser Gly Gly Gly Leu Val Lys Pro Gly Gly
1               5                   10                  15

Ser Leu Arg Leu Ser Cys Ala Ala Ser Ser Phe Ile Phe Ser Asp Ala
            20                  25                  30

Trp Met Lys Trp Val Arg Gln Ala Pro Gly Lys Gly Leu Glu Trp Val
        35                  40                  45

Gly His Phe Lys Thr Lys Thr Asp Gly Gly Thr Thr Asp Tyr Ala Ala
    50                  55                  60

Pro Val Lys Gly Arg Phe Ser Ile Ser Arg Asp Asp Ser Lys Ser Thr
65                  70                  75                  80

Leu His Val Gln Met Asn Ser Leu Lys Thr Glu Asp Thr Ala Val Tyr
                85                  90                  95

Tyr Cys Thr Thr Ala Gly Ala Ser Tyr Val
            100                 105

<210> SEQ ID NO 241
<211> LENGTH: 89
<212> TYPE: PRT
<213> ORGANISM: Artificial sequence
<220> FEATURE:
<223> OTHER INFORMATION: Synthetic amino acid sequence

<400> SEQUENCE: 241

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Thr
            20                  25                  30

Tyr Leu Ala Trp Tyr Gln Gln Lys Pro Gly Gln Ala Pro Arg Leu Leu
        35                  40                  45

Ile Tyr Ala Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys
                85

<210> SEQ ID NO 242
<211> LENGTH: 125
<212> TYPE: PRT
<213> ORGANISM: Artificial sequence
<220> FEATURE:
<223> OTHER INFORMATION: Synthetic amino acid sequence

<400> SEQUENCE: 242

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Lys Tyr
```

```
                 20                  25                  30
Thr Ile His Trp Val Arg Gln Ala Pro Gly Gln Arg Leu Glu Trp Val
             35                  40                  45

Gly Gly Ile Tyr Ala Gly Tyr Gly Asn Thr Arg Tyr Ser Gln Lys Phe
         50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Phe Glu Asp Phe Asp Ser Trp Thr Gly Tyr Tyr Ser Trp
            100                 105                 110

Leu His Trp Gly Gln Gly Thr Leu Val Thr Val Ser Ser
            115                 120                 125

<210> SEQ ID NO 243
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 243

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
             20                  25                  30

Tyr Leu Ala Trp Tyr Gln Gln Lys Pro Gly Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Thr Arg Leu Glu
 65                  70                  75                  80

Pro Glu Asp Phe Ala Met Tyr Phe Cys Gln Gln Tyr Asp Ser Ser Pro
                 85                  90                  95

Ser Ile Thr Phe Gly Gln Gly Thr Arg Leu Glu Ile Lys
            100                 105

<210> SEQ ID NO 244
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 244

Gln Val Gln Leu Gln Gln Trp Gly Ala Gly Leu Leu Lys Pro Ser Glu
 1               5                  10                  15

Thr Leu Ser Leu Thr Cys Ala Val His Gly Gly Ser Phe Ser Gly Tyr
             20                  25                  30

Phe Trp Ser Trp Ile Arg Gln Pro Pro Gly Lys Gly Leu Glu Trp Ile
         35                  40                  45

Gly Glu Met Asn His Ser Gly Ser Thr Asn Tyr Asn Pro Ser Leu Lys
     50                  55                  60

Ser Arg Val Thr Ile Ser Val Asp Thr Ser Lys Lys Gln Phe Ser Leu
 65                  70                  75                  80

Lys Leu Asn Ser Val Thr Ala Ala Asp Thr Ala Val Tyr Tyr Cys Ala
                 85                  90                  95
```

Arg Thr Ala Arg Thr Val Arg Tyr Phe Glu Asn Trp Gly Gln Gly Thr
            100                 105                 110

Leu Val Thr Val Ser Ser
        115

<210> SEQ ID NO 245
<211> LENGTH: 113
<212> TYPE: PRT
<213> ORGANISM: Artificial sequence
<220> FEATURE:
<223> OTHER INFORMATION: Synthetic amino acid sequence

<400> SEQUENCE: 245

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Asn
            20                  25                  30

Ser Asn Asn Tyr Ser Tyr Leu Thr Trp Tyr Gln Gln Lys Pro Gly Gln
        35                  40                  45

Pro Pro Arg Val Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asn Val Ala Leu Tyr Tyr Cys Gln Gln
                85                  90                  95

Tyr Tyr Ser Thr Pro Trp Thr Phe Gly Gln Gly Thr Lys Val Asp Ile
            100                 105                 110

Lys

<210> SEQ ID NO 246
<211> LENGTH: 127
<212> TYPE: PRT
<213> ORGANISM: Artificial sequence
<220> FEATURE:
<223> OTHER INFORMATION: Synthetic amino acid sequence

<400> SEQUENCE: 246

Gln Val Gln Leu Val Glu Ser Gly Gly Gly Leu Val Lys Pro Gly Gly
1               5                   10                  15

Ser Leu Lys Ile Ser Cys Ala Ala Asn Arg Phe Thr Phe Ser Asn Tyr
            20                  25                  30

Tyr Met Ser Trp Ile Arg Gln Gly Pro Gly Lys Glu Pro Glu Trp Ile
        35                  40                  45

Ser Tyr Ile Ser Ser Arg Ser Arg Tyr Thr Asn Tyr Ala Asp Ser Val
    50                  55                  60

Lys Gly Arg Phe Thr Ile Ser Arg Asp Asn Thr Lys Asn Ser Leu Phe
65                  70                  75                  80

Leu Gln Met Asn Asp Leu Arg Ala Glu Asp Thr Ala Val Tyr Tyr Cys
                85                  90                  95

Ala Arg Gly Gly Gly Tyr Cys Gly Gly Thr Thr Cys Ser Met Gly His
            100                 105                 110

Ala Phe Asp Ile Trp Gly Gln Gly Thr Val Val Thr Val Ser Ser
        115                 120                 125

<210> SEQ ID NO 247
<211> LENGTH: 97
<212> TYPE: PRT
<213> ORGANISM: Artificial sequence
<220> FEATURE:

-continued

<223> OTHER INFORMATION: Synthetic amino acid sequence

<400> SEQUENCE: 247

```
Glu Val Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ile Arg Ser Thr Asp Ile Pro Asp Arg Phe Ser
    50                  55                  60

Gly Ser Glu Ser Gly Thr Asp Phe Thr Tyr Thr Ile Ser Arg Pro Glu
65                  70                  75                  80

His Glu Asp Phe Ala Leu Tyr Phe Cys Gln Gln Tyr Gly Ser Ser Pro
                85                  90                  95

Tyr
```

<210> SEQ ID NO 248
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 248

```
Gln Val Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Thr Pro Ser Leu
    50                  55                  60

Lys Ser Arg Val Thr Ile Ser Leu Asp Lys Ser Lys Asn Gln Phe Ser
65                  70                  75                  80

Leu Lys Leu Ser Ser Val Thr Ala Ala Asp Thr Ala Met Tyr Tyr Cys
                85                  90                  95

Ala Arg Asn Phe Tyr Pro Gly Tyr Leu Gln Tyr Trp Gly Gln Gly Thr
            100                 105                 110

Leu Val Thr Val Ser Ser
        115
```

<210> SEQ ID NO 249
<211> LENGTH: 73
<212> TYPE: PRT
<213> ORGANISM: Artificial sequence
<220> FEATURE:
<223> OTHER INFORMATION: Synthetic amino acid sequence

<400> SEQUENCE: 249

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ile Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Lys Arg Pro Ser Gly Val Ser Asn Arg Phe
    50                  55                  60
```

```
Ser Gly Ser Lys Ser Gly Asn Thr Val
 65                 70
```

<210> SEQ ID NO 250
<211> LENGTH: 123
<212> TYPE: PRT
<213> ORGANISM: Artificial sequence
<220> FEATURE:
<223> OTHER INFORMATION: Synthetic amino acid sequence

<400> SEQUENCE: 250

```
Gln Val Gln Leu Val Glu Ser Gly Gly Gly Val Val Gln Pro Gly Glu
  1               5                  10                  15

Ser Leu Lys Ile Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ile Asn Lys Tyr Tyr Ala Asp Ser Val
     50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                 85                  90                  95

Ala Lys Glu Ala Gly Gly Gly Asp Cys Tyr Ser Asn Tyr Phe His Tyr
            100                 105                 110

Trp Gly Gln Gly Thr Leu Val Thr Val Ser Ser
        115                 120
```

<210> SEQ ID NO 251

<400> SEQUENCE: 251

000

<210> SEQ ID NO 252
<211> LENGTH: 123
<212> TYPE: PRT
<213> ORGANISM: Artificial sequence
<220> FEATURE:
<223> OTHER INFORMATION: Synthetic amino acid sequence

<400> SEQUENCE: 252

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Asn Ser
             20                  25                  30

Gly Met His Trp Val Arg Gln Ala Pro Gly Lys Gly Leu Glu Trp Val
         35                  40                  45

Ala Val Ile Trp Phe Asp Gly Thr Asn Lys Tyr Tyr Ala Asp Ser Val
     50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                 85                  90                  95

Ala Arg Val Pro Cys Gly Gly Asp Cys Tyr Ser Gly Tyr Leu Gln His
            100                 105                 110

Trp Gly Gln Gly Thr Leu Val Thr Val Ser Ser
        115                 120
```

```
<210> SEQ ID NO 253
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 253

Ala Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Thr
            20                  25                  30

Leu Ala Trp Tyr Gln Gln Lys Pro Gly Gln Ala Pro Arg Leu Leu Ile
        35                  40                  45

Tyr Gly Ala Ser Thr Lys Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Asn Asn Trp Pro Pro
                85                  90                  95

Leu Leu Thr Phe Gly Gly Gly Thr Lys Val Asp Ile Lys
            100                 105

<210> SEQ ID NO 254
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 254

Glu Val Gln Leu Val Glu Ser Gly Gly Gly Leu Val Gln Pro Gly Glu
1               5                   10                  15

Ser Leu Lys Ile Ser Cys Ala Ala Thr Gly Phe Thr Phe Ser Ser Tyr
            20                  25                  30

Trp Met His Trp Val Arg Gln Ala Pro Gly Lys Gly Leu Val Trp Val
        35                  40                  45

Ser Gly Ile Asn Ser Asp Gly Ser Ser Thr Ser Tyr Ala Asp Ser Val
50                  55                  60

Lys Gly Arg Phe Thr Ile Ala Arg Asp Asn Ala Lys Gly Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ala Val Arg Ile Ala Ala Ala Pro Asp Tyr Trp
            100                 105                 110

Gly Gln Gly Thr Leu Val Thr Val Ser Ser
        115                 120

<210> SEQ ID NO 255
<211> LENGTH: 113
<212> TYPE: PRT
<213> ORGANISM: Artificial sequence
<220> FEATURE:
<223> OTHER INFORMATION: Synthetic amino acid sequence

<400> SEQUENCE: 255

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
```

```
                    20                  25                  30
Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Asp Ile
            100                 105                 110

Lys

<210> SEQ ID NO 256
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 256

Gln Val Gln Leu Gln Gln Trp Gly Ala Gly Leu Leu Lys Pro Ser Glu
1               5                   10                  15

Thr Leu Ser Leu Thr Cys Ala Ile Tyr Gly Gly Ser Leu Ser Gly Gln
            20                  25                  30

Tyr Trp Ser Trp Ile Arg Gln Pro Pro Gly Arg Gly Leu Glu Trp Ile
            35                  40                  45

Gly Glu Ile His His Lys Gly Arg Thr Asn Tyr Asn Pro Ser Leu Lys
    50                  55                  60

Ser Arg Val Thr Ile Ser Ile Asp Thr Ser Gln Arg Gln Phe Ser Leu
65                  70                  75                  80

Arg Leu Thr Ser Val Ser Ala Ala Asp Thr Ala Val Tyr Tyr Cys Ala
                85                  90                  95

Ser Gly Asn Tyr Arg Leu Gly Gln Gly Thr Leu Val Thr Phe
            100                 105                 110

<210> SEQ ID NO 257
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 257

Asp Val Val Leu Thr Gln Ser Pro Leu Thr Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asp Thr Tyr Leu Asn Trp Phe Gln Gln Arg Pro Gly Gln Ala
            35                  40                  45

Pro Arg Arg Leu Ile Tyr Lys Val Ser Lys Arg Asp Phe Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Met Gln Gly
                85                  90                  95

Thr His Trp Pro Arg Thr Phe Gly Gln Gly Thr Gln Val Asp Ile Lys
```

<210> SEQ ID NO 258
<211> LENGTH: 127
<212> TYPE: PRT
<213> ORGANISM: Artificial sequence
<220> FEATURE:
<223> OTHER INFORMATION: Synthetic amino acid sequence

<400> SEQUENCE: 258

Gln Leu Gln Leu Gln Glu Ser Gly Pro Gly Leu Val Lys Pro Ser Glu
1               5                   10                  15

Thr Leu Ser Leu Ser Cys Thr Val Ser Gly Gly Ser Ile Asn Ser Arg
            20                  25                  30

Thr Tyr Tyr Trp Gly Trp Ile Arg Gln Pro Pro Gly Lys Gly Pro Glu
        35                  40                  45

Trp Ile Gly Thr Val Phe His Asn Val Ser Thr Leu Tyr Thr Ser Ser
    50                  55                  60

Leu Arg Ser Arg Val Thr Ile Ser Val Asp Thr Ser Lys Asn Arg Phe
65                  70                  75                  80

Ser Leu Lys Leu Thr Ser Val Thr Ala Ala Asp Thr Ala Val Tyr Phe
                85                  90                  95

Cys Gly Arg Leu Thr Pro Arg Asn Leu Phe Arg Gly Thr Leu Val Arg
            100                 105                 110

Trp Val Asp Pro Trp Gly Gln Gly Ile Leu Val Thr Val Ser Ser
        115                 120                 125

<210> SEQ ID NO 259
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 259

Glu Ile Val Leu Ala Gln Ser Pro Gly Thr Leu Ser Leu Ser Pro Gly
1               5                   10                  15

Glu Arg Ala Thr Leu Ser Cys Arg Ala Ser His Asn Leu Asn Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Thr
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Gly Ser Leu
                85                  90                  95

Thr Phe Gly Gly Gly Thr Lys Val Asp Ile Lys
            100                 105

<210> SEQ ID NO 260
<211> LENGTH: 126
<212> TYPE: PRT
<213> ORGANISM: Artificial sequence
<220> FEATURE:
<223> OTHER INFORMATION: Synthetic amino acid sequence

<400> SEQUENCE: 260

Gln Val Gln Leu Gln Gln Ser Gly Pro Gly Leu Val Lys Pro Ser Gln
1               5                   10                  15

```
Thr Leu Ser Leu Thr Cys Ala Ile Ser Gly Asp Ser Val Ser Ser Asn
            20                  25                  30

Ser Ala Ala Trp Ile Trp Ile Arg Gln Ser Pro Ser Arg Gly Leu Glu
        35                  40                  45

Trp Leu Gly Thr Thr Tyr Tyr Arg Ser Glu Trp Tyr Ser Asp Tyr Pro
    50                  55                  60

Ala Ser Val Lys Ser Arg Val Thr Ile Asn Ala Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ile Thr Val Gly Tyr Asn Ser Pro His Leu Arg
            100                 105                 110

Val Thr Arg Gly Trp Leu Asp Pro Trp Gly Pro Gly Asn Pro
        115                 120                 125

<210> SEQ ID NO 261
<211> LENGTH: 113
<212> TYPE: PRT
<213> ORGANISM: Artificial sequence
<220> FEATURE:
<223> OTHER INFORMATION: Synthetic amino acid sequence

<400> SEQUENCE: 261

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Ile Ala Trp Tyr Gln Gln Lys Pro Gly Gln
        35                  40                  45

Ala Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asn Phe Thr Leu Ala
65                  70                  75                  80

Ile Ser Ser Leu Gln Ala Glu Asp Val Ala Val Tyr Tyr Cys Gln Gln
                85                  90                  95

Tyr Tyr Ser Ser Pro Leu Thr Phe Gly Gly Gly Thr Lys Val Asp Ile
            100                 105                 110

Lys

<210> SEQ ID NO 262
<211> LENGTH: 98
<212> TYPE: PRT
<213> ORGANISM: Artificial sequence
<220> FEATURE:
<223> OTHER INFORMATION: Synthetic amino acid sequence

<400> SEQUENCE: 262

Gln Val Gln Leu Val Glu Ser Gly Gly Gly Val Val Gln Pro Gly Arg
1               5                   10                  15

Ser Leu Lys Ile Ser Cys Ala Ala Ser Gly Phe Thr Phe Ser Thr Tyr
            20                  25                  30

Thr Met His Trp Val Arg Gln Ala Pro Gly Lys Gly Leu Glu Trp Val
        35                  40                  45

Ala Thr Ile Ser Tyr Asp Gly Ile Asn Glu Tyr Tyr Ala Asp Ser Val
    50                  55                  60

Lys Gly Arg Phe Thr Ile Phe Arg Asp Asn Ser Lys Asn Met Leu Tyr
65                  70                  75                  80
```

-continued

Leu Gln Met Asn Ser Leu Arg Pro Glu Asp Thr Ala Met Phe Tyr Cys
                85                  90                  95

Ala Arg

<210> SEQ ID NO 263
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 263

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ile Asn
                20                  25                  30

Tyr Val His Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Lys Val Phe Gly Gly Gly Thr Gln Val Thr Val Leu
                100                 105                 110

<210> SEQ ID NO 264
<211> LENGTH: 114
<212> TYPE: PRT
<213> ORGANISM: Artificial sequence
<220> FEATURE:
<223> OTHER INFORMATION: Synthetic amino acid sequence

<400> SEQUENCE: 264

Gln Val Gln Leu Val Glu Ser Gly Gly Gly Val Val Gln Pro Gly Arg
1               5                   10                  15

Ser Leu Lys Ile Ser Cys Val Ala Ser Gly Phe Thr Phe Ser Ser Tyr
                20                  25                  30

Ala Ile His Trp Val Arg Gln Ala Pro Gly Lys Gly Leu Glu Trp Val
            35                  40                  45

Ala Phe Ile Ser Asn Asp Gly Ser Ser Lys Lys Leu Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Arg Gly Tyr Phe Gly His Trp Gly Gln Gly Thr Leu
                100                 105                 110

Val Thr

<210> SEQ ID NO 265

<400> SEQUENCE: 265

000

<210> SEQ ID NO 266

```
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 266

Gln Val Gln Leu Val Gln Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Tyr Ile
        35                  40                  45

Gly His Ile Tyr Tyr Ser Gly Thr Lys Tyr Asn Pro Ser Leu Arg
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Leu Ala Gly Arg Lys Pro Asp Ala Asp Ser Trp Gly Gln Gly Thr
            100                 105                 110

Leu Val Thr Val Ser Ser
            115

<210> SEQ ID NO 267
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 267

Gln Pro Val Leu Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Phe Phe Pro Asn Trp Leu Gln Gln Lys Pro Gly Gln Ala Pro Arg Ala
        35                  40                  45

Leu Ile Tyr Ser Thr Asn Asn Lys His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Tyr Tyr Gly Gly
                85                  90                  95

Val Val Val Phe Gly Gly Gly Thr Lys Leu Thr Val Leu
            100                 105

<210> SEQ ID NO 268
<211> LENGTH: 123
<212> TYPE: PRT
<213> ORGANISM: Artificial sequence
<220> FEATURE:
<223> OTHER INFORMATION: Synthetic amino acid sequence

<400> SEQUENCE: 268

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Ile Phe Ser Asn Tyr
            20                  25                  30
```

Ala Met Gly Trp Val Arg Gln Ala Pro Gly Lys Gly Leu Glu Trp Val
            35                  40                  45

Ser Ala Leu Ser Ala Ser Asp Gly Val Thr Ser Tyr Ala Asp Ser Val
 50                  55                  60

Lys Gly Arg Phe Thr Ile Ser Arg Asp Asn Ser Lys Asn Thr Met Tyr
 65                  70                  75                  80

Leu Gln Met Asn Arg Leu Arg Thr Glu Asp Thr Ala Ile Tyr Phe Cys
                 85                  90                  95

Ala Lys Gly Arg Ala Arg Val Asn Asn Ile Tyr Arg Tyr Phe Asp His
            100                 105                 110

Trp Gly Gln Gly Thr Leu Val Thr Val Ser Ser
            115                 120

<210> SEQ ID NO 269
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 269

Gln Ser Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ala Tyr
             20                  25                  30

Thr Phe Val Ser Trp Tyr Gln His Pro Gly Lys Ala Pro Lys Leu
            35                  40                  45

Ile Ile Tyr Glu Val Ser Asn Arg Pro Ser Gly Val Ser Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Asn Ser Tyr Thr Thr Thr
                 85                  90                  95

Ser Pro Trp Val Phe Gly Gly Gly Thr Gln Leu Thr Val Leu
            100                 105                 110

<210> SEQ ID NO 270
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 270

Glu Val Gln Leu Leu Glu Ser Gly Gly Gly Leu Val Gln Pro Gly Glu
 1               5                  10                  15

Ser Leu Lys Ile Ser Cys Ala Val Ser Gly Phe Ser Phe Lys Ser Tyr
             20                  25                  30

Ala Met Ser Trp Val Arg Gln Ala Pro Gly Lys Gly Leu Glu Trp Val
            35                  40                  45

Ser Thr Ile Gly Val Ser Gly Ala Ser Thr Tyr Phe Ala Asp Pro Val
 50                  55                  60

Lys Gly Arg Phe Thr Ile Ser Arg Asp Asn Ser Lys Asp Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Thr Tyr Tyr Tyr Asp Ser Arg Ile Trp Tyr Phe Gly Leu
            100                 105                 110

Trp Gly Arg Gly Thr
            115

<210> SEQ ID NO 271

<400> SEQUENCE: 271

000

<210> SEQ ID NO 272
<211> LENGTH: 126
<212> TYPE: PRT
<213> ORGANISM: Artificial sequence
<220> FEATURE:
<223> OTHER INFORMATION: Synthetic amino acid sequence

<400> SEQUENCE: 272

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Val Ile Ser Trp Val Arg Gln Ala Pro Gly Gln Gly Pro Glu Trp Met
            35                  40                  45

Gly Arg Ile Ile Val Met Leu Gly Val Thr Asn Tyr Ala Gln Lys Phe
        50                  55                  60

Gln Gly Arg Val Ser Ile Thr Ala Asp Lys Ser Thr Asn Thr Ala Tyr
65                  70                  75                  80

Met Glu Leu Asn Ser Leu Arg Ser Glu Asp Thr Ala Val Tyr Tyr Cys
                85                  90                  95

Ala Arg Ala Val Ile Thr Met Val Arg Gly Asp Ile Pro Leu Gly Trp
            100                 105                 110

Phe Asp Pro Trp Gly Gln Gly Thr Leu Val Thr Val Ser Ser
            115                 120                 125

<210> SEQ ID NO 273
<211> LENGTH: 100
<212> TYPE: PRT
<213> ORGANISM: Artificial sequence
<220> FEATURE:
<223> OTHER INFORMATION: Synthetic amino acid sequence

<400> SEQUENCE: 273

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Asn
            20                  25                  30

Tyr Leu Ala Trp Tyr Gln Gln Lys Pro Gly Gln Ala Pro Arg Leu Leu
            35                  40                  45

Phe Tyr Gly Ala Ser Ser Arg Ala Thr Gly Ile Pro Asp Arg Phe Ser
        50                  55                  60

Gly Ser Gly Ser Ala Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Thr Ser Ala
            100

<210> SEQ ID NO 274
<211> LENGTH: 123

```
<212> TYPE: PRT
<213> ORGANISM: Artificial sequence
<220> FEATURE:
<223> OTHER INFORMATION: Synthetic amino acid sequence

<400> SEQUENCE: 274

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Ile Asn Thr Gly
            20                  25                  30

Gly Gln Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ala
    50                  55                  60

Leu Arg Ser Arg Leu Thr Ile Thr Lys Gly Thr Ser Lys Asn Gln Val
65                  70                  75                  80

Val Leu Thr Met Thr Lys Met Asp Pro Val Asp Thr Ala Thr Tyr Tyr
                85                  90                  95

Cys Ala His Arg Ser Val Ala Gly Arg Arg Asp Leu Ala Phe Asp Ile
            100                 105                 110

Trp Gly Gln Gly Thr Leu Val Thr Val Ser Ser
        115                 120

<210> SEQ ID NO 275
<211> LENGTH: 105
<212> TYPE: PRT
<213> ORGANISM: Artificial sequence
<220> FEATURE:
<223> OTHER INFORMATION: Synthetic amino acid sequence

<400> SEQUENCE: 275

Gln Ser Val Leu Thr Gln Pro Ala Ser Val Ser Gly Ser Pro Gly Gln
1               5                   10                  15

Ser Ile Thr Ile Ser Cys Thr Gly Thr Thr Ser Asp Ile Gly Thr Tyr
            20                  25                  30

Asp Tyr Val Ser Trp Tyr Gln Gln His Pro Gly Arg Ala Pro Lys Leu
        35                  40                  45

Met Ile Tyr Asp Val Ser Lys Arg Pro Ser Gly Val Ser Gly Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ser His Tyr Tyr Leu Gln Leu His Ile Pro Ser
                85                  90                  95

Gly Leu Thr Trp Val Phe Gly Gly Gly
            100                 105

<210> SEQ ID NO 276
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 276

Glu Val Gln Leu Val Glu Ser Gly Gly Gly Leu Val Lys Pro Gly Glu
1               5                   10                  15

Ser Leu Lys Ile Ser Cys Ala Ala Ser Gly Phe Ser Phe Asn Asn Ala
            20                  25                  30

Trp Met Asn Trp Val Arg Gln Ala Pro Gly Lys Gly Leu Glu Trp Val
```

```
                35                  40                  45
Gly Arg Ile Lys Thr His Ala Asp Gly Gly Thr Thr Asp Tyr Ala Ala
        50                  55                  60

Pro Val Thr Gly Arg Phe Thr Ile Ser Arg Asp Asp Ser Lys Asn Thr
65                  70                  75                  80

Leu Ser Leu Gln Met Ser Ser Leu Lys Thr Glu Asp Thr Ala Val Tyr
                85                  90                  95

Tyr Cys Thr Thr Ser Phe Thr Phe Pro Arg Arg Ile Phe Ala Tyr Trp
            100                 105                 110

Gly Gln Gly Thr Leu Val
            115

<210> SEQ ID NO 277
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 277

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Leu Ala Val Tyr Tyr Cys Gln Leu Arg Asn Ser Trp Pro Pro
                85                  90                  95

Thr Phe Gly Pro Gly Thr Lys Val Asp Ile Lys
            100                 105

<210> SEQ ID NO 278
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 278

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Arg Ser Asn
            20                  25                  30

Gly Ile Ser Trp Val Arg Gln Ala Pro Gly Gln Gly Phe Glu Trp Leu
        35                  40                  45

Gly Trp Ile Ala Ala Tyr Asn Gly Asp Thr Lys Tyr Val Gln Lys Phe
    50                  55                  60

Gln Gly Arg Leu Thr Met Thr Thr Asp Thr Ser Thr Asp Thr Ala Tyr
65                  70                  75                  80

Met Glu Leu Trp Ser Leu Arg Ser Asp Thr Ala Val Tyr Tyr Cys
                85                  90                  95

Ala Arg Asp Pro Lys Leu Gly Arg Gly Ser Ala Phe Asp Ile Trp
            100                 105                 110
```

```
Gly Gln Gly Thr Leu Val Ile Val Ser Ser
        115                 120
```

<210> SEQ ID NO 279
<211> LENGTH: 106
<212> TYPE: PRT
<213> ORGANISM: Artificial sequence
<220> FEATURE:
<223> OTHER INFORMATION: Synthetic amino acid sequence

<400> SEQUENCE: 279

```
Glu Ile Val Leu Thr Gln Ser Pro Ala Thr Leu Ser Leu Ser Pro Gly
1               5                   10                  15

Gly Arg Ala Thr Leu Ser Cys Arg Ala Ser Gln Ser Val Gly Asn Tyr
            20                  25                  30

Leu Thr Trp Tyr Gln Gln Lys Pro Gly Gln Ala Pro Arg Leu Leu Ile
        35                  40                  45

Phe Asp Gly Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Leu Gln Arg Ser Asp Leu Tyr Thr
                85                  90                  95

Phe Gly Gln Gly Thr Lys Val Asp Ile Lys
            100                 105
```

<210> SEQ ID NO 280
<211> LENGTH: 124
<212> TYPE: PRT
<213> ORGANISM: Artificial sequence
<220> FEATURE:
<223> OTHER INFORMATION: Synthetic amino acid sequence

<400> SEQUENCE: 280

```
Glu Val Gln Leu Leu Glu Ser Gly Gly Leu Val Gln Pro Gly Glu
1               5                   10                  15

Ser Leu Lys Ile Ser Cys Val Gly Ser Glu Phe Thr Phe Ser Ser Tyr
            20                  25                  30

Ala Met Ser Trp Val Arg Gln Pro Pro Gly Lys Gly Leu Glu Trp Val
        35                  40                  45

Ser Gly Ile Ser Asp Ser Gly Arg Leu Tyr Val Ala Asp Ser Val
    50                  55                  60

Lys Gly Arg Phe Thr Val Ser Arg Asp Asn Ser Lys Asn Thr Leu Tyr
65                  70                  75                  80

Leu Glu Met Asn Ser Leu Arg Gly Glu Asp Thr Ala Ile Tyr Tyr Cys
                85                  90                  95

Ala Lys Asp Arg Val Val Gly Ala Thr Tyr Pro Arg Gly Val Phe Asp
            100                 105                 110

Ile Trp Gly Gln Gly Thr Met Val Thr Val Ser Ser
        115                 120
```

<210> SEQ ID NO 281

<400> SEQUENCE: 281

000

<210> SEQ ID NO 282
<211> LENGTH: 120
<212> TYPE: PRT

```
<213> ORGANISM: Artificial sequence
<220> FEATURE:
<223> OTHER INFORMATION: Synthetic amino acid sequence

<400> SEQUENCE: 282

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Gly Tyr Tyr Trp Gly Trp Ile Arg Gln Pro Pro Gly Lys Gly Leu Glu
        35                  40                  45

Trp Ile Ala Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Gln Ser Ser Ser Thr Gly Gly Phe His Tyr Trp Gly Gln
            100                 105                 110

Gly Thr Leu Val Thr Val Ser Ser
        115                 120

<210> SEQ ID NO 283
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 283

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln His Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asn Tyr Tyr Cys Gln Ser Tyr Asp Ser Ser
                85                  90                  95

Leu Ser Gly Arg Glu Val Phe Gly Gly Gly Thr Gln Leu Thr Val Leu
            100                 105                 110

<210> SEQ ID NO 284
<211> LENGTH: 123
<212> TYPE: PRT
<213> ORGANISM: Artificial sequence
<220> FEATURE:
<223> OTHER INFORMATION: Synthetic amino acid sequence

<400> SEQUENCE: 284

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45
```

```
Ser Gly Leu Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Lys Glu Thr Glu Lys Tyr Tyr Tyr Asp Ser Ser Gly Tyr Asp Tyr
            100                 105                 110

Trp Gly Gln Gly Thr Leu Val Thr Val Ser Ser
            115                 120

<210> SEQ ID NO 285
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 285

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ile
                20                  25                  30

Tyr Leu Ala Trp Tyr Gln Gln Lys Pro Gly Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Arg Gly
                85                  90                  95

Thr Phe Gly Gln Gly Thr Lys Leu Glu Ile Lys
            100                 105

<210> SEQ ID NO 286
<211> LENGTH: 116
<212> TYPE: PRT
<213> ORGANISM: Artificial sequence
<220> FEATURE:
<223> OTHER INFORMATION: Synthetic amino acid sequence

<400> SEQUENCE: 286

Gln Val Gln Leu Val Gln Ser Gly Gly Gly Leu Ile Gln Pro Gly Gly
 1               5                  10                  15

Ser Leu Arg Leu Ser Cys Val Val Ser Gly Phe Asn Val Ala Thr Asn
                20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
        50                  55                  60

Gly Arg Phe Thr Ile Ser Arg Asp Asn Ser Lys Asn Thr Val Phe Leu
 65                  70                  75                  80

Gln Met Asn Ser Leu Arg Pro Glu Asp Thr Ala Ala Tyr Tyr Cys Ala
                85                  90                  95

Lys Gly Gly Gly Leu Gly Leu Asp Tyr Trp Gly Gln Gly Thr Leu Val
            100                 105                 110

Thr Val Ser Ser
```

```
<210> SEQ ID NO 287
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 287

Gln Ser Ala Leu Thr Gln Pro Pro Ser Ala Ser Gly Ser Pro Gly Gln
1               5                   10                  15

Ser Val Thr Ile Thr Cys Thr Gly Ser Ser Ser Asp Val Gly Gly Tyr
            20                  25                  30

Asn Tyr Val Ser Trp Tyr Gln Gln His Pro Gly Lys Ala Pro Lys Val
        35                  40                  45

Val Ile Tyr Glu Val Asn Lys Arg Pro Ser Gly Val Pro His Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Thr
                85                  90                  95

Glu Thr Val Ala Phe Gly Gly Gly Thr Lys Leu Thr Val Leu
            100                 105                 110

<210> SEQ ID NO 288
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 288

Gln Val Gln Leu Val Gln Ser Gly Ala Glu Val Lys Lys Pro Gly Ser
1               5                   10                  15

Ser Val Lys Val Ser Cys Lys Ala Ser Gly Gly Arg Phe Ser Thr Gln
            20                  25                  30

His Ile Asn Trp Met Arg Gln Ala Pro Gly His Gly Leu Glu Trp Met
        35                  40                  45

Gly Gly Ile Ile Pro Ile Phe Ala Thr Ala Asp Tyr Ala Gln Lys Phe
    50                  55                  60

Gln Gly Arg Ile Thr Ile Thr Ala Asp Glu Ser Thr Ser Thr Ala Tyr
65                  70                  75                  80

Met Glu Met Ser Ser Leu Arg Ser Glu Asp Thr Ala Ile Tyr Tyr Cys
                85                  90                  95

Gly Val Tyr Asn Ala Asn Trp Gly Gln Gly Thr Leu Val
            100                 105

<210> SEQ ID NO 289
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 289

Asp Ile Gln Met Thr Gln Ser Pro Ser Ser Leu Pro Ala Ser Val Gly
1               5                   10                  15

Asp Arg Val Thr Ile Thr Cys Arg Ala Ser Gln Asp Ile Arg Asn Asn
            20                  25                  30
```

Leu Gly Trp Tyr Gln Gln Lys Pro Gly Lys Ala Pro Glu Arg Leu Ile
            35                  40                  45

Tyr Gly Thr Ser Asn Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Phe Gly Arg Gly Thr Lys Val Glu Ile Lys
            100                 105

<210> SEQ ID NO 290
<211> LENGTH: 115
<212> TYPE: PRT
<213> ORGANISM: Artificial sequence
<220> FEATURE:
<223> OTHER INFORMATION: Synthetic amino acid sequence

<400> SEQUENCE: 290

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ser Met His Trp Val Arg Gln Ala Pro Gly Lys Gly Leu Glu Trp Val
        35                  40                  45

Ala Val Ile Ser Phe Asp Gly Arg Ser Asn Tyr Tyr Ala Asp Ser Val
    50                  55                  60

Arg Gly Arg Phe Thr Ile Ser Arg Asp Asn Ser Lys Lys Thr Met Tyr
65                  70                  75                  80

Leu Gln Met Asn Ser Leu Arg Leu Ala Asp Thr Ala Val Tyr Tyr Cys
                85                  90                  95

Ala Arg Gly Gly Ile Gly Ala Pro Asp Pro Pro Glu Arg Tyr Gly Arg
            100                 105                 110

Leu Gly Pro
        115

<210> SEQ ID NO 291
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 291

Asp Ile Gln Met Ile Gln Ser Pro Ser Ser Leu Ser Ala Ser Val Gly
1               5                   10                  15

Asp Arg Val Thr Ile Ser Cys Gln Ala Thr Gln Asp Ile Ser Asn Ser
            20                  25                  30

Val Asn Trp Tyr Gln Gln Lys Pro Gly Lys Ala Pro Lys Leu Leu Ile
        35                  40                  45

Tyr Asp Ala Ser Thr Leu Glu Thr Gly Val Pro Ser Arg Phe Ser Gly
    50                  55                  60

Gly Gly Ser Gly Thr His Phe Thr Phe Thr Ile Ser Ser Leu Gln Pro
65                  70                  75                  80

Glu Asp Ile Ala Thr Tyr Tyr Cys Gln Gln Phe His Ser Leu Pro Pro
                85                  90                  95

Thr Phe Gly Gln Gly Pro Lys Gly Ile Ser Lys

<210> SEQ ID NO 292
<211> LENGTH: 120
<212> TYPE: PRT
<213> ORGANISM: Artificial sequence
<220> FEATURE:
<223> OTHER INFORMATION: Synthetic amino acid sequence

<400> SEQUENCE: 292

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Gly Ile Ile Trp Val Arg Gln Ala Pro Gly Gln Gly Leu Glu Trp Met
        35                  40                  45

Gly Trp Ile Ser Val Tyr Asn Asp Asn Thr Asn Ser Ala Gln Lys Phe
    50                  55                  60

Gln Asp Arg Val Thr Met Thr Thr Ala Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Ser Ser Gly Pro Arg Tyr Tyr Tyr Gly Met Asp Val
            100                 105                 110

Trp Gly Gln Gly Thr Thr Ser Pro
        115                 120

<210> SEQ ID NO 293
<211> LENGTH: 111
<212> TYPE: PRT
<213> ORGANISM: Artificial sequence
<220> FEATURE:
<223> OTHER INFORMATION: Synthetic amino acid sequence

<400> SEQUENCE: 293

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Ala Val His Trp Tyr Tyr Gln Leu Pro Gly Ile Ala Pro Lys Leu
        35                  40                  45

Leu Ile Phe Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Thr Gln Val Thr Val Leu
            100                 105                 110

<210> SEQ ID NO 294
<211> LENGTH: 123
<212> TYPE: PRT
<213> ORGANISM: Artificial sequence
<220> FEATURE:
<223> OTHER INFORMATION: Synthetic amino acid sequence

<400> SEQUENCE: 294

Glu Val Gln Leu Leu Glu Ser Gly Gly Gly Leu Val Gln Pro Gly Glu
1               5                   10                  15

```
Ser Leu Arg Leu Ser Cys Ala Ala Ser Gly Phe Thr Leu Arg Asn Tyr
            20                  25                  30

Ala Met Ser Trp Val Arg Gln Thr Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Thr Ser Lys Asn Thr Leu Tyr
65                  70                  75                  80

Val Gln Met Asn Ser Leu Arg Ala Glu Asp Thr Ala Val Tyr Tyr Cys
                85                  90                  95

Ala Lys Ile Arg Leu Asp Ser Ser Gly Tyr Ser Gly Ala Phe Asp Ile
            100                 105                 110

Trp Gly Gln Gly Thr Arg Val Thr Val Ser Ser
            115                 120
```

<210> SEQ ID NO 295
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 295

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Ser Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Pro Val Val Phe Gly Gly Gly Thr Gln Leu Thr Val Leu
            100                 105
```

<210> SEQ ID NO 296
<211> LENGTH: 123
<212> TYPE: PRT
<213> ORGANISM: Artificial sequence
<220> FEATURE:
<223> OTHER INFORMATION: Synthetic amino acid sequence

<400> SEQUENCE: 296

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Gly Thr Ala Tyr
65                  70                  75                  80

Met Glu Leu Thr Ser Leu Arg Ser Glu Asp Thr Ala Ile Tyr Tyr Cys
```

```
                85                  90                  95
Ala Arg Ala Ser Glu Gln Trp Leu Ala Ser Ile Asn Trp Phe Asp Pro
            100                 105                 110

Trp Gly Gln Gly Thr Leu Val Thr Val Ser Ser
        115                 120

<210> SEQ ID NO 297
<211> LENGTH: 110
<212> TYPE: PRT
<213> ORGANISM: Artificial sequence
<220> FEATURE:
<223> OTHER INFORMATION: Synthetic amino acid sequence

<400> SEQUENCE: 297

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Ala Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Leu Val Phe Gly Gly Gly Thr Gln Val Thr Val Leu
            100                 105                 110

<210> SEQ ID NO 298
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 298

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Asn Ser Gly Asp Arg Thr Phe Tyr Ala Asp Ser Ala
    50                  55                  60

Lys Gly Arg Phe Thr Ile Phe Arg Asp Asn Ser Asn Asn Arg Leu Tyr
65                  70                  75                  80

Leu Gln Met Asn Ser Leu Arg Ala Ala Asp Thr Ala Val Tyr Tyr Cys
                85                  90                  95

Ala Lys Trp Gly Arg Phe Glu Ser Gly Ala Phe Trp Gly Gln Gly Val
            100                 105                 110

Leu Val Thr Val Ser Ser
        115

<210> SEQ ID NO 299
<211> LENGTH: 108
<212> TYPE: PRT
<213> ORGANISM: Artificial sequence
<220> FEATURE:
```

<223> OTHER INFORMATION: Synthetic amino acid sequence

<400> SEQUENCE: 299

Ser Tyr Glu Leu Thr Gln Ser Pro Ser Val Ser Pro Gly Gln
1               5                   10                  15

Thr Ala Arg Ile Thr Cys Ser Gly Asp Ala Leu Pro Glu Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
50                  55                  60

Gly Ser Gly Thr Thr Val Thr Leu Thr Ile Thr Gly Val Gln Ala Glu
65                  70                  75                  80

Asp Glu Ala Asp Tyr Tyr Cys Gln Ser Ala Asp Asn Ser Gly Thr Tyr
                85                  90                  95

Glu Val Phe Gly Thr Gly Thr Lys Val Thr Val Leu
            100                 105

<210> SEQ ID NO 300
<211> LENGTH: 121
<212> TYPE: PRT
<213> ORGANISM: Artificial sequence
<220> FEATURE:
<223> OTHER INFORMATION: Synthetic amino acid sequence

<400> SEQUENCE: 300

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ile Ser Ser
            20                  25                  30

Ser Tyr Tyr Trp Gly Trp Ile Arg Gln Pro Pro Gly Lys Gly Leu Glu
        35                  40                  45

Trp Leu Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Val Thr Ser Val Thr Ala Ala Asp Thr Ala Val Tyr Tyr
                85                  90                  95

Cys Ala Arg Gln Ile Ser Lys Ala Ala Ala Gly Ser Ile Asp Tyr Trp
            100                 105                 110

Gly Gln Gly Thr Leu Val Thr Val Ser
        115                 120

<210> SEQ ID NO 301
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 301

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Ser

```
                    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                     85                  90                  95

Leu Gln Thr Pro Ile Thr Phe Gly Gln Gly Thr Arg Leu Glu Ile Lys
                 100                 105                 110

<210> SEQ ID NO 302
<211> LENGTH: 119
<212> TYPE: PRT
<213> ORGANISM: Artificial sequence
<220> FEATURE:
<223> OTHER INFORMATION: Synthetic amino acid sequence

<400> SEQUENCE: 302

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Thr Gly Gly Asn Thr Tyr Tyr Ala Asp Ser Val
         50                  55                  60

Lys Gly Arg Phe Thr Ile Ser Arg Asp Lys Ser Lys Asn Thr Leu Tyr
 65                  70                  75                  80

Leu Gln Met His Ser Leu Arg Ala Glu Asp Thr Ala Val Tyr Tyr Cys
                 85                  90                  95

Ala Thr Ser Leu Ile Trp Trp Leu Gln Ser Asp Tyr Trp Gly Gln Gly
                100                 105                 110

Thr Leu Val Thr Val Ser Ser
            115

<210> SEQ ID NO 303
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 303

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ala Ser Tyr
                 20                  25                  30

Leu Ile Trp Tyr Gln Gln Lys Pro Gly Asn Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Gln
                 85                  90                  95

Thr Phe Gly Gln Gly Thr Lys Val Asp Ile Lys
                100                 105

<210> SEQ ID NO 304
<211> LENGTH: 118
```

```
<212> TYPE: PRT
<213> ORGANISM: Artificial sequence
<220> FEATURE:
<223> OTHER INFORMATION: Synthetic amino acid sequence

<400> SEQUENCE: 304

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn His
            20                  25                  30

Trp Ile Ala Trp Val Arg Gln Val Pro Gly Lys Gly Leu Asp Trp Met
        35                  40                  45

Gly Ile Ile Tyr Pro Gly Asp Ser Asp Ile Arg Tyr Ser Pro Ser Phe
    50                  55                  60

Gln Gly Gln Val Thr Ile Ser Ala Asp Asn Ser Ile Asn Thr Ala Tyr
65                  70                  75                  80

Leu Gln Trp Arg Ser Leu Lys Ala Ser Asp Thr Ala Met Tyr Tyr Cys
                85                  90                  95

Ala Arg Ala Met Thr Thr Val Thr Pro Phe Asp Tyr Trp Gly Gln Gly
            100                 105                 110

Thr Leu Val Thr Phe Ser
        115

<210> SEQ ID NO 305
<211> LENGTH: 106
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (83)..(83)
<223> OTHER INFORMATION: Xaa can be any naturally occurring amino acid

<400> SEQUENCE: 305

Ser Tyr Glu Leu Thr Gln Ala Pro Ser Val Ala Val Ser Ser Gly Gln
1               5                   10                  15

Thr Ala Ser Ile Thr Cys Ser Gly Asp Lys Leu Gly Asp Thr Tyr Thr
            20                  25                  30

Phe Trp Tyr Gln Gln Lys Pro Gly Gln Ser Pro Val Val Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Thr Gly Thr Gln Ser Met
65                  70                  75                  80

Asp Glu Xaa Asp Tyr Tyr Cys Gln Ala Trp Asp Ser Ala Thr Val Val
                85                  90                  95

Phe Gly Gly Gly Thr Gln Val Thr Val Leu
            100                 105

<210> SEQ ID NO 306
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 306

Gln Leu Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Ser Arg
            20                  25                  30

Asn Phe Phe Trp Ala Trp Ile Arg Gln Pro Pro Gly Lys Gly Leu Glu
        35                  40                  45

Phe Ile Gly Ser Ile Phe Tyr Ser Gly Gly Thr Tyr Tyr Asn Pro Ser
    50                  55                  60

Leu Lys Ser Arg Leu Ser Ile Ser Val Asp Thr Ser Arg Asn Gln Phe
65              70                  75                  80

Ser Leu Arg Leu Ser Ser Val Thr Ala Ala Asp Thr Ala Val Tyr Tyr
                85                  90                  95

Cys Ala Arg His Met Ile Val Val Leu Pro Gly Val Pro Ile Ser Thr
                100                 105                 110

Ser Phe Asp Pro Trp Gly Gln Gly Thr Leu
            115                 120

<210> SEQ ID NO 307
<211> LENGTH: 115
<212> TYPE: PRT
<213> ORGANISM: Artificial sequence
<220> FEATURE:
<223> OTHER INFORMATION: Synthetic amino acid sequence

<400> SEQUENCE: 307

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ser Asn
            20                  25                  30

Ser Asn Asn Lys Asn Tyr Leu Ala Trp Tyr Gln Gln Lys Pro Gly Gln
        35                  40                  45

Pro Pro Arg Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65              70                  75                  80

Ile Ile Ser Leu Gln Pro Glu Asp Val Ala Val Tyr Tyr Cys Gln Gln
                85                  90                  95

Tyr Tyr Ser Pro Pro Ala Glu Leu Ser Phe Gly Gly Gly Thr Lys Val
                100                 105                 110

Asp Ile Lys
        115

<210> SEQ ID NO 308
<211> LENGTH: 98
<212> TYPE: PRT
<213> ORGANISM: Artificial sequence
<220> FEATURE:
<223> OTHER INFORMATION: Synthetic amino acid sequence

<400> SEQUENCE: 308

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Leu His Trp Val Arg Gln Ala Pro Gly Lys Gly Leu Glu Trp Val
        35                  40                  45

Ala Leu Ile Trp Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65              70                  75                  80
```

```
Leu Gln Met Asn Ser Leu Thr Ala Glu Asp Thr Ala Val Tyr Tyr Cys
                85                  90                  95

Ala Arg
```

<210> SEQ ID NO 309
<211> LENGTH: 86
<212> TYPE: PRT
<213> ORGANISM: Artificial sequence
<220> FEATURE:
<223> OTHER INFORMATION: Synthetic amino acid sequence

<400> SEQUENCE: 309

```
Ser Tyr Glu Leu Thr Gln Pro Pro Ala Val Ser Val Ala Pro Gly Lys
1               5                   10                  15

Thr Ala Arg Ile Thr Cys Gly Gly Asp Asp Ile Gly Phe Lys Gly Val
            20                  25                  30

His Trp Tyr Gln Gln Lys Pro Gly Gln Ala Pro Val Leu Val Val Tyr
        35                  40                  45

Asp Asp Arg Asp Arg Pro Ser Gly Ile Pro Asp Arg Leu Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr
                85
```

<210> SEQ ID NO 310
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 310

```
Glu Val Gln Leu Val Glu Ser Gly Gly Gly Leu Val Gln Pro Gly Glu
1               5                   10                  15

Ser Leu Lys Ile Ser Cys Ser Ala Ser Gly Phe Thr Phe Ser Asp Tyr
            20                  25                  30

Ala Met His Trp Val Arg Gln Ala Pro Gly Gln Gly Leu Gln Tyr Val
        35                  40                  45

Ser Ala Ile Ser Ser Asn Gly His Ser Thr Tyr Tyr Ala Asp Ser Val
    50                  55                  60

Lys Gly Arg Phe Thr Phe Ser Arg Asp Asn Ser Lys Asn Thr Leu Tyr
65                  70                  75                  80

Leu Gln Met Ser Ser Leu Arg Pro Glu Asp Thr Ala Val Tyr Tyr Cys
                85                  90                  95

Val Arg Cys Leu Leu Arg Gly Leu Ile Ser Pro Phe Tyr Trp Gly
            100                 105                 110

Gln Gly Thr Leu Val
        115
```

<210> SEQ ID NO 311
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 311

```
Gln Ser Val Leu Thr Gln Pro Pro Ser Val Ser Glu Ala Pro Arg Gln
```

```
                1               5                  10                  15
            Arg Val Thr Ile Ser Cys Ser Gly Ser Ser Asn Ile Gly Asn Asn
                               20                  25                  30

Ala Val Asn Trp Tyr Gln Gln Leu Pro Gly Lys Ala Pro Lys Leu Leu
                           35                  40                  45

Ile Tyr Tyr Asp Asp Leu Leu Pro Ser Gly Val Ser Asp Arg Phe Ser
                50                  55                  60

Gly Ser Lys Ser Gly Thr Thr Ala Ser Leu Thr Ile Ser Gly Pro Pro
            65                  70                  75                  80

Glu Asp Glu Ala Asp Phe Tyr Cys Ser Thr Trp Asp Tyr Ser Leu Ser
                            85                  90                  95

Ala Arg Val Phe Gly Gly Gly Thr Gln Val Thr Val Leu
                        100                 105
```

<210> SEQ ID NO 312
<211> LENGTH: 120
<212> TYPE: PRT
<213> ORGANISM: Artificial sequence
<220> FEATURE:
<223> OTHER INFORMATION: Synthetic amino acid sequence

<400> SEQUENCE: 312

```
            Gln Val Gln Leu Val Gln Ser Gly Gly Val Val Gln Pro Gly Arg
            1               5                  10                  15

Ser Leu Thr Leu Ser Cys Ser Ala Ser Gly Phe Ile Phe Thr Arg Tyr
                           20                  25                  30

Gly Leu His Trp Val Arg Gln Ala Pro Gly Lys Gly Leu Glu Trp Val
                        35                  40                  45

Ala Val Ile Ser Ser Asp Gly Thr Asn Arg His Tyr Ala Asp Ser Val
                50                  55                  60

Lys Gly Arg Phe Thr Val Ser Arg Asp Asn Ser Lys Ser Thr Leu Tyr
            65                  70                  75                  80

Val Gln Met Asn Ser Leu Arg Asn Glu Asp Thr Ala Val Tyr Tyr Cys
                            85                  90                  95

Ala Arg Leu Ser Leu Glu Ala Ala Trp Tyr Phe Asp Leu Trp Gly Arg
                        100                 105                 110

Gly Thr Leu Val Thr Val Ser Ser
                        115                 120
```

<210> SEQ ID NO 313
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 313

```
            Gln Ser Val Val Thr Gln Pro Pro Ser Val Ser Gly Ala Pro Gly Gln
            1               5                  10                  15

Arg Val Thr Ile Ser Cys Thr Gly Ser Ser Ser Asn Ile Gly Ala Gly
                           20                  25                  30

Tyr Asp Val His Trp Tyr Gln His Leu Pro Gly Thr Ala Pro Lys Val
                        35                  40                  45

Leu Ile Tyr Gly Asn Thr Asn Arg Pro Ser Gly Val Pro Asp Arg Phe
                50                  55                  60

Ser Gly Ser Lys Ser Gly Thr Ser Ala Ser Leu Ala Ile Thr Gly Leu
            65                  70                  75                  80
```

Gln Ala Glu Asp Glu Ala Asp Tyr Tyr Cys Gln Ser Tyr Asp Asn Ser
                85                  90                  95

Leu Asn Gly Pro Trp Val Phe Gly Thr Gly Thr Gln
            100                 105

<210> SEQ ID NO 314
<211> LENGTH: 120
<212> TYPE: PRT
<213> ORGANISM: Artificial sequence
<220> FEATURE:
<223> OTHER INFORMATION: Synthetic amino acid sequence

<400> SEQUENCE: 314

Glu Val Gln Leu Leu Glu Ser Gly Gly Gly Leu Val Gln Pro Gly Glu
1               5                   10                  15

Ser Leu Lys Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Asn Tyr Tyr Tyr Gly Met Asp Val Trp Gly Gln Gly
            100                 105                 110

Gly Thr Thr Val Thr Val Ser Ser
        115                 120

<210> SEQ ID NO 315
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 315

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Met Phe Gly Gln Gly Thr Lys Val Asp Ile Lys
            100                 105

<210> SEQ ID NO 316
<211> LENGTH: 123
<212> TYPE: PRT
<213> ORGANISM: Artificial sequence
<220> FEATURE:
<223> OTHER INFORMATION: Synthetic amino acid sequence

<400> SEQUENCE: 316

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ala Arg Asp Tyr Ser Asn Ile Phe Asp Ala Phe Asp Ile
            100                 105                 110

Trp Gly Gln Gly Thr Leu Val Thr Val Ser Ser
        115                 120

<210> SEQ ID NO 317
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 317

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 318
<211> LENGTH: 98
<212> TYPE: PRT
<213> ORGANISM: Artificial sequence
<220> FEATURE:
<223> OTHER INFORMATION: Synthetic amino acid sequence

<400> SEQUENCE: 318

Thr Val Ser Gly Gly Ser Ile Ser Ser Arg Ser Tyr Tyr Trp Gly Trp
1               5                   10                  15

Ile Arg Gln Pro Pro Gly Lys Gly Leu Glu Trp Ile Gly Ser Ile Tyr
            20                  25                  30

Tyr Ser Gly Ser Thr Tyr Tyr Asn Pro Ser Leu Lys Ser Arg Val Thr
        35                  40                  45

Ile Ser Val Asp Thr Ser Lys Asn Gln Phe Ser Leu Lys Leu Ser Ser
    50                  55                  60

```
Val Thr Ala Ala Asp Thr Ala Val Tyr Tyr Cys Val Arg Ile Ala Val
 65                  70                  75                  80

Ala Ala Ala Gly Thr Asp Tyr Trp Gly Gln Gly Thr Leu Val Thr Val
                 85                  90                  95

Ser Ser

<210> SEQ ID NO 319
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 319

Glu Ile Val Met Thr Gln Ser Pro Asp Thr Leu Ser Val Ser Pro Gly
  1               5                  10                  15

Glu Arg Ala Thr Val Ser Cys Arg Ala Ser Gln Ser Ile Ser Ser Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Ile Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Pro
                 85                  90                  95

Tyr Thr Phe Gly Gln Gly Thr Lys Val Asp Ile Lys
            100                 105

<210> SEQ ID NO 320
<211> LENGTH: 127
<212> TYPE: PRT
<213> ORGANISM: Artificial sequence
<220> FEATURE:
<223> OTHER INFORMATION: Synthetic amino acid sequence

<400> SEQUENCE: 320

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Asn Leu Thr Thr Tyr
                 20                  25                  30

Asp Ile Val Trp Val Arg Gln Ala Ala Gly Gln Gly Leu Glu Trp Met
             35                  40                  45

Gly Trp Met Asn Pro Lys Ser Gly Asn Thr Ala Tyr Ala Glu Arg Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Leu Asp Ser Leu Arg Phe Leu Glu Trp Phe His Gln Asn
            100                 105                 110

Tyr Tyr Tyr Phe Met Asp Val Trp Gly Lys Gly Thr Thr Val Thr
            115                 120                 125

<210> SEQ ID NO 321
<211> LENGTH: 103
<212> TYPE: PRT
<213> ORGANISM: Artificial sequence
<220> FEATURE:
```

<223> OTHER INFORMATION: Synthetic amino acid sequence

<400> SEQUENCE: 321

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Ile Gly Gly Tyr
            20                  25                  30

Leu Ala Trp Tyr Gln Gln Ile Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Leu Arg Ser Thr Phe Gly Gly
                85                  90                  95

Gly Thr Lys Val Asp Ile Lys
            100

<210> SEQ ID NO 322
<211> LENGTH: 121
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (66)..(66)
<223> OTHER INFORMATION: Xaa can be any naturally occurring amino acid

<400> SEQUENCE: 322

Glu Val Gln Leu Val Glu Ser Gly Gly Gly Leu Val Gln Pro Gly Arg
1               5                   10                  15

Ser Leu Arg Leu Ser Cys Lys Ala Ser Gly Ile Pro Phe Gly Asp Tyr
            20                  25                  30

Ala Met Thr Trp Phe Arg Gln Ala Pro Gly Lys Gly Leu Glu Trp Val
        35                  40                  45

Gly Phe Ile Lys Ser Lys Ala Tyr Gly Gly Thr Pro Glu Tyr Ala Ala
    50                  55                  60

Ser Xaa Lys Gly Arg Phe Thr Ile Ser Arg Asp Asn Ser Arg Ser Thr
65                  70                  75                  80

Ala Tyr Leu Gln Met Asn Ser Leu Lys Thr Asp Asp Thr Ala Val Tyr
                85                  90                  95

Tyr Cys Ser Ala Thr Leu Thr Arg Gly Glu Leu Phe Asp Tyr Trp Gly
            100                 105                 110

Gln Gly Thr Leu Val Thr Val Ser Ser
        115                 120

<210> SEQ ID NO 323
<211> LENGTH: 101
<212> TYPE: PRT
<213> ORGANISM: Artificial sequence
<220> FEATURE:
<223> OTHER INFORMATION: Synthetic amino acid sequence

<400> SEQUENCE: 323

Glu Ile Val Leu Thr Gln Ser Pro Asp Thr Leu Ser Leu Ser Leu Gly
1               5                   10                  15

Glu Arg Ala Thr Leu Ser Cys Arg Ala Ser Gln Ser Val Ser Asn Tyr
            20                  25                  30

```
Leu Ala Trp Tyr Gln Gln Lys Pro Gly Gln Ala Pro Arg Leu Leu Ile
            35                  40                  45

Tyr Asp Ala Ser Ser Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                85                  90                  95

Thr Phe Gly Gly Gly
            100
```

<210> SEQ ID NO 324
<211> LENGTH: 127
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (22)..(22)
<223> OTHER INFORMATION: Xaa can be any naturally occurring amino acid

<400> SEQUENCE: 324

```
Gln Val Gln Leu Gln Glu Ser Gly Pro Gly Leu Val Lys Pro Ser Glu
 1               5                  10                  15

Thr Leu Ser Leu Thr Xaa Thr Val Ser Gly Asp Ser Val Asn Ser Gly
            20                  25                  30

Ser Phe Tyr Trp Ser Trp Ile Arg Gln Ala Pro Gly Lys Gly Leu Glu
            35                  40                  45

Trp Ile Gly Phe Ile Tyr Tyr Ser Gly Thr Thr Asn Tyr Asn Pro Ser
 50                  55                  60

Leu Lys Arg Arg Val Thr Ile Ser Leu Ile Thr Ser Lys Asn Gln Phe
 65                  70                  75                  80

Ser Leu Arg Leu Gly Ser Val Thr Ala Ala Asp Thr Ala Val Tyr Tyr
                85                  90                  95

Cys Val Arg Glu Trp Pro Arg His Tyr Asp Asn Arg Gly Tyr His Thr
            100                 105                 110

Leu Pro Gly Thr Trp Gly Gln Gly Thr Leu Val Thr Val Ser Ser
            115                 120                 125
```

<210> SEQ ID NO 325
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 325

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Asn Leu Leu Ile
            35                  40                  45

Tyr Lys Ala Ser Thr Leu Glu Ser Gly Val Pro Ser Arg Phe Ser Gly
 50                  55                  60

Ser Gly Ser Gly Thr Glu Phe Thr Leu Thr Ile Asn Ser Leu His Pro
 65                  70                  75                  80

Asp Asp Phe Ala Thr Tyr Tyr Cys Gln Gln Tyr Asn Thr Asp Ser Ser
```

```
                    85                  90                  95

Arg Thr Phe Gly Gln Gly Thr Lys Val Asp Ile Lys
                100                 105
```

<210> SEQ ID NO 326
<211> LENGTH: 116
<212> TYPE: PRT
<213> ORGANISM: Artificial sequence
<220> FEATURE:
<223> OTHER INFORMATION: Synthetic amino acid sequence

<400> SEQUENCE: 326

```
Gln Val Gln Leu Val Glu Ser Gly Gly Val Val Gln Pro Gly Arg
1               5                   10                  15

Ser Leu Arg Leu Ser Cys Thr Ala Ser Gly Phe Asn Phe Ser Tyr Tyr
                20                  25                  30

Gly Ile His Trp Val Arg Gln Ala Pro Gly Lys Gly Leu Gln Trp Val
                35                  40                  45

Ala Leu Ile Ser Tyr Asp Gly Ser Asp Lys Tyr Tyr Ala Asp Ser Val
            50                  55                  60

Lys Gly Arg Phe Thr Val Ser Arg Asp Tyr Ser Lys Asn Thr Leu Phe
65                  70                  75                  80

Leu Gln Met Asn Ser Leu Arg Gly Asp Asp Thr Ala Val Tyr Tyr Cys
                85                  90                  95

Gln Met Val Lys Val Pro Phe Tyr Phe Trp Gly Gln Gly Thr Met Val
                100                 105                 110

Thr Leu Ser Ser
        115
```

<210> SEQ ID NO 327
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 327

```
Ser Tyr Glu Leu Thr Gln Pro Pro Ser Val Ser Val Ser Pro Gly Gln
1               5                   10                  15

Thr Ala Arg Ile Thr Cys Ser Gly Asp Glu Leu Pro Lys Arg Tyr Ala
                20                  25                  30

Tyr Trp Tyr Gln Gln Lys Ser Gly Gln Ala Pro Val Leu Val Ile Tyr
                35                  40                  45

Glu Asp Thr Lys Arg Pro Ser Gly Ile Pro Glu Arg Phe Ser Gly Ser
            50                  55                  60

Ser Ser Gly Thr Val Ala Thr Leu Thr Ile Ser Gly Ala Gln Val Asp
65                  70                  75                  80

Asp Glu Ala Asp Tyr Tyr Cys Tyr Ser Thr Asp Ser Thr Ser Asn His
                85                  90                  95

Lys Arg Val Phe Gly Gly Gly Thr Gln Val Thr Val Leu
                100                 105
```

<210> SEQ ID NO 328
<211> LENGTH: 121
<212> TYPE: PRT
<213> ORGANISM: Artificial sequence
<220> FEATURE:
<223> OTHER INFORMATION: Synthetic amino acid sequence

<400> SEQUENCE: 328

Gln Val Gln Leu Val Gln Ser Gly Ala Glu Val Lys Lys Pro Gly Ser
1               5                   10                  15

Ser Val Lys Val Ser Cys Lys Gly Ser Gly Asp Ser Phe Arg Ser Tyr
            20                  25                  30

Ala Ile Ser Trp Val Arg Gln Ala Pro Gly Gln Gly Leu Glu Trp Met
        35                  40                  45

Gly Gly Ile Ile Pro Arg Phe Gly Thr Thr Asn Tyr Ala Gln Lys Phe
    50                  55                  60

Gln Asp Arg Val Thr Ile Thr Ala Asp Lys Ser Thr Thr Thr Ala Tyr
65                  70                  75                  80

Met Glu Leu Arg Ser Leu Lys Cys Glu Asp Thr Gly Val Tyr Tyr Cys
                85                  90                  95

Ala Arg Pro Gln Ser Ala Tyr Asp Phe Gly Pro Phe Asp His Trp Gly
            100                 105                 110

Gln Gly Thr Leu Val Thr Val Ser Ser
        115                 120

<210> SEQ ID NO 329
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 329

Ser Tyr Glu Leu Thr Gln Pro Pro Ser Leu Ser Val Ala Pro Gly Lys
1               5                   10                  15

Thr Ala Arg Ile Thr Cys Gly Gly Asp Asn Ile Gly Ser Lys Gly Val
            20                  25                  30

His Trp Tyr Gln Gln Lys Pro Gly Gln Ala Pro Val Val Ile Ser
        35                  40                  45

Tyr Asp Ser Asp Arg Pro Ser Gly Ile Pro Glu Arg Phe Ser Gly Ser
    50                  55                  60

Asn Ser Gly Asp Thr Ala Thr Leu Thr Ile Ser Arg Val Glu Ala Gly
65                  70                  75                  80

Asp Glu Ala Asp Tyr Tyr Cys His Val Trp His Thr Thr Asp His
                85                  90                  95

Tyr Val Phe Gly Thr Gly Thr Lys Val Thr Val Leu
            100                 105

<210> SEQ ID NO 330
<211> LENGTH: 120
<212> TYPE: PRT
<213> ORGANISM: Artificial sequence
<220> FEATURE:
<223> OTHER INFORMATION: Synthetic amino acid sequence

<400> SEQUENCE: 330

Gln Val Gln Leu Val Glu Ser Gly Gly Gly Val Val Gln Pro Gly Arg
1               5                   10                  15

Ser Leu Arg Leu Ser Cys Ala Ala Phe Gly Phe Thr Ile Ser Ser Tyr
            20                  25                  30

Gly Met His Trp Val Arg Gln Ala Pro Gly Lys Gly Leu Glu Trp Val
        35                  40                  45

Ala Phe Ile Trp Tyr Asp Gly Thr Asn Lys Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Val Arg Thr Gln Gln Val Ile Arg Pro Phe Phe Asp His Trp Gly Gln
                100                 105                 110

Gly Thr Leu Val Thr Val Ser Ser
            115                 120
```

<210> SEQ ID NO 331
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 331

```
Glu Ile Val Met Thr Gln Ser Pro Ala Thr Leu Ser Val Ser Pro Gly
1               5                   10                  15

Asp Arg Val Thr Leu Ser Cys Arg Ala Ser Gln Ser Ile Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Ser Ile Ser Ser Leu Gln Ser
65                  70                  75                  80

Glu Asp Phe Ala Val Tyr Tyr Cys Gln Gln Tyr Lys Asn Trp Pro Pro
                85                  90                  95

Trp Thr Phe Gly Gln Gly Thr Lys Val Asp Ile Lys
                100                 105
```

<210> SEQ ID NO 332
<211> LENGTH: 129
<212> TYPE: PRT
<213> ORGANISM: Artificial sequence
<220> FEATURE:
<223> OTHER INFORMATION: Synthetic amino acid sequence

<400> SEQUENCE: 332

```
Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Asn Tyr
                20                  25                  30

Ser Ile Thr Trp Val Arg Gln Ala Pro Gly Gln Gly Leu Glu Trp Met
            35                  40                  45

Gly Gly Ile Ile Pro Ile Ser Gly Thr Ala Lys Tyr Ala Gln Lys Phe
    50                  55                  60

Gln Gly Arg Val Thr Ile Ser Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Cys Tyr Gly Val Phe Trp Ser Gly Tyr Phe Ser Arg Cys
                100                 105                 110

His Phe Gly Met Asp Val Trp Gly Gln Gly Thr Thr Val Thr Val Ser
            115                 120                 125

Ser
```

```
<210> SEQ ID NO 333
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 333

Glu Ile Glu Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

His Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Thr Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Gly Ser Pro
                85                  90                  95

Leu Leu Thr Phe Gly Gly Gly Thr Lys Val Asp Ile Lys
            100                 105

<210> SEQ ID NO 334
<211> LENGTH: 121
<212> TYPE: PRT
<213> ORGANISM: Artificial sequence
<220> FEATURE:
<223> OTHER INFORMATION: Synthetic amino acid sequence

<400> SEQUENCE: 334

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Phe Ser Gly Thr Gly Gly Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Arg Gly Ile Val Gly Thr Thr Arg Phe Asp Ser Trp Gly
            100                 105                 110

Gln Gly Thr Leu Val Thr Val Ser Ser
        115                 120

<210> SEQ ID NO 335
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 335

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30
```

```
Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Pro
                85                  90                  95

Ile Thr Phe Gly Gln Gly Thr Arg Leu Glu Ile Lys
            100                 105

<210> SEQ ID NO 336
<211> LENGTH: 131
<212> TYPE: PRT
<213> ORGANISM: Artificial sequence
<220> FEATURE:
<223> OTHER INFORMATION: Synthetic amino acid sequence

<400> SEQUENCE: 336

Gln Val Gln Leu Val Glu Ser Gly Gly Gly Leu Val Gln Leu Gly Glu
1               5                   10                  15

Ser Leu Lys Ile Ser Cys Val Ala Ser Gly Phe Ala Phe Ser Gly Ser
            20                  25                  30

Ala Met His Trp Val Arg Gln Ala Ser Gly Lys Gly Leu Glu Trp Leu
        35                  40                  45

Gly Arg Ile Arg Asn Lys Pro Asn Asn Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Ala Gly Val Tyr
                85                  90                  95

Tyr Cys Thr Arg Arg Met Asp His Ala Arg Arg Pro Ala Arg Glu Asp
            100                 105                 110

Tyr Tyr Asn Asn Gly Met Asp Ile Trp Gly Gln Gly Thr Thr Val Thr
        115                 120                 125

Val Ser Ser
    130

<210> SEQ ID NO 337
<211> LENGTH: 107
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (103)..(103)
<223> OTHER INFORMATION: Xaa can be any naturally occurring amino acid

<400> SEQUENCE: 337

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln His Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60
```

Gly Ser Gly Ser Gly Ala Glu Tyr Thr Leu Thr Ile Ser Arg Leu Glu
65                  70                  75                  80

Pro Glu Asp Phe Ala Val Tyr Tyr Cys Gln Gln Tyr Ser Ser Pro
                85                  90                  95

Thr Phe Gly Pro Gly Thr Xaa Gly Gly Tyr Gln
            100                 105

<210> SEQ ID NO 338
<211> LENGTH: 121
<212> TYPE: PRT
<213> ORGANISM: Artificial sequence
<220> FEATURE:
<223> OTHER INFORMATION: Synthetic amino acid sequence

<400> SEQUENCE: 338

Gln Val Gln Leu Val Glu Ser Gly Gly Val Val Gln Pro Gly Gly
1               5                   10                  15

Ser Leu Arg Leu Ser Cys Ala Ala Ser Gly Phe Ser Phe Ser Asn Tyr
                20                  25                  30

Gly Val His Trp Val Arg Gln Ala Pro Gly Arg Ala Leu Glu Trp Val
            35                  40                  45

Ala Phe Ile Arg Phe Asp Gly Thr Asp Lys Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Lys Asp Leu Ala Met Met Ile Ala Asn Pro Leu Asp Cys Trp Gly
            100                 105                 110

Gln Gly Ile Leu Val Thr Val Ser Ser
        115                 120

<210> SEQ ID NO 339
<211> LENGTH: 106
<212> TYPE: PRT
<213> ORGANISM: Artificial sequence
<220> FEATURE:
<223> OTHER INFORMATION: Synthetic amino acid sequence

<400> SEQUENCE: 339

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Asp Ala Ser Thr Arg Ala Thr Gly Ile Pro Val Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys Gln Gln Tyr Lys Asn Trp Gly Thr
                85                  90                  95

Phe Gly Gln Gly Thr Lys Val Asp Ile Lys
            100                 105

<210> SEQ ID NO 340
<211> LENGTH: 116
<212> TYPE: PRT
<213> ORGANISM: Artificial sequence
<220> FEATURE:
<223> OTHER INFORMATION: Synthetic amino acid sequence

<400> SEQUENCE: 340

Gln Val Gln Leu Val Gln Ser Gly Ala Glu Val Lys Pro Gly Ser
1               5                   10                  15

Ser Val Lys Val Ser Cys Lys Ala Ser Gly Gly Thr Phe Asn Ser Phe
            20                  25                  30

Ala Ile Thr Trp Val Arg Gln Ala Pro Gly Gln Gly Leu Glu Trp Met
        35                  40                  45

Gly Gly Ile Ile Pro Leu Phe Gly Thr Thr Asn Tyr Ala Gln Lys Phe
    50                  55                  60

Gln Asp Arg Val Thr Ile Thr Thr Asp Asp Ser Met Ser Thr Phe Tyr
65                  70                  75                  80

Met Glu Leu Lys Ser Leu Arg Ser Glu Asp Thr Ala Val Tyr Tyr Cys
                85                  90                  95

Ala Arg Val Phe Ser Ala Ala Gly His Trp Gly Gln Gly Thr Leu Val
            100                 105                 110

Thr Val Ser Ser
        115

<210> SEQ ID NO 341
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 341

Asp Ile Gln Met Thr Pro Ser Pro Ser Ser Leu Ser Ala Ser Val Gly
1               5                   10                  15

Asp Arg Val Thr Ile Thr Cys Arg Ala Ser Gln Ser Ile Ala Ser Tyr
            20                  25                  30

Leu Ile Trp Asp Gln Gln Lys Pro Gly Asn Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Gly Ser Leu Gln Pro
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Asp Ile Lys
            100                 105

<210> SEQ ID NO 342
<211> LENGTH: 130
<212> TYPE: PRT
<213> ORGANISM: Artificial sequence
<220> FEATURE:
<223> OTHER INFORMATION: Synthetic amino acid sequence

<400> SEQUENCE: 342

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Ala Met His Trp Val Arg Gln Ala Pro Gly Lys Gly Leu Glu Trp Val
        35                  40                  45

```
Ala Val Ile Ser Tyr Asp Ala Asn Asn Glu Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Thr Leu Arg Pro Glu Asp Thr Ala Val Tyr Tyr Cys
                 85                  90                  95

Ala Arg Gly Leu Ile Pro Ser Ala Glu Gln Trp Gln Ala Arg Gly Gly
                100                 105                 110

Pro Asp Tyr Tyr Tyr Tyr Tyr Gly Met Ala Val Trp Gly Gln Gly Thr
                115                 120                 125

Thr Val
    130
```

<210> SEQ ID NO 343

<400> SEQUENCE: 343

000

<210> SEQ ID NO 344
<211> LENGTH: 122
<212> TYPE: PRT
<213> ORGANISM: Artificial sequence
<220> FEATURE:
<223> OTHER INFORMATION: Synthetic amino acid sequence

<400> SEQUENCE: 344

```
Gln Val Gln Leu Val Gln Ser Gly Ala Glu Val Lys Lys Pro Gly Ser
 1               5                  10                  15

Ser Val Lys Val Ser Cys Lys Ala Ser Gly Ala Thr Phe Ser Ser Tyr
                 20                  25                  30

Val Phe Ser Trp Val Arg Gln Ala Pro Gly Gln Gly Leu Glu Trp Met
                 35                  40                  45

Gly Arg Ile Leu Pro Ile Leu Asp Ile Pro Asn Tyr Ala Gln Lys Phe
             50                  55                  60

Gln Gly Arg Val Thr Ile Thr Ala Asp Lys Ser Thr Ser Thr Ala Tyr
 65                  70                  75                  80

Met Glu Leu Gly Ser Leu Arg Ser Glu Asp Thr Ala Val Tyr Tyr Cys
                 85                  90                  95

Ala Arg Gly Gly Gly Ala Val Thr Gly Arg Gly Tyr Tyr Phe Asp Tyr
                100                 105                 110

Trp Gly Gln Gly Thr Leu Val Thr Phe Ser
            115                 120
```

<210> SEQ ID NO 345
<211> LENGTH: 96
<212> TYPE: PRT
<213> ORGANISM: Artificial sequence
<220> FEATURE:
<223> OTHER INFORMATION: Synthetic amino acid sequence

<400> SEQUENCE: 345

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                 20                  25                  30

Leu His Trp Tyr Gln Gln Arg Pro Gly Lys Ala Pro Lys Leu Leu Ile
                 35                  40                  45

Tyr Ala Ala Ser Ser Leu Gln Ser Gly Val Pro Ser Arg Phe Ser Gly
```

```
                        50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

<210> SEQ ID NO 346
<211> LENGTH: 118
<212> TYPE: PRT
<213> ORGANISM: Artificial sequence
<220> FEATURE:
<223> OTHER INFORMATION: Synthetic amino acid sequence

<400> SEQUENCE: 346

Gln Val Gln Leu Val Gln Ser Gly Ala Glu Val Lys Lys Pro Gly Ser
 1               5                  10                  15

Ser Val Lys Val Ser Cys Lys Leu Ser Gly Gly Thr Leu Asn Ser Tyr
                20                  25                  30

Ala Val Ser Trp Val Arg Gln Ala Pro Gly Gln Gly Leu Glu Trp Ile
             35                  40                  45

Gly Arg Ile Ile Pro Met Val Gly Met Ala His Tyr Ala Gln Lys Phe
         50                  55                  60

Gln Gly Arg Val Thr Ile Thr Ala Asp Lys Ser Thr Ser Ser Val Tyr
 65                  70                  75                  80

Met Glu Leu Ser Thr Leu Arg Ser Glu Asp Thr Ala Met Tyr His Cys
                 85                  90                  95

Ala Arg Glu Gln Lys Leu Val Gly Gly Gly Trp Phe Asp Pro Trp Gly
                100                 105                 110

Gln Gly Thr Leu Val Thr
            115

<210> SEQ ID NO 347
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 347

Glu Ile Val Leu Thr Gln Ser Pro Gly Thr Leu Ser Leu Ser Pro Gly
 1               5                  10                  15

Glu Ser Ala Thr Leu Ser Cys Arg Ala Ser Gln Ser Val Asn Ser Asp
                20                  25                  30

Tyr Leu Ala Trp Tyr Gln Gln Lys Pro Gly Gln Ala Pro Arg Leu Leu
             35                  40                  45

Ile Tyr Gly Val Ser Ser Arg Ala Thr Gly Ile Pro Asp Arg Phe Ser
         50                  55                  60

Gly Ser Gly Ser Glu Thr Asp Phe Thr Leu Thr Ile Ser Arg Leu Glu
 65                  70                  75                  80

Pro Glu Asp Phe Gly Val Phe Tyr Cys Gln Gln Tyr Gly His Ser Pro
                 85                  90                  95

Tyr Thr Phe Gly Gln Gly Thr Lys Val Asp Ile Lys
                100                 105

<210> SEQ ID NO 348
<211> LENGTH: 124
<212> TYPE: PRT
<213> ORGANISM: Artificial sequence
<220> FEATURE:
```

<223> OTHER INFORMATION: Synthetic amino acid sequence

<400> SEQUENCE: 348

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Asn Ser
            20                  25                  30

Ala Ile Asn Trp Val Arg Gln Ala Pro Gly Gln Gly Leu Glu Trp Met
        35                  40                  45

Gly Arg Ile Ile Pro Ile Leu Gly Ile Pro Asn Tyr Ala Gln Lys Phe
50                  55                  60

Glu Gly Arg Val Thr Ile Thr Ala Asp Lys Ser Thr Ser Thr Ala Tyr
65                  70                  75                  80

Met Glu Leu Asn Ser Leu Arg Ser Glu Asp Thr Ala Val Tyr Tyr Cys
                85                  90                  95

Ala Ser Pro Gln Arg Val Leu Arg Phe Leu Gln Trp Ser Pro Phe Asp
            100                 105                 110

Tyr Trp Gly Gln Gly Thr Leu Val Thr Val Ser Ser
        115                 120

<210> SEQ ID NO 349
<211> LENGTH: 98
<212> TYPE: PRT
<213> ORGANISM: Artificial sequence
<220> FEATURE:
<223> OTHER INFORMATION: Synthetic amino acid sequence

<400> SEQUENCE: 349

Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Val Leu Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Tyr Ala Ile Ser Pro
                85                  90                  95

Asn Thr

<210> SEQ ID NO 350
<211> LENGTH: 119
<212> TYPE: PRT
<213> ORGANISM: Artificial sequence
<220> FEATURE:
<223> OTHER INFORMATION: Synthetic amino acid sequence

<400> SEQUENCE: 350

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Val Arg Met Thr Thr Ser Leu Asp Tyr Trp Gly Gln Gly
            100                 105                 110

Thr Leu Val Thr Val Ser Ser
            115

<210> SEQ ID NO 351
<211> LENGTH: 111
<212> TYPE: PRT
<213> ORGANISM: Artificial sequence
<220> FEATURE:
<223> OTHER INFORMATION: Synthetic amino acid sequence

<400> SEQUENCE: 351

Gln Ser Val Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Asp Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Asp Asp Glu Ala Asp Tyr Tyr Cys Ser Ser Tyr Thr Thr Ile
                 85                  90                  95

Ser Thr Leu Gly Val Phe Gly Gly Gly Thr Gln Val Thr Val Leu
            100                 105                 110

<210> SEQ ID NO 352
<211> LENGTH: 124
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (120)..(120)
<223> OTHER INFORMATION: Xaa can be any naturally occurring amino acid

<400> SEQUENCE: 352

Gln Val Gln Leu Gln Glu Ser Gly Pro Gly Leu Val Lys Pro Ser Glu
  1               5                  10                  15

Thr Leu Ser Leu Thr Cys Ile Val Ser Gly Gly Ser Ile Ser Ser Tyr
                 20                  25                  30

Tyr Trp Ser Trp Ile Arg Gln Ser Pro Gly Lys Gly Leu Glu Trp Ile
             35                  40                  45

Gly Tyr Met Ser His Ser Gly Ser Thr Asn Tyr Asn Pro Ser Leu Lys
 50                  55                  60

Ser Arg Val Thr Ile Ser Val Asp Met Ser Lys Asn Gln Phe Ser Leu
 65                  70                  75                  80

Lys Leu Thr Ser Val Thr Ala Ala Asp Thr Ala Ala Tyr Tyr Cys Ala
                 85                  90                  95

Arg Gly Val Gly Gly Val Tyr Asp Ile Leu Thr Gly Tyr Trp Gly Pro
            100                 105                 110
```

```
Asn Trp Phe Asp Pro Trp Gly Xaa Gly Thr Leu Val
        115                 120
```

<210> SEQ ID NO 353
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 353

```
Gln Ser Val Val Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ala Asn Thr Asn Arg Pro Ser Gly Val Pro Asp Arg Phe
    50                  55                  60

Ser Gly Ser Lys Ser Asp Thr Ser Ala Ser Leu Ala Ile Thr Gly Leu
65                  70                  75                  80

Gln Ala Glu Asp Glu Gly Asp Tyr Tyr Cys Gln Ser Phe Asp Ser Ser
                85                  90                  95

Leu Arg Gly Ser Val Val Phe Gly Gly Gly Thr Gln Val Thr Val Leu
            100                 105                 110
```

<210> SEQ ID NO 354
<211> LENGTH: 121
<212> TYPE: PRT
<213> ORGANISM: Artificial sequence
<220> FEATURE:
<223> OTHER INFORMATION: Synthetic amino acid sequence

<400> SEQUENCE: 354

```
Gln Val Gln Leu Val Glu Ser Gly Gly Gly Leu Val Lys Pro Gly Glu
1               5                   10                  15

Ser Leu Lys Ile Ser Cys Ser Val Ser Gly Phe Thr Phe Ser Asp Tyr
            20                  25                  30

Tyr Met Ser Trp Ile Arg Gln Thr Pro Gly Lys Gly Leu Glu Trp Ile
        35                  40                  45

Ser Tyr Ile Ser Gly Gly Gly Asn Thr Ile Tyr Tyr Thr Asp Ser Val
    50                  55                  60

Lys Gly Arg Phe Thr Ile Ser Arg Asp Asn Ser Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Arg Ala Ala Gly Val Asn Tyr Phe Tyr Phe Tyr Tyr
            100                 105                 110

Met Asp Val Trp Gly Lys Gly Pro Arg
        115                 120
```

<210> SEQ ID NO 355
<211> LENGTH: 100
<212> TYPE: PRT
<213> ORGANISM: Artificial sequence
<220> FEATURE:
<223> OTHER INFORMATION: Synthetic amino acid sequence

<400> SEQUENCE: 355

```
Glu Ile Val Leu Thr Gln Ser Pro Ala Thr Leu Ser Leu Ser Pro Gly
```

-continued

```
                1               5                  10                 15
Glu Arg Ala Thr Leu Ser Cys Arg Ala Ser Gln Ser Val Ser Ser
                20                 25                 30

Leu Ala Trp Tyr Gln Gln Arg Pro Gly Arg Ala Pro Arg Leu Leu Ile
            35                 40                 45

Tyr Asp Ala Ser Asn Arg Ala Thr Gly Ile Pro Ala Arg Phe Ser Gly
        50                 55                 60

Ser Gly Ser Gly Thr Asp Phe Asn Leu Thr Ile Ser Ser Leu Glu Pro
65                 70                 75                 80

Glu Asp Phe Ala Val Tyr Tyr Cys Gln Gln Arg Gly Lys Trp Pro Pro
                85                 90                 95

Trp Thr Ser Ala
            100
```

<210> SEQ ID NO 356
<211> LENGTH: 119
<212> TYPE: PRT
<213> ORGANISM: Artificial sequence
<220> FEATURE:
<223> OTHER INFORMATION: Synthetic amino acid sequence

<400> SEQUENCE: 356

```
Gln Val Gln Leu Val Gln Ser Gly Ala Glu Val Lys Lys Pro Gly Ala
1               5                  10                 15

Ser Val Lys Val Ser Cys Lys Ala Ser Gly Tyr Thr Ser Met Ser Asp
            20                 25                 30

Tyr Ile Glu Trp Val Arg Gln Ala Pro Gly Gln Gly Leu Glu Trp Met
        35                 40                 45

Gly Ile Met Asn Pro Leu Gly Gly Ser Thr Ser Tyr Ala Gln Lys Leu
    50                 55                 60

Gln Gly Arg Val Thr Met Thr Arg Asp Thr Ser Thr Ser Thr Val Tyr
65                 70                 75                 80

Met Glu Leu Ser Ser Leu Arg Ser Asp Asp Thr Ala Val Tyr Tyr Cys
                85                 90                 95

Val Val Ser Ser Gly Phe Gln Gln Trp Phe Asp Pro Trp Gly Gln Gly
            100                105                110

Thr Leu Val Thr Val Ser Ser
        115
```

<210> SEQ ID NO 357
<211> LENGTH: 107
<212> TYPE: PRT
<213> ORGANISM: Artificial sequence
<220> FEATURE:
<223> OTHER INFORMATION: Synthetic amino acid sequence

<400> SEQUENCE: 357

```
Glu Ile Val Met Thr His Ser Pro Ala Thr Leu Ser Val Ser Pro Gly
1               5                  10                 15

Glu Arg Ala Ile Leu Ser Cys Arg Ala Ser Gln Ser Leu Thr Thr Asn
            20                 25                 30

Leu Ala Trp Tyr Gln Gln Lys Pro Gly Gln Ala Pro Arg Leu Leu Ile
        35                 40                 45

Tyr Arg Ala Ser Thr Arg Ala Thr Gly Ile Pro Ala Arg Phe Ser Gly
    50                 55                 60

Ser Gly Ser Gly Thr Glu Phe Thr Leu Thr Ile Ser Ser Leu Gln Ser
65                 70                 75                 80
```

-continued

Glu Asp Phe Ala Ile Tyr Tyr Cys Gln Gln Tyr Asn Asn Trp Pro Arg
                85                  90                  95

Thr Phe Gly Gln Gly Thr Lys Val Asp Ile Lys
            100                 105

<210> SEQ ID NO 358
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 358

Gly Gly Ser Phe Ser Gly Tyr Phe
1               5

<210> SEQ ID NO 359
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 359

Ile Asn His Ser Gly Ser Thr
1               5

<210> SEQ ID NO 360
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 360

Ala Arg Val Met Thr Gly Ile Thr Asn Tyr Tyr Tyr Tyr Gly Met
1               5                   10                  15

Asp Val

<210> SEQ ID NO 361
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 361

Gly Gly Ser Phe Ser Gly Tyr Tyr
1               5

<210> SEQ ID NO 362
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 362

Ile Asn His Ser Gly Ser Thr
1               5

<210> SEQ ID NO 363
<211> LENGTH: 21
<212> TYPE: PRT
<213> ORGANISM: Artificial sequence
<220> FEATURE:

<223> OTHER INFORMATION: Synthetic amino acid sequence

<400> SEQUENCE: 363

Ala Arg Ala Thr Gln Gly Ser Gly Thr Tyr Lys Leu Phe Phe Tyr Ser
1               5                   10                  15

Tyr Gly Met Asp Val
            20

<210> SEQ ID NO 364
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 364

Gly Asp Ser Ile Ser Ser Asn Asn Tyr Tyr
1               5                   10

<210> SEQ ID NO 365
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 365

Ile Tyr Tyr Ser Gly Ser Thr
1               5

<210> SEQ ID NO 366
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 366

Ala Arg His Arg Arg Val Leu Leu Trp Phe Gly Glu Phe Gln Leu
1               5                   10                  15

<210> SEQ ID NO 367
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 367

Gly Gly Ser Met Ser Ser Tyr Phe
1               5

<210> SEQ ID NO 368
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 368

Ile Ser Tyr Ser Gly Gly Thr
1               5

<210> SEQ ID NO 369
<211> LENGTH: 10
<212> TYPE: PRT

```
<213> ORGANISM: Artificial sequence
<220> FEATURE:
<223> OTHER INFORMATION: Synthetic amino acid sequence

<400> SEQUENCE: 369

Ala Arg Glu Asp Arg Gly Ser Pro Asp Tyr
1               5                   10

<210> SEQ ID NO 370
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 370

Gly Tyr Thr Phe Thr Ser Tyr Asp
1               5

<210> SEQ ID NO 371
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 371

Met Asn Pro Asn Ser Gly Asn Thr
1               5

<210> SEQ ID NO 372
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 372

Ala Arg Thr Pro Phe Asp Gly Ser Gly Tyr Tyr Tyr
1               5                   10

<210> SEQ ID NO 373
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 373

Gly Tyr Thr Phe Thr Ser Tyr Asp
1               5

<210> SEQ ID NO 374
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 374

Met Asn Pro Asn Ser Gly Asn Thr
1               5

<210> SEQ ID NO 375
<211> LENGTH: 12
<212> TYPE: PRT
<213> ORGANISM: Artificial sequence
```

```
<220> FEATURE:
<223> OTHER INFORMATION: Synthetic amino acid sequence

<400> SEQUENCE: 375

Ala Arg Thr Pro Phe Asp Asp Ile Gly Tyr Tyr Tyr
1               5                   10

<210> SEQ ID NO 376
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 376

Gly Tyr Thr Phe Thr Asp Tyr Tyr
1               5

<210> SEQ ID NO 377
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 377

Leu Asp Pro Leu Asp Gly Glu Thr
1               5

<210> SEQ ID NO 378
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 378

Ala Arg Glu Leu Thr Gly Tyr Leu Asn Tyr
1               5                   10

<210> SEQ ID NO 379
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 379

Gly Phe Ser Leu Ser Asn Ala Arg Met Arg
1               5                   10

<210> SEQ ID NO 380
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 380

Ile Phe Ser Asn Asp Glu Lys
1               5

<210> SEQ ID NO 381
<211> LENGTH: 14
<212> TYPE: PRT
<213> ORGANISM: Artificial sequence
<220> FEATURE:
```

<223> OTHER INFORMATION: Synthetic amino acid sequence

<400> SEQUENCE: 381

Ala Arg Met Arg Gly Glu Tyr Asn Ser Tyr Tyr Phe Asp Ser
1               5                   10

<210> SEQ ID NO 382
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 382

Gly Phe Thr Leu Asp Asp Tyr Ala
1               5

<210> SEQ ID NO 383
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 383

Ile Ser Trp Asn Ser Gly Gly Met
1               5

<210> SEQ ID NO 384
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 384

Ala Lys Asp Val Gly Val Val Thr Gly Gly Tyr Trp Asp Asp Ala
1               5                   10                  15

Leu Asp Ile

<210> SEQ ID NO 385
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 385

Gly Gly Ser Ile Ser Ser Phe Tyr
1               5

<210> SEQ ID NO 386
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 386

Ile Tyr Tyr Ser Gly Ser Thr
1               5

<210> SEQ ID NO 387
<211> LENGTH: 18
<212> TYPE: PRT
<213> ORGANISM: Artificial sequence

```
<220> FEATURE:
<223> OTHER INFORMATION: Synthetic amino acid sequence

<400> SEQUENCE: 387

Ala Arg Leu Arg Gly Asn Tyr Ala Ser Ser Gly Tyr Tyr Tyr Asn Phe
1               5                   10                  15

Asp Tyr

<210> SEQ ID NO 388
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 388

Gly Gly Ser Ile Ser Ser Ser Ser Tyr Tyr
1               5                   10

<210> SEQ ID NO 389
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 389

Ile Tyr Tyr Arg Gly Ser Thr
1               5

<210> SEQ ID NO 390
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 390

Ala Arg His Leu Arg Val Leu Leu Trp Phe Gly Glu Leu Leu Glu
1               5                   10                  15

<210> SEQ ID NO 391
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 391

Gly Tyr Thr Phe Thr Gly Tyr Tyr
1               5

<210> SEQ ID NO 392
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 392

Ile Asn Pro Asn Ser Gly Gly Thr
1               5

<210> SEQ ID NO 393
<211> LENGTH: 11
<212> TYPE: PRT
```

```
<213> ORGANISM: Artificial sequence
<220> FEATURE:
<223> OTHER INFORMATION: Synthetic amino acid sequence

<400> SEQUENCE: 393

Ala Arg Val Pro Pro Asp Ser Ser Ser Trp Lys
1               5                   10

<210> SEQ ID NO 394
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 394

Gly Phe Thr Phe Ser Ser Tyr Ser
1               5

<210> SEQ ID NO 395
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 395

Ile Thr Ser Ser Ser Ser Tyr Ile
1               5

<210> SEQ ID NO 396
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 396

Ala Ser Arg Pro Gly Ile Ala Pro Ala Gly Pro Gln Ala Glu Gly Tyr
1               5                   10                  15

<210> SEQ ID NO 397
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 397

Gly Tyr Thr Leu Thr Glu Leu Ser
1               5

<210> SEQ ID NO 398
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 398

Phe Asp Pro Glu Asp Gly Glu Thr
1               5

<210> SEQ ID NO 399
<211> LENGTH: 11
<212> TYPE: PRT
<213> ORGANISM: Artificial sequence
```

```
<220> FEATURE:
<223> OTHER INFORMATION: Synthetic amino acid sequence

<400> SEQUENCE: 399

Ala Arg Glu Ser Trp Leu Arg Gly Phe Asp Tyr
1               5                   10

<210> SEQ ID NO 400
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 400

Gly Gly Ser Ile Ser Arg Gly Ile Tyr Tyr
1               5                   10

<210> SEQ ID NO 401
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 401

Ile Tyr Thr Ser Gly Ser Thr
1               5

<210> SEQ ID NO 402
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 402

Ala Arg Asp Gly Trp Tyr Gly Trp Tyr Leu Asp Leu
1               5                   10

<210> SEQ ID NO 403
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 403

Gly Phe Thr Phe Ser Asn Tyr Trp
1               5

<210> SEQ ID NO 404
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 404

Ile Lys Gln Asp Gly Ser Lys Lys
1               5

<210> SEQ ID NO 405
<211> LENGTH: 17
<212> TYPE: PRT
<213> ORGANISM: Artificial sequence
<220> FEATURE:
```

<223> OTHER INFORMATION: Synthetic amino acid sequence

<400> SEQUENCE: 405

Ala Thr Leu Asn Leu Glu Leu Ala Val Asp Ala Ile Ser Glu Ala Leu
1               5                   10                  15

Lys

<210> SEQ ID NO 406
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 406

Gly Gly Ser Ile Ser Ser Gly Gly Tyr Tyr
1               5                   10

<210> SEQ ID NO 407
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 407

Met Ser Tyr Ser Gly Asp Thr
1               5

<210> SEQ ID NO 408
<211> LENGTH: 22
<212> TYPE: PRT
<213> ORGANISM: Artificial sequence
<220> FEATURE:
<223> OTHER INFORMATION: Synthetic amino acid sequence

<400> SEQUENCE: 408

Ala Arg Gly Arg Tyr Cys Asn Asp Asp Ser Cys Tyr Ser Glu Glu Ser
1               5                   10                  15

Ala Ile Trp Phe Asp Pro
            20

<210> SEQ ID NO 409
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 409

Gly Gly Thr Phe Ser Ser Leu Ala
1               5

<210> SEQ ID NO 410
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 410

Ile Ile Pro Ile Phe Gly Lys Ala
1               5

<210> SEQ ID NO 411

```
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 411

Ala Thr Gly Gly Asn Ile Arg Val His Asp Phe Asp Ile
1               5                   10

<210> SEQ ID NO 412
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 412

Gly Gly Ser Phe Ser Gly Tyr Tyr
1               5

<210> SEQ ID NO 413
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 413

Ile Asn Tyr Ser Gly Ser Thr
1               5

<210> SEQ ID NO 414
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 414

Ala Arg Ile Ser Ser Gly Trp Ile Gly Phe Pro Arg Tyr His Tyr Tyr
1               5                   10                  15

Leu Asp Val

<210> SEQ ID NO 415
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 415

Gly Glu Thr Phe Ser Arg Tyr Ala
1               5

<210> SEQ ID NO 416
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 416

Ile Ile Pro Phe Ile Asp Ile Pro
1               5
```

-continued

```
<210> SEQ ID NO 417
<211> LENGTH: 23
<212> TYPE: PRT
<213> ORGANISM: Artificial sequence
<220> FEATURE:
<223> OTHER INFORMATION: Synthetic amino acid sequence

<400> SEQUENCE: 417

Ala Ser Ser Leu Pro Ser Thr Tyr Tyr Phe Gly Ser Gly Asn Tyr Pro
1               5                   10                  15

Trp Gly Asn Trp Leu Asp Pro
            20

<210> SEQ ID NO 418
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 418

Gly Gly Ser Phe Ser Gly Tyr Tyr
1               5

<210> SEQ ID NO 419
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 419

Ile Asn Tyr Val Gly Ser Thr
1               5

<210> SEQ ID NO 420
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 420

Ala Arg Gly Leu Arg Gly Asn Ser Val Cys Phe Asp
1               5                   10

<210> SEQ ID NO 421
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 421

Gly Phe Thr Phe Ser Ser Phe Ser
1               5

<210> SEQ ID NO 422
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 422

Ile Ser Ser Ser Ser Ser Thr Ile
1               5
```

```
<210> SEQ ID NO 423
<211> LENGTH: 21
<212> TYPE: PRT
<213> ORGANISM: Artificial sequence
<220> FEATURE:
<223> OTHER INFORMATION: Synthetic amino acid sequence

<400> SEQUENCE: 423

Ala Arg Arg Ser Val Gly Cys Ser Gly Gly Asn Cys Tyr Ala Tyr Tyr
1               5                   10                  15

Tyr Gly Met Asp Val
            20

<210> SEQ ID NO 424
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 424

Gly Phe Thr Phe Ser Asp Tyr Tyr
1               5

<210> SEQ ID NO 425
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 425

Ile Ser Thr Ser Gly Ser Thr Ile
1               5

<210> SEQ ID NO 426
<211> LENGTH: 21
<212> TYPE: PRT
<213> ORGANISM: Artificial sequence
<220> FEATURE:
<223> OTHER INFORMATION: Synthetic amino acid sequence

<400> SEQUENCE: 426

Ala Arg Asp Gly Asp Gly Ser Gly Ser Tyr Thr Pro Pro Tyr Tyr Tyr
1               5                   10                  15

Tyr Gly Leu Asp Val
            20

<210> SEQ ID NO 427
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 427

Gly Phe Thr Phe Ser Ser Tyr Ser
1               5

<210> SEQ ID NO 428
<211> LENGTH: 8
<212> TYPE: PRT
<213> ORGANISM: Artificial sequence
<220> FEATURE:
<223> OTHER INFORMATION: Synthetic amino acid sequence
```

<400> SEQUENCE: 428

Ile Thr Ser Ser Ser Ser Tyr Ile
1               5

<210> SEQ ID NO 429

<400> SEQUENCE: 429

000

<210> SEQ ID NO 430
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 430

Gly Phe Thr Phe Ser Ser Tyr Ser
1               5

<210> SEQ ID NO 431
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 431

Ile Ser Ser Ile Ser Ser Tyr Ile
1               5

<210> SEQ ID NO 432
<211> LENGTH: 23
<212> TYPE: PRT
<213> ORGANISM: Artificial sequence
<220> FEATURE:
<223> OTHER INFORMATION: Synthetic amino acid sequence

<400> SEQUENCE: 432

Ala Arg Asp Arg Pro Arg Ser Arg Pro Asn Ser Gly Ser Tyr Phe Trp
1               5                   10                  15

Tyr Tyr Tyr Gly Met Asp Val
            20

<210> SEQ ID NO 433
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 433

Gly Gly Thr Phe Ser Thr Tyr Ala
1               5

<210> SEQ ID NO 434
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 434

Ile Ile Pro Ile Leu Gly Thr Ala 1               5

<210> SEQ ID NO 435
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 435

Ala Arg Arg Gly Gly Glu Gly Ala Ala His Gly Met Asp Val
1               5                   10

<210> SEQ ID NO 436
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 436

Gly Tyr Thr Phe Thr Thr Tyr Ala
1               5

<210> SEQ ID NO 437
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 437

Pro Gly Asp Gly Asp Thr
1               5

<210> SEQ ID NO 438
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 438

Ala Arg Pro Arg Ala Ser Leu Leu Arg Tyr Phe Asp Trp Leu Phe Glu
1               5                   10                  15
Gln

<210> SEQ ID NO 439
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 439

Gly Gly Ser Phe Thr Asn Tyr Tyr
1               5

<210> SEQ ID NO 440
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 440

Ile Asp His Ser Gly Ser Ala
1               5

<210> SEQ ID NO 441
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 441

Ala Arg Asp Val Tyr Gly Ser Gly Thr Tyr Tyr Trp Phe Asp Pro
1               5                   10                  15

<210> SEQ ID NO 442
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 442

Gly Gly Ser Ile Ser Thr Arg Thr Trp
1               5

<210> SEQ ID NO 443
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 443

Ile Tyr Gln Ser Gly Ser Thr
1               5

<210> SEQ ID NO 444
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 444

Ala Arg Ser Gly Arg Tyr Ser Ser Val Thr Pro Phe Asp Tyr
1               5                   10

<210> SEQ ID NO 445
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 445

Gly Phe Thr Phe Ser Asp Ser Gly
1               5

<210> SEQ ID NO 446
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 446

Ile Trp Tyr Asp Gly Ser Thr Lys

```
<210> SEQ ID NO 447
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 447

Ala Arg Glu Leu Gly Tyr Cys Ser Gly Gly Thr Cys Tyr Ser Met Gly
1               5                   10                  15

Ala Phe Asp Ile
            20

<210> SEQ ID NO 448
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 448

Ser Phe Ile Phe Ser Asp Ala Trp
1               5

<210> SEQ ID NO 449
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 449

Phe Lys Thr Lys Thr Asp Gly Gly Thr Thr
1               5                   10

<210> SEQ ID NO 450

<400> SEQUENCE: 450

000

<210> SEQ ID NO 451
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 451

Gly Tyr Thr Phe Thr Lys Tyr Thr
1               5

<210> SEQ ID NO 452
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 452

Ile Tyr Ala Gly Tyr Gly Asn Thr
1               5

<210> SEQ ID NO 453
```

```
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 453

Ala Arg Asp Phe Glu Asp Phe Asp Ser Trp Thr Gly Tyr Tyr Ser Trp
1               5                   10                  15

Leu His

<210> SEQ ID NO 454
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 454

Gly Gly Ser Phe Ser Gly Tyr Phe
1               5

<210> SEQ ID NO 455
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 455

Met Asn His Ser Gly Ser Thr
1               5

<210> SEQ ID NO 456
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 456

Ala Arg Thr Ala Arg Thr Val Arg Tyr Phe Glu Asn
1               5                   10

<210> SEQ ID NO 457
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 457

Arg Phe Thr Phe Ser Asn Tyr Tyr
1               5

<210> SEQ ID NO 458
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 458

Ile Ser Ser Arg Ser Arg Tyr Thr
1               5
```

```
<210> SEQ ID NO 459
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 459

Ala Arg Gly Gly Gly Tyr Cys Gly Gly Thr Thr Cys Ser Met Gly His
1               5                   10                  15

Ala Phe Asp Ile
            20

<210> SEQ ID NO 460
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 460

Gly Gly Ser Ile Ser Ser Ser Asn Trp
1               5

<210> SEQ ID NO 461
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 461

Ile Tyr His Ser Gly Ser Thr
1               5

<210> SEQ ID NO 462
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 462

Ala Arg Asn Phe Tyr Pro Gly Tyr Leu Gln Tyr
1               5                   10

<210> SEQ ID NO 463
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 463

Gly Phe Thr Phe Ser Ser Tyr Gly
1               5

<210> SEQ ID NO 464
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 464

Ile Trp Tyr Asp Gly Ile Asn Lys
1               5
```

<210> SEQ ID NO 465
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 465

Ala Lys Glu Ala Gly Gly Gly Asp Cys Tyr Ser Asn Tyr Phe His Tyr
1               5                   10                  15

<210> SEQ ID NO 466
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 466

Gly Phe Thr Phe Ser Asn Ser Gly
1               5

<210> SEQ ID NO 467
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 467

Ile Trp Phe Asp Gly Thr Asn Lys
1               5

<210> SEQ ID NO 468
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 468

Ala Arg Val Pro Cys Gly Gly Asp Cys Tyr Ser Gly Tyr Leu Gln His
1               5                   10                  15

<210> SEQ ID NO 469
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 469

Gly Phe Thr Phe Ser Ser Tyr Trp
1               5

<210> SEQ ID NO 470
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 470

Ile Asn Ser Asp Gly Ser Ser Thr
1               5

-continued

<210> SEQ ID NO 471
<211> LENGTH: 15
<212> TYPE: PRT
<213> ORGANISM: Artificial sequence
<220> FEATURE:
<223> OTHER INFORMATION: Synthetic amino acid sequence

<400> SEQUENCE: 471

Ala Arg Val Gly Ala Val Arg Ile Ala Ala Ala Ala Pro Asp Tyr
1               5                   10                  15

<210> SEQ ID NO 472
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 472

Gly Gly Ser Leu Ser Gly Gln Tyr
1               5

<210> SEQ ID NO 473
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 473

Ile His His Lys Gly Arg Thr
1               5

<210> SEQ ID NO 474
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 474

Ala Ser Gly Asn Tyr Arg
1               5

<210> SEQ ID NO 475
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 475

Gly Gly Ser Ile Asn Ser Arg Thr Tyr Tyr
1               5                   10

<210> SEQ ID NO 476
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 476

Val Phe His Asn Val Ser Thr
1               5

```
<210> SEQ ID NO 477
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 477

Gly Arg Leu Thr Pro Arg Asn Leu Phe Arg Gly Thr Leu Val Arg Trp
1               5                   10                  15

Val Asp Pro

<210> SEQ ID NO 478
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 478

Gly Asp Ser Val Ser Ser Asn Ser Ala Ala
1               5                   10

<210> SEQ ID NO 479
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 479

Thr Tyr Tyr Arg Ser Glu Trp Tyr Ser
1               5

<210> SEQ ID NO 480
<211> LENGTH: 21
<212> TYPE: PRT
<213> ORGANISM: Artificial sequence
<220> FEATURE:
<223> OTHER INFORMATION: Synthetic amino acid sequence

<400> SEQUENCE: 480

Ala Arg Ile Thr Val Gly Tyr Asn Ser Pro His Leu Arg Val Thr Arg
1               5                   10                  15

Gly Trp Leu Asp Pro
            20

<210> SEQ ID NO 481
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 481

Gly Phe Thr Phe Ser Thr Tyr Thr
1               5

<210> SEQ ID NO 482
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 482
```

Ile Ser Tyr Asp Gly Ile Asn Glu
1               5

<210> SEQ ID NO 483

<400> SEQUENCE: 483

000

<210> SEQ ID NO 484
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 484

Gly Phe Thr Phe Ser Ser Tyr Ala
1               5

<210> SEQ ID NO 485
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 485

Ile Ser Asn Asp Gly Ser Ser Lys
1               5

<210> SEQ ID NO 486
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 486

Ala Arg Ala Asp Arg Gly Tyr Phe Gly His
1               5                   10

<210> SEQ ID NO 487
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 487

Gly Gly Ser Ile Ser Ser Tyr Tyr
1               5

<210> SEQ ID NO 488
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 488

Ile Tyr Tyr Ser Gly Gly Thr
1               5

<210> SEQ ID NO 489
<211> LENGTH: 12
<212> TYPE: PRT

```
<213> ORGANISM: Artificial sequence
<220> FEATURE:
<223> OTHER INFORMATION: Synthetic amino acid sequence

<400> SEQUENCE: 489

Ala Arg Leu Ala Gly Arg Lys Pro Asp Ala Asp Ser
1               5                   10

<210> SEQ ID NO 490
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 490

Gly Phe Ile Phe Ser Asn Tyr Ala
1               5

<210> SEQ ID NO 491
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 491

Leu Ser Ala Ser Asp Gly Val Thr
1               5

<210> SEQ ID NO 492
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 492

Ala Lys Gly Arg Ala Arg Val Asn Asn Ile Tyr Arg Tyr Phe Asp His
1               5                   10                  15

<210> SEQ ID NO 493
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 493

Gly Phe Ser Phe Lys Ser Tyr Ala
1               5

<210> SEQ ID NO 494
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 494

Ile Gly Val Ser Gly Ala Ser Thr
1               5

<210> SEQ ID NO 495
<211> LENGTH: 16
<212> TYPE: PRT
<213> ORGANISM: Artificial sequence
```

```
<220> FEATURE:
<223> OTHER INFORMATION: Synthetic amino acid sequence

<400> SEQUENCE: 495

Ala Arg Asp Thr Tyr Tyr Tyr Asp Ser Arg Ile Trp Tyr Phe Gly Leu
1               5                   10                  15

<210> SEQ ID NO 496
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 496

Gly Gly Thr Phe Ser Ser Tyr Val
1               5

<210> SEQ ID NO 497
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 497

Ile Ile Val Met Leu Gly Val Thr
1               5

<210> SEQ ID NO 498
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 498

Ala Arg Ala Val Ile Thr Met Val Arg Gly Asp Ile Pro Leu Gly Trp
1               5                   10                  15

Phe Asp Pro

<210> SEQ ID NO 499
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 499

Gly Phe Ser Ile Asn Thr Gly Gly Gln Gly
1               5                   10

<210> SEQ ID NO 500
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 500

Ile Tyr Trp Asp Asp Asp Lys
1               5

<210> SEQ ID NO 501
<211> LENGTH: 15
<212> TYPE: PRT
```

<213> ORGANISM: Artificial sequence
<220> FEATURE:
<223> OTHER INFORMATION: Synthetic amino acid sequence

<400> SEQUENCE: 501

Ala His Arg Ser Val Ala Gly Arg Arg Asp Leu Ala Phe Asp Ile
1               5                   10                  15

<210> SEQ ID NO 502
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 502

Gly Phe Ser Phe Asn Asn Ala Trp
1               5

<210> SEQ ID NO 503
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 503

Ile Lys Thr His Ala Asp Gly Gly Thr Thr
1               5                   10

<210> SEQ ID NO 504
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 504

Thr Thr Ser Phe Thr Phe Pro Arg Arg Ile Phe Ala Tyr
1               5                   10

<210> SEQ ID NO 505
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 505

Gly Tyr Ser Phe Arg Ser Asn Gly
1               5

<210> SEQ ID NO 506
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 506

Ile Ala Ala Tyr Asn Gly Asp Thr
1               5

<210> SEQ ID NO 507
<211> LENGTH: 15
<212> TYPE: PRT
<213> ORGANISM: Artificial sequence

```
<220> FEATURE:
<223> OTHER INFORMATION: Synthetic amino acid sequence

<400> SEQUENCE: 507

Ala Arg Asp Pro Lys Leu Gly Arg Lys Gly Ser Ala Phe Asp Ile
1               5                   10                  15

<210> SEQ ID NO 508
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 508

Glu Phe Thr Phe Ser Ser Tyr Ala
1               5

<210> SEQ ID NO 509
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 509

Ile Ser Asp Ser Gly Gly Arg Leu
1               5

<210> SEQ ID NO 510
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 510

Ala Lys Asp Arg Val Val Gly Ala Thr Tyr Pro Arg Gly Val Phe Asp
1               5                   10                  15

Ile

<210> SEQ ID NO 511
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 511

Gly Gly Ser Ile Ser Ser Gly Gly Tyr Tyr
1               5                   10

<210> SEQ ID NO 512
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 512

Ile Tyr Tyr Ser Gly Ser Thr
1               5

<210> SEQ ID NO 513
<211> LENGTH: 12
<212> TYPE: PRT
```

```
<213> ORGANISM: Artificial sequence
<220> FEATURE:
<223> OTHER INFORMATION: Synthetic amino acid sequence

<400> SEQUENCE: 513

Ala Arg Gln Ser Ser Ser Thr Gly Gly Phe His Tyr
1               5                   10

<210> SEQ ID NO 514
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 514

Gly Phe Thr Phe Asp Asp Tyr Ala
1               5

<210> SEQ ID NO 515
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 515

Leu Ser Trp Asn Ser Gly Ser Ile
1               5

<210> SEQ ID NO 516
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 516

Ala Lys Glu Thr Glu Lys Tyr Tyr Tyr Asp Ser Ser Gly Tyr Asp Tyr
1               5                   10                  15

<210> SEQ ID NO 517
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 517

Gly Phe Asn Val Ala Thr Asn Tyr
1               5

<210> SEQ ID NO 518
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 518

Ile Tyr Ser Gly Gly Ser Thr
1               5

<210> SEQ ID NO 519
<211> LENGTH: 10
<212> TYPE: PRT
<213> ORGANISM: Artificial sequence
```

```
<220> FEATURE:
<223> OTHER INFORMATION: Synthetic amino acid sequence

<400> SEQUENCE: 519

Ala Lys Gly Gly Gly Leu Gly Leu Asp Tyr
1               5                   10

<210> SEQ ID NO 520
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 520

Gly Gly Arg Phe Ser Thr Gln His
1               5

<210> SEQ ID NO 521
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 521

Ile Ile Pro Ile Phe Ala Thr Ala
1               5

<210> SEQ ID NO 522
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 522

Gly Val Tyr Asn Ala Asn
1               5

<210> SEQ ID NO 523
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 523

Gly Phe Thr Phe Ser Ser Tyr Ser
1               5

<210> SEQ ID NO 524
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 524

Ile Ser Phe Asp Gly Arg Ser Asn
1               5

<210> SEQ ID NO 525
<211> LENGTH: 16
<212> TYPE: PRT
<213> ORGANISM: Artificial sequence
<220> FEATURE:
```

<223> OTHER INFORMATION: Synthetic amino acid sequence

<400> SEQUENCE: 525

Ala Arg Gly Gly Ile Gly Ala Pro Asp Pro Arg Asn Gly Leu Glu Val
1               5                   10                  15

<210> SEQ ID NO 526
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 526

Gly Tyr Thr Phe Thr Ser His Gly
1               5

<210> SEQ ID NO 527
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 527

Ile Ser Val Tyr Asn Asp Asn Thr
1               5

<210> SEQ ID NO 528
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 528

Ala Arg Ser Ser Ser Gly Pro Arg Tyr Tyr Tyr Gly Met Asp Val
1               5                   10                  15

<210> SEQ ID NO 529
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 529

Gly Phe Thr Leu Arg Asn Tyr Ala
1               5

<210> SEQ ID NO 530
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 530

Ile Ser Gly Ser Gly Gly Ser Thr
1               5

<210> SEQ ID NO 531
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 531

Ala Lys Ile Arg Leu Asp Ser Ser Gly Tyr Ser Gly Ala Phe Asp Ile
1               5                   10                  15

<210> SEQ ID NO 532
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 532

Gly Gly Thr Phe Ser Ser Tyr Ala
1               5

<210> SEQ ID NO 533
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 533

Ile Ile Pro Ile Phe Gly Thr Ala
1               5

<210> SEQ ID NO 534
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 534

Ala Arg Ala Ser Glu Gln Trp Leu Ala Ser Ile Asn Trp Phe Asp Pro
1               5                   10                  15

<210> SEQ ID NO 535
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 535

Gly Phe Ser Phe Ser Ser Tyr Ala
1               5

<210> SEQ ID NO 536
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 536

Ile Gly Asn Ser Gly Asp Arg Thr
1               5

<210> SEQ ID NO 537
<211> LENGTH: 11
<212> TYPE: PRT
<213> ORGANISM: Artificial sequence
<220> FEATURE:
<223> OTHER INFORMATION: Synthetic amino acid sequence

```
<400> SEQUENCE: 537

Ala Lys Trp Gly Arg Phe Glu Ser Gly Ala Phe
1               5                   10

<210> SEQ ID NO 538
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 538

Gly Gly Ser Ile Ile Ser Ser Ser Tyr Tyr
1               5                   10

<210> SEQ ID NO 539
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 539

Ile Tyr Tyr Ser Gly Ser Thr
1               5

<210> SEQ ID NO 540
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 540

Ala Arg Gln Ile Ser Lys Ala Ala Ala Gly Ser Ile Asp Tyr
1               5                   10

<210> SEQ ID NO 541
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 541

Gly Phe Thr Phe Ser Ser Tyr Ala
1               5

<210> SEQ ID NO 542
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 542

Ile Ser Gly Thr Gly Gly Asn Thr
1               5

<210> SEQ ID NO 543
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 543
```

```
Ala Thr Ser Leu Ile Trp Trp Leu Gln Ser Asp Tyr
1               5                   10
```

<210> SEQ ID NO 544
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 544

```
Gly Tyr Ser Phe Thr Asn His Trp
1               5
```

<210> SEQ ID NO 545
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 545

```
Pro Gly Asp Ser Asp Ile
1               5
```

<210> SEQ ID NO 546
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 546

```
Ala Arg Ala Met Thr Thr Val Thr Pro Phe Asp Tyr
1               5                   10
```

<210> SEQ ID NO 547
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 547

```
Gly Gly Ser Ile Ser Ser Arg Asn Phe Phe
1               5                   10
```

<210> SEQ ID NO 548
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 548

```
Ile Phe Tyr Ser Gly Gly Thr
1               5
```

<210> SEQ ID NO 549
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 549

```
Ala Arg His Met Ile Val Val Leu Pro Gly Val Pro Ile Ser Thr Ser
1               5                   10                  15

Phe Asp Pro

<210> SEQ ID NO 550
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 550

Gly Phe Thr Phe Ser Asn Tyr Gly
1               5

<210> SEQ ID NO 551
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 551

Ile Trp Phe Asp Gly Ser Asn Lys
1               5

<210> SEQ ID NO 552

<400> SEQUENCE: 552

000

<210> SEQ ID NO 553
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 553

Gly Phe Thr Phe Ser Asp Tyr Ala
1               5

<210> SEQ ID NO 554
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 554

Ile Ser Ser Asn Gly His Ser Thr
1               5

<210> SEQ ID NO 555
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 555

Val Arg Cys Leu Leu Arg Gly Leu Ile Ser Pro Phe Asp Tyr
1               5                   10

<210> SEQ ID NO 556
```

```
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 556

Gly Phe Ile Phe Thr Arg Tyr Gly
1               5

<210> SEQ ID NO 557
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 557

Ile Ser Ser Asp Gly Thr Asn Arg
1               5

<210> SEQ ID NO 558
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 558

Ala Arg Leu Ser Leu Glu Ala Ala Trp Tyr Phe Asp Leu
1               5                   10

<210> SEQ ID NO 559
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 559

Gly Phe Thr Phe Ser Ser Tyr Ala
1               5

<210> SEQ ID NO 560
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 560

Ile Ser Gly Ser Gly Gly Ser Thr
1               5

<210> SEQ ID NO 561
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 561

Ala Lys Asp Asn Asn Tyr Tyr Tyr Tyr Gly Met Asp Val
1               5                   10

<210> SEQ ID NO 562
<211> LENGTH: 8
```

```
<212> TYPE: PRT
<213> ORGANISM: Artificial sequence
<220> FEATURE:
<223> OTHER INFORMATION: Synthetic amino acid sequence

<400> SEQUENCE: 562

Gly Phe Thr Phe Ser Ser Tyr Gly
1               5

<210> SEQ ID NO 563
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 563

Ile Trp Phe Asp Gly Ser Asn Lys
1               5

<210> SEQ ID NO 564
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 564

Ala Arg Val Ala Arg Asp Tyr Ser Asn Ile Phe Asp Ala Phe Asp Ile
1               5                   10                  15

<210> SEQ ID NO 565
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 565

Gly Gly Ser Ile Ser Ser Arg Ser Tyr Tyr
1               5                   10

<210> SEQ ID NO 566
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 566

Ile Tyr Tyr Ser Gly Ser Thr
1               5

<210> SEQ ID NO 567
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 567

Val Arg Ile Ala Val Ala Ala Ala Gly Thr Asp Tyr
1               5                   10

<210> SEQ ID NO 568
<211> LENGTH: 8
<212> TYPE: PRT
```

<210> SEQ ID NO 568
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 568

Gly Tyr Asn Leu Thr Thr Tyr Asp
1               5

<210> SEQ ID NO 569
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 569

Met Asn Pro Lys Ser Gly Asn Thr
1               5

<210> SEQ ID NO 570
<211> LENGTH: 23
<212> TYPE: PRT
<213> ORGANISM: Artificial sequence
<220> FEATURE:
<223> OTHER INFORMATION: Synthetic amino acid sequence

<400> SEQUENCE: 570

Ala Arg Ser Leu Asp Ser Leu Arg Phe Leu Glu Trp Phe His Gln Asn
1               5                   10                  15

Tyr Tyr Tyr Phe Met Asp Val
            20

<210> SEQ ID NO 571
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 571

Gly Ile Pro Phe Gly Asp Tyr Ala
1               5

<210> SEQ ID NO 572
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 572

Ile Lys Ser Lys Ala Tyr Gly Gly Thr Pro
1               5                   10

<210> SEQ ID NO 573
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 573

Ser Ala Thr Leu Thr Arg Gly Glu Leu Phe Asp Tyr
1               5                   10

<210> SEQ ID NO 574

```
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 574

Gly Asp Ser Val Asn Ser Gly Ser Phe Tyr
1               5                   10

<210> SEQ ID NO 575
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 575

Ile Tyr Tyr Ser Gly Thr Thr
1               5

<210> SEQ ID NO 576
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 576

Val Arg Glu Trp Pro Arg His Tyr Asp Asn Arg Gly Tyr His Thr Leu
1               5                   10                  15

Pro Gly Thr

<210> SEQ ID NO 577
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 577

Gly Phe Asn Phe Ser Tyr Tyr Gly
1               5

<210> SEQ ID NO 578
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 578

Ile Ser Tyr Asp Gly Ser Asp Lys
1               5

<210> SEQ ID NO 579
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 579

Gln Met Val Lys Val Pro Phe Tyr Phe
1               5
```

```
<210> SEQ ID NO 580
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 580

Gly Asp Ser Phe Arg Ser Tyr Ala
1               5

<210> SEQ ID NO 581
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 581

Ile Ile Pro Arg Phe Gly Thr Thr
1               5

<210> SEQ ID NO 582
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 582

Ala Arg Pro Gln Ser Ala Tyr Asp Phe Gly Pro Phe Asp His
1               5                   10

<210> SEQ ID NO 583
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 583

Gly Phe Thr Ile Ser Ser Tyr Gly
1               5

<210> SEQ ID NO 584
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 584

Ile Trp Tyr Asp Gly Thr Asn Lys
1               5

<210> SEQ ID NO 585
<211> LENGTH: 13
<212> TYPE: PRT
<213> ORGANISM: Artificial sequence
<220> FEATURE:
<223> OTHER INFORMATION: Synthetic amino acid sequence

<400> SEQUENCE: 585

Val Arg Thr Gln Gln Val Ile Arg Pro Phe Phe Asp His
1               5                   10

<210> SEQ ID NO 586
```

-continued

```
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 586

Gly Gly Thr Phe Ser Asn Tyr Ser
1               5

<210> SEQ ID NO 587
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 587

Ile Ile Pro Ile Ser Gly Thr Ala
1               5

<210> SEQ ID NO 588
<211> LENGTH: 22
<212> TYPE: PRT
<213> ORGANISM: Artificial sequence
<220> FEATURE:
<223> OTHER INFORMATION: Synthetic amino acid sequence

<400> SEQUENCE: 588

Ala Arg Asp Cys Tyr Gly Val Phe Trp Ser Gly Tyr Phe Ser Arg Cys
1               5                   10                  15

His Phe Gly Met Asp Val
            20

<210> SEQ ID NO 589
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 589

Gly Phe Thr Phe Ser Asn Tyr Ala
1               5

<210> SEQ ID NO 590
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 590

Phe Ser Gly Thr Gly Gly Ser Thr
1               5

<210> SEQ ID NO 591
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 591

Ala Lys Asp Arg Gly Ile Val Gly Thr Thr Arg Phe Asp Ser
1               5                   10
```

<210> SEQ ID NO 592
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 592

Gly Phe Ala Phe Ser Gly Ser Ala
1               5

<210> SEQ ID NO 593
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 593

Ile Arg Asn Lys Pro Asn Asn Tyr Ala Thr
1               5                   10

<210> SEQ ID NO 594
<211> LENGTH: 22
<212> TYPE: PRT
<213> ORGANISM: Artificial sequence
<220> FEATURE:
<223> OTHER INFORMATION: Synthetic amino acid sequence

<400> SEQUENCE: 594

Thr Arg Arg Met Asp His Ala Arg Arg Pro Ala Arg Glu Asp Tyr Tyr
1               5                   10                  15

Asn Asn Gly Met Asp Ile
            20

<210> SEQ ID NO 595
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 595

Gly Phe Ser Phe Ser Asn Tyr Gly
1               5

<210> SEQ ID NO 596
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 596

Ile Arg Phe Asp Gly Thr Asp Lys
1               5

<210> SEQ ID NO 597
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 597

Ala Lys Asp Leu Ala Met Met Ile Ala Asn Pro Leu Asp Cys

```
1               5                    10
```

<210> SEQ ID NO 598
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 598

```
Gly Gly Thr Phe Asn Ser Phe Ala
1               5
```

<210> SEQ ID NO 599
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 599

```
Ile Ile Pro Leu Phe Gly Thr Thr
1               5
```

<210> SEQ ID NO 600
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 600

```
Ala Arg Val Phe Ser Ala Ala Gly His
1               5
```

<210> SEQ ID NO 601
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 601

```
Gly Phe Thr Phe Arg Ser Tyr Ala
1               5
```

<210> SEQ ID NO 602
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 602

```
Ile Ser Tyr Asp Ala Asn Asn Glu
1               5
```

<210> SEQ ID NO 603
<211> LENGTH: 27
<212> TYPE: PRT
<213> ORGANISM: Artificial sequence
<220> FEATURE:
<223> OTHER INFORMATION: Synthetic amino acid sequence

<400> SEQUENCE: 603

```
Ala Arg Gly Leu Ile Pro Ser Ala Glu Gln Trp Gln Ala Arg Gly Gly
1               5                   10                  15
```

Pro Asp Tyr Tyr Tyr Tyr Gly Met Ala Val
            20                  25

<210> SEQ ID NO 604
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 604

Gly Ala Thr Phe Ser Ser Tyr Val
1               5

<210> SEQ ID NO 605
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 605

Ile Leu Pro Ile Leu Asp Ile Pro
1               5

<210> SEQ ID NO 606
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 606

Ala Arg Gly Gly Gly Ala Val Thr Gly Arg Gly Tyr Tyr Phe Asp Tyr
1               5                   10                  15

<210> SEQ ID NO 607
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 607

Gly Gly Thr Leu Asn Ser Tyr Ala
1               5

<210> SEQ ID NO 608
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 608

Ile Ile Pro Met Val Gly Met Ala
1               5

<210> SEQ ID NO 609
<211> LENGTH: 14
<212> TYPE: PRT
<213> ORGANISM: Artificial sequence
<220> FEATURE:
<223> OTHER INFORMATION: Synthetic amino acid sequence

<400> SEQUENCE: 609

Ala Arg Glu Gln Lys Leu Val Gly Gly Gly Trp Phe Asp Pro
1               5                   10

<210> SEQ ID NO 610
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 610

Gly Gly Thr Leu Ser Asn Ser Ala
1               5

<210> SEQ ID NO 611
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 611

Ile Ile Pro Ile Leu Gly Ile Pro
1               5

<210> SEQ ID NO 612
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 612

Ala Ser Pro Gln Arg Val Leu Arg Phe Leu Gln Trp Ser Pro Phe Asp
1               5                   10                  15

Tyr

<210> SEQ ID NO 613
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 613

Gly Phe Ser Leu Ser Ser Tyr Gly
1               5

<210> SEQ ID NO 614
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 614

Ile Trp Tyr Asp Gly Ser Asn Lys
1               5

<210> SEQ ID NO 615
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 615

Ala Arg Gly Val Arg Met Thr Thr Ser Leu Asp Tyr
1               5                   10

<210> SEQ ID NO 616
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 616

Gly Gly Ser Ile Ser Ser Tyr Tyr
1               5

<210> SEQ ID NO 617
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 617

Met Ser His Ser Gly Ser Thr
1               5

<210> SEQ ID NO 618
<211> LENGTH: 22
<212> TYPE: PRT
<213> ORGANISM: Artificial sequence
<220> FEATURE:
<223> OTHER INFORMATION: Synthetic amino acid sequence

<400> SEQUENCE: 618

Ala Arg Gly Val Gly Gly Val Tyr Asp Ile Leu Thr Gly Tyr Trp Gly
1               5                   10                  15

Pro Asn Trp Phe Asp Pro
            20

<210> SEQ ID NO 619
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 619

Gly Phe Thr Phe Ser Asp Tyr Tyr
1               5

<210> SEQ ID NO 620
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 620

Ile Ser Gly Gly Gly Asn Thr Ile
1               5

<210> SEQ ID NO 621
<211> LENGTH: 19
<212> TYPE: PRT
<213> ORGANISM: Artificial sequence
<220> FEATURE:
<223> OTHER INFORMATION: Synthetic amino acid sequence -continued

```
<400> SEQUENCE: 621

Ala Arg Asn Leu Arg Ala Ala Gly Val Asn Tyr Phe Tyr Phe Tyr Tyr
1               5                   10                  15
Met Asp Val

<210> SEQ ID NO 622
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 622

Gly Tyr Thr Ser Met Ser Asp Tyr
1               5

<210> SEQ ID NO 623
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 623

Met Asn Pro Leu Gly Gly Ser Thr
1               5

<210> SEQ ID NO 624
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 624

Val Val Ser Ser Gly Phe Gln Gln Trp Phe Asp Pro
1               5                   10

<210> SEQ ID NO 625
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 625

Gln Asp Ile Ser Ser Tyr
1               5

<210> SEQ ID NO 626
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 626

Ala Ala Ser
1

<210> SEQ ID NO 627
<211> LENGTH: 11
<212> TYPE: PRT
<213> ORGANISM: Artificial sequence
<220> FEATURE:
```

<223> OTHER INFORMATION: Synthetic amino acid sequence

<400> SEQUENCE: 627

Gln His Leu Asn Ser Tyr Pro Arg Gly Tyr Thr
1               5                   10

<210> SEQ ID NO 628
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 628

Gln Ser Ile Thr Ser Trp
1               5

<210> SEQ ID NO 629
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 629

Lys Ala Ser
1

<210> SEQ ID NO 630
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 630

Gln Gln Tyr Asn Ser Tyr Pro Tyr Thr
1               5

<210> SEQ ID NO 631
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 631

Ser Ser Asn Ile Gly Ala Gly Tyr Asp
1               5

<210> SEQ ID NO 632
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 632

Gly Asn Ile
1

<210> SEQ ID NO 633
<211> LENGTH: 11
<212> TYPE: PRT
<213> ORGANISM: Artificial sequence
<220> FEATURE:
<223> OTHER INFORMATION: Synthetic amino acid sequence

```
<400> SEQUENCE: 633

Gln Ser Tyr Asp Ser Ser Leu Ser Gly Ala Leu
1               5                   10

<210> SEQ ID NO 634
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 634

Ser Ser Asn Ile Gly Asn Asn Tyr
1               5

<210> SEQ ID NO 635
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 635

Asp Asn Tyr
1

<210> SEQ ID NO 636
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 636

Gly Thr Trp Asp Leu Ser Leu Ser Ala Gly Val
1               5                   10

<210> SEQ ID NO 637
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 637

Gln Ser Leu Leu His Ser Asn Gly Tyr Asn Tyr
1               5                   10

<210> SEQ ID NO 638
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 638

Leu Gly Ser
1

<210> SEQ ID NO 639
<211> LENGTH: 9
<212> TYPE: PRT
<213> ORGANISM: Artificial sequence
<220> FEATURE:
<223> OTHER INFORMATION: Synthetic amino acid sequence
```

<400> SEQUENCE: 639

Met Leu Ala Leu Arg Thr Pro Gly Ala
1               5

<210> SEQ ID NO 640
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 640

Gln Ser Leu Leu His Ser Asn Gly Tyr Asn Tyr
1               5                   10

<210> SEQ ID NO 641
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 641

Leu Gly Ser
1

<210> SEQ ID NO 642
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 642

Met Gln Ala Leu Gln Thr Pro Gly Ala
1               5

<210> SEQ ID NO 643
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 643

Pro Gly Ile Cys Asn Tyr
1               5

<210> SEQ ID NO 644
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 644

Ala Ala Ser
1

<210> SEQ ID NO 645
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 645

```
Gln Lys Tyr Asn Ser Ala Pro His Thr
1               5
```

<210> SEQ ID NO 646
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 646

```
Ala Leu Pro Asn Gln Tyr
1               5
```

<210> SEQ ID NO 647
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 647

```
Lys Asp Ser
1
```

<210> SEQ ID NO 648
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 648

```
Gln Ser Ala Asp Ser Ser Gly Thr Ser Val Val
1               5                   10
```

<210> SEQ ID NO 649
<211> LENGTH: 7
<212> TYPE: PRT
<213> ORGANISM: Artificial sequence
<220> FEATURE:
<223> OTHER INFORMATION: Synthetic amino acid sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 649

```
Gln Ser Val Thr Ser Xaa Tyr
1               5
```

<210> SEQ ID NO 650
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 650

```
Ser Ala Ser
1
```

<210> SEQ ID NO 651
<211> LENGTH: 10
<212> TYPE: PRT
<213> ORGANISM: Artificial sequence
<220> FEATURE:

<223> OTHER INFORMATION: Synthetic amino acid sequence

<400> SEQUENCE: 651

Gln Gln Tyr Gly Ser Ser Pro Pro Tyr Thr
1               5                   10

<210> SEQ ID NO 652
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 652

Ser Ser Asn Ile Gly Asn Asn Tyr
1               5

<210> SEQ ID NO 653
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 653

Asp Asn Asn
1

<210> SEQ ID NO 654
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 654

Gly Thr Trp Asp Ser Ser Leu Ser Ala Tyr Val
1               5                   10

<210> SEQ ID NO 655
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 655

Ser Ser Asn Ile Gly Ala Asp Tyr Asp
1               5

<210> SEQ ID NO 656
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 656

Gly Asn Ser
1

<210> SEQ ID NO 657
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 657

Gln Ser His Asp Ser Ser Leu Ser Gly Tyr Val
1               5                   10

<210> SEQ ID NO 658
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 658

Gln Ser Leu Leu His Arg Asn Gly Tyr Asn Tyr
1               5                   10

<210> SEQ ID NO 659
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 659

Leu Gly Ser
1

<210> SEQ ID NO 660

<400> SEQUENCE: 660

000

<210> SEQ ID NO 661
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 661

Gln Ser Val Ser Ser Asn
1               5

<210> SEQ ID NO 662
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 662

Gly Ala Ser
1

<210> SEQ ID NO 663

<400> SEQUENCE: 663

000

<210> SEQ ID NO 664
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 664

Gln Ser Val Ser Ser Tyr
1               5

<210> SEQ ID NO 665
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 665

Gly Ala Ser
1

<210> SEQ ID NO 666
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 666

Gln Ser Leu Val Asn Ser Asp Gly Asn Thr Tyr
1               5                   10

<210> SEQ ID NO 667
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 667

Lys Val Ser
1

<210> SEQ ID NO 668
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 668

Met Gln Gly Thr His Trp Pro Pro Arg Trp Thr
1               5                   10

<210> SEQ ID NO 669
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 669

Val Leu Arg Asp Asn Tyr
1               5

<210> SEQ ID NO 670
<211> LENGTH: 3
<212> TYPE: PRT
<213> ORGANISM: Artificial sequence
<220> FEATURE:
<223> OTHER INFORMATION: Synthetic amino acid sequence -continued

```
<400> SEQUENCE: 670

Lys Asp Glu
1

<210> SEQ ID NO 671

<400> SEQUENCE: 671

000

<210> SEQ ID NO 672
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 672

Ser Ser Asn Ile Gly Asn Asn Tyr
1               5

<210> SEQ ID NO 673
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 673

Asp Asn Asn
1

<210> SEQ ID NO 674
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 674

Gly Thr Trp Asp Ser Ser Leu Ser Glu Val Val
1               5                   10

<210> SEQ ID NO 675
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 675

Gln Ser Val Ser Ser Asn
1               5

<210> SEQ ID NO 676
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 676

Gly Ala Ser
1

<210> SEQ ID NO 677
```

```
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 677

Gln Gln Tyr Asn Asn Trp Pro Arg Thr
1               5

<210> SEQ ID NO 678
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 678

Gln Asn Leu Leu His Ser Asn Gly Tyr Asn Tyr
1               5                   10

<210> SEQ ID NO 679
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 679

Leu Gly Ser
1

<210> SEQ ID NO 680
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 680

Met Gln Ala Leu Gln Thr Pro Ile Thr
1               5

<210> SEQ ID NO 681
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 681

Gln Ser Ile Arg Asn Tyr
1               5

<210> SEQ ID NO 682
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 682

Ala Ala Ser
1

<210> SEQ ID NO 683
<211> LENGTH: 10
```

```
<212> TYPE: PRT
<213> ORGANISM: Artificial sequence
<220> FEATURE:
<223> OTHER INFORMATION: Synthetic amino acid sequence

<400> SEQUENCE: 683

Gln Gln Ser Tyr Ser Thr Pro Pro Leu Thr
1               5                   10

<210> SEQ ID NO 684
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 684

Gln Ser Val Ser Ser Ser Tyr
1               5

<210> SEQ ID NO 685
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 685

Gly Ala Ser
1

<210> SEQ ID NO 686
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 686

Gln Gln Tyr Gly Ser Ser Pro Tyr Thr
1               5

<210> SEQ ID NO 687
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 687

Asn Ile Gly Ser Lys Ser
1               5

<210> SEQ ID NO 688
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 688

Asp Asp Ser
1

<210> SEQ ID NO 689

<400> SEQUENCE: 689
```

000

<210> SEQ ID NO 690
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 690

Gln Ser Leu Leu His Ser Asn Gly Tyr Asn Tyr
1               5                   10

<210> SEQ ID NO 691
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 691

Leu Gly Ser
1

<210> SEQ ID NO 692
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 692

Leu Gln Ala Leu Gln Thr Leu Pro Ile Thr
1               5                   10

<210> SEQ ID NO 693
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 693

Gln Ser Ile His His Asn Tyr
1               5

<210> SEQ ID NO 694
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 694

Gly Ala Ser
1

<210> SEQ ID NO 695
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 695

Gln Gln Tyr Gly Asn Ser Val Pro Tyr Ser 1               5                    10

<210> SEQ ID NO 696
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 696

Gln Arg Ile Ser Ser His
1               5

<210> SEQ ID NO 697
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 697

Val Ala Ser
1

<210> SEQ ID NO 698
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 698

Gln Gln Ser Tyr Thr Thr Pro Tyr Thr
1               5

<210> SEQ ID NO 699
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 699

Gln Ser Ile Gly Asn Tyr
1               5

<210> SEQ ID NO 700
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 700

Asp Ala Ser
1

<210> SEQ ID NO 701
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 701

Gln Gln Arg Ser His Trp Pro Ala
1               5

```
<210> SEQ ID NO 702
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 702

Ser Ser Asp Val Gly Ser Tyr Asn Leu
1               5

<210> SEQ ID NO 703
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 703

Glu Val Ser
1

<210> SEQ ID NO 704
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 704

Cys Ser Tyr Val Gly Ser Ser Thr Ser Val
1               5                   10

<210> SEQ ID NO 705
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 705

Gln Ser Val Ser Asn Thr Tyr
1               5

<210> SEQ ID NO 706
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 706

Ala Ala Ser
1

<210> SEQ ID NO 707

<400> SEQUENCE: 707

000

<210> SEQ ID NO 708
<211> LENGTH: 7
<212> TYPE: PRT
<213> ORGANISM: Artificial sequence
<220> FEATURE:
```

<223> OTHER INFORMATION: Synthetic amino acid sequence

<400> SEQUENCE: 708

Gln Ser Val Ser Ser Thr Tyr
1               5

<210> SEQ ID NO 709
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 709

Gly Ala Ser
1

<210> SEQ ID NO 710
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 710

Gln Gln Tyr Asp Ser Ser Pro Ser Ile Thr
1               5                   10

<210> SEQ ID NO 711
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 711

Gln Thr Val Leu Tyr Asn Ser Asn Asn Tyr Ser Tyr
1               5                   10

<210> SEQ ID NO 712
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 712

Trp Ala Ser
1

<210> SEQ ID NO 713
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 713

Gln Gln Tyr Tyr Ser Thr Pro Trp Thr
1               5

<210> SEQ ID NO 714
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 714

Gln Ser Val Thr Ser Ser Tyr
1               5

<210> SEQ ID NO 715
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 715

Gly Ala Ser
1

<210> SEQ ID NO 716

<400> SEQUENCE: 716

000

<210> SEQ ID NO 717
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 717

Ile Ser Asp Val Gly Gly Tyr Asn Tyr
1               5

<210> SEQ ID NO 718
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 718

Asp Val Asn
1

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 723

Gln Ser Val Ser Ser Thr
1               5

<210> SEQ ID NO 724
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 724

Gly Ala Ser
1

<210> SEQ ID NO 725
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 725

Gln His Tyr Asn Asn Trp Pro Pro Leu Leu Thr
1               5                   10

<210> SEQ ID NO 726
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 726

Gln Ser Val Leu Tyr Ser Ser Asn Asn Lys Asn Tyr
1               5                   10

<210> SEQ ID NO 727
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 727

Trp Ala Ser
1

<210> SEQ ID NO 728
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 728

Gln Gln Tyr Tyr Ser Thr Pro Trp Thr
1               5

```
<210> SEQ ID NO 729
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 729

Gln Ser Leu Val Tyr Ser Asp Gly Asp Thr Tyr
1               5                   10

<210> SEQ ID NO 730
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 730

Lys Val Ser
1

<210> SEQ ID NO 731
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 731

Met Gln Gly Thr His Trp Pro Arg Thr
1               5

<210> SEQ ID NO 732
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 732

His Asn Leu Asn Ser Asn Tyr
1               5

<210> SEQ ID NO 733
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 733

Gly Ala Ser
1

<210> SEQ ID NO 734
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 734

Gln Gln Tyr Ala Gly Ser Leu Thr
1               5
```

```
<210> SEQ ID NO 735
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 735

Gln Ser Val Leu Tyr Ser Ser Asn Asn Lys Asn Tyr
1               5                   10

<210> SEQ ID NO 736
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 736

Trp Ala Ser
1

<210> SEQ ID NO 737
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 737

Gln Gln Tyr Tyr Ser Ser Pro Leu Thr
1               5

<210> SEQ ID NO 738
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 738

Ser Ser Asn Ile Gly Ile Asn Tyr
1               5

<210> SEQ ID NO 739
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 739

Arg Asn Asn
1

<210> SEQ ID NO 740
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 740

Ala Ala Trp Asp Asp Ser Leu Ser Gly Lys Val
1               5                   10

<210> SEQ ID NO 741
```

```
<400> SEQUENCE: 741

000

<210> SEQ ID NO 742

<400> SEQUENCE: 742

000

<210> SEQ ID NO 743

<400> SEQUENCE: 743

000

<210> SEQ ID NO 744
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 744

Thr Gly Ala Val Thr Ser Gly Phe Phe
1               5

<210> SEQ ID NO 745
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 745

Ser Thr Asn
1

<210> SEQ ID NO 746
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 746

Leu Leu Tyr Tyr Gly Gly Val Val Val
1               5

<210> SEQ ID NO 747
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 747

Ser Ser Asp Val Gly Ala Tyr Thr Phe
1               5

<210> SEQ ID NO 748
<211> LENGTH: 3
<212> TYPE: PRT
<213> ORGANISM: Artificial sequence
<220> FEATURE:
<223> OTHER INFORMATION: Synthetic amino acid sequence
```

```
<400> SEQUENCE: 748

Glu Val Ser
1

<210> SEQ ID NO 749
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 749

Asn Ser Tyr Thr Thr Thr Ser Pro Trp Val
1               5                   10

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 753

Gln Ser Val Arg Ser Asn Tyr
1               5

<210> SEQ ID NO 754
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 754

Gly Ala Ser
1

<210> SEQ ID NO 755
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 755

Gln Gln Tyr Gly Ser Ser Pro Pro Thr
1               5
```

```
<210> SEQ ID NO 756
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 756

Thr Ser Asp Ile Gly Thr Tyr Asp Tyr
1               5

<210> SEQ ID NO 757
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 757

Asp Val Ser
1

<210> SEQ ID NO 758
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 758

Ser Ser Tyr Thr Ser Gly Leu Thr Trp Val
1               5                   10

<210> SEQ ID NO 759
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 759

Gln Ser Val Ser Ser Tyr
1               5

<210> SEQ ID NO 760
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 760

Asp Thr Ser
1

<210> SEQ ID NO 761
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 761

Gln Leu Arg Asn Ser Trp Pro Pro Thr
1               5

<210> SEQ ID NO 762
```

```
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 762

Gln Ser Val Gly Asn Tyr
1               5

<210> SEQ ID NO 763
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 763

Asp Gly Ser
1

<210> SEQ ID NO 764
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 764

Leu Gln Arg Ser Asp Leu Tyr Thr
1               5

<210> SEQ ID NO 765

<400> SEQUENCE: 765

000

<210> SEQ ID NO 766

<400> SEQUENCE: 766

000

<210> SEQ ID NO 767

<400> SEQUENCE: 767

000

<210> SEQ ID NO 768
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 768

Ser Ser Asn Ile Gly Ala Gly Tyr Asp
1               5

<210> SEQ ID NO 769
<211> LENGTH: 3
<212> TYPE: PRT
<213> ORGANISM: Artificial sequence
<220> FEATURE:
<223> OTHER INFORMATION: Synthetic amino acid sequence
```

```
<400> SEQUENCE: 769

Gly Asn Ser
1

<210> SEQ ID NO 770
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 770

Gln Ser Tyr Asp Ser Ser Leu Ser Gly Arg Glu Val
1               5                   10

<210> SEQ ID NO 771
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 771

Gln Ser Val Ser Ser Ile Tyr
1               5

<210> SEQ ID NO 772
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 772

Gly Ala Ser
1

<210> SEQ ID NO 773
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 773

Gln Gln Tyr Gly Ser Arg Gly Thr
1               5

<210> SEQ ID NO 774
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 774

Ser Ser Asp Val Gly Gly Tyr Asn Tyr
1               5

<210> SEQ ID NO 775
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 775
```

```
Glu Val Asn
1

<210> SEQ ID NO 776
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 776

Ser Ser Tyr Ala Gly Thr Glu Thr Val Ala
1               5                   10

<210> SEQ ID NO 777
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 777

Gln Ser Leu Leu His Tyr Asn Gly Asn Asn Tyr
1               5                   10

<210> SEQ ID NO 778
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 778

Leu Gly Ser
1

<210> SEQ ID NO 779
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 779

Met Gln Ala Arg His Thr Pro
1               5

<210> SEQ ID NO 780
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 780

Gln Asp Ile Ser Asn Ser
1               5

<210> SEQ ID NO 781
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 781
```

Asp Ala Ser
1

<210> SEQ ID NO 782
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 782

Gln Gln Phe His Ser Leu Pro Pro Thr
1               5

<210> SEQ ID NO 783
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 783

Ser Ser Asn Ile Gly Ala Gly Tyr Ala
1               5

<210> SEQ ID NO 784
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 784

Gly Asn Asn
1

<210> SEQ ID NO 785
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 785

Gln Ser Tyr Asp Ser Ser Leu Ser Gly Trp Val
1               5                   10

<210> SEQ ID NO 786
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 786

Ala Leu Pro Lys Gln Tyr
1               5

<210> SEQ ID NO 787
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 787

Lys Asp Ser

```
<210> SEQ ID NO 788
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 788

Gln Ser Ala Asp Ser Ser Gly Thr Tyr Pro Val Val
1               5                   10

<210> SEQ ID NO 789
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 789

Ser Ser Asp Val Gly Ser Tyr Asn Leu
1               5

<210> SEQ ID NO 790
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 790

Glu Val Ser
1

<210> SEQ ID NO 791
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 791

Cys Ser Tyr Ala Gly Ser Ser Thr Leu Val
1               5                   10

<210> SEQ ID NO 792
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 792

Ala Leu Pro Glu Gln Tyr
1               5

<210> SEQ ID NO 793
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 793

Lys Asp Ser
1
```

```
<210> SEQ ID NO 794
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 794

Gln Ser Ala Asp Asn Ser Gly Thr Tyr Glu Val
1               5                   10

<210> SEQ ID NO 795
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 795

Gln Ser Leu Leu His Ser Asn Gly Tyr Asn Tyr
1               5                   10

<210> SEQ ID NO 796
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 796

Leu Gly Ser
1

<210> SEQ ID NO 797
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 797

Met Gln Ala Leu Gln Thr Pro Ile Thr
1               5

<210> SEQ ID NO 798
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 798

Gln Ser Ile Ala Ser Tyr
1               5

<210> SEQ ID NO 799
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 799

Ala Ala Ser
1
```

<210> SEQ ID NO 800
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 800

Gln Gln Ser Tyr Ser Thr Pro Gln Thr
1               5

<210> SEQ ID NO 801
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 801

Lys Leu Gly Asp Thr Tyr
1               5

<210> SEQ ID NO 802
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 802

Gln Asp Thr
1

<210> SEQ ID NO 803
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 803

Gln Ala Trp Asp Ser Ala Thr Val Val
1               5

<210> SEQ ID NO 804
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 804

Gln Ser Val Leu Ser Asn Ser Asn Asn Lys Asn Tyr
1               5                   10

<210> SEQ ID NO 805
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 805

Trp Ala Ser
1

```
<210> SEQ ID NO 806
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 806

Gln Gln Tyr Tyr Ser Pro Pro Ala Glu Leu Ser
1               5                   10

<210> SEQ ID NO 807
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 807

Asp Ile Gly Phe Lys Gly
1               5

<210> SEQ ID NO 808
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 808

Asp Asp Arg
1

<210> SEQ ID NO 809

<400> SEQUENCE: 809

000

<210> SEQ ID NO 810
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 810

Ser Ser Asn Ile Gly Asn Asn Ala
1               5

<210> SEQ ID NO 811
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 811

Tyr Asp Asp
1

<210> SEQ ID NO 812
<211> LENGTH: 11
<212> TYPE: PRT
<213> ORGANISM: Artificial sequence
<220> FEATURE:
<223> OTHER INFORMATION: Synthetic amino acid sequence
```

```
<400> SEQUENCE: 812

Ser Thr Trp Asp Tyr Ser Leu Ser Ala Arg Val
1               5                   10

<210> SEQ ID NO 813
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 813

Ser Ser Asn Ile Gly Ala Gly Tyr Asp
1               5

<210> SEQ ID NO 814
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 814

Gly Asn Thr
1

<210> SEQ ID NO 815
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 815

Gln Ser Tyr Asp Asn Ser Leu Asn Gly Pro Trp Val
1               5                   10

<210> SEQ ID NO 816
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 816

Gln Gly Ile Arg Asn Asp
1               5

<210> SEQ ID NO 817
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 817

Ala Ala Ser
1

<210> SEQ ID NO 818
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 818
```

```
Leu Gln Asp Tyr Asn Tyr Pro Arg Met
1               5

<210> SEQ ID NO 819
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 819

Arg Ser Ile Ser Thr Tyr
1               5

<210> SEQ ID NO 820
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 820

Ala Ala Ser
1

<210> SEQ ID NO 821
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 821

Gln Gln Ser Tyr Ser Thr Pro Ile Thr
1               5

<210> SEQ ID NO 822
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 822

Gln Ser Ile Ser Ser Asn
1               5

<210> SEQ ID NO 823
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 823

Gly Ala Ser
1

<210> SEQ ID NO 824
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 824
```

```
Gln Gln Tyr Asn Asn Trp Pro Pro Tyr Thr
1               5                   10

<210> SEQ ID NO 825
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 825

Gln Thr Ile Gly Gly Tyr
1               5

<210> SEQ ID NO 826
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 826

Asp Ala Ser
1

<210> SEQ ID NO 827
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 827

Gln Leu Arg Ser Thr
1               5

<210> SEQ ID NO 828
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 828

Gln Ser Val Ser Asn Tyr
1               5

<210> SEQ ID NO 829
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 829

Asp Ala Ser
1

<210> SEQ ID NO 830
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 830

Gln Gln Arg Ser Asn Trp Pro Leu Thr
```

```
1               5

<210> SEQ ID NO 831
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 831

Gln Ser Ile Ser Ser Trp
1               5

<210> SEQ ID NO 832
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 832

Lys Ala Ser
1

<210> SEQ ID NO 833
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 833

Gln Gln Tyr Asn Thr Asp Ser Ser Arg Thr
1               5                   10

<210> SEQ ID NO 834
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 834

Glu Leu Pro Lys Arg Tyr
1               5

<210> SEQ ID NO 835
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 835

Glu Asp Thr
1

<210> SEQ ID NO 836
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 836

Tyr Ser Thr Asp Ser Thr Ser Asn His Lys Arg Val
1               5                   10
```

```
<210> SEQ ID NO 837
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 837

Asn Ile Gly Ser Lys Gly
1               5

<210> SEQ ID NO 838
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 838

Tyr Asp Ser
1

<210> SEQ ID NO 839
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 839

His Val Trp His Thr Thr Thr Asp His Tyr Val
1               5                   10

<210> SEQ ID NO 840
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 840

Gln Ser Ile Ser Ser Asn
1               5

<210> SEQ ID NO 841
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 841

Gly Ala Ser
1

<210> SEQ ID NO 842
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 842

Gln Gln Tyr Lys Asn Trp Pro Pro Trp Thr
1               5                   10
```

<210> SEQ ID NO 843
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 843

Gln Ser Val Arg Ser Ser His
1               5

<210> SEQ ID NO 844
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 844

Gly Ala Ser
1

<210> SEQ ID NO 845
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 845

Gln Gln Tyr Gly Gly Ser Pro Leu Leu Thr
1               5                   10

<210> SEQ ID NO 846
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 846

Gln Ser Val Ser Ser Asn
1               5

<210> SEQ ID NO 847
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 847

Gly Ala Ser
1

<210> SEQ ID NO 848
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 848

Gln Gln Tyr Ser Asn Trp Pro Pro Ile Thr
1               5                   10

```
<210> SEQ ID NO 849
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 849

Gln Ser Val Ser Ser Ser Phe
1               5

<210> SEQ ID NO 850
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 850

Asp Ala Ser
1

<210> SEQ ID NO 851
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 851

Gln Gln Tyr Ser Ser Ser Pro Thr
1               5

<210> SEQ ID NO 852
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 852

Gln Ser Val Ser Ser Asn
1               5

<210> SEQ ID NO 853
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 853

Asp Ala Ser
1

<210> SEQ ID NO 854
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 854

Gln Gln Tyr Lys Asn Trp Gly Thr
1               5

<210> SEQ ID NO 855
```

```
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 855

Gln Ser Ile Ala Ser Tyr
1               5

<210> SEQ ID NO 856
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 856

Ala Ala Ser
1

<210> SEQ ID NO 857
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 857

Gln Gln Ser Tyr Ser Thr Pro Gln Thr
1               5

<210> SEQ ID NO 858

<400> SEQUENCE: 858

000

<210> SEQ ID NO 859

<400> SEQUENCE: 859

000

<210> SEQ ID NO 860

<400> SEQUENCE: 860

000

<210> SEQ ID NO 861
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 861

Gln Ser Ile Ser Ser Tyr
1               5

<210> SEQ ID NO 862
<211> LENGTH: 3
<212> TYPE: PRT
<213> ORGANISM: Artificial sequence
<220> FEATURE:
<223> OTHER INFORMATION: Synthetic amino acid sequence
```

```
<400> SEQUENCE: 862

Ala Ala Ser
1

<210> SEQ ID NO 863
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 863

Gln Gln Ser Tyr Ser Thr Pro Pro
1               5

<210> SEQ ID NO 864
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 864

Gln Ser Val Asn Ser Asp Tyr
1               5

<210> SEQ ID NO 865
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 865

Gly Val Ser
1

<210> SEQ ID NO 866
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 866

Gln Gln Tyr Gly His Ser Pro Tyr Thr
1               5

<210> SEQ ID NO 867
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 867

Gln Ser Val Ser Ser Ser Tyr
1               5

<210> SEQ ID NO 868
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 868
```

Asp Val Leu
1

<210> SEQ ID NO 869
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 869

Gln Gln Tyr Ala Ile Ser Pro Asn Thr
1               5

<210> SEQ ID NO 870
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 870

Ser Ser Asp Val Gly Gly Tyr Asn Tyr
1               5

<210> SEQ ID NO 871
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 871

Asp Val Ser
1

<210> SEQ ID NO 872
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 872

Ser Ser Tyr Thr Thr Ile Ser Thr Leu Gly Val
1               5                   10

<210> SEQ ID NO 873
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 873

Ser Ser Asn Ile Gly Ala Gly Tyr Asp
1               5

<210> SEQ ID NO 874
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 874

Ala Asn Thr
1

<210> SEQ ID NO 875
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 875

Gln Ser Phe Asp Ser Ser Leu Arg Gly Ser Val Val
1               5                   10

<210> SEQ ID NO 876
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 876

Gln Ser Val Ser Ser Ser
1               5

<210> SEQ ID NO 877
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 877

Asp Ala Ser
1

<210> SEQ ID NO 878
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 878

Gln Gln Arg Gly Lys Trp Pro Pro Trp Thr
1               5                   10

<210> SEQ ID NO 879
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 879

Gln Ser Leu Thr Thr Asn
1               5

<210> SEQ ID NO 880
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 880

Arg Ala Ser
1

<210> SEQ ID NO 881
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 881

Gln Gln Tyr Asn Asn Trp Pro Arg Thr
1               5

<210> SEQ ID NO 882
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 882
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcccgatct atttgggttc taatcgggcc     180
gccggggtcc ctgacaggtt cattggcagt ggatcaggca cagattttac actgaaaatc     240
ggcatattgg aggctgagga tgttggggtt tattattgca tgctcgctct acgaactccg     300
ggggctttcg gccctgggac caaggtggat ataaga                               336

<210> SEQ ID NO 883
<211> LENGTH: 379
<212> TYPE: DNA
<213> ORGANISM: Artificial sequence
<220> FEATURE:
<223> OTHER INFORMATION: Synthetic oligonucleotide

<400> SEQUENCE: 883
gaagtgcagc tggtggagtc tgggggaggc ttggtacagc ctggcaggtc cctgagactc      60
tcctgtgcag tctctggatt caccccttgat gattatgcca tgcactgggt ccggcaacct    120
ccagggaagg gcctggagtg ggtcacaggt attagttgga atagtggtgg catgggctat    180
gcggactctg tgaagggccg attcaccatc tccagagaca cgccaagaa ctccctctat     240 ctacaaatga acagtctgag agttgaggac acggccttct actactgtgc aaaagatgtt    300
ggaggggtgg tgactggagg ttattgggat gatgctcttg atatctgggg ccaagggaca    360
atggtcaccg tctcctcag                                                  379

<210> SEQ ID NO 884
<211> LENGTH: 382
<212> TYPE: DNA
<213> ORGANISM: Artificial sequence
<220> FEATURE:
<223> OTHER INFORMATION: Synthetic oligonucleotide

<400> SEQUENCE: 884
caggtgcagc tgcaggagtc gggcccagga ctggtgaagc cttcacagac cctgtccctc      60
acctgtactg tctctggtgg ctccatcagc agtggtggtt actactggag ttggatccgc    120
cagtacccag ggaagggcct ggagtggatc gggcacatgt cttatagtgg ggacaccttc    180
ttcaacccgt ccctcaagag tcgagctacc atatcagcgg acacgtctaa gcaccagttc    240

```
tccctgatgc tgagatctgt gactgccgcg acacggccg tgtatttatg tgcgagaggc    300
agatattgta atgatgacag ctgctactcc gaggagtctg ctatctggtt cgacccctgg    360
ggccagggaa ccctggtcac ct                                              382
```

<210> SEQ ID NO 885
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 885

```
cagcctgtgc tgactcagcc tgcctccgtg tctgggtctc ctggacagtc gatcaccatc     60
tcctgcactg gaaccaccag tgacattggt acttatgact atgcctcctg gtatcaacag    120
cacccaggca gaccccccaa actcatgatt tatgatgtca gtaagcggcc ctcagggggtt   180 tctggtcgct ctctctggctc caagtctggc aacacggcct ccctgaccat ctctggcctc   240
cagactgagg acgagtctca ttattactgc agctcatata aagcggcct cacttgggtg    300 ttcggcggag ggaccaagct gaccgtccta g                                   331
```

<210> SEQ ID NO 886
<211> LENGTH: 111
<212> TYPE: PRT
<213> ORGANISM: Artificial sequence
<220> FEATURE:
<223> OTHER INFORMATION: Synthetic amino acid

<400> SEQUENCE: 886

```
Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
Pro Gln Leu Pro Ile Tyr Leu Gly Ser Asn Arg Ala Ala Gly Val Pro
    50                  55                  60
Asp Arg Phe Ile Gly Ser Gly Ser Gly Thr Asp Phe Thr Leu Lys Ile
65                  70                  75                  80
Gly Ile Leu Ala Glu Asp Val Gly Val Tyr Tyr Cys Met Leu Ala Leu
                85                  90                  95
Arg Thr Pro Gly Ala Phe Gly Pro Gly Thr Lys Val Asp Ile Arg
            100                 105                 110
```

<210> SEQ ID NO 887
<211> LENGTH: 126
<212> TYPE: PRT
<213> ORGANISM: Artificial sequence
<220> FEATURE:
<223> OTHER INFORMATION: Synthetic amino acid

<400> SEQUENCE: 887

```
Glu Val Gln Leu Val Glu Ser Gly Gly Gly Leu Val Gln Pro Gly Arg
1               5                   10                  15
Ser Leu Arg Leu Ser Cys Ala Val Ser Gly Phe Thr Leu Asp Asp Tyr
            20                  25                  30
Ala Met His Trp Val Arg Gln Pro Pro Gly Lys Gly Leu Glu Trp Val
        35                  40                  45
Thr Gly Ile Ser Trp Asn Ser Gly Gly Met Gly Tyr Ala Asp Ser Val
```

```
                50                  55                  60
Lys Gly Arg Phe Thr Ile Ser Arg Asp Ser Ala Lys Asn Ser Leu Tyr
 65                  70                  75                  80

Leu Gln Met Asn Ser Leu Arg Val Glu Asp Thr Ala Phe Tyr Tyr Cys
                 85                  90                  95

Ala Lys Asp Val Gly Val Val Thr Gly Gly Tyr Trp Asp Asp Ala
                100                 105                 110

Leu Asp Ile Trp Gly Gln Gly Thr Met Val Thr Val Ser Ser
            115                 120                 125

<210> SEQ ID NO 888
<211> LENGTH: 127
<212> TYPE: PRT
<213> ORGANISM: Artificial sequence
<220> FEATURE:
<223> OTHER INFORMATION: Synthetic amino acid

<400> SEQUENCE: 888

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Tyr Trp Ser Trp Ile Arg Gln Tyr Pro Gly Lys Gly Leu Glu
         35                  40                  45

Trp Ile Gly His Met Ser Tyr Ser Gly Asp Thr Phe Phe Asn Pro Ser
 50                  55                  60

Leu Lys Ser Arg Ala Thr Ile Ser Ala Asp Thr Ser Lys His Gln Phe
 65                  70                  75                  80

Ser Leu Met Leu Arg Ser Val Thr Ala Ala Asp Thr Ala Val Tyr Leu
                 85                  90                  95

Cys Ala Arg Gly Arg Tyr Cys Asn Asp Asp Ser Cys Tyr Ser Glu Glu
                100                 105                 110

Ser Ala Ile Trp Phe Asp Pro Trp Gly Gln Gly Thr Leu Val Thr
            115                 120                 125

<210> SEQ ID NO 889
<211> LENGTH: 108
<212> TYPE: PRT
<213> ORGANISM: Artificial sequence
<220> FEATURE:
<223> OTHER INFORMATION: Synthetic amino acid

<400> SEQUENCE: 889

Asp Ile Val Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Arg Pro
 65                  70                  75                  80

Asp Asp Phe Ala Thr Tyr Tyr Cys Gln Gln Tyr Asn Thr Tyr Ser Trp
                 85                  90                  95

Trp Thr Phe Gly Gln Gly Thr Lys Val Glu Ile Lys
                100                 105
```

```
<210> SEQ ID NO 890
<211> LENGTH: 110
<212> TYPE: PRT
<213> ORGANISM: Artificial sequence
<220> FEATURE:
<223> OTHER INFORMATION: Synthetic amino acid

<400> SEQUENCE: 890

Gln Pro Val Leu Thr Gln Pro Ala Ser Val Ser Gly Ser Pro Gly Gln
1               5                   10                  15

Ser Ile Thr Ile Ser Cys Thr Gly Thr Thr Ser Asp Ile Gly Thr Tyr
            20                  25                  30

Asp Tyr Ala Ser Trp Tyr Gln Gln His Pro Gly Arg Ala Pro Lys Leu
        35                  40                  45

Met Ile Tyr Asp Val Ser Lys Arg Pro Ser Val Ser Gly Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ser His Tyr Tyr Cys Ser Ser Tyr Thr Ser Gly
                85                  90                  95

Leu Thr Trp Val Phe Gly Gly Gly Thr Lys Leu Thr Val Leu
            100                 105                 110

<210> SEQ ID NO 891
<211> LENGTH: 8
<212> TYPE: PRT
<213> ORGANISM: Artificial sequence
<220> FEATURE:
<223> OTHER INFORMATION: Synthetic amino acid

<400> SEQUENCE: 891

Gly Tyr Thr Phe Ala Ser Tyr Asp
1               5

<210> SEQ ID NO 892
<211> LENGTH: 8
<212> TYPE: PRT
<213> ORGANISM: Artificial sequence
<220> FEATURE:
<223> OTHER INFORMATION: Synthetic amino acid

<400> SEQUENCE: 892

Ser Tyr Ser Gly Asn Gly Asn Thr
1               5

<210> SEQ ID NO 893
<211> LENGTH: 17
<212> TYPE: PRT
<213> ORGANISM: Artificial sequence
<220> FEATURE:
<223> OTHER INFORMATION: Synthetic amino acid

<400> SEQUENCE: 893

Ala Ser Arg Asp Ile Val Val Thr Ala Thr Arg Ser Pro Phe Asp
1               5                   10                  15

Tyr

<210> SEQ ID NO 894
<211> LENGTH: 8
<212> TYPE: PRT
<213> ORGANISM: Artificial sequence
<220> FEATURE:
<223> OTHER INFORMATION: Synthetic amino acid
```

```
<400> SEQUENCE: 894

Gly Gly Ser Phe Ser Gly Tyr Tyr
1               5

<210> SEQ ID NO 895
<211> LENGTH: 7
<212> TYPE: PRT
<213> ORGANISM: Artificial sequence
<220> FEATURE:
<223> OTHER INFORMATION: Synthetic amino acid

<400> SEQUENCE: 895

Ile Asn His Ser Gly Ser Thr
1               5

<210> SEQ ID NO 896
<211> LENGTH: 19
<212> TYPE: PRT
<213> ORGANISM: Artificial sequence
<220> FEATURE:
<223> OTHER INFORMATION: Synthetic amino acid

<400> SEQUENCE: 896

Ala Arg Val Leu Ser Gly Trp Leu Pro Phe Pro Asn Tyr Tyr Tyr Tyr
1               5                   10                  15

Met Asp Val

<210> SEQ ID NO 897
<211> LENGTH: 11
<212> TYPE: PRT
<213> ORGANISM: Artificial sequence
<220> FEATURE:
<223> OTHER INFORMATION: Synthetic amino acid

<400> SEQUENCE: 897

Gln Ser Leu Leu His Ser Asn Gly Tyr Asn Tyr
1               5                   10

<210> SEQ ID NO 898
<211> LENGTH: 3
<212> TYPE: PRT
<213> ORGANISM: Artificial sequence
<220> FEATURE:
<223> OTHER INFORMATION: Synthetic amino acid

<400> SEQUENCE: 898

Leu Gly Ser
1

<210> SEQ ID NO 899

<400> SEQUENCE: 899

000

<210> SEQ ID NO 900
<211> LENGTH: 9
<212> TYPE: PRT
<213> ORGANISM: Artificial sequence
<220> FEATURE:
<223> OTHER INFORMATION: Synthetic amino acid

<400> SEQUENCE: 900

Gln Gln Tyr Gly Ser Ser Pro Arg Thr
1               5
```

```
<210> SEQ ID NO 901
<211> LENGTH: 6
<212> TYPE: PRT
<213> ORGANISM: Artificial sequence
<220> FEATURE:
<223> OTHER INFORMATION: Synthetic amino acid

<400> SEQUENCE: 901

Gln Ser Val Ser Ser Asp
1               5

<210> SEQ ID NO 902
<211> LENGTH: 3
<212> TYPE: PRT
<213> ORGANISM: Artificial sequence
<220> FEATURE:
<223> OTHER INFORMATION: Synthetic amino acid

<400> SEQUENCE: 902

Gly Ala Ser
1

<210> SEQ ID NO 903
<211> LENGTH: 9
<212> TYPE: PRT
<213> ORGANISM: Artificial sequence
<220> FEATURE:
<223> OTHER INFORMATION: Synthetic amino acid

<400> SEQUENCE: 903

Gln Gln Tyr Asn Asn Trp Pro Gly Thr
1               5

<210> SEQ ID NO 904
<211> LENGTH: 6
<212> TYPE: PRT
<213> ORGANISM: Artificial sequence
<220> FEATURE:
<223> OTHER INFORMATION: Synthetic amino acid

<400> SEQUENCE: 904

Ala Leu Pro Lys Gln Phe
1               5

<210> SEQ ID NO 905
<211> LENGTH: 3
<212> TYPE: PRT
<213> ORGANISM: Artificial sequence
<220> FEATURE:
<223> OTHER INFORMATION: Synthetic amino acid

<400> SEQUENCE: 905

Lys Asp Ser
1

<210> SEQ ID NO 906
<211> LENGTH: 11
<212> TYPE: PRT
<213> ORGANISM: Artificial sequence
<220> FEATURE:
<223> OTHER INFORMATION: Synthetic amino acid

<400> SEQUENCE: 906

Gln Ser Val Asp Asn Ser Gly Thr Tyr Glu Val
1               5                   10
```

```
<210> SEQ ID NO 907
<211> LENGTH: 6
<212> TYPE: PRT
<213> ORGANISM: Artificial sequence
<220> FEATURE:
<223> OTHER INFORMATION: Synthetic amino acid

<400> SEQUENCE: 907

Gln Asp Ile Arg Asn Asn
1               5

<210> SEQ ID NO 908
<211> LENGTH: 3
<212> TYPE: PRT
<213> ORGANISM: Artificial sequence
<220> FEATURE:
<223> OTHER INFORMATION: Synthetic amino acid

<400> SEQUENCE: 908

Gly Thr Ser
1

<210> SEQ ID NO 909
<211> LENGTH: 9
<212> TYPE: PRT
<213> ORGANISM: Artificial sequence
<220> FEATURE:
<223> OTHER INFORMATION: Synthetic amino acid

<400> SEQUENCE: 909

Leu Gln His Asn Ser Tyr Pro Pro Thr
1               5

<210> SEQ ID NO 910
<211> LENGTH: 9
<212> TYPE: PRT
<213> ORGANISM: Artificial sequence
<220> FEATURE:
<223> OTHER INFORMATION: Synthetic amino acid

<400> SEQUENCE: 910

Thr Ser Asp Ile Gly Thr Tyr Asp Tyr
1               5

<210> SEQ ID NO 911
<211> LENGTH: 3
<212> TYPE: PRT
<213> ORGANISM: Artificial sequence
<220> FEATURE:
<223> OTHER INFORMATION: Synthetic amino acid

<400> SEQUENCE: 911

Asp Val Ser
1

<210> SEQ ID NO 912
<211> LENGTH: 11
<212> TYPE: PRT
<213> ORGANISM: Artificial sequence
<220> FEATURE:
<223> OTHER INFORMATION: Synthetic amino acid

<400> SEQUENCE: 912

Gln Leu His Ile Pro Ser Gly Leu Thr Trp Val
1               5                   10
```

```
<210> SEQ ID NO 913
<211> LENGTH: 6
<212> TYPE: PRT
<213> ORGANISM: Artificial sequence
<220> FEATURE:
<223> OTHER INFORMATION: Synthetic amino acid

<400> SEQUENCE: 913

Gln Ser Ile Ser Ser Trp
1               5

<210> SEQ ID NO 914
<211> LENGTH: 3
<212> TYPE: PRT
<213> ORGANISM: Artificial sequence
<220> FEATURE:
<223> OTHER INFORMATION: Synthetic amino acid

<400> SEQUENCE: 914

Asp Ala Ser
1

<210> SEQ ID NO 915
<211> LENGTH: 10
<212> TYPE: PRT
<213> ORGANISM: Artificial sequence
<220> FEATURE:
<223> OTHER INFORMATION: Synthetic amino acid

<400> SEQUENCE: 915

Gln Gln Tyr Asn Thr Tyr Ser Trp Trp Thr
1               5                   10

<210> SEQ ID NO 916
<211> LENGTH: 352
<212> TYPE: DNA
<213> ORGANISM: Artificial sequence
<220> FEATURE:
<223> OTHER INFORMATION: Synthetic oligonucleotide

<400> SEQUENCE: 916
gaggtccagc tggtacagtc tggggctgag gtgaagaagg atctggcctc agtgaaggtc      60
tcctgcaagg tttctggata caccttcacc gactactaca tgcactgggt gcaacaggcc     120
cctggaaaag ggcttgagtg gatgggactt gttgatcctc aagaaggtga acaacatac     180 gcagagaagt tccagggcag agtcaccata accgcggaca cgtctacaga cacagcctat     240
atggagctga gcagcctgag atctgaggac acggccgtgt attactgtgc aaaagaatca     300
tttgggatcc cccacttctg gggccaggga accctggtca ccgtctcctc ag             352

<210> SEQ ID NO 917
<211> LENGTH: 117
<212> TYPE: PRT
<213> ORGANISM: Artificial sequence
<220> FEATURE:
<223> OTHER INFORMATION: Synthetic amino acid

<400> SEQUENCE: 917

Glu Val Gln Leu Val Gln Ser Gly Ala Glu Val Lys Lys Asp Leu Ala
1               5                   10                  15

Ser Val Lys Val Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45
```

Gly Leu Val Asp Pro Gln Glu Gly Glu Thr Thr Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Lys Glu Ser Phe Gly Ile Pro His Phe Trp Gly Gln Gly Thr Leu
            100                 105                 110

Val Thr Val Ser Ser
        115

<210> SEQ ID NO 918
<211> LENGTH: 8
<212> TYPE: PRT
<213> ORGANISM: Artificial sequence
<220> FEATURE:
<223> OTHER INFORMATION: Synthetic amino acid

<400> SEQUENCE: 918

Gly Tyr Thr Phe Thr Asp Tyr Tyr
1               5

<210> SEQ ID NO 919
<211> LENGTH: 8
<212> TYPE: PRT
<213> ORGANISM: Artificial sequence
<220> FEATURE:
<223> OTHER INFORMATION: Synthetic amino acid

<400> SEQUENCE: 919

Val Asp Pro Gln Glu Gly Glu Thr
1               5

<210> SEQ ID NO 920
<211> LENGTH: 10
<212> TYPE: PRT
<213> ORGANISM: Artificial sequence
<220> FEATURE:
<223> OTHER INFORMATION: Synthetic amino acid

<400> SEQUENCE: 920

Ala Lys Glu Ser Phe Gly Ile Pro His Phe
1               5                   10

<210> SEQ ID NO 921
<211> LENGTH: 20
<212> TYPE: PRT
<213> ORGANISM: Artificial sequence
<220> FEATURE:
<223> OTHER INFORMATION: Synthetic amino acid

<400> SEQUENCE: 921

Ala Arg Ala Thr Gln Gly Ser Gly Thr Asn Lys Leu Phe Phe Tyr Ser
1               5                   10                  15

Gly Met Asp Val
            20

<210> SEQ ID NO 922
<211> LENGTH: 16
<212> TYPE: PRT
<213> ORGANISM: Artificial sequence
<220> FEATURE:
<223> OTHER INFORMATION: Synthetic amino acid

<400> SEQUENCE: 922

```
Ala Ser Arg Pro Gly Ile Ala Pro Ala Gly Pro Pro Gly Gly Gly Leu
1               5                   10                  15

<210> SEQ ID NO 923
<211> LENGTH: 16
<212> TYPE: PRT
<213> ORGANISM: Artificial sequence
<220> FEATURE:
<223> OTHER INFORMATION: Synthetic amino acid

<400> SEQUENCE: 923

Ala Lys Glu Ala Cys Gly Gly Asp Cys Tyr Ser Asn Tyr Phe His Tyr
1               5                   10                  15

<210> SEQ ID NO 924
<211> LENGTH: 19
<212> TYPE: PRT
<213> ORGANISM: Artificial sequence
<220> FEATURE:
<223> OTHER INFORMATION: Synthetic amino acid

<400> SEQUENCE: 924

Gly Pro Leu Thr Pro Gly Asn Leu Phe Pro Gly Thr Leu Val Arg Trp
1               5                   10                  15

Val Asp Pro

<210> SEQ ID NO 925
<211> LENGTH: 15
<212> TYPE: PRT
<213> ORGANISM: Artificial sequence
<220> FEATURE:
<223> OTHER INFORMATION: Synthetic amino acid

<400> SEQUENCE: 925

Ala Arg Gly Arg Gly Val Val Met Thr Ala Ile Thr Arg Arg Leu
1               5                   10                  15

<210> SEQ ID NO 926
<211> LENGTH: 12
<212> TYPE: PRT
<213> ORGANISM: Artificial sequence
<220> FEATURE:
<223> OTHER INFORMATION: Synthetic amino acid

<400> SEQUENCE: 926

Ala Arg Leu Ala Gly Arg Lys Pro Asp Ala Asn Ser
1               5                   10

<210> SEQ ID NO 927
<211> LENGTH: 10
<212> TYPE: PRT
<213> ORGANISM: Artificial sequence
<220> FEATURE:
<223> OTHER INFORMATION: Synthetic amino acid

<400> SEQUENCE: 927

Gly Lys Gly Gly Arg Leu Gly Leu Asp Tyr
1               5                   10

<210> SEQ ID NO 928
<211> LENGTH: 16
<212> TYPE: PRT
<213> ORGANISM: Artificial sequence
<220> FEATURE:
<223> OTHER INFORMATION: Synthetic amino acid
```

```
<400> SEQUENCE: 928

Ala Arg Gly Gly Ile Gly Ala Pro Gly Pro Glu Arg Tyr Gly Arg
1               5                   10                  15

<210> SEQ ID NO 929
<211> LENGTH: 16
<212> TYPE: PRT
<213> ORGANISM: Artificial sequence
<220> FEATURE:
<223> OTHER INFORMATION: Synthetic amino acid

<400> SEQUENCE: 929

Ala Arg Pro Arg Gln Val Gly Ala Asn Arg Gly Tyr Tyr Phe Asp Tyr
1               5                   10                  15

<210> SEQ ID NO 930
<211> LENGTH: 13
<212> TYPE: PRT
<213> ORGANISM: Artificial sequence
<220> FEATURE:
<223> OTHER INFORMATION: Synthetic amino acid

<400> SEQUENCE: 930

Ala Arg Leu Ile Leu Glu Ala Ala Trp Tyr Phe Asp Leu
1               5                   10

<210> SEQ ID NO 931
<211> LENGTH: 8
<212> TYPE: PRT
<213> ORGANISM: Artificial sequence
<220> FEATURE:
<223> OTHER INFORMATION: Synthetic amino acid

<400> SEQUENCE: 931

Met Gln Ala Leu Gln Thr Pro Pro
1               5

<210> SEQ ID NO 932
<211> LENGTH: 8
<212> TYPE: PRT
<213> ORGANISM: Artificial sequence
<220> FEATURE:
<223> OTHER INFORMATION: Synthetic amino acid

<400> SEQUENCE: 932

Gln Tyr Asn Asn Cys Ser Leu Tyr
1               5

<210> SEQ ID NO 933
<211> LENGTH: 10
<212> TYPE: PRT
<213> ORGANISM: Artificial sequence
<220> FEATURE:
<223> OTHER INFORMATION: Synthetic amino acid

<400> SEQUENCE: 933

Gln Val Trp Asp Ser Asn Ser Asp His Arg
1               5                   10

<210> SEQ ID NO 934
<211> LENGTH: 8
<212> TYPE: PRT
<213> ORGANISM: Artificial sequence
<220> FEATURE:
<223> OTHER INFORMATION: Synthetic amino acid

<400> SEQUENCE: 934
```

```
Gln Gln Tyr Gly Ser Ser Pro Arg
1               5

<210> SEQ ID NO 935
<211> LENGTH: 8
<212> TYPE: PRT
<213> ORGANISM: Artificial sequence
<220> FEATURE:
<223> OTHER INFORMATION: Synthetic amino acid

<400> SEQUENCE: 935

Gln Gln Tyr Gly Ser Ser Pro Tyr
1               5

<210> SEQ ID NO 936
<211> LENGTH: 8
<212> TYPE: PRT
<213> ORGANISM: Artificial sequence
<220> FEATURE:
<223> OTHER INFORMATION: Synthetic amino acid

<400> SEQUENCE: 936

Gln Gln Tyr Gly Ser Ser Pro Pro
1               5

<210> SEQ ID NO 937
<211> LENGTH: 10
<212> TYPE: PRT
<213> ORGANISM: Artificial sequence
<220> FEATURE:
<223> OTHER INFORMATION: Synthetic amino acid

<400> SEQUENCE: 937

Gln Leu Ile Tyr Gln Ala Ala Ser Leu Gly
1               5                   10

<210> SEQ ID NO 938
<211> LENGTH: 7
<212> TYPE: PRT
<213> ORGANISM: Artificial sequence
<220> FEATURE:
<223> OTHER INFORMATION: Synthetic amino acid

<400> SEQUENCE: 938

Leu Gln Ala Arg His Thr Pro
1               5

<210> SEQ ID NO 939
<211> LENGTH: 10
<212> TYPE: PRT
<213> ORGANISM: Artificial sequence
<220> FEATURE:
<223> OTHER INFORMATION: Synthetic amino acid

<400> SEQUENCE: 939

Cys Ser Tyr Ala Gly Ser Ser Phe Leu Val
1               5                   10

<210> SEQ ID NO 940
<211> LENGTH: 10
<212> TYPE: PRT
<213> ORGANISM: Artificial sequence
<220> FEATURE:
<223> OTHER INFORMATION: Synthetic amino acid

<400> SEQUENCE: 940
```

```
Gln Val Trp Asp Ser Ser Ser Asp His Pro
1               5                   10

<210> SEQ ID NO 941
<211> LENGTH: 12
<212> TYPE: PRT
<213> ORGANISM: Artificial sequence
<220> FEATURE:
<223> OTHER INFORMATION: Synthetic amino acid

<400> SEQUENCE: 941

Tyr Ser Thr Asp Ser Thr Ser Asn Gln Lys Arg Val
1               5                   10

<210> SEQ ID NO 942
<211> LENGTH: 10
<212> TYPE: PRT
<213> ORGANISM: Artificial sequence
<220> FEATURE:
<223> OTHER INFORMATION: Synthetic amino acid

<400> SEQUENCE: 942

Gln Gln Tyr Asp Asn Leu Pro Ser Gly Ala
1               5                   10

<210> SEQ ID NO 943
<211> LENGTH: 8
<212> TYPE: PRT
<213> ORGANISM: Artificial sequence
<220> FEATURE:
<223> OTHER INFORMATION: Synthetic amino acid

<400> SEQUENCE: 943

Gln Gln Ser Tyr Ser Thr Pro Pro
1               5
```

HUMAN ORTHOPOXVIRUS ANTIBODIES AND METHODS OF USE THEREFOR

This application is a national phase application under 35 U.S.C. § 371 of International Application No. PCT/US2017/057150, filed Oct. 18, 2017, which claims benefit of priority to U.S. Provisional Application Ser. No. 62/410,207, filed Oct. 19, 2016, the entire contents of each of which is hereby incorporated by reference.

This invention was made with government support under grant number HHSN272200900047C awarded by the National Institute of Allergy and Infectious Diseases and the National Institutes of Health. The government has certain rights in the invention.

BACKGROUND

1. Field of the Disclosure

The present disclosure relates generally to the fields of medicine, infectious disease, and immunology. More particular, the disclosure relates to human antibodies binding to orthopoxvirus.

2. Background

Naturally-occurring members of the Orthopoxvirus genus, cowpox virus (CPXV), monkeypox virus (MPXV) and *Variola* virus (VARV), cause severe infections in humans. VARV exclusively causes human infections, with an estimated 300-500 million deaths during the 20th century before the initiation of the global smallpox vaccination campaign (Smith and McFadden, 2002). MPXV and CPXV are emerging zoonotic infections with a sporadic occurrence worldwide (McCollum et al., 2015; Reed et al., 2004; Vorou et al., 2008). There is no licensed specific treatment for these infections, and the only method of prevention is vaccination using vaccinia virus (VACV). Vaccinations against smallpox were discontinued in the late 1970s, leaving a large proportion of the current human population vulnerable to orthopoxviruses. The fear that smallpox could potentially re-emerge following a bioterror or biowarfare action (Smith and McFadden, 2002), the sporadic outbreaks of zoonotic MPXV and CPXV, and the increasing prevalence of immunocompromised individuals who cannot be vaccinated safely (Kemper et al., 2002), has stimulated renewed interest in research on orthopoxvirus protective immunity and treatment.

Poxviruses have a large and complex proteome containing over 200 proteins. During infection, the virus exists in two antigenically distinct forms, designated mature virions (MV) or enveloped virions (EV), which contain ~25 or 6 surface proteins, respectively (Moss, 2011). Monkeypox and smallpox are select agents and subject to the select agent regulations under (42 C.F.R. § 73). Various poxvirus species share many genetic and antigenic features (Hughes et al., 2010; Ichihashi and Oie, 1988; Stanford et al., 2007), and an infection with an orthopoxvirus of any one species may confer substantial protection against infection with the other orthopoxviruses (McConnell et al., 1964). Vaccination with VACV protects against disease caused by VARV, MPXV, or CPXV (Hammarlund et al., 2005). The immunologic mechanisms underlying cross-protection by immunization with VACV likely are diverse, but include neutralizing antibodies (Moss, 2011). A critical role for antibodies (Abs) in poxvirus immunity was suggested by historical cases in which passive transfer of serum from VARV- or VACV-immune subjects protected exposed individuals against smallpox (Kempe et al., 1961). Recent studies in non-human primate or murine models of experimental infection showed that polyclonal Abs are necessary and sufficient for protection against lethal challenge with MPXV or VACV (Belyakov et al., 2003; Edghill-Smith et al., 2005). The level of neutralizing activity in immune serum is thought to be the best laboratory predictor of protective immunity to orthopoxvirus infections in humans (Mack et al., 1972). Human vaccinia immune globulin (VIG) has been used for the prevention and treatment of some smallpox and vaccine-related complications with limited success (Wittek, 2006). The level of efficacy is uncertain due to lot-to-lot variation in potency and a lack of understanding of the molecular determinants of protection.

Percutaneous inoculation with VACV elicits a broad and heterogeneous serum Ab response that targets a large number of antigenic determinants of VACV (Davies et al., 2005a; Davies et al., 2007). The viral inhibitory activity of serum from immune subjects with cross-neutralizing activity to VACV, MPXV, and VARV likely is composed of Abs to diverse specificities (Hughes et al., 2012; Kennedy et al., 2011). Abs in VIG recognize many antigen targets, including surface proteins of both EV and MV virion forms of VACV (Davies et al., 2005a). Study of polyclonal Abs in poxvirus-immune sera of rabbits revealed the pattern of recognition for each poxvirus was unique, but also suggested that different poxvirus species shared common neutralizing determinants (Baxby, 1982). Studies in murine infection models identified targets for neutralizing and protective mouse monoclonal Abs (mAbs), which included the MV surface proteins A27, L1, H3, D8, A28, A13 and A17, and the EV surface proteins B5 and A33 (Moss, 2011). Protection of mice against systemic and respiratory infection with murine Abs required clones specific to antigens of both MV and EV forms of VACV (Lustig et al., 2005). These studies suggest complex patterns of recognition by Abs protecting against infection and disease in experimental animal models, but the molecular basis for neutralization and cross-reactive poxvirus immunity in humans are poorly understood.

SUMMARY

Thus, in accordance with the present disclosure, there is provided a method of detecting a orthopoxvirus infection in a subject comprising (a) contacting a sample from said subject with an antibody or antibody fragment having clone-paired heavy and light chain CDR sequences from Tables 3 and 4, respectively; and (b) detecting orthopoxvirus in said sample by binding of said antibody or antibody fragment to a orthopoxvirus antigen in said sample. The sample may be a body fluid, and may be blood, sputum, tears, saliva, mucous or serum, urine, exudate, transudate, tissue scrapings or feces. Detection may comprise ELISA, RIA or Western blot. The antibody fragment may be a recombinant ScFv (single chain fragment variable) antibody, Fab fragment, F(ab')$_2$ fragment, or Fv fragment. The method may further comprise performing steps (a) and (b) a second time and determining a change in orthopoxvirus antigen levels as compared to the first assay.

The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

In another embodiment, there is provided a method of treating a subject infected with orthopoxvirus, or reducing the likelihood of infection of a subject at risk of contracting orthopoxvirus, comprising delivering to the subject an antibody or antibody fragment having clone-paired heavy and light chain CDR sequences from Tables 3 and 4, respectively. The antibody fragment may be a recombinant ScFv (single chain fragment variable) antibody, Fab fragment, $F(ab')_2$ fragment, or Fv fragment. The antibody may be an IgG. The antibody may be is a chimeric antibody. The antibody or antibody fragment may be administered prior to infection, or may be administered after infection. Delivering may comprise antibody or antibody fragment administration, or genetic delivery with an RNA or DNA sequence or vector encoding the antibody or antibody fragment.

The antibody or antibody fragment may be encoded by clone-paired light and heavy chain variable sequences as set forth in Table 1, may be encoded by clone-paired light and heavy chain variable sequences having 95% identify to as set forth in Table 1, and may be encoded by light and heavy chain variable sequences having 70%, 80%, or 90% identity to clone-paired sequences from Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

Also provided is a monoclonal antibody, wherein the antibody or antibody fragment is characterized by clone-paired heavy and light chain CDR sequences from Tables 3 and 4, respectively. The antibody fragment may be a recombinant ScFv (single chain fragment variable) antibody, Fab fragment, $F(ab')_2$ fragment, or Fv fragment. The antibody may be a chimeric antibody, or is bispecific antibody. The antibody may be an IgG. The antibody or antibody fragment may further comprise a cell penetrating peptide and/or is an intrabody.

The antibody or antibody fragment may be encoded by clone-paired light and heavy chain variable sequences as set forth in Table 1, may be encoded by clone-paired light and heavy chain variable sequences having 95% identify to as set forth in Table 1, and may be encoded by light and heavy chain variable sequences having 70%, 80%, or 90% identity to clone-paired sequences from Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

In yet another embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody fragment may be a recombinant ScFv (single chain fragment variable) antibody, Fab fragment, $F(ab')_2$ fragment, or Fv fragment. The antibody may be a chimeric antibody or a bispecific antibody. The antibody may be an IgG. The antibody or antibody fragment may further comprise a cell penetrating peptide and/or is an intrabody.

The antibody or antibody fragment may be encoded by clone-paired light and heavy chain variable sequences as set forth in Table 1, may be encoded by clone-paired light and heavy chain variable sequences having 95% identify to as set forth in Table 1, and may be encoded by light and heavy chain variable sequences having 70%, 80%, or 90% identity to clone-paired sequences from Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

A further embodiment comprises a vaccine formulation comprising two or more antibodies or antibody fragments characterized by clone-paired heavy and light chain CDR sequences from Tables 3 and 4, respectively. At least one of said two or more antibody fragments may be a recombinant ScFv (single chain fragment variable) antibody, Fab fragment, $F(ab')_2$ fragment, or Fv fragment. At least one of said antibodies may be a chimeric antibody, or is bispecific antibody. At least one of said antibodies may be an IgG. At least one of said antibodies or antibody fragments further comprises a cell penetrating peptide and/or is an intrabody.

At least one of the two or more antibodies or antibody fragments may be encoded by clone-paired light and heavy chain variable sequences as set forth in Table 1, may be encoded by clone-paired light and heavy chain variable sequences having 95% identify to as set forth in Table 1, and may be encoded by light and heavy chain variable sequences having 70%, 80%, or 90% identity to clone-paired sequences from Table 1. At least one of the two or more antibodies or antibody fragments may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The vaccine formulation may comprise antibodies or antibody fragments that bind to MV and EV forms of vaccinia virus, such as where formulation comprises at least two antibodies or antibody fragments that bind to each of MV and EV forms of vaccinia virus. The vaccine formulation may comprise antibodies that bind to two or more of the orthopox antigens selected from the group consisting of A27, D8, L1, B5, A33 and H3, such as wherein said formulation may comprise antibodies or antibody fragments that bind to MV proteins A27 and L1 and EV proteins B5 and A33, and may further comprise antibodies or antibody fragments that bind to MV proteins D8 and H3.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-D. Panel of Poxvirus-Specific Human MAbs. A panel of 89 human mAbs was generated based on reactivity to VACV-infected cell lysate or to VACV protein antigens. Individual mAbs were assessed for cross reactivity using CPXV, MPXV, and VARV-infected cell lysates or antigens. (FIG. 1A) Antigen specificity of purified mAbs. Reactivity of Abs of unknown antigen specificity that bound to inactivated VACV-infected cell lysate only is designated as "VACV lysate only". (FIG. 1B) Representation of mAbs in the panel from FIG. 1A that bound only to VACV-infected cell lysate, recombinant VACV proteins, or both, VACV infected cell lysate and recombinant VACV proteins. Binding of individual mAbs is listed in Table S3 and S4. (FIG. 1C) Cross-reactivity of mAbs that bound to VACV lysates from FIG. 1B to VACV-, CPXV-, MPXV- or VARV-infected cell lysates. See also Figure S2. (FIG. 1D) Cross-reactivity of mAbs that bound to VACV antigens from FIG. 1B to the respective 12 ortholog proteins of VARV. Four mAbs with low expression were not tested.

FIGS. 2A-D. Neutralizing and Cross-neutralizing Potency of Human MAbs. Individual mAbs were assessed for neutralization using MV or EV forms of VACV, CPXV, or MPXV. (FIG. 2A) Representation of individual mAbs within the panel that neutralized at least one of three Orthopoxvirus species. Cross-neutralizing activity of individual mAbs is listed in Table S5. (FIG. 2B) Relative abundance (shown in colors and with percent on the top of each bar) and number of VACV-neutralizing mAbs for each antigen specificity from FIG. 2A. Anti-I1 and unknown specificity mAbs neutralized MPXV only. (FIG. 2C) Cross-neutralization of VACV, CPXV or MPXV by individual mAbs from FIG. 2A. (FIG. 2D) Cross-neutralizing potency of individual neutralizing mAbs from FIG. 2A, where each dot represents the mean±SD of triplicate $E_{max}$ values of individual mAbs. Antibodies later tested for protection in vivo (detailed below) are indicated in red.

FIGS. 3A-B. Mixtures of Four or Six MAbs Possess High Cross-Neutralizing Activity for VACV, CPXV, MPXV and VARV. Neutralizing activity of mAbs or VIGIV was assessed using MV- and EV-neutralization assays. Mix6 included anti-L1, -H3, -A27, -D8, -B5 and -A33 mAbs. Mix4 included anti-L1, -A27, -B5 and -A33 mAbs. (FIG. 3A) VACV neutralization by individual mAbs or their mixtures, compared with VIGIV. MAb mixtures designations are listed in Table S6. (FIG. 3B) Cross-neutralizing activity of Mix4, Mix6 and VIGIV for VACV, CPXV, MPXV or VARV (only the MV form was tested for VARV). Data represent one of two independent experiments, shown as mean±SD of assay triplicates. See also Figure S3.

FIGS. 4A-D. Mix6 Provides Superior Protection Against Lethal VACV Infection in vivo. Groups of C57BL/6 or BALB/c SCID mice representing, respectively, lower respiratory tract (FIG. 4A) or systemic dissemination (FIG. 4C) infection models, were inoculated IP with 1.2 mg of Mix6 or with 5 mg of VIGIV, or 1.2 mg of an irrelevant anti-dengue virus neutralizing mAb. The next day (d0) mice were challenged with a lethal dose of VACV and monitored for protection. (FIG. 4A) Protection from respiratory VACV infection that was mediated by Mix6, VIGIV, or vaccination with live VACV three weeks prior with a sub-lethal dose of VACV. (FIG. 4B) VACV titers assessed in the lungs of infected mice from FIG. 4A on day 7 p.i., shown as mean±SEM; data represent one of two independent experiments with n=5-10 mice per group. Dotted line indicates limit of detection (LOD) for the assay. (FIG. 4C) Protection from systemically disseminated lethal VACV infection that was mediated by Mix6. (FIG. 4D) Human mAb concentration in blood of treated mice from FIG. 4C at different times after treatment, shown as mean concentration ±SEM. One of two independent experiments, n=3-5 mice per group.

FIGS. 5A-C. Human MAb Specificities that Contribute to Protection Against Lethal Respiratory VACV Infection. C57BL/6 mice were inoculated IP one day prior to VACV challenge with 0.2 mg of individual mAbs or one of several mixtures designed to de-convolute protective mAbs specificities within Mix6. The next day (d0), mice were challenged IN with VACV and monitored for protection. (FIG. 5A) Protective capacity of individual mAbs of Mix6. Anti-D8 and -H3 specificities were inoculated as a mixture of 3-5 mAbs to those proteins from different competition-binding groups. (FIG. 5B) Protective capacity of mixtures that were based on Mix6 but had removal of a mAb for a single specificity, either L1, A27, D8, H3, A33, or B5. (FIG. 5C) Protective capacity of mixtures based on Mix4, Mix4 lacking anti-L1 mAb but with a two-fold excess of anti-A27 mAb, or Mix4 lacking anti-B5 mAb but with a two-fold excess of anti-A33 mAb. Data shown indicate mean±SEM from one of two independent experiments using 5 to 10 mice per group. MAb mixtures designations are listed in Table S6. See also Figure S4 and S5.

(FIG. 9A) Examples of mAbs within the panel that exhibited cross-reactivity to VACV, CPXV, MPXV, and VARV-infected cell lysates. Reactivity to VARV-infected cell lysate was measured at single mAb dilution as detailed in Table S3, ND indicates not determined. (FIG. 9B) Examples of four mAbs within the panel that exhibited cross-reactivity to VACV and VARV protein antigen orthologs. These four mAbs were included in mAb mixtures Mix4 and Mix6, which later were assessed for protective capacity in vivo. Data represent one of two independent experiments, shown as mean±SD of assay triplicates.

Figure 10:
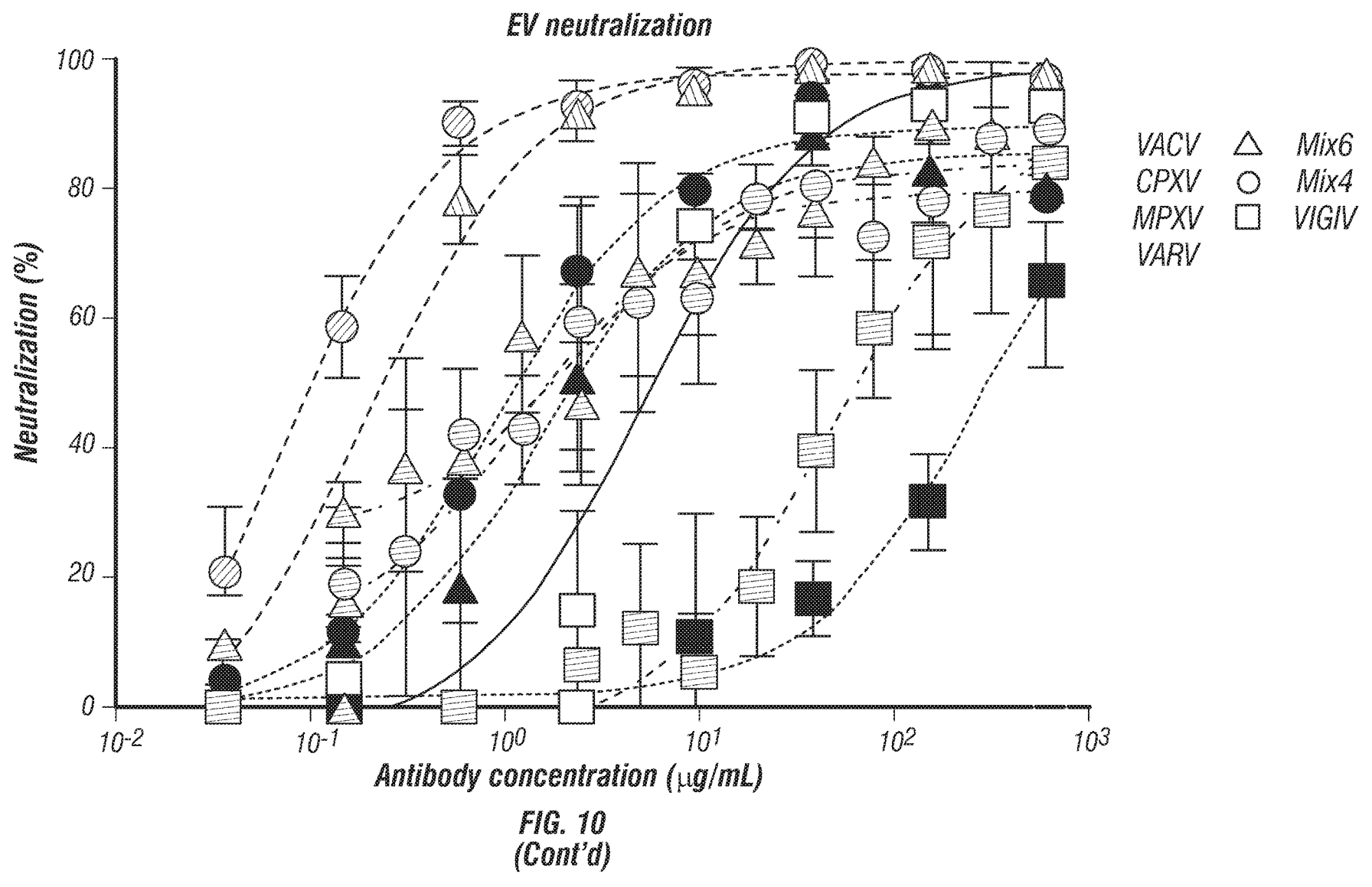

FIG. 10. Cross-Neutralizing Activity of Human mAb Mixtures, Related to FIGS. 3A-B. Cross-neutralizing activity of Mix6, Mix4, or VIGIV was assessed using MV- and EV-neutralization assays for VACV, CPXV, MPXV and VARV (MV form only for VARV). Data represent one of two independent experiments, shown as mean±SD of assay triplicates.

(FIG. 11A) Protection from respiratory VACV infection that was mediated by Mix6 (ΔEV). (FIG. 11B) Protection from respiratory VACV infection that was mediated by Mix6(ΔMV); Data represent one of two independent experiments with n=5-10 mice per group. Percent (%) indicates survival by day 7.

FIGS. 12A-B. Human mAb Specificities That Participate in Protection Against of Lethal Respiratory VACV Infection, Related to FIGS. 5A-C. (FIG. 12A) B6 mice were inoculated IP one day prior to VACV challenge with 0.2 mg of individual anti-D8, -H3, -A27, or -L1 mAbs. The next day (day 0), mice were anesthetized and challenged IN with VACV under conditions promoting less severe upper airway infection ($2\times10^5$ pfu VACV in 10 µL of PBS) and monitored for protection. Previously reported protective mouse anti-B5 mAb B126 and anti-H3 #41 (Benhnia et al., 2009; McCausland et al., 2010) served as control treatment for protection. (FIG. 12B) B6 mice received 400 µg of mAbs in the mixture designated as Mix4(ΔB5) (200 µg of anti-A33, 100 µg of anti-A27, and anti-L1) and was challenged with ten-fold higher ($10^6$ pfu) dose of VACV next day. Mice were monitored for protection and survival. Body weight is shown only for animals that survived. Percent figures near each curve indicate survival by day 7 based on endpoint criteria for euthanasia. Data showed mean±SEM from one of two independent experiments using 5 to 10 mice per group

DESCRIPTION OF ILLUSTRATIVE EMBODIMENTS

Figure 6:
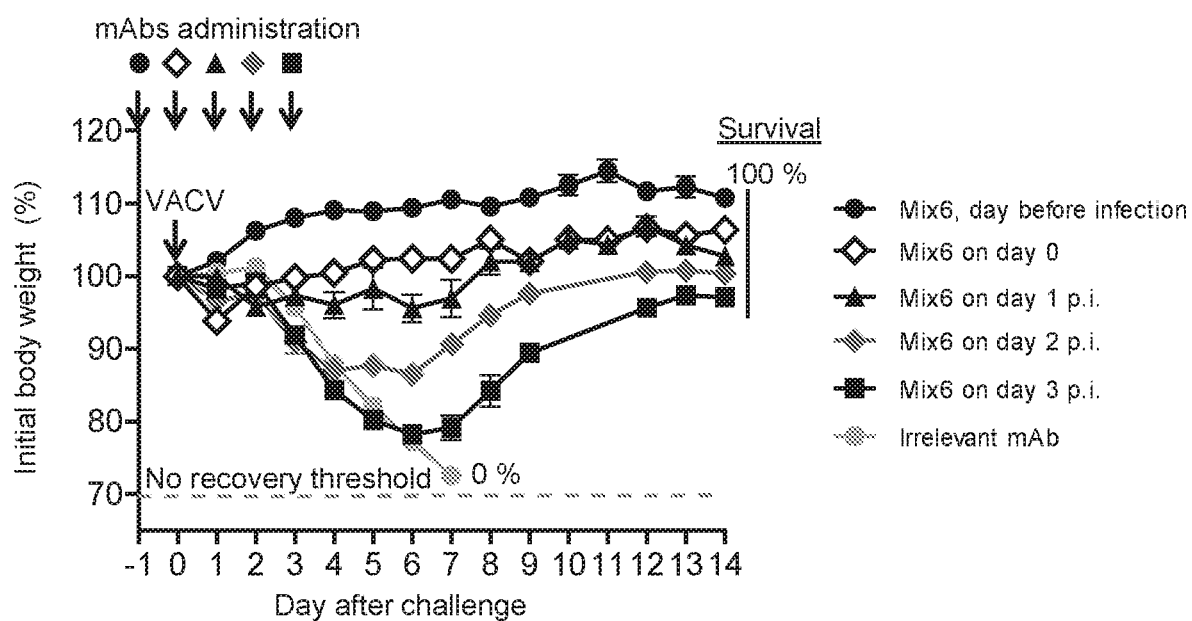
FIG. 6. Efficient Post-Exposure Treatment Effect Mediated by Mix6 MAbs. C57BL/6 mice were inoculated IP with 1.2 mg of Mix6 on the day before (d-1), or on the day of (d0), or day one to day three (d1-d3) after lethal IN challenge with VACV. The control group included mice pre-treated one day before challenge with 1.2 mg of an anti-dengue virus mAb. Body weight loss kinetics. Data are presented as mean±SEM, using 5 to 10 mice per group. Percent indicate survival based on endpoint criteria for euthanasia.

As discussed above, immunization with vaccinia virus (VACV) induces long lasting cross-protective immunity to *Variola* virus (VARV) and other clinically important orthopoxviruses, such as cowpox virus (CPXV) and monkeypox virus (MPXV). The appearance of serum neutralizing antibodies (Abs) induced by VACV may be a correlate of immunity for orthopoxviruses. However, the molecular basis of broadly neutralizing antibody responses for diverse orthopoxviruses in humans remains unknown. The inventors generated a large panel of orthopoxvirus-specific human monoclonal Abs from VACV-immunized subjects or from a subject with history of naturally-acquired MPXV infection. Detailed analysis revealed the principal neutralizing antibody specificities that are cross-reactive for VACV, CPXV, MPXV and VARV and that are determinants of protection in murine challenge models. Optimal protection against infection and disease following respiratory or systemic infection required a mixture of Abs that targeted several membrane proteins, including proteins on enveloped and mature virion forms of virus, and the presence of complement. This work reveals the principal targets for human Abs that mediate cross-protective immunity to diverse orthopoxviruses, using complementary and cooperative neutralizing activities. These and other aspects of the disclosure are described in detail below.

I. POXVIRUSES

Four genera of poxviruses may infect humans: orthopoxvirus, parapoxvirus, yatapoxvirus, and molluscipoxvirus. Orthopox include smallpox virus (*Variola*), vaccinia virus, cowpox virus, and monkeypox virus. Parapox include orf virus, pseudocowpox, and bovine papular stomatitis virus. Yatapox include tanapox virus and yaba monkey tumor virus; Molluscipox include molluscum contagiosum virus (MCV). The most common are vaccinia (seen on Indian subcontinent) and molluscum contagiosum, but monkeypox infections are rising (seen in west and central African rainforest countries). Smallpox has largely been eradicated by vaccination, but concerns remain in light of the growing unvaccinated population.

Poxviridae viral particles (virions) are generally enveloped (external enveloped virion-EEV), though the intracellular mature virion (IMV) form of the virus, which contains different envelope, is also infectious. They vary in their shape depending upon the species but are generally shaped like a brick or as an oval form similar to a rounded brick because they are wrapped by the endoplasmic reticulum. The virion is exceptionally large, its size is around 200 nm in diameter and 300 nm in length and carries its genome in a single, linear, double-stranded segment of DNA. By comparison, Rhinovirus is $\frac{1}{10}$ as large as a typical Poxviridae virion.

Replication of the poxvirus involves several stages. The first thing the virus does is to bind to a receptor on the host cell surface; the receptors for the poxvirus are thought to be glycosaminoglycans (GAGs). After binding to the receptor, the virus enters the cell where it uncoats. Uncoating of the virus is a two-step process. Firstly the outer membrane is removed as the particle enters the cell; secondly the virus particle (without the outer membrane) fuses with the cellular membrane to release the core into the cytoplasm. The pox viral genes are expressed in two phases. The early genes encode the non-structural protein, including proteins necessary for replication of the viral genome, and are expressed before the genome is replicated. The late genes are expressed after the genome has been replicated and encode the structural proteins to make the virus particle. The assembly of the virus particle occurs in five stages of maturation that lead to the final exocytosis of the new enveloped virion. After the genome has been replicated, the immature virion (IV) assembles the A5 protein to create the intracellular mature virion (IMV). The protein aligns and the brick-shaped envelope of the intracellular enveloped virion (IEV). These IEV particles are then fused to the cell plasma to form the cell-associated enveloped virion (CEV). Finally, the CEV encounters the microtubules and the virion prepares to exit the cell as an extracellular enveloped virion (EEV). The assembly of the virus particle occurs in the cytoplasm of the cell and is a complex process that is currently being researched to understand each stage in more depth. Considering the fact that this virus is large and complex, replication is relatively quick taking approximately 12 hours until the host cell dies by the release of viruses.

The replication of poxvirus is unusual for a virus with double-stranded DNA genome (dsDNA) because it occurs in the cytoplasm, although this is typical of other large DNA viruses. Poxvirus encodes its own machinery for genome transcription, a DNA dependent RNA polymerase, which makes replication in the cytoplasm possible. Most dsDNA viruses require the host cell's DNA-dependent RNA polymerase to perform transcription. These host DNA are found in the nucleus, and therefore most dsDNA viruses carry out a part of their infection cycle within the host cell's nucleus.

The ancestor of the poxviruses is not known but structural studies suggest it may have been an adenovirus or a species related to both the poxviruses and the adenoviruses. Based on the genome organisation and DNA replication mechanism it seems that phylogenetic relationships may exist between the rudiviruses (Rudiviridae) and the large eukaryal DNA viruses: the African swine fever virus (Asfarviridae), Chlorella viruses (Phycodnaviridae) and poxviruses (Poxviridae). The mutation rate in these genomes has been estimated to be $0.9$-$1.2 \times 10^{-6}$ substitutions per site per year. A second estimate puts this rate at $0.5$-$7 \times 10^{-6}$ nucleotide substitutions per site per year. A third estimate places the rate at $4$-$6 \times 10^{-6}$.

The last common ancestor of the extant poxviruses that infect vertebrates existed 0.5 million years ago. The genus Avipoxvirus diverged from the ancestor 249±69 thousand years ago. The ancestor of the genus Orthopoxvirus was next to diverge from the other clades at 0.3 million years ago. A second estimate of this divergence time places this event at 166,000±43,000 years ago. The division of the Orthopox into the extant genera occurred 14,000 years ago. The genus Leporipoxvirus diverged 137,000±35,000 years ago. This was followed by the ancestor of the genus Yatapoxvirus. The last common ancestor of the Capripoxvirus and Suipoxvirus diverged 111,000±29,000 years ago. An isolate from a fish—Salmon Gill Poxvirus—appears to be the earliest branch in the Chordopoxvirinae.

A. Taxonomy

The name of the family, Poxviridae, is a legacy of the original grouping of viruses associated with diseases that produced poxes in the skin. Modern viral classification is based on phenotypic characteristics; morphology, nucleic acid type, mode of replication, host organisms, and the type of disease they cause. The smallpox virus remains as the most notable member of the family.

The species in the subfamily Chordopoxvirinae infect vertebrates and those in the subfamily Entomopoxvirinae infect insects. There are 10 recognized genera in the Chordopoxvirinae and 3 in the Entomopoxvirinae. Both subfamilies also contain a number of unclassified species for which new genera may be created in the future. Cotia virus is an unusual virus that may belong to a new genus.

The GC-content of these genomes differs considerably. Avipoxvirus, Capripoxvirus, Cervidpoxvirus, Orthopoxvirus, Suipoxvirus, Yatapoxvirus and one Entomopox genus (Betaentomopoxvirus) along with several other unclassified Entomopoxviruses have a low G+C content while others—Molluscipoxvirus, Orthopoxvirus, Parapoxvirus and some unclassified Chordopoxvirus—have a relatively high G+C content. The reasons for these differences are not known.

Phylogenetic analysis of 26 Chordopoxviruses genomes has shown that the central region of the genome is conserved and contains ~90 genes. The termini in contrast are not conserved between species. Of this group Avipoxvirus is the most divergent. The next most divergent is Molluscipoxvirus. Capripoxvirus, Leporipoxvirus, Suipoxvirus and Yatapoxvirus genera cluster together: Capripoxvirus and Suipoxvirus share a common ancestor and are distinct from the genus Orthopoxvirus. Within the Othopoxvirus genus Cowpox virus strain Brighton Red, Ectromelia virus and Monkeypox virus do not group closely with any other member. Variola virus and Camelpox virus form a subgroup. Vaccinia virus is most closely related to CPV-GRI-90.

B. Vaccinia Virus

The prototypial poxvirus is vaccinia virus, known for its role as the active agent in the eradication of smallpox. The vaccinia virus is an effective tool for foreign protein expression, as it elicits a strong host immune-response. The vaccinia virus enters cells primarily by cell fusion, although currently the receptor responsible is unknown. Vaccinia virus is closely related to the virus that causes cowpox; historically the two were often considered to be one and the same. The precise origin of vaccinia virus is unknown due to the lack of record-keeping as the virus was repeatedly cultivated and passaged in research laboratories for many decades. The most common notion is that vaccinia virus, cowpox virus, and *Variola* virus (the causative agent of smallpox) were all derived from a common ancestral virus. There is also speculation that vaccinia virus was originally isolated from horses.

In addition to the morbidity of uncomplicated primary vaccination, transfer of infection to other sites by scratching, and post vaccinial encephalitis, other complications of vaccinia infections may be divided into the following types: Generalized vaccinia, Eczema vaccinatum, Progressive vaccinia (Vaccinia gangrenosum, Vaccinia necrosum) and Roseola vaccinia.

Vaccinia contains three classes of genes: early, intermediate and late. These genes are transcribed by viral RNA polymerase and associated transcription factors. Vaccinia replicates its genome in the cytoplasm of infected cells, and after late-stage gene expression undergoes virion morphogenesis, which produces IMV contained within an envelope membrane. The exact origin of the envelope membrane is still unknown. The IMV is then transported to the Golgi apparatus where it is wrapped with an additional two membranes, becoming the Intracellular Enveloped Virus (IEV). The IEV is transported along cytoskeletal microtubules to reach the cell periphery, where it fuses with the plasma membrane to become the Cell-associated Enveloped Virus (CEV). This triggers actin tails on cell surfaces or is released as EEV.

Vaccinia virus is able to undergo multiplicity reactivation. MR is the process by which two, or more, virus genomes containing otherwise lethal damage interact within an infected cell to form a viable virus genome. Abel found that vaccinia viruses exposed to doses of UV light sufficient to prevent progeny formation when single virus particles infected host chick embryo cells, could still produce viable progeny viruses when host cells were infected by two or more of these inactivated viruses; that is, MR could occur. Researchers have demonstrated MR of vaccinia virus after treatment with UV-light, nitrogen mustard, and X-rays or gamma rays.

Vaccinia contains within its genome several proteins that give the virus resistance to interferons. K3L is a protein with homology to the protein eukaryotic initiation factor 2 (eIF-2alpha). K3L protein inhibits the action of PKR, an activator of interferons. E3L is another protein encoded by Vaccinia. E3L also inhibits PKR activation; and is also able to bind to double stranded RNA.

C. Smallpox

Smallpox was an infectious disease caused by either of two virus variants, *Variola major* and *Variola minor*. The disease is also known by the Latin names *Variola* or *Variola vera*, derived from *varius* ("spotted") or *varus* ("pimple"). The disease was originally known in English as the "pox" or "red plague"; the term "smallpox" was first used in Britain in the 15th century to distinguish *Variola* from the "great pox" (syphilis). The last naturally occurring case of smallpox (*Variola minor*) was diagnosed on 26 Oct. 1977.

Infection with smallpox is focused in small blood vessels of the skin and in the mouth and throat before disseminating. In the skin it results in a characteristic maculopapular rash and, later, raised fluid-filled blisters. *V. major* produced a more serious disease and had an overall mortality rate of 30-35 percent. *V. minor* caused a milder form of disease (also known as alastrim, cottonpox, milkpox, whitepox, and Cuban itch) which killed about 1 percent of its victims. Long-term complications of *V. major* infection included characteristic scars, commonly on the face, which occur in 65-85 percent of survivors. Blindness resulting from corneal ulceration and scarring, and limb deformities due to arthritis and osteomyelitis were less common complications, seen in about 2-5 percent of cases.

Smallpox vaccination within three days of exposure will prevent or significantly lessen the severity of smallpox symptoms in the vast majority of people. Vaccination four to seven days after exposure can offer some protection from disease or may modify the severity of disease. Other than vaccination, treatment of smallpox is primarily supportive, such as wound care and infection control, fluid therapy, and possible ventilator assistance. Flat and hemorrhagic types of smallpox are treated with the same therapies used to treat shock, such as fluid resuscitation. People with semi-confluent and confluent types of smallpox may have therapeutic issues similar to patients with extensive skin burns.

No drug is currently approved for the treatment of smallpox. However, antiviral treatments have improved since the last large smallpox epidemics, and studies suggest that the antiviral drug cidofovir might be useful as a therapeutic agent. The drug must be administered intravenously, however, and may cause serious kidney toxicity.

The overall case-fatality rate for ordinary-type smallpox is about 30 percent, but varies by pock distribution: ordinary type-confluent is fatal about 50-75 percent of the time, ordinary-type semi-confluent about 25-50 percent of the time, in cases where the rash is discrete the case-fatality rate is less than 10 percent. The overall fatality rate for children younger than 1 year of age is 40-50 percent. Hemorrhagic and flat types have the highest fatality rates. The fatality rate for flat-type is 90 percent or greater and nearly 100 percent is observed in cases of hemorrhagic smallpox. The case-fatality rate for *Variola minor* is 1 percent or less. There is no evidence of chronic or recurrent infection with *Variola* virus.

In fatal cases of ordinary smallpox, death usually occurs between the tenth and sixteenth days of the illness. The cause of death from smallpox is not clear, but the infection is now known to involve multiple organs. Circulating immune complexes, overwhelming viremia, or an uncontrolled immune response may be contributing factors. In early hemorrhagic smallpox, death occurs suddenly about six days after the fever develops. Cause of death in hemorrhagic cases involved heart failure, sometimes accompanied by pulmonary edema. In late hemorrhagic cases, high and sustained viremia, severe platelet loss and poor immune response were often cited as causes of death. In flat smallpox modes of death are similar to those in burns, with loss of fluid, protein and electrolytes beyond the capacity of the body to replace or acquire, and fulminating sepsis.

Complications of smallpox arise most commonly in the respiratory system and range from simple bronchitis to fatal pneumonia. Respiratory complications tend to develop on about the eighth day of the illness and can be either viral or bacterial in origin. Secondary bacterial infection of the skin is a relatively uncommon complication of smallpox. When this occurs, the fever usually remains elevated.

Other complications include encephalitis (1 in 500 patients), which is more common in adults and may cause temporary disability; permanent pitted scars, most notably on the face; and complications involving the eyes (2 percent of all cases). Pustules can form on the eyelid, conjunctiva, and cornea, leading to complications such as conjunctivitis, keratitis, corneal ulcer, iritis, iridocyclitis, and optic atrophy. Blindness results in approximately 35 percent to 40 percent of eyes affected with keratitis and corneal ulcer. Hemorrhagic smallpox can cause subconjunctival and retinal hemorrhages. In 2 to 5 percent of young children with smallpox, virions reach the joints and bone, causing osteomyelitis variolosa. Lesions are symmetrical, most common in the elbows, tibia, and fibula, and characteristically cause separation of an epiphysis and marked periosteal reactions. Swollen joints limit movement, and arthritis may lead to limb deformities, ankylosis, malformed bones, flail joints, and stubby fingers.

Smallpox is believed to have emerged in human populations about 10,000 BC. The earliest physical evidence of it is probably the pustular rash on the mummified body of Pharaoh Ramses V of Egypt. The disease killed an estimated 400,000 Europeans annually during the closing years of the 18th century (including five reigning monarchs), and was responsible for a third of all blindness. Of all those infected, 20-60 percent—and over 80 percent of infected children—died from the disease. Smallpox was responsible for an estimated 300-500 million deaths during the 20th century. As recently as 1967, the World Health Organization (WHO) estimated that 15 million people contracted the disease and that two million died in that year. After vaccination campaigns throughout the 19th and 20th centuries, the WHO certified the global eradication of smallpox in 1979. Smallpox is one of two infectious diseases to have been eradicated, the other being rinderpest, which was declared eradicated in 2011.

D. Monkeypox

Monkeypox virus (MPV) is a double-stranded DNA, zoonotic virus and a species of the genus Orthopoxvirus in the family Poxviridae. It is one of the human orthopoxviruses that includes *Variola* (VARY), cowpox (CPX), and vaccinia (VACV) viruses. But it is not a direct ancestor to, nor a direct descendent of, the *Variola* virus which causes smallpox. The monkeypox virus causes a disease that is similar to smallpox, but with a milder rash and lower death rate. Variation in virulence of the virus has been observed in isolates from Central Africa where strains are more virulent than those from Western Africa.

Monkeypox is carried by both animals and humans. It was first identified by Preben von Magnus in Copenhagen, Denmark in 1958 in crab-eating macaque monkeys (*Macaca fascicularis*) being used as laboratory animals. It has also been identified in the giant Gambian rat which was the source of a 2003 outbreak in the United States. Monkeypox virus causes the disease in both humans and animals. The crab-eating macaque is often used for neurological experiments. The virus is mainly found in tropical rainforest regions of central and West Africa.

The virus can spread both from animal to human and from human to human. Infection from animal to human can occur via an animal bite or by direct contact with an infected animal's bodily fluids. The virus can spread from human to human by both droplet respiration and contact with fomites from an infected person's bodily fluids. Incubation period is 10-14 days. Prodromal symptoms include swelling of lymph nodes, muscle pain, headache, fever, prior to the emergence of the rash.

The virus is mainly found in the tropical rainforests of Central Africa and West Africa. It was first discovered in monkeys in 1958, and in humans in 1970. Between 1970 and 1986, over 400 cases in humans were reported. Small viral outbreaks with a death rate in the range of 10% and a secondary human to human infection rate of about the same amount occur routinely in equatorial Central and West Africa. The primary route of infection is thought to be contact with the infected animals or their bodily fluids. The first reported outbreak in the United States occurred in 2003 in the midwestern states of Illinois, Indiana, and Wisconsin, with one occurrence in New Jersey. The outbreak was traced to prairie dogs infected from an imported Gambian pouch rat. No deaths occurred.

E. Cowpox

Cowpox is an infectious disease caused by the cowpox virus. The virus, part of the orthopoxvirus family, is closely related to the vaccinia virus. The virus is zoonotic, meaning that it is transferable between species, such as from animal to human. The transferal of the disease was first observed in dairymaids who touched the udders of infected cows and consequently developed the signature pustules on their hands. Cowpox is more commonly found in animals other than bovines, such as rodents. Cowpox is similar to, but much milder than, the highly contagious and often deadly smallpox disease. Its close resemblance to the mild form of smallpox and the observation that dairymaids were immune from smallpox inspired the first smallpox vaccine, created and administered by English physician Edward Jenner.

The word "vaccination," coined by Jenner in 1796, is derived from the Latin root *vaccinus*, meaning of or from the cow. Once vaccinated, a patient develops antibodies that make him/her immune to cowpox, but they also develop immunity to the smallpox virus, or Variola virus. The cowpox vaccinations and later incarnations proved so successful that in 1980, the World Health Organization announced that smallpox was the first disease to be eradicated by vaccination efforts worldwide. Other orthopox viruses remain prevalent in certain communities and continue to infect humans, such as the cowpox virus (CPXV) in Europe, vaccinia in Brazil, and monkeypox virus in Central and West Africa.

Today, the virus is found in Europe, mainly in the UK. Human cases are very rare (though in 2010 a laboratory worker contracted cowpox) and most often contracted from domestic cats. Human infections usually remain localized and self-limiting, but can become fatal in immunosuppressed patients. The virus is not commonly found in cattle; the reservoir hosts for the virus are woodland rodents, particularly voles. Domestic cats contract the virus from these rodents. Symptoms in cats include lesions on the face, neck, forelimbs, and paws, and, less commonly, upper respiratory tract infections. Symptoms of infection with cowpox virus in humans are localized, pustular lesions generally found on the hands and limited to the site of introduction. The incubation period is 9 to 10 days. The virus is most prevalent in late summer and autumn.

Immunity to cowpox is gained when the smallpox vaccine is administered. Though the vaccine now uses vaccinia virus, the poxviruses are similar enough that the body becomes immune to both cow- and smallpox.

II. MONOCLONAL ANTIBODIES AND PRODUCTION THEREOF

A. General Methods

It will be understood that monoclonal antibodies binding to Poxvirus will have several applications. These include the production of diagnostic kits for use in detecting and diagnosing Poxvirus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

In the case of human antibodies against natural pathogens, a suitable approach is to identify subjects that have been exposed to the pathogens, such as those who have been diagnosed as having contracted the disease, or those who have been vaccinated to generate protective immunity against the pathogen. Circulating anti-pathogen antibodies can be detected, and antibody producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. In one aspect, there are provided monoclonal antibodies having clone-paired CDR's from the heavy and light chains as illustrated in Tables 3 and 4, respectively. Such antibodies may be produced by the clones discussed below in the Examples section using methods described herein.

In a second aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (0 the amino acids may vary from those set out above by permitting conservative substitutions (discussed below). Each of the foregoing applies to the nucleic acid sequences set forth as Table 1 and the amino acid sequences of Table 2.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies were generated by subcloning heavy and light chain Fv DNAs from the cloning vector into an IgG plasmid vector, transfected into 293 Freestyle cells or CHO cells, and antibodies were collected an purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (–0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (–0.4), sulfur containing amino acids: cysteine (–1.0) and methionine (–1.3); hydrophobic, nonaromatic amino acids:

valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the VII C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

F. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. ACTIVE/PASSIVE IMMUNIZATION AND TREATMENT/PREVENTION OF POXVIRUS INFECTION

A. Formulation and Administration

The present disclosure provides pharmaceutical compositions comprising anti-Poxvirus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Active vaccines are also envisioned where antibodies like those disclosed are produced in vivo in a subject at risk of Poxvirus infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, or by nebulizer. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

IV. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNC12, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetraacetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxy benzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting Poxvirus and its associated antigens. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of Poxvirus antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing Poxvirus, and contacting the sample with a first antibody in accordance with the present disclosure, as the case may be, under conditions effective to allow the formation of immunocomplexes.

These methods include methods for purifying Poxvirus or related antigens from a sample. The antibody will preferably be linked to a solid support, such as in the form of a column matrix, and the sample suspected of containing the Poxvirus or antigenic component will be applied to the immobilized antibody. The unwanted components will be washed from the column, leaving the Poxvirus antigen immunocomplexed to the immobilized antibody, which is then collected by removing the organism or antigen from the column.

The immunobinding methods also include methods for detecting and quantifying the amount of Poxvirus or related components in a sample and the detection and quantification of any immune complexes formed during the binding process. Here, one would obtain a sample suspected of containing Poxvirus or its antigens, and contact the sample with an antibody that binds Poxvirus or components thereof, followed by detecting and quantifying the amount of immune complexes formed under the specific conditions. In terms of antigen detection, the biological sample analyzed may be any sample that is suspected of containing Poxvirus or Poxvirus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to Poxvirus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate.

Then, a test composition suspected of containing the Poxvirus or Poxvirus antigen is added to the wells. After binding and washing to remove non-specifically bound immune complexes, the bound antigen may be detected. Detection may be achieved by the addition of another anti-Poxvirus antibody that is linked to a detectable label. This type of ELISA is a simple "sandwich ELISA." Detection may also be achieved by the addition of a second anti-Poxvirus antibody, followed by the addition of a third antibody that has binding affinity for the second antibody, with the third antibody being linked to a detectable label.

In another exemplary ELISA, the samples suspected of containing the Poxvirus or Poxvirus antigen are immobilized onto the well surface and then contacted with the anti-Poxvirus antibodies of the disclosure. After binding and washing to remove non-specifically bound immune complexes, the bound anti-Poxvirus antibodies are detected. Where the initial anti-Poxvirus antibodies are linked to a detectable label, the immune complexes may be detected directly. Again, the immune complexes may be detected using a second antibody that has binding affinity for the first anti-Poxvirus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of Poxvirus antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventors propose the use of labeled Poxvirus monoclonal antibodies to determine the amount of Poxvirus antibodies in a sample. The basic format would include contacting a known amount of Poxvirus monoclonal antibody (linked to a detectable label) with Poxvirus antigen or particle. The Poxvirus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only.

Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, the present disclosure concerns immunodetection kits for use with the immunodetection methods described above. As the antibodies may be used to detect Poxvirus or Poxvirus antigens, the antibodies may be included in the kit. The immunodetection kits will thus comprise, in suitable container means, a first antibody that binds to Poxvirus or Poxvirus antigen, and optionally an immunodetection reagent.

In certain embodiments, the Poxvirus antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the Poxvirus or Poxvirus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

VI. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Donors. PBMCs were obtained from subjects vaccinated with Dryvax (Wyeth), IMVAMUNE (Bavarian Nordic), or ACAM2000 (Acambis). The VRC 201 study was approved by the NIAID IRB under the intramural number 02-I-0316. The ClinicalTrials.gov number was NCT00046397. One sample was obtained from a U.S. survivor of naturally-acquired MPXV infection (Lewis et al., 2007). The studies were approved by the Institutional Review Boards of Vanderbilt University Medical Center, Oregon Health Sciences University, and the National Institute of Allergy and Infectious Diseases.

Mice. C57BL/6 and CBy.Smn.CB17PRKdc SCID/J (BALB/c SCID) mice were purchased from Jackson Laboratories (Bar Harbor). BALB/c SCID mice received Laboratory Autoclavable Rodent Diet #5010 (LabDiet). Breeding, maintenance and experimentation complied with Institutional Animal Care and Use Committee regulations.

Cell lines and viruses. VACV Dryvax (NIH, Lot #4008284), VACV Western Reserve (VACV-WR; ATCC VR-119) and CPXV Brighton Red (BEI Resources, NR-88) were propagated and titered in monolayer cultures of BSC-40 cells (ATCC CRL-2761). MPXV Zaire was propagated in BSC-40 cells and titered on Vero cells (ATCC CCL-81). Bangladesh 1974 Solaiman strain of VARV was propagated in monolayer cultures of Vero E6 cells (ATCC CRL-1586). VACV and CPXV were manipulated under BSL-2 conditions by vaccinated personnel. MPXV was manipulated under BSL-2 conditions with BSL-3 precautions by vaccinated personnel. All experiments with live VARV were reviewed and approved by the World Health Organization Advisory Committee on Variola Virus Research (WHO ACVVR). Experiments with VARV were conducted in accordance with WHO ACVVR guidelines and within a biosafety level 4 laboratory.

Antigens. Recombinant VACV proteins A27, A33, L1, B5, A28, L5, A21, H2, F9, J5, and VARV proteins 12, A31.5, A36, M1, B6, A31 were produced using a baculovirus expression system or purchased from BEI Resources. Truncated monomeric D8 protein was kindly provided by Dr. D. M. Zajonc and Dr. Y. Xiang. Recombinant VACV H3 protein was kindly provided by Dr. Crotty. DNA encoding the MPXV ortholog of the A27 VACV protein was purchased from BEI Resources. H3 and D8 protein orthologs of VARV were produced after WHO approval, as described previously (Davies et al., 2005b; Matho et al., 2012). Cell lysates infected with VACV (NYCBOH), CPXV, MPXV were prepared and inactivated as described previously (Amanna et al., 2012). A VACV-WR protein array was acquired from Antigen Discovery, Inc. The VARV protein microarray was prepared as described previously (Davies et al., 2005b).

Generation of human hybridomas. Human hybridomas were generated as described previously (Crowe, 2009). Briefly, cryopreserved samples were transformed with Epstein-Barr virus. Cultures were incubated in 384-well culture plates for 10 days and then expanded using cell culture medium containing irradiated heterologous human PBMCs (Nashville Red Cross). Plates were screened for VACV recombinant antigen- or VACV-infected cell lysate-specific antibody secreting cell lines using ELISA. Cells from wells with supernatants containing Abs that reacted to antigen or infected cell lysate were fused with HMMA2.5 myeloma cells using an established electrofusion technique (Yu et al., 2008).

ELISA protocol. For screening ELISA, plates were coated with antigen at 1 µg/mL, or 1:400 dilution of a lysate in PBS. After blocking, plates were incubated with culture supernatants followed by incubation with anti-human IgG conjugated with alkaline phosphatase (Meridian, Life Science Inc.) or HRP (Pharmigen). Plates were developed and supernatants were counted as VACV-reactive or recombinant protein antigen-reactive if their absorbance was 2.5-fold above the background from wells containing medium or coated with uninfected cell lysate, respectively. For binding kinetics and cross-reactivity assays, purified mAbs were assessed at concentrations ranging from 100 µg/mL to 20 pg/mL, in triplicate. $EC_{50}$ values were determined using Prism 5.0 software (GraphPad) after log transformation of antibody concentration using sigmoidal dose-response non-linear fit analysis with $R^2$ values greater than 0.85, as described previously (Thornburg et al., 2013). Binding of purified mAbs to VARV-infected cell lysate was determined at a single dilution of 100 µg/mL, in triplicate.

MAb isotype analysis. The isotype and subclass of secreted antibodies were determined using murine anti-human IgG1-IgG4 AP-conjugated antibodies (Southern Biotech).

Protein arrays and mAb target analysis. The Orthopoxvirus (VACV strain WR) protein array was acquired from Antigen Discovery, Inc. (ADI). The VARV protein microarray was fabricated in a similar manner as described previously (Davies et al., 2005b). Briefly, individual open reading frames encoded by the viral genome were amplified and cloned into T7 expression vectors by homologous recombination. Proteins were produced using an *Escherichia* coli-based cell-free coupled transcription/translation reactions (RTS 100 kits; 5 Prime, Gaithersburg, USA) according to the manufacturer's instructions. Proteins were printed without further purification on nitrocellulose-coated glass slides (Whatman). Protein expression was monitored using hemagglutinin or His tags present on the protein termini; quantification of the amount of protein spotted was not possible. No-DNA control spots containing the reaction mixture but lacking template DNA were included throughout the array to correct for background binding to *E. coli* proteins found in the transcription-translation mixture.

MAbs were probed on the VACV strain WR or VARV protein arrays at dilutions between 1:25 and 1:100, according to the manufacturer's instructions and reagents (ADI). Briefly, arrays were probed with antibody overnight at 4° C., then with biotin-conjugated goat anti-human antibodies for 1 hour at RT, then with a streptavidin-conjugated fluorophore for 1 hour at RT. Arrays were scanned using a GenePix 4100A scanner (Molecular Devices) with laser setting at 100% and photomultiplier (PMT) gain of 400. Image analysis was performed with GenePix Pro 5.0 software (Molecular Devices). Spot intensity was calculated as the median spot value minus local spot background. A secondary correction for background binding to *E. coli* proteins in the reaction mixture was done by subtracting an average of the no-DNA spots from the background-corrected spot value. Since mAb affinity, protein sequence conservation, and protein expression levels vary, a simple evaluation for highest fluorescent intensity, and a correlation between the two chips, if needed, was used to identify protein targets.

Biolayer interferometry analysis. Experiments were performed on an Octet RED biosensor instrument (Pall ForteBio; Menlo Park) essentially as described previously (Smith et al., 2014). Briefly, biosensors were pre-wetted in running buffer containing DPBS, 0.1% BSA, and 0.05% Tween-20. Human mAbs were loaded onto Protein G biosensor tips (ForteBio) at a concentration of 105 µg/mL and then washed. Biosensors were incubated with a 0.2 mL volume of recombinant protein solution at a 90 µg/mL concentration and washed. Antibody-antigen association/disassociation was determined as wavelength shift in nm.

For competition-binding studies, mAb-antigen complexes were tested for the ability to bind a second mAb in sandwich assay as described previously (Smith et al., 2014). The extent of antibody-antigen association was determined as wavelength shift in nm and calculated as a percentage after normalization, where 0% was the wavelength shift in nm for self-blocking control and 100% was the maximal wavelength shift in nm. Experiments were performed in duplicate. Antibodies were considered to be members of the same competition-binding group if they competed for binding to antigen and exhibited a similar blocking pattern to other antibodies in the panel.

MAb isoype and gene sequence analysis. The isotype and subclass of secreted antibodies were determined using murine anti-human IgG1-IgG4 antibodies followed by secondary anti-mouse HRP-conjugated antibody (Southern Biotech). Nucleotide sequences of variable gene segments were determined by Sanger sequencing from cloned cDNA generated by reverse transcription PCR of mRNA, using variable gene-specific primers designed to amplify antibody genes from all gene families (Weitkamp et al., 2003). Identity of the gene segments and mutations from the germline sequences were determined by alignment using the ImMunoGeneTics database (world-wide-web at imgt.org) (Ruiz et al., 2000).

MAb production and purification. Hybridoma cells secreting VACV-specific mAbs were grown in serum-free medium (Gibco). MAbs were purified from culture supernatants using a HiTrap MabSelect Sure column (GE Healthcare).

Virus neutralization assays. Neutralizing activity of mAbs was determined using MV or EV forms of VACV strain NYCBOH, CPXV, or MPXV, or MV of VARV in a plaque reduction neutralization (PRNT) assay. Neutralization was performed in the presence of complement for all viruses except VARV MV. All experiments with live VARV were reviewed and approved by the World Health Organization Advisory Committee on Variola Virus Research (WHO ACVVR). Experiments with VARV were conducted in accordance with WHO ACVVR guidelines within a biosafety level 4 laboratory. $E_{max}$ was determined as a maximum of neutralization mAb effect (%); $IC_{50}$ and $E_{max}$ values were determined using Prism 5.0 software (GraphPad) after log transformation of antibody concentration using a 3-parameter nonlinear fit analysis of antibody $\log_{10}$ concentration versus response with $R^2$ values greater than 0.85, as described previously (Thornburg et al., 2013).

In vivo protection study. To test the effect of mAbs on respiratory tract infection, six- to eight-week old male B6 mice were injected IP with 100-200 µg of individual mAbs or designated mixtures of mAbs (100-200 µg of each mAb), or 5 mg of VIGIV (BEI Resources). Human anti-dengue virus mAb served as mock-vaccinated control. In ABSL-2 facilities, ketamine-xylazine anesthetized mice were inoculated IN with $10^5$ PFU VACV-WR in 50 µL, or in some experiments in 10 µL of PBS. In some experiments, mice were inoculated with $10^6$ PFU VACV. For virus titer determination, lungs from individual mice were homogenized and plated on confluent BSC-40 cell monolayer cultures. To test the effect of mAbs on disseminated VACV infection, eight- to ten-week old female BALB/c SCID mice were given Abs IP either prior to or after VACV inoculation, as detailed in the text. For lethal challenge, mice were inoculated IP with $10^5$ PFU VACV-WR in 100 µL PBS. Mice were weighed and monitored daily for morbidity, and those losing over 30% of initial body weight were euthanized, per IACUC requirements.

Quantification and Statistical Analysis. The descriptive statistics mean±SEM or mean±SD were determined for continuous variables as noted. Comparisons were performed using Wilcoxon rank sum test or the post hoc group comparisons in ANOVA; all tests were two-tailed and unpaired. Survival curves were estimated using the Kaplan Meier method and curves compared using the log rank test with subjects right censored, if they survived until the end of the study. * –$p<0.05$; ** – was used to reject a "null hypothesis". *=$p<0.05$; =$p<0.01$; * –=$p<0.001$; ns—non-significant. Statistical analyses were performed using Prism v5.0 (GraphPad).

Example 2—Results

Poxvirus infection in humans elicits a complex B cell response encoding large numbers of clones reactive with antigens from diverse Orthopoxvirus species. The inventors obtained peripheral blood mononuclear cells (PBMCs) from a donor who had recovered from a naturally-occurring MPXV infection or from otherwise healthy subjects previously immunized with one of three different vaccine formulations (Table S1), IMVAMUNE (live attenuated modified vaccinia Ankara virus), Dryvax (a freeze-dried calf lymph produced vaccinia virus), or ACAM2000 (Vero cell culture produced vaccinia virus) (Verardi et al., 2012). To identify poxvirus-specific B cell cultures, PBMCs were transformed with Epstein-Barr virus, and the supernatants from the resulting lymphoblastoid cell lines were screened by ELISA for binding to poxvirus antigens. Hybridomas secreting human antigen-specific mAbs were generated from B cell lines secreting virus-specific antibodies, as previously described (Crowe, 2009). For screening, the inventors used 12 recombinant VACV proteins antigens designated A21, A27, A28, A33, B5, D8, F9, J5, H2, H3, L1, and L5. The A33 and B5 proteins are surface antigens on the EV form of virus, while the remaining ten proteins are surface antigens on MV particles. The inventors also screened supernatants for binding to inactivated lysates of VACV-infected BSC-40 cell monolayer cultures.

Figure 8:
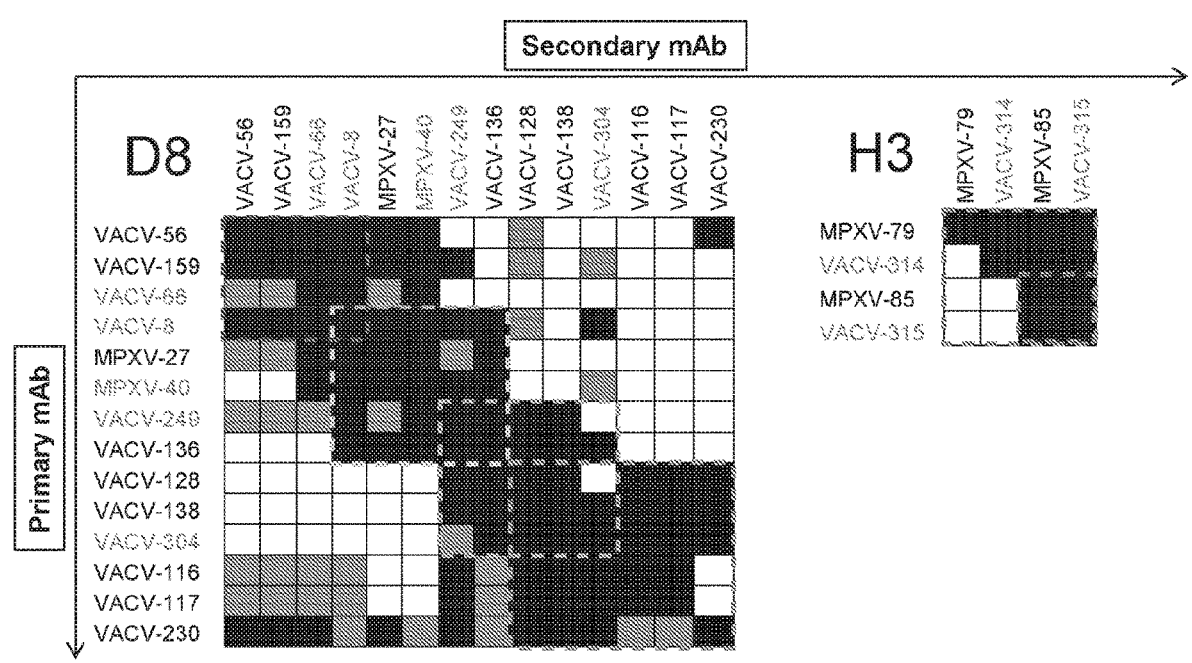
FIG. 8. Human Anti-D8 and Anti-H3 mAbs Targeted Diverse Epitopes of the Major VACV Surface Antigens, Related to FIGS. 1A_D. Anti-D8 and anti-H3 mAbs from the panel were assessed for competitive binding to D8 and H3 proteins by biolayer interferometry. MAbs were judged to compete for the same site if maximum binding of second antibody was reduced to ≤39% of its un-competed binding (shown in black boxes). The mAbs were considered non-competing if maximum binding of second mAb was ≥61% of its un-competed binding (shown in white boxes). Gray boxes indicate an intermediate phenotype (competition resulted in between 40% and 60% of un-competed binding). Dashed lines indicate designated competition groups. Antibodies that were selected for in vivo protection studies shown in lighter color. Two anti-H3 mAbs, MPXV-72 and MPXV-1, did not bind to antigen in biolayer interferometry and were distinguished as separate group from other anti-H3 mAbs.

A total of 89 cloned hybridoma cell lines secreting human mAbs were isolated, including 44 lines from vaccinees and 45 from the donor with a history of MPXV infection (Table S1). The 89 mAbs were independent clones that displayed a high degree of sequence diversity, including a unique HCDR3 sequence for each mAb (Table S2). Thirty-two mAbs in the panel bound in ELISA to inactivated VACV-infected cell lysates only, and thus their protein antigen specificity was uncertain initially. Binding of these mAbs was reassessed using VACV protein antigen microarrays, which revealed additional mAbs specific to D8, H3 A21, A25, H5 and I1 VACV proteins. Therefore, the mAb panel contained Abs to at least 12 antigens: D8, B5, A33, H3, L1, A27, I1, A25, F9, A28, A21, and H5 (FIG. 1A). The majority (62 of 89-70%) of purified mAbs reacted to one of six VACV antigens that were reported previously as major targets for neutralizing Abs in mice or humans (Moss, 2011), specifically A27, H3, D8, L1, B5 and A33. Sixteen percent (14 of 89) of mAbs in the panel reacted with VACV-infected cell lysate but not with a recombinant protein antigen, therefore they remain of unknown specificity (FIG. 1A). MAbs that targeted the antigens VACV D8 and B5 were over-represented in the panel (35 of 75 mAbs) accounting for 47% of mAbs with known antigen specificity. Further analysis revealed several competition-binding groups among Ab specificities that bind to H3 or D8 antigens (FIG. 8), indicating the presence of mAbs to several antigenic sites on these antigens.

The inventors next assessed the cross-reactivity of individual VACV-reactive mAbs to CPXV, MPXV or VARV by testing binding to CPXV-, MPXV- or VARV-infected cell lysates or to recombinant VARV protein antigens that are orthologs of the identified VACV targets. A large fraction (45 of 73-62%) of mAbs that bound to VACV antigens in virus-infected cell lysate (FIG. 1B) bound in a cross-reactive manner to the virus-infected lysates of all four Orthopoxvirus species tested, and the majority (70 of 73-96%) of mAbs cross-reacted with at least two orthopoxviruses (FIG. 1C; Table S3). Remarkably, a large fraction (47 of 71-66%) of the mAbs with an established protein antigen specificity for VACV cross-reacted with the orthologous VARV antigens (FIG. 1D; Table S3). The mAbs bound to recombinant antigens and/or infected cell lysates in a concentration-dependent manner (FIGS. 9A-B and data not shown), and the majority of them possessed 50% maximal effective concentration ($EC_{50}$) binding values of 1 μg/mL or lower, confirming their antigen-specific binding phenotype (Table S4). Therefore, the majority of mAbs in the panel exhibited binding patterns that suggested the potential to neutralize several Orthopoxvirus species that are infectious for humans.

The majority of human neutralizing mAbs recognized one of six antigens and exhibited cross-neutralization for several Orthopoxvirus species. The inventors next tested the mAbs in virus neutralization assays using MV or EV forms of VACV, CPXV, or MPXV. Neutralization potency of mAbs was assessed based on the half-maximal inhibitory concentration ($IC_{50}$) and the maximum of neutralization effect ($E_{max}$) values. More than half (48 of 89-54%) of the mAbs possessed neutralizing activity ($E_{max} \geq 50\%$) at 100 μg/mL or lower concentration for at least one orthopoxvirus; 16 or 32 mAbs neutralized the EV or MV form of VACV, respectively (FIG. 2A). Of note, neutralizing activity for the majority of these Abs required complement (Table S5). Most (46 of 48-98%) of the neutralizing mAbs recognized one of six proteins, D8, L1, B5 A33, A27 or H3 (FIG. 2B). Two remaining mAbs were from the subject with prior wild-type MPXV infection and recognized I1 or an undetermined MPXV antigen (Table S5).

A majority (38 of 48-79%) of neutralizing mAbs cross-neutralized at least two Orthopoxvirus species (mainly VACV and CPXV), and 12 of 48 (25%) mAbs neutralized three orthopoxviruses—VACV, CPXV and MPXV (FIG. 2C). Regardless of their antigen specificity, the neutralizing mAbs varied widely in their neutralization potency. $IC_{50}$ values of individual mAbs ranged from ~0.02 to 100 μg/mL, and $E_{max}$ values varied from 50% (the designated cut-off threshold to identify potent neutralizing clones) to 99.5% (FIG. 2D, Table S5). Most of the neutralizing mAbs reduced plaque number only by ~60-80% at the highest tested concentration, regardless of antigen or form of virus targeted. The neutralizing activity of MV-targeted anti-D8, L1, A27 or H3, and EV-targeted anti-B5 mAbs were similar for VACV and CPXV, and two of six VACV and MPXV-neutralizing anti-A33 mAbs neutralized CPXV. None of the anti-D8 or -B5 mAbs neutralized MPXV, despite the ability of these mAbs to bind the corresponding MPXV ortholog protein. In contrast, the broadest cross-neutralizing activity (neutralization of VACV, CPXV and MPXV), was detected in mAbs directed to A33, L1, A27 or H3 antigens (FIG. 2D). Cross-neutralizing mAbs were isolated from most orthopoxvirus-immune subjects (Table S5). Together, these data indicate that mAbs induced by VACV immunization or MPXV infection that recognize any of six neutralizing determinants can inhibit several Orthopoxvirus species, and also suggest that the broadest cross-neutralization is mediated predominantly by four Ab specificities.

Figure 3A:
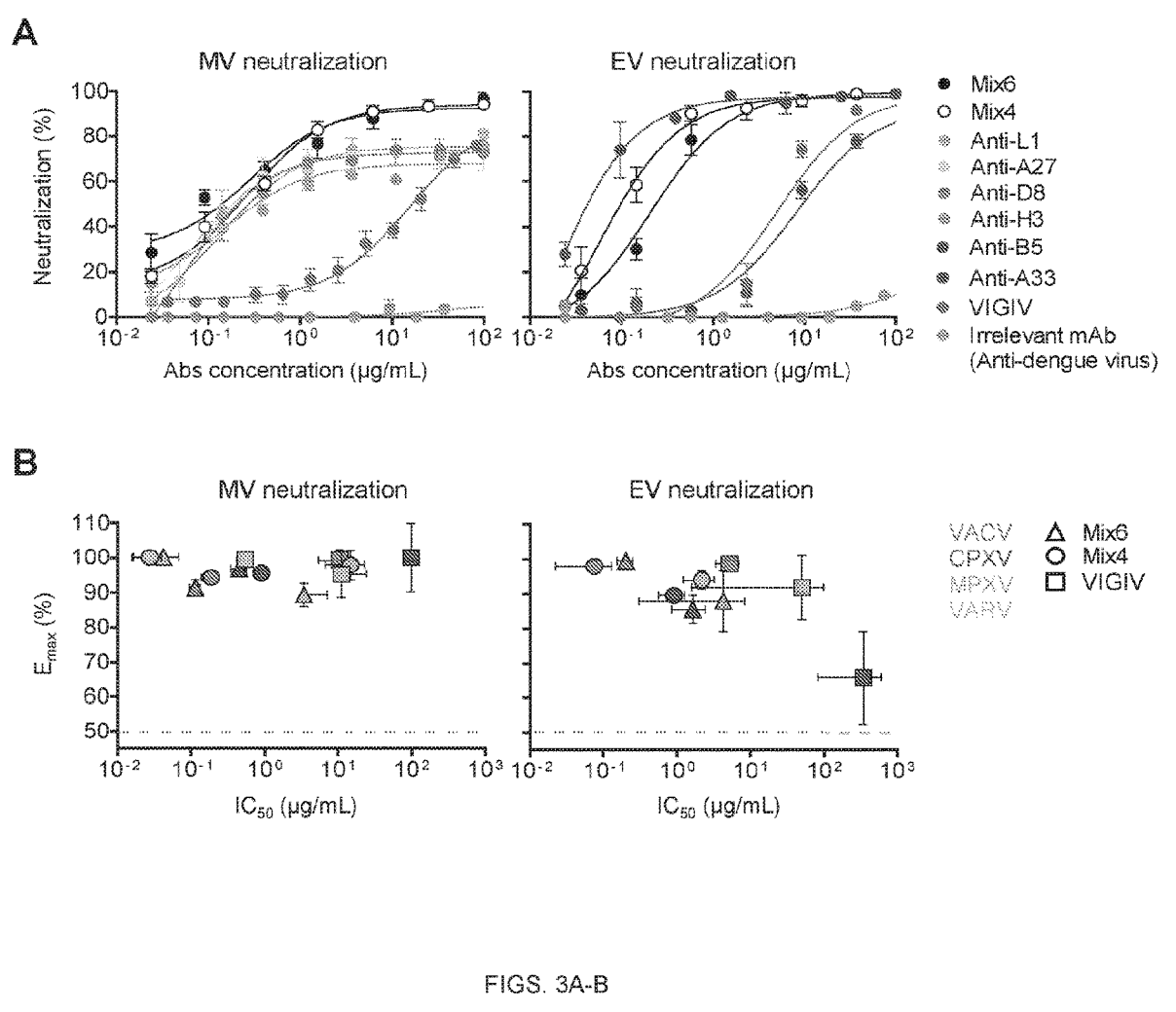
Figure 9A:
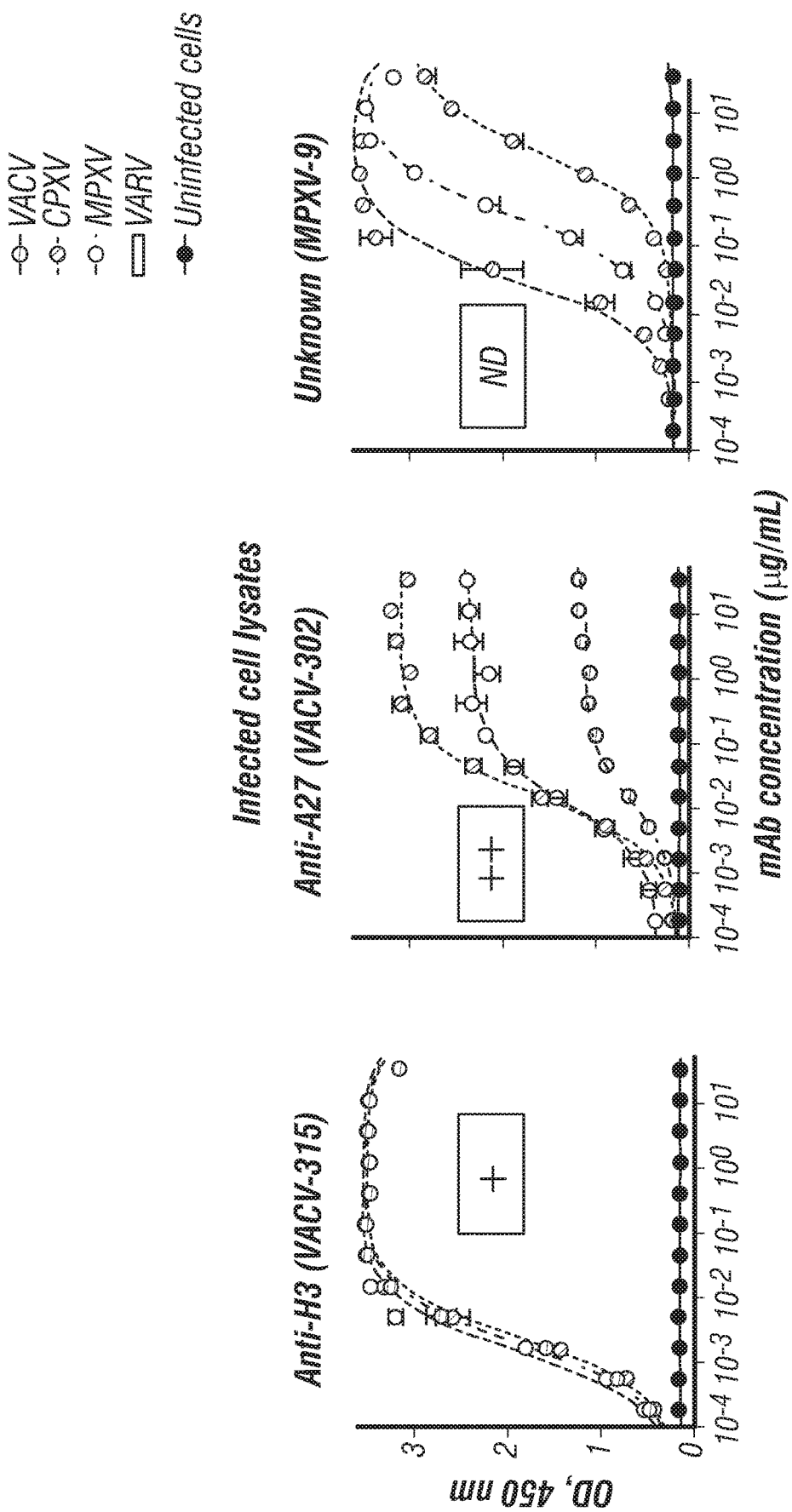
FIGS. 9A-B. Cross-Reactivity of Human mAbs to Poxviruses, Related to FIGS. 1A-D. Cross-reactivity of individual mAbs to different poxviruses were assessed by ELISA using infected cell lysates or purified recombinant protein antigens.
Figure 9B:
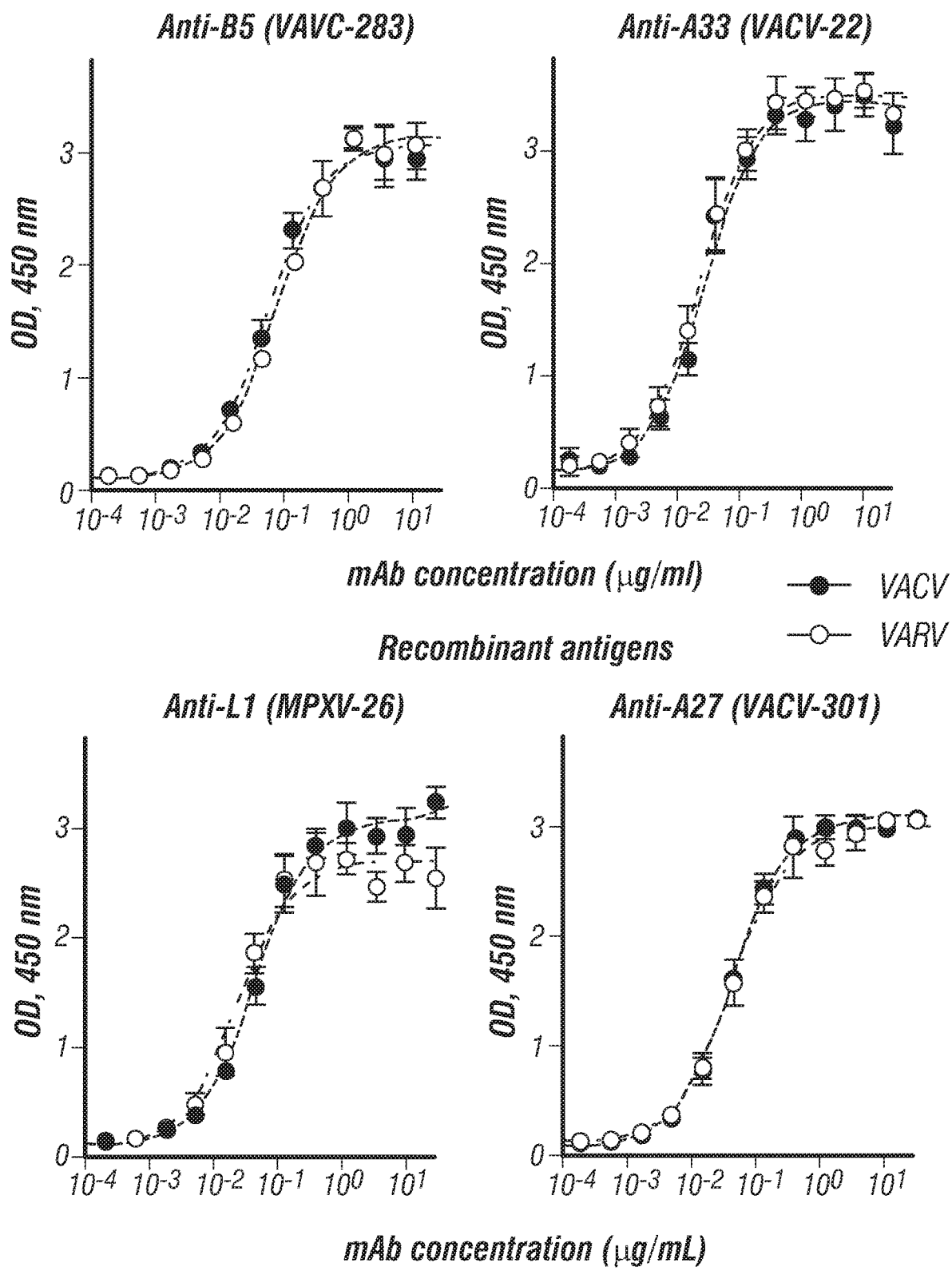

Mixtures of diverse mAb specificities possess superior cross-neutralizing activity for VACV, CPXV, MPXV, and VARV. The inventors next designed two mixtures of mAbs, designated Mix6 and Mix4, containing diverse specificities with high neutralizing and cross-neutralizing activities to both MV and EV forms of virus (FIG. 2D). Mix6 contained single neutralizing mAbs directed to each of six antigens that targeted by neutralizing mAbs-MV proteins D8, A27, H3, and L1, and EV proteins B5 and A33. Mix4 was similar to Mix6, containing mAbs to A27, L1, B5 and A33, but lacked anti-D8 and H3 mAbs (Table S6). Both mixtures included four mAbs that exhibited similar binding for VACV proteins and the corresponding VARV protein orthologs (FIGS. 9A-B). The neutralizing activity of Mix6 and Mix4 for VACV were higher than that of individual mAbs or VIGIV (FIG. 3A). Moreover, Mix6 and Mix4 cross-neutralized VACV, CPXV, MPXV and VARV more potently than did VIGIV in EV and MV neutralization assays (FIG. 3B, S3; VARV could only be tested in the MV assay, without complement). Therefore, neutralization and cross-neutralization are more efficiently achieved with mixtures of diverse mAbs specificities than with individual potently neutralizing mAbs.

Superior in vivo protection against VACV infection was achieved by administration of a mixture of human mAbs that targeted multiple viral antigens. The inventors next evaluated the protective capacity of Mix6. Single-dose treatment with Mix6 one day before lethal intranasal (IN) challenge of C57BL/6 (B6) mice with VACV provided complete protection against weight loss and mortality (FIG. 4A). Mock-treated mice experienced severe illness and succumbed by day 7 post-inoculation (p.i.). The protection was associated with a profound (~$10^6$-fold) reduction of viral load in the lungs on day 7 p.i., when compared to the mock-treated group (FIG. 4B). Notably, the level of protection provided by Mix6 was comparable to, if not higher than, that provided by prior immunization with a sub-lethal dose of VACV. In contrast, pre-treatment with VIGIV did not protect mice under the challenge conditions used. These mice were unable to control VACV replication in the lungs and succumbed by day 7 p.i., similarly to the mock-treated group (FIG. 4B). These data indicate a high prophylactic potency of Mix6 for prevention of respiratory tract infection.

To further characterize the protective efficacy of Mix6, the inventors tested it in a lethal model of systemic VACV dissemination using severe combined immunodeficiency (SCID) mice that lack adaptive immune responses but retain a functional complement system (Bosma and Carroll, 1991). Initially, they assessed the prophylactic effect of Mix6 given to mice by the IP route one day prior to lethal IP virus challenge. Remarkably, single-dose pre-treatment with Mix6 provided sterilizing immunity in this model (FIG. 4C). Mice pre-treated with a human mAb of irrelevant specificity succumbed to the disease by day 20 p.i., when the group of animals pre-treated with Mix6 was completely protected from death and any signs of disease. Clearance of human mAbs from animal blood rendered healthy mice susceptible to VACV re-infection (FIGS. 4C-D), demonstrating that the sterilizing immunity observed during primary VACV infection was mediated solely by the administered Mix6.

In summary, these findings demonstrate the high prophylactic potency of Mix6 for prevention of respiratory- and systemically-disseminated VACV infections.

Figure 11A:
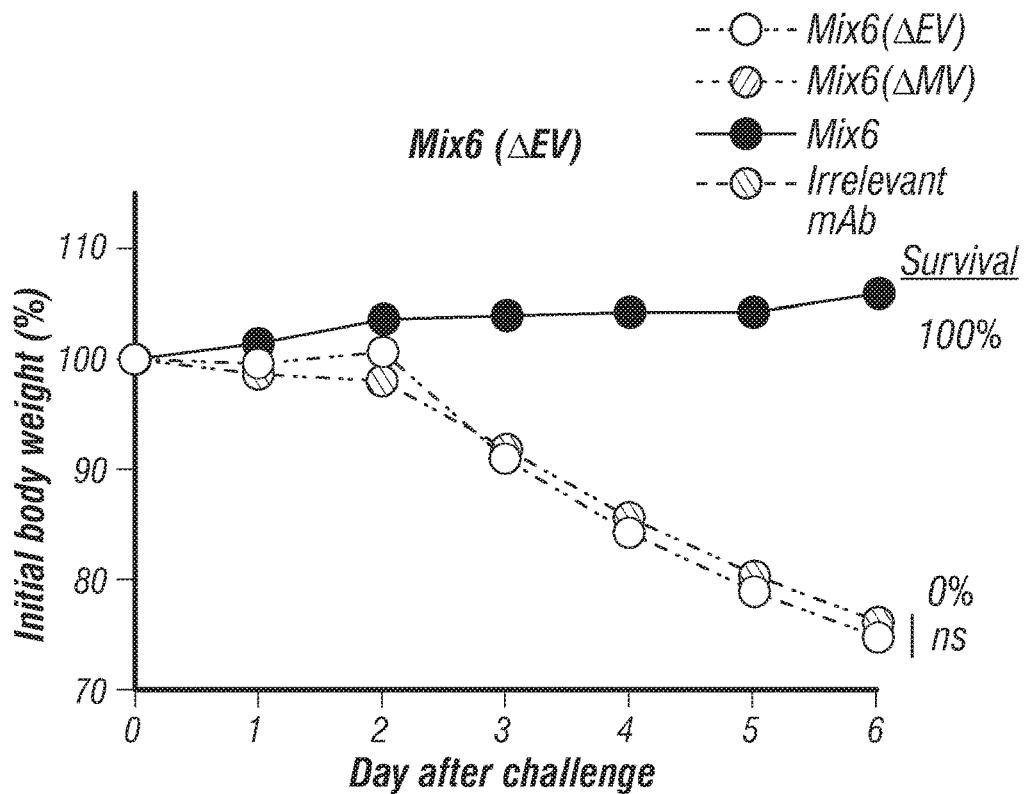
FIGS. 11A-B. Protection Against of Lethal Respiratory VACV Infection is Mediated Principally by EV-Targeted mAbs, Related to FIGS. 5A-C. Groups of C57BL/6 mice were inoculated IP with 1.2 mg of Mix6, or with 0.8 mg of Mix6 lacking two anti-EV mAbs (designated as Mix6 (ΔEV)), or 0.4 mg of Mix6 lacking four anti-MV mAbs (designated as Mix6(ΔMV)), or 1.2 mg of an irrelevant anti-dengue virus neutralizing mAb. The next day (d0) mice were challenged by the IN route with a lethal dose of VACV and monitored for protection.
Figure 11B:
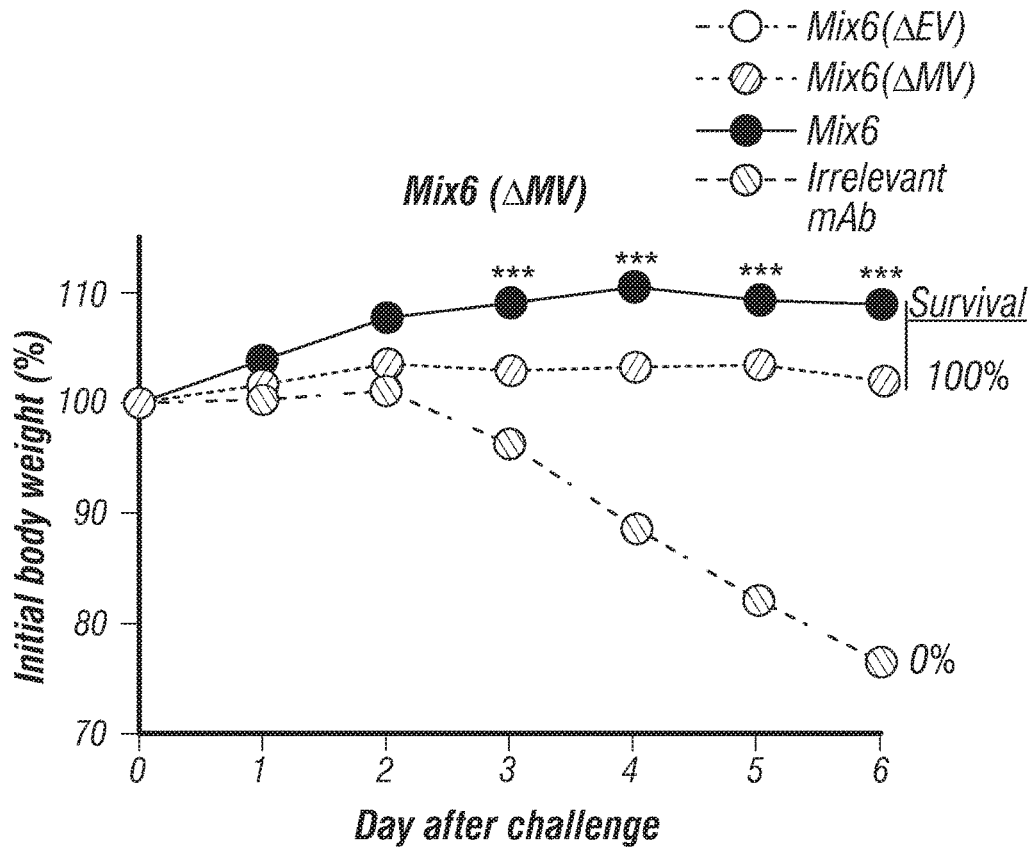
Figure 12A:
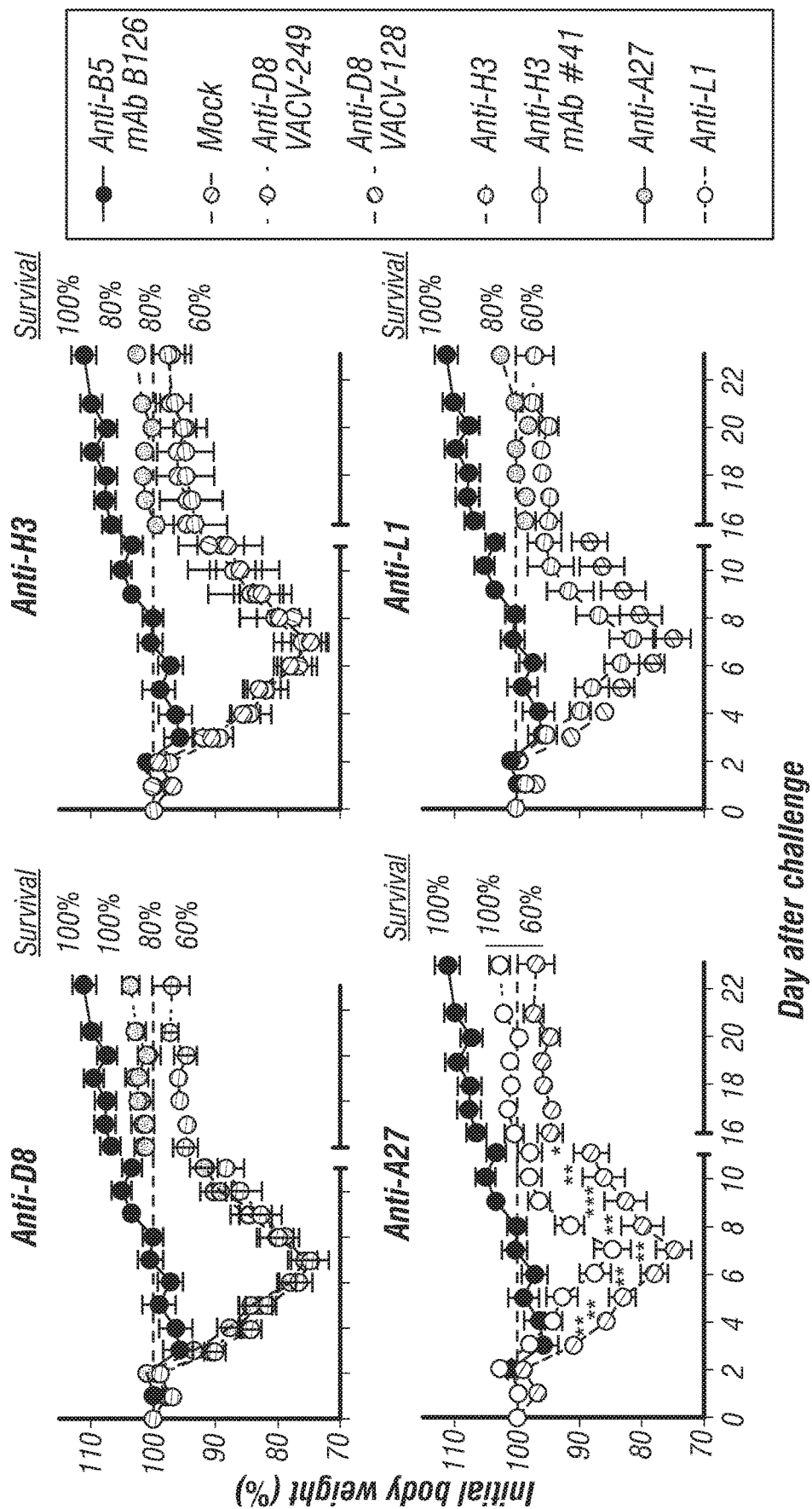

Four principal antibody specificities participated in protection against respiratory VACV challenge when used in mixture. The inventors next determined the contribution of individual mAbs within Mix6 by assessing the protective capacity of single mAbs or their mixtures (Table S6). Both of the EV-targeted antibodies, anti-A33 and -B5, protected B6 mice from death and severe weight loss when administered alone or as a mixture (Mix6(delta MV)) one day before IN VACV challenge. In contrast, none of the MV-targeted mAbs, or their mixture (Mix6(delta EV)), protected mice in the same conditions (FIG. 5A and FIGS. 11A-B). A possible explanation for this result was that the VACV challenge conditions used in this model are quite stringent and likely do not allow detection of moderate levels of protection by some mAbs. The other possibility was that the selected mAb clones may bind to non-protective epitopes of their antigens. To investigate further, the inventors assessed protection using a less severe upper airways infection mouse model (FIG. 12A). These conditions resulted in milder disease and less mortality. In addition, anti-D8 and H3 mAbs were tested as mixtures of five or three different epitope specificities that incorporated mAbs from different competition-binding groups for D8 or H3 antigens, respectively. These single antigen-specific mixtures thus recognized diverse epitopes in D8 or H3 antigen. In this less stringent challenge setting, anti-A27 mAbs prevented mortality and severe weight loss, showing these mAbs may contribute to the protective efficiency by Mix6. Anti-L1 mAbs and mixtures of anti-D8 or anti-H3 mAbs still were not protective (FIG. 12A). Therefore, these monotherapy studies suggested three protective human mAbs specificities in this model—anti-B5, -A33 and -A27.

It was possible that some of the six Ab specificities contributed to protection in mixtures only in a cooperative manner that would not be detected by monotherapy studies. To detect such activity, the inventors designed mixtures that were variants of the Mix6 that each lacked one mAb specificity (Table S6). Each of the Mix6 variant mixtures lacking one of the mAbs was protective, although mixtures lacking anti-L1, anti-A27, anti-A33 and -B5 were less efficient in protection against weight loss than Mix6 (FIG. 5B). Removal of the protective MV-targeted anti-A27 mAb from Mix6 did not affect the outcome of challenge substantially. However, exclusion of the MV-targeted anti-L1 mAb from Mix6 resulted in detectable weight loss upon infection, which was comparable to that seen when mice were pre-treated with Mix6 lacking either of the most potent EV-targeted mAbs (anti-A33 or -B5) identified in the monotherapy studies (FIGS. 5A-B). Moreover, Mix4 containing anti-L1, -A27, -B5 and -A33 mAbs conferred a level of protection equivalent to that of Mix6 (FIG. 5C). Therefore, the mAbs in Mix4 appear to cooperate in achieving their protective effect.

One possible explanation for the diminished protection observed when a mAb mixture lacked a single MV- or EV-targeted mAb specificity was the decrease in total amount of mAb per treatment. Therefore, the inventors next examined whether the lack of one mAb specificity in protective Mix4 could be compensated for by using a mixture containing the same total amount of Ab by adding an equivalent amount of one of the retained mAb specificities targeting the same virion form. The monotherapy results suggested higher potency of anti-A33 and -A27 mAbs when compared to the EV- or MV-specific anti-B5 and anti-A27 mAbs (FIG. 5A and FIG. 12A). Therefore, groups of mice were treated before VACV challenge with a variant of Mix4 that contained a two-fold higher amount of the anti-A27 or anti-A33 mAb and lacked anti-B5 (designated as Mix4 (ΔB5)), or -L1 (designated as Mix4(ΔL1)) mAb, respectively. An excess of anti-A27 or anti-A33 mAb did not restore the initial activity of Mix4 in absence of mAbs with anti-L1 or anti-B5 specificities, although the effect was minor under the challenge conditions used (FIG. 5C). However, in more stringent challenge conditions, mice pre-treated with Mix4 exhibited significantly higher resistance to the disease and recovered faster compared to mice that received the Mix4 (ΔB5) containing a two-fold higher amount of anti-A33 mAb (FIG. 12B). This finding suggested Mix4 as a potent therapeutic mixture. Together, these results showed that four principal mAb specificities in Mix4 contributed to, and were required for, efficient protection against lethal respiratory tract VACV infection in the mouse model.

Therapeutic effect of Mix6 when given up to three days after infection by the respiratory route. The inventors next determined how long after respiratory infection Mix6 would exhibit a therapeutic effect, when treatment was delayed. For these studies, mice were immunized passively with MIX6 one day before or on the day of virus challenge, or one, two or three days after virus challenge (FIG. 6). As expected, the treatment was most efficient when administered before disease onset. Mice given Mix6 showed significant protection from weight loss if the treatment was given one day before, on the day of challenge or one day after infection. When the treatment was delayed until day three, the time point when untreated animals developed disease due to profound virus burden in the lungs (data not shown), the inventors observed protection from death, but only partial protection from weight loss (FIG. 6). These data demonstrated that Mix6 mediated a therapeutic effect even when treatment was delayed, especially against lethality.

Figure 7A:
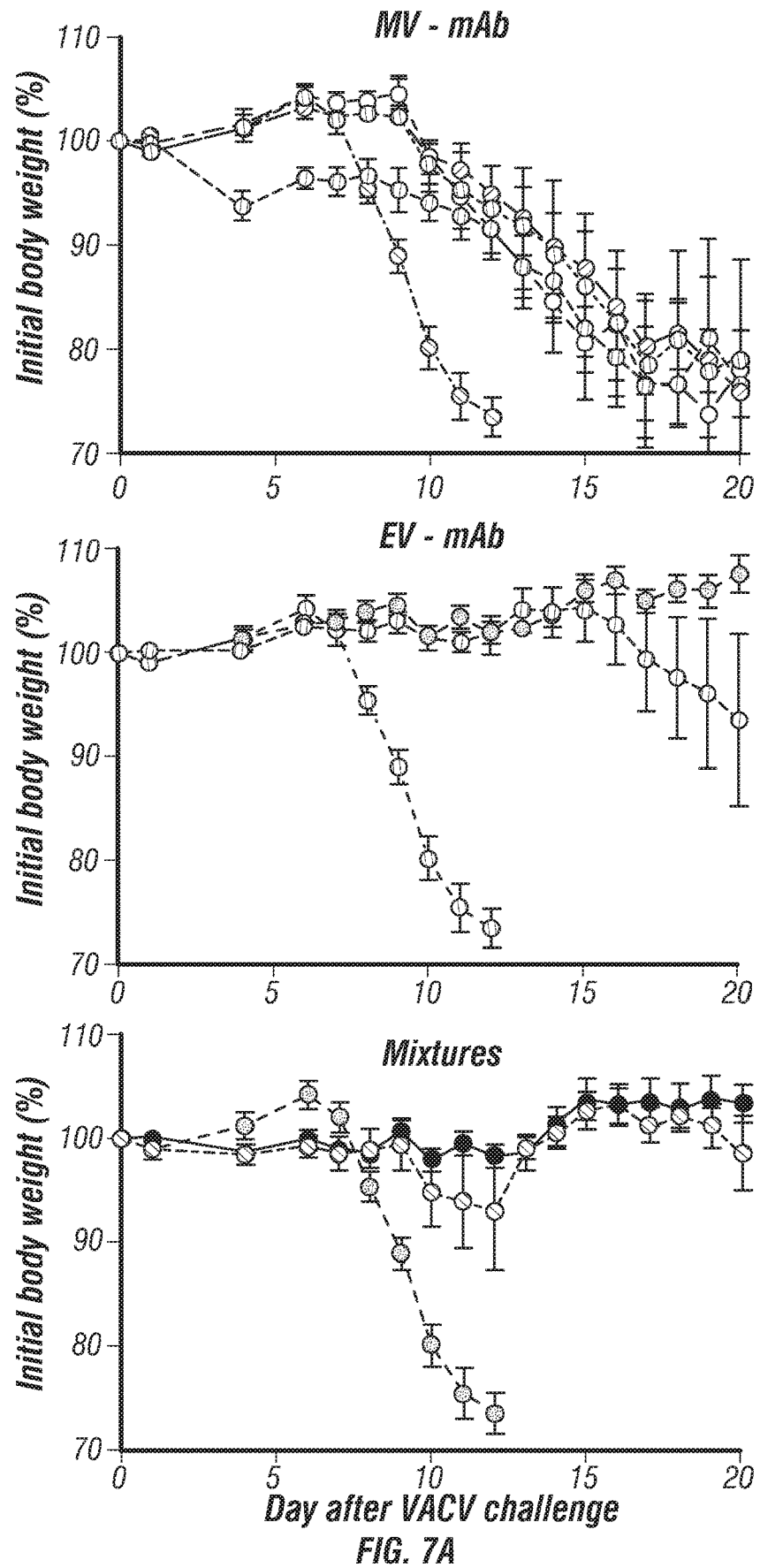
FIGS. 7A-B. Human MAb Specificities that Contribute to Protection Against Progressive Systemic VACV Infection. BALB/c SCID mice were challenged IP with $10^5$ pfu VACV. The next day, mice were inoculated IP with 1.2 mg of Mix6, 5 mg of VIGIV, or 0.2 mg anti-L1, -A27, -D8, -H3, -B5, -A33, or irrelevant mAb. Body weight loss kinetics (FIG. 7A) and survival (FIG. 7B). Data in FIG. 7A show body weight only for the animals that survived. Mean±SEM, n=5-6 mice per group. Each curve was compared to that of the irrelevant mAb-treated group on FIG. 7B.
Figure 7B:
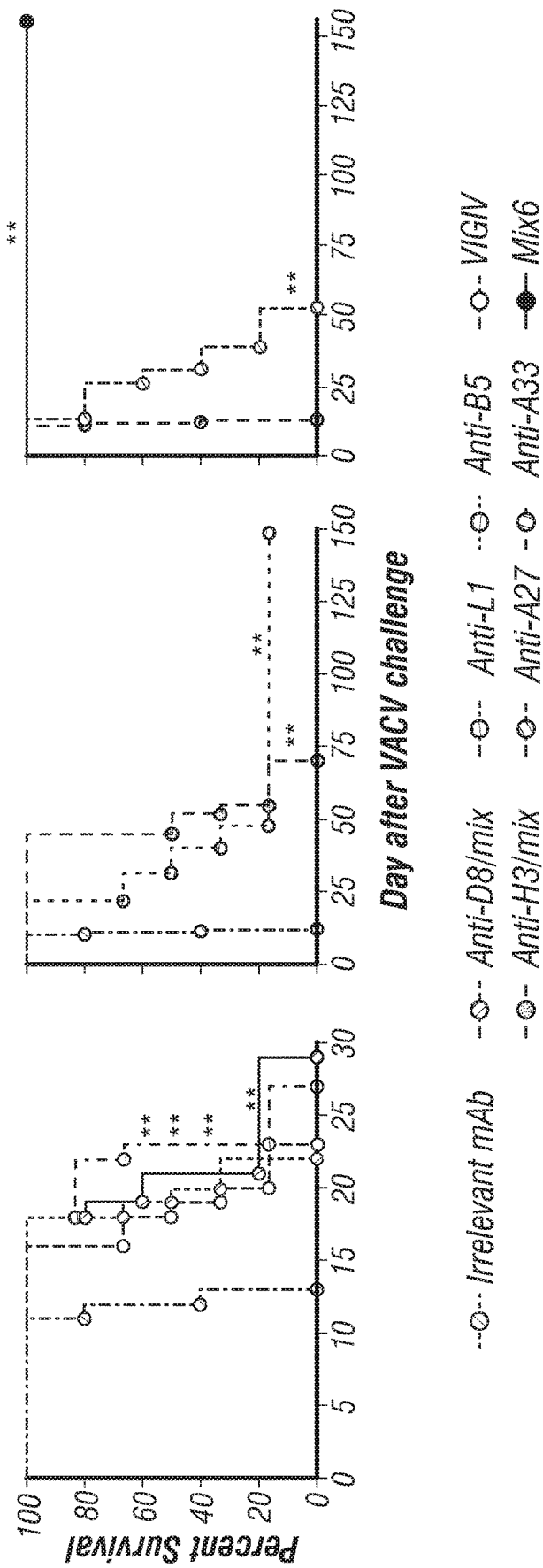

Diverse human Ab specificities participate in protection against systemic VACV infection. The experiments described above showed that a single dose of Mix6 given prior to systemic inoculation with a lethal dose of VACV conferred sterilizing protective immunity in SCID mice, which lack adaptive immunity (FIG. 4C). Using this model, the inventors next assessed the efficacy of monotherapy with individual mAbs, Mix6 or VIGIV that were given to mice one day after inoculation with a lethal dose of VACV (FIGS. 7A-B). Similar to the respiratory challenge study, anti-H3 or -D8 mAbs were used as mixtures of several epitope specificities. Each of the Abs tested, including those identified as non-protective in respiratory tract infection, delayed morbidity and mortality in mice when compared to the animals in the mock-treated group. Moreover, delayed treatment with Mix6 conferred sterilizing immunity to inoculated mice, which all survived and lacked signs of illness for >155 days after VACV inoculation (FIGS. 7A-B). Together these results demonstrated a high therapeutic potency of Mix6 and showed that diverse mAbs specificities may contribute to protection against systemically disseminated VACV infection.

Example 3—Discussion

In this study, the inventors elucidated the breadth and specificity of human cross-neutralizing mAbs against the clinically relevant orthopoxviruses VACV, CPXV, MPXV, and VARV. In addition, they identified protective specificities for human mAbs and demonstrated that superior protection in mouse challenge models could be achieved with a defined mAb mixture that targeted a limited number of poxvirus protein antigens.

Studying protective antibody-mediated immunity for poxvirus infections has been challenging because of the lack of clonal human Abs representing the naturally-occurring human B cell response to poxvirus infection or immunization. In the current work, using a cohort of orthopoxvirus-immune subjects, the inventors showed that orthopoxvirus infection elicits a complex B cell response encoding large numbers of clones reactive to antigens from diverse orthopoxvirus species. Further analysis of individual clones revealed the importance of six major neutralizing mAb specificities that targeted both MV (anti-H3, -A27, -D8 and -L1) and EV (anti-B5 and -A33) infectious forms of poxvirus and required complement for optimal activity.

In studies of human mAbs to other viruses, such as HIV, influenza, or dengue virus, the inventors have found that the percentage of neutralizing mAbs among the total number of mAbs induced by infection or vaccination varies according to the agent. For example, typically less than 1% of the mAbs induced by dengue virus infection neutralize virus (Smith et al., 2012), whereas a large proportion of influenza-specific mAbs neutralize (Thornburg et al., 2013). For orthopoxviruses, the inventors found here that a high fraction of the mAbs from the panel (54%) possessed neutralizing activity. Given the high level of sequence homology among the surface proteins from VACV, CPXV, MPXV and VARV (89-100%), such a robust and diverse neutralizing Ab response likely explains the efficient cross-protection induced by VACV immunization against heterologous orthopoxvirus infections. The inventors' finding that a large fraction of poxvirus-specific mAbs of the panel exhibited cross-binding and/or cross-neutralizing activity for VACV, CPXV, MPXV, and VARV further substantiates this model. The broadest cross-neutralization was achieved by mAbs targeting four antigens in the MV form of VACV, namely A33, A27, L1 and H3 (or the ortholog proteins in the other three viruses), thus identifying the principal determinants of Ab-mediated cross-protective immunity to orthopoxviruses. Of note, the presence of complement enhanced the inhibitory activity of mAbs targeting most neutralizing determinants.

Information about the protective potential of human Abs has been limited mostly to the study of varying lots of VIGIV, which has been used with partial success for post-exposure treatment and for management of some severe adverse reactions to smallpox vaccination (Wittek, 2006). Multiple antigen specificities appear to contribute to neutralization of the MV form of VACV by VIGIV or immune serum IgG (Benhnia et al., 2008; Moss, 2011). Abs to B5 were thought responsible for much of the neutralization activity against VACV EV forms of virus (Bell et al., 2004). Animal studies suggested that protection is not readily achieved by administration of a single neutralizing mAb, and requires both EV- and MV-targeted mAbs (Lustig et al., 2005). Reconstituting (or improving) the protective activity of VIGIV with mAbs has been attempted empirically, using a mixture of anti-H3 and -B5 mAbs (McCausland et al., 2010), or a complex mixture of 26 human mAbs directed to fourteen antigens (Lantto et al., 2011; Zaitseva et al., 2011). These data suggest that a mixture containing mAbs of only two specificities (anti-H3 and anti-B5) likely would fail to cross-protect efficiently, since the inventors observed that anti-B5 mAbs fail to neutralize the EV form of MPXV. In contrast, the previous mixture of 26 mAbs likely includes redundant or noncontributory mAbs, because this composition contains a number of mAbs that are directed to antigenic specificities without an apparent role in cross-neutralization or protection. To make a potent neutralizing and protective human Ab mixture by rational design that recognizes the four major poxvirus threats to humans, the inventors combined potent cross-neutralizing human mAbs targeting six major poxvirus antigenic proteins: the MV antigens H3, A27, D8 and L1 and the EV antigens B5 and A33. Remarkably, M$_{IX}$6 or its derivative M$_{IX}$4 cross-neutralized all four clinically relevant orthopoxviruses, including live VARV, and exhibited superiority compared to conventional VIGIV.

Poxviruses transmit by several routes of infection, and cause diverse clinical syndromes in humans (Smith and McFadden, 2002), which can be modeled in part using different animal models (Chapman et al., 2010). The inventors sought here to compare the prophylactic and treatment efficiency of human mAbs and their mixtures in several well-established VACV lethal challenge murine models using either mild or severe respiratory tract infection or, alternatively, systemic inoculation resulting in disseminated infection (Belyakov et al., 2003; Flexner et al., 1987; Wyatt et al., 2004). The resulting data revealed that the contribution of individual specificities to protection varied depending on the route of virus inoculation. Four specificities (anti-A33, -B5, -L1 and -A27), contributed significantly to protection against respiratory tract infection, while in contrast, all six tested specificities contributed to protection in the model of systemic infection. Moreover, the inventors observed that the major contribution to protection in both models was provided by EV-targeted anti-B5 and -A33 human mAbs, consistent with previous studies of mouse mAbs (Lustig et al., 2005). Thus, cross-protection against all clinically important orthopoxviruses is most likely achieved when incorporating both EV-neutralizing anti-B5 and -A33 mAbs, which may compensate for some species cross-neutralization deficiencies of the other. M$_{IX}$6 and M$_{IX}$4 exhibited superiority in protection against VACV compared to VIGIV, suggesting novel efficient mixtures of mAbs for therapeutic use in humans.

Using naturally occurring human mAbs isolated using hybridoma technology, this study revealed six principal cross-neutralizing human mAb specificities for VACV, CPXV, MPXV and VARV, and Ab specificities that are necessary and sufficient determinants of protection in murine challenge models. This work suggests that a mixture of these Abs could mediate cross-protective immunity to orthopoxviruses. As with most studies, there are several limitations of this work that the inventors would like to point out. First, the antibody discovery platform used likely allowed us to identify mAbs only from the most frequent classes of B cell memory clones that occur in human peripheral blood. Therefore, less frequent clones could be missing from the inventors' analysis. Second, it remains unknown to what extent the B cell memory repertoire in the blood that the inventors have studied corresponds to the antigen-reactive antibody protein repertoire in the serum that is secreted by long-lived plasma cells in the bone marrow. Future proteomics studies using emerging technologies might be able to address this question. And third, future development for use in humans of individual mAbs or mixtures described here against VACV, CPXV, and MPXV or VARV should include studies of larger animal models, such as non-human primates.

TABLE 1

NUCLEOTIDE SEQUENCES FOR ANTIBODY VARIABLE REGIONS

| Clone | Variable Sequence Region | SEQ ID NO: |
|---|---|---|
| VACV-8 heavy | CAGGTGCAGCTACAGCAGTGGGGCGCAGGACTGTTGAAGCCTTCGGAGACCCTGTCCCTCACCTGCGC TGGCTATGGTGGGTCCTTCAGTGGTTATTTCTGGAGCTGGATCCGCCAGCCCCCAGGGAAGGGGCTGG AATGGATTGGGGAGATCAATCATAGTGGCAGCACCGACTACAACCCGTCCCTCAAGAGTCGAGTCACC ATATCACTGGACACGTCCAAGACCCAGTTCTCCCTGAAGCTGAGCTCTGTGACCGCCGCGGACACGGCT GTCTATTACTGTGCGAGAGTGATGACTGGAATTACGAATTACTACTACTATTACGGTATGGACGTCTGG GGCCAAGGGACCACGGTCACCTTCT | 1 |
| VACV-8 light | GACATCCAGTTGACCCAGTCTCCATCCTTCCTGTCTGCATCTGTAGGAGACAGAGTCACCATCACTTGCC GGGCCAGTCAGGACATTAGCAGTTATTTAGCCTGGTATCAGCAAAAACCAGGGAAAGCCCCTAAGCTC CTGATCTATGCTGCATCCACTTTGCAAAGTGGGGTCCCCTCAAGGTTCAGCGGCAGTGAATCTGGGACA GAATTCACTCTCACAATCAGCAGCCTGCAGCCTGAAAATTTTGCAACTTATTACTGTCAACACCTTAATA GTTACCCCCGGGGGTACACTTTTGGCCAGGGGACCAAGGTGGATATCAAA | 2 |
| VACV-56 heavy | CAGGTGCAGCTACAGCAGTGGGGCGCAGGACTGTTGAAGCCTTCGGAGACCCTCTCACTCACCTGTGC TGTCTATGGTGGGTCCTTCAGTGGTTACTACTGGAGCTGGATCCGCCAGCCCCCAGGGAAGGGGCTGG AGTGGATTGGGGAAATCAATCATAGTGGAAGCACCAACTACAACCCGTCCCTCAAGAGTCGAGTCACC ATATCAGTAGACACGTCCAAGAGCCAGTTCTCCCTGAAGCTGAGCTCTGTGACCGCCGCGGACACGGCT GTGTATTACTGTGCGAGAGCCACCCAGGGTTCGGGGACCTATAAGTTATTCTTTTACTCCTACGGTATG GACGTCTGGGGCCAAGGGACCACGGTCACCGTCTCCTCA | 3 |
| VACV-56 light | GACATCCAGATGACCCAGTCTCCTTCCACCCTGTCTGCATCTGTAGGAGACAGAGTCACCATCACTTGCC GGGCCAGTCAGAGTATTACTAGCTGGTTGGCCTGGTATCAGCAGAAACCAGGGAAAGCCCCTAAGCTC CTGATCTATAAGGCGTCTAGTTTAGAAAGTGGGGTCCCATCAAGGTTCAGCGGCAGTGGATCTGGGAC AGAATTCACTCTCACCATCAGCAGCCTGCAGCCTGATGATTTTGCAACTTATTACTGCCAACAGTATAAT AGTTATCCGTACACTTTTGGCCAGGGGACACGACTGGAGATTAAA | 4 |
| VACV-66 heavy | CAGCTGCAGCTGCAGGAGTCGGGCCCAGGACTGGTGAAGCCTTCGGAGACCCTGTCCCTCACCTGCAC TGTCTCTGGTGACTCCATCAGCAGTAATAATTACTACTGGGGCTGGATCCGCCAGCCCCCAGGGAAGGG ACTGGAGTGGATTGGGAGTATCTATTACAGTGGGAGCACCTACTACAACCCGTCCCTCAAGAGTCGAGT CACCCATATCCGTAGACACGTCCAAGAACCAGTTCTCCCTGAAGCTGAGCTCTGTGACCGCCGCAGACAC GGCTGTGTATTACTGTGCGAGACACCGTCGAGTATTACTATGGTTCGGGGAGTTCCAACTCTGGGCCA GGGAACCCTGGTCACCGTCTCCTCAG | 5 |
| VCV-66 light | CAGTCTGCCCTGACGCAGCCGCCCTCAGTGTCTGGGGCCCAGGGCAGAGGGTCACCATCTCCTGCACT GGGAGCAGCTCCAACATCGGGGCAGGTTATGATGTACACTGGTACCAGCAGCTTCCAGGAACAGCCCC CAAACTCCTCATCTATGGTAACATCAATCGGCCCTCAGGGGTCCCTGACCGATTCTCTGGCTCCAAGTCT GGCACCTCAGCCTCCCTGGCCATCACTGGGCTCCAGGCTGAGGATGAGGCTGATTATTACTGCCAGTCC TATGACAGCAGCCTGAGTGGTGCCTTATTCGGCGGAGGGACCCAGCTGACCGTCCTAT | 6 |
| VACV-77 heavy | CAGGTGCAGCTGCAGGAGTCGGGCCCAGGACTGGTGAAGCCTTCGGAGACCCTGTCCCTCACCTGCAC TGTCTCTGGTGGCTCCATGAGTAGTTACTTCTGGAGCTGGATCCGCCAGCCCCCAGGGAAGGGACTGG AGTGGATTGGGTATATCTCTTACAGTGGGGGCACCAACTACAACCCCTCCCTCAAGAGTCGAGTCACCA TATCAGTAGACACGTCCAAGAACCAGTTCTCCCTGAAGCTGACCTCTGTGACCGCTGCGGACACGGCCG TTTATTACTGTGCGAGAGAGGACCGCGGCTCGCCTGACTATTGGGGCCAGGGAACCCTGGTCACCGTCT CCTCAG | 7 |
| VACV-77 light | CAGTCTGTGTTGACGCAGCCGCCCTCAGTGTCTGCGGCCCCAGGACGGAAGGTCACCATCTCCTGCTCT GGAAGCAGCTCCAACATTGGGAATAATTATGTATCCTGGTACCAGCAGCTCCCAGGAACAGCCCCCAAA CTCCTCATTTATGACAATTATAAGCGACCCTCAGGGATTCCTGACCGATTCTCTGGCTCCAAGTCTGGCA CGTCAGCCACCCTGGGCATCACCGGACTCCAGACTGGGGACGAGGCCGATTATTACTGCGGAACATGG GATCTCAGCCTGAGTGCTGGGGTGTTCGGCGGAGGGACCAAGCTGACCGTCCTAG | 8 |
| VACV-116 heavy | CAGGTGCAGCTGGTGCAGTCTGGGGCTGAGGTGAAGAAGCCTGGGGCCTCAGTGAAGGTCTCCTGCA AGGCTTCTGGATACACCTTCACCAGTTATGATATCAACTGGGTGCGACAGGCCACTGGACAAGGGCTTG AGTGGCTGGGATGGATGAACCCTAACAGTGGTAACACAAAGTCTGCACAGAAGGTCAAGGGCAGAGT CACCATGACCAGGGACACCTCCATAAGCACAGCCTACATGGAGCTGAGCAGCCTGAGATCTGAGGACA CGGCCGTGTATTACTGTGCGAGAACCCCCTTTGATGGTAGTGGTTATTATTACTGGGGCCAGGGAACCC TGGTCACCGTCTCCTCAG | 9 |
| VACV-116 light | LC#1<br>GATATTGTGATGACTCAGTCTCCACTCTCCCTGTCCGTCACCCCTGGAGAGCCGGCCTCCATCTCCTGCA GGTCGAGTCAGAGCCTCCTGCATAGTAATGGATACAACTATTTGGATTGGTACCTGCAGAAGCCAGGG CAGTCTCCACAGCTCCTGATCTATTTGGGTTCTAATCGGGCCTCCGGGGTCCCTGACAGGTTCAGTGGC AGTGGATCAGGCACAGATTTTACACTGAAAATCAGCAGAGTGGAGGCTGAGGATGTTGGGGTTTATTA TTGCATGCAAGCTCTACAAACTCCGGGGGCTTCGGCCCTGGACCAAGGTGGATATCAAA | 10 |
| | LC#2<br>GATATTGTGATGACTCAGTCTCCACTCTCCCTGCCCGTCACCCCTGGAGAGCCGGCCTCCATCTCCTGCA GGTCTAGTCAGAGCCTCCTGCATAGTAATGGATACAACTATTTGGATTGGTACCTGCAGAAGCCAGGGC AGTCTCCACAGCTCCCGATCTATTTGGGTTCTAATCGGCCGCGGGGTCCCTGACAGGTTCATTGGCA GTGGATCAGGCACAGATTTTACACTGAAAATCGGCATATTGGAGGCTGAGGATGTTGGGGTTTATTATT GCATGCTGCTCTACGAACTCCGGGGCTTTCGGCCCTGGGACCAAGGTGGATATAAGA | 882 |
| VACV-117 heavy | CAGGTGCAGCTGGTGCAGTCTGGGGCTGAGGTGAAGAAGCCTGGGGCCTCAGTGAAGGTCTCCTGCA AGGCTTCTGGATACACCTTCACCAGTTATGATATCAACTGGGTGCGACAGGCCACTGGACAAGGGCTTG AGTGGCTGGGATGGATGAACCCTAACAGTGGTAACACAAAGTCTGCACAGAAGGTCAAGGGCAGAGT | 11 |

TABLE 1-continued

NUCLEOTIDE SEQUENCES FOR ANTIBODY VARIABLE REGIONS

| Clone | Variable Sequence Region | SEQ ID NO: |
|---|---|---|
|  | CACCATGACCAGGGACACCTCCATAAGCACAGCCTACATGGAGCTGAGCAGCCTGAGATCTGAGGACA CGGCCGTGTATTACTGTGCGAGAACCCCCTTTGATGATATTGGTTATTATTACTGGGGCCAGGGAACCC TGGTCACCGTCTCCTC |  |
| VACV-117 light | GATATTGTGATGACTCAGTCTCCACTCTCCCTGTCCGTCACCCCTGGAGAGCCGGCCTCCATCTCCTGCA GGTCGAGTCAGAGCCTCCTGCATAGTAATGGATACAACTATTTGGATTGGTACCTGCAGAAGCCAGGG CAGTCTCCACAGCTCCTGATCTATTTGGGTTCTAATCGGGCCTCCGGGGTCCCTGACAGGTTCATTGGCA GTGGATCAGGCACAGATTTTACACTGAAAATCAGCATAGTGGAGGCTGAGGATGTTGGGGTTTATTATT GCATGCAAGCTCTACAAACTCCGGGGGCTTTCGGCCCTGGGACCAAGGTGGATATCAAA | 12 |
| VACV-128 heavy | GAGGTCCAGCTGGTACAGTCTGGGGCTGAGGTGAAGAAGCCTGGGGCTACAGTGAAAATCTCCTGCA AGGTTTCTGGATACACCTTCACCGACTACTACATGCACTGGGTGCAACAGGCCCCTGGAAAAGGGCTTA AGTGGATGGGACTTCTTGATCCTCTAGATGGTGAAACAATATACTCAGAGAAGTTCCAGGGCAAAGTC ACCATAACCGCGGACACATCTACAGACACAGCCTACATGGAACTGAGCAGCCTGAGATCTGAGGACAC GGCCGTGTATTACTGTGCAAGAGAGTTGACTGGTTACCTCAACTACTGGGGCCAGGGAACCCTGGTCA CCGTCTCCTCAG | 13 |
| VACV-128 light | GACATCCAGATGACCCAGTCTCCATCCTCCCTGTCTGCATCTGTAGGAGACAGAGTCACCATCACTTGCC GGGCGAGTCCCGGCATTTGCAATTATTTAGCCTGGTATCAACATAAACCAGGGAAAGTTCCTAAACTCC TGATCTATGCTGCATCCACTTTGCAATCAGGGGTCCCATCTCACTGGCGTTGGATCTGGGACAA ATTTCACTCTCACCATCAACAATTTGCCTCCTGAAAATGTTGCAACTTATTACTGTCAAAAGTATAACAGT GCCCCTCACACGTTCGGCCAAGGGACAAAAGTGGATATCAAA | 14 |
| VACV-136 heavy | CAGGTCACCTTGAAGGAGTCTGGTCCTGTGCTGGTGAACCCCACAGAGACCCTCACGCTGACCTGCACC GTCTCTGGATTCTCACTCAGCAATGCTAGAATGCGTGTGAGCTGGATCCGTCAGCCCCCAGGGAAGGCC CTGGAGTGGCTTGCACACATTTTTTTCGAATGACGAAAAATCCTACAGCACATCTCTGAAGAGCAGGCTC ACCATCTCCAAGGACACCTCCAAAAGCCAGGTGGTCCTTACCATGACCAACATGGACCCTGTGGACACA GCCTCATATTACTGTGCCCGGATGAGGGGGGAGTACAACTCGTACTACTTTGACTCCTGGGGCCAGGG AACCCTGGTCACCGTCTCCTC | 15 |
| VACV-136 light | TCCTATGAGCTGACACAGCCACCCTCGGTGTCAGTGTCCCAGGACAGACGGCCAGGATCACCTGCTCT GGAGATGCATTGCCAAACCAATATGCTTATTGGTACCAGCAGAAGCCAGGCCAGGCCCCTGTGCTGGT GATATATAAAGACAGTGAGAGGCCCTCAGGGATCCCTGAGCGATTCTCTGGCTCCAGCTCAGGGACAA CAGTCACGTTGACCATCAGTGGAGTCCAGGCAGAAGACGAGGCTGACTATTACTGTGCAATCAGCAGAC AGCAGTGGTACTTCTGTGGTATTCGGCGGAGGGACCCAGGTGACCGTCCT | 16 |
| VACV-138 heavy | HC#1<br>CAGGTGCAGCTGGTGCAGTCTGGGGCTGAGGTGAAGAAGCCTGGGGCCTCAGTGAAGGTTTCCTGCA AGGCATCTGGATACACCTTCGCCAGCTACGACATTCACTGTGTGCGACAGGCCCCTGGACAAGGGTTTG AATGGATGGTAGGGAGCTACTCTGGCAATGGTAACACAGGCTATGCACAGAAGTTTCAGGGCAGAGTC ACCATGACCAGGGACACGTCCACGAGCACAGCCTACATGGAGCTGAGCAGCCTAGAGATCTGAGGACAT AGATGTGTACTACTGTGCGAGTAGGGATATTGTGGTGGTGACTGCTACCCGCTCCCCCTTTGACTACTG GGGCCAGGGAACCCTGGTCACCGTCTCCTCA<br>HC#2<br>GAAGTGCAGCTGGTGGAGTCTGGGGGAGGCTTGGTACAGCCTGGCAGGTCCCTGAGACTCTCCTGTGC AGTCTCTGGATTCACCCTTGATGATTATGCCATGCACTGGGTCCGGCAACCTCCAGGGAAGGGCCTGGA GTGGGTCACAGGTATTAGTTGGAATAGTGGTGGCATGGGCTATGCGGACTCTGTGAAGGGCCGATTCA CCATCTCCAGAGACAGCGCCAAGAACTCCCTCTATCTACAAATGAACAGTCTGAGAGTTGAGGACACGG CCTTCTACTACTGTGCAAAAGATGTTGGAGGGGTGGTGACTGGAGGTTATTGGGATGATGCTCTTGATA TCTGGGGCCAAGGGACAATGGTCACCGTCTCCTCAG<br>HC#3<br>GAGGTCCAGCTGGTACAGTCTGGGGCTGAGGTGAAGAAGGATCTGGCCTCAGTGAAGGTCTCCTGCAA GGTTTCTGGATACACCTTCACCGACTACTACATGCACTGGGTGCAACAGGCCCCTGGAAAAGGGCTTGA GTGGATGGGACTTGTTGATCCTCAAGAAGGTGAAACAACATACGCAGAGAAGTTCCAGGGCAGAGTCA CCATAACCGCGGACACGTCTACAGACACAGCCTATATGGAGCTGAGCAGCCTGAGATCTGAGGACACG GCCGTGTATTACTGTGCAAAAGAATCATTTGGGATCCCCCACTTCTGGGGCCAGGGAACCCTGGTCACC GTCTCCTCAG | 17<br><br>883<br><br><br><br><br><br><br><br>916 |
| VACV-138 light | GAAATTGTGTTGACGCAGTCTCCAGGCACCCTGTCTTTGTCTCCAGGGGAAAGAGCCACCCTCTCCTGC AGGGCCAGTCAGAGTGTTACCAGCACCTACTTAGCCGGGCACCAGCAAAAACCTGGCCAGGCTCCAAG GCTCCTCATCTATAGTGCATCCAGCAGGGCCACTGGCATCCCAGACAGGTTCAGTGGCAGTGGGTCTGG GACAGACTTCACTCTCACCATCAGCAGACTGGAGCCTGAAGATTTTGCAGTGTATTACTGTCAGCAATAT GGTAGCTCACCTCCGTACACTTTTGGCCAGGGGACCAAGGTGGATATCAAA | 18 |
| VACV-168 heavy | CAGGTGCAGCTGCAGGAGTCGGGCCCAGGACTGGTGAAGCCTTCGGAGACCCTGTCCCTCACCTGCAC TGTCTCTGGTGGCTCCATCAGTAGTTTCTACTGGAGCTGGATCCGGCAGCCCCCAGGGAAGGGACTGG AGTGGATTGGGTATATCTATTACAGTGGGAGCACCAACTACAACCCCTCCCTCAAGAGTCGAGTCACCA TATCAGTAGACACGTCCAAGAACCAGTTCTCCCTGAAGCTGAGCTCTGTGACCGCTGCGGACACGGCCG TGTATTACTGTGCGAGATAAGAGGGAACTATGCTAGTAGTGGTTATTACTACAACTTTGACTACTGGG GCCAGGGAACCCTGGTCACCGTCTCCTCAG | 19 |
| VACV-168 light | CAGTCTGTGGTGACGCAGCCGCCCTCAGTGTCTGCGGCCCCAGGACAGAAGGTCACCATCTCCTGCTCT GGAAGCAGCTCCAACATTGGGAATAATTATGTATCCTGGTACCAGCAGCTCCCAGGAACAGCCCCCAAA CTCCTCATTTATGACAATAATAAGCGACCCTCAGGGATTCCTGACCGATTCTCTGGCTCCAAGTCTGGCA | 20 |

TABLE 1-continued

NUCLEOTIDE SEQUENCES FOR ANTIBODY VARIABLE REGIONS

| Clone | Variable Sequence Region | SEQ ID NO: |
|---|---|---|
| | CGTCAGCCACCCTGGGCATCACCGGACTCCAGACTGGGGACGAGGCCGATTATTACTGCGGAACATGG<br>GATAGCAGCCTGAGTGCTTATGTCTCGGAAACTGGGACCAAGGTCACCGTCCTAG | |
| VACV-159<br>heavy | CAGCTGCAGCTGCAGGAGTCGGGCCCAGGACTGGTGAAGCCTTCGGAGACCCTGTCCCTCACCTGCAC<br>TGTCTCTGGTGGCTCCATCAGCAGTAGTAGTTACTACTGGGGCTGGATCCGCCAGCCCCCAGGGAAGG<br>GGCTGGAGTGGATTGGGAGTATCTATTATCGTGGGAGCACCTACTACAACCCGTCCCTCAAGAGTCGA<br>ATCACCATATCCGTAGACACGTCCAAGAACCAGTTCTCCCTGAAGCTGAGGTCTGTGACCGCCGCAGAC<br>ACGGCTGTGTATTACTGTGCGAGACATTTGCAGAGTATTACTATGGTTCGGGGAGTTATTGGAATGGGG<br>CCAAGGGACCACGGTCACCGTCTCCTCAG | 21 |
| VACV-159<br>light | CAGTCTGCCCTGACGCAGCCGCCCTCAGTGTCTGGGGCCCCAGGGCAGAGGGTCACAATCTCCTGCACT<br>GGGAGCAGCTCCAACATCGGGGCAGATTATGATGTACACTGGTACCAGCAGCTTCCAGGAACAGCCCC<br>CAAACTCCTCATCTATGGTAACAGCAATCGGCCCTCAGGGGTCCCTGACCGATTCTCTGGCTCCAAGTCT<br>GGCACCTCAGCCTCCCTGGCCATCACTGGGCTCCAGGCTGAGGATGAGGCTGATTATTACTGCCAGTCC<br>CATGACAGCAGCCTGAGTGGTTATGTCTTCGGAACTGGGACCAAGGTCACCGTCCTAT | 22 |
| VACV-199<br>heavy | CAGGTGCAGCTGGTGCAGTCTGGGGCTGAGGTGAAGAAGCCTGGGGCCTCAGTGAAGGTCTCCTGCA<br>AGGCTTCTGGATACACCTTCACCGGCTACTATATGCACTGGGTGCGACAGGCCCCTGGACAAGGGCTTG<br>AGTGGATGGGATGGATCAACCCAAACAGTGGTGGCACAAACTATGCACAGAAGTTTCAGGGCAGGGT<br>CACCATGACCAGGGACACGCCCATCAGCACAGCCTACATGGAGCTGAGCAGGCTGAGATCTGACGACA<br>CGGCCGTGTATTACTGTGCGAGAGTGCCCCCYGATAGCAGCAGCTGGAAGTGGGGCCAGGGAACCCTG<br>GTCACCGTCTCCT | 23 |
| VACV-199<br>light | GATATTGTGATGACTCAGTCTCCACTCTCCCTGCCCGTCACCCCTGGAGAGCCGGCCTCCATCTCCTGCA<br>GGTCTAGTCAGAGCCTCCTGCATAGAAATGGATACAACTATTTGGATTGGTACCTGCAGAAGCCAGGG<br>CAGTCTCCACAGCTCCTGATCTATTTGGGTTCTAATCGGGCCTCCGGGGTCCCTGACAGGTTCAGTGGC<br>AGTGGATCAGGCACAGATTTTACACTGAAAATCAGCAGAGTGGAGGCTGAGGATGTTGGGGTTTATTA<br>CTGCATGCAAGCTCTACAAACTCCTCCGACGTCGGCCAAGGAC | 24 |
| VACV-228<br>heavy | GAGGTGCAGCTGGTGGAGTCTGGGGGAGGCCTGGTCAAGCCTGGGGGGTCCCTGAGACTCTCCTGTG<br>CAGCCTCTGGATTCACCCTTCAGTAGCTATAGCATGAACTGGGTCCGCCAGCCTCCAGGGAAGGGGCTG<br>GAGTGGGTCTCATCCATTACTAGTAGTAGTAGTTACATATACTACGCAGACTCAGTGAAGGGCCGATTC<br>ACCATCTCCAGAGACAACGCCAAGAACTCACTGTATCTGCAAATGAACAGCCTGAGAGCCGAGGACAC<br>GGCTGTGTATTATTGTGCGAGCCGACCGGGTATAGCACCAGCTGGCCCCCAGGCGGAGGGCTACTGGG<br>GCCAGGGAACCCTGGTCACCTTC | 25 |
| VACV-228<br>light | GAAATAGTGATGACGCAGTCTCCAGCCACCCTGTCTGTGTCTCCAGGGGAAAGAGCCACCCTCTCCTGC<br>AGGGCCAGTCAGAGTGTCAGCAGCAACTTAGCCTGGTACCAGCAGAAACCTGGCCAGGCTCCCAGGCT<br>CCTCATCTATGGTGCATCCACCAGGGCACTGGCATCCCAGCCAGGTTCAGTGCCAGTGGGTCTGGGAC<br>AGAGTTCACTCTCACCATCAGCAGCCTGCAGCCTGAAGATTTTGCAGTGTATTACTGTCAGCAGTAT | 26 |
| VACV-230<br>heavy | CAGGTCCAGCTGGTACAGTCTGGGGCTGAGGTGAAGAAGCCTGGGGCCTCAGTGAAGGTCTCCTGCAA<br>GGTCTCCGGATACACCCTCACTGAATTATCCATGCACTGGGTGCGACAGGCTCCTGGAAAAGGGCTTGA<br>GTGGCTGGGAGGTTTTGATCCTGAAGATGGTGAAACAATCTACGCACAGAAGTTCCAGGGCAGAGTCA<br>CCATGACCGAGGACACATCTACAGACACAGCCTACATGGAACTGAGCAGCCTGAGATCTGAGGACACG<br>GCCGTGTATTACTGTGCAAGAGAAAGCTGGCTCAGGGGGTTTGACTACTGGGGCCAGGGAACCCTGGT<br>CACCGTCTCCTC | 27 |
| VACV-230<br>light | GAAATTGTGTTGACGCAGTCTCCAGGCACCCTGTCTTTGTCTCCAGGGGAAAGAGCCACCCTCTCCTGC<br>AGGGCCAGTCAGAGTGTTAGCAGCAGCTACTTAGCCTGGTACCAGCAGAAACCTGGCCAGGCTCCCAG<br>GCTCCTCCTCTATGGTGCATCCAGCAGGGCCACTGGCATCCCAGACAGGTTCAGTGGCAGTGGGTCTG<br>GGACAGACTTCACTCTCACCATCAGCAGACTGGAGCCTGAAAATTTTGCAGTGTATTACTGTCAGCAGT<br>ATGGTAGCTCCTCGGACGTTCGGCCAAGGGACCAAGGTGGATATCAAA | 28 |
| VACV-249<br>heavy | CAAGTGCAGCTGGTGGAGTCGGGCCCAGGACTGGTGAAGCCTTCACAGACCCTGTCCCTCACCTGCACT<br>GTCTCTGGTGGCTCCATCAGCCGTGGTATTACTACTGGAGCTGGATCCGGCAGCCCGCCGGGAAGGG<br>ACTGGAGTGGATTGGGCGTATCTATACCAGTGGGAGCACCAACTACAACCCCTCCCTCAAGAGTCGAGT<br>CACCATATCAGTAGACACGTCCAAGAACCAGTTCTCCCTGAAGCTGAGCTCTGTGACCGCCGCAGACAC<br>GGCCGTGTATTACTGTGCGAGAGATGGCTGGTACGGGTGGTACTTAGATCTCTGGGCCGTGGCACCCC<br>TGGTCACCGTCTCCTCAG | 29 |
| VACV-249<br>light | GAAATAGTGATGACGCAGTCTCCAGCCACCCTGTCTGTGTCTCCAGGGGAAAGAGCCACCCTCTCCTGC<br>AGGGCCAGTCAGAGTGTTAGCAGCGACTTAGCCTGGTACCAGCAGAAACCTGGCCAGGCTCCCAGGCT<br>CCTCATCTATGGTGCATCCACCAGGGCACTGGTATCCCAGCCAGGTTCAGTGGCAGTGGGTCTGGGAC<br>AGAGTTCACTCTCACCATCAGCAGCCTGCAGTCTGAAGATTTTGCAGTTTATTACTGTCAGCAGTATAAT<br>AACTGGCCGGGTACTTTCGGCGGAGGGACCAAGGTGGATATCAAA | 30 |
| VACV-304<br>heavy | GAGGTGCAGCTGGTGGAGTCTGGGGGAGGCTTGGTCCAGCCTGGGGGGTCCCTGAGACTCTCCTGTG<br>TAGTCTCTGGATTCACCTTTAGTAATTATTGGATGAGTTGGGTCCGCCAGGCTCCAGGGAAGGGGCTGG<br>AGTGGGTGGCCAACATAAAGCAAGATGGTAGTAAGAAATACTATGTGGACTCTGTGACGGGCCGATTC<br>ACCATCTCCAGAGACAACGCCAAGAACTCACTGTATCTGCAAATGAACAGCCTGAGAGCCGAGGACAC<br>GGCTGTGTATTACTGTGCGACCTTAAATCTTGAATTAGCAGTGGATGCTATCTCGGAGGCCCTTAAGTG<br>GGGCCAGGGAACCCTGGTCACCGTCTCCTCAG | 31 |

TABLE 1-continued

NUCLEOTIDE SEQUENCES FOR ANTIBODY VARIABLE REGIONS

| Clone | Variable Sequence Region | SEQ ID NO: |
|---|---|---|
| VACV-304 light | TCCTATGAGCTGACACAGCCACCCTCGGTGTCAGTGTCCCCAGGACAGACGGCCAGGATCACCTGCTCT GGAGATGCATTGCCAAAACAATTTGCTTATTGGTACCAGCAGAAGCCAGGCCAGGCCCCTGTAGTGAT GATATATAAAGACAGTGAGAGGCCCTCAGGGATCCCTGAGCGATTCTCTGGCTCCAGTTCAGGGACAA CAGTCACGTTGACCATCAGTGGAGTCCAGGCAGAAGACGAGGCTGACTATTACTGTCAATCAGTAGAC AACAGTGGTACTTATGAGGTGTTCGGCGGAGGGACCCAGCTGACCGTCCTAT | 32 |
| MPXV-27 heavy | HC#1<br>CAGGTGCAGCTACAGCAGTGGGGCGCAGGACTGTTGAAGCCTTCGGAGACCCTGTCCCTCACCTGTGA TGTCTATGGTGGGTCCTTCAGTGGTTACTACTGGAGCTGGATCCGCCAGCCCCCAGGGAAGGGGCTGG AGTGGATTGGGGAAATCAATCATAGTGGAAGCACCACCTACACCCCGTCCCTCAGGAGTCGAGTCACC ATATCAGTAGACACGTCCAAGAACCAGTTCTCCCTGAAGCTGAGCTCTGTGACCGCCGCGGACACGGCT GTGTATTACTGTGCGAGAGTTTTGTCAGGGTGGCTACCATTTCCCAACTACTACTACTACATGGACGTCT GGGGCAAAGGNACCACGGTCACCT | 33 |
| | HC#2<br>CAGGTGCAGCTGCAGGAGTCGGGCCCAGGACTGGTGAAGCCTTCACAGACCCTGTCCCTCACCTGTACT GTCTCTGGTGGCTCCATCAGCAGTGGTGGTTACTACTGGAGTTGGATCCGCCAGTACCCAGGGAAGGG CCTGGAGTGGATCGGGCACATGTCTTATAGTGGGGACACCTTCTTCAACCCGTCCCTCAAGAGTCGAGC TACCCATATCAGCGGACACGTCTAAGCACCAGTTCTCCCTGATGCTGAGATCTGTGACTGCCGCGGACAC GGCGTGTATTTATGTGCGAGAGGCAGATATTGTAATGATGACAGCTGCTACTCCGAGGAGTCTGCTAT CTGGTTCGACCCCTGGGGCCAGGGAACCCTGGTCACCT | 884 |
| MPXV-27 light | GACATCCAGATGACTCAGTCTCCATCGTCCCTGCCTGCATCTGTAGGAGACAGGGTCACCATCACTTGCC GGGCAAGTCAGGACATTAGAAATAATTTAGGCTGGTATCAGCAGAAACCAGGGAAAGCCCCTGAGCG CCTGATCTATGAACCTCCAATTTGCAGAGTGGGGTCCCGTCAAGGTTCAGCGGCAGTGGATCTGGGA CAGAATTCACTCTCACAATCAGCAGCCTGCAGCCTGAAGATTTTGCAACTTATTACTGTCTACAGCATAA TAGTTACCCTCCCACGTTCGGCCGCGGGACCAAGGTGGAAATCAAAC | 34 |
| MPXV-30 heavy | CAGGTCCAGCTGGTGCAGTCTGGGGCTGAGGTGAAGAAGCCTGGGTCCTCAGTGAAGGTCTCCTGCAA GGTTTCTGGAGGCACCTTCAGCAGTTTAGCTATCAACTGGGTGCGACAGGCCCCTGGACAGGGGCTTG AGTGGATGGGAGGCATCATCCCCATCTTTGGTAAAGCAAACTACGCACAGAAGTTCCAGGGCAGAGTG TCAATTATCGCGGACGAATCCACGAGCACAGCCTACATGGACCTGAGCAGCCTGAGATTTGAGGACAC GGCCGTGTATTACTGTGCGACTGGTGGGAACATTAGGGTTCATGATTTTGATATCTGGGGCCAAGGGA CACTGGTCATCGTCTCTTCA | 35 |
| MPXV-30 light | GATGTTGTGATGACTCAGTCTCCACTCTCCCTGCCCGTCACCCTTGGACAGCCGGCCTCCATCTCCTGCA GGTCTAGTCAAAGCCTCGTAAACAGCGATGGAAATACCTACTGGTTTCAGCAGAGGCCAGGC CAATCTCCAAGGCGCCTAATTTATAAGGTTTCTAACCGGGACTCTGGGGTCCCAGACAGATTCAGCGGC AGTGGGTCAGGCACTGATTTCACACTGAACATCAGCAGGGTGGAGGCTGAGGATGTTGGGGTTTATTA CTGCATGCAAGGTACACACTGGCCTCCGAGGTGGACGTTCGGCCAAGGGACCAAGGTGGATATCAAA | 36 |
| MPXV-40 heavy | CAGGTGCAGCTACAGCAGTGGGGCGCAGGACTGTTGAAGCCTTCGGAGACCCTGTCCCTCACCTGCGC TGTCTATGGTGGGTCCTTCAGTGGTTACTACTGGAGCTGGATTCGCCAGCCCCCAGGGAAGGGGCTGG AGTGGATTGGGGAAATCAATTACAGTGGAAGCACCGACTACAACCCGTCCCTCAGAGTCGAGTCACC ATATCAGTARACGCGTCCAAGAACCACTTCTCCCTGAACTTGAACTCTGTGACCGCCGCGGACACGGTT GTGTATTACTGTGCGAGAATTTCAAGCGGCTGGATTGGATTTCCCCGATACCACTACTACTTGGACGTCT GGGGCAAAGGGACCACGGTCACCGTCTCCT | 37 |
| MPXV-40 light | TCCTATGAGCTGACACAGCCACCCCGCGGTGTCAGTGTCCCCAGGACAGACAGCCAGGATCAGCTGCTCT GGAGATGTACTGAGAGATAATTATGCTGACTGGTACCCGCAAAAGCCAGGCCAGGCCCCTGTGCTGGT GATATATAAAGATGAACAATCCCTGGGTGTCGGCGGAGGGACCCAGCTGACCGTCCTAGATCGGAAGA GCGTCGTG | 38 |
| MPXV-61 heavy | CAGGTCCAGCTGGTGCAGTCTGGGGCTGAGGTGAAGAAGCCTGGGTCCTCAGTGAAGGTCTCCTGCAA GGCTTCTGGAGAGACCTTCAGCAGATATGCTTTCAGCTGGGTGCGACTGGCCCCTGGACAAGGCCTTG AGTGGTTGGGAAGGATCATCCCCTTTCATTGATATACCAAACTACGCACAGAAGTTCCAGGGGAGAGTC ACCATTACCGCGGACAAATCCACGAGCACAGCCTACATGGAGCTGAGTAGCCTGAGATCTGAAGACAC GGCCGTCTATTACTGTGCGAGTTCGCTCCCCTCCACATATTCTTTGTTCGGGGAATTATCCCTGGGGA AACTGGCTCGACCCCTGGGGCCAGGGAACCCTGGTCACCGTCTCCTCAG | 39 |
| MPXV-61 light | CAGTCTGTGGTGACGCAGCCGCCCTCAGTGTCTGCGGCCCCCGGACAGAACGTCACCATCTCCTGCTCT GGAAGCAGCTCCAACATTGGGAATAATTATGTATCCTGGTACCATCAGCTCCCAGGAACAGCCCCCAAA CTCCTCATTTATGACAATGATAAGCGACCCTCAGGGATTCCTGACCGATTCTCTGGCTCCAAGTCTGGCA CGTCAGCCACCCTGGGCATCACCGGACTCCAGACTGGGGACGAGGCCGATTATTACTGCGGAACATGG GATAGCAGCCTGAGTGAAGTAGTGTTCGGCGGAGGGACCCAGGTGACCGTCCTA | 40 |
| MPXV-96 heavy | CAGGTGCAGCTACAGCAGTGGGGCGCAGGACTGTTGATATCTTCGGAGACCCTGTCCCTCACCTGTGGT GTGTATGGTGGGTCCTTCAGTGGTTACTACTGGACCTGGATCCGTCAGCCCCCGGGAAGGGGCTGGA GTGGATTGGTGAAATCAATTATGTTGGAAGCACCAACTACAACCCGTCCCTCAAGAGTCGAGTCACCAT GTCAGTAGACACGTCCAAGAACCACTTCTCCCTGAGCCTGAGCTCTGTGACCGCCGCTGACACGGCTGT CTATTACTGTGCGAGAGGCCTTCGTGGAAATAGTGTCTGCTTTGACTGGGGCCCTGGAACCCTGGTCAC TGTCTCCTC | 41 |
| MPXV-96 light | GAGTTAGTGATGACGCAGTCTCCAGCCACCCTGTCTGTGTCTCCAGGGGAAAGAGCCTCCCTCTCCTGC AGGGCCAGTCAGAGTGTTAGCAGCAACTTAGCCTGGTACCAGCAGAAACCTGGCCAGGCTCCCAGGCT | 42 |

TABLE 1-continued

NUCLEOTIDE SEQUENCES FOR ANTIBODY VARIABLE REGIONS

| Clone | Variable Sequence Region | SEQ ID NO: |
|---|---|---|
| | CCTCATCTATGGTGCATCCACCAGGGCCACTGGTCTCCCAGCCAGGTTCAGTGGCAGTGGGTCTGGGAC AGAGTTCACTCTCACCATCAGCAGCCTGCAGTCTGAAGATTTTGCAATTTATTACTGTCAGCAGTATAAT AACTGGCCGAGAACTTTTGGCCAGGGGACCAAGGTGGATATCA | |
| VACV-1 heavy | GAGGTGCAGCTGGTGGAGTCTGGGGGAGGCTTGGTACAGCCTGGGGAGTCTCTGAAGATCTCCTGTG CAGCCTCTGGATTCACCTTCAGTAGCTTTAGCATGAACTGGGTCCGCCAGGCTCCAGGGAAGGGGCTG GAGTGGGTTTCATACATTAGTAGTAGTAGTAGTACCATATACTACGCAGACTCTGTGAAGGGCCGATTC ACCATCTCCAGAGACAATGCCAAGAACTCACTGTATCTACAAATGAACAGCCTGAGAGACGAGGACAC GGCTGTGTATTACTGTGCGAGACGGTCAGTTGGTTGTAGTGGTGGTAACTGCTACGCATACTACTACGG TATGGACGTCTGGGGCCAAGGGACCACGGTCACCGTCTCCTC | 43 |
| VACV-1 light | GATATTGTGATGACTCAGTCTCCACTCTCCCTGCCCGTCACCCCTGGAGAGCCGGCCTCCATCTCCTGCA GGTCTAGTCAGAACCTCCTGCATAGTAATGGATACAACTATTTGGATTGGTACCTGCAGAAGCCAGGGC AGTCTCCACAGCTCCTGATCTATTTGGGTTCTAATCGGGCCTCCGGGGTCCCTGACAGGTTCAGTGGCA GTGGATCAGGCACAGATTTTACACTGAAAATCAGCAGAGTGGAGGCTGAGGATGTTGGACTTTATTAC TGCATGCAAGCTCTACAAACTCCTATCACCTTCGGCCAAGGGACACGACTGGAGATTAAA | 44 |
| VACV-59 heavy | CAGGTGCAGCTGGTGCAGTCTGGGGGAGGCTTGGTCAAGCCTGGAGGGTCCCTGAGACTCTCCTGTGC AGCCTCTGGATTCACCTTCAGTGACTACTACATGAGCTGGATCCGCCAGGCTCCAGGGAAGGGGCTGG AGTGGGTTTCATACATTAGTACTAGTGGTAGTACCATATACTACGCAGACTCTGTGAAGGGCCGATTCA CCATCTCCAGGGACAACGCCAAGAACTCACTGTATCTGCAAATGAACAGCCTGAGAGCCGAGGACACG GCCATGTATTACTGTGCGAGAGATGGTGATGGTTCGGGGAGTTATACCCCTCCTTACTATTACTACGGT CTGGACGTCTGGGGCCAAGGGACCACGGTCACCGTCTCCTCA | 45 |
| VACV-59 light | GACATCCAGATGACCCAGTCTCCATCCTCCCTGTCTGCATCTGTAGGAGACAGAGTCACCATCACTTGCC GGGCAAGTCAGAGCATTCGCAACTATTTAAATTGGTATCAGCAGAAATCAGGGAAAGCCCCTAAGCTC CTGATCTATGCTGCATCCAGTTTGCAAAGTGGGGTCCCATCAAGGTTCAGTGGCAGTGGATCTGGGACA GATTTCACTCTCACCATCAGCAGTCTGCACCCTGAAGATTTTGCAACTTACTACTGTCAACAGAGTTACA GTACCCCTCCGCTCACTTTCGGCGGAGGGACCAAGGTAGAGATCAAAC | 46 |
| VACV-151 heavy | GAGGTGCAGCTGGTGGAGTCTGGGGGAGGCCTGGTCAAGCCTGGGGGGTCCCTGAGACTCTCCTGTG CAGCCTCTGGATTCACCTTCAGTAGCTATAGCATGAACTGGGTCCGCCAGCCTCCAGGGAAGGGGCTG GAGTGGGTCTCATCCATTACTAGTAGTAGTAGTTACATATACTACGCAGACTCAGTGAAGGGCCGATTC ACCATCTCCAGAGACAACGCCAAGAACTCACTGTATCTGCAAATGAACAGCCTGAGAGCCGAGGACAC GGCTGTGTATTATTGTGCGAGCCGACCGGGTATAGCACCAGCTGGCCCCCCAGGCGGAGGGCTACTGG GGCCC | 47 |
| VACV-151 light | GAAATTGTGTTGACGCAGTCTCCAGGCACCCTGTCTTTGTCTCCAGGGGAAAGAGCCACCCTCTCCTGC AGGGCCAGTCAGAGTGTTAGCAGCAGCTACTTAGCCTGGTACCAGCAGAAACCTGGCCAGGCTCCCAG GCTCCTCATCTATGGTGCATCCCGCAGGGCCACTGGCATCCCAGACAGGTTCAGTGCCAGTGGGTCTGG GACAGACTTCACTCTCACCATCAGCAGACTGGAGCCTGAAGATTTTGCAGTGTATTACTGTCAGCAGTA TGGTAGCTCACCGTACACTTTTGGCCGGGGGACCCAGGTGGATATCAAAA | 48 |
| VACV-282 heavy | GAGGTGCAGCTGGTGGAGTCTGGGGGAGGCCTGGTCAAGCCTGGGGGGTCCCTGAGACTCTCCTGTG CAGCCTCTGGATTCACCTTCAGTAGTTATAGCATGAACTGGGTCCGCCAGGCTCCAGGGAAGGGGCTG GAGTGGGTCTCATCCATTAGTAGTATTAGTAGCTACATATACTACGCAGACTCAGTCAAGGGCCGATTC ACCATCTCCAGAGACAACGCCAAGAACTCACTGTATCTGCAAATGAACAGCCTGAGAGCCGAGGACAC GGCTGTGTATTACTGTGCGAGAGATAGGCCACGGTCAAGGCCCAATTCGGGGAGTTATTTCTGGTACTA CTACGGTATGGACGTCTGGGG | 49 |
| VACV-282 light | TCCTATGAGCTGACTCAGCCACCCTCGGTGTCAGTGGCCCCAGGACAGACGGCCAGGATTACCTGTGG GGGAAACAACATTGGAAGTAAAAGTGTGCACTGGTACCAGCAGAAGCCAGGCCAGGCCCCTGTGCTG GTCGTCTATGATGATAGCGACCGGCCCTCAGGGATCCCTGAGCGATTCTCTGGCTCCAACTCTGGGAAC ACGGCCACCCTGACCATCAGCAGGGTCGAAGCCGGGGATGAGGCCGACTATTACTGTCAGGTGTGGG ATAGTAATAGTGATCATCGGGTATCGGCG | 50 |
| VACV-283 heavy | CAGGTCCAGCTGGTGCAGTCTGGGGCTGAGGTGAAGAAGCCTGGGTCCTCAGTGAAGGTCTCCTGCAA GGCTTCTGGAGGCACCTTCAGCACCTATGCTATCAACTGGGTGCGACAGGCCCCTGGACAAGGGCTTG AGTGGATGGGAAGGATCATCCCTATCCTTGGTACGGCAAACTACGCACAGAAGTTCCAGGGCAGAGTC ACGATTACCGCGGACAAATCCACGAGCACAGCCTACATGGAGCTGAGCAGCCTGAGATCTGAGGACAC GGCCGTGTATTACTGTGCGAGACGGGGGGGCGAGGGCGCCGCACACGGTATGGACGTCTGGGGCCAA GGGACCACGGTCACCGTCTCCTCA | 51 |
| VACV-283 light | GATATTGTGATGACTCAGTCTCCACTCTCCCTGCCCGTCACCCCTGGAGAGCCGGCCTCCATCTCCTGCA GGTCTAGTCAGAGCCTCCTGCATAGTAATGGATACAACTATTTGGATTGGTACCTGCAGAAGCCAGGGC AGTCTCCACAGCTCCTGATCTATTTGGGTTCTAATCGGGCCTCCGGGGTCCCTGACAGGTTCAGTGGCA GTGGATCAGGCACAGATTTTACACTGAAAATCAGCAGAGTGGAGGCTGAGGATGTTGGGGTTTATTAC TGCTTGCAGGCTCTACAAACTCTTCCGATCACCTTCGGCCAAGGGACACGACTGGAGATTAA | 52 |
| MPXV-2 heavy | CAGGTCCAGCTTGTGCAGTCTGGGGCTGAGGTGAAGAAGCCTGGGGCCTCAGTGAAGGTCTCCTGCAA GACTTCTGGATACACCTTCACTACCTATGTGTTCATTGGGTGCGCCAGGCCCCCGGACAAAGGCTTGA GTGGATGGGATGGATCAACCCTGGCGATGTGACACAAGATATGCCCAGAAGTTCCAGGACAGAGTC ACCATTAGTAGTGACACATCCGCGACCACAGTGTACATGGAACTGAGCAGCCTGAGATCTGAGGACAC GGCTGTGTATTCTGTGCGAGACCTCGTGCCAGTCTATTACGATATTTTGACTGGCTGTTTGAACAGTGG GGCCAGGGAAACCCTGGTCACCGTCTCCTCA | 53 |

TABLE 1-continued

| NUCLEOTIDE SEQUENCES FOR ANTIBODY VARIABLE REGIONS | | |
|---|---|---|
| Clone | Variable Sequence Region | SEQ ID NO: |
| MPXV-2 light | GAAATTGTGTTGACGCAGTCTCCAGGCACCCTGTCTTTGTCTCCAGGGGACAGAGCCACCCTCTCCTGC<br>GGGGCCAGTCAGAGCATTCACCACAACTACGTAGCCTGGTACCAGCAGAGACCTGGCCAGGCTCCCAG<br>GCTCCTCATCTTTGGTGCTTCCAGTAGGGCCACTGGCATCCCAGACAGGTTCACTGGCAGTGGGTCTGG<br>GACAGAATTCACTCTCACCATCAACAGACTGGAGCCTGAAGATTTTGCAGTGTATTACTGTCAGCAGTA<br>TGGCAACTCAGTTCCGTACTCCTTTGGCCAGGGGACCAAGGTGGATATCAAAA | 54 |
| MPXV-12 heavy | CAGGTGCAGCTACAGCAGTGGGGCGCAGGACTGTTGAAGCCTTCGGAGACCCTGTCCCTCACCTGTGC<br>TGTCTATGGTGGGTCCTTCACGAACTACTACTGGAGCTGGATCCGCCAGTTCCCAGGGAAGGGGCTGG<br>AGTACATTGGGGAAATCGATCATAGTGGAAGCGCCAACTACAACCCGTCCCTGAAGAGTCGAGTCACC<br>ATATCACTAGACACGTCCAAGAACCAATTCTCCCTGAGGCTGAGCTCTGTGACCGCCGCGGACACGGCT<br>GTGTATTTCTGTGCGAGGGATGTCTATGGTTCGGGGACTTATTACTGGTTCGATCCCTGGGGCCAGGGA<br>ACCCTGGTCACCGTCTCCTCAG | 55 |
| MPXV-12 light | GACATCCAGATGACCCAGTCTCCAACCTCCCTGTCTGCATCTGTAGGAGACAGAGTCACCATCACTTGCC<br>GGGCAAGTCAGAGGATTAGCAGCCATTTAAATTGGTATCAACAGAAACCAGGGAAAGCCCCTAAACTC<br>CTGATTTATGTCGCATCCAGTTTGCAAAGTGGGGTCCCATCAAGGTTCAGTGGCAGTGGATCTGGGACA<br>GATTACACTCTCACCATCAGCAGTCTGCAACCTGAAGATTTTGCAACTTACTTCTGTCAACAGAGTTACA<br>CTACCCCGTACACTTTTGGCCAGGGGACCAACCTGCAAATGAAAC | 57 |
| MPXV-13 heavy | CAGGTGCAGCTGCAGGAGTCGGGCCCAGGACTGGTGAAGCCTTCGGAGACCCTGTCCCTCACCTGCGC<br>TGTCTCTGGTGGCTCCATCAGCACTAGAACCTGGTGGACTTGGGTCCGCCAGCCCCCAGGGAAGGGGC<br>TGGAGTGGATTGGAGAAATCTATCAGAGTGGGAGCACCAACTACAACCCGTCCCTCAAGAGTCGAGTC<br>ACCATATCAATAGACACGTCCAAGAACCAGTTCTCCCTGAAGCTGAGCTCTGTGACCGCCGCGGACACG<br>GCCCTGTATTACTGTGCGAGAAGTGGCAGATATAGCAGTGTCACTCCTTTTGACTACTGGGGCCAGGGA<br>ACCCTGGTCACT | 58 |
| MPXV-13 light | GAAATTGTGTTGACACAGTCCCCAGCCACCCTGGTCTTTGTCTCCGGGCAAAGAGCCACCCTCTCCTGCA<br>GGGCCAGTCAAAGTATTGGCAACTACTTAGCCTGGTACCAACAGAAACCTGGCCAGGCTCCCAGGCTCC<br>TCATCTATGATGCATCCAACAGGGCCACTGGCATCCCAGCCAGGTTCAGTGGCAGTGGGTCTGGGACA<br>GACTTCACTCTCACCATCAGCAGCCTAGAGCCTGAAGATTTTGCAGTTTATTACTGTCAGCAGCGTAGCC<br>ACTGGCCGGCTTTCGGCCCTGGGACCAAGGTGGATATCAAAA | 59 |
| MPXV-25 heavy | CAGGTGCAGCTGGTGGAGTCTGGGGGAGGCGTGGTCCAGCCTGGGAGGTCTCTGAAGATCTCCTGTG<br>CAGCCTCTGGATTCACCTTCAGTGACTCTGGCTTACACTGGGTCCGCCAGGCTCCAGGCAAGGGGCTGG<br>AGTGCGTGGCATTTATATGGTATGATGGAAGTACTAAATACTATGCAGACTCCGTGAAGGGCCGATTCA<br>CCATCTCCAGAGACAATTCCAGGAACACACTGTATCTTCAAATGAAGAGCCTGAGAGCCGAGGACACG<br>GCTGTGTATTACTGTGCGAGAGAGCTAGGATATTGTAGTGGTGGTACCTGCTACTCCATGGGTGCTTTT<br>GATATCTGGGGCCAAGGGACACTGGTCACCGTCTCTCAGT | 60 |
| MPXV-25 light | CAGTCTGTGCTGACTCAGCCTGCCTCCGTGTCTGGGTCTCCTGGACAGTCGATCACCATCTCCTGCACTG<br>GAACCAGCAGTGATGTTGGGAGTTATAACCTTGTCTCCTGGTACCAACAGCACCCAGGCAAAGCCCCCA<br>AACTCATGATTTATGAGGTCAGTAAGCGGCCCTCAGGGGTTTCTAATCGCTTCTCTGGCTCCAAGTCTGA<br>CAACACGGCCTCCCTGACAATCTCTGGGCTCCAGGCTGAGGACGAGGCTGATTATTACTGCTGCTCATA<br>TGTAGGTAGTAGCACTTCCGTGTTCGGCGGAGGGACCCAGGTGACCGTCCTA | 61 |
| MPXV-38 heavy | GAGGTGCAGCTGGTGGAGTCTGGGGGAGGCTTGGTAAAGCCTGGGGGGTCCCTTAGACTCTCCTGTG<br>CAGCCTCTAGTTTCATTTTCAGTGACGCCTGGATGAAGTGGGTCCGCCAGGCTCCAGGGAAGGGGCTG<br>GAGTGGGTCGGCCATTTTAAAACCAAAACTGATGGTGGGACAACAGACTACGCTGCACCCGTGAAAGG<br>CAGATTCAGCATCTCAAGAGATGATTCAAAATCCACGCTGCATGTGCAAATGAACAGCCTGAAAACCGA<br>GGACACAGCCGTGTATTACTGTACCACAGCCGGGGCAAGTTACGTC | 62 |
| MPXV-38 light | GAAATTGTGTTGACGCAGTCTCCAGGCACCCTGTCTTTGTCTCCAGGGGAAAGAGCCACCCTCTCCTGC<br>AGGGCCAGTCAGAGTGTTAGCAACACGTACTTAGCCTGGTACCAGCAGAAACCTGGCCAGGCTCCCAG<br>GCTCCTCATCTATGCTGCATCCAACAGGGCCACTGGCATCCCAGACAGGTTCAGTGGCAGTGGGTCTGG<br>GACAGACTTCACTCTCACCATCAGCAGACTGGAGCCTGAAGATTTTGCAGTGTATTACTGTCAACCAGT<br>ATGG | 63 |
| MPXV-43 heavy | CAGGTCCAGCTTGTGCAGTCTGGGGCTGAGGTGAAGAAGCCTGGGGCCTCAGTGAAGGTCTCCTGCAA<br>GGCTTCTGGATACACCTTCACTAAATATACTATACATTGGGTGCGCCAGGCCCCCGGACAAAGGCTTGA<br>GTGGGTGGGAGGGATCTACGCTGGCTATGGCAACACAAGATACTCACAGAAGTTCCAGGGCAGAGTC<br>ACCATTACCAGGGACACATCCGCGAGCACAGCCTACATGGAGCTGAGCAGCCTGAGATCTGAAGACAC<br>GGCTGTGTATTTCTGTGCGAGAGATTTCGAGGATTTCGATTCCTGGACTGGTTATTATTT-<br>CATGGCTTTCAC<br>TGGGGCCAGGGAACCCTGGTCACCGTCTCCTCAG | 64 |
| MPXV-43 light | GAAATTGTGTTGACGCAGTCTCCCGGCACCCTGTCTTTGTCTCCAGGGGAAAGAGCCACCCTCTCCTGC<br>AGGGCCAGTCAGAGTGTTAGCAGCACCTACTTAGCCTGGTACCAGCAAAAACCTGGCCAGGCTCCCAG<br>GCTCCTCATCTATGGTGCCTCCAGCAGGGCCACTGGCATCCCAGACAGGTTCAGTGGCAGTGGGTCTG<br>GGACAGACTTCACTCTCACCATCACCAGACTGGAGCCTGAAGATTTTGCAATGTATTTCTGTCAGCAGTA<br>TGATAGCTCCCCTTCGATCACCTTCGGCCAAGGGACACGACTGGAGATTAAA | 65 |
| MPXV-66 heavy | CAGGTGCAGCTACAGCAGTGGGGCGCAGGACTGTTGAAGCCTTCGGAGACCCTGTCCCTCACCTGCGC<br>TGTCCATGGTGGGTCCTTCAGTGGTTACTTCTGGAGCTGGATCCGCCAGCCCCCAGGGAAGGGGCTGG<br>AATGGATTGGGGAAATGAATCATAGTGGCAGCACCAACTATAACCCATCCCTCAAGAGTCGAGTCACCA | 66 |

TABLE 1-continued

NUCLEOTIDE SEQUENCES FOR ANTIBODY VARIABLE REGIONS

| Clone | Variable Sequence Region | SEQ ID NO: |
|---|---|---|
| | TATCAGTAGACACGTCCAAGAAGCAGTTCTCCCTGAAGCTGAACTCTGTGACCGCCGCGGACACGGCTG<br>TGTATTACTGTGCGAGAACAGCTCGTACGGTGAGGTACTTTGAAAACTGGGGCCAGGGAACCCTGGTC<br>ACCGTCTCCTCA | |
| MPXV-66 light | GACATCGTGATGACCCAGTCTCCAGACTCCCTGGCTGTGTCTCTGGGCGAGAGGGCCACCATCAACTGC<br>AAGTCCAGCCAGACTGTTTTATACAACTCCAACAATTACAGCTACTTAACTTGGTACCAGCAGAAACCAG<br>GACAGCCTCCTAGGGTGCTCATTTACTGGGCATCTACCCGGGAATCCGGGGTCCCTGACCGATTCAGTG<br>GCAGCGGGTCTGGGACAGATTTCACTCTCACCATCAGCAGCCTGCAGGCTGAAAATGTGGCCCTTTTATT<br>ACTGTCAGCAGTATTACAGTACTCCTTGGACGTTCGGCCAAGGGACCAAGGTGGATATCAAAA | 67 |
| MPXV-70 heavy | CAGGTGCAGCTGGTGGAGTCTGGGGGAGGCTTGGTCAAGCCTGGAGGGTCTCTGAAGATCTCCTGTGC<br>AGCCAACAGATTCACCTTCAGCAACTACTACATGAGCTGGATCCGCCAGGGTCCAGGGAAGGAGCCGG<br>AGTGGATTTCATACATTAGTAGTAGAAGTCGTTACACAAATTACGCAGACTCTGTGAAGGGCCGATTCA<br>CCATCTCCAGAGACAACACCAAGAATTCACTGTTTCTGCAAATGAACGACCTGCGAGCCGAGGACACGG<br>CTGTCTATTACTGTGCGAGAGGGGGGGATATTTGTGGCGGTACTACTTGTTCCATGGGACATGCTTTTTG<br>ATATCTGGGGTCAAGGGACAGTGGTCACCGTCTCTTTCAG | 68 |
| MPXV-70 light | GAAGTTGTGTTGACGCAGTCTCCAGGCACCCTGTCTTTGTCTCCAGGGGAAAGAGCCACCCTCTCCTGC<br>AGGGCCAGTCAGAGTGTGACCAGCAGCTACTTAGCCTGGTACCAACAGAAGCCTGGCCAGGCTCCCAG<br>GCTCCTCATCTATGGTGCATCTATCAGGTCCACTGACATCCCAGACAGGTTCAGTGGCAGTGAGTCTGG<br>GACAGACTTCACTTACACCATCAGCAGACCGGAGCATGAAGATTTTGCTCTGTATTTTCTGTCAGCAGTAT<br>GGTAGCTCACCGTACAC | 69 |
| MPXV-92 heavy | CAAGTGCAGCTGGTGGAGTCGGGCCCAGGACTGGTGAAGCCTTCGGGGACGCTGTCCCTCACCTGCGC<br>TGTCTCTGGTGGCTCCATCAGCAGTAGTAACTGGTGGAGTTGGGTCCGCCAGCCCCCAGGGAAGGGGC<br>TGGAGTGGATTGGGGAAATCTATCATAGTGGGAGCACCAACTACACCCCGTCCCTCAAGAGTCGAGTC<br>ACCATATCATTAGACAAGTCCAAGAACCAGTTCTCCCTGAAGCTGAGCTCTGTGACCGCCGCGGACACG<br>GCCATGTATTACTGTGCGAGAAACTTCTATCCCGGATACCTCCAGTACTGGGGCCAGGGCACCCTGGTC<br>ACCGTCTCCTCAG | 70 |
| MPXV-92 light | CAGTCTGCTCTGACCCAGCCTGCCAGTGTGAGTGGATCTCCTGGACAGTCTATTACCATTTCTTGTACCG<br>GAACCATTAGCGACGTGGGCGGGTACAACTACGTGAGCTGGTACCAGCAGCACCCAGGCAAGGCTCCC<br>AAACTGATGATCTATGACGTGAACAAGCGGCCTTCAGGGGTCAGCAATAGATTCTCAGGAAGCAAATC<br>CGGCAATACTGTACG | 71 |
| VACV-5 heavy | CAGGTGCAGCTGGTGGAGTCTGGGGGAGGCGTGGTCCAGCCTGGGGAGTCTCTGAAGATCTCCTGTG<br>CAGCCTCTGGATTCACCTTCAGTAGCTATGGCATGCACTGGGTCCGCCAGGCTCCAGGCAAGGGGCTG<br>GAGTGGGTGGCAGTTATATGGTATGATGGAATTAATAAATACTATGCAGACTCCGTGAAGGGCCGATT<br>CACCCATCTCCAGAGACAATTCCAAGAACACGCTGTATCTGCAAATGAACAGCCTGAGAGCTGAGGACAC<br>GGCTGTGTATTACTGTGCGAAAGAGGCGGGTGGTGGTGACTGCTATTCCAACTACTTTCACTACTGGGG<br>CCAGGGAACCCTGGTCACCGTCTCCTCA | 72 |
| VACV-5 light | ND | 73 |
| VACV-22 heavy | CAGGTGCAGCTGGTGGAGTCTGGGGGAGGCGTGGTCCAGCCTGGGAGGTCCCTGAGACTCTCCTGTG<br>CAGCGTCTGGATTCACCTTCAGTAACTCTGGCATGCACTGGGTCCGCCAGGCTCCAGGCAAGGGGCTG<br>GAGTGGGTGGCAGTTATATGGTTTGATGGAACTAATAAATACTATGCAGACTCCGTGAAGGGCCGATT<br>CACCATCTCCAGAGACAATTCCAAGAACACGCTGTATCTGCAAATGAACAGCCTGAGAGCCGAGGACA<br>CGGCTGTGTATATTACTGTGCGAGAGTGCCTTGGTGGTGGTGACTGCTATTCCGGGTACCTCCAGCACTGGG<br>GCCAGGGCACCCTGGTCACCGTCTCCTCA | 74 |
| VACV-22 light | GCAATAGTGATGACGCAGTCTCCAGCCACCCTGTCTGTGTCTCCAGGGGAAAGAGCCACCCTCTCCTGC<br>AGGGCCAGTCAGAGTGTTAGCAGCACCTTAGCCTGGTACCAGCAGAAACCTGGCCAGGCTCCCAGGCT<br>CCTCATCTATGGTGCATCCACCAAGGCCACTGGTATCCCAGCCAGGTTCAGTGGCAGTGGGTCTGGGAC<br>AGAGTTCACTCTCACCATCAGCAGCCTGCAGTCTGAAGATTTTGCAGTTTATTACTGTCAGCACTATAAT<br>AACTGGCCTCCCCTGCTCACTTTCGGCGGAGGGACCAAGGTGGATATCAAAT | 75 |
| VACV-80 heavy | GAGGTGCAGCTGGTGGAGTCCGGGGGAGGCTTAGTTCAGCCTGGGGAGTCTCTGAAGATCTCCTGTGC<br>AGCCACTGGATTCACCTTCAGTAGCTACTGGATGCACTGGGTCCGCCAAGCTCCAGGGAAGGGACTGG<br>TGTGGGTCTCAGGTATTAATAGTGATGGCAGTAGCACAAGTTACGCGGACTCCGTGAAGGGCCGATTC<br>ACCATCGCCAGAGACAACGCCAAGGGCACGCTGTATCTGCAAATGAACAGTCTGAGAGCCGAGGACAC<br>GGCTGTATATTACTGTGCAAGAGTCGGCGCCGTCCGTATAGCAGCAGCTGCCCCTGACTACTGGGGCCA<br>GGGAACCCTGGTCACCGTCTCCTCA | 76 |
| VACV-80 light | GACATCGTGATGACCCAGTCTCCAGACTCCCTGGCTGTGTCTCTGGGCGAGAGGGCCACCATCAACTGC<br>AAGTCCAGCCAGAGTGTTTTATACAGCTCCAACAATAAGAACTACTTAGCTTGGTACCAGCAGAAACCA<br>GGACAGCCTCCTAAGCTGCTCATTTACTGGGCATCTACCCGGGAATCCGGGGTCCCTGACCGATTCAGT<br>GGCAGCGGGTCTGGGACAGATTTCACTCTCACCATCAGCAGCCTGCAGGCTGAAGATGTGGCAGTTTA<br>TTACTGTCAGCAATATTATAGTACTCCGTGGACGTTCGGCCAAGGGACCAAGGTGGATATCAAAA | 77 |
| MPXV-39 heavy | CAGGTGCAGCTACAGCAGTGGGGCGCAGGACTGTTGAAGCCTTCGGAGACCCTGTCCCTCACCTGTGC<br>TATTTATGGTGGGTCCCTCAGTGGTCAGTACTGGATTGGATCCGCCAGCCCCCCGGGAGGGGCCTGG<br>AGTGGATTGGGGAGATCCATCATAAGGGACGCACCAACTACAACCCGTCCCTCAAGAGTCGAGTCACC | 78 |

TABLE 1-continued

NUCLEOTIDE SEQUENCES FOR ANTIBODY VARIABLE REGIONS

| Clone | Variable Sequence Region | SEQ ID NO: |
|---|---|---|
| | ATATCAATTGACACGTCGCAGAGGCAGTTCTCCCTGAGGCTGACCTCTGTGAGCGCCGCGGACACGGCT<br>GTGTATTACTGTGCGAGTGGAAACTACAGACTGGGCCAGGGAACCCTGGTCACCTTC | |
| MPXV-39 light | GATGTTGTGCTGACTCAGTCTCCACTCACCCTGCCCGTCACCCTTGGACAGCCGGCCTCCATCTCCTGCA<br>GGTCTAGTCAAAGCCTCGTATACAGTGATGGAGACACCTACTTGAATTGGTTTCAGCAGAGGCCAGGCC<br>AAGCTCCGAGGCGCCTAATTTATAAGGTTTCTAAACGGGACTTTGGGGTCCCAGACAGATTCAGCGGCA<br>GTGGGTCA7GGCACTGATTTCACACTGAGAATCAGCAGGGTGGAGGCTGAGGATGTTGGGGTTTATTA<br>CTGCATGCAAGGTACACACTGGCCTCGAACTTTTGGCCAGGGGACCCAAGTGGATATTAAA | 79 |
| MPXV-51 heavy | CAGCTGCAGCTGCAGGAGTCGGGCCCAGGACTGGTGAAGCCTTCGGAGACCCTGTCCCTCTCCTGCAC<br>CGTCTCTGGTGGCTCCATCAACAGTCGTACTTACTACTGGGGCTGGATCCGCCAGCCCCCAGGGAAGGG<br>GCCGGAGTGGATTGGGACTGTCTTTCATAATGTGAGCACCTTGTACACCTCGTCCCTCAGGAGTCCAGT<br>CACCATCTCCGTAGACACCTCCAAGAACCGGTTCTCCCTGAAATTGACCTCTGTGACCGCCGCGGACAC<br>GGCTGTTTATTTCTGTGGGAGACTAACTCCGCGCAATTTATTTCGTGGGACGTTAGTGAGATGGGTCGA<br>CCCCTGGGGCCAGGGAATCCTGGTCACCGTCTCCTCAG | 80 |
| MPXV-51 light | GAAATAGTGTTGGCGCAGTCTCCAGGCACCCTGTCTTTGTCTCCAGGGGAAAGAGCCACCCTCTCCTGC<br>AGGGCCAGTCACAATCTTAACAGCAACTACTTAGCCTGGTACCAGCAGAAACCTGGCCAGGCTCCCAG<br>GCTCCTCATCTATGGTGCATCCAGCAGGGCCACTGGCATCCCAGACAGGTTCACTGGCAGTGGGTCTGG<br>GACAGACTTCACTCTCACCATCAGCAGACTGGAGCCTGAAGATTTTGCAGTGTATTACTGTCAGCAGTA<br>TGCTGGCTCACTCACTTTCGGCGGAGGGACCAAGGTGGATATCAAA | 81 |
| MPXV-56 heavy | CAGGTACAGCTGCAGCAGTCAGGTCCAGGACTGGTGAAGCCCTCGCAGACCCTGTCACTCACCTGTGCC<br>ATCTCCGGGGACAGTGTCTCTAGCAACAGTGCTGCTTGGATCTGGATCAGGCAGTCCCCATCCGAGAGG<br>CCTTGAGTGGCTGGGAACGACATACTACAGGTCCGAGTGGTATAGTGATTATCCAGCATCTGTGAAAA<br>GTCGAGTAACCATCAACGCAGACACATCCAAGAACCAGTTCTCCCTGCAGCTGAACTCTGTGACTCCCG<br>AGGACACGGCTGTGTATTATTGTGCAAGAATAACCGTCGGGTATAACAGCCCTCACCTGCGGGTAACTC<br>GAGGCTGGCTCGACCCCTGGGGCCAGGGAACCCTGGTCACCTCCTCCTCAG | 82 |
| MPXV-56 light | GACATCGTGATGACCCAGTCTCCAGACTCCCTGGCTGTGTCTCTGGGCGAGAGGGCCACCATCAACTGC<br>AAGTCCAGCCAGAGTGTTTTATACAGCTCCAACAATAAGAACTACATTGCATGGTACCAGCAGAAGCCA<br>GGACAGGCTCCTAAGCTGCTCATTTACTGGGCATCTACCCGGGAATCCGGGGTCCCTGACCGATTCAGT<br>GGCAGCGGGTCTGGGACAAATTTCACTCTCGCCATCAGCAGCCTGCAGGCTGAAGATGTGGCAGTTTA<br>TTACTGTCAGCAATATTATAGTTCTCCCCTCACTTTCGGCGGAGGGACCAAGGTGGATATCAAA | 83 |
| MPXV-91 heavy | CAGGTGCAGCTGGTGGAGTCTGGGGGAGGCGTGGTCCAGCCTGGGAGGTCTCTGAAGATCTCCTGTG<br>CAGCCTCTGGATTCACCTTCAGTACCTATACTATGCACTGGGTCCGCCAGGCTCCAGGCAAGGGGCTAG<br>AGTGGGTGGCAACTATATCATATGATGGCATTAATGAATACTACGCAGACTCCGTGAAGGGCCGATTCA<br>CCATCTTCAGAGACAATTCCAAGAACATGCTGTATCTGCAAATGAACAGCCTGAGACCTGAGGACACGG<br>CTATGTTTTACTGTGCGAGAGGGAGGGGAGTGGTGATGACTGCTATTACCAGACGACTTCTGGGGC | 84 |
| MPXV-91 light | CAGTCTGTGCTGACTCAGCCNCCCTCAGCGTCTGGGACCCCCGGGCAGAGGGTCACCATCTCTTGTTCT<br>GGAAGCAGCTCCAACATCGGAATTAATTATGTACACTGGTACCAGCAGCTCCCAGGAACGGCCCCAAA<br>CTCCTCATCTATAGGAATAATCAGCGGCCCTCAGGGGTCCCTGACCGATTCTCTGGCTCCAAGTCTGGCA<br>CCTCAGCCTCCCTGGCCATCAGTGGGCTCCGGTCCGAGGATGAGGCTGATTATTACTGTGCAGCATGGG<br>ATGACAGCCTGAGTGGTAAAGTGTTCGGCGGAGGGACCCAGGTGACCGTCCTA | 85 |
| MPXV-99 heavy | CAGGTGCAGCTGGTGGAGTCTGGGGGAGGCGTGGTCCAGCCTGGGAGGTCTCTGAAGATCTCCTGTG<br>TAGCCTCTGGATTCACCTTCAGCAGTTATGCAATACACTGGGTCCGCCAGGCTCCAGGCAAGGGGCTAG<br>AGTGGGTGGCGTTTATCTCAAATGATGGAAGTAGTAAAAAGTTGGCAGACTCCGTGAAGGGCCGATTC<br>ACCATCTCCAGAGACAATTCCAAGAACACGCTGTATCTGCAAATGAACAGCCTGAGAGCTGAGGACAC<br>GGCTGTATATTATTGTGCGAGAGCGGATCGAGGGTACTTTGGCCACTGGGGCCAGGGAACCCTGGTCA<br>CC | 86 |
| MPXV-99 light | ND | 87 |
| VACV-314 heavy | CAGGTGCAGCTGGTGCAGTCGGGCCCAGGACTGGTGAAGCCTTCGGAGACACTGTCCCTCACCTGCAC<br>TGTCTCTGGTGGCTCCATCAGTAGTTACTACTGGAGCTGGATCCGGCAGCCCCCAGGGAAGGGACTGG<br>AGTACATTGGGCATATCTATTACAGCGGGGGCACCAAGTACAACCCCTCCCTCAGGAGTCGCGTCACCA<br>TATCAGTAGACACGTCCAAGAACCAGTTCTCCCTGAAGCTGACCTCTGTGACCGCCGCAGACACGGCCG<br>TGTATTACTGTGCGAGACTGGCCGGGAGAAAACCTGACGCGGACTCCTGGGGCCAGGGAACCCTGGTC<br>ACCGTCTCCTCAG | 88 |
| VACV-314 light | CAGCCTGTGCTGACTCAGGAGCCCTCACTGACTGTGTCCCCAGGAGGGACAGTCACTCTCACCTGTGCT<br>TCCAGCACTGGAGCAGTCACCAGTGGTTTCTTTCCAAACTGGCTCCAGCAGAAACCTGGACAAGCTCCC<br>AGGGCACTGATTTATAGTACAAACAACAAACACTCCTGGACCCCTGCCCGGTTCTCAGGCTCCCTCCTTG<br>GGGGCAAAGCTGCCCTGACACTGTCAGGTGTGCAGCCTGAGGACGAGGCTGAGTATTACTGCCTGCTC<br>TACTATGGTGGTGTCGTGGTATTCGGCGGAGGGACCAAGCTGACCGTCCTAG | 89 |
| VACV-315 heavy | GAGGTGCAGCTGTTGGAGTCTGGGGGAGGCTTGGTACAGCCTGGGGGGTCTCTGAAGCTCTCCTGTGC<br>AGCCTCTGGATTCATCTTTAGCAACTATGCCATGGGCTGGGTCCGCCAGGCTCCAGGGAAGGGGCTGG<br>AGTGGGTCTCAGCTCTTAGTGCTAGTGATGGTGTCACTTCCTACGCAGACTCCGTGAAGGGCCGGTTCA<br>CCATCTCCAGAGACAATTCCAAGAACACGATGTATTTGCAAATGAACAGGCTGAGAACCGAAGACACG<br>GCCATATATTTCTGTGCGAAAGGCCGCGCTCGGGTAAACAACATCTACCGCTACTTTGACCACTGGGGC<br>CAGGGAACCCTGGTCACCGTCTCCTCA | 90 |

TABLE 1-continued

NUCLEOTIDE SEQUENCES FOR ANTIBODY VARIABLE REGIONS

| Clone | Variable Sequence Region | SEQ ID NO: |
|---|---|---|
| VACV-315 light | CAGTCTGTGCTGACTCAGCCTGCCTCCGTGTCTGGGTCTCCTGGACAGTCGATCACCATCTCCTGCACTG GAACCAGCAGTGACGTTGGTGCTTATACCTTTGTCTCCTGGTACCAACATCACCCGGGCAAAGCCCCCA AACTCATCATTTATGAGGTCAGTAATCGGCCCTCCGGGGTTTCTGATCGCTTCTCTGGCTCCAAGTCTGG CAACACGGCCTCCCTGACCATCTCTGGGCTCCAGGCTGAGGACGAGGCTGATTATTACTGCAATTCATA TACAACCACCAGTCCCTGGGTGTTCGGCGGAGGGACCCAGCTGACCGTCCTA | 91 |
| MPXV-1 heavy | GAGGTGCAGCTGTTGGAGTCTGGGGGAGGCTTGGTACAGCCTGGGGAGTCTCTGAAGATCTCCTGTGC AGTCTCTGGATTCTCCTTTAAGAGTTATGCCATGAGCTGGGTCCGCCAGGCTCCAGGGAAGGGGCTCGA GTGGGTCTCCACTATTGGTGTGAGTGGTGCTAGCACATACTTCGCAGACCCCGTGAAGGGCCGATTCAC AATCTCCAGAGACAACTCCAAGGACACTCTGTATCTGCAAATGAACAGCCTGAGAGCCGAGGACACGG CCGTCTATTACTGTGCGAGAGACACATATTACTATGATAGTAGAATCTGGTACTTCGGTCTCTGGGGCC GTGGCACCC | 92 |
| MPXV-1 light | ND | 93 |
| MPXV-29 heavy | CAGGTCCAGCTGGTGCAGTCTGGGGCTGAGGTGAAGAAGCCTGGGTCCTCAGTGAAGGTCTCCTGCAA GGCTTCTGGAGGCACCTTCAGCAGCTATGTTATCAGTTGGGTGCGACAGGCCCCTGGACAAGGGCCTG AGTGGATGGGAAGGATCATCGTTATGCTTGGTGTAACAAACTACGCACAGAAGTTCCAGGGCAGAGTC TCGATTACCGCGGACAAATCCACAAACACAGCCTACATGGAGCTGAACAGCCTGAGATCTGAGGACAC GGCCGTGTATTACTGTGCGAGGGCCGTCATTACTATGGTTCGGGGAGATATACCCCTCGGGTGGTTCG ACCCCTGGGGCCAGGGAACCCTGGTCACCGTCTCCTCAG | 94 |
| MPXV-29 light | GAAATTGTGTTGACGCAGTCTCCAGGCACCCTGTCTTTGTCTCCAGGGGAAAGAGCCACCCTCTCCTGC AGGGCCAGTCAGAGTGTTAGAAGCAACTACTTAGCCTGGTACCAGCAGAAACCTGGCCAGGCTCCCAG GCTCCTCTTCTATGGTGCATCCAGCAGGGCCACTGGCATCCCAGACAGGTTCAGTGGCAGTGGGTCTGC GACAGACTTCACTCTCACCATCAGCAGACTGGAGCCTGAAGATTTTGCAGTGTATTACTGTCAGCAGTA TGGTAGCTCACCCCCGACGTCGGCCCAAGGGACCAAGGTGGAAATCAAA | 95 |
| MPXV-72 heavy | CAGGTCACCTTGAAGGAGTCTGGTCCTACGCTGGTGAAACCCACACAGACCCTCACGCTGACCTGCACC TTCTCTGGGTTCTCAATCAACAGGTGGACAGGGTGTGGGCTGGATCCGGCAGCCCCCAGGAAAGGC CCTGGAGTGGCTTGCGCTCATTTATTGGGATGATGATAAGCGCTACAGCCCGGCTCTGAGGAGCAGAC TCACCATCACCAAGGGCACCTCCAAAAACCAGGTGGTCCTAACAATGACCAAAATGGACCCTGTGGACA CAGCCACATATTACTGTGCACACCGTTCAGTGGCTGGTAGGAGGGACTTGGCTTTTGATATCTGGGGCC AAGGGACCCTGGTCACCGTCTCCTCAG | 96 |
| MPXV-72 light | LC#1<br>CAGTCTGTGCTGACTCAGCCTGCCTCCGTGTCTGGGTCTCCTGGACAGTCGATCACCATCTCCTGCACTG GAACCACCAGTGACATTGGTACTTATGACTATGTCTCCTGGTATCAACAGCACCCAGGCAGAGCCCCCA AACTCATGATTTATGATGTCAGTAAGCGGCCCTCAGGGGTTTCTGGTCGCTTCTCTGGCTCCAAGTCTGG CAACACGGCCTCCCTGACCATCTCTGGCCTCCAGACTGAGGACGAGTCTCATTATTATCTGCAGCTTCAT ATACCAAGCGGCCTCACTTGGGTGTTCGGCGGAGGG | 97 |
| | LC#2<br>GACATCGTGATGACCCAGTCTCCTTCCACCCTGTCTGCATCTGTAGGAGACAGAGTCACCATCACTTGCC GGGCCAGTCAGAGTATTAGTAGCTGGTTGGCCTGGTATCAGCAGAAACCAGGGAAAGCCCCTAAACTC CTGATCTATGATGCCTCCAGTTTGGAAAGTGGGGTCCCATCAAGGTTCAGCGGCAGTGGATCTGGGAC AGAATTCACTCTCACCATCAGCAGCCTGCGGCCTGATGATTTTGCAACTTATTACTGCCAACAGTATAAT ACTTATTCTTGGTGGACGTTCGGCCAAGGGACCAAGGTGGAAATCAAAC | 56 |
| | LC#3<br>CAGCCTGTGCTGACTCAGCCTGCCTCCGTGTCTGGGTCTCCTGGACAGTCGATCACCATCTCCTGCACTG GAACCACCAGTGACATTGGTACTTATGACTATGCCTCCTGGTATCAACAGCACCCAGGCAGAGCCCCCA AACTCATGATTTATGATGTCAGTAAGCGGCCCTCAGGGGTTTCTGGTCGCTTCTCTGGCTCCAAGTCTGG CAACACGGCCTCCCTGACCATCTCTGGCCTCCAGACTGAGGACGAGTCTCATTATTACTGCAGCTCATAT ACAAGCGGCCTCACTTGGGTGTTCGGCGGAGGGACCAAGCTGACCGTCCTAG | 885 |
| MPXV-76 heavy | GAGGTGCAGCTGGTGGAGTCTGGGGGAGGCTTGGTAAAGCCTGGGGAGTCTCTGAAGATCTCCTGTG CAGCCTCTGGTTTCAGTTTCAATAACGCCTGGATGAACTGGGTCCGCCAGGCTCCAGGGAAGGGGCTG GAGTGGGTCGGCCGTATTAAAACTCATGCTGATGGTGGGACAACTGACTACGCTGCACCCGTGACAGG CAGATTCACCATCTCGAGAGATGATTCAAAAAACACGCTGTCTCTCCAAATGAGCAGCCTGAAAACCGA GGACACAGCCGTGTATTACTGTACCACAAGTTTTACGTTCCCCCGCAGGATCTTTGCTTACTGGGGCCAG GGAACCCTGGTCACCGTCTCCTCAG | 98 |
| MPXV-76 light | GAAATTGTGTTGACACAGTCTCCAGCCACCCTGTCTTTGTCTCCAGGGGAAAGAGCCACCCTCTCCTGCA GGGCCAGTCAGAGTGTTAGCAGCTACTTAGCCTGGTACCAACAAAAACCTGGCCAGGCTCCCAGACTCC TCATCTATGATCATCCAACAGGGCCACTGGCATCCCAGCCAGGTTCAGTGGCAGTGGGTCTGGGACA GACTTCACTCTCACCATCAGCAGCCTAGAGCCTGAGGATCTTGCAGTTTATTACTGTCAACTTCGAAACA GCTGGCCTCCAACTTTCGGCCCTGGGACCAAGGTGGATATCAAA | 99 |
| MPXV-79 heavy | CAGGTTCAGCTGGTGCAGTCTGGAGCTGAGGTGAAGAAGCCTGGGGCCTCAGTGAAGGTCTCCTGCAA GGCCTCTGGTTATTCCTTTAGAAGCAACGGCATCAGCTGGGTGCGACAGGCCCCTGGACAAGGATTTG AGTGGCTGGGATGGATCGCCGCTTACAATGGTGACACAAAATATGTGCAGAAGTTTCAGGGCAGACTC ACCATGACCACGGACACTTCCACGGACACAGCCTACATGGAGCTGTGGAGCCTGAGATCTGACGACAC GGCCGTCTATTACTGTGCGAGAGATCCCAAACTGGGGAGAAAGGGAAGTGCT98TTTGATATCTGGGG CCAAGGGACACTGGTCATCGTCTCGTCA | 100 |

TABLE 1-continued

NUCLEOTIDE SEQUENCES FOR ANTIBODY VARIABLE REGIONS

| Clone | Variable Sequence Region | SEQ ID NO: |
|---|---|---|
| MPXV-79 light | GAAATTGTGTTGACACAGTCTCCAGCCACCCTGTCTTTGTCTCCAGGGGAAGAGCCACCCTCTCCTGCA<br>GGGCCAGTCAGAGTGTTGGCAACTACTTAACTTGGTACCAACAGAAACCTGGCCAGGCTCCCAGGCTCC<br>TCATCTTTGATGGGTCCACCAGGGCCACTGGCATCCCAGCCAGGTTCAGTGGCAGTGGGTCTGGGACA<br>GACTTCACTCTCACCATCAGCAGCCTAGAGCCTGAAGATTTTGCAGTTTATTACTGTCTACAGCGTAGCG<br>ACTTGTACACTTTTGGCCAGGGGACCAAGGTGGATATCAAA | 101 |
| MPXV-85 heavy | GAGGTGCAGCTGTTGGAGTCTGGGGGAGGCTTGGTACAGCCTGGGGAGTCTCTGAAGATCTCCTGTGT<br>AGGCTCTGAATTCACATTTAGTAGTTATGCCATGAGCTGGGTCCGCCAGCCTCCAGGGAAGGGGCTGG<br>AGTGGGTCTCAGGTATTAGTGATAGTGGTGGAAGATTGTACGTCGCAGACTCCGTGAAGGGCCGCTTC<br>ACCGTCTCCAGAGACAATTCCAAGAACACGCTGTATCTGGAAATGAATAGCCTGAGAGGCGAGGACAC<br>GGCCCATATATTACTGTGCGAAAGACCGGGTTGTGGGAGCAACTTACCCGCGGGGCGTTTTTGATATCTG<br>GGGCCAAGGGACAATGGTCACCGTCTCTTCA | 102 |
| MPXV-85 light | ND | 103 |
| VACV-33 heavy | CAGCTGCAGCTGCAGGAGTCGGGCCCAGGACTGGTGAAGCCTTCGGAGACCCTGTCCCTCACCTGCAC<br>TGTCTCTGGTGGCTCCATCAGCAGTGGTGGTTACTACTGGGGCTGGATCCGCCAGCCCCCAGGGAAGG<br>GGCTGGAGTGGATTGCGAGTATCTATTATAGTGGGAGCACCTACTACAACCCGTCCCTCAAGAGTCGA<br>GTCACCATATCAGTAGACACGTCCAAGACCCAGTTCTCCCTGAAGCTGAGCTCTGTGACCGCCGCGGAC<br>ACGGCCGTGTATTATTGTGCGAGGCAGAGCAGCTCGACGGGGGGCTTCCACTACTGGGGCCAGGGAA<br>CCCTGGTCACCGTCTCCTCA | 104 |
| VACV-33 light | CAGTCTGTGCTGACGCAGCCGCCCTCAGTGTCTGGGGCCCCAGGGCAGAGGGTCACCATCTCCTGCACT<br>GGGAGCAGCTCCAACATCGGGGCAGGTTATGATGTACACTGGTACCAGCATCTTCCAGGAACAGCCCC<br>CAAACTCCTCATCTATGGTAACAGCAATCGGCCCTCAGGGGTCCCTGACCGATTCTCTGGCTCCAAGTCT<br>GGCACCTCAGCCTCCCTGGCCATCACTGGGCTCCAGGCTGAGGATGAGGCTAATTATTACTGCCAGTCC<br>TATGACAGCAGCCTGAGTGGTCGGGAGGTGTTCGGCGGAGGGACCCAGCTGACCGTCCTA | 105 |
| VACV-34 heavy | CAAGTGCAGCTGGTGGAGTCTGGGGGAGGCTTGGTACAGCCTGGCAGGTCCCTGAGACTCTCCTGTGC<br>AGCCTCTGGATTCACCTTTGATGATTATGCCATGCACTGGGTCCGGCAAGCTCCAGGGAAGGGCCTGGA<br>GTGGGTCTCAGGTCTTAGTTGGAATAGTGGTAGCATAGGCTATGCTGACTCTGTGAAGGGCCGATTCA<br>CCATCTCCAGAGACAACGCCAAGAACTCCCTGTATCTGCAAATGAACAGTCTGAGAGCTGAGGACACG<br>GCCTTGTATTACTGTGCAAAAGAGACCGAGAAATATTACTATGATAGTAGTGGTTATGACTACTGGGGC<br>CAGGGAACCCTGGTCACCGTCTCCTCAG | 106 |
| VACV-34 light | GAAATTGTGTTGACTCAGTCTCCAGGCACCCTGTCTTTGTCTCCAGGGGAAAGAGCCACCCTCTCCTGCA<br>GGGCCAGTCAGAGTGTTAGCAGCATCTACTTAGCCTGGTACCAGCAGAAACCTGGCCAGGCTCCCAGG<br>CTCCTCATCTATGGTGCATCCAGCAGGGCCACTGGCATCCCAGACAGGTTCAGTGGCAGTGGGTCTGG<br>GACAGACTTCACTCTCACCATCAGCAGACTGGAGCCTGAAGATTTTGCAGTGTATTACTGTCAGCAGTA<br>TGGTAGCCGAGGGACTTTTGGCCAGGGGACCAAGCTGGAGATCAAAC | 107 |
| MPXV-26 heavy | CAGGTGCAGCTGGTGCAGTCTGGAGGAGGCCTGATCCAGCCTGGGGGGTCCCTGAGACTCTCCTGTGT<br>AGTCTCTGGGTTCAACGTCGCTACTAATTATATGAGTTGGGTCCGCCAGGCTCCAGGGAAGGGGCTGG<br>AGTGGGTCTCAGTTATTTATAGCGGCGGTAGTACATACTACGCAGACTCCGTGAAGGGCCGATTCACCA<br>TCTCCAGAGACAATTCCAAGAACACGGTGTTTCTTCAAATGAACAGCTGAGACCCGAAGACACGGCCG<br>CGTATTATTGTGCGAAGGGGGGAGGATTGGGTCTGGACTACTGGGGCCAGGGAACCCTGGTCACCGT<br>CTCCTCA | 108 |
| MPXV-26 light | CAGTCTGCCCTGACTCAGCCTCCCTCCGCGTCGGGTCTCCTGGACAGTCAGTCACCATCACATGCACTG<br>GAAGCAGCAGTGACGTTGGTGGTTATAACTATGTGCCTGGTACCAACAACACCCAGGCAAAGCCCCC<br>AAAGTCGTGATTTATGAGGTCAATAAGCGGCCCTCAGGGGTCCCTCATCGCTTCTCTGGCTCCAAGTCT<br>GGCAACACGGCCTCCCTGACCGTCTCTGGCCTCCAGGCTGAGGATGAGGCTGATTATTACTGCAGCTCA<br>TATGCAGGCACCGAAACCGTGGCATTCGGCGGAGGGACCAAGCTGACCGTCCTAC | 109 |
| MPXV-74 heavy | CAGGTCCAGCTGGTGCAGTCTGGGGCTGAGGTGAAGAAGCCTGGGTCCTCAGTGAAGGTCTCCTGCAA<br>GGCTTCTGGAGGCAGATTCAGCACTCAACATATCAACTGGATGCGACAGGCCCCTGGACATGGACTTG<br>AGTGGATGGGAGGGATCATCCCCATCTTTGCTACAGCAGACTACGCACAGAAGTTCCAGGGCAGAATC<br>ACAATTACCGCGGACGAATCTACCAGCACAGCCTACATGGAAATGAGCAGCCTGAGATCTGAGGACAC<br>GGCCATATATTATTGTGGTGTCTACAATGCAAACTGGGGCCAGGGAACCCTGGTCACCGTCTCCTCAG | 110 |
| MPXV-74 light | GATATTGTGATGACTCAGTCTCCACTCTCCCTGCCCGTCACCCCTGGAGAGCCGGCCTCCTTCTCCTGTA<br>GGTCTAGTCAGAGCCTCCTGCATTATAATGGAAATAACTATTTGAATTGGTACCTGCAGAAGCCAGGGC<br>AGTCTCCACAACTCCTGATCTATTTGGGTTCTAATCGGGCCTCCGGGGTCCCTGACAGGTTCAGTGGCA<br>GTGGATCAGGCACAGATTTTACACTGAAAATCAGTAGAGTGGAGGCTGACGATGTTGGGATTTACTACT<br>GCATGCAAGCTCGACACACCCCGTGGTCGGCCCAAGGGACCAAGGTGGAAATCAAA | 111 |
| MPXV-83 heavy | CAGGTGCAGCTGGTGGAGTCTGGGGGAGGCGTGGTCCAGCCTGGGAGGTCCCTGAGACTCTCCTGTG<br>CAGCCTCTGGATTCACCTTCAGTAGCTATAGTATGCACTGGGTCCGCCAGGCTCCAGGGAAGGGGCTG<br>AATGGGTGGCAGTTATATCATTTGATGGGAGAAGTAATTACTACGCAGACTCCGTGAGGGGCCGCTTC<br>ACCATCTCCAGAGACAACTCCAAGAAAACGATGTATCTGCAAATGAACAGCTGAGACTTGCGGACAC<br>GGCTGTGTATTACTGTGCGAGAGGTGGAATAGGTGCCCCGGACCCCCGGAACGGTTTGGAAGTTTGGG<br>GGCGAGGGGCCCCGGTCACCCTCTCCTCC | 112 |

TABLE 1-continued

NUCLEOTIDE SEQUENCES FOR ANTIBODY VARIABLE REGIONS

| Clone | Variable Sequence Region | SEQ ID NO: |
|---|---|---|
| MPXV-83 light | GACATTCAGATGATCCAGTCTCCATCCTCCCTGTCTGCATCTGTAGGAGACAGAGTCACCATCTCCTGCC AGGCGACTCAAGACATTAGCAACTCTGTAAATTGGTATCAGCAGAAACCAGGGAAAGCCCCCAAACTC CTGATCTACGATGCGTCCACTTTGGAAACAGGGGTCCCTTCAAGGTTCAGTGAGGTGGATCTGGGAC ACATTTTACTTTCACCATCAGCAGCCTGCAGCCTGAAGACATTGCAACATATTACTGTCAACAGTTTCAT AGTCTCCCTCCGACNTTTGGCCAGGGGCCCAAGGGGATATCCAAAC | 113 |
| MPXV-87 heavy | CAGGTTCAGCTGGTGCAGTCTGGAGCTGAGGTGAAGAAGCCTGGGGCCTCAGTGAAGGTCTCCTGCAA GGCTTCTGGTTACACCTTTACGAGCCACGGTATCATCTGGGTGCGACAGGCCCCTGGACAAGGGCTTGA GTGGATGGGATGGATCAGCGTTTACAATGACAACACAAACTCTGCACAGAAGTTCCAGGACAGAGTCA CCATGACCACAGCCACATCCACGAGCACAGCCTACATGGAGCTGAGGAGCCTGAGATCTGACGACACG GCCGTTTATTACTGTGCGAGAAGTAGCAGTGGCCCCCGGTATTACTACTACGGTATGGACGTCTGGGGC CAAGGGACCACGTCACCTGTCTCCTCA | 114 |
| MPXV-87 light | CAGTCTGTGGTGACGCAGCCGCCCTCAGTGTCTGGGGCCCAGGGCAGAGGGTCACCATCTCCTGCAC TGGGAGCAGCTCCAACATCGGGGCAGGTTATGCTGTACACTGGTACTACCAGCTTCCAGGAATAGCCCC CAAACTCCTCATCTTTGGTAACAACAATCGGCCCTCAGGGGTCCCTGACCGCTTCTCTGGCTCCAAGTCT GGCACCTCAGCCTCCCTGGCCATCACTGGGCTCCAGGCTGAGGATGAGGCTGATTATTACTGCCAGTCC TATGACAGCAGCCTGAGTGGTTGGGTGTTCGGCGGAGGGACCCAGGTGACCGTCCTA | 115 |
| VACV-154 heavy | GAGGTGCAGCTGTTGGAGTCTGGGGGAGGCTTGGTACAGCCTGGGGAGTCTCTGAGACTCTCCTGTGC AGCCTCTGGATTCACCCTTAGGAACTATGCCATGAGCTGGGTCCGCCAGACTCCAGGGAAGGGGCTGG AGTGGGTCTCAGCTATTAGTGGTAGTGGTGGTAGCACATACTACGCAGACTCCGTGAAGGGCCGGTTC ACCATCTCCAGAGACACTTCCAAGAACACGCTGTATGTGCAAATGAACAGCCTGAGAGCCGAGGACAC GGCCGTATATTACTGTGTGCGAAAATAAGATTAGATAGTAGTGGTTATTCAGGTGCTTTTGATATCTGGGG CCAAGGGACAAGGGTCACCGTCTCCTCA | 116 |
| VACV-154 light | TCCTATGAGCTGACACAGCCACCCTCGGTGTCAGTGTCCCAGGACAGACGGCCAGGATCACCTGCTCT GGAGATGCATTGCCAAAGCAATATGCTTCTTGGTACCAGCAGAAGCCAGGCCAGGCCCCTGTGCTGGT GATATATAAAGACAGTGAGAGGCCCTCAGGGATCCCTGAGCGATTCTCTGGCTCCAGCTCAGGGACAA CAGTCACGTTGACCATCAGTGGAGTCCAGGCAGAAGACGAGGCTGACTATTACTGTCAATCAGCAGAC AGCAGTGGTACTTATCCGGTGGTTTTCGGCGGAGGGACCCAGCTGACCGTCCTA | 117 |
| VACV-300 heavy | CAGGTCCAGCTGGTGCAGTCTGGGGCTGAGGTGAAGAAGCCTGGGTCCTCAGTGAAGGTCTCCTGCAA GGCTTCTGGAGGCACCTTCAGCAGCTATGCTATCAGTTGGGTGCGACAGGCCCCTGGACAAGGGCTTG AGTGGATGGGAGGATCATCCCTATCTTTGGTACAGCAAACTACGCACAGAAGTTCCAGGGCAGAGTC ACGATTACCGCGGACGAATCCACGGGCACAGCCTACATGGAGCTGACCAGCCTGAGATCTGAGGACAC GGCCATATATTACTGTGCGAGAGCGTCGGAGCAGTGGCTGGCCTCAATCAACTGGTTCGACCCCTGGG GCCAGGGAACCCTGGTCACCGTCTCCTCA | 118 |
| VACV-300 light | CAGTCTGCCCTGACTCAGCCTGCCTCCGTGTCTGGGTCTCCTGGACAGTCGATCACCATCTCCTGCACTG GAACCAGCAGTGATGTTGGGAGTTATAACCTTGTCTCCTGGTACCAACAACACCCAGGCAAAGCCCCA AACTCATGATTTATGAGGTCAGTAAGCGGCCCTCAGGGGTTTCTAATCGCTTCTCTGCCTCCAAGTCTGG CAACACGGCCTCCCTGACAATCTCTGGGCTCCAGGCTGAGGACGAGGCTGATTATTACTGCTGCTCATA TGCAGGTAGTAGCACTTTGGTGTTCGGCGGAGGGACCCAGGTCACCGTCCTA | 119 |
| VACV-301 heavy | GAGGTGCAGCTGTTGGAGTCTGGGGGAGGCTTGGTACAGCCTGGGGGGTCCCTGAGACTCTCCTGTGC AGCCTCTGGATTCAGCTTCAGCAGCTATGCCATGAGTTGGGTCCGCCAGGCTCCAGGGAAGGGACTGG AGTGGGTCTCAGGGATTGGTAATAGTGGTGATAGGACATTTTACGCAGACTCCGCGAAGGGCCGGTTC ACCATCTTTAGAGACAATTCCAACAATAGGTTGTATCTGCAAATGAACAGCCTGAGAGCCGCGGACACG GCCGTGTATTACTGTGCGAAGTGGGGCAGATTTGAAAGTGGCGCCTTTTGGGGCCAGGGAGTCCTGGT CACCGTCTCCTCA | 120 |
| VACV-301 light | TCCTATGAGCTGACACAGTCACCCTCGGTGTCAGTGTCCCAGGACAGACGGCCAGGATCACCTGCTCT GGAGATGCATTGCCAGAGCAGTATGCTTATTGGTACCAGCAGAAGCCAGGCCAGGCCCCCAGTGTTGGT AATATATAAAGACAGTGAGAGGCCCTCAGGGATCCCTGAGCGATTCTCTGGCTCCGGCTCAGGGACAA CAGTCACGTTGACCATTACTGGAGTCCAGGCAGAAGACGAGGCTGACTATTACTGTCAATCCGCAGACA ACAGTGGTACTTATGAAGTCTTCGGAACTGGGACCAAGGTCACCGTCCTA | 121 |
| VACV-302 heavy | CAGCTGCAGCTGCAGGAGTCGGGCCCAGGACTGGTGAAGCCTTCGGAGACCCTGTCCCTCACCTGCAC TGTCTCTGGTGGCTCCATCATCAGTAGTAGTTACTACTGGGGCTGGATCCGCCAGCCCCCAGGGAAGGG GCTGGAGTGGCTTGGGAGTATCTATTATAGTGGGAGCACCTACTACAACCCGTCCCTCAAGAGTCGAGT CACCATATCCGTAGACACGTCCAAGAACCAGTTCTCCCTGAAGGTGACCTCTGTGACCGCCGCAGACAC GGCTGTGTATTACTGTGCGAGACAAATTTCCAAAGCAGCAGCTGGTTCTATTGACTACTGGGGCCAGGG AACCCTGGTCACCGTCTCC | 122 |
| VACV-302 light | GATATTGTGATGACTCAGTCTCCACTCTCCCTGCCCGTCACCCCTGGAGAGCCGGCCTCCATCTCCTGCA GGTCTAGTCAGAGCCTCCTGCATAGTAATGGATACAACTATTTGGATTGGTACCTGCAGAAGCCAGGGC AGTCTCCACAGCTCCTGATCTATTTGGGTTCTAATCGGGCCTCCGGGGTCTCTGACAGGTTCAGTGGCA GTGGATCAGGCACAGATTTTACACTGAAAATCAGCAGAGTAGAGGCTGAGGATGTTGGGGTTTATTAC TGCATGCAAGCTCTACAAACTCCGATCACCTTCGGCCAAGGGACACGACTGGAGATTAAA | 123 |
| VACV-303 heavy | GAGGTGCAGCTGTTGGAGTCTGGGGGAGGCTTGGTACAGCCTGGGGGGTCCCTGAGACTCTCCTGTGC AGCCTCTGGATTCACCCTTAGCAGCTATGCCATGAGCTGGGTCCGCCAGGCTCCAGGGAAGGGGCTGG AGTGGGTCTCAGCTATTAGTGGCACTGGTGGAAATACATACTACGCAGACTCCGTGAAGGGCCGGTTC ACCATCTCCAGAGACAAGTCCAAGAACACGCTATATCTGCAAATGCACAGCCTGAGAGCCGAGGACAC | 124 |

TABLE 1-continued

NUCLEOTIDE SEQUENCES FOR ANTIBODY VARIABLE REGIONS

| Clone | Variable Sequence Region | SEQ ID NO: |
|---|---|---|
| | GGCCGTATATTACTGTGCGACGTCCCTGATATGGTGGCTACAGTCTGACTACTGGGGCCAGGGAACCCT<br>GGTCACCGTCTCCTCA | |
| VACV-303 light | GACATCCAGATGACCCAGTCTCCATCCTCCCTGTCTGCATCTGTAGGAGACAGAGTCACCATCACTTGCC<br>GGGCAAGTCAGAGCATTGCCAGCTATTTAATTTGGTATCAGCAGAAACCAGGGAACGCCCCTAAGCTCC<br>TGATCTATGCTGCATCCAGTTTGCAAAGTGGGGTCCCATCAAGGTTCAGTGGCAGTGGATCTGGGACA<br>GATTTCACTCTCACCATCAGCAGTCTGCAACCTGAAGATTTTGCAACTTACTACTGTCAACAGAGTTACA<br>GTACCCCTCAAACGTTCGGCCAAGGGACCAAGGTGGATATCAAA | 125 |
| MPXV-10 heavy | GAGGTGCAGCTGGTGCAGTCTGGAGCAGAGGTGAAAAAGCCCGGGGAGTCTCTGAAGATCTCCTGTA<br>AGGGTTCTGGATACAGCTTTACCAACCACTGGATCGCCTGGGTGCGCCAGGTGCCCGGGAAAGGCCTG<br>GATTGGATGGGGATCATCTATCCTGGTGACTCTGATATCAGATACAGCCCGTTCCTTCCAAGGCCAGGTC<br>ACCATTTCAGCCGACAACTCCATCAACACCGCCTACTTGCAGTGGAGGAGCCTGAAGGCCTCGGACACC<br>GCCATGTATTACTGTGCGAGAGCCATGACGACGGTGACTCCTTTTGACTACTGGGGCCAGGGAACCCTG<br>GTCACCTTCTCC | 126 |
| MPXV-10 light | TCCTATGAGCTGACTCAGGCACCCTCAGTGGCCGTGTCTTCAGGACAGACAGCCAGCATCACCTGCTCT<br>GGAGATAAATTGGGGGATACATATACTTTCTGGTATCAGCAGAAGCCAGGCCAGTCCCCTGTGGTGGT<br>CATCTATCAAGATACCAAGCGGCCCTCAGGGATCCCTGAGCGATTCTCTGGCTCCAACTCTGGGAACAC<br>AGCCACTCTGACCATCACCGGGACCCAGTCTATGGATGAAGCTGACTATTACTGTCAGGCGTGGGACA<br>GCGCCACTGTGGTTTTCGGCGGAGGGACCCAGGTGACCGTCCTA | 127 |
| MPXV-31 heavy | CAGCTGCAGCTGCAGGAGTCGGGCCCAGGACTGGTGAAGCCTTCGGAGACCCTGTCCCTCACCTGCAC<br>TGTCTCTGGTGGCTCCATCAGCAGTAGGAATTTCTTCTGGGCGTGGATCCGCCAGCCCCCAGGGAAGG<br>GACTGGAGTTCATTGGGAGTATTTTTTATAGTGGGGGCACCTACTACAACCCGTCCCTCAAGAGTCGAC<br>TCTCCATATCCGTAGACACGTCTAGGAACCAGTTCTCCCTGAGGCTGAGTTCTGTGACCGCCGCAGATA<br>CGGCTGTATACTACTGTGCGAGACATATGATTGTAGTCCTACCAGGTGTCCCGATTTCCACCTCGTTCGA<br>CCCCTGGGGCCAGGGAACCCTGGTCACCGTCTCCTCAG | 128 |
| MPXV-31 light | GACATCGTGATGACCCAGTCGCCAGACTCCCTGGCTGTGTCTCTGGGCGAGAGGGCCACCATCAACTGC<br>AAGTCCAGTCAGAGTGTTTTATCCAACTCCAACAATAAGAACTACTTAGCTTGGTACCAGCAGAAACCA<br>GGACAGCCTCCTAGGCTGCTCATTTACTGGGCATCTGCCCGGGAATCCGGGGTCCCTGACCGATTCAGT<br>GGCAGCGGGTCTGGGACAGATTTCACTCTCACCATCATCAGCCTGCAGCTGAAGATGTGGCAGTTTAT<br>TACTGTCAGCAGTATTATAGTCCTCCTGCGGAGCTCTCTTTCGGCGGAGGGACCAAGGTGGATATCAAA | 129 |
| MPXV-53 heavy | CAGGTGCAGCTGGTGGAGTCTGGGGGAGGCGTGGTCCAGCCTGGGAGGTCCCTGAGACTCTCCTGTG<br>CAGCGTCTGGATTCACCTTCAGTAACTATGGCCTGCACTGGGTCCGCCAGGCTCCAGGCAAGGGGCTG<br>GAGTGGGTGGCACTTATATGGTTTGATGGAAGTAATAAATACTATGCAGACTCCGTGAAGGGCCGATT<br>CACCATCTCCAGAGACAATTCCAAGAACACACTGTATCTGCAAATGAACAGCCTGACAGCCGAGGACAC<br>GGCTGTGTATTACTGTGCGAGAGAGACAGTA | 130 |
| MPXV-53 light | TCCTATGAGCTGACTCAGCCACCCGCGGTGTCAGTGGCCCCAGGAAAGACGGCCAGGATTACCTGTGG<br>GGGAGACGACATTGGATTTAAAGGTGTGCACTGGTACCAGCAGAAGCCAGGCCAGGCCCCTGTACTGG<br>TCGTCTATGATGATCGCGACCGGCCCTCAGGGATCCCTGACCGATTATCTGGCTCCAACTCTGGGAACA<br>CGGCCACCCTGACCATCAGCAGGGTCGAAGCCGGGGATGAGGCCGACTATTAC | 131 |
| MPXV-71 heavy | GAGGTGCAGCTGGTGGAGTCTGGGGGAGGCTTGGTCCAGCCTGGGGAGTCTCTGAAGATCTCCTGTTC<br>AGCCTCTGGATTCACCTTCAGTGACTATGCTATGCACTGGGTCCGCCAGGCTCCAGGGCAGGGACTGCA<br>ATATGTTTCAGCTATTAGTAGTAATGGACATAGTACATATTACGCAGACTCCGTGAAGGGCAGATTCAC<br>CTTCTCCAGAGACAATTCCAAGAATACGCTGTATCTTCAAATGAGCAGTCTGAGACCTGAAGACACGGC<br>TGTATATTACTGTGTGAGGTGTCTGCTTCGGGGACTTATTAGCCCCTTTGACTACTGGGGCCAGGGAAC<br>CCTGGTCACCGTCTCCTCAG | 132 |
| MPXV-71 light | CAGTCTGTGCTGACTCAGCCACCCTCGGTGTCTGAAGCCCCAGGCAGAGGGTCACCATCTCCTGTTCT<br>GGAAGCAGCTCCAACATCGGAAATAATGCTGTAAACTGGTACCAGCAGCTCCCAGGAAAGGCTCCCAA<br>ACTCCTCATCTATTATGATGATCTGCTGCCCTCAGGGGTCTCTGACCGCTTCTCTGGCTCAAAGTCTGGG<br>ACCACAGCCTCCCTGACTATCTCGGGCCCCAGCCTGAGGACGAGGCTGATTTTTACTGTTCAACATGG<br>GACTACAGCCTCAGTGCTCGGGTGTTCGGCGGAGGGACCCAGGTGACCGTCCTAG | 133 |
| MPXV-97 heavy | CAGGTTCAGCTGGTGCAGTCTGGGGGAGGTGTAGTCCAGCCTGGGAGGTCCCTCACACTCTCCTGTTCA<br>GCCTCTGGATTCATCTTCACTAGATATGGTCTCCACTGGGTCCGCCAGGCTCCAGGCAAGGGGCTAGAG<br>TGGGTGGCAGTTATTTCATCTGATGAACGAATAGACACTACGCAGACTCCGTGAAGGGCCGATTCACC<br>GTCTCCAGAGACAATTCCAAAAGCACATTATATGTGCAGATGAACAGCCTGAGAAATGAGGACACGGC<br>TGTATATTACTGTGCGAGACTAAGTCTAGAAGCGGCGTGGTACTTCGATCTCTGGGGCCGTGGTACCCT<br>GGTCACCGTCTCCTCAG | 134 |
| MPXV-97 light | CAGTCTGTGGTGACGCAGCCGCCCTCAGTGTCTGGGGCCCAGGGCAGAGGGTCACCATCTCCTGCAC<br>TGGGAGCAGCTCCAACATCGGGGCAGGTTATGATGTACACTGGTACCAGCATCTTCCAGGAACAGCCC<br>CCAAAGTCCTCATCTATGGCAACACCAATCGGCCCTCAGGGGTCCCTGACCGGTTCTCTGGCTCTAAGTC<br>TGGCACCTCAGCCTCCCTGGCCATCACTGGGCTCCAGGCTGAGGATGAGGCTGATTATTACTGCCAGTC<br>CTATGACAACAGCCTGAATGGCCCTTGGGTCTTCGGAACTGGGACCCAG | 135 |
| VACV-309 heavy | GAGGTGCAGCTGTTGGAGTCTGGGGGAGGCTTGGTACAGCCTGGGGAGTCCCTGAAACTCTCCTGTGC<br>AGCCTCTGGATTCACCTTTAGCAGCTATGCCATGAACTGGGTCCGCCAGGCTCCAGGGAAGGGGCTGG<br>AGTGGGTCTCAGGTATTAGTGGTAGTGGTGGTAGCACATACTACGCAGACTCCGTGAAGGGCCGGTTC | 136 |

TABLE 1-continued

NUCLEOTIDE SEQUENCES FOR ANTIBODY VARIABLE REGIONS

| Clone | Variable Sequence Region | SEQ ID NO: |
|---|---|---|
| | ACCGTCTCCAGAGACAATTCCAAGAACACGCTGTATCTGCAAATGAACAGCCTGAGAGCCGAGGACAC<br>GGCCGTATATTACTGTGCGAAAGACAACAACTACTACTACTACGGTATGGACGTCTGGGGCCAAGGGA<br>CCACGGTCACCGTCTCCTCA | |
| VACV-309<br>light | GCCATCCAGATGACCCAGTCTCCATCCTCCCTGTCTGCATCTGTAGGAGACAGAGTCACCATCACTTGCC<br>GGGCAAGTCAGGGCATTAGAAATGATTTAGGCTGGTATCAGCAGAAACCAGGGAAAGCCCCTAAGCTC<br>CTGATCTATGCTGCATCCAGTTTACAAAGTGGGGTCCCATCAAGGTTCAGCGGCAGTGGATCTGGCACA<br>GATTTCACTCTCACCATCAGCAGCCTGCAGCCTGAAGATTTTGCAACTTATTACTGTCTACAAGATTACA<br>ATTATCCTCGAATGTTCGGCCAAGGGACCAAGGTGGATATCAAA | 137 |
| VACV-312<br>heavy | CAGGTGCAGCTGGTGGAGTCTGGGGGAGGCGTGGTCCAGCCTGGGAGGTCCCTGAGACTCTCCTGTG<br>CAGCGTCTGGATTCACCTTCAGTAGCTATGGCATGCACTGGGTCCGCCAGGCTCCAGGCAAGGGGCTG<br>GAGTGGGTGGCAGTTATATGGTTTGATGGAAGTAATAAATACTATGCAGACTCCGTGAAGGGCCGATT<br>CACCATCTCCAGAGACAATTCCAAGAACACGCTGTATCTCCAAATGAACAGCCTGAGAGCCGAGGACAC<br>GGCTGTGTATTACTGTGCGAGAGTCGCCCGGGACTACAGTAACATCTTTGATGCTTTTGATATCTGGGG<br>CCAAGGGACACTGGTCACCGTCTCCTCA | 138 |
| VACV-312<br>light | GACATCCAGATGACCCAGTCTCCATCCTCCCTGTCTGCATCTGTAGGAGACAGAGTCACCATCACTTGCC<br>GGGCAAGTCGGAGCATTAGCACCTATTTAAATTGGTATCAGCAGAAACCAGGGAAAGCCCCTAAGCTC<br>CTGATCTATGCTGCATCCAGTTTGCACAGTGGGGTCCCATCAAGGTTCAGTGGCAGTGGATCTGGGACA<br>GATTTCACTCTCACCATCAGCAGTCTGCAACCTGAAGATTTTGCAACTTACTACTGTCAACAGAGTTACA<br>GTACCCCGATCACCTTCGGCCAAGGGACACGACTGGAGATTAAA | 139 |
| VACV-313<br>heavy | CAGCTGCAGCTGCAGGAGTCGGGCCCAGGACTGGTGAAGCCTTCGGAGACCCTGTCCCTCACCTGCAC<br>TGTCTCTGGTGGCTCCATCAGCAGTAGAAGTTACTACTGGGGCTGGATCCGCCAGCCCCCAGGGAAGG<br>GGCTGGAGTGGATTGGGAGTATCTATTATAGTGGGAGCACCTACTACAACCCGTCTCTCAAGAGTCGA<br>GTCACCATATCCGTAGACACGTCCAAGAACCAGTTCTCCCTGAAGCTGAGCTCTGTGACCGCCGCAGAC<br>ACGGCTGTGTATTACTGTGTGAGAATAGCCGTAGCAGCAGCTGGCACAGACTACTGGGGCCAGGGAAC<br>CCTGGTCACCGTCTCCTCA | 140 |
| VACV-313<br>light | GAGATAGTGATGACGCAGTCTCCAGACACCCTGTCTGTGTCTCCAGGGGAAAGAGCCACCGTCTCCTGC<br>AGGGCCAGTCAGAGTATTAGCAGCAACTTAGCCTGGTACCAGCAGAAACCTGGCCAGGCTCCCAGGCT<br>CCTCATCTATGGTGCATCCACCAGGGCCATTGGTATCCCAGCCAGGTTCAGTGGCAGTGGGTCTGGGAC<br>AGAGTTCACTCTCACCATCAGCAGCCTGCAGTCTGAAGATTTTGCAGTTTATTACTGTCAGCAGTATAAT<br>AACTGGCCTCCGTACACTTTTGGCCAGGGGACCAAGGTGGATATCAAAA | 141 |
| MPXV-9<br>heavy | CAGGTGCAGCTGGTGCAGTCTGGGGCTGAGGTGAAGAAGCCTGGGGCCTCAGTGAAGGTCTCCTGCA<br>AGGCTTCTGGATACAACCTCACCACCTATGATATCGTTTGGGTGCGACAGGCCGCTGGACAAGGGCTTG<br>AGTGGATGGGATGGATGAATCCTAAAAGTGGTAACACAGCCTACGCAGAGAGGTTCCAGGGCAGAGT<br>CACCATGACCAGGAACACCTCCATAAGCACAGCCTACATGGAGCTGAGCAGCCTGAGATCTGAGGACA<br>CGGCCGTGTATTACTGTGCGAGAAGTCTGGATTCATTACGATTTTTGGAGTGGTTCCACCAGAACTACT<br>ACTACTTCATGGACGTCTGGGGCAAAGGGACCACGGTCACCGTCTCCTCA | 142 |
| MPXV-9<br>light | GAAATTGTGTTGACACAGTCTCCAGCCACCCTGTCTTTGTCTCCAGGGGAAAGAGCCACCCTCTCCTGCA<br>GGGCCAGTCAGACTATTGGCGGCTACTTAGCCTGGTATCAACAGAAACCTGGCCAGGCTCCCAGGCTC<br>TCATCTATGATGCATCCAACAGGGCCACTGGCATCCCAGCCAGGTTCAGTGGCAGTGGGTCTGGGACA<br>GACTTCACTCTCACCATCAGCAGCCTGGAGCCTGAAGATTTTGCAGTTTATTACTGTCAGCTGCGTAGCA<br>CTTTCGGCGGAGGGACCAAGGTGGATATCAAAA | 143 |
| MPXV-41<br>heavy | GAGGTGCAGCTGGTGGAGTCTGGGGGAGGCTTGGTACAGCCAGGCGGTCCCTGAGACTCTCCTGTA<br>AAGCCTCTGGAATCCCCTTTGGTGATTATGCTATGACCTGGTTCCGCCAGGCTCCAGGGAAGGGACTGG<br>AGTGGGTAGGTTTCATTAAGAGCAAAGCTTATGGTGGGACACCGGAATACGCCGCGTCTKTGAAGGGC<br>AGATTCACCATCTCAAGAGATAATTCCAGAAGCACCGCCTACCTGCAAATGAACAGCCTGAAAACCGAC<br>GACACAGCCGTGTATTACTGTAGTGCAACATTGACTAGAGGGGAGCTGTTTGACTACTGGGGCCAGGG<br>AACCCTGGTCACCGTCTCCTCA | 144 |
| MPXV-41<br>light | GAAATTGTGTTGACACAGTCTCCAGACACCCTGTCTTTGTCTCTAGGGGAAAGAGCCACCCTCTCCTGCA<br>GGGCCAGTCAGAGTGTTAGTAACTACTTAGCCTGGTATCAACAGAAACCTGGCCAGGCTCCCAGGCTCC<br>TCATCTATGATGCGTCCAGCAGGGCCACTGGCATCCCAGCCAGGTTCAGTGGCAGTGGGTCTGGGACA<br>GACTTCACTCTCACCATCAGCAGCCTAGAGCCTGAAGATTTTGCAGTTTATTACTGTCAGCAGCGTTCCA<br>ACTGGCCGCTCACTTTCGGCGGAGGA | 145 |
| MPXV-49<br>heavy | CAGGIGCAGCTGCAGGAGTCGGGCCCAGGACTGGTGAAGCCTTCGGAGACCCTGTCCCTCACCTGSAC<br>TGTCTCTGGTGACTCCGTCAACAGTGGTAGTTTCTACTGGAGCTGGATCCGGCAGCCCCCAGGGAAGG<br>GACTGGAGTGGATTGGTTTTATCTATTACAGTGGGACCACCAACTACAACCCCTCCCTCAAGAGACGAG<br>TCACCATATCATTAATCACGTCCAAGAACCAGTTTCCCTGAAGCTGGGCTCTGTGACCGCTGCGGACAC<br>GGCCGTCTATTACTGTGTGAGAGTGGCCTAGGCACTATGATAATAGAGGTTACCACACGTTGCCGG<br>GGACCTGGGGCCAGGGAACCCTGGTCACCGTCTCCTCAG | 146 |
| MPXV-49<br>light | GACATCCAGATGACCCAGTCTCCTTCCACCCTGTCTGCATCTGTAGGAGACAGAGTCACCATCACTTGCC<br>GGGCCAGTCAGAGTATTAGTAGCGTTGGCCTGGTATCAGCAGAAACCAGGGAAAGCCCCTAACCTTT<br>CTGATCTATAAGGCGTCTACTTTAGAAAGTGGGGTCCCATCACGGTTCAGCGGCAGTGGATCTGGGAC<br>AGAGTTCACTCTCACCATCAACAGCCTGCACCCTGATGATTTTGCAACTTATTACTGCCAACAATATAAT<br>ACTGATTCTTCCCGGACGTTCGGCCAAGGGACCAAGGTGGATATCAAAA | 147 |

TABLE 1-continued

NUCLEOTIDE SEQUENCES FOR ANTIBODY VARIABLE REGIONS

| Clone | Variable Sequence Region | SEQ ID NO: |
|---|---|---|
| VACV-318 heavy | CAGGTGCAGCTGGTGGAGTCTGGGGGAGGCGTGGTCCAGCCTGGGAGGTCCCTGAGACTCTCCTGTA CAGCCTCTGGATTCAACTTCAGTTACTATGGCATACACTGGGTCCGCCAGGCTCCAGGCAAGGGGCTGC AGTGGGTGGCACTTATATCATATGATGGAAGTGATAAATACTATGCAGACTCCGTGAAGGGCCGATTC ACCGTCTCCAGAGACTATTCCAAGAACACACTGTTTCTGCAAATGAACAGCCTGAGAGGTGACGATACG GCTGTGTATTATTGTCAAATGGTTAAGGTGCCTTTTTATTTCTGGGGCCAAGGGACAATGGTCACCCTCT CCTCC | 148 |
| VACV-318 light | TCCTATGAGCTGACACAGCCACCCTCGGTGTCAGTGTCCCCAGGACAAACGGCCAGGATCACCTGCTCT GGAGATGAATTGCCAAAAGATATGCTTATTGGTACCAGCAGAAGTCAGGCCAGGCCCCTGTGCTGGT CATCTATGAGGACACCAAACGACCCTCCGGGATCCCTGAAAGATTCTCTGGCTCCAGCTCAGGGACAGT GGCCACCTTGACTATCAGCGGGGCCCAGGTGGACGATGAAGCTGACTACTACTGTTACTAACAGACA GTACTAGTAATCATAAGAGGGTGTTCGGCGGAGGGACCCAGGTGACCGTCCTA | 149 |
| VACV-308 heavy | CAGGTGCAGCTGGTGCAGTCTGGGGCTGAGGTGAAGAAGCCTGGGTCCTCGGTGAAGGTCTCCTGCA AGGGTTCTGGAGACAGCTTCAGAAGTTATGCTATCAGTTGGGTGCGACAGGCCCCTGGACAAGGGCTT GAGTGGATGGGAGGGATCATCCCTAGGTTTGGTACAACAAACTACGCACAGAAGTTCCAGGACAGAGT CACGATTACCGCAGACAAGTCCACGACTACAGCCTACATGGAACTGCGCAGCCTCAAATGTGAGGACA CGGGCGTGTATTACTGTGCGAGGCCACAAAGTGCCTACGATTTCGGGCCTTTTGACCACTGGGGCCAG GGAACCCTGGTCACCGTCTCCTCA | 150 |
| VACV-308 light | TCCTATGAGCTGACTCAGCCACCCTCACTGTCAGTGGCCCCAGGAAAGACGGCCAGAATTACCTGTGGG GGAGACAACATTGGAAGTAAAGGTGTTCACTGGTACCAGCAGAAGCCAGGCCAGGCCCCTGTGGTAGT CATCTCTTATGATAGCGACCGGCCCTCAGGGATCCCTGAGCGATTCTCTGGCTCCAATTCTGGGGACAC GGCCACCCTGACCATCAGCAGGGTCGAAGCCGGGGATGAGGCCGACTATTACTGTCACGTGTGGCATA CTACTACTGATCATTATGTCTTCGGAACTGGGACCAAGGTCACCGTCCTAG | 151 |
| VACV-305 heavy | CAGGTGCAGCTGGTGGAGTCTGGGGGAGGCGTGGTCCAGCCTGGGAGGTCCCTGAGACTCTCCTGTG CCGCGTTTGGATTCACCATCAGTAGCTATGGCATGCACTGGGTCCGCCAGGCTCCAGGCAAGGGCTG GAGTGGGTGGCATTTATATGGTATGATGGAACTAATAAATACTATGCAGACTCCGTGAAGGGCCGATT CACCATCTCCAGAGACAATTCCAAGAACACGCTGTATCTGCAAATGAACAGCCTCAGAGCCGAGGACAC GGCCGTGTATTACTGTGTGAGGACCCAGCAGGTTATACGCCCTTTTTTCGACCACTGGGGCCAGGGAAC CCTGGTCACCGTCTCCTCA | 152 |
| VACV-305 light | GAAATAGTGATGACGCAGTCTCCAGCCACCCTGTCTGTGTCTCCAGGGGATAGAGTCACCCTCTCCTGC AGGGCCAGTCAGAGTATTAGCAGCAACTTAGCCTGGTACCAGCAGAAACCTGGCCAGGCTCCCAGGCT CCTCATCTATGGTGCATCCACCAGGGCCACTGGTATCCCAGCCAGGTTCAGTGGCAGTGGGTCTGGGAC AGAGTTCACTCTCAGCATCAGCAGCCTGCAGTCTGAAGATTTTGCAGTTTATTACTGTCAGCAGTATAAA AACTGGCCTCCGTGGACGTTCGGCCAAGGGACCAAGGTGGATATCAAA | 153 |
| VACV-306 heavy | CAGGTGCAGCTGGTGCAGTCTGGGGCTGAGGTGAAGAAGCCTGGGTCCTCGGTGAAGGTCTCCTGCA AGACTTCTGGAGGCACCTTCAGCAATTATTCTATCACCTGGGTGCGACAGGCCCCTGGACAAGGGCTTG AGTGGATGGGAGGGATCATCCCTATCTCTGGAACAGCAAAATACGCACAGAAGTTCCAGGGCAGAGTC ACGATTAGCGCGGACAAATCCACGAGCACAGCCTACATGGAACTGAGCAGCCTGAGATCTGAGGACAC GGCCGTATATTACTGTGCGAGAGACTGTTACGGGGTTTTTTGGAGTGGTTATTTTAGCAGGTGCCACTT CGGTATGGACGTCTGGGGCCAAGGGACCACGGTCACCGTCTCCTCA | 154 |
| VACV-306 light | GAAATTGAGTTGACGCAGTCTCCAGGCACCCTGTCTTTGTCTCCAGGGGAAAGAGCCACCCTCTCCTGC AGGGCCAGTCAGAGCGTTAGAAGCAGCCACTTAGCCTGGTACCAGCAGAAACCTGGCCAGGCTCCCAG GCTCCTCATCTATGGTGCATCCAACAGGGCCACTGGCATCCCAGACAGATTCAGTGGCAGTGGGACTG GGACAGACTTCACTCTCACCATCAGCAGACTGGAGCCTGAAGATTTTGCAGTGTATTACTGTCAGCAGT ATGGTGGCTCACCTTTGCTCACTTTCGGCGGAGGGACCAAGGTGGATATCAAA | 155 |
| VACV-307 heavy | GAGGTGCAGCTGTTGGAGTCTGGGGGAGGCTTGGTACAGCCTGGGGGGTCCCTGAAACTCTCCTGTGC AGCCTCTGGATTCACATTTAGCAACTATGCCATGAGCTGGGTCCGCCAGGCTCCAGGGAAGGGGCTGG AGTGGGTCTCAGCTTTTAGTGGCACTGGTGGTAGCACATACTACGCAGACTCCGTGAAGGGCCGGTTC AGCATCTCCAGAGACAATTCCAAGAACACGCTGTATCTGCAAATGAACAGCCTGAGAGTCGAGGACAC GGCCGTATATTACTGTGCGAAAGATAGGGGAATAGTGGGAACTACCCGATTTGACTCCTGGGGCCAGG GAACCCTGGTCACCGTCTCCTCA | 156 |
| VACV-307 light | GAAATAGTGATGACGCAGTCTCCAGCCACCCTGTCTGTGTCTCCAGGGGAAAGAGCCACCCTCTCCTGC AGGGCCAGTCAGAGTGTTAGCAGCAACTTAGCCTGGTACCAGCAGAAACCTGGCCAGGCTCCCAGGCT CCTCATCTATGGTGCATCCACCAGGGCCACTGGTATCCCAGCCAGGTTCAGTGGCAGTGGGTCTGGGAC AGAGTTCACTCTCACCATCAGCAGCCTGCAGTCTGAAGATTTTGCAGTTTATTACTGTCAGCAGTATAGT AACTGGCCTCCGATCACCTTCGGCCAAGGGACACGACTGGAGATTAAA | 157 |
| VACV-311 heavy | CAGGTGCAGCTGGTGGAGTCTGGGGGAGGCTTGGTCCAGCTCGGGGAGTCTCTGAAGATCTCCTGTGT AGCCTCTGGCTTCGCCTTCAGTGGCTCTGCTATGCACTGGGTCCGCCAGGCTTCCGGGAAAGGGCTGGA GTGGCTTGGCCGTATAAGAAATAAGCCGAACAACTACGCGACAGCATATGCTGCGTCGGTGAAAGGCA GGTTCACCATCTCCAGAGATGATTCAAAGAACACGGCTATCTACAAATGAACAGCCTGAAAACCGAG GACGGGCGTGTATTATTGTACTAGACGAATGGACATGCTCGTCGGCCCGCTCGGGAGGACTACTA CAACAACGGTATGGACATCTGGGGCCAAGGGACCACGGTCACCGTCTCCTCA | 158 |
| VACV-311 light | GAAATTGTGTTGACGCAGTCTCCAGGCACCCTGTCTTTGTCTCCAGGGGAAAGAGCCACCCTCTCCTGC AGGGCCAGTCAGAGTGTTAGCAGCAGCTTCTTAGCCTGGTACCAGCACAAACCTGGCCAGGCTCCCAG GCTCCTCATCTATGATGCGTCCAGCAGGGCACTGGCATCCCAGACAGGTTCAGTGGCAGTGGGTCTG | 159 |

TABLE 1-continued

NUCLEOTIDE SEQUENCES FOR ANTIBODY VARIABLE REGIONS

| Clone | Variable Sequence Region | SEQ ID NO: |
|---|---|---|
| | GGGCAGAGTACACTCTCACCATCAGCAGACTGGAGCCTGAAGACTTTGCAGTGTATTACTGTCAGCAGT ATAGTAGCTCACCCACCTTCGGCCCTGGGACCAAAGGTGGATATCAA | |
| VACV-316 heavy | CAGGTGCAGCTGGTGGAGTCTGGGGGAGGCGTGGTCCAGCCTGGGGGGTCCCTGAGACTCTCCTGTG CAGCGTCTGGATTCAGCTTCAGTAACTATGGCGTGCACTGGGTCCGCCAGGCTCCAGGCAGGGCGCTG GAGTGGGTCGCTTTTATACGGTTTGATGGAACTGATAAATACTATGCAGACTCCGTGGAGGGCCGATTC ACCATCTCCAGAGACAATTCCAAGAACACACTGTATCTCCAAATGAACAACCTGAGAGCTGAGGACACG GCTGTGTATTACTGTGCGAAGGATTTGGCGATGATGATTGCAAACCCCCTTGACTGCTGGGGCCAGGG AATCCTGGTCACCGTCTCCTCA | 160 |
| VACV-316 light | GAAATAGTGATGACGCAGTCTCCAGCCACCCTGTCTGTGTCTCCAGGGGAAAGAGCCACCCTCTCCTGC AGGGCCAGTCAGAGTGTTAGTAGCAACTTAGCCTGGTACCAGCAGAAACCTGGCCAGGCTCCCAGGCT CCTCATCTATGATGCATCCACCAGGGCCACTGGTATCCCAGTCAGGTTCAGTGGCAGTGGGTCTGGGAC AGAGTTCACTCTCACCATCAGCAGCCTGCAGTCTGAAGATTTTGCAATTTATTACTGTCAGCAGTATAAA AACTGGGGACGTTCGGCCAAGGGACCAAGGTGGATATCAAA | 161 |
| VACV-310 heavy | CAGGTCCAGCTGGTGCAGTCTGGGGCTGAGGTGAAGAAGCCTGGGTCCTCGGTGAAGGTCTCCTGCAA GGCTTCTGGAGGCACTTTCAACAGTTTTGCTATCACCTGGGTGCGACAGGCCCCTGGACAAGGGCTTGA GTGGATGGGGGGGATCATTCCTCTCTTGGTACCACGAACTACGCACAGAAGTTCCAGGACAGAGTCA CGATTACCACGGACGAATTCCATGAGTACATTTTACATGGAGTTGAAAAGCCTGAGATCTGAGGACACG GCCGTCTATTACTGTGCGAGAGTGTTCTCCGCGGCTGGACACTGGGGCCAGGGAACCCTGGTCACCGT CTCCTCAG | 162 |
| VACV-310 light | GACATCCAGATGACCCCTTCTCCATCCTCCCTGTCTGCATCTGTAGGAGACAGAGTCACCATCACTTGCC GGGCAAGTCAGAGCATTGCCAGCTATTTAATTTGGGATCAGCAGAAACCAGGGAACGCCCCTAAGCTC CTGATCTATGCTGCATCCAGTTTGCAAAGTGGGGTCCCATCAAGGTTCAGTGGCAGTGGATCTGGGACA GATTTCACTCTCACCATCGGCAGTCTGCAACCTGAAGATTTTGCAACTTACTACTGTCAACAGAGTTACA GTACCCCTCAAACGTTCGGCCAAGGGACCAAGGTGGATATCAAAA | 163 |
| MPXV-8 heavy | CAGGTGCAGCTGGTGGAGTCTGGGGAGGCGTGGTCCAGCCTGGGAGGTCCCTGAGACTCTCCTGTG CAGCCTCTGGATTCACCTTCCGTAGCTATGCTATGCACTGGGTCCGCCAGGCTCCAGGCAAGGGGCTAG AGTGGGTGGCAGTTATCTCATATGATGCGAATAATGAATACTACGCAGACTCCGTGAAGGGCCGATTC ACCATCTCCAGAGACAATTCCAAGAACACGCTGTATCTGCAAATGAACACCCTGAGACCTGAGGACACG GCTGTATATTACTGTGCGAGAGGGCTCATTCCTTCCGCAGAGCAGTGGCAGGCCAGGGGGGGACCTGA TTACTACTACTACGGTATGGCCGTCTGGGGCCAAGGGACCACGGTC | 164 |
| MPXV-8 light | ND | 165 |
| MPXV-28 heavy | CAGGTCCAGCTGGTGCAGTCTGGGGCTGAGGTGAAGAAGCCTGGGTCCTCAGTGAAGGTCTCCTGCAA GGCTTCTGGAGGCACCTTCAGCAGCTATGTTTTCAGCTGGGTGCGACAGGCCCCTGGACAAGGGCTTGA GTGGATGGGAAGGATCCTCCCTATCCTTGATATACCAAACTACGCACAGAAGTTCCAGGGCAGAGTCAC GATTACCGCGGACAAATCCACGAGCACAGCCTACATGGAGCTGGGCAGCCTGAGATCTGAGGACACG GCCGTGTATTACTGTGCGAGAGGCGGAGGCGCAGTGACTGGACGGGGGTATTATTTTGACTACTGGG GCCAGGGAACCCTGGTCACCTTCTCC | 166 |
| MPXV-28 light | GACATCCAGATGACCCAGTCTCCATCCTCCCTGTCTGCATCTGTAGGAGACAGAGTCACCATCACTTGCC GGGCAAGTCAGAGCATTAGCAGCTATTTACATTGGTATCAACAGAGACCAGGGAAAGCCCCTAAGCTC CTGATCTATGCTGCATCCAGTTTGCAAAGTGGGGTCCCATCAAGGTTTCAGTGGCAGTGGATCTGGGACA GATTTCACTCTCACCATCAGCAGTCTGCAACCTGAAGATTTTGCAACTTACTACTGTCAACAGAGTTACA GTACCCCTCCCACTTTCGGCGGAGGGACCAAGGTGGAGATCAAAC | 167 |
| MPXV-42 heavy | CAGGTCCAGCTGGTGCAGTCTGGGGCTGAGGTGAAGAAGCCTGGGTCCTCGGTGAAGGTCTCCTGCAA GCTTTCCGGAGGCACCCTCAACAGTTATGCTGTCAGCTGGGTGCGACAGGCCCCGGGACAAGGGCTTG AGTGGATAGGAAGGATCATCCCTATGGTTGGCATGGCACACTATGCACAGAAGTTTCAGGGCAGAGTC ACAATTACCGCGGACAAATCCACGAGTTCAGTCTACATGGAGCTGAGTACCCTGAGATCCGAAGACAC GGCCATGTATCATTGTGCGAGAGAGCAGAAGTTGGTGGGGGGGCTGGTTCGACCCCTGGGGCCAG GGAACCCTGGTCACC | 168 |
| MPXV-42 light | GAAATTGTATTGACGCAGTCTCCAGGCACCCTGTCTTTGTCTCCAGGGGAAAGCGCCACCCTCTCCTGCA GGGCCAGTCAGAGTGTTAACAGCGACTACTTAGCCTGGTACCAACAGAAGCCTGGCCAGGCTCCCAGG CTCCTCATCTATGGTGTATCCAGCAGGGCCACTGGCATCCCAGACAGGTTCAGTGGCAGTGGGTCTGAG ACAGACTTCACTCTCACCATTAGTAGACTGGAGCCTGAAGATTTTGGTGTATTTTACTGTCAGCAGTATG GTCACTCACCGTACACTTTTGGCCAGGGGACCAAGGTGGATATCAAA | 169 |
| MPXV-45 heavy | CAGGTCCAGCTGGTGCAGTCTGGGGCTGAGGTGAAGAAGCCTGGGTCCTCGGTGAAGGTCTCCTGCAA GGCTTCTGGAGGCACCCTCAGCAATTCTGCTATCAACTGGGTGCGACAGGCCCCTGGACAAGGGCTTG AGTGGATGGGAAGGATCATCCCTATCCTTGGTATACCAAACTACGCACAGAAGTTCGAGGGCAGAGTC ACGATTACCGCGGACAAATCCACGAGCACAGCCTACATGGAGCTGAACAGCCTGAGATCTGAGGACAC GGCCGTGTATTACTGTGCGAGCCCTCAGAGAGTATTACGATTTTTGCAGTGGTCACCCTTTGACTACTG GGGCCAGGGAACCCTGGTCACCGTCTCCTCAG | 170 |
| MPXV-45 light | GAAATTGTGTTGACGCAGTCTCCAGGCACCCTGTCTTTGTCTCCAGGGGAAAGAGTTACCCTCTCCTGCA GGGCCAGTCAGAGTGTTAGCAGCAGCTACTTAGCCTGGTACCAGCAGAAACCTGGCCAGGCTCCCAGG CTCCTCATCTATGATGTATTAAGCAGAGCCACTGGCATCCCAGACAGGTTCAGTGGCAGTGGGTCTGGG | 171 |

TABLE 1-continued

NUCLEOTIDE SEQUENCES FOR ANTIBODY VARIABLE REGIONS

| Clone | Variable Sequence Region | SEQ ID NO: |
|---|---|---|
| | ACAGACTTCACTCTCACCATCAGCAGACTGGAGCCTGAAGATTTTGCAGTGTATTTCTGTCAGCAGTATG CTATCTCACCTAACACTTTTGGCCAGGGGACCAAGCTGGAGATCAAAC | |
| MPXV-82 heavy | CAGGTGCAGCTGGTGGAGTCTGGGGGAGGCGTGGTCCAGCCTGGGAGGTCCCTGAGACTCTCCTGTG CAGCCTCTGGATTCAGCCTCAGTAGCTATGGCATGCACTGGGTCCGCCAGGCTCCAGGCAAGGGGCTG GAGTGGGTGGCAGTTATATGGTATGATGGAAGTAATAAATACTATGCAGACTCCGTGAAGGGCCGATT CACCATCTCCAGAGACAATTCCAAGAACACGCTGTATCTGCAAATGAACAGCCTGAGAGCCGAGGACA CGGCTGTGTATTACTGTGCGAGAGGGGTTCGAATGACTACAAGCCTTGACTACTGGGGCCAGGGAACC CTGGTCACCGTCTCCTCA | 172 |
| MPXV-82 light | CAGTCTGTGCTGACTCAGCCTGCCTCCGTGTCTGGGTCTCCTGGACAGTCGATCACCATCTCCTGCACTG GAACCAGCAGTGACGTTGGTGGTTATAACTATGTCTCCTGGTACCAACAGCACCCAGGCAAAGCCCCA AACTCATGATTTATGATGTCAGTAAGCGGCCCTCAGGGGTTTCTAATCGCTTCTCTGGCTCCAAGTCTGG CAACACGGCCTCCCTGACCATCTCTGGGCTCCAGGCTGACGACGAGGCTGATTATTACTGCAGCTCATA TACAACCATCAGCACTTTAGGGGTGTTCGGCGGAGGGACCCAGGTGACCGTCCTA | 173 |
| MPXV-86 heavy | CAGGTGCAGCTGCAGGAGTCGGGCCCAGGACTGGTGAAGCCTTCGGAGACCCTGTCCCTCACCTGCAT TGTCTCTGGTGGCTCCATCAGTAGTTACTACTGGAGTTGGATCCGGCAATCCCCAGGGAAGGGACTGG AGTGGATTGGGTATATGTCTCACAGTGGGAGCACCAACTACAACCCCTCCCTCAAGAGTCGAGTCACCA TATCAGTAGACATGTCCAAGAACCAGTTTTCCCTGAAGTTGACCTCTGTGACCGCTGCGGACACGGCCG CGTATTATTGTGCGAGAGGAGTGGGTGGCGTTTACGATATTTTGACTGGTTATTGGGGCCCCAACTGGT TCGACCCCTGGGGCCAGGGAACCCTGGTCACCGTCTCCTCAG | 174 |
| MPXV-86 light | CAGTCTGTGGTGACGCAGCCGCCCTCAGTGTCTGGGGCCCCAGGGCAGAGGGTCACCATCTCCTGCAC TGGGAGCAGCTCCAACATCGGGGCAGGTTATGATGTACACTGGTACCAACAGCTTCCAGGAACAGCCC CCAAACTCCTCATCTATGCTAACACCAATCGGCCCTCAGGGGTCCCTGACCGATTCTCTGGCTCCAAGTC TGACACCTCAGCCTCCCTGGCCATCACTGGGCTCCAGGCTGAGGATGAGGGTGATTATTACTGCCAGTC CTTTGACAGCAGCCTGAGGGGTTCCGTGGTATTCGGCGGAGGGACCCAGGTGACCGTCCTAG | 175 |
| MPXV-88 heavy | CAGGTGCAGCTGGTGGAGTCTGGGGGAGGCTTGGTCAAGCCTGGGGAGTCTCTGAAGATCTCCTGTTC AGTCTCTGGATTCACCTTCAGTGACTACTACATGAGCTGGATCCGCCAGACTCCAGGGAAGGGGCTGG AGTGGATTTCATACATTAGTGGTGGTGTAATACCATATACTATACAGACTCTGTGAAGGGCCGATTCA CCATCTCCAGGGACAACTCCAAGAAGTCACTGTATCTGCAAATGAACAGCCTGAGAGCCGAGGACACG GCCGTGTATTACTGTGCGCGGAACCTTAGGGCTGCAGGTGTTAATTATTTCTACTTCTACTACATGGACG TCTGGGGCAAAGGACCACGGTC | 176 |
| MPXV-88 light | GAAATTGTGTTGACACAGTCTCCAGCCACCCTGTCTTTGTCTCCAGGGGAAAGAGCCACCCTCTCCTGCA GGGCCAGTCAGAGTGTTAGCAGCTCCTTAGCCTGGTATCAACAGAGACCTGGCCGGGCGCCCAGGCTC CTCATCTATGATGCATCCAATAGGGCCACTGGCATCCCAGCCAGGTTCAGTGGCAGTGGGTCTGGGACA GACTTCAATCTCACCATCAGCAGCCTGGAGCCTGAAGATTTTGCAGTTTATTACTGTCAGCAGCGTGGC AAGTGGCCTCCGTGGACGTCGGCC | 177 |
| MPXV-98 heavy | CAGGTGCAGCTGGTGCAGTCTGGGGCTGAGGTGAAGAAGCCTGGGGCCTCAGTGAAGGTCTCCTGCA AGGCATCTGGATACACCTCGATGAGCGACTATATAGAATGGGTGCGACAGGCCCCTGGACAAGGGCTT GAGTGGATGGGAATAATGAACCCTCTTGGTGGCAGCAAGCTACGCACAGAAGTTGCAGGGCAGAG TCACCATGACCAGGGACACGTCCACGAGCACAGTGTACATGGAGCTGAGCAGCCTGAGATCTGACGAC ACGGCCGTCTATTATTGTGTAGTTAGTAGTGGTTTTCAACAGTGGTTCGACCCCTGGGGCCAGGGAACC CTGGTCACCGTCTCTTCA | 178 |
| MPXV-98 light | GAAATAGTGATGACGCATTCTCCAGCCACCCTGTCTGTGTCTCCAGGGGAAAGAGCCATCCTCTCCTGC AGGGCCAGTCAGAGTCTCACCACCAACTTAGCCTGGTACCAGCAGAAACCTGGCCAGGCTCCCAGGCT CCTCATCTATCGTGCATCCACCAGGGCCACTGGTATCCCAGCCAGGTTCAGTGGCAGTGGGTCTGGGAC AGAGTTCACTCTCACCATCAGCAGCCTGCAATCTGAAGATTTTGCAATTTATTACTGTCAACAGTATAAT AACTGGCCTCGGACGTTCGGCCAAGGGACCAAGGTGGATATCAAA | 179 |

TABLE 2

PROTEIN SEQUENCES FOR ANTIBODY VARIABLE REGIONS

| Clone | Variable Sequence | SEQ ID NO: |
|---|---|---|
| VACV-8 heavy | QVQLQQWGAGLLKPSETLSLTCAGYGGSFSGYFWSWIRQPPGKGLEWIGEINHSGSTDYNPSLKSRVTISLD TSKTQFSLKLSSVTAADTAVYYCARVMTGITNYYYYGMDVWGQGTTVTF | 180 |
| VACV-8 light | DIQLTQSPSFLSASVGDRVTITCRASQDISSYLAWYQQKPGKAPKLLIYAASTLQSGVPSRFSGSESGTEFTLTIS SLQPENFATYYCQHLNSYTPRGYTFGQGTKVDIK | 181 |
| VACV-56 heavy | QVQLQQWGAGLLKPSETLSLTCAVYGGSFSGYYWSWIRQPPGKGLEWIGEINHSGSTNYNPSLKSRVTISVD TSKSQFSLKLSSVTAADTAVYYCARATQGSGYTKLFFYSYGMDVWGQGTTVTSS | 182 |
| VACV-56 light | DIQMTQSPSTLSASVGDRVTITCRASQSITSWLAWYQQKPGKAPKWYKASSLESGVPSRFSGSGSGTEFTLTI SSLQPDDFATYYCQQYNSYPYTFGQGTRLEIK | 183 |
| VACV-66 heavy | QLQLQESGPGLVKPSETLSLTCTVSGDSISSNNYYWGWIRQPPGKGLEWIGSIYYSGSTYYNPSLKSRVTISVD TSKNQFSLKLSSVTAADTAVYYCARHRRVLLWFGEFQLMGQGTLVTVSS | 184 |
| VACV-66 light | QSALTQPPSVSGAPGQRVTISCTGSSSNIGAGYDVHWYQQLPGTAPKLLIYGNINRPSGVPDRFSGSKSGTSA SLAITGLQAEDEADYYCQSYDSSLSGALFGGGTQLTVL | 185 |
| VACV-77 heavy | QVQLQESGPGLVKPSETLSLTCTVSGGSMSSYFWSWIRQPPGKGLEWIGYISYSGGINYNPSLKSRVTISVDT SKNQFSLKLTSVTAADTAVYYCAREDRGSPDYWGQGTLVTVSS | 186 |
| VACV-77 light | QSVLTQPPSVSAAPGRKVTISCSGSSSNIGNNVSWYQQLPGTAPKWDNYKRPSGIPDRFSGSKSGTSATL GITGLQTGDEADYYCGTWDLSLSAGVFGGGTKLTVL | 187 |
| VACV-116 heavy | QVQLVQSGAEVKKPGASVKVSCKASGYTFTSYDINWVRQATGQGLEWLGWMNPNSGNTKSAQKVKGRV TMRDTSISTAYMELSSLRSEDTAVYYCARTPFDGSGYYYWGQGTLVTVSS | 188 |
| VACV-116 light | LC#1<br>DIVMTQSPLSLSVTPGEPASISCRSSQSLLHSNGYNYLDWYLQKPGQSPQLLIYLGSNRASGVPDRFSGSGSGT DFTLKISRVEAEDVGVYCMQALQTPGASALDQGGYQ<br>LC#2<br>DIVMTQSPLSLPVTPGEPASISCRSSQSLLHSNGYNYLDWYLQKPGQSPQLPIYLGSNRAAGVPDRFIGSGSG TDFTLKIGILEAEDVGVYYCMLALRTPGAFGPGTKVDIR | 189<br><br><br>886 |
| VACV-117 heavy | QVQLVQSGAEVKKPGASVKVSCKASGYTFTSYDINWVRQATGQGLEWLGWMNPNSGNTKSAQKVKGXV TMRDTSISTAYMELSSLRSEDTAVYYCARTPFDDIGYYYWGQGTLVTVS | 190 |
| VACV-117 light | DIVMTQSPLSLSVTPGEPASISCRSSQSLLHSNGYNYLDWYLQKPGQSPQLLIYLGSNRASGVPDRFIGSGSGT DFTLKISIVEAEDVGVYYCMQALQTPGAFGPGTKVDIK | 191 |
| VACV-128 heavy | EVQLVQSGAEVKKPGATVKISCKVSGYTFTDYYMHWVQQAPGKGLKMGLLLDPLDGETIYSEKFQGKVTIT ADTSTDTAYMELSSLRSEDTAVYYCARELTGYLNYWGQGTLVTVSS | 192 |
| VACV-128 light | DIQMTQSPSSLSASVGDRVTITCRASPGICNYLAWYQHKPGKVPKLLIYAASTLQSGVPSRFTGVGSGTNFTLT INNLPPENVATYYCQKNSAPHTFGQGTKVDIK | 193 |

TABLE 2-continued

PROTEIN SEQUENCES FOR ANTIBODY VARIABLE REGIONS

| Clone | Variable Sequence | SEQ ID NO: |
|---|---|---|
| VACV-136 heavy | QVTLKESGPVLVNPTETLLTCTVSGFSLSNARMRVSWIRQPPGKALEWLAHIFSNDEKSYSTSLKSRLTISKDT SKSQVVLTMTNMDPVDTASYYCARMRGEYNSYYFDSWGQGTLVTVS | 194 |
| VACV-136 light | SYELTQPPSVSVSPGQTARITCSGDALPNQYAYWYQQKPGQAPVLVIYKDSERPSGIPERFSGSSSGTTVTLTI SGVQAEDEADYYCQSADSSGTSVVEGGGTQVTV | 195 |
| VACV-138 heavy | HC#1<br>QVQLVQSGAEVKKPGASVKVSCKASGYTFASYDIHCVRQAPQGFEMWVGSYSGNGNIGYAQKFQGRVT MTRDTSTSTAYMELSSQRSEDIDVYYCASRDIVVVTATRSPFDYWGQGTLV<br>HC#2 | 196 |
| | EVQLVESGGGLVQPGRSLRLSCAVSGFTLDDYAMHWVRQPPGKGLEWTGISWNSGGMGYADSVKGRFT ISRDSAKNSLYLQMNSLRVEDTAFYYCAKDVGGVVTGGYWDDALDIWGQGTMVTVSS<br>HC# | 887 |
| | EVQLVQSGAEVKKDLASVKVSCKVSGYTFTDYYMHWVQQAPGKGLEWMGLVDPQEGETTYAEKFQGRVT ITADTSTDTAYMELSSLRSEDTAVYYCAKESEGIPHFWGQGTLVTVSS | 917 |
| VACV-138 light | EIVLTQSPGTLSLSPGERATLSCRASQSVTSTYLAGHQQKPGQAPRLLIYSASSRATGIPDRESGSGSGTDFTLTI SRLEPEDFAVYYCQQYGSSPPYTEGQGTKVDIK | 197 |
| VACV-168 heavy | QVQLQESGPGLVKPSETLSLTCTVSGGSISSFYWSWIRQPPGKGLEWIGYIYYSGSTNYNPSLKSRVTISVDTSK NQFSLKLSSVTAADTAVYYCARLRGNYASSGYYYNEDYWGQGTLVTVSS | 198 |
| VACV-168 light | QSVVTQPPSVSAAPGQKVTISCSGSSSNIGNNVVSWYQQLPGTAPKWDNNKRPSGIPDRESGSKSGTSAT LGITGLQTGDEADYYCGTWDSSLSAYVSETGTKVTVL | 199 |
| VACV-159 heavy | QLQLQESGPGLVKPSETLSLTCTVSGGSISSSSYYWGWIRQPPGKGLEWIGSIYYRGSTYYNPSLKSRITISVDTS KNQFSLKLRSVTAADTAVYYCARHLRVLLWEGELLEWGQGTTVTVL | 200 |
| VACV-159 light | QSALTQPPSVSGAPGQRVTISCTGSSSNIGADYDVHWYQQLPGTAPKLLIYGNSNRPSGVPDRFSGSKSGTS ASLAITGLQAEDEADYYCQSHDSSLSGVFGTGTKVTVL | 201 |
| VACV-199 heavy | QVQLVQSGAEVKKPGASVKVSCKASGYTFGYYMHWVRQAPGQGLEWMGWINPNSGGTNYAQKFQGR VTMTRDTPISTAYMELSRLRSDDTAVYYCARVPPDSSSWKWQQGTLVTVS | 202 |
| VACV-199 light | DIVMTQSPLSLPVTPGEPASISCRSSQSLLHRNGYNYLDWYLQKPGQSQLLIYLGSNRASGVPDRFSGSGSG TDFTLKISRVEAEDVGVYYCMQALQTPPTSAKD | 203 |
| VACV-228 heavy | EVQLVESGGGLVKPGGSLRLSCAASGFTFSSYSMNWVRQPPGKGLEWVSSITSSSSYIYYADSVKGRFTISRD NAKNSLYLQMNSLRAEDTAVYYCASRPGIAPAGPQAEGYWGQGTLVTF | 204 |
| VACV-228 light | EIVMTQSPATLSVSPGERATLSCRASQSVSSNLAWYQQKPGQAPRLLIYGASTRATGIPARFSASGSTEFTLT ISSLQPEDFAVYYCQQY | 205 |
| VACV-230 heavy | QVQLVQSGAEVKKPGASVKVSCKVSGYTLTELSMHWVRQAPGKGLEWLGGFDPEDGETIYAQKFQGRVT MTEDTSTDTAYMELSSLRSEDTAVYYCARESWLRGFDYWGQGTLVTVS | 206 |
| VACV-230 light | EIVLTQSPGTLSLSPGERATLSCRASQSVSSSYLAWYQQKPGQAPRLLIYGASSRATGIPDRFSGSGSGTDFLT ISRLEPENFAVYYCQQYGSSPRITFGQGTKVDIK | 207 |

TABLE 2-continued

PROTEIN SEQUENCES FOR ANTIBODY VARIABLE REGIONS

| Clone | Variable Sequence | SEQ ID NO: |
|---|---|---|
| VACV-249 heavy | QVQLVESGPGLVKPSQTLSLTCTVSGGSISRGIYYWSWIRQPAGKGLEWIGRIYTSGSTNYNPSLKSRVTISVDTSKNQFSLKLSSVTAADTAVYYCARDGWYGWYLDLWGRGTLVTVSS | 208 |
| VACV-249 light | EIVMTQSPATLSVSPGERATLSCRASQSVSSDLAWYQQKPGQAPRLLIYGASTRATGIPARFSGSGSGTEFTLTISSLQSEDFAVYYCQQYNNWPGTFGGGTKVDIK | 209 |
| VACV-304 heavy | EVQLVESGGGLVQPGGSLRLSCVVSGFTFSNYWMSWVRQAPGKGLEWVANIKQDGSKKYYVDSVTGRFTISRDNAKNSLYLQMNSLRAEDTAVYYCATLNLELAVDAISEALKWGQGTLVTVSS | 210 |
| VACV-304 light | SYELTQPPSVSVSPGQTARITCSGDALPKQFAYWYQQKPGQAPVVMIYKDSERPSGIPERFSGSSSGTTVTLTISGVQAEDEADYTCQSVDNSGTTEVFGGGTQLTVL | 211 |
| MPXV-27 heavy | HC#1<br>QVQLQQWGAGLLKPSETLSLTCDVYGGSFSGYYWSWIRQPPGKGLEWIGEINHSGSTTYTPSLRSRVTISVDTSKNQFSLKLSSVTAADTAVYYCARVLSGWLPFPNYYYMDVWGKGTTVT<br>HC#2<br>QVQLQESGPGLVKPSQTLSLTCVSGGSISSGGYYWSWIRQYPGKGLEWIGHMSYSGDTFFNPSLKSRATISADTSKHQFSIMLRSVTAADTAVYLCARGRYCNDDSCYSESAIWFDPWGQGTLVT | 212<br><br>888 |
| MPXV-27 light | DIQMTQSPSSLPASVGDRVTITCRASQDIRNNLGWYQQKPGKAPERLLYGTSNLQSGVPSRFSGSGSGTEFTLTISSLQPEDFATYYCLQHNSYPPTFGRGTKVEIK | 213 |
| MPXV-30 heavy | QVQLVQSGGAEVKKPGSSVKVSCKVSGGTFSSLAINWVRQAPGQGLEWMGGIIPIFGKANYAQKFQGRVSIIADESTSTAYMDLSSLRFEDTAVYYCATGNIRVHDFDIWGQGTLVTVSS | 214 |
| MPXV-30 light | DVVMTQSPLSLPVTLGQPASISCRSSQSLVNSDGNTYLNWFQQRPGQSPRRLIYKVSNRDSGVPDRFSGSGSGTDFTLNISRVEARDVGVYCMQGTHWPPRWTFGQGTKVDIK | 215 |
| MPXV-40 heavy | QVQLQQWGAGLLKPSETLSLTCAVYGGSFSGYYWSWIRQPPGKGLEWIGEINYSGSTDYNPSLESRVTISVXASKNHFSLNLNSVTAADTVVYYCARISSGWIGFPRYHYLDVWGKGTVTVS | 216 |
| MPXV-40 light | SYELTQPPAVSVSPGQTARISCSGDVLRDNYADWYPQKPGQAPVLVIYKDEQSLGVGGGTQLTLVDRKSVV | 217 |
| MPXV-61 heavy | QVQLVQSGGAEVKKPGSSVKVSCKASGETFSRYAPSWVRLAPGQGLEWLGRIIPFIDIPNYAQKFQGRVTITADKSTSTAYMELSSLRSEDTAVYYCASSLPSTYYFGSGNYPWGNWLDPWGQGTLVTVSS | 218 |
| MPXV-61 light | QSVVTQPPSVSAAPGQNVTISCGSGSSNIGNNYVVSWYHQLPGTAPKLLIYDNDKRPSGIPDRFSGSKSGTSATLGITGLQTGDEADYYCGTWDSSLSEVVFGGGTQVTVL | 219 |
| MPXV-96 heavy | QVQLQQWGAGLLISSETLSLTCGVYGGSFSGYYWTWIRQPPGKGLEWIGEINVVGSTNYNPSLKSRVTMSVDTSKNHFSLSLSSVTAADTAVYYCARGLRGNSVCFDWGPGTLVTVS | 220 |
| MPXV-96 light | ELVMTQSPATLSVSPGERASLSCRASQSVSSNLAWYQQKPGQAPRLLIYGASTRATGLPARFSGSGSGTEFTLTISSLQSEDFAIYYCQQYNNWPRTFGQGTKVDI | 221 |

TABLE 2-continued

PROTEIN SEQUENCES FOR ANTIBODY VARIABLE REGIONS

| Clone | Variable Sequence | SEQ ID NO: |
|---|---|---|
| VACV-1 heavy | EVQLVESGGGLVQPGESLKISCAASGFTFSSFSMNWVRQAPGKGLEWVSYISSSSSTIYYADSVKGRFTISRDN AKNSLYLQMNSLRDEDTAVYYCARRSVGCSGGNCYAYYYGMDVWGQGTTVTVS | 222 |
| VACV-1 light | DIVMTQSPLSLPVTPGEPASISCRSSQNLLHSNGYNYLDWYLQKPGQSPQLLIYLGSNRASGVPDRFSGSGSG TDFTLKISRVEAEDVGLYYCMQALQTPITFGQGTRLEIK | 223 |
| VACV-59 heavy | QVQLVQSGGGLVKPGGSLRLSCAASGFTFSDYYMSWIRQAPGKGLEWVSYISTSGSTIYYADSVKGRFTISRD NAKNSLYLQMNSLRAEDTAMYYCARDGDGSGSYTPPYYYYGLDVWGQGTTVTVSS | 224 |
| VACV-59 light | DIQMTQSPSSLSASVGDRVTITCRASQSIRNYLNWYQQKSGKAPKLLIYAASSLQSGVPSRFSGSGSGTDFTLT ISSLHPEDFATYYCQQSYSTPPLTFGGGTKVEIK | 225 |
| VACV-151 heavy | EVQLVESGGGLVKPGGSLRLSCAASGFTFSSYSMNWVRQPPGKGLEWVSSITSSSSYIYYADSVKGRFTISRD NAKNSLYLQMNSLRAEDTAVYYCASRPGIAPAGPPGGGLLGP | 226 |
| VACV-151 light | EIVLTQSPGTLSLSPGERATLSCRASQSVSSSYLAWYQQKPGQAPRLLIYGASRRATGIPDRFSASGSGTDFTLT ISRLEPEDFAVYYCQQYGSSPYTFGRGTQVDIK | 227 |
| VACV-282 heavy | EVQLVESGGGLVKPGGSLRLSCAASGFTFSSYSMNWVRQAPGKGLEWVSSISSISSYIYYADSVKGRFTISRDN AKNSLYLQMNSLRAEDTAVYYCARDRPRSRPNSGSYFWYYYGMDVW | 228 |
| VACV-282 light | SYELTQPPSVSVAPGQTARITCGGNNIGSKSVHWYQQKPGQAPVLVVYDDSDRPSGIPERFSGSNSGNTATL TISRVEAGDEADYYCQVWDSNSDHRVSA | 229 |
| VACV-283 heavy | QVQLVQSGAEVKKPGSSVKVSCKASGGTFSTYAINWVRQAPGQGLEWMGRIIPILGTANYAQKFQGRVTIT ADKSTSTAYMELSSLRSEDTAVYYCARRGGEGAAHGMDVWGQGTTVTVSS | 230 |
| VACV-283 light | DIVMTQSPLSLPVTPGEPASISCRSSQSLLHSNGYNYLDWYLQKPGQSPQLLIYLGSNRASGVPDRFSGSGSG TDFTLKISRVEAEDVGVYYCLQALQTLPITFGQGTRLEI | 231 |
| MPXV-2 heavy | QVQLVQSGAEVKKPGASVKVSCKTSGYTFTTYAVHWVRQAPGQRLEWMGWINPGDGDTRYAQKFQDRV TISSDTSATTVYMELSSLRSEDTAVYFCARPRASLLRYFDWLFEQWGQETLVTVSS | 232 |
| MPXV-2 light | EIVLTQSPGTLSLSPGDRATLSCGASQSIHHNYVAWYQQRPGQAPRLLIFGASSRATGIPDRFTGSGSGTEFTL TINRLEPEDFAVYYCQQYGNSVPYSFGQGTKVDIK | 233 |
| MPXV-12 heavy | QVQLQQWGAGLLKPSETLSLTCAVYGGSFTNYYWSWIRQFPGKGLEYIGEIDHSGSANYNPSLKSRVTISLDT SKNQFSLRLSSVTAADTAVYFCARDVYGSGTYYWFDPWGQGTLVTVSS | 234 |
| MPXV-12 light | DIQMTQSPTSLSASVGDRVTITCRASQRISSHLNWYQQKPGKAPKLLIYVASSLQSGVPSRFSGSGSGTDYTLT ISSLQPEDFATYFCQQSYTTPYTFGQGTNLQMK | 235 |
| MPXV-13 heavy | QVQLQESGPGLVKPSETLSLTCAVSGGSISTRTWWTWVRQPPGKGLEWIGEIYQSGSTNYNPSLKSRVTISID TSKNQFSLKLSSVTAADTALYYCARSGRYSSVTPFDYWGQGTLVT | 236 |
| MPXV-13 light | EIVLTQSPATLVFVSGQRATLSCRASQSIGNYLAWYQQKPGQAPRLLIYDASNRATGIPARFSGSGSGTDFTLT ISSLEPEDFAVYYCQQRSHWPAFGPGTKVDIK | 237 |

TABLE 2-continued

| PROTEIN SEQUENCES FOR ANTIBODY VARIABLE REGIONS | | |
|---|---|---|
| Clone | Variable Sequence | SEQ ID NO: |
| MPXV-25 heavy | QVQLVESGGGVVQPGRSLKISCAASGFTFSDSGLHWVRQAPGKGLECVAFIWYDGSTKYYADSVKGRFTISR DNSRNTLYLQMKSLRAEDTAVYYCARELGYCSGGTCYSMGAFDIWGQGTLVTVSQ | 238 |
| MPXV-25 light | QSVLTQPASVSGSPGQSITISCTGTSSDVGSYNLVSWYQQHPGKAPKLMIYEVSKRPSGVSNRFSGSKSDNTA SLTISGLQAEDEADYYCCSYVGSSTSVGGGGTQVTVL | 239 |
| MPXV-38 heavy | EVQLVESGGGLVKPGGSLRLSCAASSFIFSDAWMKWVRQAPGKGLEWVGHFKTKTDGGTTDYAAPVKGRF SISRDDSKSTLHVQMNSLKTEDTAVYYCTTAGASYV | 240 |
| MPXV-38 light | EIVLTQSPGTLSLSPGERATLSCRASQSVSNTYLAWYQQKPGQAPRLLIYAASNRATGIPDRFSGSGSGTDFTL TISRLEPEDFAVYYC | 241 |
| MPXV-43 heavy | QVQLVQSGAEVKKPGASVKVSCKASGYTFTKYTIHWVRQAPGQRLEWVGGIYAGYGNTRYSQKFQGRVTIT RDTSASTAYMELSSLRSEDTAVYFCARDFEDFDSWIGYYSWLHWGQGTLVTVSS | 242 |
| MPXV-43 light | EIVLTQSPGTLSLSPGERATLSCRASQSVSSTYLAWYQQKPGQAPRLLIYGASSRATGIPDRFSGSGSGTDFTLT ITRLEPEDFAMYFCQQYDSSPSITFGQGTRLEIK | 243 |
| MPXV-66 heavy | QVQLQQWGAGLLKPSETLSLTCAVHGGSFSGYFWSWIRQPPGKGLEWIGEMNHSGSTNYNPSLKSRVTISV DTSKKQFSLKLNSVTAADTAVYYCARTARTVRYFENWGQGTLVTVSS | 244 |
| MPXV-66 light | DIVMTQSPDSLAVSLGERATINCKSSQTVLYNSNNYSYLTWYQQKPGQPPRVLIYWASTRESGVPDRFSGSG SGTDFTLTISSLQAENVALYYCQQYYSTPWTFGQGTKVDIK | 245 |
| MPXV-70 heavy | QVQLVESGGGLVKPGGSLKISCAANRFTFSNYYMSWIRQGPGKEPEWISYISSRSRYTNYADSVKGRFTISRD NTKNSLFLQMNDLRAEDTAVYYCARGGGYCGGTTCSMGHAFDIWGQGTVVTVSS | 246 |
| MPXV-70 light | EVVLTQSPGTLSLSPGERATLSCRASQSVTSSYLAWYQQKPGQAPRLLIYGASIRSTDIPDRFSGSESGTDFTYTI SRPEHEDFALYFCQQYGSSPY | 247 |
| MPXV-92 heavy | QVQLVESGPGLVKPSGTLSLTCAVSGGSISSSNWWSWVRQPPGKGLEWIGEIYHSGSTNYTPSLKSRVTISLD KSKNQFSLKLSSVTAADTAMYYCARNFYPGYLQYWGQGTLVTVSS | 248 |
| MPXV-92 light | QSALTQPASVSGSPGQSITISCTGTISDVGGYNYVSWYQQHPGKAPKLMIYDVNKRPSGVSNRFSGSKSGNT V | 249 |
| VACV-5 heavy | QVQLVESGGGVVQPGESLKISCAASGFTFSSYGMHWVRQAPGKGLEWVAVIWYDGINKYYADSVKGRFTIS RDNSKNTLYLQMNSLRAEDTAVYYCAKEAGGGDCYSNYFHYWGQGTLVTVSS | 250 |
| VACV-5 light | ND | 251 |
| VACV-22 heavy | QVQLVESGGGVVQPGRSLRLSCAASGFTFSNSGMHWVRQAPGKGLEWVAVIWFDGTNKYYADSVKGRFT ISRDNSKNTLYLQMNSLRAEDTAVYYCARVPCGGDCYSGYLQHWGQGTLVTVSS | 252 |
| VACV-22 light | AIVMTQSPATLSVSPGERATLSCRASQSVSSTLAWYQQKPGQAPRLLIYGASTKATGIPARFSGSGSGTEFTLT ISSLQSEDFAVYYCQHYNNWPPLLTFGGGTKVDIK | 253 |

TABLE 2-continued

| PROTEIN SEQUENCES FOR ANTIBODY VARIABLE REGIONS | | |
|---|---|---|
| Clone | Variable Sequence | SEQ ID NO: |
| VACV-80 heavy | EVQLVESGGGLVQPGESLKISCAATGFTFSSYWMHWVRQAPGKGLVWVSGINSDGSSTSYADSVKGRFTIA RDNAKGTLYLQMNSLRAEDTAVYYCARVGAVRIAAAAPDYWGQGTLVTVSS | 254 |
| VACV-80 light | DIVMTQSPDSLAVSLGERATINCKSSQSVLYSSNNKNYLAWYQQKPGQPPKLLIYWASTRESGVPDRFSGSG SGTDFTLTISSLQAEDVAVYYCQQYYSTPWTFGQGTKVDIK | 255 |
| MPXV-39 heavy | QVQLQQWGAGLLKPSETLSLTCAIYGGSLSGQYWSWIRQPPGRGLEWIGEIHHKGRTNYNPSLKSRVTISIDT SQRQFSLRLTSVSAADTAVYYCASGNYRLGQGTLVTF | 256 |
| MPXV-39 light | DVVLTQSPLTLPVTLGQPASISCRSSQSLVYSDGDTYLNWFQQRPGQAPRRLIYKVSKRDFGVPDRFSGSGSG TDFTLRISRVEAEDVGVYYCMQGTHWPRTFGQGTQVDIK | 257 |
| MPXV-51 heavy | QLQLQESGPGLVKPSETLSLSCTVSGGSINSRTYYWGWIRQPPGKGPEWIGTVFHNVSTLYTSSLRSRVTISVD TSKNRFSLKLTSVTAADTAVYFCGRLTPRNLFRGTLVRWVDPWGQGILVTVSS | 258 |
| MPXV-51 light | EIVLAQSPGTLSLSPGERATLSCRASHNLNSNYLAWYQQKPGQAPRLLIYGASSRATGIPDRFTGSGSGTDFTL TISRLEPEDFAVYYCQQYAGSLTFGGGTKVDIK | 259 |
| MPXV-56 heavy | QVQLQQSGPGLVKPSQTLSLTCAISGDSVSSNSAAWIWIRQSPSRGLEWLGTTYYRSEWYSDYPASVKSRVTI NADTSKNQFSLQLNSVTPEDTAVYYCARITVGYNSPHLRVTRGWLDPWGQGTLVTSSS | 260 |
| MPXV-56 light | DIVMTQSPDSLAVSLGERATINCKSSQSVLYSSNNKNYIAWYQQKPGQAPKLLIYWASTRESGVPDRFSGSGS GTNFTLAISSLQAEDVAVYYCQQYYSSPLTEGGGTKVDIK | 261 |
| MPXV-91 heavy | QVQLVESGGGVVQPGRSLKISCAASGFTFSTYTMHWVRQAPGKGLEWVATISYDGINEYYADSVKGRFTIFR DNSKNMLYLQMNSLRPEDTAMFYCAR | 262 |
| MPXV-91 light | QSVLTQPPSASGTPGQRVTISCSGSSSNIGINYVHWYQQLPGTAPKLLIYRNNQRPSGVPDRFSGSKSGTSAS LAISGLRSEDEADYYCAAWDDSLSGKVFGGGTQVTVL | 263 |
| MPXV-99 heavy | QVQLVESGGGVVQPGRSLKISCVASGFTFSSYAIHWVRQAPGKGLEWVAFISNDGSSKKLADSVKGRFTISR DNSKNTLYLQMNSLRAEDTAVYYCARADRGYFGHWGQGTLVT | 264 |
| MPXV-99 light | ND | 265 |
| VACV-314 heavy | QVQLVQSGPGLVKPSETLSLTCTVSGGSISSYYWSWIRQPPGKGLEYIGHIYYSGGTKYNPSLRSRVTISVDTSK NQFSLKLTSVTAADTAVYYCARLAGRKPDADSWGQGTLVTVSS | 266 |
| VACV-314 light | QPVLTQEPSLTVSPGGTVTLTCASSTGAVTSGFFPNWLQQKPGQAPRALIYSTNNKHSWTPARFSGSLLGGK AALTLSGVQPEDEAEYYCLLYYGGVVVEGGGTKLTVL | 267 |
| VACV-315 heavy | EVQLLESGGGLVQPGGSLKLSCAASGFIFSNYAMGWVRQAPGKGLEWVSALSASDGVTSYADSVKGRFTISR DNSKNTMYLQMNRLRTEDTAIYFCAKGRARVNNIYRYFDHWGQGTLVTVSS | 268 |
| VACV-315 light | QSVLTQPASVSGSPGQSITISCTGTSSDVGAYTFVSWYQHHPGKAPKLIIYEVSNRPSGVSDRFSGSKSGNTAS LTISGLQAEDEADYYCNSYTTTSPWVFGGGTQLTVL | 269 |

TABLE 2-continued

PROTEIN SEQUENCES FOR ANTIBODY VARIABLE REGIONS

| Clone | Variable Sequence | SEQ ID NO: |
|---|---|---|
| MPXV-1 heavy | EVQLLESGGGLVQPGESLKISCAVSGFSFKSYAMSWVRQAPGKGLEWVSTIGVSGASTYFADPVKGRFTISRD NSKDTLYLQMNSLRAEDTAVYYCARDTYYYDSRIWYFGLWGRGT | 270 |
| MPXV-1 light | ND | 271 |
| MPXV-29 heavy | QVQLVQSGAEVKKPGSSVKVSCKASGGIFSSYVISWVRQAPGQGPEWMGRIIVMLGVTNYAQKFQGRVSI TADKSTNTAYMELNSLRSEDTAVYYCARAVITMVRGDIPLGWFDPWGQGTLVTVSS | 272 |
| MPXV-29 light | EIVLTQSPGTLSLSPGERATLSCRASQSVRSNYLAWYQQKPGQAPRLLFYGASSRATGIPDRFSGSGSATDFTL TISRLEPEDFAVYYCQQYGSSPPTSAQGTKVEIK | 273 |
| MPXV-72 heavy | QVTLKESGPTLVKPTQTLTLTCTFSGFSINTGGQGVGWIRQPPGKALEWLALIYWDDDKRYSPALRSRLTITK GTSKNQVVLTMTKMDPVDTATYYCAHRSVAGRRDLAFDIWGQGTLVTVSS | 274 |
| MPXV-72 light | LC#1<br>QSVLTQPASVSGSPGQSITISCTGTTSDIGTYDYVSWYQQHPGRAPKLMIYDVSKRPSGVSGRFSGSKSGNTA SLTISGLQTEDESHYYLQLHIPSGLTWVFGGG<br>LC#2<br>DIVMTQSPSTLSASVGDRVTITCRASQSISSWLAWYQQKPGKAPKLLIYDASSLESGVPSRFSGSGSGTEFTLTI SSLRPDDFATYYCQQYNTYSWWTFGQGTKVEIK<br>LC#3<br>QPVLTQPASVSGSPGQSITISCTGTTSDIGTYDYASWYQQHPGRAPKLMIYDVSKRPSGVSGRFSGSKSGNTA SLTISGLQTEDESHYYCSSYTSGLTWVEGGGTKLTVL | 275<br><br><br><br><br>889<br><br>890 |
| MPXV-76 heavy | EVQLVESGGGLVKPGESLKISCAASGFSFNNAWMNWVRQAPGKGLEWVGRIKTHADGGTTDYAAPVTGR FTISRDDSKNTLSLQMSSLKTEDTAVYYCTTSFTFPRRIFAYWGQGTLVTVSS | 276 |
| MPXV-76 light | EIVLTQSPATLSLSPGERATLSCRASQSVSSYLAWYQQKPGQAPRLLIYDTSNRATGIPARFSGSGSGTDFTLTI SSLEPEDLAVYYCQLRNSWPPTFGPGTKVDIK | 277 |
| MPXV-79 heavy | QVQLVQSGAEVKKPGASVKVSCKASGYSFRSNGISWVRQAPGQGFEWLGWIAAYNGDTKYVQKFQGRLT MTTDTSTDTAYMELWSLRSDDTAVYYCARDPKLGRKGSAFDIWGQGTLVIVSS | 278 |
| MPXV-79 light | EIVLTQSPATLSLSPGGRATLSCRASQSVGNYLTWYQQKPGQAPRLLIFDGSTRATGIPARFSGSGSGTDFTLTI SSLEPEDFAVYYCLQRSDLYTFGQGTKVDIK | 279 |
| MPXV-85 heavy | EVQLLESGGGLVQPGESLKISCVGSEFTFSSYAMSWVRQPPGKGLEWVSGISDSGGRLYVADSVKGRFTVSR DNSKNTLYLEMNSLRGEDTAIYYCAKDRVVGATYPRGVFDIWGQGTMVTVSS | 280 |
| MPXV-85 light | ND | 281 |
| VACV-33 heavy | QLQLQESGPGLVKPSETLSLTCTVSGGSISSGGYYWGWIRQPPGKGLEWIASIYYSGSTYYNPSLKSRVTISVDT SKTQFSLKLSSVTAADTAVYYCARQSSSIGGFHYWGQGTLVTVSS | 282 |

TABLE 2-continued

| PROTEIN SEQUENCES FOR ANTIBODY VARIABLE REGIONS | | |
|---|---|---|
| Clone | Variable Sequence | SEQ ID NO: |
| VACV-33 light | QSVLTQPPSVSGAPGQRVTISCTGSSSNIGAGYDVHWYQHLPGTAPKWYGNSNRPSGVPDRFSGSKSGTS<br>ASLAITGLQAEDEANYYCQSYDSSLSGREVFGGGTQLTVL | 283 |
| VACV-34 heavy | QVQLVESGGGLVQPGRSLRLSCAASGFTFDDYAMHWVRQAPGKGLEWVSGLSWNSGSIGYADSVKGRFTI<br>SRDNAKNSLYLQMNSLRAEDTALYYCAKETEKYYYDSSGYDYWGQGTLVTVSS | 284 |
| VACV-34 light | EIVLTQSPGTLSLSPGERATLSCRASQSVSSIYLAWYQQKPGQAPRLLIYGASSRATGIPDRFSGSGSGTDFILTI<br>SRLEPEDFAVYYCQQYGSRGTFGQGTKLEIK | 285 |
| MPXV-26 heavy | QVQLVQSGGGLIQPGGSLRLSCVVSGFNVATNYMSWVRQAPGKGLEWVSVIYSGGSTYYADSVKGRFTISR<br>DNSKNTVFLQMNSLRPEDTAAYYCAKGGGLGLDYWGQGTLVTVSS | 286 |
| MPXV-26 light | QSALTQPPSASGSPGQSVTITCTGSSSDVGGYNYVSWYQQHPGKAPKVVIYEVNKRPSGVPHRFSGSKSGNT<br>ASLTVSGLQAEDEADYYCSSYAGTETVAFGGGTKLTVL | 287 |
| MPXV-74 heavy | QVQLVQSGAEVKKPGSSVKVSCKASGGRFSTQHINWMRQAPGHGLEWMGGIIPIFATADYAQKFQGRITIT<br>ADESTSTAYMEMSSLRSEDTAIYYCGVYNANWGQGTLVTVSS | 288 |
| MPXV-74 light | DIVMTQSPLSLPVTPGEPASFSCRSSQSLLHYNGNNYLNWYLQKPGQSPQLLIYLGSNRASGVPDRFSGSGSG<br>TDFTLKISKVEADDVGIYYCMQARHTPWSAQGTKVEIK | 289 |
| MPXV-83 heavy | QVQLVESGGGVVQPGRSLRLSCAASGFTFSSYSMHWVRQAPGKGLEWVAVISFDGRSNYYADSVRGRFTIS<br>RDNSKKTMYLQMNSLRLADTAVYYCARGGIGAPDPRNGLEVWGRGAPVTLSS | 290 |
| MPXV-83 light | DIQMIQSPSSLSASVGDRVTISCQATQDISNSVNWYQQKPGKAPKWYDASTLETGVPSRFSGGGSGTHFTF<br>TISSLQPEDIATYYCQQFHSLPPTFGQGPKGISK | 291 |
| MPXV-87 heavy | QVQLVQSGAEVKKPGASVKVSCKASGYTFTSHGIIWVRQAPGQGLEWMGWISVYNDNINSAQKFQDRVT<br>MTTATSTSTAYMELRSLRSDDTAVYYCARSSSGPRYYYYGMDVWGQGTTSPVSS | 292 |
| MPXV-87 light | QSVVTQPPSVSGAPGQRVTISCIGSSSNIGAGYAVHWYYQLPGIAPKLLIFGNNNRPSGVPDRFSGSKSGTSA<br>SLAITGLQAEDEADYYCQSYDSSLSGWVEGGGTQVTVL | 293 |
| VACV-154 heavy | EVQLLESGGGLVQPGESLRLSCAASGFTLRNYAMSWVRQTPGKGLEWVSAISGSGGSTYYADSVKGRFTISR<br>DTSKNTLYVQMNSLRAEDTAVYYCAKIRLDSSGYSGAFDIWGQGTRVTVSS | 294 |
| VACV-154 light | SYELTQPPSVSVSPGQTARITCSGDALPKQYASWYQQKPGQAPVLVIYKDSERPSGIPERFSGSSSGTTVTLTIS<br>GVQAEDEADYYCQSADSSGTYPVVEGGGTQLTVL | 295 |
| VACV-300 heavy | QVQLVQSGAEVKKPGSSVKVSCKASGGIFSSYAISWVRQAPGQGLEWMGGIIPIFGTANYAQKFQGRVTIT<br>ADESTGTAYMELTSLRSEDTAIYYCARASEQWLASINWFDPWGQGTLVTVSS | 296 |
| VACV-300 light | QSALTQPASVSGSPGQSITISCTGTSSDVGSYNLVSWYQQHPGKAPKLMIYEVSKRPSGVSNRFSASKSGNTA<br>SLTISGLQAEDEADYYCCSYAGSSTLVEGGGTQVTVL | 297 |
| VACV-301 heavy | EVQLLESGGGLVQPGGSLRLSCAASGFSFSSYAMSWVRQAPGKGLEWVSGIGNSGDRIFYADSAKGRFTIFR<br>DNSNNRLYLQMNSLRAADTAVYYCAKWGRFESGAFWGQGVLVTVSS | 298 |

TABLE 2-continued

| PROTEIN SEQUENCES FOR ANTIBODY VARIABLE REGIONS | | |
|---|---|---|
| Clone | Variable Sequence | SEQ ID NO: |
| VACV-301 light | SYELTQSPSVSVSPGQTARITCSGDALPEQYAYWYQQKPGQAPVLVIYKDSERPSGIPERFSGSGSGTTVTLTIT GVQAEDEADYYCQSADNSGTYEVFGTGTKVTVL | 299 |
| VACV-302 heavy | QLQLQESGPGLVKPSETLSLTCTVSGGSIISSSYYWGWIRQPPGKGLEWLGSIYYSGSTYYNPSLKSRVTISVDT SKNQFSLKVTSVTAADTAVYYCARQISKAAAGSIDYWGQGTLVTVS | 300 |
| VACV-302 light | DIVMTQSPLSLPVTPGEPASISCRSSQSLLHSNGYNYLDWYLQKPGQSPQLLIYLGSNRASGVSDRFSGSGSGT DFTLKISRVEAEDVGVYYCMQALQTPITFGQGTRLEIK | 301 |
| VACV-303 heavy | EVQLLESGGGLVQPGGSLRLSCAASGFTESSYAMSWVRQAPGKGLEWVSAISGTGGNTYYADSVKGRFTISR DKSKNTLYLQMHSLRAEDTAVYYCATSLIWWLQSDYWGQGTLVTVSS | 302 |
| VACV-303 light | DIQMTQSPSSLSASVGDRVTITCRASQSIASYLIWYQQKPGNAPKWYAASSLQSGVPSRFSGSGSGTDFTLTI SSLQPEDFATYYCQQSYSTPQTFGQGTKVDIK | 303 |
| MPXV-10 heavy | EVQLVQSGAEVKKPGESLKISCKGSGYSFTNHWIAWVRQVPGKGLDWMGIIYPGDSDIRYSPSFQGQVTISA DNSINTAYLQWRSLKASDTAMYYCARAMTTVTPFDYWGQGTLVTFS | 304 |
| MPXV-10 light | SYELTQAPSVAVSSGQTASITCSGDKLGDTYTFWYQQKPGQSPVVVIYQDTKRPSGIPERFSGSNSGNTATLTI TGTQSMDEADYYCQAWDSATVVFGGGTQVTVL | 305 |
| MPXV-31 heavy | QLQLQESGPGLVKPSETLSLTCTVSGGSISSRNEFWAWIRQPPGKGLEFIGSIFYSGGTYYNPSLKSRLSISVDTS RNQFSLRLSSVTAADTAVYYCARHMIVVLPGVPISTSFDPWGQGTLVTVSS | 306 |
| MPXV-31 light | DIVMTQSPDSLAVSLGERATINCKSSQSVLSNSNNKNYLAWYQQKPGQPPRLLIYWASARESGVPDRESGSG SGTDFTLTIISLQPEDVAVYYCQQYYSPPAELSEGGGTKVDIK | 307 |
| MPXV-53 heavy | QVQLVESGGGVVQPGRSLRLSCAASGFTFSNYGLHWVRQAPGKGLEWVALIWFDGSNKYVADSVKGRFTIS RDNSKNTLYLQMNSLTAEDTAVYYCAR | 308 |
| MPXV-53 light | SYELTQPPAVSVAPGKTARITCGGDDIGFKGVHWYQQKPGQAPVLVVYDDRDRPSGIPDRLSGSNSGNTAT LTISRVEAGDEADYY | 309 |
| MPXV-71 heavy | EVQLVESGGGLVQPGESLKISCSASGFTFSDYAMHWVRQAPGQGLQYVSAISSNGHSTYYADSVKGRFTFSR DNSKNTLYLQMSSLRPEDTAVYYCVRCLLRGLISPFDYWGQGTLVTVSS | 310 |
| MPXV-71 light | QSVLTQPPSVSEAPRQRVTISCSGSSSNIGNNAVNWYQQLPGKAPKWYYDDLLPSGVSDRFSGSKSGTTASL TISGPQPEDEADFYCSTWDYSLSARVEGGGTQVTVL | 311 |
| MPXV-97 heavy | QVQLVQSGGGVVQPGRSLTLSCSASGFIFTRYGLHWVRQAPGKGLEWVAVISSDGTNRHYADSVKGRFTVS RDNSKSTLYVQMNSLRNEDTAVYYCARLSLEAAWYFDLWGRGTLVTVSS | 312 |
| MPXV-97 light | QSVVTQPPSVSGAPGQRVTISCTGSSSNIGAGYDVHWYQHLPGTAPKVLIYGNTNRPSGVPDRFSGSKSGTS ASLAITGLQAEDEADYYCQSYDNSLNGPWVFGTGTQ | 313 |
| VACV-309 heavy | EVQLLESGGGLVQPGESLKLSCAASGFTFSSYAMNWVRQAPGKGLEWVSGISGSGGSTYYADSVKGRFTVS RDNSKNTLYLQMNSLRAEDTAVYYCAKDNNYVYYGMDVWGQGTTVTVSS | 314 |

TABLE 2-continued

| PROTEIN SEQUENCES FOR ANTIBODY VARIABLE REGIONS | | |
|---|---|---|
| Clone | Variable Sequence | SEQ ID NO: |
| VACV-309 light | AIQMTOSPSSLSASVGDRVTITCRASQGIRNDLGWYQQKPGKAPKWYAASSLQSGVPSRFSGSGSGTDFTL TISSLQPEDFATYYCLQDYNYPRMFGQGTKVDIK | 315 |
| VACV-312 heavy | QVQLVESGGGVVQPGRSLRLSCAASGFTFSSYGMHWVRQAPGKGLEWVAVIWFDGSNKYVADSVKGRFTI SRDNSKNTLYLQMNSLRAEDTAVYYCARVARDYSNIFDAFDIWGQGTLVTVSS | 316 |
| VACV-312 light | DIQMTQSPSSLSASVGDRVTITCRASRSISTYLNWYQQKPGKAPKLLIYAASSLHSGVPSRFSGSGSGTDFTLTI SSLQPEDFATYYCQQSYSTPITFGQGTRLEIK | 317 |
| VACV-313 heavy | QLQLQESGPGLVKPSETLSLTCTVSGGSISSRSYYWGWIRQPPGKGLEWIGSIYYSGSTYYNPSLKSRVTISVDT SKNQFSLKLSSVTAADTAVYYCVRIAVAAAGTDYWGQGTLVTVSS | 318 |
| VACV-313 light | EIVMTQSPDTLSVSPGERATVSCRASQSISSNLAWYQQKPGQAPRLLIYGASTRAIGIPARFSGSGSGTEFTLTI SSLQSEDFAVYYCQQYNNWPPYTFGQGTKVDIK | 319 |
| MPXV-9 heavy | QVQLVQSGAEVKKPGASVKVSCKASGYNLTTYDIVWVRQAAGQGLEWMGWMNPKSGNTAYAERFQGR VTMTRNTSISTAYMELSSLRSEDTAVYYCARSLDSLRFLEWFHQNYYYFMDVWGKGTTVTVSS | 320 |
| MPXV-9 light | EIVLTQSPATLSLSPGERATLSCRASQTIGGYLAWYQQIPGQAPRLLIYDASNRATGIPARFSGSGSGTDFTLTIS SLEPEDFAVYYCQLRSTEGGGTKVDIK | 321 |
| MPXV-41 heavy | EVQLVESGGGLVQPGRSLRLSCKASGIPFGDYAMTWFRQAPGKGLEWVGFIKSKAYGGTPEYAASXKGRFTI SRDNSRSTAYLQMNSLKTDDTAVYYCSATLTRGELFDYWGQGTLVTVSS | 322 |
| MPXV-41 light | EIVLTQSPDTLSLSLGERATLSCRASQSVSNYLAWYQQKPGQAPRLLIYDASSRATGIPARFSGSGSGTDFTLTI SSLEPEDFAVYYCQQRSNWPLTEGGG | 323 |
| MPXV-49 heavy | QVQLQESGPGLVKPSETLSLTXTVSGDSVNSGSFYWSWIRQAPGKGLEWIGFIYYSGTTNYNPSLKRRVTISLI TSKNQFSLRLGSVTAADTAVYYCVREWPRHYDNRGYHTLPGTWGQGTLVTVSS | 324 |
| MPXV-49 light | DIQMTQSPSTLSASVGDRVTITCRASQSISSWLAWYQQKPGKAPNLLIYKASTLESGVPSRFSGSGSGTEFTLTI NSLHPDDFATYYCQQYNTDSSRTFGQGTKVDIK | 325 |
| VACV-318 heavy | QVQLVESGGGVVQPGRSLRLSCTASGFNFSYYGIHWVRQAPGKGLQWVALISYDGSDKYYADSVKGRFTVS RDYSKNTLFLQMNSLRGDDTAVYYCQMVKVPFYFWGQGTMVTLSS | 326 |
| VACV-318 light | SYELTQPPSVSVSPGQTARITCSGDELPKRYAYWYQQKSGQAPVLVIYEDTKRPSGIPERFSGSSSGTVATLTIS GAQVDDEADYYCYSTDSTSNHKRVFGGGTQVTVL | 327 |
| VACV-308 heavy | QVQLVQSGAEVKKPGSSVKVSCKGSGDSFRSYAISWVRQAPGQGLEWMGGIIPRFGTTNYAQKFQDRVTIT ADKSITTAYMELRSLKCEDTGVYYCARPQSAYDFGPFDHWGQGTLVTVSS | 328 |
| VACV-308 light | SYELTQPPSLSVAPGKTARITCGGDNIGSKGVHWYQQKPGQAPVVVISYDSDRPSGIPERFSGSNSGDTATLT ISRVEAGDEADYYCHVWHTTTDHYVFGTGTKVTVL | 329 |
| VACV-305 heavy | QVQLVESGGGVVQPGRSLRLSCAAFGFTISSYGMHWVRQAPGKGLEWVAFIWYDGTNKYYADSVKGRFTI SRDNSKNTLYLQMNSLRAEDTAVYYCVRTQQVIRPFFDHWGQGTLVTVSS | 330 |

TABLE 2-continued

| PROTEIN SEQUENCES FOR ANTIBODY VARIABLE REGIONS | | |
|---|---|---|
| Clone | Variable Sequence | SEQ ID NO: |
| VACV-305 light | EIVMTQSPATLSVSPGDRVTLSCRASQSISSNLAWYQQKPGQAPRLLIYGASTRATGIPARFSGSGSGTEFTLSI SSLQSEDFAVYYCQQYKNWPPWTFGQGTKVDIK | 331 |
| VACV-306 heavy | QVQLVQSGAEVKKPGSSVKVSCKTSGGTFSNYSITWVRQAPGQGLEWMGGIIPISGTAKYAQKFQGRVTISA DKSTSTAYMELSSLRSEDTAVYYCARDCYGVEWSGYFSRCHFGMDVWGQGTTVTVSS | 332 |
| VACV-306 light | EIELTQSPGILSLSPGERATLSCRASQSVRSSHLAWYQQKPGQAPRLLIYGASNRATGIPDRFSGSGTGTDFTL TISRLEPEDFAVYYCQQYGGSPLLTFGGGTKVDIK | 333 |
| VACV-307 heavy | EVQLLESGGGLVQPGGSLKLSCAASGFTFSNYAMSWVRQAPGKGLEWVSAFSGTGGSTYYADSVKGRFSIS RDNSKNTLYLQMNSLRVEDTAVYYCAKDRGIVGTTRFDSWGQGTLVTVSS | 334 |
| VACV-307 light | EIVMTQSPATLSVSPGERATLSCRASQSVSSNLAWYQQKPGQAPRLLIYGASTRATGIPARFSGSGSGTEFTLT ISSLQSEDFAVYYCQQYSNWPPITFGQGTRLEIK | 335 |
| VACV-311 heavy | QVQLVESGGGLVQLGESLKISCVASGFAFSGSAMHWVRQASGKGLEWLGRIRNKPNNYATAYAASVKGRFT ISRDDSKNTAYLQMNSLKTEDAGVYYCTRRMDHARRPAREDYYNNGMDIWGQGTTVTVSS | 336 |
| VACV-311 light | EIVLTQSPGTLSLSPGERATLSCRASQSVSSSFLAWYQHKPGQAPRLLIYDASSRATGIPDRFSGSGSGAEYTLTI SRLEPEDFAVYYCQQYSSSPTFGPGTKGGYQ | 337 |
| VACV-316 heavy | QVQLVESGGGVVQPGGSLRLSCAASGFSFSNYGVHWVRQAPGRALEWVAFIRFDGTDKYYADSVEGRFTIS RDNSKNTLYLQMNNLRAEDTAVYYCAKDLAMMIANPLDCWGQGILVTVSS | 338 |
| VACV-316 light | EIVMTQSPATLSVSPGERATLSCRASQSVSSNLAWYQQKPGQAPRLLIYDASTRATGIPVRFSGSGSGTEFTLT ISSLQSEDFAIYYCQQYKNWGTFGQGTKVDIK | 339 |
| VACV-310 heavy | QVQLVQSGAEVKKPGSSVKVSCKASGGTENSFAITWVRQAPGQGLEWMGGIIPLFGTTNYAQKFQDRVTIT TDDSMSTFYMELKSLRSEDTAVYYCARVFSAAGHWGQGTLVTVSS | 340 |
| VACV-310 light | DIQMTPSPSSLSASVGDRVTITCRASQSIASYLIWDQQKPGNAPKLLIYAASSLQSGVPSRFSGSGSGTDFTLTI GSLQPEDFATYYCQQSYSTPQTFGQGTKVDIK | 341 |
| MPXV-8 heavy | QVQLVESGGGVVQPGRSLRLSCAASGFTFRSYAMHWVRQAPGKGLEWVAVISYDANNEYYADSVKGRFTI SRDNSKNTLYLQMNTLRPEDTAVYYCARGLIPSAEQWQARGGPDYYYYYGMAVWGQGTTV | 342 |
| MPXV-8 light | ND | 343 |
| MPXV-28 heavy | QVQLVQSGAEVKKPGSSVKVSCKASGATFSSYVFSWVRQAPGQGLEWMGRILPILDIPNYAQKFQGRVTITA DKSTSTAYMELGSLRSEDTAVYYCARGGGAVTGRGYYFDYWGQGTLVT FS | 344 |
| MPXV-28 light | DIQMTQSPSSLSASVGDRVTITCRASQSISSYLHWYQQRPGKAPKLLIYAASSLQSGVPSRFSGSGSGTDFTLTI SSLQPEDFATYYCQQSYSTPPTFGGGTKVEIK | 345 |

TABLE 2-continued

| PROTEIN SEQUENCES FOR ANTIBODY VARIABLE REGIONS | | |
|---|---|---|
| Clone | Variable Sequence | SEQ ID NO: |
| MPXV-42 heavy | QVQLVQSGAEVKKPGSSVKVSCKLSGGTLNSYAVSWVRQAPGQGLEWIGRIIPMVGMAHYAQKFQGRVTI TADKSTSSVYMELSTLRSEDTAMYHCAREQKLVGGGWFDPWGQGTLVT | 346 |
| MPXV-42 light | EIVLTQSPGTLSLSPGESATLSCRASQSVNSDYLAWYQQKPGQAPRLLIYGVSSRATGIPDRFSGSGSETDFILT ISRLEPEDFGVFYCQQYGHSPYTFGQGTKVDIK | 347 |
| MPXV-45 heavy | QVQLVQSGAEVKKPGSSVKVSCKASGGILSNSAINWVRQAPGQGLEWMGRIIPILGIPNYAQKFEGRVTITA DKSTSTAYMELNSLRSEDTAVYYCASPQRVLRFLQWSPFDYWGQGTLVTVSS | 348 |
| MPXV-45 light | EIVLTQSPGTLSLSPGERVTLSCRASQSVSSSYLAWYQQKPGQAPRLLIYDVLSRATGIPDRFSGSGSGTDFTLTI SRLEPEDFAVYFCQQYAISPNTFGQGTKLEIK | 349 |
| MPXV-82 heavy | QVQLVESGGGVVQPGRSLRLSCAASGFSLSSYGMHWVRQAPGKGLEWVAVIWYDGSNKYYADSVKGRFTI SRDNSKNTLYLQMNSLRAEDTAVYYCARGVRMTTSLDYWGQGTLVTVSS | 350 |
| MPXV-82 light | QSVLTPASVSGSPGQSITISCTGTSSDVGGYNYVSWYQQHPGKAPKLMIYDVSKRPSGVSNRFSGSKSGNT ASLTISGLQADDEADYYCSSYTTISTLGVEGGGTQVTVL | 351 |
| MPXV-86 heavy | QVQLQESGPGLVKPSETLSLTCIVSGGSISSYYWSWIRQSPGKGLEWIGYMSHSGSTNYNPSLKSRVTISVDM SKNQFSLKLTSVTAADTAAYYCARGVGGVYDILTGYWGPNWFDPWGQGTLVTVSS | 352 |
| MPXV-86 light | QSVVTQPPSVSGAPGQRVTISCTGSSSNIGAGYDVHWYQQLPGTAPKLLIYANTNRPSGVPDRFSGSKSDTS ASLAITGLQAEDEGDYYCQSFDSSLRGSVVFGGGTQVTVL | 353 |
| MPXV-88 heavy | QVQLVESGGGLVKPGESLKISCSVSGFTFSDYYMSWIRQTPGKGLEWISYISGGGNTIYYTDSVKGRFTISRDN SKKSLYLQMNSLRAEDTAVYYCARNLRAAGVNYFYFYYMDVWGKGPR | 354 |
| MPXV-88 light | EIVLTQSPATLSLSPGERATLSCRASQSVSSSLAWYQQRPGRAPRLLIYDASNRATGIPARFSGSGSGTDFNLTI SSLEPEDFAVYYCQQRGKWPPWTSA | 355 |
| MPXV-98 heavy | QVQLVQSGAEVKKPGASVKVSCKASGYTSMSDYIEWVRQAPGQGLEWMGIMNPLGGSTSYAQKLQGRVT MTRDTSTSTVYMELSSLRSDDTAVYYCVVSSGFQQWFDPWGQGTLVTVSS | 356 |
| MPXV-98 light | EIVMTHSPATLSVSPGERAILSCRASQSLTTNLAWYQQKPGQAPRLLIYRASTRATGIPARFSGSGSGTEFTLTI SSLQSEDFAIYYCQQYNNWPRTFGQGTKVDIK | 357 |

TABLE 3

| | CDR HEAVY CHAIN SEQUENCES | | |
|---|---|---|---|
| Antibody | CDRH1 (SEQ ID NO:) | CDRH2 (SEQ ID NO:) | CDRH3 (SEQ ID NO:) |
| VACV-8 | GGSFSGYF (358) | INHSGST (359) | ARVMTGITNYYYYGMDV (360) |
| VACV-56 | GGSFSGYY (361) | INHSGST (362) | ARATQGSGTYKLFFYSYGMDV (363) |
| VACV-66 | GDSISSNNYY (364) | IYYSGST (365) | ARHRRVLLWFGEFQL (366) |
| VACV-77 | GGSMSSYF (367) | ISYSGGT (368) | AREDRGSPDY (369) |
| VACV-116 | GYTFTSYD (370) | MNPNSGNT (371) | ARTPFDGSGYYY (372) |
| VACV-117 | GYTFTSYD (373) | MNPNSGNT (374) | ARTPFDDIGYYY (375) |
| VACV-128 | GYTFTDYY (376) | LDPLDGET (377) | ARELTGYLNY (378) |
| VACV-136 | GFSLSNARMR (379) | IFSNDEK (380) | ARMRGEYNSYYFDS (381) |
| VACV-138 | HC#1 GYTFASYD (891) HC#2 GFTLDDYA (382) HC#3 GYTFTDYY (918) | HC#1 SYSGNGNT (892) HC#2 ISWNSGGM (383) HC#3 VDPQEGET (919) | HC#1 ASRDIVVVTATRSPFDY (893) HC#2 AKDVGGVVTGGYWDDALDI (384) HC#3 AKESFGIPHF (920) |
| VACV-168 | GGSISSFY (385) | IYYSGST (386) | ARLRGNYASSGYYYNFDY (387) |
| VACV-159 | GGSISSSSYY (388) | IYYRGST (389) | ARHLRVLLWFGELLE (390) |
| VACV-199 | GYTFTGYY (391) | INPNSGGT (392) | ARVPPDSSSWK (393) |
| VACV-228 | GFTFSSYS (394) | ITSSSSYI (395) | ASRPGIAPAGPQAEGY (396) |
| VACV-230 | GYTLTE LS (397) | FDPEDGET (398) | ARESWLRGFDY (399) |
| VACV-249 | GGSISRGIYY (400) | IYTSGST (401) | ARDGWYGWYLDL (402) |
| VACV-304 | GFTFSNYW (403) | IKQDGSKK (404) | ATLNLELAVDAISEALK (405) |
| MPXV-27 | HC#1 GGSFSGYY (894) HC#2 GGSISSGGYY (406) | HC#1 INHSGST (895) HC#2 MSYSGDT (407) | HC#1 ARVLSGWLPFPNYYYYMDV (896) HC#2 ARGRYCNDDSCYSEESAIWFDP (408) |
| MPXV-30 | GGIFSSLA (409) | IIPIFGKA (410) | ATGGNIRVHDFDI (411) |
| MPXV-40 | GGSFSGYY (412) | INYSGST (413) | ARISSGWIGFPRYHYYLDV (414) |
| MPXV-61 | GETFSRYA (415) | IIPFIDIP (416) | ASSLPSTYYFGSGNYPWGNWLDP (417) |
| MPXV-96 | GGSFSGYY (418) | INYVGST (419) | ARGLRGNSVCFD (420) |

TABLE 3-continued

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| VACV-1 | GFTFSSFS (421) | ISSSSSTI (422) | ARRSVGCSGGNCYAYYYGMDV (423) |
| VACV-59 | GFTFSDYY (424) | ISTSGSTI (425) | ARDGDSGSYTPPYYYYGLDV (426) |
| VACV-151 | GFTFSSYS (427) | ITSSSSYI (428) | ND (429) |
| VACV-282 | GFTFSSYS (430) | ISSISSYI (431) | ARDRPRSRPNSGSYFWYYYGMDV (432) |
| VACV-283 | GGTFSTYA (433) | IIPILGTA (434) | ARRGGEGAAHGMDV (435) |
| MPXV-2 | GYTFTTYA (436) | PGDGDT (437) | ARPRASLLRYFDWLFEQ (438) |
| MPXV-12 | GGSFTNYY (439) | IDHSGSA (440) | ARDVYGSGTYYWFDP (441) |
| MPXV-13 | GGSISTRTW (442) | IYQSGST (443) | ARSGRYSSVTPFDY (444) |
| MPXV-25 | GFTFSDSG (445) | IWYDGSTK (446) | ARELGYCSGGTCYSMGAFDI (447) |
| MPXV-38 | SFIFSDAW (448) | FKTKTDGGTT (449) | ND (450) |
| MPXV-43 | GYTFTKYT (451) | IYAGYGNT (452) | ARDFEDFDSWTGYYSWLH (453) |
| MPXV-66 | GGSFSGYF (454) | MNHSGST (455) | ARTARTVRYFEN (456) |
| MPXV-70 | RFTFSNYY (457) | ISSRSRYT (458) | ARGGGYCGGTTCSMGHAFDI (459) |
| MPXV-92 | GGSISSSNW (460) | IYHSGST (461) | ARNFYPGYLQY (462) |
| VACV-5 | GFTFSSYG (463) | IWYDGINK (464) | AKEAGGGDCYSNYFHY (465) |
| VACV-22 | GFTFSNSG (466) | IWFDGTNK (467) | ARVPCGGDCYSGYLQH (468) |
| VACV-80 | GFTFSSYW (469) | INSDGSST (470) | ARVGAVRIAAAAPDY (471) |
| MPXV-39 | GGSLSGQY (472) | IHHKGRT (473) | ASGNYR (474) |
| MPXV-51 | GGSINSRTYY (475) | VFHNVST (476) | GRLTPRNLFRGTLVRWVDP (477) |
| MPXV-56 | GDSVSSNSAA (478) | TYYRSEWYS (479) | ARITVGYNSPHLRVTRGWLDP (480) |
| MPXV-91 | GFTFSTYT (481) | ISYDGINE (482) | ND (483) |
| MPXV-99 | GFTFSSYA (484) | ISNDGSSK (485) | ARADRGYFGH (486) |
| VACV-314 | GGSISSYY (487) | IYYSGGT (488) | ARLAGRKPDADS (489) |
| VACV-315 | GFIFSNYA (490) | LSASDGVT (491) | AKGRARVNNIYRYFDH (492) |
| MPXV-1 | GFSFKSYA (493) | IGVSGAST (494) | ARDTYYYDSRIWYFGL (495) |

TABLE 3-continued

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| MPXV-29 | GGIFSSYV (496) | IIVMLGVT (497) | ARAVITMVRGDIPLGWFDP (498) |
| MPXV-72 | GFSINTGGQG (499) | IYWDDDK (500) | AHRSVAGRRDLAFDI (501) |
| MPXV-76 | GFSFNNAW (502) | IKTHADGGTT (503) | TTSFTFPRRIFAY (504) |
| MPXV-79 | GYSFRSNG (505) | IAAYNGDT (506) | ARDPKLGRKGSAFDI (507) |
| MPXV-85 | EFTFSSYA (508) | ISDSGGRL (509) | AKDRVVGATYPRGVFDI (510) |
| VACV-33 | GGSISSGGYY (511) | IYYSGST (512) | ARQSSSTGGFHY (513) |
| VACV-34 | GFTFDDYA (514) | LSWNSGSI (515) | AKETEKYYYDSSGYDY (516) |
| MPXV-26 | GFNVATNY (517) | IYSGGST (518) | AKGGGLGLDY (519) |
| MPXV-74 | GGRFSTQH (520) | IIPIFATA (521) | GVYNAN (522) |
| MPXV-83 | GFTFSSYS (523) | ISFDGRSN (524) | ARGGIGAPDPRNGLEV (525) |
| MPXV-87 | GYTFTSHG (526) | ISVYNDNT (527) | ARSSSGPRYYYYGMDV (528) |
| VACV-154 | GFTLRNYA (529) | ISGSGGST (530) | AKIRLDSSGYSGAFDI (531) |
| VACV-300 | GGIFSSYA (532) | IIPIFGTA (533) | ARASEQWLASINWFDP (534) |
| VACV-301 | GFSFSSYA (535) | IGNSGDRT (536) | AKWGRFESGAF (537) |
| VACV-302 | GGSIISSSYY (538) | IYYSGST (539) | ARQISKAAAGSIDY (540) |
| VACV-303 | GFTFSSYA (541) | ISGTGGNT (542) | ATSLIWWLQSDY (543) |
| MPXV-10 | GYSFTNHW (544) | PGDSDI (545) | ARAMTTVTPFDY (546) |
| MPXV-31 | GGSISSRNFF (547) | IFYSGGT (548) | ARHMIVVLPGVPISTSFDP (549) |
| MPXV-53 | GFTFSNYG (550) | IWFDGSNK (551) | ND (552) |
| MPXV-71 | GFTFSDYA (553) | ISSNGHST (554) | VRCLLRGLISPFDY (555) |
| MPXV-97 | GFIFTRYG (556) | ISSDGTNR (557) | ARLSLEAAWYFDL (558) |
| VACV-309 | GFTFSSYA (559) | ISGSGGST (560) | AKDNNYYYYGMDV (561) |
| VACV-312 | GFTFSSYG (562) | IWFDGSNK (563) | ARVARDYSNIFDAFDI (564) |
| VACV-313 | GGSISSRSYY (565) | IYYSGST (566) | VRIAVAAAGTDY (567) |
| MPXV-9 | GYNLTTYD (568) | MNPKSGNT (569) | ARSLDSLRFLEWFHQNYYYFMDV (570) |

TABLE 3-continued

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| MPXV-41 | GIPFGDYA (571) | IKSKAYGGTP (572) | SATLTRGELFDY (573) |
| MPXV-49 | GDSVNSGSFY (574) | IYYSGTT (575) | VREWPRHYDNRGYHTLPGT (576) |
| VACV-318 | GFNFSYYG (577) | ISYDGSDK (578) | QMVKVPFYF (579) |
| VACV-308 | GDSFRSYA (580) | IIPRFGTT (581) | ARPQSAYDFGPFDH (582) |
| VACV-305 | GFTISSYG (583) | IWYDGTNK (584) | VRTQQVIRPFFDH (585) |
| VACV-306 | GGTFSNYS (586) | IIPISGTA (587) | ARDCYGVFWSGYFSRCHFGMDV (588) |
| VACV-307 | GFTFSNYA (589) | FSGTGGST (590) | AKDRGIVGTTRFDS (591) |
| VACV-311 | GFAFSGSA (592) | IRNKPNNYAT (593) | TRRMDHARRPAREDYYNNGMDI (594) |
| VACV-316 | GFSGSNYG (595) | IRFDGTDK (596) | AKDLAMMIANPLDC (597) |
| VACV-310 | GGTFNSFA (598) | IIPLFGTT (599) | ARVFSAAGH (600) |
| MPXV-8 | GFTFRSYA (601) | ISYDANNE (602) | ARGLIPSAEQWQARGGPDYYYYYGMAV (603) |
| MPXV-28 | GATFSSYV (604) | ILPILDIP (605) | ARGGGAVTGRGYYFDY (606) |
| MPXV-42 | GGTLNSYA (607) | IIPMVGMA (608) | AREQKLVGGGWFDP (609) |
| MPXV-45 | GGTLSNSA (610) | IIPILGIP (611) | ASPQRVRFLQWSPFDY (612) |
| MPXV-82 | GFSLSSYG (613) | IWYDGSNK (614) | ARGVRMTTSLDY (615) |
| MPXV-86 | GGSISSYY (616) | MSHSGST (617) | ARGVGGVYDILTGYWGPNWFDP (618) |
| MPXV-88 | GFTFSDYY (619) | ISGGGNTI (620) | ARNLRAAGVNYFYFYYMDV (621) |
| MPXV-98 | GYTSMSDY (622) | MNPLGGST (623) | VVSSGFQQWFDP (624) |

TABLE 4

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| VACV-8 | QDISSY (625) | AAS (626) | QHLNSYPRGYT (627) |
| VACV-56 | QSITSW (628) | KAS (629) | QQYNSYPYT (630) |
| VACV-66 | SSNIGAGYD (631) | GNI (632) | QSYDSSLSGAL (633) |

TABLE 4-continued

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| VACV-77 | SSNIGNNY (634) | DNY (635) | GTWDLSLSAGV (636) |
| VACV-116 | LC#1 QSLLHSNGYNY (897) LC#2 QSLLHSNGYNY (637) | LC#1 LGS (898) LC#2 LGS (638) | LC#1 Not identified (899) LC#2 MLALRTPGA (639) |
| VACV-117 | QSLLHSNGYNY (640) | LGS (641) | MQALQTPGA (642) |
| VACV-128 | PGICNY (643) | AAS (644) | QKYNSAPHT (645) |
| VACV-136 | ALPNQY (646) | KDS (647) | QSADSSGTSVV (648) |
| VACV-138 | QSVISTY (649) | SAS (650) | QQYGSSPPYT (651) |
| VACV-168 | SSNIGNNY (652) | DNN (653) | GTWDSSLSAYV (654) |
| VACV-159 | SSNIGADYD (655) | GNS (656) | QSHDSSLSGYV (657) |
| VACV-199 | QSLLHRNGYNY (658) | LGS (659) | ND (660) |
| VACV-228 | QSVSSN (661) | GAS (662) | ND (663) |
| VACV-230 | QSVSSSY (664) | GAS (665) | QQYGSSPRT (900) |
| VACV-249 | QSVSSD (901) | GAS (902) | QQYNNWPGT (903) |
| VACV-304 | ALPKQF (904) | KDS (905) | QSVDNSGTYEV (906) |
| MPXV-27 | QDIRNN (907) | GTS (908) | LQHNSYPPT (909) |
| MPXV-30 | QSLVNSDGNTY (666) | KVS (667) | MQGTHWPPRWT (668) |
| MPXV-40 | VLRDNY (669) | KDE (670) | ND (671) |
| MPXV-61 | SSNIGNNY (672) | DNN (673) | GTWDSSLSEVV (674) |
| MPXV-96 | QSVSSN (675) | GAS (676) | QQYNNWPRT (677) |
| VACV-1 | QNLLHSNGYNY (678) | LGS (679) | MQALQTPIT (680) |
| VACV-59 | QSIRNY (681) | AAS (682) | QQSYSTPPLT (683) |
| VACV-151 | QSVSSSY (684) | GAS (685) | QQYGSSPYT (686) |
| VACV-282 | NIGSKS (687) | DDS (688) | ND (689) |
| VACV-283 | QSLLHSNGYNY (690) | LGS (691) | LQALQTLPIT (692) |

TABLE 4-continued

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| MPXV-2 | QSIHHNY (693) | GAS (694) | QQYGNSVPYS (695) |
| MPXV-12 | QRISSH (696) | VAS (697) | QQSYTTPYT (698) |
| MPXV-13 | QSIGNY (699) | DAS (700) | QQRSHWPA (701) |
| MPXV-25 | SSDVGSYNL (702) | +VS (703) | CSYVGSSTSV (704) |
| MPXV-38 | QSVSNTY (705) | AAS (706) | ND (707) |
| MPXV-43 | QSVSSTY (708) | GAS (709) | QQYDSSPSIT (710) |
| MPXV-66 | QTVLYNSNNYSY (711) | WAS (712) | QQYYSTPWT (713) |
| MPXV-70 | QSVISSY (714) | GAS (715) | ND (716) |
| MPXV-92 | ISDVGGYNY (717) | DVN (718) | ND (719) |
| VACV-5 | ND (720) | ND (721) | ND (722) |
| VACV-22 | QSVSST (723) | GAS (724) | QHYNNWPPLLT (725) |
| VACV-80 | QSVLYSSNNKNY (726) | WAS (727) | QQYYSTPWT (728) |
| MPXV-39 | QSLVYS.DGDTY (729) | KVS (730) | MQGTHWPRT (731) |
| MPXV-51 | HNLNSNY (732) | GAS (733) | QQYAGSLT (734) |
| MPXV-56 | QSVLYSSNNKNY (735) | WAS (736) | QQYYSSPLT (737) |
| MPXV-91 | SSNIGINY (738) | RNN (739) | AAWDDSLSGKV (740) |
| MPXV-99 | ND (741) | ND (742) | ND (743) |
| VACV-314 | TGAVTSGFF (744) | SIN (745) | LLYYGGVVV (746) |
| VACV-315 | SSDVGAYTF (747) | +VS (748) | NSYTTTSPWV (749) |
| MPXV-1 | ND (750) | ND (751) | ND (752) |
| MPXV-29 | QSVRSNY (753) | GAS (754) | QQYGSSPPT (755) |
| MPXV-72 | LC#1 TSDIGTYDY (910) LC#2 QSISSW (913) LC#3 TSDIGTYDY (756) | LC#1 DVS (911) LC#2 DAS (914) LC#3 DVS (757) | LC#1 QLHIPSGLTWV (912) LC#2 QQYNTYSWWT (915) LC#3 SSYTSGLTWV 758) |

TABLE 4-continued

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| MPXV-76 | QSVSSY (759) | DTS (760) | QLRNSWPPT (761) |
| MPXV-79 | QSVGNY (762) | DGS (763) | LQRSDLYT (764) |
| MPXV-85 | ND (765) | ND (766) | ND (767) |
| VACV-33 | SSNIGAGYD (768) | GNS (769) | QSYDSSLSGREV (770) |
| VACV-34 | QSVSSIY (771) | GAS (772) | QQYGSRGT (773) |
| MPXV-26 | SSDVGGYNY (774) | EVN (775) | SSYAGTETVA (776) |
| MPXV-74 | QSLLHYNGNNY (777) | LGS (778) | MQARHTPW (779) |
| MPXV-83 | QDISNS (780) | DAS (781) | QQFHSLPPT (782) |
| MPXV-87 | SSNIGAGYA (783) | GNN (784) | QSYDSSLSGWV (785) |
| VACV-154 | ALPKQY (786) | KDS (787) | QSADSSGTYPVV (788) |
| VACV-300 | SSDVGSYNL (789) | +VS (790) | CSYAGSSTLV (791) |
| VACV-301 | ALPEQY (792) | KDS (793) | QSADNSGTYEV (794) |
| VACV-302 | QSLLHSNGYNY (795) | LGS (796) | MQALQTPIT (797) |
| VACV-303 | QSIASY (798) | AAS (799) | QQSYSTPQT (800) |
| MPXV-10 | KLGDTY (801) | QDT (802) | QAWDSATVV (803) |
| MPXV-31 | QSVLSNSNNKNY (804) | WAS (805) | QQYYSPPAELS (806) |
| MPXV-53 | DIGFKG (807) | DDR (808) | ND (809) |
| MPXV-71 | SSNIGNNA (810) | YDD (811) | STWDYSLSARV (812) |
| MPXV-97 | SSNIGAGYD (813) | GNT (814) | QSYDNSLNGPWV (815) |
| VACV-309 | QGIRND (816) | AAS (817) | LQDYNYPRM (818) |
| VACV-312 | RSISTY (819) | AAS (820) | QQSYSTPIT (821) |
| VACV-313 | QSISSN (822) | GAS (823) | QQYNNWPPYT (824) |
| MPXV-9 | QTIGGY (825) | DAS (826) | QLRST (827) |
| MPXV-41 | QSVSNY (828) | DAS (829) | QQRSNWPLT (830) |
| MPXV-49 | QSISSW (831) | KAS (832) | QQYNTDSSRT (833) |

TABLE 4-continued

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| VACV-318 | ELPKRY (834) | EDT (835) | YSTDSTSNHKRV (836) |
| VACV-308 | NIGSKG (837) | YDS (838) | HVWHTTTDHYV (839) |
| VACV-305 | QSISSN (840) | GAS (841) | QQYKNWPPWT (842) |
| VACV-306 | QSVRSSH (843) | GAS (844) | QQYGGSPLLT (845) |
| VACV-307 | QSVSSN (846) | GAS (847) | QQYSNWPPIT (848) |
| VACV-311 | QSVSSSF (849) | DAS (850) | QQYSSSPT (851) |
| VACV-316 | QSVSSN (852) | DAS (853) | QQYKNWGT (854) |
| VACV-310 | QSIASY (855) | AAS (856) | QQSYSTPQT (857) |
| MPXV-8 | ND (858) | ND (859) | ND (860) |
| MPXV-28 | QSISSY (861) | AAS (862) | QQSYSTPPT (863) |
| MPXV-42 | QSVNSDY (864) | GVS (865) | QQYGHSPYT (866) |
| MPXV-45 | QSVSSSY (867) | DVL (868) | QQYAISPNT (869) |
| MPXV-82 | SSDVGGYNY (870) | DVS (871) | SSYTTISTLGV (872) |
| MPXV-86 | SSNIGAGYD (873) | ANT (874) | QSFDSSLRGSVV (875) |
| MPXV-88 | QSVSSS (876) | DAS (877) | QQRGKWPPWT (878) |
| MPXV-98 | QSLTTN (879) | RAS (880) | QQYNNWPRT (881) |

TABLE S1

Generation of Human B Cell Hybridomas from PBMCs of Vaccinia-Immunized Subjects or from a Subject Who had a History of Naturally-Acquired Monkeypox Infection

| Subject | Vaccine or infection | Time post-exposure when blood was taken | Serum neutralizing reciprocal titer[a], (fold dilution) | Number of individual hybridomas generated from sample |
|---|---|---|---|---|
| MVA 1 | Modified Vaccinia Ankara (MVA) vaccine | Day 14 after booster vaccination | ND | 16 |
| MVA 3 | | | ND | 1 |
| MVA 4 | | | ND | 3 |
| MVA 12 | | | ND | 2 |
| MVA 19 | | | ND | 1 |
| MVA 21 | | | ND | 3 |
| VRC-201-003-09 | Dryvax vaccine | 9 months | 1,000 | 1 |
| VRC-201-040-05 | | 5 months | 693 | 9 |
| VRC-201-044-06 | | 6 months | 638 | 1 |
| VRC-201-020-08 | | 8 months | 610 | 6 |
| 18 | Acam2000 vaccine | 21 days | 10 | 1 |

TABLE S1-continued

Generation of Human B Cell Hybridomas from PBMCs of Vaccinia-Immunized Subjects or from a Subject Who had a History of Naturally-Acquired Monkeypox Infection

| Subject | Vaccine or infection | Time post-exposure when blood was taken | Serum neutralizing reciprocal titer[a], (fold dilution) | Number of individual hybridomas generated from sample |
|---|---|---|---|---|
| MSK452 | Monkeypox virus infection | 1 year | 108 | 45 |

[a]Based on plaque reduction neutralizing test performed using VACV strain WR.
ND indicates not determined

TABLE S2

Sequence Diversity of Antibody Variable Genes Encoding Poxvirus-Specific mAbs, Related to FIGS. 1A-D

| | | | Heavy chain variable gene sequence | | | | | | Light chain variable sequence | | | | |
|---|---|---|---|---|---|---|---|---|---|---|---|---|---|
| Antigen | Donor | mAb | $V_H$ gene | $V_H$ region nucleo-tide % homology to $V_H$ gene | $D_H$ gene | $J_H$ gene | HCDR3 amino acids (aa) [SEQ ID NO:] | CDR3 length (aa) | $V_L$ gene | $V_L$ region nucleo-tide % homology to $V_L$ gene | $J_L$ gene | LCDR3 amino acids (aa) [SEQ ID NO:] | CDR3 length (aa) |
| D8 | MVA 1 | VACV-8 | 4-34 | 92 | 1-7 | 6 | ARVMTGITNYYYYGMDV [360] | 18 | 1-9 | 91 | 2 | QHLNSYPRGYT [627] | 11 |
| | | VACV-56 | 4-34 | 90 | 3-10 | 6 | ARATQGSGTNKLFFYSGMDV [921] | 21 | 1-5 | 99 | 2 | QQYNSYPYT [630] | 9 |
| | | VACV-66 | 4-39 | 87 | 3-10 | 5 | ARHRRVLLWFGEFQL [366] | 18 | 1-40 | 98 | 2 | QSYDSSLSGAL [633] | 11 |
| | | VACV-77 | 4-59 | 88 | 6-6 | 4 | AREDRGSPDY [369 | 10 | 1-51 | 98 | 3 | GTWDLSLSAGV [636] | 11 |
| | | VACV-116 | 1-8 | 96 | 3-22 | 4 | ARTPFDGSGYYY [372] | 12 | 2-28 or 2D-28 | 99 | 1 or 3 | MQALQTPGA [642] | 9 |
| | | VACV-117 | 1-8 | 93 | 3-22 | 4 | ARTPFDDIGYYY [375] | 12 | 2-28 or 2D-28 | 81.5 | 1 or 3 | Identical to VACV-116 | 9 |
| | | VACV-128 | 1-f*01 | 83 | 3-9 | 4 | ARELTGYLNY [378] | 10 | 1-27 | 78 | 1 or 3 | QKYNSAPHT [645] | 9 |
| | | VACV-136 | 2-26 | 95 | 1-1 | 4 | ARMRGEYNSYYFDS [381] | 14 | 3-25 | 98 | 2 or 3 | QSADSSGTSVV [648] | 11 |
| | | VACV-138 | 1-46 | 75 | 2-21 | 4 | ASRDIVVVTATRSPFDY [893] | 17 | 3-20 | 99 | 2 | QQYGSSPPYT [651] | 10 |
| | MVA 3 | VACV-168 | 4-59 | 96 | 3-22 | 4 | ARLRGNYASSGYYYNFDY [387] | 18 | 1-51 | 99 | 1 | GTWDSSLSAYV [654] | 11 |
| | MVA 4 | VACV-159 | 4-39 | 88 | 3-10 | 4 | ARHLRVLLWFGELLE [390] | 15 | 1-40 | 98 | 1 | QSHDSSLSGYV [657] | 11 |
| | MVA 19 | VACV-199 | 1-2 | 92 | 6-13 | 5 | ARVPPDSSSWK [393] | 11 | 2-28 or 2D-28 | 99 | 2 | MQALQTPP [931] | 8 |
| | MVA 21 | VACV-228 | 3-21 | 85 | 6-13 | 4 | ASRPGIAPAGPQAEGY [396] | 16 | 3-20 | 83 | 4 | QYNNCSLY [932] | 8 |
| | | VACV-230 | 1-24 | 92 | 3-10 | 4 | ARESWLRGFDY [399] | 11 | 3-20 | 74 | 1 | QQYGSSPRT [900] | 9 |
| | | VACV-249 | 4-61 | 86 | 6-19 | 2 | ARDGWYGWYLDL [402] | 12 | 3-15 | 99 | 4 | QQYNNWPGT [903] | 9 |
| | VRC-201-040-05 | VACV-304 | 3-7 | 87 | 6-19 | 4 | ATLNLELAVDAISEALK [405] | 17 | 3-25 | 82 | 2 | QSVDNSGTYEV [906] | 11 |
| | MSK452 | MPXV-27 | 4-34 | 93 | 5-12 | 6 | ARVLSGWLPFPNYYYYMDV [896] | 19 | ND | ND | ND | ND | ND |
| | | MPXV-30 | 1-69 | 82 | 4-23 | 3 | ATGGNIRVHDFDI [411] | 13 | 2-30 | 98 | 1 | MQGTHWPPRWT [668] | 11 |
| | | MPXV-40 | 4-34 | 82 | 2-21 | 6 | ARISSGWIGFPRYHYYLDV [414] | 19 | 3-13 | 85 | 3 | ND | ND |
| | | MPXV-61 | 1-69 | 92 | 3-10 | 5 | ASSLPSTYYFGSGNYPWGNWLDP [417] | 23 | 1-51 | 94 | 2 or 3 | GTWDSSLSEVV [674] | 11 |
| | | MPXV-96 | 4-34 | 86 | 5-21 | 4 | ARGLRGNSVCFD [420] | 12 | 3-15 | 98 | 2 | QQYNNPRT [667] | 9 |
| B5 | MVA 1 | VACV-1 | 3-48 | 86 | 2-15 | 6 | ARRSVGCSGGNCYAYYGMDV [423] | 21 | 2-28 or 2D-28 | 99 | 5 | MQALQTPIT [680] | 9 |
| | | VACV-59 | 3-11 | 86 | 3-10 | 6 | ARDGDGSGSYTPPYYYYGLDV [426] | 21 | 1-39 or 2D-39 | 98 | 4 | QQSYSTPPLT [683] | 10 |
| | MVA 4 | VACV-151 | 3-21 | 85 | 6-13 | 5 | ASRPGIAPAGPPGGGL [9222] | 16 | 3-20 | 99 | 2 | QQYGSSPYT [686] | 9 |
| | MVA 12 | VACV-282 | 3-21 | 84 | 3-10 | 6 | ARDRPRSRPNGSYFWYYYGMDV [432] | 23 | 3-21 | 98 | 2 or 3 | QVWDSNDHR [933] | 10 |
| | | VACV-283 | 1-69 | 84 | 3-16 | 6 | ARRGGEGAAHGMVD [435] | 14 | 2-28 or 2D-28 | 99 | 5 | LQALQTLPIT [692]10 | |
| | MSK452 | MPXV-2 | 1-3 | 87 | 3-9 | 5 | ARPRASLLRYFDWLFEQ [438] | 17 | 3-20 | 85 | 2 | QQYGNSVPYS [695] | 10 |
| | | MPXV-12 | 4-34 | 85 | 3-10 | 6 | ARDVYGSGTYYWFDP [441] | 15 | 1-39 or 1D-39 | 96 | 2 | QQSYTTPYT [698] | 9 |
| | | MPXV-13 | 4-4 | 89 | 6-19 | 4 | ARSGRYSSVTPFDY [444] | 14 | 3-11 | 85 | 3 | QQRSHWPA [701] | 8 |
| | | MPXV-25 | 3-33 | 84 | 2-15 | 3 | ARELGYCSGGTCYSMGAFDI [447] | 20 | 2-23 | 98.5 | 3 | CSYVGSSTSV [704] | 10 |

TABLE S2-continued

Sequence Diversity of Antibody Variable Genes Encoding Poxvirus-Specific mAbs, Related to FIGS. 1A-D

| Antigen | Donor | mAb | Heavy chain variable gene sequence | | | | | | Light chain variable sequence | | | | |
|---|---|---|---|---|---|---|---|---|---|---|---|---|---|
| | | | $V_H$ gene | $V_H$ region nucleotide % homology to $V_H$ gene | $D_H$ gene | $J_H$ gene | HCDR3 amino acids (aa) [SEQ ID NO:] | CDR3 length (aa) | $V_L$ gene | $V_L$ region nucleotide % homology to $V_L$ gene | $J_L$ gene | LCDR3 amino acids (aa) [SEQ ID NO:] | CDR3 length (aa) |
| | | MPXV-38 | 3-15 | 82 | 3-22 | 4 | ND | ND | 3-20 | 97 | 1 | QQYGSSPR [934] | 8 |
| | | MPXV-43 | 1-3 | 93 | 3-3 | 1 | ARDFEDFDSWTGYYSWLH [453] | 18 | 3-20 | 97 | 5 | QQYDSSPSIT [710] | 10 |
| | | MPXV-66 | 4-34 | 94 | 6-13 | 1 | ARTARTVRYFEN [456] | 12 | 4-1 | 90 | 1 | QQYYSTPWT [713] | 9 |
| | | MPXV-70 | 3-11 | 85 | 2-2 | 3 | ARGGGYCGGTTCSMGHAFDI [459] | 20 | 3-20 | 93 | 1 or 2 | QQYGSSPY [935] | 8 |
| | | MPXV-92 | 4-4 | 88 | 2-21 | 1 | ARNFYPGYLQY [462] | 11 | ND | ND | ND | ND | ND |
| A33 | MVA 1 | VACV-5 | 3-30 | 91 | 2-21 | 4 | AKEACGDCYSNYFHY [923] | 16 | ND | ND | ND | ND | ND |
| | | VACV-22 | 3-33 | 85 | 2-21 | 4 | ARVPCGGDCYSGYLQH [468] | 16 | 3-15 | 98 | 4 | QHYNNWPPLLT [725] | 11 |
| | | VACV-80 | 3-74 | 84 | 6-13 | 4 | ARVGAVRIAAAAPDY [471] | 15 | 4-1 | 99 | 1 | QQYYSTPWT [728] | 9 |
| | MSK452 | MPXV-39 | 4-34 | 81 | 1-7 | 5 | ASGNYR [474] | 6 | 2-30 | 97 | 2 | MQGTHWPRT [731] | 9 |
| | | MPXV-51 | 4-39 | 87 | 3-10 | 5 | GPLTPGNLFPGTLVRMVDP [924] | 19 | 3-20 | 96 | 4 | QQYAGSLT [734] | 8 |
| | | MPXV-56 | 6-1 | 85 | 6-13 | 5 | ARITVGNSPHLRVTRGMLDP [480] | 21 | 4-1 | 97 | 4 | QQYYSSPLT [737] | 9 |
| | | MPXV-91 | 3-30 | 80 | 2-21 | 4 | ARGRGVVMTAITRRL [925] | 15 | 1-47 | 98 | 3 | SSEFFD;DHLB [740] | 11 |
| | | MPXV-99 | 3-30 | 84 | 3-10 | 4 | ARADRGYFGH [486] | 10 | ND | ND | ND | ND | ND |
| H3 | VRC-201-020-08 | VACV-314 | 4-59 | 78 | 3-10 | 4 | ARLAGRKPDANS [926] | 12 | 7-43 | 98 | 5 | LLYYGGVVV [746] | 9 |
| | MSK452 | VACV-315 | 3-23 | 81 | 4-11 | 4 | AKGRARVNNIYRYFDH [492] | 16 | 2-14 | 98 | 3 | NSYTTTSPWV [749] | 10 |
| | | MPXV-1 | 3-23 | 87 | 3-22 | 2 | ARDTYYDSRIWYFGL [495] | 15 | ND | ND | ND | ND | ND |
| | | MPXV-29 | 1-69 | 87 | 3-10 | 5 | ARAVITMVRGDIPLGWFDP [498] | 19 | 3-20 | 98 | 5 | QQYGSSPP [936] | 8 |
| | | MPXV-72 | 2-5 | 88 | 6-19 | 3 | AHRSVAGRRDLAFDI [501] | 15 | 2-14 | 88 | 4 | QLIYQAASLG [937] | 10 |
| | | MPXV-76 | 3-15 | 90 | 3-10 | 4 | TTSFTFPRRIFAY [504] | 13 | 3-11 | 90 | 3 | QLRNSWPPT [761] | 9 |
| | | MPXV-79 | 1-18 | 84 | 7-27 | 3 | ARDFKLGRKGSAFDI [507] | 15 | 3-11 | 94 | 2 | LQRSDLYT [764] | 8 |
| | | MPXV-85 | 3-23 | 84 | 1-26 | 3 | AKDRVVGATYPRGVFDI [510] | 17 | ND | ND | ND | ND | ND |
| L1 | MVA 1 | VACV-33 | 4-39 | 83 | 6-6 | 4 | ARQSSSTGGFHY [513] | 12 | 1-40 | 97 | 2 | QSYDSSLSGREV [770] | 12 |
| | | VACV-34 | 3-9 | 85 | 3-22 | 4 | AKETEKYYYDSSGYDY [516] | 16 | 3-20 | 99 | 2 | QQYGSRGT [773] | 8 |
| | MSK452 | MPXV-26 | 3-53 | 80 | 1-26 | 4 | GKGGRLGLDY [927] | 10 | 2-8 | 70 | 2 or 3 | SSYAGTETVA [776] | 10 |
| | | MPXV-74 | 1-69 | 80 | 5-24 | 4 | GVYNAN [522] | 6 | 2-28 or 2D-28 | 95 | ND | LQARMTP [938] | 7 |
| | | MPXV-83 | 3-30 | 79 | 1-1 | 6 | ARGGIGAPGPPERYGR [928] | 16 | 1-33 or 1D-33 | 94 | 3 | QQFHSLPPT [782] | 9 |
| A27 | MVA 4 | MPXV-87 | 1-18 | 83 | 6-19 | 6 | ARSSSGPRYYYYGMDV [528] | 16 | 1-40 | 93 | 3 | QSYDSSLSGWV [785] | 11 |
| | VRC-201-040-05 | VACV-154 | 3-23 | 85 | 3-22 | 3 | AKIRLDSSGYSGAFDI [531] | 16 | 3-25 | 99 | 2 or 3 | QSADSSGTYPVV [788] | 12 |
| | | VACV-300 | 1-69 | 93 | 6-19 | 5 | ARASEQMLASINWFDP [534] | 16 | 2-23 | 90 | 3 | CSYAGSSFLV [939] | 10 |
| | | VACV-301 | 3-23 | 79 | 3-16 | 4 | AKWGRFESGAF [537] | 11 | 3-25 | 96 | 1 | QSADNSGTYEV [794] | 11 |
| | | VACV-302 | 4-39 | 88 | 6-13 | 4 | ARQISKAAAGSIDY [540] | 14 | 2-28 or 2D-28 | 99 | 5 | MQALQTPIT [797] | 9 |
| | | VACV-303 | 3-23 | 87 | 5-12 | 4 | ATSLIWWLQSDY [543] | 12 | 1-39 or 1D-39 | 98 | 1 | QQYSTPQT [800] | 9 |

TABLE S2-continued

Sequence Diversity of Antibody Variable Genes Encoding Poxvirus-Specific mAbs, Related to FIGS. 1A-D

| Antigen | Donor | mAb | Heavy chain variable gene sequence | | | | | | Light chain variable sequence | | | | |
|---|---|---|---|---|---|---|---|---|---|---|---|---|---|
| | | | $V_H$ gene | $V_H$ region nucleotide % homology to $V_H$ gene | $D_H$ gene | $J_H$ gene | HCDR3 amino acids (aa) [SEQ ID NO:] | CDR3 length (aa) | $V_L$ gene | $V_L$ region nucleotide % homology to $V_L$ gene | $J_L$ gene | LCDR3 amino acids (aa) [SEQ ID NO:] | CDR3 length (aa) |
| I1 | MSK452 | MPXV-10 | 5-51 | 88 | 4-17 | 4 | ARAMTVTPFDY [546] | 12 | 3-1 | 86 | 2 or 3 | QAWDSATVV [803] | 9 |
| | | MPXV-31 | 5-51 | 81 | 1-26 | 4 | ARPRQVGANRGYYFDY [929] | 16 | 4-1 | 94 | 4 | QQYYSPPAELS [806] | 11 |
| | | MPXV-53 | 3-33 | 91 | 6-19 | 4 | ND | ND | 3-21 | 95 | 2 | QVWDSSSDHP [940] | 10 |
| | | MPXV-71 | 3-64 | 81 | 3-10 | 4 | VRCLLRGLISPFDY [555] | 14 | 1-36 | 54 | 3 | STWDYSLSARV [812] | 11 |
| | | MPXV-97 | 3-30 | 84 | 3-3 | 2 | ARLILEAAWYFDL [930] | 13 | 1-40 | 93 | 1 | QSYDNSLNGPWV [815] | 12 |
| A25 | VRC-201-040-05 | VACV-309 | 3-23 | 86 | 1-1 | 6 | AKDNNYYYYGMDV [561] | 13 | 1-6 | 100 | 1 | LQDYNYPRM [818] | 9 |
| | VRC-201-044-06 | VACV-312 | 3-33 | 88 | 4-11 | 3 | ARVARDYSNIFDAFDI [564] | 16 | 1-39 or 1D-39 | 98 | 5 | QQSYSTPIT [821] | 8 |
| | VRC-201-020-08 | VACV-313 | 4-39 | 88 | 6-13 | 4 | VARIAVAAGTDY [567] | 12 | 3-15 | 97 | 2 | QQYNNWPPYT [824] | 10 |
| | MSK452 | MPXV-9 | 1-8 | 92 | 3-3 | 6 | ARSLDSLRFLEMFHQNYYYFMDV [570] | 23 | 3-11 | 88 | 4 | QLRST [827] | 5 |
| F9 | MSK452 | MPXV-41 | 3-49 | 85 | 4-23 | 4 | SATLTRGELFDY [573] | 12 | 3-11 | 96 | 4 | QQSNWPLT [830] | 9 |
| A28 | MSK452 | MPXV-49 | 4-61 | 90 | 3-22 | 5 | VREWPRHYDNRGYHTLPGT [576] | 19 | 1-5 | 92 | 1 | QQYNTDSSRT [833] | 10 |
| A21 | VRC-201-020-08 | VACV-318 | 3-30 | 74 | 5-12 | 3 | QMVKVPFYF [579] | 9 | 3-10 | 84 | 3 | YSTDSTSNQKRV [941] | 12 |
| H5 | VRC-201-003-09 | VACV-308 | 1-69 | 78 | 5-12 | 4 | ARPQSAVDFGPFDH [582] | 14 | 3-21 | 94 | 1 | HVWHTTTDHYV [839] | 11 |
| Unknown | VRC-201-040-05 | VACV-305 | 3-30 | 83 | 6-3 | 5 | VRTQQVIRPFFDH [858] | 13 | 315 | 98 | 1 | QQYKNWPPWT [842] | 10 |
| | | VACV-306 | 1-69 | 83 | 3-3 | 6 | ARDCYGVFWSGYFSRCHFGMDV [588] | 22 | 3-20 | 97 | 4 | QQYGGSPLLT [845] | 10 |
| | | VACV-307 | 3-23 | 85 | 1-26 | 4 | AKDRGIVGTTRFDS [591] | 14 | 3-15 | 99 | 5 | QQYSNWPPIT [848] | 10 |
| | VRC-201-020-08 | VACV-311 | 3-73 | 84 | 2-8 | 6 | TRRMDHARRPAREDYTNNGMDI [594] | 22 | 3-20 | 87 | 3 | QQYSSSPT [851] | 8 |
| | | VACV-316 | 3-30 | 82 | 2-21 | 4 | ADKLAWMLANPLDC [597] | 14 | 3-15 | 98 | 1 | QQYKNWGT [854] | 8 |
| | | VACV-310 | 1-69 | 78 | 6-13 | 4 | ARVFSAAGH [600] | 9 | 1-33 | 94 | 2 | QQYDNLPSGA [942] | 10 |
| | 18 | MPXV-8 | 3-30 | 83 | 6-19 | 6 | ARGLIPSAEQWQARGGPDYYYYG MAV [603] | 27 | ND | ND | ND | ND | ND |
| | MSK452 | MPXV-28 | 1-69 | 85 | 6-19 | 4 | ARGGGAVTGRGYYFDY [606] | 16 | 1-39 or 1D-39 | 99 | 2 | QQYGHSPYT [866] | 9 |
| | | MPXV-42 | 1-69 | 83 | 6-13 | 5 | AREQKLVGGWFDP [609] | 14 | 3-20 | 94 | 2 | QQYAISPNT [869] | 9 |
| | | MPXV-45 | 1-69 | 95 | 3-3 | 4 | ASPQRVLRFLQWSPFDY [612] | 17 | 3-20 | 96 | 2 | SSYTTISTLGV [872] | 11 |
| | | MPXV-82 | 3-33 | 86 | 5-24 | 4 | ARGVRMTTSLDY [615] | 12 | 2-14 | 98 | 3 | QSFDSLRGSVV [875] | 12 |
| | | MPXV-86 | 4-59 | 84 | 3-9 | 5 | ARGVGGVYDILTGYWGPNWFDP [618] | 22 | 1-40 | 97 | 2 or 3 | | |

TABLE S2-continued

Sequence Diversity of Antibody Variable Genes Encoding Poxvirus-Specific mAbs, Related to FIGS. 1A-D

| | | Heavy chain variable gene sequence | | | | | | Light chain variable sequence | | | | |
|---|---|---|---|---|---|---|---|---|---|---|---|---|
| Antigen Donor | mAb | $V_H$ gene | $V_H$ region nucleotide % homology to $V_H$ gene | $D_H$ gene | $J_H$ gene | HCDR3 amino acids (aa) [SEQ ID NO:] | CDR3 length (aa) | $V_L$ gene | $V_L$ region nucleotide % homology to $V_L$ gene | $J_L$ gene | LCDR3 amino acids (aa) [SEQ ID NO:] | CDR3 length (aa) |
| | MPXV-88 | 3-11 | 83 | 6-13 | 6 | ARNLRAAGVNFYFYYMDV [621] | 19 | 3-11 | 96 | 1 | QQRGKWPPWT [878] | 10 |
| | MPXV-98 | 1-46 | 86 | 3-22 | 5 | VVSSGFQQWFP [624] | 12 | 3-15 | 96 | 1 | Identical to MPVX-96 | 9 |

ND indicates not determined

TABLE S3

Reactivity and Cross-Reactivity of Poxvirus-Specific mAbs, Related to FIGS. 1A-D

| Antigen | Donor | mAb | Reactivity in screen to VACV | | Cross-reactivity | | | | | |
|---|---|---|---|---|---|---|---|---|---|---|
| | | | | | CPXV | | MPXV | | VARV[a] | |
| | | | Antigen | Lysate | Antigen | Lysate | Antigen | Lysate | Antigen | Lysate |
| D8 | MVA 1 | VACV-8 | Yes | Yes | ND | Yes | ND | Yes | no | Yes (++) |
| | | VACV-56 | Yes | Yes | ND | no | ND | Yes | no | Yes (+++) |
| | | VACV-66 | Yes | Yes | ND | no | ND | Yes | no | Yes (++++) |
| | | VACV-77[b] | Yes | ND | ND | ND | ND | ND | ND | ND |
| | | VACV-116 | Yes | Yes | ND | Yes | ND | Yes | no | ND |
| | | VACV-117 | Yes | Yes | ND | Yes | ND | Yes | no | ND |
| | | VACV-128 | Yes | Yes | ND | Yes | ND | no | no | Yes (++++) |
| | | VACV-136 | Yes | Yes | ND | Yes | ND | Yes | no | Yes (++++) |
| | | VACV-138 | Yes | Yes | ND | Yes | ND | Yes | Yes | Yes (+) |
| | MVA 3 | VACV-168 | Yes | Yes | ND | Yes | ND | Yes | Yes | no |
| | MVA 4 | VACV-159 | Yes | Yes | ND | Yes | ND | Yes | no | Yes (+++) |
| | MVA 19 | VACV-199 | Yes | Yes | ND | Yes | ND | Yes | Yes | no |
| | MVA 21 | VACV-228[b] | Yes | ND | ND | ND | ND | ND | ND | ND |
| | | VACV-230 | Yes | Yes | ND | Yes | ND | Yes | no | Yes (++) |
| | | VACV-249 | Yes | Yes | ND | Yes | ND | Yes | Yes | Yes (+++) |
| | VRC-201-040-05 | VACV-304 | Yes | Yes | ND | Yes | ND | Yes | Yes | Yes (++) |
| | MSK452 | MPXV-27 | Yes | Yes | ND | Yes | ND | Yes | Yes | Yes (++) |
| | | MPXV-30 | Yes | Yes | ND | Yes | ND | Yes | Yes | Yes (+) |
| | | MPXV-40 | Yes | Yes | ND | Yes | ND | Yes | Yes | Yes (+++++) |
| | | MPXV-61 | Yes | Yes | ND | Yes | ND | Yes | no | Yes (++) |
| | | MPXV-96 | Yes | Yes | ND | Yes | ND | Yes | no | Yes (+) |
| B5 | MVA 1 | VACV-1 | Yes | no | ND | no | ND | no | Yes | Yes (+) |
| | | VACV-59 | Yes | no | ND | Yes | ND | no | Yes | Yes (+) |
| | MVA 4 | VACV-151 | Yes | no | ND | no | ND | no | Yes | Yes (++) |
| | MVA 12 | VACV-282 | Yes | no | ND | no | ND | no | Yes | Yes (++) |
| | | VACV-283 | Yes | Yes | ND | Yes | ND | Yes | Yes | Yes (+++) |
| | MSK452 | MPXV-2 | Yes | Yes | ND | Yes | ND | Yes | Yes | Yes (++) |
| | | MPXV-12 | Yes | Yes | ND | Yes | ND | Yes | Yes | no |
| | | MPXV-13 | Yes | Yes | ND | Yes | ND | Yes | Yes | Yes (++) |
| | | MPXV-25 | Yes | Yes | ND | Yes | ND | Yes | Yes | Yes (++) |
| | | MPXV-38 | Yes | Yes | ND | Yes | ND | Yes | Yes | no |
| | | MPXV-43 | Yes | Yes | ND | Yes | ND | no | Yes | no |
| | | MPXV-66 | Yes | Yes | ND | Yes | ND | Yes | Yes | Yes (++) |
| | | MPXV-70 | Yes | Yes | ND | Yes | ND | Yes | no | Yes (+++) |
| | | MPXV-92 | Yes | Yes | ND | Yes | ND | Yes | Yes | Yes (+++++) |
| A33 | MVA 1 | VACV-5 | Yes | no | ND | no | ND | no | Yes | ND |
| | | VACV-22 | Yes | Yes | ND | Yes | ND | Yes | Yes | no |
| | | VACV-80 | Yes | Yes | ND | no | ND | no | no | no |
| | MSK452 | MPXV-39 | Yes | no | ND | no | ND | Yes | no | no |
| A33 | MSK452 | MPXV-51 | Yes | Yes | ND | Yes | ND | Yes | Yes | no |
| | | MPXV-56 | Yes | Yes | ND | Yes | ND | Yes | Yes | Yes (+) |
| | | MPXV-91 | Yes | no | ND | Yes | ND | no | Yes | Yes (+++++) |
| | | MPXV-99 | Yes | Yes | ND | Yes | ND | Yes | Yes | Yes (++) |
| H3 | VRC-201-020-08 | VACV-314 | Yes | Yes | ND | Yes | ND | Yes | Yes | Yes (+++++) |
| | | VACV-315 | Yes | Yes | ND | Yes | ND | Yes | no | Yes (+) |
| | MSK452 | MPXV-1 | Yes | Yes | ND | Yes | ND | Yes | no | Yes (+) |
| | | MPXV-29 | Yes | Yes | ND | Yes | ND | Yes | Yes | Yes (+) |
| | | MPXV-72 | Yes | Yes | ND | Yes | ND | Yes | no | Yes (+) |
| | | MPXV-79 | Yes | Yes | ND | Yes | ND | Yes | no | Yes (+) |
| | | MPXV-76 | Yes | Yes | ND | Yes | ND | Yes | no | no |
| | | MPXV-85 | Yes | Yes | ND | Yes | ND | Yes | no | no |
| L1 | MVA 1 | VACV-33 | Yes | no | ND | Yes | ND | no | Yes | Yes (+) |
| | | VACV-34 | Yes | no | ND | no | ND | no | Yes | Yes (+) |
| | MSK452 | MPXV-26 | Yes | no | ND | Yes | ND | no | Yes | Yes (+) |
| | | MPXV-83 | Yes | no | ND | Yes | ND | no | Yes | ND |
| | | MPXV-74 | Yes | Yes | ND | Yes | ND | Yes | ND | Yes (+++) |
| | | MPXV-87 | Yes | Yes | ND | Yes | ND | Yes | Yes | Yes (++) |
| A27 | MVA 4 | VACV-154 | Yes | Yes | ND | Yes | Yes | Yes | no | no |
| | VRC-201-040-05 | VACV-300 | Yes | Yes | ND | Yes | Yes | Yes | Yes | Yes (++) |
| | | VACV-301 | Yes | Yes | ND | Yes | Yes | Yes | Yes | no |
| | | VACV-302 | Yes | Yes | ND | Yes | Yes | Yes | no | Yes (++) |
| | | VACV-303 | Yes | Yes | ND | Yes | Yes | Yes | no | no |
| I1 | MSK452 | MPXV-10 | Yes | Yes | ND | Yes | ND | Yes | Yes | no |
| | | MPXV-31 | Yes | Yes | ND | Yes | ND | Yes | Yes | no |
| | | MPXV-53 | Yes | Yes | ND | Yes | ND | Yes | no | no |
| | | MPXV-71 | Yes | Yes | ND | Yes | ND | Yes | no | Yes (+++) |
| | | MPXV-97 | Yes | Yes | ND | Yes | ND | Yes | no | Yes (+++) |
| A25 | VRC-201-040-05 | VACV-309 | Yes | Yes | ND | Yes | ND | Yes | Yes | Yes (+) |
| | VRC-201-044-06 | VACV-312 | Yes | Yes | ND | Yes | ND | no | Yes | Yes (+) |
| | VRC-201-020-08 | VACV-313 | Yes | Yes | ND | Yes | ND | no | Yes | Yes (+) |
| | MSK452 | MPXV-9 | Yes | Yes | ND | Yes | ND | Yes | Yes | no |

TABLE S3-continued

Reactivity and Cross-Reactivity of Poxvirus-Specific mAbs, Related to FIGS. 1A-D

| | | | Reactivity in screen to VACV | | Cross-reactivity | | | | | |
|---|---|---|---|---|---|---|---|---|---|---|
| | | | | | CPXV | | MPXV | | VARV[a] | |
| Antigen | Donor | mAb | Antigen | Lysate | Antigen | Lysate | Antigen | Lysate | Antigen | Lysate |
| F9 | MSK452 | MPXV-41 | Yes | no | ND | no | ND | no | ND | no |
| A28 | MSK452 | MPXV-49 | Yes | no | ND | no | ND | no | ND | Yes (+) |
| A21 | VRC-201-020-08 | VACV-318 | Yes | no | ND | no | ND | no | no | no |
| H5 | VRC-201-003-09 | VACV-308 | Yes | Yes | ND | Yes | ND | Yes | Yes | no |

ND indicates not determined
Yes: mAb reactivity was confirmed by ELISA or protein microarray or biolayer Interferometry
No: mAb was tested and found as not reactive
[a]Range of mAb binding efficiency to VARV-infected cell lysate, where numbers indicate optical density from ELISA:
+ (0-0.099 OD);
++ (0.1-0.299 OD);
+++ (0.3-0.499 OD);
++++ (0.5-0.799 OD);
+++++ (>0.8 OD)
[b]MAbs with low expression that were excluded from the analysis

TABLE S4

Binding of Poxvirus-Specific mAbs to Purified Antigens or Infected Cell Lysates, Related to FIGS. IA-D

| | | | $EC_{50}$ (µg/mL) | | | | | | | |
|---|---|---|---|---|---|---|---|---|---|---|
| | | | Purified antigen | | | | Virus-infected cell lysate | | | |
| Antigen | Donor | mAb | VACV | CPXV | MPXV | VARV | VACV | CPXV | MPXV | VARV |
| D8 | MVA 1 | VACV-8 | ND | ND | ND | ND | 0.04 | 0.1 | 0.06 | ND |
| | | VACV-56 | ND | ND | ND | ND | 0.01 | > | 0.008 | ND |
| | | VACV-66 | ND | ND | ND | ND | 0.01 | > | >0.3 | ND |
| | | VACV-77 | ND | ND | ND | ND | ND | ND | ND | ND |
| | | VACV-116 | 1.8 | ND | ND | ND | 0.01 | 0.01 | >26 | ND |
| | | VACV-117 | 1.8 | ND | ND | ND | 0.01 | 0.01 | >26 | ND |
| | | VACV-128 | 1.1 | ND | ND | ND | 0.3 | 0.25 | > | ND |
| | | VACV-136 | ND | ND | ND | ND | 0.06 | 0.05 | 0.04 | ND |
| | | VACV-138 | 0.5 | ND | ND | ND | 0.08 | 0.04 | 0.1 | ND |
| | MVA 3 | VACV-168 | ND | ND | ND | ND | 0.4 | 0.8 | 0.5 | ND |
| | MVA 4 | VACV-159 | ND | ND | ND | ND | 0.009 | >28 | >14 | ND |
| | MVA 19 | VACV-199 | ND | ND | ND | ND | 0.008 | 0.008 | >19 | ND |
| | MVA 21 | VACV-228 | ND | ND | ND | ND | ND | ND | ND | ND |
| | | VACV-230 | ND | ND | ND | ND | 0.6 | 3.3 | 1 | ND |
| | | VACV-249 | 2.8 | ND | ND | ND | 0.3 | 0.4 | 0.1 | ND |
| | VRC-201-040-05 | VACV-304 | 0.05 | ND | ND | ND | 0.04 | 0.05 | 0.1 | ND |
| | MSK452 | MPXV-27 | 0.09 | ND | ND | ND | 0.02 | 0.02 | 0.02 | ND |
| | | MPXV-30 | ND | ND | ND | ND | 0.004 | 0.004 | 0.003 | ND |
| | | MPXV-40 | 0.09 | ND | ND | ND | 0.01 | 0.02 | 0.01 | ND |
| | | MPXV-61 | ND | ND | ND | ND | 0.007 | 0.009 | 0.004 | ND |
| | | MPXV-96 | ND | ND | ND | ND | 0.001 | 0.003 | 0.001 | ND |
| B5 | MVA 1 | VACV-1 | 0.02 | ND | ND | 0.02 | > | > | > | ND |
| | | VACV-59 | 0.14 | ND | ND | 0.18 | > | 0.78 | > | ND |
| | MVA 4 | VACV-151 | 0.04 | ND | ND | 0.04 | > | > | > | ND |
| | MVA 12 | VACV-282 | 0.155 | ND | ND | 3.15 | > | > | > | ND |
| | | VACV-283 | 0.06 | ND | ND | 0.08 | >48 | >41 | >50 | ND |
| | MSK452 | MPXV-2 | 0.03 | ND | ND | 0.06 | >6 | >13 | >6 | ND |
| | | MPXV-12 | 0.1 | ND | ND | 0.1 | 5.85 | 12.62 | 5.62 | ND |
| | | MPXV-13 | >10 | ND | ND | 0.03 | >0.1 | 0.004 | >0.1 | ND |
| | | MPXV-25 | 0.19 | ND | ND | 0.19 | 0.066 | 0.05 | >0.24 | ND |
| | | MPXV-38 | 0.08 | ND | ND | 0.08 | >50 | >50 | >50 | ND |
| | | MPXV-43 | 10.1 | ND | ND | 10.8 | 0.011 | >62.8 | > | ND |
| | | MPXV-66 | 0.1 | ND | ND | 0.16 | >33 | >29 | >16 | ND |
| | | MPXV-70 | 0.1 | ND | ND | > | >9 | >24 | >13 | ND |
| | | MPXV-92 | 0.7 | ND | ND | 1.2 | 0.064 | 0.014 | 0.046 | ND |
| A33 | MVA 1 | VACV-5 | 0.03 | ND | ND | 0.01 | > | > | > | ND |
| | | VACV-22 | 0.03 | ND | ND | 0.02 | >0.008 | >0.009 | >0.006 | ND |
| | | VACV-80 | 0.065 | ND | ND | > | >69 | > | > | ND |
| | MSK452 | MPXV-39 | 0.07 | ND | ND | > | > | > | >47 | ND |
| | | MPXV-51 | 0.04 | ND | ND | 0.04 | 0.05 | 0.024 | 0.025 | ND |
| | | MPXV-56 | 0.06 | ND | ND | 0.05 | >0.07 | >0.07 | >26 | ND |
| | | MPXV-91 | 0.03 | ND | ND | 0.03 | > | 0.26 | > | ND |
| | | MPXV-99 | 0.01 | ND | ND | 0.04 | >49 | >18 | >0.008 | ND |

TABLE S4-continued

Binding of Poxvirus-Specific mAbs to Purified Antigens or Infected Cell Lysates, Related to FIGS. IA-D

| | | | \multicolumn{8}{c}{$EC_{50}$ (μg/mL)} | | | | | | | |
|---|---|---|---|---|---|---|---|---|---|---|
| | | | \multicolumn{4}{c}{Purified antigen} | \multicolumn{4}{c}{Virus-infected cell lysate} |
| Antigen | Donor | mAb | VACV | CPXV | MPXV | VARV | VACV | CPXV | MPXV | VARV |
| H3 | VRC-201-020-08 | VACV-314 | 0.1 | ND | ND | ND | 0.003 | 0.004 | 0.003 | ND |
| | VRC-201-020-08 | VACV-315 | 0.2 | ND | ND | ND | 0.002 | 0.002 | 0.001 | ND |
| | MSK452 | MPXV-1 | 0.4 | ND | ND | ND | 0.009 | 0.011 | 0.005 | ND |
| H3 | MSK452 | MPXV-29 | ND | ND | ND | ND | 0.001 | 0.002 | 0.001 | ND |
| | | MPXV-72 | 0.04 | ND | ND | ND | 0.005 | 0.003 | 0.003 | ND |
| | | MPXV-79 | 0.06 | ND | ND | ND | 0.004 | 0.004 | 0.003 | ND |
| | | MPXV-76 | ND | ND | ND | ND | 0.008 | 0.01 | 0.006 | ND |
| | | MPXV-85 | 0.04 | ND | ND | ND | 0.003 | 0.002 | 0.002 | ND |
| L1 | MVA 1 | VACV-33 | 0.02 | ND | ND | 0.02 | > | 0.06 | > | ND |
| | | VACV-34 | 0.04 | ND | ND | 0.02 | > | > | > | ND |
| | MSK452 | MPXV-26 | 0.05 | ND | ND | 0.02 | > | 0.05 | > | ND |
| | | MPXV-83 | 0.065 | ND | ND | 0.065 | > | 0.03 | > | ND |
| | | MPXV-74 | ND | ND | ND | ND | 0.02 | 0.02 | 0.02 | ND |
| | | MPXV-87 | 0.3 | ND | ND | 0.3 | 0.01 | 0.003 | 0.001 | ND |
| A27 | MVA 4 | VACV-154 | 0.06 | ND | 0.06 | 0.3 | >0.1 | 0.02 | 0.02 | ND |
| | VRC-201-040-05 | VACV-300 | 0.22 | ND | 0.14 | 0.79 | >0.37 | 0.06 | >0.68 | ND |
| | | VACV-301 | 0.03 | ND | 0.04 | 0.11 | >21 | >1.4 | >5.6 | ND |
| | | VACV-302 | 0.08 | ND | 0.04 | 0.55 | 0.01 | 0.01 | 0.01 | ND |
| | | VACV-303 | 0.02 | ND | 0.02 | 0.16 | 0.05 | 0.004 | 0.004 | ND |
| I1 | MSK452 | MPXV-10 | ND | ND | ND | ND | 0.003 | 0.006 | >0.02 | ND |
| | | MPXV-31 | ND | ND | ND | ND | 0.01 | 0.01 | 0.04 | ND |
| | | MPXV-53 | ND | ND | ND | ND | 0.008 | 0.011 | >0.08 | ND |
| | | MPXV-71 | ND | ND | ND | ND | 0.022 | 0.014 | 0.006 | ND |
| | | MPXV-97 | ND | ND | ND | ND | 0.008 | >50 | 0.001 | ND |
| A25 | VRC-201-040-05 | VACV-309 | ND | ND | ND | ND | 0.005 | 0.005 | 0.001 | ND |
| | VRC-201-044-06 | VACV-312 | ND | ND | ND | ND | 0.002 | >50 | > | ND |
| | VRC-201-020-08 | VACV-313 | ND | ND | ND | ND | 0.001 | 1.172 | > | ND |
| | MSK452 | MPXV-9 | ND | ND | ND | ND | 0.022 | 0.876 | 0.107 | ND |
| F9 | MSK452 | MPXV-41 | 0.008 | ND | ND | ND | > | > | > | ND |
| A28 | MSK452 | MPXV-49 | 0.02 | ND | ND | ND | > | > | > | ND |
| A21 | VRC-201-020-08 | VACV-318 | 1.3 | ND | ND | ND | > | > | > | ND |
| H5 | VRC-201-003-09 | VACV-308 | ND | ND | ND | ND | 0.006 | 0.002 | 0.003 | ND |
| Unknown | VRC-201-040-05 | VACV-305 | ND | ND | ND | ND | 0.003 | 0.001 | 0.002 | ND |
| | | VACV-306 | ND | ND | ND | ND | 0.003 | 0.001 | 0.001 | ND |
| | | VACV-307 | ND | ND | ND | ND | 0.004 | 0.003 | 0.002 | ND |
| | VRC-201-020-08 | VACV-311 | ND | ND | ND | ND | 0.517 | > | > | ND |
| | | VACV-316 | ND | ND | ND | ND | 3.521 | > | > | ND |
| | 18 | VACV-310 | ND | ND | ND | ND | 0.027 | 0.004 | > | ND |
| | MSK452 | MPXV-8 | ND | ND | ND | ND | 0.118 | 0.058 | 0.039 | ND |
| | | MPXV-28 | ND | ND | ND | ND | 0.001 | >16 | 0.001 | ND |
| | | MPXV-42 | ND | ND | ND | ND | 0.017 | 0.036 | 0.018 | ND |
| | | MPXV-45 | ND | ND | ND | ND | 0.0002 | 0.0004 | 0.0001 | ND |
| | | MPXV-82 | ND | ND | ND | ND | 0.003 | 0.004 | 0.002 | ND |
| | | MPXV-86 | ND | ND | ND | ND | ND | ND | ND | ND |
| | | MPXV-88 | ND | ND | ND | ND | >62 | 0.03 | 0.05 | ND |
| | | MPXV-98 | ND | ND | ND | ND | 0.014 | 0.006 | 0.004 | ND |

> indicates that binding was not detected even when mAb was tested at the highest concentration of 100 μg/mL
ND indicates not determined

TABLE S5

Neutralizing Activity of Poxvirus-Specific mAbs, Related to FIGS. 2A-D

| | | | | \multicolumn{12}{c}{$IC_{50}$ given as μg/mL/($E_{Max}$ given as %)} |
| | | | | \multicolumn{4}{c}{VACV} | \multicolumn{4}{c}{CPXV} | \multicolumn{4}{c}{MPXV} |
| Antigen | Donor | mAb | Isotype | MV | MV + C' | EV | EV + C' | MV | MV + C' | EV | EV + C' | MV | MV + C' | EV | EV + C' |
|---|---|---|---|---|---|---|---|---|---|---|---|---|---|---|---|
| D8 | MVA 1 | VACV-8 | IgG1 | < | 0.3 (74) | ND | ND | < | 2 (58) | ND | ND | < | < | ND | ND |
| | | VACV-56 | IgG1 | < | 0.04 (81) | ND | ND | < | < | ND | ND | < | < | ND | ND |
| | | VACV-66 | IgG1 | < | 0.1 (83) | ND | ND | < | < | ND | ND | < | < | ND | ND |
| | | VACV-77 | ND | ND | ND | ND | ND | ND | ND | ND | ND | ND | ND | ND | ND |
| | | VACV-116 | IgG1 | < | 0.2 (82) | ND | ND | < | 0.1 (70) | ND | ND | < | < | ND | ND |

TABLE S5-continued

Neutralizing Activity of Poxvirus-Specific mAbs, Related to FIGS. 2A-D

| | | | | \multicolumn{12}{c}{$IC_{50}$ given as µg/mL/($E_{Max}$ given as %)} |
| | | | | VACV | | | | CPXV | | | | MPXV | | | |
| Antigen | Donor | mAb | Isotype | MV | MV + C' | EV | EV + C' | MV | MV + C' | EV | EV + C' | MV | MV + C' | EV | EV + C' |
|---|---|---|---|---|---|---|---|---|---|---|---|---|---|---|---|
| | | VACV-117 | IgG1 | ND | ND | ND | ND | ND | ND | ND | ND | ND | ND | ND | ND |
| | | VACV-128 | IgG1 | < | 0.5 (86) | ND | ND | < | 0.3 (71) | ND | ND | < | < | ND | ND |
| | | VACV-136 | IgG1 | < | 0.4 (84) | ND | ND | < | 0.2 (75) | ND | ND | < | < | ND | ND |
| | | VACV-138 | IgG1 | < | 0.3 (80) | ND | ND | < | 0.3 (70) | ND | ND | < | < | ND | ND |
| | MVA 3 | VACV-168 | IgG1 | ND | ND (66) | < | < | < | 0.5 (73) | < | < | < | < | < | < |
| | MVA 4 | VACV-159 | IgG1 | < | 0.04 (84) | ND | ND | < | < | ND | ND | < | < | ND | ND |
| | MVA 19 | VACV-199 | IgG1 | < | 3.4 (63) | < | < | ND | ND | < | < | < | < | < | < |
| | MVA 21 | VACV-228 | ND | ND | ND | ND | ND | ND | ND | ND | ND | ND | ND | ND | ND |
| | | VACV-230 | IgG1 | < | 0.1 (77) | ND | ND | < | 2 (71) | ND | ND | < | < | ND | ND |
| | | VACV-249 | IgG1 | < | 0.2 (70) | ND | ND | < | 0.5 (75) | ND | ND | < | < | ND | ND |
| | VRC-201-040-05 | VACV-304 | IgG1 | < | 0.02 (69) | ND | ND | < | 0.1 (79) | ND | ND | < | < | ND | ND |
| | MSK452 | MPXV-27 | IgG1 | < | 0.1 (70) | ND | ND | < | 0.08 (75) | ND | ND | < | < | ND | ND |
| | | MPXV-30 | IgG1 | < | < | < | < | < | < | < | < | < | < | < | < |
| | | MPXV-40 | IgG1 | < | 0.08 (70) | ND | ND | < | 0.1 (74) | ND | ND | < | < | ND | ND |
| | | MPXV-61 | IgG1 | < | < | < | < | < | < | < | < | < | < | < | < |
| | | MPXV-96 | IgG1 | < | < | < | < | < | < | < | < | < | < | < | < |
| B5 | MVA 1 | VACV-1 | IgG1 | < | < | < | < | ND | ND | < | < | ND | ND | < | < |
| | | VACV-59 | IgG2 | ND | ND | < | 0.2 (72) | ND | ND | < | 0.006 (86) | ND | ND | < | < |
| | MVA 4 | VACV-151 | IgG1 | < | < | < | 100 (55) | ND | ND | < | 0.46 (86) | ND | ND | < | < |
| | MVA 12 | VACV-282 | IgG1 | < | < | < | < | ND | ND | < | < | ND | ND | < | < |
| | | VACV-283 | IgG1 | ND | ND | < | 0.7 (76) | ND | ND | < | 0.2 (86) | ND | ND | < | < |
| | MSK452 | MPXV-2 | IgG1 | < | < | < | 1 (67) | ND | ND | < | 0.07 (80) | < | < | < | < |
| | | MPXV-12 | IgG3 | < | < | < | < | ND | ND | < | ND | < | < | < | < |
| | | MPXV-13 | IgG1 | < | < | < | 0.01 (80) | ND | ND | < | 0.002 (97) | < | < | < | < |
| | | MPXV-25 | IgG1 | < | < | < | 0.02 (77) | ND | ND | < | < | < | < | < | < |
| | | MPXV-38 | IgG1 | < | < | < | < | ND | ND | < | < | < | < | < | < |
| | | MPXV-43 | IgG1 | < | < | < | < | ND | ND | < | < | < | < | < | < |
| | | MPXV-66 | IgG1 | < | < | < | 0.01 (87) | ND | ND | < | 0.03 (86) | < | < | < | < |
| | | MPXV-70 | IgG1 | < | < | < | 0.01 (85) | ND | ND | < | 0.002 (87) | < | < | < | < |
| | | MPXV-92 | IgG1 | ND | ND | < | 0.08 (86) | < | ND | < | 0.5 (90) | < | ND | < | < |
| A33 | MVA 1 | VACV-5 | IgG1 | < | < | < | < | ND | ND | < | < | ND | ND | < | < |
| | | VACV-22 | IgG1 | < | < | < | 9.7 (87) | ND | ND | < | < | ND | ND | < | 50 (72) |
| | | VACV-80 | IgG1 | < | < | < | < | ND | ND | < | < | ND | ND | < | < |
| | MSK452 | MPXV-39 | IgG3 | < | < | < | < | ND | ND | < | < | < | < | < | 100 (56) |
| | | MPXV-51 | IgG1 | < | < | < | 0.1 (50) | ND | ND | < | < | < | < | < | 0.8 (77) |
| | | MPXV-56 | IgG2 | < | < | < | 0.16 (56) | ND | ND | < | 0.6 (61) | < | < | < | 12.5 (75) |
| | | MPXV-91 | IgG3 | < | < | < | < | ND | ND | < | 1.3 (58) | < | < | < | 1.6 (51) |
| | | MPXV-99 | IgG1 | < | < | < | < | ND | ND | < | < | < | < | < | 0.8 (84) |
| H3 | VRC-201-020-08 | VACV-314 | IgG3 | < | 0.1 (74) | ND | ND | < | 0.7 (85) | ND | ND | < | 0.8 (84) | ND | ND |
| | | VACV-315 | IgG1 | < | 2.2 (72) | ND | ND | < | 2.8 (70) | ND | ND | < | < | ND | ND |
| | MSK452 | MPXV-1 | IgG1 | < | < | ND | ND | < | 2.4 (53) | ND | ND | 25 (77) | 3 (85) | ND | ND |

TABLE S5-continued

Neutralizing Activity of Poxvirus-Specific mAbs, Related to FIGS. 2A-D

| | | | | IC$_{50}$ given as μg/mL/(E$_{Max}$ given as %) | | | | | | | | | | | | |
|---|---|---|---|---|---|---|---|---|---|---|---|---|---|---|---|
| | | | | VACV | | | | CPXV | | | | MPXV | | | |
| Antigen | Donor | mAb | Isotype | MV | MV + C' | EV | EV + C' | MV | MV + C' | EV | EV + C' | MV | MV + C' | EV | EV + C' |
| | | MPXV-29 | IgG1 | < | < | < | < | < | < | ND | ND | < | < | < | < |
| | | MPXV-72 | IgG1 | < | 11.4 (66) | ND | ND | < | 1.7 (84) | ND | ND | < | 6.2 (64) | ND | ND |
| | | MPXV-76 | IgG1 | < | < | < | < | < | < | ND | ND | < | < | < | < |
| | | MPXV-79 | IgG1 | < | 4.7 (62) | ND | ND | < | 0.2 (81) | ND | ND | 12.5 (67) | < | ND | ND |
| | | MPXV-85 | IgG1 | < | 3.4 (63) | ND | ND | < | 0.6 (82) | ND | ND | 12.5 (77) | 100 (51) | ND | ND |
| L1 | MVA 1 | VACV-33 | IgG1 | 0.3 (56) | 0.7 (71) | ND | ND | 0.5 (74) | 0.2 (75) | ND | ND | 70 (50) | < | ND | ND |
| | | VACV-34 | IgG1 | 3.3 (76) | 0.96 (78) | ND | ND | 2.7 (88) | 7 (88) | ND | ND | 63 (64) | < | ND | ND |
| | MSK452 | MPXV-26 | IgG1 | 0.3 (95) | 0.7 (80) | ND | ND | 0.07 (99) | 0.2 (93) | ND | ND | 3 (96) | 6.2 (97) | ND | ND |
| | | MPXV-83 | IgG1 | 0.3 (56) | 0.2 (75) | ND | ND | 0.2 (69) | 0.1 (78) | ND | ND | < | 12.5 (67) | ND | ND |
| | | MPXV-74 | IgG1 | < | 0.09 (79) | ND | ND | < | 0.08 (71) | ND | ND | < | < | ND | ND |
| | | MPXV-87 | IgG1 | 5 (61) | 0.8 (72) | ND | ND | 0.8 (63) | 0.6 (82) | ND | ND | 50 (57) | 50 (65) | ND | ND |
| A27 | MVA 4 | VACV-154 | IgG1 | < | < | ND | ND | < | < | ND | ND | 15 (66) | 14 (69) | ND | ND |
| | VRC-201-040-05 | VACV-300 | IgG1 | < | < | ND | ND | < | < | ND | ND | < | < | ND | ND |
| | | VACV-301 | IgG3 | 0.5 (61) | 0.1 (77) | ND | ND | < | 4 (86) | ND | ND | 1.6 (84) | 0.8 (92) | ND | ND |
| | | VACV-302 | IgG1 | 12.3 (81) | 0.1 (53) | ND | ND | 11 (93) | 0.2 (81) | ND | ND | 0.1 (88) | 6.3 (82) | ND | ND |
| | | VACV-303 | IgG1 | < | < | ND | ND | < | < | ND | ND | 25 (51) | 15 (64) | ND | ND |
| I1 | MSK452 | MPXV-10 | IgG1 | < | < | < | < | ND | ND | ND | ND | < | < | < | < |
| | | MPXV-31 | IgG1 | < | < | < | < | ND | ND | ND | ND | < | < | < | < |
| | | MPXV-53 | IgG1 | < | < | < | < | ND | ND | ND | ND | < | < | < | < |
| | | MPXV-71 | IgG1 | < | < | < | < | ND | ND | ND | ND | < | < | < | < |
| | | MPXV-97 | IgG1 | < | < | < | < | < | < | ND | ND | 0.02 (96) | 0.02 (76) | < | < |
| A25 | VRC-201-040-05 | VACV-309 | IgG1 | < | < | < | < | ND | ND | ND | ND | < | < | < | < |
| | VRC-201-044-06 | VACV-312 | IgG1 | < | < | < | < | ND | ND | ND | ND | ND | ND | < | < |
| | VRC-201-020-08 | VACV-313 | IgG1 | < | < | < | < | ND | ND | ND | ND | < | < | < | < |
| | MSK452 | MPXV-9 | IgG1 | < | < | < | < | ND | ND | ND | ND | < | < | < | < |
| F9 | MSK452 | MPXV-41 | IgG1 | < | < | < | < | ND | ND | ND | ND | < | < | < | < |
| A28 | MSK452 | MPXV-49 | IgG1 | < | < | < | < | ND | ND | ND | ND | < | < | < | < |
| A21 | VRC-201-020-08 | VACV-318 | IgG1 | < | < | < | < | ND | ND | ND | ND | < | < | < | < |
| H5 | VRC-201-003-09 | VACV-308 | IgG1 | < | < | < | < | ND | ND | ND | ND | < | < | < | < |
| Un-known | VRC-201-040-05 | VACV-305 | IgG1 | < | < | < | < | ND | ND | ND | ND | < | < | < | < |
| | | VACV-306 | IgG1 | < | < | < | < | ND | ND | ND | ND | < | < | < | < |
| | | VACV-307 | IgG1 | < | < | < | < | ND | ND | ND | ND | < | < | < | < |
| | VRC-201-020-08 | VACV-311 | IgG1 | < | < | < | < | < | < | ND | ND | < | < | < | < |
| | | VACV-316 | IgG1 | < | < | < | < | ND | ND | ND | ND | < | < | < | < |
| | 18 | VACV-310 | IgG1 | < | < | < | < | ND | ND | ND | ND | < | < | < | < |
| | MSK452 | MPXV-8 | IgG1 | < | < | < | < | ND | ND | ND | ND | < | < | < | < |
| | | MPXV-28 | IgG1 | < | < | < | < | ND | ND | ND | ND | < | < | < | < |
| | | MPXV-42 | IgG1 | < | < | < | < | ND | ND | ND | ND | < | < | < | < |
| | | MPXV-45 | IgG1 | < | < | < | < | ND | ND | ND | ND | < | < | < | < |
| | | MPXV-82 | IgG1 | < | < | < | < | ND | ND | ND | ND | < | < | < | < |
| | | MPXV-86 | ND | < | < | < | < | ND | ND | ND | ND | < | < | < | < |
| | | MPXV-88 | ND | < | < | < | < | ND | ND | ND | ND | < | < | < | 3.1 (78) |
| | | MPXV-98 | IgG1 | < | < | < | < | ND | ND | ND | ND | < | < | < | < |

< indicates that the E$_{max}$ was below 50% even at the highest concentration of 100 μg/mL
ND indicates not determined
C' indicates neutralization assay was performed in the presence of complement

TABLE S6

Composition of mAb Mixtures, Related to FIGS. 3A-B and FIGS. 5A-C

| Mixture | Human mAb specificity | | | | | | Ratio | Total amount of mAbs per mouse, mg | mAb clones included |
|---|---|---|---|---|---|---|---|---|---|
| | Anti-A27 | Anti-D8 | Anti-H3 | Anti-L1 | Anti-A33 | Anti-B5 | | | |
| Mix6 | 1 | 1 | 1 | 1 | 1 | 1 | 1:1:1:1:1:1 | 1.2 | VACV-301, VACV-249, MPXV-72, MPXV-26, VACV-22, VACV-283 |
| Mix6 (ΔD8) | 1 | — | 1 | 1 | 1 | 1 | 1:1:1:1:1 | 1 | VACV-301 MPXV-72, MPXV-26, VACV-22, VACV-283 |
| Mix6 (ΔL1) | 1 | 1 | 1 | — | 1 | 1 | 1:1:1:1:1 | 1 | VACV-301, VACV-249, MPXV-72, VACV-22, VACV-283 |
| Mix6 (ΔA27) | — | 1 | 1 | 1 | 1 | 1 | 1:1:1:1:1 | 1 | VACV-249, MPXV-72, MPXV-26, VACV-22, VACV-283 |
| Mix6 (ΔH3) | 1 | 1 | — | 1 | 1 | 1 | 1:1:1:1:1 | 1 | VACV-301, VACV-249, MPXV-26, VACV-22, VACV-283 |
| Mix6 (ΔA33) | 1 | 1 | 1 | 1 | — | 1 | 1:1:1:1:1 | 1 | VACV-301, VACV-249, MPXV-72, MPXV-26, VACV-283 |
| Mix6 (ΔB5) | 1 | 1 | 1 | 1 | 1 | — | 1:1:1:1:1 | 1 | VACV-301, VACV-249, MPXV-72, MPXV-26, VACV-22 |
| Anti-D8/mix | — | 5 | — | — | — | — | 1:1:1:1:1 | 1 | VACV-249, VACV-8, VACV-304, VACV-66, MPXV-40 |
| Anti-H3/mix | — | — | 3 | — | — | — | 1:1:1 | 0.6 | VACV-314, VACV-315, MPXV-72 |
| Mix4 | 1 | — | — | 1 | 1 | 1 | 1:1:1:1 | 0.8 | VACV-301, MPXV-26, VACV-22, VACV-283 |
| Mix4 (ΔL1) | 1 | — | — | — | 1 | 1 | 2:1:1 | 0.8 | VACV-301, VACV-22, VACV-283 |
| Mix4 (ΔB5) | 1 | — | — | 1 | 1 | — | 1:1:2 | 0.8 | VACV-301, MPXV-26, VACV-22 |
| Mix6 (ΔEV) | 1 | 1 | 1 | 1 | — | — | 1:1:1:1 | 0.8 | VACV-301, VACV-249, MPXV-72, MPXV-26 |
| Mix6 (ΔMV) | — | — | — | — | 1 | 1 | 1:1 | 0.4 | VACV-22, VACV-283 |

An entry using the "—" symbol above indicates that the mAb listed in the column header was not included in the mix listed to the left.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

"Antibodies: A Laboratory Manual," Cold Spring Harbor Press, Cold Spring Harbor, N.Y., 1988.
Abbondanzo et al., Am. J. Pediatr. Hematol. Oncol., 12(4), 480-489, 1990.
Allred et al., Arch. Surg., 125(1), 107-113, 1990.
Atherton et al., Biol. of Reproduction, 32, 155-171, 1985.
Austin et al., PLoS Pathog 8, e1002930, 2012.
Brehin, et al., Virology 371:185-195, 2008.
Brown et al., J. Immunol. Meth., 12; 130(1), 111-121, 1990.
Campbell, In: Monoclonal Antibody Technology, Laboratory Techniques in Biochemistry and Molecular Biology, Vol. 13, Burden and Von Knippenberg, Eds. pp. 75-83, Amsterdam, Elsevier, 1984.
Capaldi et al., Biochem. Biophys. Res. Comm., 74(2):425-433, 1977.
Christian et al., Proc Natl Acad Sci USA, 110:18662-18667, 2013.
Couderc et al., J. Infect. Dis. 200, 516-523, 2009.
De Jager et al., Semin. Nucl. Med. 23(2), 165-179, 1993.
Dholakia et al., J. Biol. Chem., 264, 20638-20642, 1989.
Doolittle and Ben-Zeev, Methods Mol. Biol., 109, 215-237, 1999.
Edwards & Brown, J. Gen. Virol. 67 (Pt 2), 377-380, 1986.
Edwards et al., J. Gen. Virol. 67 (Pt 2), 377-380, 1986.
Fong et al., J. Virol. 88:14364-14379, 2014.
Fric et al., J. Infect. Dis. 207:319-322, 2013.
Gefter et al., Somatic Cell Genet., 3:231-236, 1977.
Goh et al., Clin. Immunol. 149:487-497, 2013.
Gulbis and Galand, Hum. Pathol. 24(12), 1271-1285, 1993.
Guo et al., Sci. Transl. Med. 3:99 ra85, 2001.
Hallengard, et al., J. Virol. 88:13333-13343, 2014.
Hawman et al., J. Virol. 87, 13878-13888, 2013.
Hong et al., J. Virol. 87:12471-12480, 2013.
Kam et al., EMBO Mol. Med. 4, 330-343, 2012b.
Kam et al., J. Virol. 86, 13005-13015, 2012a.
Kam et al., PLoS One 9, e95647, 2014.
Khatoon et al., Ann. of Neurology, 26, 210-219, 1989.
Kielian et al., Viruses 2:796-825, 2010.
King et al., J. Biol. Chem., 269, 10210-10218, 1989.
Kohler and Milstein, Eur. J. Immunol., 6, 511-519, 1976.
Kohler and Milstein, Nature, 256, 495-497, 1975.
Krause et al., J. Immunol. 187:3704-3711, 2011b.
Krause et al., J. Virol. 84:3127-3130, 2010.

Krause et al., *J. Virol.* 85:10905-10908, 2011a.
Krause et al., *J. Virol.* 86:6334-6340, 2012.
Kyte and Doolittle, *J. Mol. Biol.,* 157(1):105-132, 1982.
Lanciotti & Valadere, *Emerg Infect Dis* 20, 2014.
Lee et al., *PLoS Pathog.* 7:e1002390, 2011.
Levitt et al., *Vaccine* 4, 157-162, 1986.
Lum et al., *J. Immunol.* 190:6295-6302, 2013.
Mainou et al., *MBio* 4, 2013.
Masrinoul et al., *Virology* 464-465, 111-117, 2014.
Messer et al., *Proc. Natl. Acad. Sci. USA* 111:1939-1944, 2014.
Morrison et al., *Am J Pathol,* 178:32-40, 2011.
Nakamura et al., In: *Enzyme Immunoassays: Heterogeneous and Homogeneous Systems*, Chapter 27, 1987.
O'Shannessy et al., *J. Immun. Meth.,* 99, 153-161, 1987.
Paes et al., *J. Am. Chem. Soc.,* 131:6952-6954, 2009.
Pal et al., *J. Virol.* 88:8213-8226, 2014.
Pal et al., *PLoS Pathog* 9, e1003312, 2013.
Persic et al., *Gene* 187:1, 1997
Potter and Haley, *Meth. Enzymol.,* 91, 613-633, 1983.
Remington's Pharmaceutical Sciences, 15th Ed., 3:624-652, 1990.
R. C. Team, R Foundation for Statistical Computing, Vienna, Austria, 2014.
Schilte et al., *PLoS Negl. Trop. Dis.* 7:e2137, 2013.
Selvarajah et al., *PLoS Negl. Trop. Dis.* 7:e2423, 2013.
Sissoko et al., *PLoS Negl. Trop. Dis.* 3:e389, 2009.
Smith et al., *J. Virol.* 86, 2665-2675, 2012.
Smith et al., *J. Virol.* 88, 12233-12241, 2014.
Smith et al., *J. Virol.* 86:2665-2675, 2012.
Smith et al., *MBio* 4, e00873-00813, 2013a.
Smith et al., *J. Infect. Dis.* 207, 1898-1908, 2013b.
Staples et al., *Clin. Infect. Dis.* 49, 942-948, 2009.
Sun et al., *Elife* 2:e00435, 2013.
Sun et al., *J. Steroid Biochem.,* 26(1):83-92, 1987.
Sun et al., *J. Virol.* 88:2035-2046, 2014.
Tang et al., *J. Biol. Chem.,* 271:28324-28330, 1996.
Thornburg et al., *J. Clin. Invest.,* 123:4405-4409, 2013.
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
Vander Veen et al., *Anim Health Res Rev,* 13:1-9, 2012.
Voss et al., *Nature,* 468:709-712, 2010.
Voss et al., *Nature,* 468:709-712, 2010.
Warter et al., *J. Immunol.,* 186:3258-3264, 2011.
Warter et al., *J. Immunol.,* 186:3258-3264, 2011.
Wawrzynczak & Thorpe, In: *Immunoconjugates, Antibody Conjugates In Radioimaging And Therapy Of Cancer*, Vogel (Ed.), NY, Oxford University Press, 28, 1987.
Yu et al., *Nature* 455:532-536, 2008.
Amanna et al., *Nat Med* 18, 974-979, 2012.
Baxby, D., *J Gen Virol* 58, 251-262, 1982.
Bell et al., *Virology* 325, 425-431, 2004.
Belyakov et al., *Proc Natl Acad Sci USA* 100, 9458-9463, 2003.
Benhnia et al., *J Virol* 83, 1201-1215, 2009.
Benhnia et al., *J Virol* 82, 3751-3768, 2008.
Bosma & Carroll, *Annu Rev Immunol* 9, 323-350, 1991.
Chapman et al., *Vet Pathol* 47, 852-870, 2010.
Crowe, J. E., Jr., *Vaccine* 27 Suppl 6, G47-51, 2009.
Davies et al., *Proc Natl Acad Sci USA* 102, 547-552, 2005a.
Davies et al., *J Virol* 79, 11724-11733, 2005b.
Davies et al., *Proteomics* 7, 1678-1686, 2007.
Edghill-Smith et al., *Nat Med* 11, 740-747, 2005.
Flexner et al., *Nature* 330, 259-262, 1987.
Hammarlund et al., *Nat Med* 11, 1005-1011, 2005.
Hughes et al., *Infect Genet Evol* 10, 50-59, 2010.
Hughes et al., *Clin Vaccine Immunol* 19, 1116-1118, 2012.
Ichihashi & Oie, *Virology* 163, 133-144, 1988.
Kempe et al., *Bull World Health Organ* 25, 41-48, 1961.
Kemper et al., *Eff Clin Pract* 5, 84-90, 2002.
Kennedy et al., *J Infect Dis* 204, 1395-1402, 2011.
Lantto et al., *J Virol* 85, 1820-1833, 2011.
Lewis et al., *N Engl J Med* 356, 2112-2114, 2007.
Lustig et al., *J Virol* 79, 13454-13462, 2005.
Mack et al., *Am J Trop Med Hyg* 21, 214-218, 1972.
Matho et al., *J Virol* 86, 8050-8058, 2012.
McCausland et al., *Antivir Ther* 15, 661-675, 2010.
McCollum et al., *Am J Trop Med Hyg* 93, 718-721, 2015.
McConnell et al., *Am J Vet Res* 25, 192-195, 1964.
Moss, B., *Immunol Rev* 239, 8-26, 2011.
Reed et al., *N Engl J Med* 350, 342-350, 2004.
Ruiz et al., *Nucleic Acids Res* 28, 219-221, 2000.
Smith & McFadden, *Nat Rev Immunol* 2, 521-527, 2002.
Smith et al., *J Virol* 88, 12233-12241, 2014.
Smith et al., *J Virol* 86, 2665-2675, 2012.
Stanford et al., *Immunol Cell Biol* 85, 93-102, 2007.
Thornburg et al., *J Clin Invest* 123, 4405-4409, 2013.
Verardi et al., *Hum Vaccin Immunother* 8, 961-970, 2012.
Vorou et al., *Curr Opin Infect Dis* 21, 153-156, 2008.
Weitkamp et al., *J Immunol Methods* 275, 223-237, 2003.
Wittek, R., *Int J Infect Dis* 10, 193-201, 2006.
Wyatt et al., *Proc Natl Acad Sci USA* 101, 4590-4595, 2004.
Yu et al., *J Immunol Methods* 336, 142-151, 2008.
Zaitseva et al., *J Virol* 85, 9147-9158, 2011.

What is claimed is:

1. A method of detecting an orthopoxvirus infection in a subject comprising:

(a) contacting a sample from said subject with an antibody or antibody fragment having clone-paired heavy and light chain CDR sequences selected from the group consisting of VACV-8 (SEQ ID NOs: 358-360 and SEQ ID NOs: 625-627), VACV-56 (SEQ ID NOs: 361-363 and SEQ ID NOs: 628-630), VACV-66 (SEQ ID NOs: 364-366 and SEQ ID NOs: 631-633), VACV-77 (SEQ ID NOs: 367-369 and SEQ ID NOs: 634-636), VACV-116 (SEQ ID NOs: 370-372, SEQ ID NOs: 897-899 and SEQ ID NOs: 637-639), VACV-117 (SEQ ID NOs: 373-375 and SEQ ID NOs: 640-642), VACV-128 (SEQ ID NOs: 376-378 and SEQ ID NOs: 643-645), VACV-136 (SEQ ID NOs: 379-381 and SEQ ID NOs: 646-648), VACV-138 (SEQ ID NOs: 891-893, SEQ ID NOs: 382-384, SEQ ID NOs: 918-920 and SEQ ID NOs: 649-651), VACV-168 (SEQ ID NOs: 385-387 and SEQ ID NOs: 652-654), VACV-159 (SEQ ID NOs: 388-390 and SEQ ID NOs: 655-657), VACV-199 (SEQ ID NOs: 391-393 and SEQ ID NOs: 658-660), VACV-228 (SEQ ID NOs: 394-396 and SEQ ID NOs: 661-663), VACV-230 (SEQ ID NOs: 397-399, SEQ ID NOs: 664-665 and SEQ ID NO: 900), VACV-249 (SEQ ID NOs: 400-402 and SEQ ID NOs: 901-903), VACV-304 (SEQ ID NOs: 403-405 and SEQ ID NOs: 904-906), MPXV-27 (SEQ ID NOs: 894-896, SEQ ID NOs: 406-408 and SEQ ID NOs: 907-909), MPXV-30 (SEQ ID NOs: 409-411 and SEQ ID NOs: 666-668), MPXV-40 (SEQ ID NOs: 412-414 and SEQ ID NOs: 669-671), MPXV-61 (SEQ ID NOs: 415-417 and SEQ ID NOs: 672-674), MPXV-96 (SEQ ID NOs: 418-420 and SEQ ID NOs: 675-677), VACV-1 (SEQ ID NOs: 421-423 and SEQ ID NOs: 678-680) VACV-59 (SEQ ID NOs: 424-426 and SEQ ID NOs: 681-683), VACV-151 (SEQ ID NOs: 427-429 and SEQ ID NOs: 684-686), VACV-282 (SEQ ID NOs: 430-432 and SEQ ID NOs: 687-689), VACV-283 (SEQ ID NOs: 433-435 and SEQ ID NOs: 690-692), MPXV-2 (SEQ ID NOs: 436-438 and SEQ ID NOs: 693-695), MPXV-12 (SEQ ID NOs: 439-441 and SEQ ID NOs: 696-698), MPXV-13 (SEQ ID NOs: 442-444 and SEQ ID NOs: 699-701), MPXV-25 (SEQ ID NOs: 445-447 and SEQ ID NOs: 702-704), MPXV-38 (SEQ ID NOs: 448-450 and SEQ ID NOs: 705-707), MPXV-43 (SEQ ID NOs: 451-453 and SEQ ID NOs: 708-710), MPXV-66 (SEQ ID NOs: 454-456 and SEQ ID NOs: 711-713), MPXV-70 (SEQ ID NOs: 457-459 and SEQ ID NOs: 714-716), MPXV-92 (SEQ ID NOs: 460-462 and SEQ ID NOs: 717-719), VACV-22 (SEQ ID NOs: 466-468 and SEQ ID NOs: 723-725), VACV-80 (SEQ ID NOs: 469-471 and SEQ ID NOs: 726-728), MPXV-39 (SEQ ID NOs: 472-474 and SEQ ID NOs: 729-731) MPXV-51 (SEQ ID NOs: 475-477 and SEQ ID NOs: 732-734), MPXV-56 (SEQ ID NOs: 478-480 and SEQ ID NOs: 735-737), MPXV-91 (SEQ ID NOs: 481-483 and SEQ ID NOs: 738-740), VACV-314 (SEQ ID NOs: 487-489 and SEQ ID NOs: 744-

746), VACV-315 (SEQ ID NOs: 490-492 and SEQ ID NOs: 747-749), MPXV-29 (SEQ ID NOs: 496-498 and SEQ ID NOs: 753-755), MPXV-72 (SEQ ID NOs: 499-501, SEQ ID NOs: 910-915 and SEQ ID NOs: 756-758), MPXV-76 (SEQ ID NOs: 502-504 and SEQ ID NOs: 759-761), MPXV-79 (SEQ ID NOs: 505-507 and SEQ ID NOs: 762-764), VACV-33 (SEQ ID NOs: 511-513 and SEQ ID NOs: 768-770), VACV-34 (SEQ ID NOs: 514-516 and SEQ ID NOs: 771-773), MPXV-26 (SEQ ID NOs: 517-519 and SEQ ID NOs: 774-776), MPXV-74 (SEQ ID NOs: 520-522 and SEQ ID NOs: 777-779), MPXV-83 (SEQ ID NOs: 523-525 and SEQ ID NOs: 780-782), MPXV-87 (SEQ ID NOs: 526-528 and SEQ ID NOs: 783-785), VACV-154 (SEQ ID NOs: 529-531 and SEQ ID NOs: 786-788), VACV-300 (SEQ ID NOs: 532-534 and SEQ ID NOs: 789-791), VACV-301 (SEQ ID NOs: 535-537 and SEQ ID NOs: 792-794), VACV-302 (SEQ ID NOs: 538-540 and SEQ ID NOs: 795-797), VACV-303 (SEQ ID NOs: 541-543 and SEQ ID NOs: 798-800), MPXV-10 (SEQ ID NOs: 544-546 and SEQ ID NOs: 801-803), MPXV-31 (SEQ ID NOs: 547-549 and SEQ ID NOs: 804-806), MPXV-53 (SEQ ID NOs: 550-552 and SEQ ID NOs: 807-809), MPXV-71 (SEQ ID NOs: 553-555 and SEQ ID NOs: 810-812), MPXV-97 (SEQ ID NOs: 556-558 and SEQ ID NOs: 813-815), VACV-309 (SEQ ID NOs: 559-561 and SEQ ID NOs: 816-818), VACV-312 (SEQ ID NOs: 562-564 and SEQ ID NOs: 819-821), VACV-313 (SEQ ID NOs: 565-567 and SEQ ID NOs: 822-824), MPXV-9 (SEQ ID NOs: 568-570 and SEQ ID NOs: 825-827), MPXV-41 (SEQ ID NOs: 571-573 and SEQ ID NOs: 828-830), MPXV-49 (SEQ ID NOs: 574-576 and SEQ ID NOs: 831-833), VACV-318 (SEQ ID NOs: 577-579 and SEQ ID NOs: 834-836), VACV-308 (SEQ ID NOs: 580-582 and SEQ ID NOs: 837-839), VACV-305 (SEQ ID NOs: 583-585 and SEQ ID NOs: 840-842), VACV-306 (SEQ ID NOs: 586-588 and SEQ ID NOs: 843-845), VACV-307 (SEQ ID NOs: 589-591 and SEQ ID NOs: 846-848), VACV-311 (SEQ ID NOs: 592-594 and SEQ ID NOs: 849-851), VACV-316 (SEQ ID NOs: 595-597 and SEQ ID NOs: 852-854), VACV-310 (SEQ ID NOs: 598-600 and SEQ ID NOs: 855-857), MPXV-28 (SEQ ID NOs: 604-606 and SEQ ID NOs: 861-863), MPXV-42 (SEQ ID NOs: 607-609 and SEQ ID NOs: 864-866), MPXV-45 (SEQ ID NOs: 610-612 and SEQ ID NOs: 867-869), MPXV-82 (SEQ ID NOs: 613-615 and SEQ ID NOs: 870-872), MPXV-86 (SEQ ID NOs: 616-618 and SEQ ID NOs: 873-875), MPXV-88 (SEQ ID NOs: 619-621 and SEQ ID NOs: 876-878), MPXV-98 (SEQ ID NOs: 622-624 and SEQ ID NOs: 879-881), and (b) detecting orthopoxvirus in said sample by binding of said antibody or antibody fragment to a orthopoxvirus antigen in said sample.

2. A method of treating a subject infected with orthopoxvirus, or reducing the likelihood of infection of a subject at risk of contracting orthopoxvirus, comprising delivering to said subject an antibody or antibody fragment having clone-paired heavy and light chain CDR sequences selected from the group consisting of VACV-8 (SEQ ID NOs: 358-360 and SEQ ID NOs: 625-627), VACV-56 (SEQ ID NOs: 361-363 and SEQ ID NOs: 628-630), VACV-66 (SEQ ID NOs: 364-366 and SEQ ID NOs: 631-633), VACV-77 (SEQ ID NOs: 367-369 and SEQ ID NOs: 634-636), VACV-116 (SEQ ID NOs: 370-372, SEQ ID NOs: 897-899 and SEQ ID NOs: 637-639), VACV-117 (SEQ ID NOs: 373-375 and SEQ ID NOs: 640-642), VACV-128 (SEQ ID NOs: 376-378 and SEQ ID NOs: 643-645), VACV-136 (SEQ ID NOs: 379-381 and SEQ ID NOs: 646-648), VACV-138 (SEQ ID NOs: 891-893, SEQ ID NOs: 382-384, SEQ ID NOs: 918-920 and SEQ ID NOs: 649-651), VACV-168 (SEQ ID NOs: 385-387 and SEQ ID NOs: 652-654), VACV-159 (SEQ ID NOs: 388-390 and SEQ ID NOs: 655-657), VACV-199 (SEQ ID NOs: 391-393 and SEQ ID NOs: 658-660), VACV-228 (SEQ ID NOs: 394-396 and SEQ ID NOs: 661-663), VACV-230 (SEQ ID NOs: 397-399, SEQ ID NOs: 664-665 and SEQ ID NO: 900), VACV-249 (SEQ ID NOs: 400-402 and SEQ ID NOs: 901-903), VACV-304 (SEQ ID NOs: 403-405 and SEQ ID NOs: 904-906), MPXV-27 (SEQ ID NOs: 894-896, SEQ ID NOs: 406-408 and SEQ ID NOs: 907-909), MPXV-30 (SEQ ID NOs: 409-411 and SEQ ID NOs: 666-668), MPXV-40 (SEQ ID NOs: 412-414 and SEQ ID NOs: 669-671), MPXV-61 (SEQ ID NOs: 415-417 and SEQ ID NOs: 672-674), MPXV-96 (SEQ ID NOs: 418-420 and SEQ ID NOs: 675-677), VACV-1 (SEQ ID NOs: 421-423 and SEQ ID NOs: 678-680) VACV-59 (SEQ ID NOs: 424-426 and SEQ ID NOs: 681-683), VACV-151 (SEQ ID NOs: 427-429 and SEQ ID NOs: 684-686), VACV-282 (SEQ ID NOs: 430-432 and SEQ ID NOs: 687-689), VACV-283 (SEQ ID NOs: 433-435 and SEQ ID NOs: 690-692), MPXV-2 (SEQ ID NOs: 436-438 and SEQ ID NOs: 693-695), MPXV-12 (SEQ ID NOs: 439-441 and SEQ ID NOs: 696-698), MPXV-13 (SEQ ID NOs: 442-444 and SEQ ID NOs: 699-701), MPXV-25 (SEQ ID NOs: 445-447 and SEQ ID NOs: 702-704), MPXV-38 (SEQ ID NOs: 448-450 and SEQ ID NOs: 705-707), MPXV-43 (SEQ ID NOs: 451-453 and SEQ ID NOs: 708-710), MPXV-66 (SEQ ID NOs: 454-456 and SEQ ID NOs: 711-713), MPXV-70 (SEQ ID NOs: 457-459 and SEQ ID NOs: 714-716), MPXV-92 (SEQ ID NOs: 460-462 and SEQ ID NOs: 717-719), VACV-22 (SEQ ID NOs: 466-468 and SEQ ID NOs: 723-725), VACV-80 (SEQ ID NOs: 469-471 and SEQ ID NOs: 726-728), MPXV-39 (SEQ ID NOs: 472-474 and SEQ ID NOs: 729-731) MPXV-51 (SEQ ID NOs: 475-477 and SEQ ID NOs: 732-734), MPXV-56 (SEQ ID NOs: 478-480 and SEQ ID NOs: 735-737), MPXV-91 (SEQ ID NOs: 481-483 and SEQ ID NOs: 738-740), VACV-314 (SEQ ID NOs: 487-489 and SEQ ID NOs: 744-746), VACV-315 (SEQ ID NOs: 490-492 and SEQ ID NOs: 747-749), MPXV-29 (SEQ ID NOs: 496-498 and SEQ ID NOs: 753-755), MPXV-72 (SEQ ID NOs: 499-501, SEQ ID NOs: 910-915 and SEQ ID NOs: 756-758), MPXV-76 (SEQ ID NOs: 502-504 and SEQ ID NOs: 759-761), MPXV-79 (SEQ ID NOs: 505-507 and SEQ ID NOs: 762-764), VACV-33 (SEQ ID NOs: 511-513 and SEQ ID NOs: 768-770), VACV-34 (SEQ ID NOs: 514-516 and SEQ ID NOs: 771-773), MPXV-26 (SEQ ID NOs: 517-519 and SEQ ID NOs: 774-776), MPXV-74 (SEQ ID NOs: 520-522 and SEQ ID NOs:777-779), MPXV-83 (SEQ ID NOs: 523-525 and SEQ ID NOs: 780-782), MPXV-87 (SEQ ID NOs: 526-528 and SEQ ID NOs: 783-785), VACV-154 (SEQ ID NOs: 529-531 and SEQ ID NOs: 786-788), VACV-300 (SEQ ID NOs: 532-534 and SEQ ID NOs: 789-791), VACV-301 (SEQ ID NOs: 535-537 and SEQ ID NOs: 792-794), VACV-302 (SEQ ID NOs: 538-540 and SEQ ID NOs: 795-797), VACV-303 (SEQ ID NOs: 541-543 and SEQ ID NOs: 798-800), MPXV-10 (SEQ ID NOs: 544-546 and SEQ ID NOs: 801-803), MPXV-31 (SEQ ID NOs: 547-549 and SEQ ID NOs: 804-806), MPXV-53 (SEQ ID NOs: 550-552 and SEQ ID NOs: 807-809), MPXV-71 (SEQ ID NOs: 553-555 and SEQ ID NOs: 810-812), MPXV-97 (SEQ ID NOs: 556-558 and SEQ ID NOs: 813-815), VACV-309 (SEQ ID NOs: 559-561 and SEQ ID NOs: 816-818), VACV-312 (SEQ ID NOs: 562-564 and SEQ ID NOs: 819-821), VACV-313 (SEQ ID NOs: 565-567 and SEQ ID NOs: 822-824), MPXV-9 (SEQ ID NOs: 568-570 and SEQ ID NOs: 825-827), MPXV-41 (SEQ ID NOs: 571-573 and SEQ ID NOs: 828-830), MPXV-49 (SEQ ID NOs: 574-576 and SEQ ID NOs: 831-833), VACV-318 (SEQ ID NOs: 577-579 and SEQ ID NOs: 834-836), VACV-308 (SEQ ID NOs: 580-582 and SEQ ID NOs: 837-839), VACV-305 (SEQ ID NOs: 583-585 and SEQ ID NOs: 840-842), VACV-306 (SEQ ID NOs: 586-588 and SEQ ID NOs: 843-845), VACV-307 (SEQ ID NOs: 589-591 and SEQ ID NOs: 846-848), VACV-311 (SEQ ID NOs: 592-594 and SEQ ID NOs: 849-851), VACV-316 (SEQ ID NOs: 595-597 and SEQ ID NOs: 852-854), VACV-310 (SEQ ID NOs: 598-600 and SEQ ID NOs: 855-857), MPXV-28 (SEQ ID NOs: 604-606 and SEQ ID NOs: 861-863), MPXV-42 (SEQ ID NOs: 607-609 and SEQ ID NOs: 864-866), MPXV-45 (SEQ ID NOs: 610-612 and SEQ ID NOs: 867-869), MPXV-82 (SEQ ID NOs: 613-615 and SEQ ID NOs: 870-872), MPXV-86 (SEQ ID NOs: 616-618 and SEQ ID NOs: 873-875), MPXV-88 (SEQ ID NOs: 619-621 and SEQ ID NOs: 876-878), MPXV-98 (SEQ ID NOs: 622-624 and SEQ ID NOs: 879-881).

3. The method of claim 2, wherein the antibody or antibody fragment is encoded by clone-paired light and heavy chain variable sequences selected from the group consisting of VACV-8 heavy (SEQ ID NO: 1), VACV-8 light (SEQ ID NO: 2), VACV-56 heavy (SEQ ID NO: 3), VACV-56 light (SEQ ID NO: 4), VACV-66 heavy (SEQ ID NO: 5), VACV-66 light (SEQ ID NO: 6), VACV-77 heavy (SEQ ID NO: 7), VACV-77 light (SEQ ID NO: 8), VACV-116 heavy (SEQ ID NO: 9), VACV-116 light (SEQ ID NO: 10 and SEQ ID NO: 882), VACV-117 heavy (SEQ ID NO: 11), VACV-117 light (SEQ ID NO: 12), VACV-128 heavy (SEQ ID NO: 13), VACV-128 light (SEQ ID NO: 14), VACV-136 heavy (SEQ ID NO: 15), VACV-136 light (SEQ ID NO: 16), VACV-138 heavy (SEQ ID NO: 17, SEQ ID NO: 883 and SEQ ID NO: 916), VACV-138 light (SEQ ID NO: 18), VACV-168 heavy (SEQ ID NO: 19), VACV-168 light (SEQ ID NO: 20), VACV-159 heavy (SEQ ID NO: 21), VACV-159 light (SEQ ID NO: 22), VACV-199 heavy (SEQ ID NO: 23), VACV-199 light (SEQ ID NO: 24), VACV-228 heavy (SEQ ID NO: 25), VACV-228 light (SEQ ID NO: 26), VACV-230 heavy (SEQ ID NO: 27), VACV-230 light (SEQ ID NO: 28), VACV-249 heavy (SEQ ID NO: 29), VACV-249 light (SEQ ID NO: 30), VACV-304 heavy (SEQ ID NO: 31), VACV-304 light (SEQ ID NO: 32), MPXV-27 heavy (SEQ ID NO: 33 and SEQ ID NO: 884), MPXV-27 light (SEQ ID NO: 34), MPXV-30 heavy (SEQ ID NO: 35), MPXV-30 light (SEQ ID NO: 36), MPXV-40 heavy (SEQ ID NO: 37), MPXV-40 light (SEQ ID NO: 38), MPXV-61 heavy (SEQ ID NO: 39), MPXV-61 light (SEQ ID NO: 40), MPXV-96 heavy (SEQ ID NO: 41), MPXV-96 light (SEQ ID NO: 42), VACV-1 heavy (SEQ ID NO: 43), VACV-1 light (SEQ ID NO: 44), VACV-59 heavy (SEQ ID NO: 45), VACV-59 light (SEQ ID NO: 46), VACV-151 heavy (SEQ ID NO: 47), VACV-151 light (SEQ ID NO: 48), VACV-282 heavy (SEQ ID NO: 49), VACV-282 light (SEQ ID NO: 50), VACV-283 heavy (SEQ ID NO: 51), VACV-283 light (SEQ ID NO: 52), MPXV-2 heavy (SEQ ID NO: 53), MPXV-2 light (SEQ ID NO: 54), MPXV-12 heavy (SEQ ID NO: 55), MPXV-12 light (SEQ ID NO: 57), MPXV-13 heavy (SEQ ID NO: 58), MPXV-13 light (SEQ ID NO: 59), MPXV-25 heavy (SEQ ID NO: 60), MPXV-25 light (SEQ ID NO: 61), MPXV-38 heavy (SEQ ID NO: 62), MPXV-38 light (SEQ ID NO: 63), MPXV-43 heavy (SEQ ID NO: 64), MPXV-43 light (SEQ ID NO: 65), MPXV-66 heavy (SEQ ID NO: 66), MPXV-66 light (SEQ ID NO: 67), MPXV-70 heavy (SEQ ID NO: 68), MPXV-70 light (SEQ ID NO: 69), MPXV-92 heavy (SEQ ID NO: 70), MPXV-92 light (SEQ ID NO: 71), VACV-22 heavy (SEQ ID NO: 74), VACV-22 light (SEQ ID NO: 75), VACV-80 heavy (SEQ ID NO: 76), VACV-80 light (SEQ ID NO: 77), MPXV-39 heavy (SEQ ID NO: 78), MPXV-39 light (SEQ ID NO: 79), MPXV-51 heavy (SEQ ID NO: 80), MPXV-51 light (SEQ ID NO: 81), MPXV-56 heavy (SEQ ID NO: 82), MPXV-56 light (SEQ ID NO: 83), MPXV-91 heavy (SEQ ID NO: 84), MPXV-91 light (SEQ ID NO: 85), VACV-314 heavy (SEQ ID NO: 88), VACV-314 light (SEQ ID NO: 89), VACV-315 heavy (SEQ ID NO: 90), VACV-315 light (SEQ ID NO: 91), MPXV-29 heavy (SEQ ID NO: 94), MPXV-29 light (SEQ ID NO: 95), MPXV-72 heavy (SEQ ID NO: 96), MPXV-72 light (SEQ ID NO: 97, SEQ ID NO: 56 and SEQ ID NO: 885), MPXV-76 heavy (SEQ ID NO: 98), MPXV-76 light (SEQ ID NO: 99), MPXV-79 heavy (SEQ ID NO: 100), MPXV-79 light (SEQ ID NO: 101), VACV-33 heavy (SEQ ID NO: 104), VACV-33 light (SEQ ID NO: 105), VACV-34 heavy (SEQ ID NO: 106), VACV-34 light (SEQ ID NO: 107), MPXV-26 heavy (SEQ ID NO: 108), MPXV-26 light (SEQ ID NO: 109), MPXV-74 heavy (SEQ ID NO: 110), MPXV-74 light (SEQ ID NO: 111), MPXV-83 heavy (SEQ ID NO: 112), MPXV-83 light (SEQ ID NO: 113), MPXV-87 heavy (SEQ ID NO: 114), MPXV-87 light (SEQ ID NO: 115), VACV-154 heavy (SEQ ID NO: 116), VACV-154 light (SEQ ID NO: 117), VACV-300 heavy (SEQ ID NO: 118), VACV-300 light (SEQ ID NO: 119), VACV-301 heavy (SEQ ID NO: 120), VACV-301 light (SEQ ID NO: 121), VACV-302 heavy (SEQ ID NO: 122), VACV-302 light (SEQ ID NO: 123), VACV-303 heavy (SEQ ID NO: 124), VACV-303 light (SEQ ID NO: 125), MPXV-10 heavy (SEQ ID NO: 126), MPXV-10 light (SEQ ID NO: 127), MPXV-31 heavy (SEQ ID NO: 128), MPXV-31 light (SEQ ID NO: 129), MPXV-53 heavy (SEQ ID NO: 130), MPXV-53 light (SEQ ID NO: 131), MPXV-71 heavy (SEQ ID NO: 132), MPXV-71 light (SEQ ID NO: 133), MPXV-97 heavy (SEQ ID NO: 134), MPXV-97 light (SEQ ID NO: 135), VACV-309 heavy (SEQ ID NO: 136), VACV-309 light (SEQ ID NO: 137), VACV-312 heavy (SEQ ID NO: 138), VACV-312 light (SEQ ID NO: 139), VACV-313 heavy (SEQ ID NO: 140), VACV-313 light (SEQ ID NO: 141), MPXV-9 heavy (SEQ ID NO: 142), MPXV-9 light (SEQ ID NO: 143), MPXV-41 heavy (SEQ ID NO: 144), MPXV-41 light (SEQ ID NO: 145), MPXV-49 heavy (SEQ ID NO: 146), MPXV-49 light (SEQ ID NO: 147), VACV-318 heavy (SEQ ID NO: 148), VACV-318 light (SEQ ID NO: 149), VACV-308 heavy (SEQ ID NO: 150), VACV-308 light (SEQ ID NO: 151), VACV-305 heavy (SEQ ID NO: 152), VACV-305 light (SEQ ID NO: 153), VACV-306 heavy (SEQ ID NO: 154), VACV-306 light (SEQ ID NO: 155), VACV-307 heavy (SEQ ID NO: 156), VACV-307 light (SEQ ID NO: 157), VACV-311 heavy (SEQ ID NO: 158), VACV-311 light (SEQ ID NO: 159), VACV-316 heavy (SEQ ID NO: 160), VACV-316 light (SEQ ID NO: 161), VACV-310 heavy (SEQ ID NO: 162), VACV-310 light (SEQ ID NO: 163), MPXV-28 heavy (SEQ ID NO: 166), MPXV-28 light (SEQ ID NO: 167), MPXV-42 heavy (SEQ ID NO: 168), MPXV-42 light (SEQ ID NO: 169), MPXV-45 heavy (SEQ ID NO: 170), MPXV-45 light (SEQ ID NO: 171), MPXV-82 heavy (SEQ ID NO: 172), MPXV-82 light (SEQ ID NO: 173), MPXV-86 heavy (SEQ ID NO: 174), MPXV-86 light (SEQ ID NO: 175), MPXV-88 heavy (SEQ ID NO: 176), MPXV-88 light (SEQ ID NO: 177), MPXV-98 heavy (SEQ ID NO: 178), MPXV-98 light (SEQ ID NO: 179).

4. The method of claim 2, wherein the antibody or antibody fragment is encoded by clone-paired light and heavy chain variable sequences having 95% identity to clone-paired light and heavy chain variable sequences selected from the group consisting of VACV-8 heavy (SEQ ID NO: 1), VACV-8 light (SEQ ID NO: 2), VACV-56 heavy (SEQ ID NO: 3), VACV-56 light (SEQ ID NO: 4), VACV-66 heavy (SEQ ID NO: 5), VACV-66 light (SEQ ID NO: 6), VACV-77 heavy (SEQ ID NO: 7), VACV-77 light (SEQ ID NO: 8), VACV-116 heavy (SEQ ID NO: 9), VACV-116 light (SEQ ID NO: 10 and SEQ ID NO: 882), VACV-117 heavy (SEQ ID NO: 11), VACV-117 light (SEQ ID NO: 12), VACV-128 heavy (SEQ ID NO: 13), VACV-128 light (SEQ ID NO: 14), VACV-136 heavy (SEQ ID NO: 15), VACV-136 light (SEQ ID NO: 16), VACV-138 heavy (SEQ ID NO: 17, SEQ ID NO: 883 and SEQ ID NO: 916), VACV-138 light (SEQ ID NO: 18), VACV-168 heavy (SEQ ID NO: 19), VACV-168 light (SEQ ID NO: 20), VACV-159 heavy (SEQ ID NO: 21), VACV-159 light (SEQ ID NO: 22), VACV-199 heavy (SEQ ID NO: 23), VACV-199 light (SEQ ID NO: 24), VACV-228 heavy (SEQ ID NO: 25), VACV-228 light (SEQ ID NO: 26), VACV-230 heavy (SEQ ID NO: 27), VACV-230 light (SEQ ID NO: 28), VACV-249 heavy (SEQ ID NO: 29), VACV-249 light (SEQ ID NO: 30), VACV-304 heavy (SEQ ID NO: 31), VACV-304 light (SEQ ID NO: 32), MPXV-27 heavy (SEQ ID NO: 33 and SEQ ID NO: 884), MPXV-27 light (SEQ ID NO: 34), MPXV-30 heavy (SEQ ID NO: 35), MPXV-30 light (SEQ ID NO: 36), MPXV-40 heavy (SEQ ID NO: 37), MPXV-40 light (SEQ ID NO: 38), MPXV-61 heavy (SEQ ID NO: 39), MPXV-61 light (SEQ ID NO: 40), MPXV-96 heavy (SEQ ID NO: 41), MPXV-96 light (SEQ ID NO: 42), VACV-1 heavy (SEQ ID NO: 43), VACV-1 light (SEQ ID NO: 44), VACV-59 heavy (SEQ ID NO: 45), VACV-59 light (SEQ ID NO: 46), VACV-151 heavy (SEQ ID NO: 47), VACV-151 light (SEQ ID NO: 48), VACV-282 heavy (SEQ ID NO: 49), VACV-282 light (SEQ ID NO: 50), VACV-283 heavy (SEQ ID NO: 51), VACV-283 light (SEQ ID NO: 52), MPXV-2 heavy (SEQ ID NO: 53), MPXV-2 light (SEQ ID NO: 54), MPXV-12 heavy (SEQ ID NO: 55), MPXV-12 light (SEQ ID NO: 57), MPXV-13 heavy (SEQ ID NO: 58), MPXV-13 light (SEQ ID NO: 59), MPXV-25 heavy (SEQ ID NO: 60), MPXV-25 light (SEQ ID NO: 61), MPXV-38 heavy (SEQ ID NO: 62), MPXV-38 light (SEQ ID NO: 63), MPXV-43 heavy (SEQ ID NO: 64), MPXV-43 light (SEQ ID NO: 65), MPXV-66 heavy (SEQ ID NO: 66), MPXV-66 light (SEQ ID NO: 67), MPXV-70 heavy (SEQ ID NO: 68), MPXV-70 light (SEQ ID NO: 69), MPXV-92 heavy (SEQ ID NO: 70), MPXV-92 light (SEQ ID NO: 71), VACV-22 heavy (SEQ ID NO: 74), VACV-22 light (SEQ ID NO: 75), VACV-80 heavy (SEQ ID NO: 76), VACV-80 light (SEQ ID NO: 77), MPXV-39 heavy (SEQ ID NO: 78), MPXV-39 light (SEQ ID NO: 79), MPXV-51 heavy (SEQ ID NO: 80), MPXV-51 light (SEQ ID NO: 81), MPXV-56 heavy (SEQ ID NO: 82), MPXV-56 light (SEQ ID NO: 83), MPXV-91 heavy (SEQ ID NO: 84), MPXV-91 light (SEQ ID NO: 85), VACV-314 heavy (SEQ ID NO: 88), VACV-314 light (SEQ ID NO: 89), VACV-315 heavy (SEQ ID NO: 90), VACV-315 light (SEQ ID NO: 91), MPXV-29 heavy (SEQ ID NO: 94), MPXV-29 light (SEQ ID NO: 95), MPXV-72 heavy (SEQ ID NO: 96), MPXV-72 light (SEQ ID NO: 97, SEQ ID NO: 56 and SEQ ID NO: 885), MPXV-76 heavy (SEQ ID NO: 98), MPXV-76 light (SEQ ID NO: 99), MPXV-79 heavy (SEQ ID NO: 100), MPXV-79 light (SEQ ID NO: 101), VACV-33 heavy (SEQ ID NO: 104), VACV-33 light (SEQ ID NO: 105), VACV-34 heavy (SEQ ID NO: 106), VACV-34 light (SEQ ID NO: 107), MPXV-26 heavy (SEQ ID NO: 108), MPXV-26 light (SEQ ID NO: 109), MPXV-74 heavy (SEQ ID NO: 110), MPXV-74 light (SEQ ID NO: 111), MPXV-83 heavy (SEQ ID NO: 112), MPXV-83 light (SEQ ID NO: 113), MPXV-87 heavy (SEQ ID NO: 114), MPXV-87 light (SEQ ID NO: 115), VACV-154 heavy (SEQ ID NO: 116), VACV-154 light (SEQ ID NO: 117), VACV-300 heavy (SEQ ID NO: 118), VACV-300 light (SEQ ID NO: 119), VACV-301 heavy (SEQ ID NO: 120), VACV-301 light (SEQ ID NO: 121), VACV-302 heavy (SEQ ID NO: 122), VACV-302 light (SEQ ID NO: 123), VACV-303 heavy (SEQ ID NO: 124), VACV-303 light (SEQ ID NO: 125), MPXV-10 heavy (SEQ ID NO: 126), MPXV-10 light (SEQ ID NO: 127), MPXV-31 heavy (SEQ ID NO: 128), MPXV-31 light (SEQ ID NO: 129), MPXV-53 heavy (SEQ ID NO: 130), MPXV-53 light (SEQ ID NO: 131), MPXV-71 heavy (SEQ ID NO: 132), MPXV-71 light (SEQ ID NO: 133), MPXV-97 heavy (SEQ ID NO: 134), MPXV-97 light (SEQ ID NO: 135), VACV-309 heavy (SEQ ID NO: 136), VACV-309 light (SEQ ID NO: 137), VACV-312 heavy (SEQ ID NO: 138), VACV-312 light (SEQ ID NO: 139), VACV-313 heavy (SEQ ID NO: 140), VACV-313 light (SEQ ID NO: 141), MPXV-9 heavy (SEQ ID NO: 142), MPXV-9 light (SEQ ID NO: 143), MPXV-41 heavy (SEQ ID NO: 144), MPXV-41 light (SEQ ID NO: 145), MPXV-49 heavy (SEQ ID NO: 146), MPXV-49 light (SEQ ID NO: 147), VACV-318 heavy (SEQ ID NO: 148), VACV-318 light (SEQ ID NO: 149), VACV-308 heavy (SEQ ID NO: 150), VACV-308 light (SEQ ID NO: 151), VACV-305 heavy (SEQ ID NO: 152), VACV-305 light (SEQ ID NO: 153), VACV-306 heavy (SEQ ID NO: 154), VACV-306 light (SEQ ID NO: 155), VACV-307 heavy (SEQ ID NO: 156), VACV-307 light (SEQ ID NO: 157), VACV-311 heavy (SEQ ID NO: 158), VACV-311 light (SEQ ID NO: 159), VACV-316 heavy (SEQ ID NO: 160), VACV-316 light (SEQ ID NO: 161), VACV-310 heavy (SEQ ID NO: 162), VACV-310 light (SEQ ID NO: 163), MPXV-28 heavy (SEQ ID NO: 166), MPXV-28 light (SEQ ID NO: 167), MPXV-42 heavy (SEQ ID NO: 168), MPXV-42 light (SEQ ID NO: 169), MPXV-45 heavy (SEQ ID NO: 170), MPXV-45 light (SEQ ID NO: 171), MPXV-82 heavy (SEQ ID NO: 172), MPXV-82 light (SEQ ID NO: 173), MPXV-86 heavy (SEQ ID NO: 174), MPXV-86 light (SEQ ID NO: 175), MPXV-88 heavy (SEQ ID NO: 176), MPXV-88 light (SEQ ID NO: 177), MPXV-98 heavy (SEQ ID NO: 178), MPXV-98 light (SEQ ID NO: 179).

5. The method of claim 2, wherein said antibody or antibody fragment is encoded by light and heavy chain variable sequences having 70%, 80%, or 90% identity to clone-paired light and heavy chain sequences selected from the group consisting of VACV-8 heavy (SEQ ID NO: 1), VACV-8 light (SEQ ID NO: 2), VACV-56 heavy (SEQ ID NO: 3), VACV-56 light (SEQ ID NO: 4), VACV-66 heavy (SEQ ID NO: 5), VACV-66 light (SEQ ID NO: 6), VACV-77 heavy (SEQ ID NO: 7), VACV-77 light (SEQ ID NO: 8), VACV-116 heavy (SEQ ID NO: 9), VACV-116 light (SEQ ID NO: 10 and SEQ ID NO: 882), VACV-117 heavy (SEQ ID NO: 11), VACV-117 light (SEQ ID NO: 12), VACV-128 heavy (SEQ ID NO: 13), VACV-128 light (SEQ ID NO: 14), VACV-136 heavy (SEQ ID NO: 15), VACV-136 light (SEQ ID NO: 16), VACV-138 heavy (SEQ ID NO: 17, SEQ ID NO: 883 and SEQ ID NO: 916), VACV-138 light (SEQ ID NO: 18), VACV-168 heavy (SEQ ID NO: 19), VACV-168 light (SEQ ID NO: 20), VACV-159 heavy (SEQ ID NO: 21), VACV-159 light (SEQ ID NO: 22), VACV-199 heavy (SEQ ID NO: 23), VACV-199 light (SEQ ID NO: 24), VACV-228 heavy (SEQ ID NO: 25), VACV-228 light (SEQ ID NO: 26), VACV-230 heavy (SEQ ID NO: 27), VACV-230 light (SEQ ID NO: 28), VACV-249 heavy (SEQ ID NO: 29), VACV-249 light (SEQ ID NO: 30), VACV-304 heavy (SEQ ID NO: 31), VACV-304 light (SEQ ID NO: 32), MPXV-27 heavy (SEQ ID NO: 33 and SEQ ID NO: 884), MPXV-27 light (SEQ ID NO: 34), MPXV-30 heavy (SEQ ID NO: 35), MPXV-30 light (SEQ ID NO: 36), MPXV-40 heavy (SEQ ID NO: 37), MPXV-40 light (SEQ ID NO: 38), MPXV-61 heavy (SEQ ID NO: 39), MPXV-61 light (SEQ ID NO: 40), MPXV-96 heavy (SEQ ID NO: 41), MPXV-96 light (SEQ ID NO: 42), VACV-1 heavy (SEQ ID NO: 43), VACV-1 light (SEQ ID NO: 44), VACV-59 heavy (SEQ ID NO: 45), VACV-59 light (SEQ ID NO: 46), VACV-151 heavy (SEQ ID NO: 47), VACV-151 light (SEQ ID NO: 48), VACV-282 heavy (SEQ ID NO: 49), VACV-282 light (SEQ ID NO: 50), VACV-283 heavy (SEQ ID NO: 51), VACV-283 light (SEQ ID NO: 52), MPXV-2 heavy (SEQ ID NO: 53), MPXV-2 light (SEQ ID NO: 54), MPXV-12 heavy (SEQ ID NO: 55), MPXV-12 light (SEQ ID NO: 57), MPXV-13 heavy (SEQ ID NO: 58), MPXV-13 light (SEQ ID NO: 59), MPXV-25 heavy (SEQ ID NO: 60), MPXV-25 light (SEQ ID NO: 61), MPXV-38 heavy (SEQ ID NO: 62), MPXV-38 light (SEQ ID NO: 63), MPXV-43 heavy (SEQ ID NO: 64), MPXV-43 light (SEQ ID NO: 65), MPXV-66 heavy (SEQ ID NO: 66), MPXV-66 light (SEQ ID NO: 67), MPXV-70 heavy (SEQ ID NO: 68), MPXV-70 light (SEQ ID NO: 69), MPXV-92 heavy (SEQ ID NO: 70), MPXV-92 light (SEQ ID NO: 71), VACV-22 heavy (SEQ ID NO: 74), VACV-22 light (SEQ ID NO: 75), VACV-80 heavy (SEQ ID NO: 76), VACV-80 light (SEQ ID NO: 77), MPXV-39 heavy (SEQ ID NO: 78), MPXV-39 light (SEQ ID NO: 79), MPXV-51 heavy (SEQ ID NO: 80), MPXV-51 light (SEQ ID NO: 81), MPXV-56 heavy (SEQ ID NO: 82), MPXV-56 light (SEQ ID NO: 83), MPXV-91 heavy (SEQ ID NO: 84), MPXV-91 light (SEQ ID NO: 85), VACV-314 heavy (SEQ ID NO: 88), VACV-314 light (SEQ ID NO: 89), VACV-315 heavy (SEQ ID NO: 90), VACV-315 light (SEQ ID NO: 91), MPXV-29 heavy (SEQ ID NO: 94), MPXV-29 light (SEQ ID NO: 95), MPXV-72 heavy (SEQ ID NO: 96), MPXV-72 light (SEQ ID NO: 97, SEQ ID NO: 56 and SEQ ID NO: 885), MPXV-76 heavy (SEQ ID NO: 98), MPXV-76 light (SEQ ID NO: 99), MPXV-79 heavy (SEQ ID NO: 100), MPXV-79 light (SEQ ID NO: 101), VACV-33 heavy (SEQ ID NO: 104), VACV-33 light (SEQ ID NO: 105), VACV-34 heavy (SEQ ID NO: 106), VACV-34 light (SEQ ID NO: 107), MPXV-26 heavy (SEQ ID NO: 108), MPXV-26 light (SEQ ID NO: 109), MPXV-74 heavy (SEQ ID NO: 110), MPXV-74 light (SEQ ID NO: 111), MPXV-83 heavy (SEQ ID NO: 112), MPXV-83 light (SEQ ID NO: 113), MPXV-87 heavy (SEQ ID NO: 114), MPXV-87 light (SEQ ID NO: 115), VACV-154 heavy (SEQ ID NO: 116), VACV-154 light (SEQ ID NO: 117), VACV-300 heavy (SEQ ID NO: 118), VACV-300 light (SEQ ID NO: 119), VACV-301 heavy (SEQ ID NO: 120), VACV-301 light (SEQ ID NO: 121), VACV-302 heavy (SEQ ID NO: 122), VACV-302 light (SEQ ID NO: 123), VACV-303 heavy (SEQ ID NO: 124), VACV-303 light (SEQ ID NO: 125), MPXV-10 heavy (SEQ ID NO: 126), MPXV-10 light (SEQ ID NO: 127), MPXV-31 heavy (SEQ ID NO: 128), MPXV-31 light (SEQ ID NO: 129), MPXV-53 heavy (SEQ ID NO: 130), MPXV-53 light (SEQ ID NO: 131), MPXV-71 heavy (SEQ ID NO: 132), MPXV-71 light (SEQ ID NO: 133), MPXV-97 heavy (SEQ ID NO: 134), MPXV-97 light (SEQ ID NO: 135), VACV-309 heavy (SEQ ID NO: 136), VACV-309 light (SEQ ID NO: 137), VACV-312 heavy (SEQ ID NO: 138), VACV-312 light (SEQ ID NO: 139), VACV-313 heavy (SEQ ID NO: 140), VACV-313 light (SEQ ID NO: 141), MPXV-9 heavy (SEQ ID NO: 142), MPXV-9 light (SEQ ID NO: 143), MPXV-41 heavy (SEQ ID NO: 144), MPXV-41 light (SEQ ID NO: 145), MPXV-49 heavy (SEQ ID NO: 146), MPXV-49 light (SEQ ID NO: 147), VACV-318 heavy (SEQ ID NO: 148), VACV-318 light (SEQ ID NO: 149), VACV-308 heavy (SEQ ID NO: 150), VACV-308 light (SEQ ID NO: 151), VACV-305 heavy (SEQ ID NO: 152), VACV-305 light (SEQ ID NO: 153), VACV-306 heavy (SEQ ID NO: 154), VACV-306 light (SEQ ID NO: 155), VACV-307 heavy (SEQ ID NO: 156), VACV-307 light (SEQ ID NO: 157), VACV-311 heavy (SEQ ID NO: 158), VACV-311 light (SEQ ID NO: 159), VACV-316 heavy (SEQ ID NO: 160), VACV-316 light (SEQ ID NO: 161), VACV-310 heavy (SEQ ID NO: 162), VACV-310 light (SEQ ID NO: 163), MPXV-28 heavy (SEQ ID NO: 166), MPXV-28 light (SEQ ID NO: 167), MPXV-42 heavy (SEQ ID NO: 168), MPXV-42 light (SEQ ID NO: 169), MPXV-45 heavy (SEQ ID NO: 170), MPXV-45 light (SEQ ID NO: 171), MPXV-82 heavy (SEQ ID NO: 172), MPXV-82 light (SEQ ID NO: 173), MPXV-86 heavy (SEQ ID NO: 174), MPXV-86 light (SEQ ID NO: 175), MPXV-88 heavy (SEQ ID NO: 176), MPXV-88 light (SEQ ID NO: 177), MPXV-98 heavy (SEQ ID NO: 178), MPXV-98 light (SEQ ID NO: 179).

6. The method of claim 2, wherein said antibody or antibody fragment comprises light and heavy chain variable sequences according to clone-paired light and heavy chain sequences selected from the group consisting of VACV-8 heavy (SEQ ID NO: 180), VACV-8 light (SEQ ID NO: 181), VACV-56 heavy (SEQ ID NO: 182), VACV-56 light (SEQ ID NO: 183), VACV-66 heavy (SEQ ID NO: 184), VACV-66 light (SEQ ID NO: 185), VACV-77 heavy (SEQ ID NO: 186), VACV-77 light (SEQ ID NO: 187), VACV-116 heavy (SEQ ID NO: 188), VACV-116 light (SEQ ID NO: 189 and SEQ ID NO: 886), VACV-117 heavy (SEQ ID NO: 190), VACV-117 light (SEQ ID NO: 191), VACV-128 heavy (SEQ ID NO: 192), VACV-128 light (SEQ ID NO: 193), VACV-136 heavy (SEQ ID NO: 194), VACV-136 light (SEQ ID NO: 195), VACV-138 heavy (SEQ ID NO: 196, SEQ ID NO: 887 and SEQ ID NO: 917), VACV-138 light (SEQ ID NO: 197), VACV-168 heavy (SEQ ID NO: 198), VACV-168 light (SEQ ID NO: 199), VACV-159 heavy (SEQ ID NO: 200), VACV-159 light (SEQ ID NO: 201), VACV-199 heavy (SEQ ID NO: 202), VACV-199 light (SEQ ID NO: 203), VACV-228 heavy (SEQ ID NO: 204), VACV-228 light (SEQ ID NO: 205), VACV-230 heavy (SEQ ID NO: 206), VACV-230 light (SEQ ID NO: 207), VACV-249 heavy (SEQ ID NO: 208), VACV-249 light (SEQ ID NO: 209), VACV-304 heavy (SEQ ID NO: 210), VACV-304 light (SEQ ID NO: 211), MPXV-27 heavy (SEQ ID NO: 212 and SEQ ID NO: 888), MPXV-27 light (SEQ ID NO: 213), MPXV-30 heavy (SEQ ID NO: 214), MPXV-30 light (SEQ ID NO: 215), MPXV-40 heavy (SEQ ID NO: 216), MPXV-40 light (SEQ ID NO: 217), MPXV-61 heavy (SEQ ID NO: 218), MPXV-61 light (SEQ ID NO: 219), MPXV-96 heavy (SEQ ID NO: 220), MPXV-96 light (SEQ ID NO: 221), VACV-1 heavy (SEQ ID NO: 222), VACV-1 light (SEQ ID NO: 223), VACV-59 heavy (SEQ ID NO: 224), VACV-59 light (SEQ ID NO: 225), VACV-151 heavy (SEQ ID NO: 226), VACV-151 light (SEQ ID NO: 227), VACV-282 heavy (SEQ ID NO: 228), VACV-282 light (SEQ ID NO: 229), VACV-283 heavy (SEQ ID NO: 230), VACV-283 light (SEQ ID NO: 231), MPXV-2 heavy (SEQ ID NO: 232), MPXV-2 light (SEQ ID NO: 233), MPXV-12 heavy (SEQ ID NO: 234), MPXV-12 light (SEQ ID NO: 235), MPXV-13 heavy (SEQ ID NO: 236), MPXV-13 light (SEQ ID NO: 237), MPXV-25 heavy (SEQ ID NO: 238), MPXV-25 light (SEQ ID NO: 239), MPXV-38 heavy (SEQ ID NO: 240), MPXV-38 light (SEQ ID NO: 241), MPXV-43 heavy (SEQ ID NO: 242), MPXV-43 light (SEQ ID NO: 243), MPXV-66 heavy (SEQ ID NO: 244), MPXV-66 light (SEQ ID NO: 245), MPXV-70 heavy (SEQ ID NO: 246), MPXV-70 light (SEQ ID NO: 247), MPXV-92 heavy (SEQ ID NO: 248), MPXV-92 light (SEQ ID NO: 249), VACV-22 heavy (SEQ ID NO: 252), VACV-22 light (SEQ ID NO: 253), VACV-80 heavy (SEQ ID NO: 254), VACV-80 light (SEQ ID NO: 255), MPXV-39 heavy (SEQ ID NO: 256), MPXV-39 light (SEQ ID NO: 257), MPXV-51 heavy (SEQ ID NO: 258), MPXV-51 light (SEQ ID NO: 259), MPXV-56 heavy (SEQ ID NO: 260), MPXV-56 light (SEQ ID NO: 261), MPXV-91 heavy (SEQ ID NO: 262), MPXV-91 light (SEQ ID NO: 263), VACV-314 heavy (SEQ ID NO: 266), VACV-314 light (SEQ ID NO: 267), VACV-315 heavy (SEQ ID NO: 268), VACV-315 light (SEQ ID NO: 269), MPXV-29 heavy (SEQ ID NO: 272), MPXV-29 light (SEQ ID NO: 273), MPXV-72 heavy (SEQ ID NO: 274), MPXV-72 light (SEQ ID NO: 275, SEQ ID NOs: 889-890), MPXV-76 heavy (SEQ ID NO: 276), MPXV-76 light (SEQ ID NO: 277), MPXV-79 heavy (SEQ ID NO: 278), MPXV-79 light (SEQ ID NO: 279), VACV-33 heavy (SEQ ID NO: 282), VACV-33 light (SEQ ID NO: 283), VACV-34 heavy (SEQ ID NO: 284), VACV-34 light (SEQ ID NO: 285), MPXV-26 heavy (SEQ ID NO: 286), MPXV-26 light (SEQ ID NO: 287), MPXV-74 heavy (SEQ ID NO: 288), MPXV-74 light (SEQ ID NO: 289), MPXV-83 heavy (SEQ ID NO: 290), MPXV-83 light (SEQ ID NO: 291), MPXV-87 heavy (SEQ ID NO: 292), MPXV-87 light (SEQ ID NO: 293), VACV-154 heavy (SEQ ID NO: 294), VACV-154 light (SEQ ID NO: 295), VACV-300 heavy (SEQ ID NO: 296), VACV-300 light (SEQ ID NO: 297), VACV-301 heavy (SEQ ID NO: 298), VACV-301 light (SEQ ID NO: 299), VACV-302 heavy (SEQ ID NO: 300), VACV-302 light (SEQ ID NO: 301), VACV-303 heavy (SEQ ID NO: 302), VACV-303 light (SEQ ID NO: 303), MPXV-10 heavy (SEQ ID NO: 304), MPXV-10 light (SEQ ID NO: 305), MPXV-31 heavy (SEQ ID NO: 306), MPXV-31 light (SEQ ID NO: 307), MPXV-53 heavy (SEQ ID NO: 308), MPXV-53 light (SEQ ID NO: 309), MPXV-71 heavy (SEQ ID NO: 310), MPXV-71 light (SEQ ID NO: 311), MPXV-97 heavy (SEQ ID NO: 312), MPXV-97 light (SEQ ID NO: 313), VACV-309 heavy (SEQ ID NO: 314), VACV-309 light (SEQ ID NO: 315), VACV-312 heavy (SEQ ID NO: 316), VACV-312 light (SEQ ID NO: 317), VACV-313 heavy (SEQ ID NO: 318), VACV-313 light (SEQ ID NO: 319), MPXV-9 heavy (SEQ ID NO: 320), MPXV-9 light (SEQ ID NO: 321), MPXV-41 heavy (SEQ ID NO: 322), MPXV-41 light (SEQ ID NO: 323), MPXV-49 heavy (SEQ ID NO: 324), MPXV-49 light (SEQ ID NO: 325), VACV-318 heavy (SEQ ID NO: 326), VACV-318 light (SEQ ID NO: 327), VACV-308 heavy (SEQ ID NO: 328), VACV-308 light (SEQ ID NO: 329), VACV-305 heavy (SEQ ID NO: 330), VACV-305 light (SEQ ID NO: 331), VACV-306 heavy (SEQ ID NO: 332), VACV-306 light (SEQ ID NO: 333), VACV-307 heavy (SEQ ID NO: 334), VACV-307 light (SEQ ID NO: 335), VACV-311 heavy (SEQ ID NO: 336), VACV-311 light (SEQ ID NO: 337), VACV-316 heavy (SEQ ID NO: 338), VACV-316 light (SEQ ID NO: 339), VACV-310 heavy (SEQ ID NO: 340), VACV-310 light (SEQ ID NO: 341), MPXV-28 heavy (SEQ ID NO: 344), MPXV-28 light (SEQ ID NO: 345), MPXV-42 heavy (SEQ ID NO: 346), MPXV-42 light (SEQ ID NO: 347), MPXV-45 heavy (SEQ ID NO: 348), MPXV-45 light (SEQ ID NO: 349), MPXV-82 heavy (SEQ ID NO: 350), MPXV-82 light (SEQ ID NO: 351), MPXV-86 heavy (SEQ ID NO: 352), MPXV-86 light (SEQ ID NO: 353), MPXV-88 heavy (SEQ ID NO: 354), MPXV-88 light (SEQ ID NO: 355), MPXV-98 heavy (SEQ ID NO: 356), MPXV-98 light (SEQ ID NO: 357).

7. The method of claim 2, wherein said antibody or antibody fragment comprises light and heavy chain variable sequences having 70%, 80% or 90% identity to clone-paired light and heavy chain sequences selected from the group consisting of VACV-8 heavy (SEQ ID NO: 180), VACV-8 light (SEQ ID NO: 181), VACV-56 heavy (SEQ ID NO: 182), VACV-56 light (SEQ ID NO: 183), VACV-66 heavy (SEQ ID NO: 184), VACV-66 light (SEQ ID NO: 185), VACV-77 heavy (SEQ ID NO: 186), VACV-77 light (SEQ ID NO: 187), VACV-116 heavy (SEQ ID NO: 188), VACV-116 light (SEQ ID NO: 189 and SEQ ID NO: 886), VACV-117 heavy (SEQ ID NO: 190), VACV-117 light (SEQ ID NO: 191), VACV-128 heavy (SEQ ID NO: 192), VACV-128 light (SEQ ID NO: 193), VACV-136 heavy (SEQ ID NO: 194), VACV-136 light (SEQ ID NO: 195), VACV-138 heavy (SEQ ID NO: 196, SEQ ID NO: 887 and SEQ ID NO: 917), VACV-138 light (SEQ ID NO: 197), VACV-168 heavy (SEQ ID NO: 198), VACV-168 light (SEQ ID NO: 199), VACV-159 heavy (SEQ ID NO: 200), VACV-159 light (SEQ ID NO: 201), VACV-199 heavy (SEQ ID NO: 202), VACV-199 light (SEQ ID NO: 203), VACV-228 heavy (SEQ ID NO: 204), VACV-228 light (SEQ ID NO: 205), VACV-230 heavy (SEQ ID NO: 206), VACV-230 light (SEQ ID NO: 207), VACV-249 heavy (SEQ ID NO: 208), VACV-249 light (SEQ ID NO: 209), VACV-304 heavy (SEQ ID NO: 210), VACV-304 light (SEQ ID NO: 211), MPXV-27 heavy (SEQ ID NO: 212 and SEQ ID NO: 888), MPXV-27 light (SEQ ID NO: 213), MPXV-30 heavy (SEQ ID NO: 214), MPXV-30 light (SEQ ID NO: 215), MPXV-40 heavy (SEQ ID NO: 216), MPXV-40 light (SEQ ID NO: 217), MPXV-61 heavy (SEQ ID NO: 218), MPXV-61 light (SEQ ID NO: 219), MPXV-96 heavy (SEQ ID NO: 220), MPXV-96 light (SEQ ID NO: 221), VACV-1 heavy (SEQ ID NO: 222), VACV-1 light (SEQ ID NO: 223), VACV-59 heavy (SEQ ID NO: 224), VACV-59 light (SEQ ID NO: 225), VACV-151 heavy (SEQ ID NO: 226), VACV-151 light (SEQ ID NO: 227), VACV-282 heavy (SEQ ID NO: 228), VACV-282 light (SEQ ID NO: 229), VACV-283 heavy (SEQ ID NO: 230), VACV-283 light (SEQ ID NO: 231), MPXV-2 heavy (SEQ ID NO: 232), MPXV-2 light (SEQ ID NO: 233), MPXV-12 heavy (SEQ ID NO: 234), MPXV-12 light (SEQ ID NO: 235), MPXV-13 heavy (SEQ ID NO: 236), MPXV-13 light (SEQ ID NO: 237), MPXV-25 heavy (SEQ ID NO: 238), MPXV-25 light (SEQ ID NO: 239), MPXV-38 heavy (SEQ ID NO: 240), MPXV-38 light (SEQ ID NO: 241), MPXV-43 heavy (SEQ ID NO: 242), MPXV-43 light (SEQ ID NO: 243), MPXV-66 heavy (SEQ ID NO: 244), MPXV-66 light (SEQ ID NO: 245), MPXV-70 heavy (SEQ ID NO: 246), MPXV-70 light (SEQ ID NO: 247), MPXV-92 heavy (SEQ ID NO: 248), MPXV-92 light (SEQ ID NO: 249), VACV-22 heavy (SEQ ID NO: 252), VACV-22 light (SEQ ID NO: 253), VACV-80 heavy (SEQ ID NO: 254), VACV-80 light (SEQ ID NO: 255), MPXV-39 heavy (SEQ ID NO: 256), MPXV-39 light (SEQ ID NO: 257), MPXV-51 heavy (SEQ ID NO: 258), MPXV-51 light (SEQ ID NO: 259), MPXV-56 heavy (SEQ ID NO: 260), MPXV-56 light (SEQ ID NO: 261), MPXV-91 heavy (SEQ ID NO: 262), MPXV-91 light (SEQ ID NO: 263), VACV-314 heavy (SEQ ID NO: 266), VACV-314 light (SEQ ID NO: 267), VACV-315 heavy (SEQ ID NO: 268), VACV-315 light (SEQ ID NO: 269), MPXV-29 heavy (SEQ ID NO: 272), MPXV-29 light (SEQ ID NO: 273), MPXV-72 heavy (SEQ ID NO: 274), MPXV-72 light (SEQ ID NO: 275, SEQ ID NOs: 889-890), MPXV-76 heavy (SEQ ID NO: 276), MPXV-76 light (SEQ ID NO: 277), MPXV-79 heavy (SEQ ID NO: 278), MPXV-79 light (SEQ ID NO: 279), VACV-33 heavy (SEQ ID NO: 282), VACV-33 light (SEQ ID NO: 283), VACV-34 heavy (SEQ ID NO: 284), VACV-34 light (SEQ ID NO: 285), MPXV-26 heavy (SEQ ID NO: 286), MPXV-26 light (SEQ ID NO: 287), MPXV-74 heavy (SEQ ID NO: 288), MPXV-74 light (SEQ ID NO: 289), MPXV-83 heavy (SEQ ID NO: 290), MPXV-83 light (SEQ ID NO: 291), MPXV-87 heavy (SEQ ID NO: 292), MPXV-87 light (SEQ ID NO: 293), VACV- 154 heavy (SEQ ID NO: 294), VACV-154 light (SEQ ID NO: 295), VACV-300 heavy (SEQ ID NO: 296), VACV-300 light (SEQ ID NO: 297), VACV-301 heavy (SEQ ID NO: 298), VACV-301 light (SEQ ID NO: 299), VACV-302 heavy (SEQ ID NO: 300), VACV-302 light (SEQ ID NO: 301), VACV-303 heavy (SEQ ID NO: 302), VACV-303 light (SEQ ID NO: 303), MPXV-10 heavy (SEQ ID NO: 304), MPXV-10 light (SEQ ID NO: 305), MPXV-31 heavy (SEQ ID NO: 306), MPXV-31 light (SEQ ID NO: 307), MPXV-53 heavy (SEQ ID NO: 308), MPXV-53 light (SEQ ID NO: 309), MPXV-71 heavy (SEQ ID NO: 310), MPXV-71 light (SEQ ID NO: 311), MPXV-97 heavy (SEQ ID NO: 312), MPXV-97 light (SEQ ID NO: 313), VACV-309 heavy (SEQ ID NO: 314), VACV-309 light (SEQ ID NO: 315), VACV-312 heavy (SEQ ID NO: 316), VACV-312 light (SEQ ID NO: 317), VACV-313 heavy (SEQ ID NO: 318), VACV-313 light (SEQ ID NO: 319), MPXV-9 heavy (SEQ ID NO: 320), MPXV-9 light (SEQ ID NO: 321), MPXV-41 heavy (SEQ ID NO: 322), MPXV-41 light (SEQ ID NO: 323), MPXV-49 heavy (SEQ ID NO: 324), MPXV-49 light (SEQ ID NO: 325), VACV-318 heavy (SEQ ID NO: 326), VACV-318 light (SEQ ID NO: 327), VACV-308 heavy (SEQ ID NO: 328), VACV-308 light (SEQ ID NO: 329), VACV-305 heavy (SEQ ID NO: 330), VACV-305 light (SEQ ID NO: 331), VACV-306 heavy (SEQ ID NO: 332), VACV-306 light (SEQ ID NO: 333), VACV-307 heavy (SEQ ID NO: 334), VACV-307 light (SEQ ID NO: 335), VACV-311 heavy (SEQ ID NO: 336), VACV-311 light (SEQ ID NO: 337), VACV-316 heavy (SEQ ID NO: 338), VACV-316 light (SEQ ID NO: 339), VACV-310 heavy (SEQ ID NO: 340), VACV-310 light (SEQ ID NO: 341), MPXV-28 heavy (SEQ ID NO: 344), MPXV-28 light (SEQ ID NO: 345), MPXV-42 heavy (SEQ ID NO: 346), MPXV-42 light (SEQ ID NO: 347), MPXV-45 heavy (SEQ ID NO: 348), MPXV-45 light (SEQ ID NO: 349), MPXV-82 heavy (SEQ ID NO: 350), MPXV-82 light (SEQ ID NO: 351), MPXV-86 heavy (SEQ ID NO: 352), MPXV-86 light (SEQ ID NO: 353), MPXV-88 heavy (SEQ ID NO: 354), MPXV-88 light (SEQ ID NO: 355), MPXV-98 heavy (SEQ ID NO: 356), MPXV-98 light (SEQ ID NO: 357).

8. The method of claim 2, encoded by light and heavy chain variable sequences having 95% identity to clone-paired light and heavy chain sequences selected from the group consisting of VACV-8 heavy (SEQ ID NO: 180), VACV-8 light (SEQ ID NO: 181), VACV-56 heavy (SEQ ID NO: 182), VACV-56 light (SEQ ID NO: 183), VACV-66 heavy (SEQ ID NO: 184), VACV-66 light (SEQ ID NO: 185), VACV-77 heavy (SEQ ID NO: 186), VACV-77 light (SEQ ID NO: 187), VACV-116 heavy (SEQ ID NO: 188), VACV-116 light (SEQ ID NO: 189 and SEQ ID NO: 886), VACV-117 heavy (SEQ ID NO: 190), VACV-117 light (SEQ ID NO: 191), VACV-128 heavy (SEQ ID NO: 192), VACV-128 light (SEQ ID NO: 193), VACV-136 heavy (SEQ ID NO: 194), VACV-136 light (SEQ ID NO: 195), VACV-138 heavy (SEQ ID NO: 196, SEQ ID NO: 887 and SEQ ID NO: 917), VACV-138 light (SEQ ID NO: 197), VACV-168 heavy (SEQ ID NO: 198), VACV-168 light (SEQ ID NO: 199), VACV-159 heavy (SEQ ID NO: 200), VACV-159 light (SEQ ID NO: 201), VACV-199 heavy (SEQ ID NO: 202), VACV-199 light (SEQ ID NO: 203), VACV-228 heavy (SEQ ID NO: 204), VACV-228 light (SEQ ID NO: 205), VACV-230 heavy (SEQ ID NO: 206), VACV-230 light (SEQ ID NO: 207), VACV-249 heavy (SEQ ID NO: 208), VACV-249 light (SEQ ID NO: 209), VACV-304 heavy (SEQ ID NO: 210), VACV-304 light (SEQ ID NO: 211), MPXV-27 heavy (SEQ ID NO: 212 and SEQ ID NO: 888), MPXV-27 light (SEQ ID NO: 213), MPXV-30 heavy (SEQ ID NO: 214), MPXV-30 light (SEQ ID NO: 215), MPXV-40 heavy (SEQ ID NO: 216), MPXV-40 light (SEQ ID NO: 217), MPXV-61 heavy (SEQ ID NO: 218), MPXV-61 light (SEQ ID NO: 219), MPXV-96 heavy (SEQ ID NO: 220), MPXV-96 light (SEQ ID NO: 221), VACV-1 heavy (SEQ ID NO: 222), VACV-1 light (SEQ ID NO: 223), VACV-59 heavy (SEQ ID NO: 224), VACV-59 light (SEQ ID NO: 225), VACV-151 heavy (SEQ ID NO: 226), VACV-151 light (SEQ ID NO: 227), VACV-282 heavy (SEQ ID NO: 228), VACV-282 light (SEQ ID NO: 229), VACV-283 heavy (SEQ ID NO: 230), VACV-283 light (SEQ ID NO: 231), MPXV-2 heavy (SEQ ID NO: 232), MPXV-2 light (SEQ ID NO: 233), MPXV-12 heavy (SEQ ID NO: 234), MPXV-12 light (SEQ ID NO: 235), MPXV-13 heavy (SEQ ID NO: 236), MPXV-13 light (SEQ ID NO: 237), MPXV-25 heavy (SEQ ID NO: 238), MPXV-25 light (SEQ ID NO: 239), MPXV-38 heavy (SEQ ID NO: 240), MPXV-38 light (SEQ ID NO: 241), MPXV-43 heavy (SEQ ID NO: 242), MPXV-43 light (SEQ ID NO: 243), MPXV-66 heavy (SEQ ID NO: 244), MPXV-66 light (SEQ ID NO: 245), MPXV-70 heavy (SEQ ID NO: 246), MPXV-70 light (SEQ ID NO: 247), MPXV-92 heavy (SEQ ID NO: 248), MPXV-92 light (SEQ ID NO: 249), VACV-22 heavy (SEQ ID NO: 252), VACV-22 light (SEQ ID NO: 253), VACV-80 heavy (SEQ ID NO: 254), VACV-80 light (SEQ ID NO: 255), MPXV-39 heavy (SEQ ID NO: 256), MPXV-39 light (SEQ ID NO: 257), MPXV-51 heavy (SEQ ID NO: 258), MPXV-51 light (SEQ ID NO: 259), MPXV-56 heavy (SEQ ID NO: 260), MPXV-56 light (SEQ ID NO: 261), MPXV-91 heavy (SEQ ID NO: 262), MPXV-91 light (SEQ ID NO: 263), VACV-314 heavy (SEQ ID NO: 266), VACV-314 light (SEQ ID NO: 267), VACV-315 heavy (SEQ ID NO: 268), VACV-315 light (SEQ ID NO: 269), MPXV-29 heavy (SEQ ID NO: 272), MPXV-29 light (SEQ ID NO: 273), MPXV-72 heavy (SEQ ID NO: 274), MPXV-72 light (SEQ ID NO: 275, SEQ ID NOs: 889-890), MPXV-76 heavy (SEQ ID NO: 276), MPXV-76 light (SEQ ID NO: 277), MPXV-79 heavy (SEQ ID NO: 278), MPXV-79 light (SEQ ID NO: 279), VACV-33 heavy (SEQ ID NO: 282), VACV-33 light (SEQ ID NO: 283), VACV-34 heavy (SEQ ID NO: 284), VACV-34 light (SEQ ID NO: 285), MPXV-26 heavy (SEQ ID NO: 286), MPXV-26 light (SEQ ID NO: 287), MPXV-74 heavy (SEQ ID NO: 288), MPXV-74 light (SEQ ID NO: 289), MPXV-83 heavy (SEQ ID NO: 290), MPXV-83 light (SEQ ID NO: 291), MPXV-87 heavy (SEQ ID NO: 292), MPXV-87 light (SEQ ID NO: 293), VACV-154 heavy (SEQ ID NO: 294), VACV-154 light (SEQ ID NO: 295), VACV-300 heavy (SEQ ID NO: 296), VACV-300 light (SEQ ID NO: 297), VACV-301 heavy (SEQ ID NO: 298), VACV-301 light (SEQ ID NO: 299), VACV-302 heavy (SEQ ID NO: 300), VACV-302 light (SEQ ID NO: 301), VACV-303 heavy (SEQ ID NO: 302), VACV-303 light (SEQ ID NO: 303), MPXV-10 heavy (SEQ ID NO: 304), MPXV-10 light (SEQ ID NO: 305), MPXV-31 heavy (SEQ ID NO: 306), MPXV-31 light (SEQ ID NO: 307), MPXV-53 heavy (SEQ ID NO: 308), MPXV-53 light (SEQ ID NO: 309), MPXV-71 heavy (SEQ ID NO: 310), MPXV-71 light (SEQ ID NO: 311), MPXV-97 heavy (SEQ ID NO: 312), MPXV-97 light (SEQ ID NO: 313), VACV-309 heavy (SEQ ID NO: 314), VACV-309 light (SEQ ID NO: 315), VACV-312 heavy (SEQ ID NO: 316), VACV-312 light (SEQ ID NO: 317), VACV-313 heavy (SEQ ID NO: 318), VACV-313 light (SEQ ID NO: 319), MPXV-9 heavy (SEQ ID NO: 320), MPXV-9 light (SEQ ID NO: 321), MPXV-41 heavy (SEQ ID NO: 322), MPXV-41 light (SEQ ID NO: 323), MPXV-49 heavy (SEQ ID NO: 324), MPXV-49 light (SEQ ID NO: 325), VACV-318 heavy (SEQ ID NO: 326), VACV-318 light (SEQ ID NO: 327), VACV-308 heavy (SEQ ID NO: 328), VACV-308 light (SEQ ID NO: 329), VACV-305 heavy (SEQ ID NO: 330), VACV-305 light (SEQ ID NO: 331), VACV-306 heavy (SEQ ID NO: 332), VACV-306 light (SEQ ID NO: 333), VACV-307 heavy (SEQ ID NO: 334), VACV-307 light (SEQ ID NO: 335), VACV-311 heavy (SEQ ID NO: 336), VACV-311 light (SEQ ID NO: 337), VACV-316 heavy (SEQ ID NO: 338), VACV-316 light (SEQ ID NO: 339), VACV-310 heavy (SEQ ID NO: 340), VACV-310 light (SEQ ID NO: 341), MPXV-28 heavy (SEQ ID NO: 344), MPXV-28 light (SEQ ID NO: 345), MPXV-42 heavy (SEQ ID NO: 346), MPXV-42 light (SEQ ID NO: 347), MPXV-45 heavy (SEQ ID NO: 348), MPXV-45 light (SEQ ID NO: 349), MPXV-82 heavy (SEQ ID NO: 350), MPXV-82 light (SEQ ID NO: 351), MPXV-86 heavy (SEQ ID NO: 352), MPXV-86 light (SEQ ID NO: 353), MPXV-88 heavy (SEQ ID NO: 354), MPXV-88 light (SEQ ID NO: 355), MPXV-98 heavy (SEQ ID NO: 356), MPXV-98 light (SEQ ID NO: 357).

9. The method of claim 2, wherein the antibody fragment is a recombinant ScFv (single chain fragment variable) antibody, Fab fragment, F(ab')$_2$ fragment, or Fv fragment.

10. The method of claim 2, wherein said antibody is an IgG.

11. The method of claim 2, wherein said antibody is a chimeric antibody.

12. The method of claim 2, wherein said antibody or antibody fragment is administered prior to infection.

13. The method of claim 2, wherein said antibody or antibody fragment is administered after infection.

14. The method of claim 2, wherein delivering comprises administering the antibody or antibody fragment, or administering an RNA or DNA sequence or vector encoding the antibody or antibody fragment.

15. A monoclonal antibody, wherein the antibody or antibody fragment is characterized by clone-paired heavy and light chain CDR sequences selected from the group consisting of VACV-8 (SEQ ID NOs: 358-360 and SEQ ID NOs: 625-627), VACV-56 (SEQ ID NOs: 361-363 and SEQ ID NOs: 628-630), VACV-66 (SEQ ID NOs: 364-366 and SEQ ID NOs: 631-633), VACV-77 (SEQ ID NOs: 367-369 and SEQ ID NOs: 634-636), VACV-116 (SEQ ID NOs: 370-372, SEQ ID NOs: 897-899 and SEQ ID NOs: 637-639), VACV-117 (SEQ ID NOs: 373-375 and SEQ ID NOs: 640-642), VACV-128 (SEQ ID NOs: 376-378 and SEQ ID NOs: 643-645), VACV-136 (SEQ ID NOs: 379-381 and SEQ ID NOs: 646-648), VACV-138 (SEQ ID NOs: 891-893, SEQ ID NOs: 382-384, SEQ ID NOs: 918-920 and SEQ ID NOs: 649-651), VACV-168 (SEQ ID NOs: 385-387 and SEQ ID NOs: 652-654), VACV-159 (SEQ ID NOs: 388-390 and SEQ ID NOs: 655-657), VACV-199 (SEQ ID NOs: 391-393 and SEQ ID NOs: 658-660), VACV-228 (SEQ ID NOs: 394-396 and SEQ ID NOs: 661-663), VACV-230 (SEQ ID NOs: 397-399, SEQ ID NOs: 664-665 and SEQ ID NO: 900), VACV-249 (SEQ ID NOs: 400-402 and SEQ ID NOs: 901-903), VACV-304 (SEQ ID NOs: 403-405 and SEQ ID NOs: 904-906), MPXV-27 (SEQ ID NOs: 894-896, SEQ ID NOs: 406-408 and SEQ ID NOs: 907-909), MPXV-30 (SEQ ID NOs: 409-411 and SEQ ID NOs: 666-668), MPXV-40 (SEQ ID NOs: 412-414 and SEQ ID NOs: 669-671), MPXV-61 (SEQ ID NOs: 415-417 and SEQ ID NOs: 672-674), MPXV-96 (SEQ ID NOs: 418-420 and SEQ ID NOs: 675-677), VACV-1 (SEQ ID NOs: 421-423 and SEQ ID NOs: 678-680) VACV-59 (SEQ ID NOs: 424-426 and SEQ ID NOs: 681-683), VACV-151 (SEQ ID NOs: 427-429 and SEQ ID NOs: 684-686), VACV-282 (SEQ ID NOs: 430-432 and SEQ ID NOs: 687-689), VACV-283 (SEQ ID NOs: 433-435 and SEQ ID NOs: 690-692), MPXV-2 (SEQ ID NOs: 436-438 and SEQ ID NOs: 693-695), MPXV-12 (SEQ ID NOs: 439-441 and SEQ ID NOs: 696-698), MPXV-13 (SEQ ID NOs: 442-444 and SEQ ID NOs: 699-701), MPXV-25 (SEQ ID NOs: 445-447 and SEQ ID NOs: 702-704), MPXV-38 (SEQ ID NOs: 448-450 and SEQ ID NOs: 705-707), MPXV-43 (SEQ ID NOs: 451-453 and SEQ ID NOs: 708-710), MPXV-66 (SEQ ID NOs: 454-456 and SEQ ID NOs: 711-713), MPXV-70 (SEQ ID NOs: 457-459 and SEQ ID NOs: 714-716), MPXV-92 (SEQ ID NOs: 460-462 and SEQ ID NOs: 717-719), VACV-22 (SEQ ID NOs: 466-468 and SEQ ID NOs: 723-725), VACV-80 (SEQ ID NOs: 469-471 and SEQ ID NOs: 726-728), MPXV-39 (SEQ ID NOs: 472-474 and SEQ ID NOs: 729-731) MPXV-51 (SEQ ID NOs: 475-477 and SEQ ID NOs: 732-734), MPXV-56 (SEQ ID NOs: 478-480 and SEQ ID NOs: 735-737), MPXV-91 (SEQ ID NOs: 481-483 and SEQ ID NOs: 738-740), VACV-314 (SEQ ID NOs: 487-489 and SEQ ID NOs: 744-746), VACV-315 (SEQ ID NOs: 490-492 and SEQ ID NOs: 747-749), MPXV-29 (SEQ ID NOs: 496-498 and SEQ ID NOs: 753-755), MPXV-72 (SEQ ID NOs: 499-501, SEQ ID NOs: 910-915 and SEQ ID NOs: 756-758), MPXV-76 (SEQ ID NOs: 502-504 and SEQ ID NOs: 759-761), MPXV-79 (SEQ ID NOs: 505-507 and SEQ ID NOs: 762-764), VACV-33 (SEQ ID NOs: 511-513 and SEQ ID NOs: 768-770), VACV-34 (SEQ ID NOs: 514-516 and SEQ ID NOs: 771-773), MPXV-26 (SEQ ID NOs: 517-519 and SEQ ID NOs: 774-776), MPXV-74 (SEQ ID NOs: 520-522 and SEQ ID NOs:777-779), MPXV-83 (SEQ ID NOs: 523-525 and SEQ ID NOs: 780-782), MPXV-87 (SEQ ID NOs: 526-528 and SEQ ID NOs: 783-785), VACV-154 (SEQ ID NOs: 529-531 and SEQ ID NOs: 786-788), VACV-300 (SEQ ID NOs: 532-534 and SEQ ID NOs: 789-791), VACV-301 (SEQ ID NOs: 535-537 and SEQ ID NOs: 792-794), VACV-302 (SEQ ID NOs: 538-540 and SEQ ID NOs: 795-797), VACV-303 (SEQ ID NOs: 541-543 and SEQ ID NOs: 798-800), MPXV-10 (SEQ ID NOs: 544-546 and SEQ ID NOs: 801-803), MPXV-31 (SEQ ID NOs: 547-549 and SEQ ID NOs: 804-806), MPXV-53 (SEQ ID NOs: 550-552 and SEQ ID NOs: 807-809), MPXV-71 (SEQ ID NOs: 553-555 and SEQ ID NOs: 810-812), MPXV-97 (SEQ ID NOs: 556-558 and SEQ ID NOs: 813-815), VACV-309 (SEQ ID NOs: 559-561 and SEQ ID NOs: 816-818), VACV-312 (SEQ ID NOs: 562-564 and SEQ ID NOs: 819-821), VACV-313 (SEQ ID NOs: 565-567 and SEQ ID NOs: 822-824), MPXV-9 (SEQ ID NOs: 568-570 and SEQ ID NOs: 825-827), MPXV-41 (SEQ ID NOs: 571-573 and SEQ ID NOs: 828-830), MPXV-49 (SEQ ID NOs: 574-576 and SEQ ID NOs: 831-833), VACV-318 (SEQ ID NOs: 577-579 and SEQ ID NOs: 834-836), VACV-308 (SEQ ID NOs: 580-582 and SEQ ID NOs: 837-839), VACV-305 (SEQ ID NOs: 583-585 and SEQ ID NOs: 840-842), VACV-306 (SEQ ID NOs: 586-588 and SEQ ID NOs: 843-845), VACV-307 (SEQ ID NOs: 589-591 and SEQ ID NOs: 846-848), VACV-311 (SEQ ID NOs: 592-594 and SEQ ID NOs: 849-851), VACV-316 (SEQ ID NOs: 595-597 and SEQ ID NOs: 852-854), VACV-310 (SEQ ID NOs: 598-600 and SEQ ID NOs: 855-857), MPXV-28 (SEQ ID NOs: 604-606 and SEQ ID NOs: 861-863), MPXV-42 (SEQ ID NOs: 607-609 and SEQ ID NOs: 864-866), MPXV-45 (SEQ ID NOs: 610-612 and SEQ ID NOs: 867-869), MPXV-82 (SEQ ID NOs: 613-615 and SEQ ID NOs: 870-872), MPXV-86 (SEQ ID NOs: 616-618 and SEQ ID NOs: 873-875), MPXV-88 (SEQ ID NOs: 619-621 and SEQ ID NOs: 876-878), MPXV-98 (SEQ ID NOs: 622-624 and SEQ ID NOs: 879-881).

16. A hybridoma or engineered non-B cell encoding an antibody or antibody fragment wherein the antibody or antibody fragment is characterized by clone-paired heavy and light chain CDR sequences selected from the group consisting of VACV-8 (SEQ ID NOs: 358-360 and SEQ ID NOs: 625-627), VACV-56 (SEQ ID NOs: 361-363 and SEQ ID NOs: 628-630), VACV-66 (SEQ ID NOs: 364-366 and SEQ ID NOs: 631-633), VACV-77 (SEQ ID NOs: 367-369 and SEQ ID NOs: 634-636), VACV-116 (SEQ ID NOs: 370-372, SEQ ID NOs: 897-899 and SEQ ID NOs: 637-639), VACV-117 (SEQ ID NOs: 373-375 and SEQ ID NOs: 640-642), VACV-128 (SEQ ID NOs: 376-378 and SEQ ID NOs: 643-645), VACV-136 (SEQ ID NOs: 379-381 and SEQ ID NOs: 646-648), VACV-138 (SEQ ID NOs: 891-893, SEQ ID NOs: 382-384, SEQ ID NOs: 918-920 and SEQ ID NOs: 649-651), VACV-168 (SEQ ID NOs: 385-387 and SEQ ID NOs: 652-654), VACV-159 (SEQ ID NOs: 388-390 and SEQ ID NOs: 655-657), VACV-199 (SEQ ID NOs: 391-393 and SEQ ID NOs: 658-660), VACV-228 (SEQ ID NOs: 394-396 and SEQ ID NOs: 661-663), VACV-230 (SEQ ID NOs: 397-399, SEQ ID NOs: 664-665 and SEQ ID NO: 900), VACV-249 (SEQ ID NOs: 400-402 and SEQ ID NOs: 901-903), VACV-304 (SEQ ID NOs: 403-405 and SEQ ID NOs: 904-906), MPXV-27 (SEQ ID NOs: 894-896, SEQ ID NOs: 406-408 and SEQ ID NOs: 907-909), MPXV-30 (SEQ ID NOs: 409-411 and SEQ ID NOs: 666-668), MPXV-40 (SEQ ID NOs: 412-414 and SEQ ID NOs: 669-671), MPXV-61 (SEQ ID NOs: 415-417 and SEQ ID NOs: 672-674), MPXV-96 (SEQ ID NOs: 418-420 and SEQ ID NOs: 675-677), VACV-1 (SEQ ID NOs: 421-423 and SEQ ID NOs: 678-680) VACV-59 (SEQ ID NOs: 424-426 and SEQ ID NOs: 681-683), VACV-151 (SEQ ID NOs: 427-429 and SEQ ID NOs: 684-686), VACV-282 (SEQ ID NOs: 430-432 and SEQ ID NOs: 687-689), VACV-283 (SEQ ID NOs: 433-435 and SEQ ID NOs: 690-692), MPXV-2 (SEQ ID NOs: 436-438 and SEQ ID NOs: 693-695), MPXV-12 (SEQ ID NOs: 439-441 and SEQ ID NOs: 696-698), MPXV-13 (SEQ ID NOs: 442-444 and SEQ ID NOs: 699-701), MPXV-25 (SEQ ID NOs: 445-447 and SEQ ID NOs: 702-704), MPXV-38 (SEQ ID NOs: 448-450 and SEQ ID NOs: 705-707), MPXV-43 (SEQ ID NOs: 451-453 and SEQ ID NOs: 708-710), MPXV-66 (SEQ ID NOs: 454-456 and SEQ ID NOs: 711-713), MPXV-70 (SEQ ID NOs: 457-459 and SEQ ID NOs: 714-716), MPXV-92 (SEQ ID NOs: 460-462 and SEQ ID NOs: 717-719), VACV-22 (SEQ ID NOs: 466-468 and SEQ ID NOs: 723-725), VACV-80 (SEQ ID NOs: 469-471 and SEQ ID NOs: 726-728), MPXV-39 (SEQ ID NOs: 472-474 and SEQ ID NOs: 729-731) MPXV-51 (SEQ ID NOs: 475-477 and SEQ ID NOs: 732-734), MPXV-56 (SEQ ID NOs: 478-480 and SEQ ID NOs: 735-737), MPXV-91 (SEQ ID NOs: 481-483 and SEQ ID NOs: 738-740), VACV-314 (SEQ ID NOs: 487-489 and SEQ ID NOs: 744-746), VACV-315 (SEQ ID NOs: 490-492 and SEQ ID NOs: 747-749), MPXV-29 (SEQ ID NOs: 496-498 and SEQ ID NOs: 753-755), MPXV-72 (SEQ ID NOs: 499-501, SEQ ID NOs: 910-915 and SEQ ID NOs: 756-758), MPXV-76 (SEQ ID NOs: 502-504 and SEQ ID NOs: 759-761), MPXV-79 (SEQ ID NOs: 505-507 and SEQ ID NOs: 762-764), VACV-33 (SEQ ID NOs: 511-513 and SEQ ID NOs: 768-770), VACV-34 (SEQ ID NOs: 514-516 and SEQ ID NOs: 771-773), MPXV-26 (SEQ ID NOs: 517-519 and SEQ ID NOs: 774-776), MPXV-74 (SEQ ID NOs: 520-522 and SEQ ID NOs:777-779), MPXV-83 (SEQ ID NOs: 523-525 and SEQ ID NOs: 780-782), MPXV-87 (SEQ ID NOs: 526-528 and SEQ ID NOs: 783-785), VACV-154 (SEQ ID NOs: 529-531 and SEQ ID NOs: 786-788), VACV-300 (SEQ ID NOs: 532-534 and SEQ ID NOs: 789-791), VACV-301 (SEQ ID NOs: 535-537 and SEQ ID NOs: 792-794), VACV-302 (SEQ ID NOs: 538-540 and SEQ ID NOs: 795-797), VACV-303 (SEQ ID NOs: 541-543 and SEQ ID NOs: 798-800), MPXV-10 (SEQ ID NOs: 544-546 and SEQ ID NOs: 801-803), MPXV-31 (SEQ ID NOs: 547-549 and SEQ ID NOs: 804-806), MPXV-53 (SEQ ID NOs: 550-552 and SEQ ID NOs: 807-809), MPXV-71 (SEQ ID NOs: 553-555 and SEQ ID NOs: 810-812), MPXV-97 (SEQ ID NOs: 556-558 and SEQ ID NOs: 813-815), VACV-309 (SEQ ID NOs: 559-561 and SEQ ID NOs: 816-818), VACV-312 (SEQ ID NOs: 562-564 and SEQ ID NOs: 819-821), VACV-313 (SEQ ID NOs: 565-567 and SEQ ID NOs: 822-824), MPXV-9 (SEQ ID NOs: 568-570 and SEQ ID NOs: 825-827), MPXV-41 (SEQ ID NOs: 571-573 and SEQ ID NOs: 828-830), MPXV-49 (SEQ ID NOs: 574-576 and SEQ ID NOs: 831-833), VACV-318 (SEQ ID NOs: 577-579 and SEQ ID NOs: 834-836), VACV-308 (SEQ ID NOs: 580-582 and SEQ ID NOs: 837-839), VACV-305 (SEQ ID NOs: 583-585 and SEQ ID NOs: 840-842), VACV-306 (SEQ ID NOs: 586-588 and SEQ ID NOs: 843-845), VACV-307 (SEQ ID NOs: 589-591 and SEQ ID NOs: 846-848), VACV-311 (SEQ ID NOs: 592-594 and SEQ ID NOs: 849-851), VACV-316 (SEQ ID NOs: 595-597 and SEQ ID NOs: 852-854), VACV-310 (SEQ ID NOs: 598-600 and SEQ ID NOs: 855-857), MPXV-28 (SEQ ID NOs: 604-606 and SEQ ID NOs: 861-863), MPXV-42 (SEQ ID NOs: 607-609 and SEQ ID NOs: 864-866), MPXV-45 (SEQ ID NOs: 610-612 and SEQ ID NOs: 867-869), MPXV-82 (SEQ ID NOs: 613-615 and SEQ ID NOs: 870-872), MPXV-86 (SEQ ID NOs: 616-618 and SEQ ID NOs: 873-875), MPXV-88 (SEQ ID NOs: 619-621 and SEQ ID NOs: 876-878), MPXV-98 (SEQ ID NOs: 622-624 and SEQ ID NOs: 879-881).

17. A vaccine formulation comprising two or more antibodies or antibody fragments characterized by clone-paired heavy and light chain CDR sequences selected from the group consisting of VACV-8 (SEQ ID NOs: 358-360 and SEQ ID NOs: 625-627), VACV-56 (SEQ ID NOs: 361-363 and SEQ ID NOs: 628-630), VACV-66 (SEQ ID NOs: 364-366 and SEQ ID NOs: 631-633), VACV-77 (SEQ ID NOs: 367-369 and SEQ ID NOs: 634-636), VACV-116 (SEQ ID NOs: 370-372, SEQ ID NOs: 897-899 and SEQ ID NOs: 637-639), VACV-117 (SEQ ID NOs: 373-375 and SEQ ID NOs: 640-642), VACV-128 (SEQ ID NOs: 376-378 and SEQ ID NOs: 643-645), VACV-136 (SEQ ID NOs: 379-381 and SEQ ID NOs: 646-648), VACV-138 (SEQ ID NOs: 891-893, SEQ ID NOs: 382-384, SEQ ID NOs: 918-920 and SEQ ID NOs: 649-651), VACV-168 (SEQ ID NOs: 385-387 and SEQ ID NOs: 652-654), VACV-159 (SEQ ID NOs: 388-390 and SEQ ID NOs: 655-657), VACV-199 (SEQ ID NOs: 391-393 and SEQ ID NOs: 658-660), VACV-228 (SEQ ID NOs: 394-396 and SEQ ID NOs: 661-663), VACV-230 (SEQ ID NOs: 397-399, SEQ ID NOs: 664-665 and SEQ ID NO: 900), VACV-249 (SEQ ID NOs: 400-402 and SEQ ID NOs: 901-903), VACV-304 (SEQ ID NOs: 403-405 and SEQ ID NOs: 904-906), MPXV-27 (SEQ ID NOs: 894-896, SEQ ID NOs: 406-408 and SEQ ID NOs: 907-909), MPXV-30 (SEQ ID NOs: 409-411 and SEQ ID NOs: 666-668), MPXV-40 (SEQ ID NOs: 412-414 and SEQ ID NOs: 669-671), MPXV-61 (SEQ ID NOs: 415-417 and SEQ ID NOs: 672-674), MPXV-96 (SEQ ID NOs: 418-420 and SEQ ID NOs: 675-677), VACV-1 (SEQ ID NOs: 421-423 and SEQ ID NOs: 678-680) VACV-59 (SEQ ID NOs: 424-426 and SEQ ID NOs: 681-683), VACV-151 (SEQ ID NOs: 427-429 and SEQ ID NOs: 684-686), VACV-282 (SEQ ID NOs: 430-432 and SEQ ID NOs: 687-689), VACV-283 (SEQ ID NOs: 433-435 and SEQ ID NOs: 690-692), MPXV-2 (SEQ ID NOs: 436-438 and SEQ ID NOs: 693-695), MPXV-12 (SEQ ID NOs: 439-441 and SEQ ID NOs: 696-698), MPXV-13 (SEQ ID NOs: 442-444 and SEQ ID NOs: 699-701), MPXV-25 (SEQ ID NOs: 445-447 and SEQ ID NOs: 702-704), MPXV-38 (SEQ ID NOs: 448-450 and SEQ ID NOs: 705-707), MPXV-43 (SEQ ID NOs: 451-453 and SEQ ID NOs: 708-710), MPXV-66 (SEQ ID NOs: 454-456 and SEQ ID NOs: 711-713), MPXV-70 (SEQ ID NOs: 457-459 and SEQ ID NOs: 714-716), MPXV-92 (SEQ ID NOs: 460-462 and SEQ ID NOs: 717-719), VACV-22 (SEQ ID NOs: 466-468 and SEQ ID NOs: 723-725), VACV-80 (SEQ ID NOs: 469-471 and SEQ ID NOs: 726-728), MPXV-39 (SEQ ID NOs: 472-474 and SEQ ID NOs: 729-731) MPXV-51 (SEQ ID NOs: 475-477 and SEQ ID NOs: 732-734), MPXV-56 (SEQ ID NOs: 478-480 and SEQ ID NOs: 735-737), MPXV-91 (SEQ ID NOs: 481-483 and SEQ ID NOs: 738-740), VACV-314 (SEQ ID NOs: 487-489 and SEQ ID NOs: 744-746), VACV-315 (SEQ ID NOs: 490-492 and SEQ ID NOs: 747-749), MPXV-29 (SEQ ID NOs: 496-498 and SEQ ID NOs: 753-755), MPXV-72 (SEQ ID NOs: 499-501, SEQ ID NOs: 910-915 and SEQ ID NOs: 756-758), MPXV-76 (SEQ ID NOs: 502-504 and SEQ ID NOs: 759-761), MPXV-79 (SEQ ID NOs: 505-507 and SEQ ID NOs: 762-764), VACV-33 (SEQ ID NOs: 511-513 and SEQ ID NOs: 768-770), VACV-34 (SEQ ID NOs: 514-516 and SEQ ID NOs: 771-773), MPXV-26 (SEQ ID NOs: 517-519 and SEQ ID NOs: 774-776), MPXV-74 (SEQ ID NOs: 520-522 and SEQ ID NOs:777-779), MPXV-83 (SEQ ID NOs: 523-525 and SEQ ID NOs: 780-782), MPXV-87 (SEQ ID NOs: 526-528 and SEQ ID NOs: 783-785), VACV-154 (SEQ ID NOs: 529-531 and SEQ ID NOs: 786-788), VACV-300 (SEQ ID NOs: 532-534 and SEQ ID NOs: 789-791), VACV-301 (SEQ ID NOs: 535-537 and SEQ ID NOs: 792-794), VACV-302 (SEQ ID NOs: 538-540 and SEQ ID NOs: 795-797), VACV-303 (SEQ ID NOs: 541-543 and SEQ ID NOs: 798-800), MPXV-10 (SEQ ID NOs: 544-546 and SEQ ID NOs: 801-803), MPXV-31 (SEQ ID NOs: 547-549 and SEQ ID NOs: 804-806), MPXV-53 (SEQ ID NOs: 550-552 and SEQ ID NOs: 807-809), MPXV-71 (SEQ ID NOs: 553-555 and SEQ ID NOs: 810-812), MPXV-97 (SEQ ID NOs: 556-558 and SEQ ID NOs: 813-815), VACV-309 (SEQ ID NOs: 559-561 and SEQ ID NOs: 816-818), VACV-312 (SEQ ID NOs: 562-564 and SEQ ID NOs: 819-821), VACV-313 (SEQ ID NOs: 565-567 and SEQ ID NOs: 822-824), MPXV-9 (SEQ ID NOs: 568-570 and SEQ ID NOs: 825-827), MPXV-41 (SEQ ID NOs: 571-573 and SEQ ID NOs: 828-830), MPXV-49 (SEQ ID NOs: 574-576 and SEQ ID NOs: 831-833), VACV-318 (SEQ ID NOs: 577-579 and SEQ ID NOs: 834-836), VACV-308 (SEQ ID NOs: 580-582 and SEQ ID NOs: 837-839), VACV-305 (SEQ ID NOs: 583-585 and SEQ ID NOs: 840-842), VACV-306 (SEQ ID NOs: 586-588 and SEQ ID NOs: 843-845), VACV-307 (SEQ ID NOs: 589-591 and SEQ ID NOs: 846-848), VACV-311 (SEQ ID NOs: 592-594 and SEQ ID NOs: 849-851), VACV-316 (SEQ ID NOs: 595-597 and SEQ ID NOs: 852-854), VACV-310 (SEQ ID NOs: 598-600 and SEQ ID NOs: 855-857), MPXV-28 (SEQ ID NOs: 604-606 and SEQ ID NOs: 861-863), MPXV-42 (SEQ ID NOs: 607-609 and SEQ ID NOs: 864-866), MPXV-45 (SEQ ID NOs: 610-612 and SEQ ID NOs: 867-869), MPXV-82 (SEQ ID NOs: 613-615 and SEQ ID NOs: 870-872), MPXV-86 (SEQ ID NOs: 616-618 and SEQ ID NOs: 873-875), MPXV-88 (SEQ ID NOs: 619-621 and SEQ ID NOs: 876-878), MPXV-98 (SEQ ID NOs: 622-624 and SEQ ID NOs: 879-881).

18. The vaccine formulation of claim 17, wherein said antibodies or antibody fragments bind to MV and EV forms of vaccinia virus.

19. The vaccine formulation of claim 17, wherein said antibodies bind to two or more of the orthopox antigens selected from the group consisting of A27, D8, L1, B5, A33 and H3.

20. The vaccine formulation of claim 17, wherein said antibodies or antibody fragments bind to MV proteins A27 and L1 and EV proteins B5 and A33.

* * * * *